United States Patent
Allen et al.

(10) Patent No.: US 11,021,493 B2
(45) Date of Patent: Jun. 1, 2021

(54) 1,4-THIAZINE DIOXIDE AND 1,2,4-THIADIAZINE DIOXIDE DERIVATIVES AS BETA-SECRETASE INHIBITORS AND METHODS OF USE

(71) Applicant: AMGEN INC., Thousand Oaks, CA (US)

(72) Inventors: Jennifer R. Allen, Newbury Park, CA (US); Matthew P. Bourbeau, Woodland Hills, CA (US); James A. Brown, Moorpark, CA (US); Ning Chen, Thousand Oaks, CA (US); Michael J. Frohn, Thousand Oaks, CA (US); Zice Fu, Foster City, CA (US); Longbin Liu, Thousand Oaks, CA (US); Qingyian Liu, Camarillo, CA (US); Liping H. Pettus, Thousand Oaks, CA (US); Wenyuan Qian, Thousand Oaks, CA (US); Corey Reeves, Sherman Oaks, CA (US); Aaron C. Siegmund, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 16/466,207

(22) PCT Filed: Dec. 13, 2017

(86) PCT No.: PCT/US2017/066197
§ 371 (c)(1),
(2) Date: Jun. 3, 2019

(87) PCT Pub. No.: WO2018/112094
PCT Pub. Date: Jun. 21, 2018

(65) Prior Publication Data
US 2020/0231601 A1 Jul. 23, 2020

Related U.S. Application Data

(60) Provisional application No. 62/434,715, filed on Dec. 15, 2016.

(51) Int. Cl.
*C07D 513/08* (2006.01)
*A61P 25/28* (2006.01)
*C07D 417/10* (2006.01)

(52) U.S. Cl.
CPC ............ *C07D 513/08* (2013.01); *A61P 25/28* (2018.01); *C07D 417/10* (2013.01)

(58) Field of Classification Search
CPC ............................ C07D 513/08; C07D 417/10
USPC ...................................................... 514/222.5
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| 5,942,400 A | 8/1999 | Anderson et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2011/0152253 A1 | 6/2011 | Motoki et al. |
| 2012/0238557 A1 | 9/2012 | Masui et al. |
| 2012/0245154 A1 | 9/2012 | Anan et al. |
| 2012/0245157 A1 | 9/2012 | Masui et al. |
| 2016/0046618 A1 | 2/2016 | Allen et al. |

FOREIGN PATENT DOCUMENTS

| | | |
|---|---|---|
| EP | 2 147 914 A1 | 1/2010 |
| EP | 2 151 435 A1 | 2/2010 |
| EP | 2 305 672 A1 | 4/2011 |
| EP | 2 703 401 A1 | 3/2014 |
| EP | 1 942 105 B1 | 4/2014 |
| WO | 2000/017369 A2 | 3/2000 |
| WO | 2009/134617 A1 | 11/2009 |
| WO | 2009/151098 A1 | 12/2009 |

(Continued)

*Primary Examiner* — Kahsay Habte
(74) *Attorney, Agent, or Firm* — Markus Bergauer

(57) ABSTRACT

The present disclosure provides a class of compounds useful for the modulation of beta-secretase enzyme (BACE) activity. The compounds have a general Formula I:

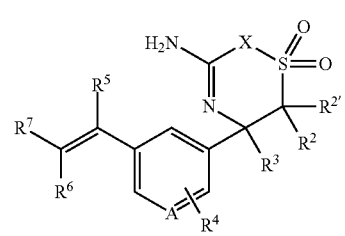

wherein variables A, X, $R^2$, $R^{2'}$, $R^3$, $R^4$, $R^5$, $R^6$, and $R^7$ of Formula I are defined herein. This disclosure also provides pharmaceutical compositions comprising the compounds, and uses of the compounds and compositions for treatment of disorders and/or conditions related to Aβ plaque formation and deposition, resulting from the biological activity of BACE. Such BACE mediated disorders include, for example, Alzheimer's Disease, cognitive deficits, cognitive impairments, and other central nervous system conditions.

33 Claims, No Drawings

(56) References Cited

FOREIGN PATENT DOCUMENTS

| | | |
|---|---|---|
| WO | 2010/013302 A1 | 2/2010 |
| WO | 2010/013794 A1 | 2/2010 |
| WO | 2011/005738 A1 | 1/2011 |
| WO | 2011/009898 A1 | 1/2011 |
| WO | 2011/029803 A1 | 3/2011 |
| WO | 2011/044081 A1 | 4/2011 |
| WO | 2011/069934 A1 | 6/2011 |
| WO | 2012/095463 A1 | 7/2012 |
| WO | 2012/095469 A1 | 7/2012 |
| WO | 2012/098213 A1 | 7/2012 |
| WO | 2012/098461 A1 | 7/2012 |
| WO | 2012/138734 A1 | 10/2012 |
| WO | 2012/139425 A1 | 10/2012 |
| WO | 2012/147762 A1 | 11/2012 |
| WO | 2012/156284 A1 | 11/2012 |
| WO | 2012/162330 A1 | 11/2012 |
| WO | 2012/162334 A1 | 11/2012 |
| WO | 2013/004676 A1 | 1/2013 |
| WO | 2013/027188 A1 | 2/2013 |
| WO | 2013/028670 A1 | 2/2013 |
| WO | 2013/030713 A1 | 3/2013 |
| WO | 2013/142613 A1 | 9/2013 |
| WO | 2013/164730 A1 | 11/2013 |
| WO | 2013/182638 A1 | 12/2013 |
| WO | 2014/013076 A1 | 1/2014 |
| WO | 2014/045162 A1 | 3/2014 |
| WO | 2014/062549 A1 | 4/2014 |
| WO | 2014/062553 A1 | 4/2014 |
| WO | 2014/065434 A1 | 5/2014 |
| WO | 2014/066132 A1 | 5/2014 |
| WO | 2014/093190 A1 | 6/2014 |
| WO | 2014/097038 A1 | 6/2014 |
| WO | 2014/098831 A1 | 6/2014 |
| WO | 2014/099788 A9 | 6/2014 |
| WO | 2014/099794 A1 | 6/2014 |
| WO | 2014/138484 A1 | 9/2014 |
| WO | 2014/143579 A1 | 9/2014 |
| WO | 2016/022724 A1 | 2/2016 |
| WO | 2016/172255 A1 | 10/2016 |
| WO | 2017/024180 A1 | 2/2017 |
| WO | 2018/112081 A1 | 6/2018 |
| WO | 2018/112083 A1 | 6/2018 |
| WO | 2018/112084 A1 | 6/2018 |
| WO | 2018/112086 A1 | 6/2018 |
| WO | 2018/112094 A1 | 6/2018 |

1,4-THIAZINE DIOXIDE AND 1,2,4-THIADIAZINE DIOXIDE DERIVATIVES AS BETA-SECRETASE INHIBITORS AND METHODS OF USE

CROSS-REFERENCE TO RELATED APPLICATIONS

This application is a national stage application under 35 U.S.C. § 371 of International Application No. PCT/US2017/066197, having an international filing date of Dec. 13, 2017, which claims the benefit of U.S. Provisional Patent Application No. 62/434,715, filed Dec. 15, 2016, which is incorporated by reference herein in its entirety.

FIELD

The present disclosure relates generally to pharmaceutically active compounds and pharmaceutical compositions thereof for the modulation of beta site amyloid precursor protein cleaving enzyme (BACE) activity. Provided herein are uses of these compounds and pharmaceutical compositions thereof for treatment of disorders and/or conditions related to beta-amyloid plaque formation and deposition, resulting from the biological activity of BACE. Such BACE mediated disorders include, for example, Alzheimer's disease, cognitive deficits, cognitive impairments, and other central nervous system conditions.

BACKGROUND

Alzheimer's disease (AD) affects greater than 12 million aging people worldwide, and, importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid (Aβ) peptide deposits in the brain (commonly referred to as Aβ "plaques" or "plaque deposits") and in cerebral blood vessels (beta amyloid angiopathy). A wealth of evidence suggests that Aβ and accompanying amyloid plaque formation is central to the pathophysiology of AD and is likely to play an early role in this intractable neurodegenerative disorder. Yan et al., *Lancet Neurol.* 13(3):319-329 (2014). The second change in AD is the formation of intraneuronal tangles, consisting of an aggregate form of the microtubule-binding protein tau. Besides being found in patients with AD, intraneuronal tangles are also found in other dementia-inducing disorders. Joachim et al., *Alzheimer. Dis. Assoc. Disord.* 6(1):7-34 (1992).

Several lines of evidence indicate that progressive cerebral deposition of Aβ peptide plays a seminal role in the pathogenesis of AD and can precede cognitive symptoms by years or even decades. Selkoe, *Neuron* 6(4):487-498 (1991). Release of Aβ peptide from neuronal cells grown in culture and the presence of Aβ peptide in cerebrospinal fluid (CSF) of both normal individuals and AD patients has been demonstrated. Seubert et al., *Nature* 359:325-327 (1992). Autopsies of AD patients have revealed large numbers of lesions comprising Aβ and tau peptides in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's syndrome, Hereditary Cerebral Hemorrhage with Amyloidosis of the Dutch-type (HCHWA-D), and other neurodegenerative disorders.

It has been hypothesized that Aβ peptide formation is a causative precursor or factor in the development of AD. More specifically, deposition of Aβ peptide in areas of the brain responsible for cognition is believed to be a major factor in the development of AD. Aβ plaques are primarily composed of Aβ peptide. Aβ peptide is derived from the proteolytic cleavage of a large transmembrane amyloid precursor protein (APP), and is a peptide comprised of about 39-42 amino acid residues. Aβ 1-42 (42 amino acids long) is thought to be the major component of these plaque deposits in the brains of AD patients. Citron, *Trends Pharmacol. Sci.* 25(2):92-97 (2004).

Similar plaques appear in some variants of Lewy body dementia and in inclusion body myositis, a muscle disease. Aβ peptides also form aggregates coating cerebral blood vessels in cerebral amyloid angiopathy. These plaques are composed of fibrillar Aβ aggregates that display a characteristic β-sheet structure, a protein fold shared by other peptides such as prions associated with protein misfolding diseases. Research on laboratory rats suggest that the dimeric, soluble form of the peptide is a causative agent in the development of AD and is the smallest synaptotoxic species of soluble amyloid beta oligomer. Shankar et al., *Nat. Med.* 14(8):837-842 (2008).

Several aspartyl proteases, including β-secretase and γ-secretase, are involved in the processing or cleavage of APP, resulting in the formation of Aβ peptide. β-Secretase (BACE, also commonly referred to as memapsin) is the first to cleave APP to generate two fragments: (1) a first N-terminus fragment (sAPPβ) and (2) a second C-99 fragment, which is subsequently cleaved by γ-secretase to generate the Aβ peptide. APP has also been found to be cleaved by α-secretase to produce sAPPα, a secreted form of APP that does not result in Aβ plaque formation. This alternate pathway precludes the formation of Aβ peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the β-secretase specific cleavage site. BACE is present in two forms, BACE 1 and BACE 2, designated as such depending upon the specific cleavage site of APP. 3-Secretase is described in Sinha et al., *Nature* 402:537-540 (1999) and International Patent Application Publication No. WO2000/017369. It has been proposed that Aβ peptide accumulates as a result of APP processing initiated by BACE. Moreover, in vivo processing of APP at the β-secretase cleavage site is thought to be a rate-limiting step in Aβ peptide production.

Sabbagh et al., *Alzheimer's Disease Review* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of Aβ peptide. BACE knockout mice do not produce Aβ peptide and are free from AD associated pathologies including neuronal loss and certain memory deficits. Cole et al., *Molecular Neurodegeneration* 2:22, pages 1-25 (2007). When crossed with transgenic mice that over express APP, the progeny of BACE deficient mice show reduced amounts of Aβ peptide in brain extracts as compared with control animals. Luo et al., *Nat. Neurosci.* 4(3):231-232 (2001). The fact that BACE initiates the formation of Aβ peptide, and the observation that BACE levels are elevated in this disease provide direct and compelling reasons to develop therapies directed at BACE inhibition, thus, reducing Aβ peptide formation and its associated toxicities. To this end, inhibition of β-secretase activity and a corresponding reduction of Aβ peptide in the brain should provide a therapeutic method for treating AD and other Aβ peptide or plaque related disorders.

Consequently, the approach of regulating or reducing Aβ peptide formation and deposition as a potential treatment for AD has received tremendous attention, support and commitment from both researchers and investors alike. A small molecule γ-secretase inhibitor, LY450139 ("Semagacestat"), an Aβ peptide lowering agent, advanced to phase III clinical trials for the treatment of AD. The pharmacokinetics of semagacestat in plasma, as well as the plasma and cerebral spinal fluid (CSF) Aβ peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (Henley et al., *Expert Opin. Pharmacother.* 10(10): 1657-1664 (2009); Siemers et al., *Clin. Neuropharmacol.* 30(6): 317-325 (2007); and Siemers et al., *Neurology* 66(4): 602-604 (2006)). Additional approaches have been taken in attempts to treat AD and plaque-related disorders. See, for example, Yan et al., *Lancet Neurology* 13(3):319-329 (2014).

Furthermore, each of the following exemplary patent application publications describes inhibitors of BACE, useful for treating AD and other β-secretase mediated disorders: WO2014/098831, WO2014/099794, WO2014/099788, WO2014/097038, WO2014/093190, WO2014/066132, WO2014/065434, WO2014/062553, WO2014/062549, WO2014/045162, WO2014/013076, WO2013/182638, WO2013/164730, WO2013/030713, WO2013/028670, WO2013/004676, WO2012/162334, WO2012/162330, WO2012/147762, WO2012/139425, WO2012/138734, US2012/0245157, US2012/0245154, US2012/0238557, WO2011/029803, WO2011/005738, US2011/0152253, WO2010/013794, WO2010/013302, US2010/0160290, US2010/0075957, WO2009/151098, WO2009/134617, US2009/0209755, US2009/0082560, EP2703401 (equivalent of WO2012/146762) and EP1942105.

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein CatD has been implicated in undesirable side effects. For instance, the inhibition of CatD is believed to be linked to adverse retinal development and retinal atrophy. Particularly, in mice it was found that CatD is essential for the metabolic maintenance of retinal photoreceptor cells and that its deficiency induces apoptosis of the cells, while the loss of inner nuclear layer (INL) neurons is mediated by nitric oxide release from microglial cells. However, in the very same mice, it was also found that no atrophic change was detected in the retina of mice deficient in Cathepsin B or L. Koike et al., *Mol. Cell Neurosci.* 22(2):146-161 (2003). Further, animal models of CatD deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers, but not neuronal cell death and neurodegeneration induced by CatD deficiency, which suggests that alterations in the macroautophagy-lysosomal degradation pathway can mediate neuronal cell death in NCL/Batten Disease in the absence of apoptosis. Shacka et al., *Autophagy* 3(5):474-476 (2007). Finally, an adverse effect of the inhibition of CatD is evident from the data presented in Folio et al., *PLoS One* 6(7):e21908 (2011). The authors of the PLoS One paper found that knock-down of CatD affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyperpigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human BACE-mediated AD clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Phase I dosing trial was terminated and people brought in for eye assessments did not show any abnormalities. (Alzheimer's Research Forum News, Mar. 31, 2011 reporting on Martin Citron's presentation at the AD/PD Conference 3-2011 in Barcelona, Spain).

Hence, it is desirable to provide compounds which modulate the activity of and are selective for BACE, while not suffering from undesirable side effects possibly due to intervention with or the reduction and/or direct or indirect inhibition of the expression and/or function of other proteins or biological pathways.

SUMMARY

The compounds disclosed herein are useful for the modulation of β-secretase activity, and as treatment of AD. Particularly, the compounds provided herein are useful for the regulation or reduction of the formation of Aβ peptide and, consequently, the regulation and/or reduction of formation of Aβ plaque both in the brain, as well as in the CNS. To this end, the compounds are useful for the treatment of AD and other (β-secretase and/or plaque-related and/or mediated disorders. For example, the compounds are useful for the prophylaxis and/or treatment, acute and/or chronic, of AD and other diseases or conditions involving the deposition or accumulation of Aβ peptide, and formation of plaque, in the brain.

First, provided herein is a compound of Formula I

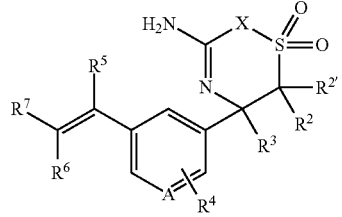

or a tautomer, or a pharmaceutically acceptable salt of said compound or tautomer, wherein A is N, CH or $CR^4$;

X is $NR^1$ or $C(R^1R^{1'})$;

$R^1$ and $R^{1'}$ independently are H or $C_{1-4}$alkyl, wherein the $C_{1-4}$alkyl is optionally substituted with 1 to 3 fluoro substituents;

provided that X is $C(R^1R^{1'})$, one of $R^1$ and $R^{1'}$ and one of $R^2$ and $R^{2'}$ together optionally form a —$CH_2CH_2$— group bridging the two carbon atoms to which $R^1$, $R^{1'}$, $R^2$, and $R^{2'}$ are attached, wherein the other of $R^1$ and $R^{1'}$ and the other of $R^2$ and $R^{2'}$ independently are H or $C_{1-4}$alkyl, wherein the $C_{1-4}$alkyl is optionally substituted with 1 to 3 fluoro substituents;

$R^1$ and $R^{1'}$ with the carbon atom to which $R^1$ and $R^{1'}$ are attached optionally form a $C_{3-6}$carbocycle;

$R^2$ and $R^{2'}$ independently are H, halogen or $C_{1-4}$alkyl;

$R^2$ and $R^{2'}$ with the carbon atom to which $R^2$ and $R^{2'}$ are attached optionally form a $C_{3-6}$carbocycle;

$R^3$ is $C_{1-4}$alkyl, wherein the $C_{1-4}$alkyl is optionally substituted with 1 to 3 fluoro substituents;

one of $R^2$ and $R^{2'}$ together with $R^3$ and the two carbon atoms to which $R^2$, $R^{2'}$, and $R^3$ are attached optionally form a 5 or 6 membered heterocycloalkane;

$R^4$ is independently at each occurrence a halogen;

$R^5$ is H or F; and one of $R^6$ and $R^7$ is F or H and the other of $R^6$ and $R^7$ is a 5 or 6 membered heterocycloalkane, phenyl, or 5 to 10-membered heterocycle, wherein the phenyl or heterocycle is optionally substituted with 1 to 3 substituents independently selected from halogen, OH, CN, $C_{1-6}$alkyl, $C_{3-6}$cycloalkyl, cyclopropylethynyl, $C_{1-6}$alkoxy, $C_{3-6}$alkenyloxy, $C_{3-6}$alkynyloxy, —$OCH_2C(O)OC_{1-6}$alkyl, —$OCH_2$—$C_{3-6}$cycloalkyl, phenoxy, benzyloxy, or —O—$C_{1-4}$alkyl-heteroaryl, wherein the $C_{1-6}$alkyl, $C_{1-6}$alkoxy or heteroaryl is optionally substituted with 1 to 5 substituents selected from F, Br, OH, methyl, methoxy, or oxetanyl.

Second, provided herein are pharmaceutical compositions comprising a compound of Formula I and a pharmaceutically acceptable excipient.

Third, provided herein are compounds of Formula I or pharmaceutical compositions thereof for use as a medicament.

Fourth, provided herein are compounds of Formula I or pharmaceutical compositions thereof for use in reducing beta amyloid peptide levels in the cerebral spinal fluid of a subject.

Fifth, provided herein are compounds of Formula I or pharmaceutical compositions thereof for use in treating Alzheimer's disease, cognitive impairment, or a combination thereof in a subject. In addition, provided herein are compounds of Formula I or pharmaceutical compositions thereof for treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Sixth, provided herein are compounds of Formula I or pharmaceutical compositions thereof for use in reducing formation of plaque in the brain of a subject.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

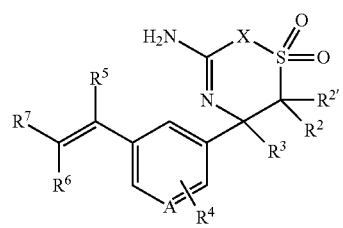

or a tautomer, or a pharmaceutically acceptable salt of said compound or tautomer, wherein A is N, CH or $CR^4$;

X is $NR^1$ or $C(R^1R^{1'})$;

$R^1$ and $R^{1'}$ independently are H or $C_{1-4}$alkyl, wherein the $C_{1-4}$alkyl is optionally substituted with 1 to 3 fluoro substituents;

provided that X is $C(R^1R^{1'})$, one of $R^1$ and $R^{1'}$ and one of $R^2$ and $R^{2'}$ together optionally form a —$CH_2CH_2$— group bridging the two carbon atoms to which $R^1$, $R^{1'}$, $R^2$, and $R^{2'}$ are attached, wherein the other of $R^1$ and $R^{1'}$ and the other of $R^2$ and $R^{2'}$ independently are H or $C_{1-4}$alkyl, wherein the $C_{1-4}$alkyl is optionally substituted with 1 to 3 fluoro substituents;

$R^1$ and $R^{1'}$ with the carbon atom to which $R^1$ and $R^{1'}$ are attached optionally form a $C_{3-6}$carbocycle;

$R^2$ and $R^{2'}$ independently are H, halogen, or $C_{1-4}$alkyl;

$R^2$ and $R^{2'}$ with the carbon atom to which $R^2$ and $R^{2'}$ are attached optionally form a $C_{3-6}$carbocycle;

$R^3$ is $C_{1-4}$alkyl, wherein the $C_{1-4}$alkyl is optionally substituted with 1 to 3 fluoro substituents;

one of $R^2$ and $R^{2'}$ together with $R^3$ and the two carbon atoms to which $R^2$, $R^{2'}$, and $R^3$ are attached optionally form a 5 or 6 membered heterocycloalkane;

$R^4$ is independently at each occurrence a halogen;
R is H or F; and
one of $R^6$ and $R^7$ is F or H and the other of $R^6$ and $R^7$ is a 5 or 6 membered heterocycloalkane, phenyl, or 5 to 10-membered heterocycle, wherein the phenyl or heterocycle is optionally substituted with 1 to 3 substituents independently selected from halogen, OH, CN, $C_{1-6}$alkyl, $C_{3-6}$cycloalkyl, cyclopropylethynyl, $C_{1-6}$alkoxy, $C_{3-6}$alkenyloxy, $C_{3-6}$alkynyloxy, —OCH$_2$C(O)OC$_{1-6}$alkyl, —OCH$_2$—C$_{3-6}$cycloalkyl, phenoxy, benzyloxy, or —O—$C_{1-4}$alkyl-heteroaryl, wherein the $C_{1-6}$alkyl, $C_{1-6}$alkoxy or heteroaryl is optionally substituted with 1 to 5 substituents selected from F, Br, OH, methyl, methoxy, or oxetanyl.

Provided herein as Embodiment 2 is the compound according to Embodiment 1, or a tautomer, or a pharmaceutically acceptable salt of said compound or tautomer, wherein the compound of Formula I is a compound of Formula II

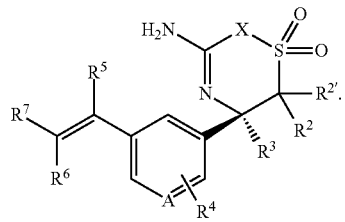

II

Provided herein as Embodiment 3 is the compound according to Embodiment 1, or a tautomer, or a pharmaceutically acceptable salt of said compound or tautomer, wherein the compound of Formula I is a compound of Formula III

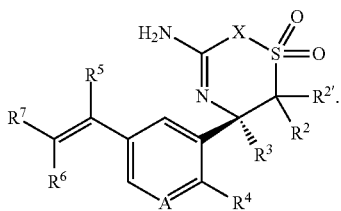

III

Provided herein as Embodiment 4 is the compound according to any one of Embodiments 1 to 3, or a tautomer, or a pharmaceutically acceptable salt of said compound or tautomer, wherein A is N.

Provided herein as Embodiment 5 is the compound according to any one of Embodiments 1 to 3, or a tautomer, or a pharmaceutically acceptable salt of said compound or tautomer, wherein A is CH.

Provided herein as Embodiment 6 is the compound according to any one of Embodiments 1 to 3, or a tautomer, or a pharmaceutically acceptable salt of said compound or tautomer, wherein A is $CR^4$.

Provided herein as Embodiment 7 is the compound according to any one of Embodiments 1 to 6, or a tautomer, or a pharmaceutically acceptable salt of said compound or tautomer, wherein X is $NR^1$.

Provided herein as Embodiment 8 is the compound according to any one of Embodiments 1 to 7, or a tautomer, or a pharmaceutically acceptable salt of said compound or tautomer, wherein $R^1$ is methyl.

Provided herein as Embodiment 9 is the compound according to any one of Embodiments 1 to 6, or a tautomer, or a pharmaceutically acceptable salt of said compound or tautomer, wherein X is $C(R^1R^{1'})$.

Provided herein as Embodiment 10 is the compound according to any one of Embodiments 1 to 6 and 9, or a tautomer, or a pharmaceutically acceptable salt of said compound or tautomer, wherein $R^1$ and $R^{1'}$ independently are H or methyl.

Provided herein as Embodiment 11 is a the compound according to any one of Embodiments 1 to 6 and 9, or a tautomer, or a pharmaceutically acceptable salt of said compound or tautomer, wherein $R^1$ and $R^{1'}$ are methyl.

Provided herein as Embodiment 12 is the compound according to any one of Embodiments 1 to 6 and 9, or a tautomer, or a pharmaceutically acceptable salt of said compound or tautomer, wherein one of $R^1$ and $R^{1'}$ and one of $R^2$ and $R^{2'}$ together optionally form a —CH$_2$CH$_2$— group bridging the two carbon atoms to which $R^1$, $R^{1'}$, $R^2$ and $R^{2'}$ are attached, wherein the other of $R^1$ and $R^{1'}$ and the other of $R^2$ and $R^{2'}$ independently are H or $C_{1-4}$alkyl, wherein the $C_{1-4}$alkyl is optionally substituted with 1 to 3 fluoro substituents.

Provided herein as Embodiment 13 is the compound of Embodiment 12, or a tautomer, or a pharmaceutically acceptable salt of said compound or tautomer, wherein the compound is a compound of Formula IV

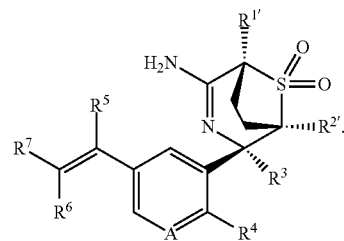

IV

Provided herein as Embodiment 14 is a the compound of Embodiment 13, or a tautomer, or a pharmaceutically acceptable salt of said compound or tautomer, wherein $R^{1'}$ is CH$_2$F and $R^{2'}$ is H.

Provided herein as Embodiment 15 is the compound according to any one of Embodiments 1 to 11, or a tautomer, or a pharmaceutically acceptable salt of said compound or tautomer, wherein $R^2$ and $R^{2'}$ independently are H, F, or methyl.

Provided herein as Embodiment 16 is the compound according to any one of Embodiments 1 to 11, or a tautomer, or a pharmaceutically acceptable salt of said compound or tautomer, wherein $R^2$ and $R^{2'}$ are H, or $R^2$ and $R^{2'}$ are F, or $R^2$ and $R^{2'}$ are methyl.

Provided herein as Embodiment 17 is the compound according to any one of Embodiments 1 to 11, or a tautomer, or a pharmaceutically acceptable salt of said compound or tautomer, wherein $R^2$ and $R^{2'}$ with the carbon atom to which $R^2$ and $R^{2'}$ are attached optionally form a $C_3$carbocycle.

Provided herein as Embodiment 18 is the compound according to any one of Embodiments 1 to 11, or a tautomer, or a pharmaceutically acceptable salt of said compound or tautomer, wherein one of $R^2$ and $R^{2'}$ together with $R^3$ and the two carbon atoms to which $R^2$, $R^{2'}$, and $R^3$ are attached optionally form a 5 membered heterocycloalkane.

Provided herein as Embodiment 19 is the compound according to any one of Embodiments 1 to 11, or a tautomer, or a pharmaceutically acceptable salt of said compound or tautomer, wherein one of $R^2$ and $R^{2'}$ together with $R^3$ and the two carbon atoms to which $R^2$, $R^{2'}$, and $R^3$ are attached optionally form a tetrahydrofuran.

Provided herein as Embodiment 20 is the compound according to any one of Embodiments 1 to 17, or a tautomer, or a pharmaceutically acceptable salt of said compound or tautomer, wherein $R^3$ is methyl, $CH_2F$, or $CHF_2$.

Provided herein as Embodiment 21 is the compound according to any one of Embodiments 1 to 17, or a tautomer, or a pharmaceutically acceptable salt of said compound or tautomer, wherein $R^3$ is methyl.

Provided herein as Embodiment 22 is the compound according to any one of Embodiments 1 to 17, or a tautomer, or a pharmaceutically acceptable salt of said compound or tautomer, wherein $R^3$ is $CH_2F$.

Provided herein as Embodiment 23 is the compound according to any one of Embodiments 1 to 19, or a tautomer, or a pharmaceutically acceptable salt of said compound or tautomer, wherein $R^4$ is F.

Provided herein as Embodiment 24 is the compound according to any one of Embodiments 1 to 23, or a tautomer, or a pharmaceutically acceptable salt of said compound or tautomer, wherein one of $R^6$ and $R^7$ is F or H and the other of $R^6$ and $R^7$ is tetrahydropyranyl, tetrahydofuranyl, thiophenyl, thiazolyl, phenyl, pyridyl, pyrazinyl, 2,3-dihydrobenzo[b][1,4]dioxinyl, 2,3-dihydro-[1,4]dioxino[2,3-c]pyridyl, [1,3]dioxolo[4,5-c]pyridyl, 3,4-dihydro-2H-pyrano[2,3-c]pyridyl, 2,3-dihydro-[1,4]dioxino[2,3-b]pyridyl, 6,7-dihydro-[1,4]dioxino[2,3-d]pyrimidinyl, isoquinolinyl, or pyrido[3,4-b]pyrazinyl, and wherein said other of $R^6$ and $R^7$ is optionally substituted.

Provided herein as Embodiment 25 is the compound according to any one of Embodiments 1 to 24, or a tautomer, or a pharmaceutically acceptable salt of said compound or tautomer, wherein one of $R^6$ and $R^7$ is F or H and the other of $R^6$ and $R^7$ is optionally substituted with 1 or 2 substituents independently selected from F, Cl, Br, OH, CN, methyl, trifluoromethyl, cyclopropyl, cyclopropylethynyl, methoxy, trifluoromethoxy, ethoxy, 2-fluoroethoxy, 2,2-difluoroethoxy, 2,2,2-trifluoroethoxy, 2-methoxyethoxy, propoxy, 2,2,3,3-tetrafluoropropoxy, 3,3,3-trifluoropropoxy, propan-1-ol-2-oxy, 2-propanoloxy, 2-cyano-2-methyl-propoxy, oxetan-3-ylmethoxy, (1-methoxypropan-2-yl)oxy, 2-methoxypropoxy, allyloxy, 2-propynyloxy, 2-butynyloxy, 3-butyn-2-yloxy, 2-butyn-4-ol-oxy, 4-fluoro-2-butynoxy, pent-1-yn-3-yloxy, pent-3-yn-2-yloxy, hex-4-yn-3-yloxy, hex-3-yn-2-yloxy, —$OCH_2C(O)OC_2H_5$, cyclopropylmethoxy, cyclobutylmethoxy, cyclopentylmethoxy, cyclohexylmethoxy, phenoxy, benzyloxy, or —$OC_{1-2}$alkyl-heteroaryl, wherein the heteroaryl is optionally substituted with one or two methyl groups or the heteroaryl is optionally substituted with one bromo.

Provided herein as Embodiment 26 is the compound according to any one of Embodiments 1 to 25, or a tautomer, or a pharmaceutically acceptable salt of said compound or tautomer, wherein one of $R^6$ and $R^7$ is F or H and the other of $R^6$ and $R^7$ is

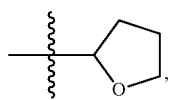

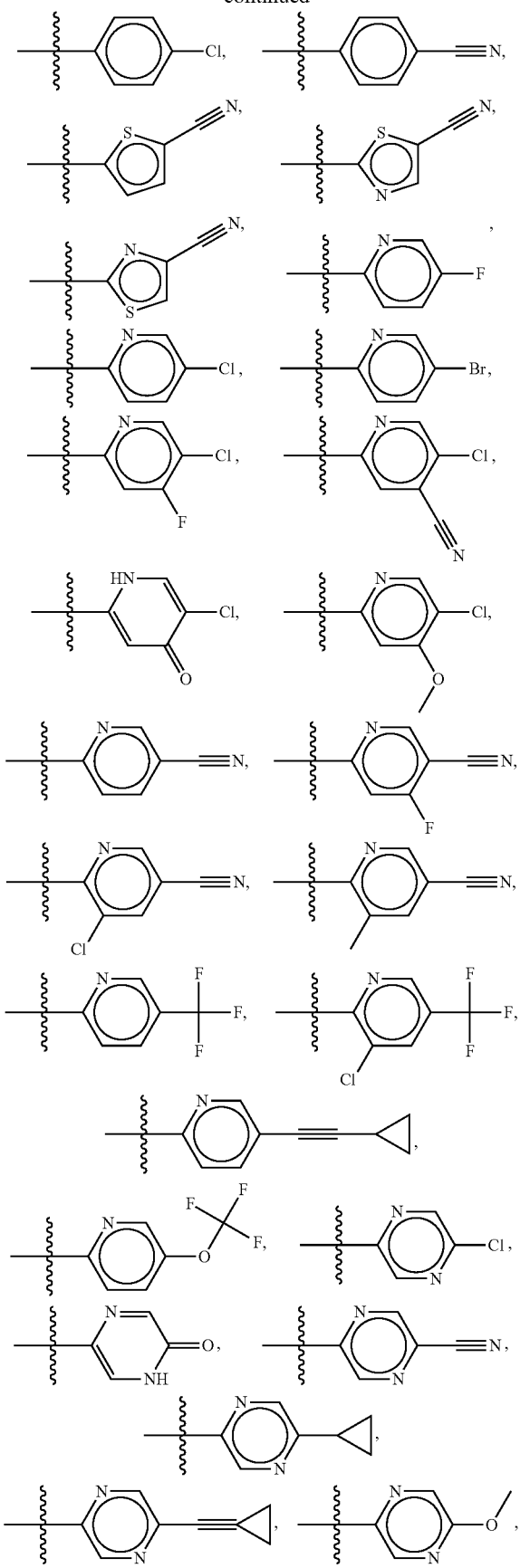

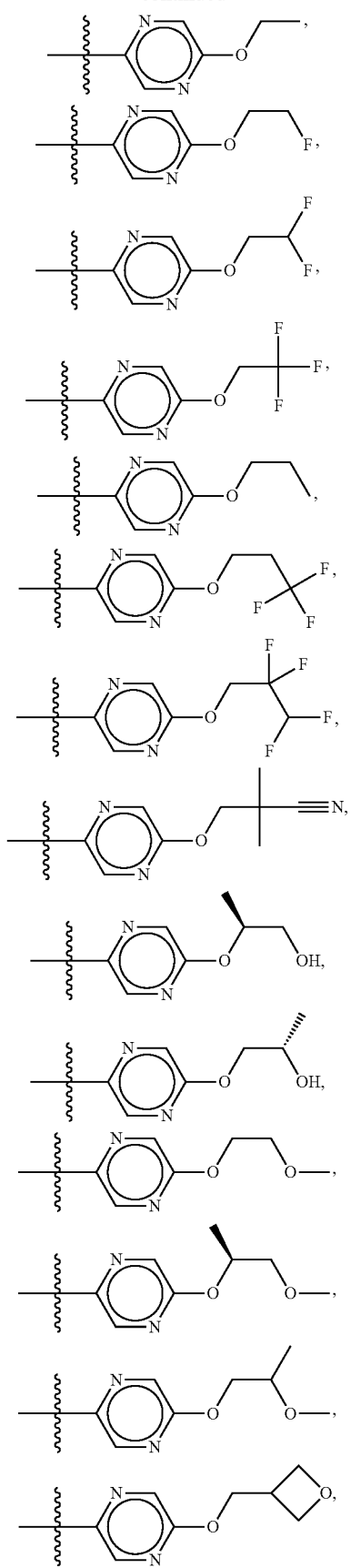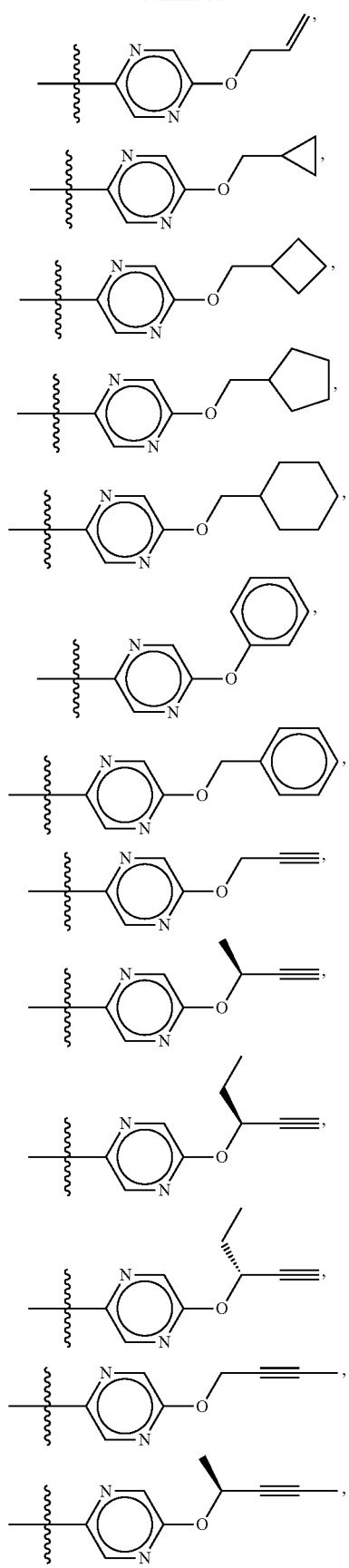

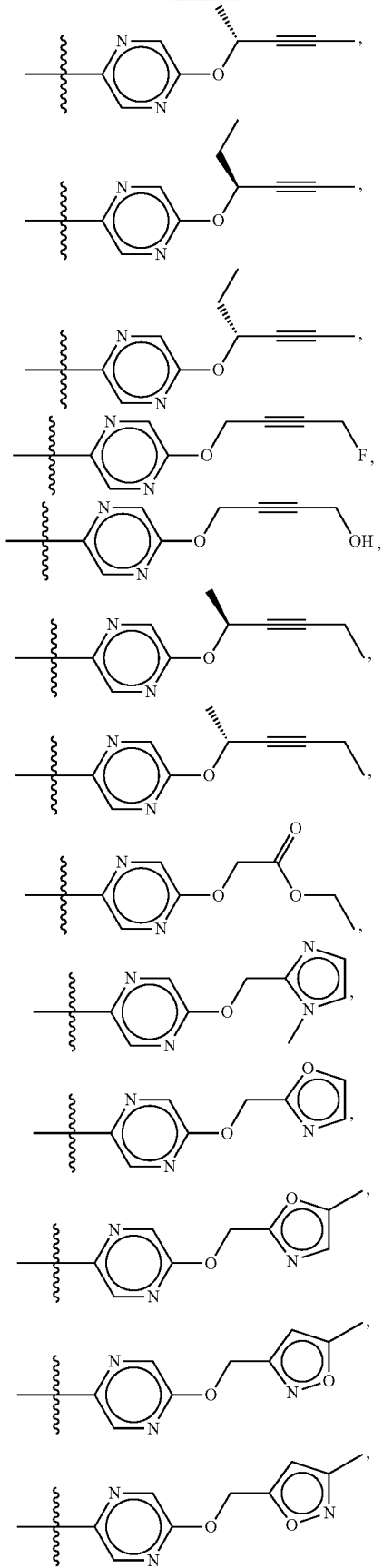
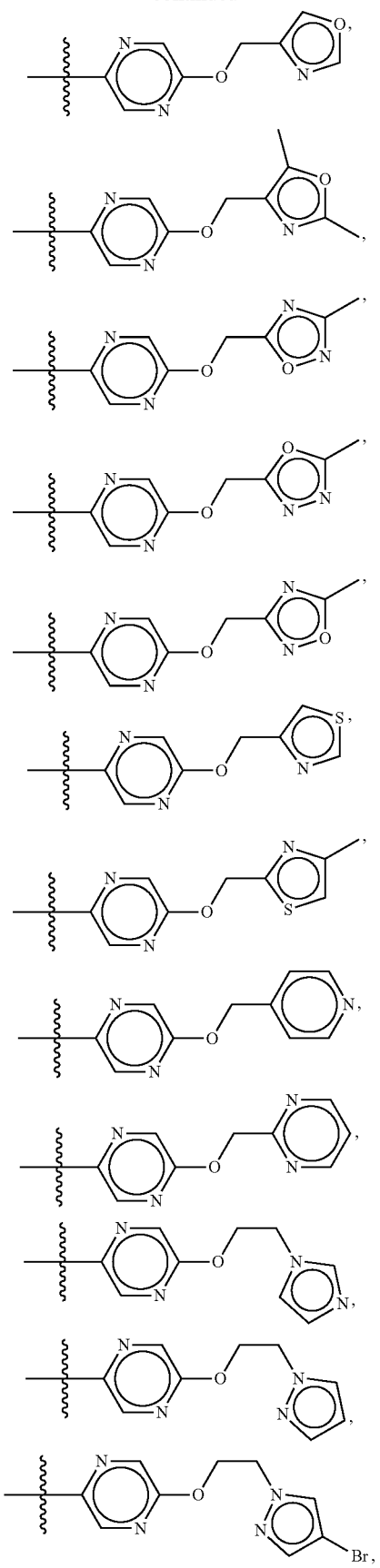

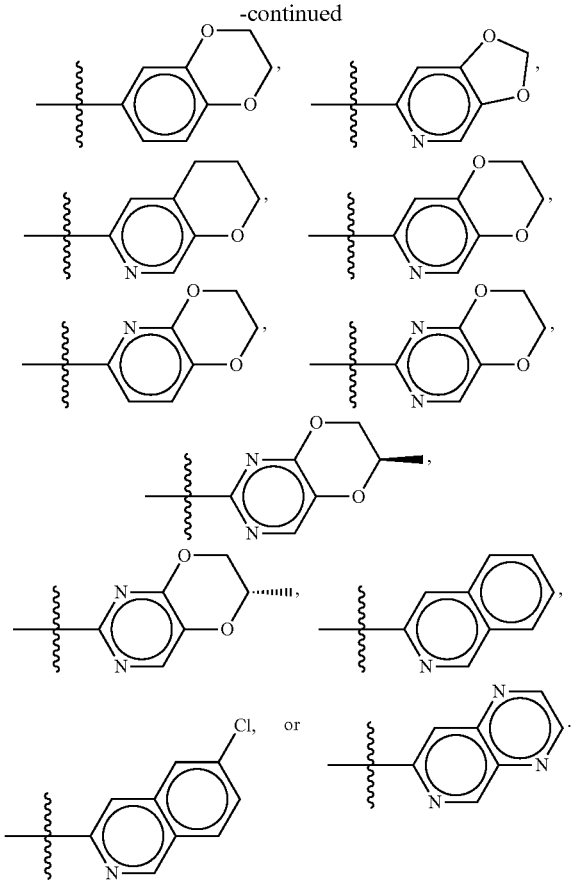

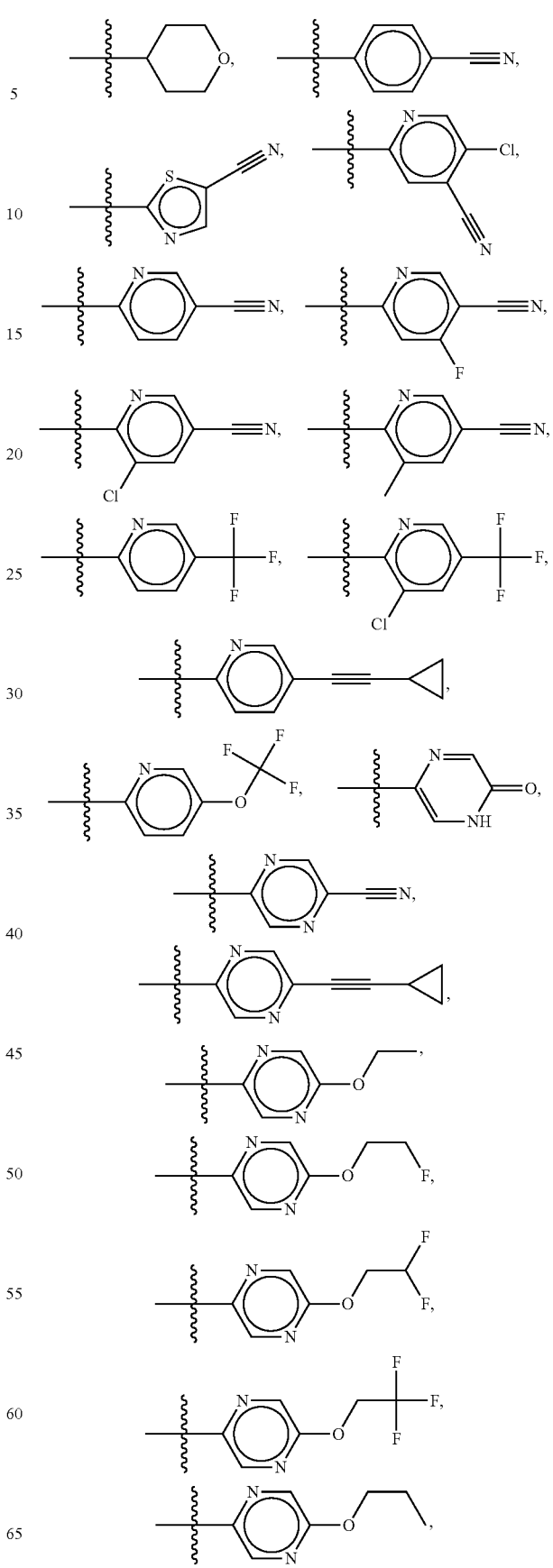

Provided herein as Embodiment 27 is the compound according to any one of Embodiments 1 to 23, or a tautomer, or a pharmaceutically acceptable salt of said compound or tautomer, wherein one of $R^6$ and $R^7$ is F or H and the other of $R^6$ and $R^7$ is tetrahydropyranyl, phenyl, pyridyl, pyrazinyl, or 6,7-dihydro-[1,4]dioxino[2,3-d]pyrimidinyl, and wherein the other of $R^6$ and $R^7$ is optionally substituted.

Provided herein as Embodiment 28 is the compound according to any one of Embodiments 1 to 23 and 27, or a tautomer, or a pharmaceutically acceptable salt of said compound or tautomer, wherein one of $R^6$ and $R^7$ is F or H and the other of $R^6$ and $R^7$ is optionally substituted with 1 or 2 substituents independently selected from OH, CN, methyl, trifluoromethyl, cyclopropylethynyl, trifluoromethoxy, ethoxy, 2-fluoroethoxy, 2,2-difluoroethoxy, 2,2,2-trifluoroethoxy, 2-methoxyethoxy, propoxy, 2,2,3,3-tetrafluoropropoxy, 3,3,3-trifluoropropoxy, propan-1-ol-2-oxy, 2-propanoloxy, 2-cyano-2-methyl-propoxy, (1-methoxypropan-2-yl)oxy, 2-methoxypropoxy, allyloxy, 2-propynyloxy, 2-butynyloxy, 3-butyn-2-yloxy, 2-butyn-4-ol-oxy, 4-fluoro-2-butynoxy, (S)-pent-1-yn-3-yloxy, hex-4-yn-3-yloxy, (S)-hex-3-yn-2-yloxy, —OCH$_2$C(O)OC$_2$H$_5$, cyclopropylmethoxy, cyclopentylmethoxy, cyclohexylmethoxy, benzyloxy, or —OCH$_2$-(5-membered-heteroaryl), wherein the 5-membered-heteroaryl is optionally substituted with one or two methyl groups or the heteroaryl is optionally substituted with one bromo.

Provided herein as Embodiment 29 is the compound according to any one of Embodiments 1 to 25, or a tautomer, or a pharmaceutically acceptable salt of said compound or tautomer, wherein one of $R^6$ and $R^7$ is F or H and the other of $R^6$ and $R^7$ is

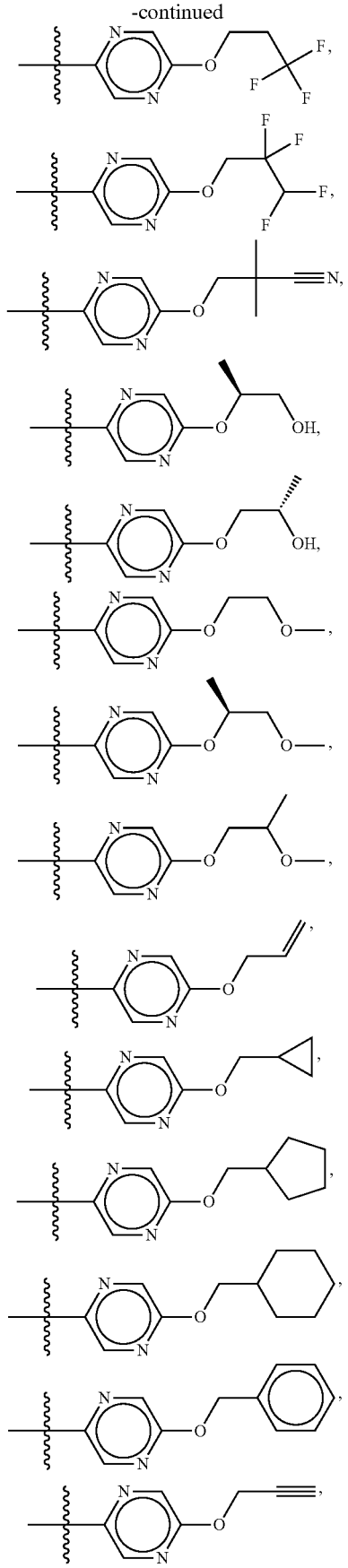
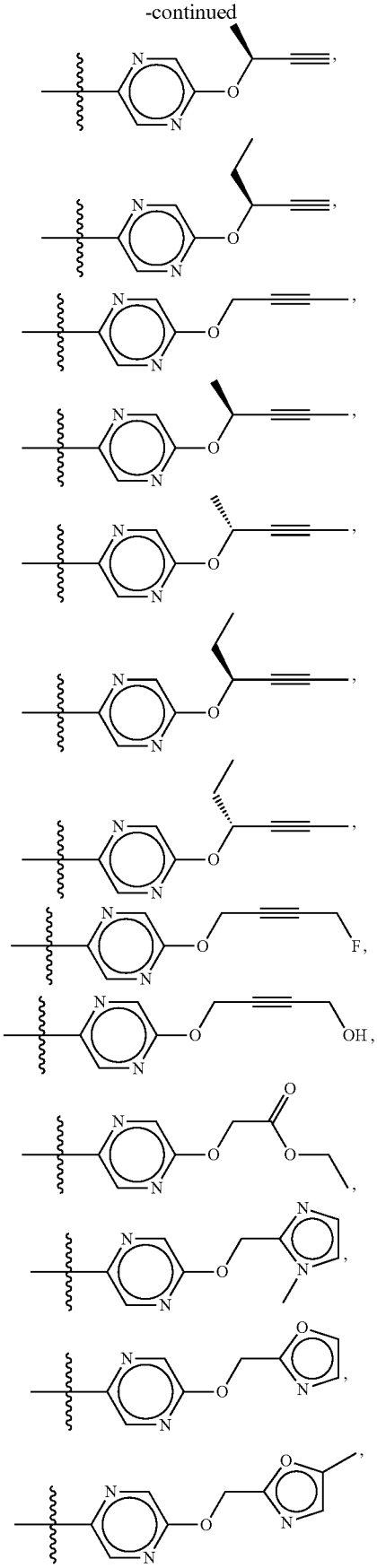

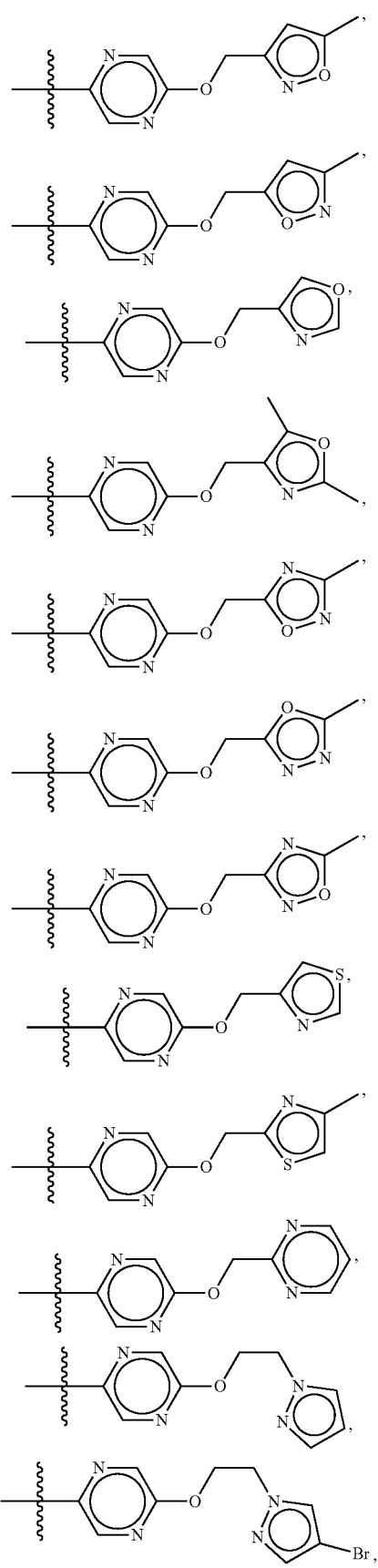

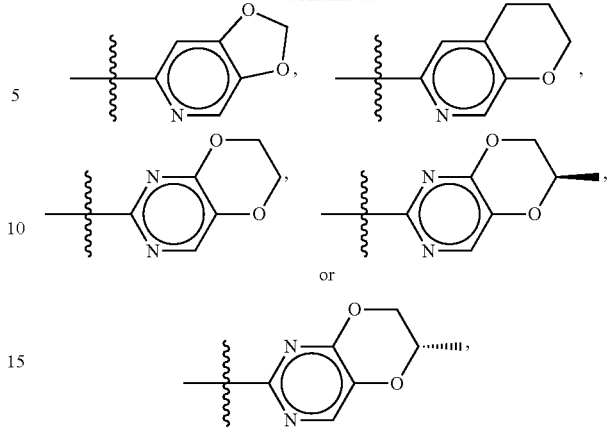

Provided herein as Embodiment 30 is the compound according to any one of Embodiments 1 to 29, or a tautomer, or a pharmaceutically acceptable salt of said compound or tautomer, wherein
$R^5$ is H; and
$R^6$ is H.

Provided herein as Embodiment 31 is the compound according to any one of Embodiments 1 to 29, or a tautomer, or a pharmaceutically acceptable salt of said compound or tautomer, wherein
$R^5$ is H; and
$R^7$ is H.

Provided herein as Embodiment 32 is the compound according to any one of Embodiments 1 to 29, or a tautomer, or a pharmaceutically acceptable salt of said compound or tautomer, wherein
$R^5$ is F; and
$R^6$ is H.

Provided herein as Embodiment 33 is the compound according to any one of Embodiments 1 to 29, or a tautomer, or a pharmaceutically acceptable salt of said compound or tautomer, wherein
$R^5$ is F; and
$R^7$ is H.

Provided herein as Embodiment 34 is the compound according to any one of Embodiments 1 to 29, or a tautomer, or a pharmaceutically acceptable salt of said compound or tautomer, wherein
$R^5$ is H; and
$R^6$ is F.

Provided herein as Embodiment 35 is the compound according to any one of Embodiments 1 to 29, or a tautomer, or a pharmaceutically acceptable salt of said compound or tautomer, wherein
$R^5$ is H; and
$R^7$ is F.

Provided herein as Embodiment 36 is the compound of Embodiment 1, or a tautomer, or a pharmaceutically acceptable salt of said compound or tautomer, selected from
(R,Z)-9-amino-7-(5-(2-(5-chloropyridin-2-yl)-2-fluorovinyl)-2-fluorophenyl)-7-methyl-5-thia-8-azaspiro[3.5]non-8-ene 5,5-dioxide;
(1R,4R,5S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide;
6-((Z)-2-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-1-fluorovinyl)nicotinonitrile;

(R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile;

(R,Z)-3-amino-5-(5-(2-(5-chloropyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(5-(2-(5-bromopyridin-2-yl)-2-fluorovinyl)-2,3-difluorophenyl)-2,5-dimethyl-5,6-dihydro-2H-1,2,4-thiadiazine 1,1-dioxide;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)nicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)nicotinonitrile;

(1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2,2,2-trifluoroethoxy)pyrazin-2-yl)vinyl)phenyl)-1-(fluoromethyl)-4-methyl-8-thia-3-azabicyclo[3.2.1]oct-2-ene 8,8-dioxide;

(R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide;

(R,Z)-3-amino-5-(5-(2-(5-chloropyrazin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile;

(R,Z)-5-amino-3-(5-(2-(5-chloropyridin-2-yl)-2-fluorovinyl)-2-fluorophenyl)-3,6,6-trimethyl-3,6-dihydro-2H-1,4-thiazine 1,1-dioxide;

(1R,4R,5S)-2-amino-4-(2-fluoro-5-((Z)-2-fluoro-2-(5-((3-methyl-1,2,4-oxadiazol-5-yl)methoxy)pyrazin-2-yl)vinyl)phenyl)-1-(fluoromethyl)-4-methyl-8-thia-3-azabicyclo[3.2.1]oct-2-ene 8,8-dioxide;

(R,Z)-3-amino-5-(2-fluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-(2,2,2-trifluoroethoxy)pyrazin-2-yl)vinyl)phenyl)-2,5-dimethyl-5,6-dihydro-2H-1,2,4-thiadiazine 1,1-dioxide;

(1R,4R,5S)-2-amino-4-(5-((Z)-2-(5-(cyclopropylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-((5-methyl-1,3,4-oxadiazol-2-yl)methoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2,2,3,3-tetrafluoropropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-methoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-fluoro-2-(5-ethoxypyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(R,Z)-5-amino-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,2-trifluoroethoxy)pyrazin-2-yl)vinyl)phenyl)-3,6,6-trimethyl-3,6-dihydro-2H-1,4-thiazine 1,1-dioxide;

(1R,4R,5S)-4-(5-((Z)-2-(5-(allyloxy)pyrazin-2-yl)-2-fluorovinyl)-2-fluorophenyl)-2-amino-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(oxetan-3-ylmethoxy)pyrazin-2-yl)vinyl)phenyl)-1-(fluoromethyl)-4-methyl-8-thia-3-azabicyclo[3.2.1]oct-2-ene 8,8-dioxide;

(R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile;

(1R,4R,5S)-2-amino-4-(5-((Z)-2-(5-((S)-but-3-yn-2-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(R,Z)-5-amino-3-(2-fluoro-5-(2-fluoro-2-(5-(oxazol-2-ylmethoxy)pyrazin-2-yl)vinyl)phenyl)-3,6,6-trimethyl-3,6-dihydro-2H-1,4-thiazine 1,1-dioxide;

(1R,4R,5S)-2-amino-4-(2-fluoro-5-((Z)-2-fluoro-2-(5-(2-methoxyethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(((S)-1-methoxypropan-2-yl)oxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(cyclobutylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-fluoroethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(2,2-difluoroethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-propoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-methoxypropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(but-2-yn-1-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(8R)-8-(2-fluoro-5-((Z)-2-fluoro-2-(5-(2-propyn-1-yloxy)-2-pyrazinyl)ethenyl)phenyl)-5,8-dimethyl-4-thia-5,7-diazaspiro[2.5]oct-6-en-6-amine 4,4-dioxide;

(8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide;

(R,Z)-5-amino-3-(2-fluoro-5-(2-fluoro-2-(5-hydroxypyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,3,3-tetrafluoropropoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(3,3,3-trifluoropropoxy)pyrazin-2-yl)vinyl)phenyl)-3,6,6-trimethyl-3,6-dihydro-2H-1,4-thiazine 1,1-dioxide;

(R,Z)-3-amino-5-(5-(2-(5-(cyclopropylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(cyclobutylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-amino-5-(2-fluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-5-(2-(3-(6-amino-5,8-dimethyl-4,4-dioxido-4-thia-5,7-diazaspiro[2.5]oct-6-en-8-yl)-4-fluorophenyl)-1-fluorovinyl)pyrazine-2-carbonitrile;

(R,Z)-3-amino-5-(2-fluoro-5-(2-fluoro-2-(5-(2,2,3,3-tetrafluoropropoxy)pyrazin-2-yl)vinyl)phenyl)-2,5-dimethyl-5,6-dihydro-2H-1,2,4-thiadiazine 1,1-dioxide;

(R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide;

(R,Z)-5-amino-3-(5-(2-(5-(cyclohexylmethoxy)pyrazin-2-yl)-2-fluorovinyl)-2-fluorophenyl)-3,6,6-trimethyl-3,6-dihydro-2H-1,4-thiazine 1,1-dioxide;

(R,E)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide;

(R,Z)-3-((5-(2-(3-(5-amino-3,6,6-trimethyl-1,1-dioxido-3,6-dihydro-2H-1,4-thiazin-3-yl)-4-fluorophenyl)-1-fluorovinyl)pyrazin-2-yl)oxy)-2,2-dimethylpropanenitrile;

(R,Z)-5-amino-3-(5-(2-(5-(but-2-yn-1-yloxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-imidazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide;

(R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-pyrazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide;

(R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide;

(R)-5-amino-3-(5-((Z)-2-(5-((S)-but-3-yn-2-yloxy)pyrazin-2-yl)-2-fluorovinyl)-2-fluorophenyl)-3,6,6-trimethyl-3,6-dihydro-2H-1,4-thiazine 1,1-dioxide;

(8R)-8-(2-fluoro-5-((Z)-2-fluoro-2-(5-((3-methyl-1,2,4-oxadiazol-5-yl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-((5-methyl-3-isoxazolyl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(2,2,2-trifluoroethoxy)-2-pyrazinyl)ethenyl)phenyl)-5,8-dimethyl-4-thia-5,7-diazaspiro[2.5]oct-6-en-6-amine 4,4-dioxide;

(R)-3-amino-5-(2-fluoro-5-((Z)-2-fluoro-2-(5-(((S)-1-methoxypropan-2-yl)oxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(but-2-yn-1-yloxy)pyrazin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2,3-difluorophenyl)-2,5-dimethyl-5,6-dihydro-2H-1,2,4-thiadiazine 1,1-dioxide hydrochloride;

(R,Z)-3-amino-5-(5-(2-(5-(but-2-yn-1-yloxy)pyrazin-2-yl)-2-fluorovinyl)-2-fluorophenyl)-2,5-dimethyl-5,6-dihydro-2H-1,2,4-thiadiazine 1,1-dioxide;

(8R)-8-(2-fluoro-5-((Z)-2-fluoro-2-(5-((5-methyl-1,3-oxazol-2-yl)methoxy)-2-pyrazinyl)ethenyl)phenyl)-5,8-dimethyl-4-thia-5,7-diazaspiro[2.5]oct-6-en-6-amine 4,4-dioxide;

(R,Z)-5-(2-(3-(5-amino-3,6,6-trimethyl-1,1-dioxido-3,6-dihydro-2H-1,4-thiazin-3-yl)-4-fluorophenyl)-1-fluorovinyl)pyrazine-2-carbonitrile;

(R)-3-amino-5-(5-((Z)-2-(5-((S)-but-3-yn-2-yloxy)pyrazin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-(5-(2-methoxypropoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(cyclobutylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(2-fluoro-5-(2-fluoro-2-(5-((3-methyl-1,2,4-oxadiazol-5-yl)methoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-((5-methyl-1,3,4-oxadiazol-2-yl)methoxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((R)-pent-1-yn-3-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide;

(R,Z)-3-amino-5-(2-fluoro-5-(2-fluoro-2-(5-(oxetan-3-ylmethoxy)pyrazin-2-yl)vinyl)phenyl)-2,5-dimethyl-5,6-dihydro-2H-1,2,4-thiadiazine 1,1-dioxide;

(R,Z)-6-(2-(3-(3-amino-2,5,6,6-tetramethyl-1,1-dioxido-5,6-dihydro-2H-1,2,4-thiadiazin-5-yl)-4-fluorophenyl)-1-fluorovinyl)nicotinonitrile;

(R,Z)-5-(2-(3-(3-amino-2,5,6,6-tetramethyl-1,1-dioxido-5,6-dihydro-2H-1,2,4-thiadiazin-5-yl)-4-fluorophenyl)-1-fluorovinyl)pyrazine-2-carbonitrile;

(R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5,6,6-tetramethyl-5,6-dihydro-2H-1,2,4-thiadiazine 1,1-dioxide;

(R,Z)-5-amino-3-(5-(2-(2,3-dihydro-[1,4]dioxino[2,3-c]
pyridin-7-yl)-2-fluorovinyl)-2-fluorophenyl)-3,6,6-trimethyl-3,6-dihydro-2H-1,4-thiazine 1,1-dioxide;
(R,Z)-3-amino-5-(5-(2-(5-(but-2-yn-1-yloxy)pyrazin-2-yl)-2-fluorovinyl)-2-fluorophenyl)-2,5,6,6-tetramethyl-5,6-dihydro-2H-1,2,4-thiadiazine 1,1-dioxide;
(R)-3-amino-5-(5-((Z)-2-(5-((S)-but-3-yn-2-yloxy)pyrazin-2-yl)-2-fluorovinyl)-2-fluorophenyl)-2,5,6,6-tetramethyl-5,6-dihydro-2H-1,2,4-thiadiazine 1,1-dioxide;
(R,Z)-3-amino-5-(5-(2-(2,3-dihydro-[1,4]dioxino[2,3-c]
pyridin-7-yl)-2-fluorovinyl)-2-fluorophenyl)-2,5-dimethyl-5,6-dihydro-2H-1,2,4-thiadiazine 1,1-dioxide;
(S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile;
(S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide;
(S,Z)-5-amino-3-(2-fluoro-5-(2-fluoro-2-(5-(prop-2-yn-1-yloxy)pyrazin-2-yl)vinyl)phenyl)-3-(fluoromethyl)-6,6-dimethyl-3,6-dihydro-2H-1,4-thiazine 1,1-dioxide;
(R,Z)-5-amino-3-(5-(2-(5-chloropyrazin-2-yl)-2-fluorovinyl)-2-fluorophenyl)-2,2-difluoro-3,6,6-trimethyl-3,6-dihydro-2H-1,4-thiazine 1,1-dioxide;
(R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile;
(R,Z)-5-amino-3-(5-(2-(5-chloropyrazin-2-yl)-2-fluorovinyl)-2,3-difluorophenyl)-3,6,6-trimethyl-3,6-dihydro-2H-1,4-thiazine 1,1-dioxide;
(S,Z)-5-amino-3-(5-(2-(5-(but-2-yn-1-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;
(S)-5-amino-3-(5-((Z)-2-(5-((S)-but-3-yn-2-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;
(R,Z)-3-amino-5-(5-(2-(2,3-dihydrobenzo[b][1,4]dioxin-6-yl)-2-fluorovinyl)-2-fluorophenyl)-2,5-dimethyl-5,6-dihydro-2H-1,2,4-thiadiazine 1,1-dioxide;
(R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile;
(R)-5-amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide;
(R)-5-amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide;
(2R,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
(2S,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
(R,Z)-5-amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
(R,Z)-5-amino-3-(5-(2-(5-chloropyrazin-2-yl)-2-fluorovinyl)-2-fluoropyridin-3-yl)-3,6,6-trimethyl-3,6-dihydro-2H-1,4-thiazine 1,1-dioxide;
(R,Z)-5-amino-3-(2,3-difluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
(R,Z)-5-amino-3-(2-fluoro-5-(2-fluoro-2-(5-(prop-2-yn-1-yloxy)pyrazin-2-yl)vinyl)pyridin-3-yl)-3,6,6-trimethyl-3,6-dihydro-2H-1,4-thiazine 1,1-dioxide;
(R,Z)-5-amino-3-(5-(2-(5-(cyclopropylmethoxy)pyrazin-2-yl)-2-fluorovinyl)-2-fluorophenyl)-3,6,6-trimethyl-3,6-dihydro-2H-1,4-thiazine 1,1-dioxide;
(R)-5-amino-3-(2-fluoro-5-((Z)-2-fluoro-2-(5-((R)-pent-3-yn-2-yloxy)pyrazin-2-yl)vinyl)phenyl)-3,6,6-trimethyl-3,6-dihydro-2H-1,4-thiazine 1,1-dioxide;
(R)-5-amino-3-(2-fluoro-5-((Z)-2-fluoro-2-(5-((S)-pent-3-yn-2-yloxy)pyrazin-2-yl)vinyl)phenyl)-3,6,6-trimethyl-3,6-dihydro-2H-1,4-thiazine 1,1-dioxide;
(R,Z)-5-amino-3-(5-(2-(5-(benzyloxy)pyrazin-2-yl)-2-fluorovinyl)-2-fluoropyridin-3-yl)-3,6,6-trimethyl-3,6-dihydro-2H-1,4-thiazine 1,1-dioxide;
(R,Z)-5-amino-3-(2-fluoro-5-(2-fluoro-2-(5-(pyridin-4-ylmethoxy)pyrazin-2-yl)vinyl)phenyl)-3,6,6-trimethyl-3,6-dihydro-2H-1,4-thiazine 1,1-dioxide;
(R,Z)-5-amino-3-(2-fluoro-5-(2-fluoro-2-(5-phenoxypyrazin-2-yl)vinyl)phenyl)-3,6,6-trimethyl-3,6-dihydro-2H-1,4-thiazine 1,1-dioxide;
(R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile;
(2S,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;
(2R,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;
(R,Z)-5-amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide;
(R)-5-amino-3-(2-fluoro-5-((Z)-2-fluoro-2-(5-((R)-hex-3-yn-2-yloxy)pyrazin-2-yl)vinyl)phenyl)-3,6,6-trimethyl-3,6-dihydro-2H-1,4-thiazine 1,1-dioxide;
(R)-5-amino-3-(2-fluoro-5-((Z)-2-fluoro-2-(5-((S)-hex-3-yn-2-yloxy)pyrazin-2-yl)vinyl)phenyl)-3,6,6-trimethyl-3,6-dihydro-2H-1,4-thiazine 1,1-dioxide;
(R)-5-amino-3-(2-fluoro-5-((Z)-2-fluoro-2-(5-(((S)-1-hydroxypropan-2-yl)oxy)pyrazin-2-yl)vinyl)phenyl)-3,6,6-trimethyl-3,6-dihydro-2H-1,4-thiazine 1,1-dioxide;
(R)-5-amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide;
(R,Z)-3-amino-5-(2,3-difluoro-5-(2-fluoro-2-(5-(thiazol-4-ylmethoxy)pyrazin-2-yl)vinyl)phenyl)-2,5-dimethyl-5,6-dihydro-2H-1,2,4-thiadiazine 1,1-dioxide;
(R,Z)-3-amino-5-(2,3-difluoro-5-(2-fluoro-2-(5-((3-methylisoxazol-5-yl)methoxy)pyrazin-2-yl)vinyl)phenyl)-2,5-dimethyl-5,6-dihydro-2H-1,2,4-thiadiazine 1,1-dioxide;
(R,Z)-3-amino-5-(5-(2-(5-chloro-4-hydroxypyridin-2-yl)-2-fluorovinyl)-2-fluorophenyl)-2,5-dimethyl-5,6-dihydro-2H-1,2,4-thiadiazine 1,1-dioxide;
(R,Z)-3-amino-5-(2,3-difluoro-5-(2-fluoro-2-(5-((5-methylisoxazol-3-yl)methoxy)pyrazin-2-yl)vinyl)phenyl)-2,5-dimethyl-5,6-dihydro-2H-1,2,4-thiadiazine 1,1-dioxide;
(R,Z)-3-amino-5-(2,3-difluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;
(R,Z)-3-amino-5-(2,3-difluoro-5-(2-fluoro-2-(5-(oxazol-4-ylmethoxy)pyrazin-2-yl)vinyl)phenyl)-2,5-dimethyl-5,6-dihydro-2H-1,2,4-thiadiazine 1,1-dioxide;
6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-4-fluoro-3-pyridinecarbonitrile;

(R,Z)-5-(5-(2-(5-(allyloxy)pyrazin-2-yl)-2-fluorovinyl)-2,3-difluorophenyl)-3-amino-2,5-dimethyl-5,6-dihydro-2H-1,2,4-thiadiazine 1,1-dioxide;

(R,Z)-3-amino-5-(2,3-difluoro-5-(2-fluoro-2-(5-(pyrimidin-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,2,4-oxadiazol-3-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-chloro-4-methoxypyridin-2-yl)-2-fluorovinyl)-2-fluorophenyl)-2,5-dimethyl-5,6-dihydro-2H-1,2,4-thiadiazine 1,1-dioxide;

(R,Z)-2-(2-(3-(3-amino-2,5-dimethyl-1,1-dioxido-5,6-dihydro-2H-1,2,4-thiadiazin-5-yl)-4-fluorophenyl)-1-fluorovinyl)-5-chloroisonicotinonitrile;

(R,Z)-3-amino-5-(5-(2-(5-chloro-4-fluoropyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-Amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R)-3-amino-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((4-methylthiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-((2,5-dimethyloxazol-4-yl)methoxy)pyrazin-2-yl)-2-fluorovinyl)-2,3-difluorophenyl)-2,5-dimethyl-5,6-dihydro-2H-1,2,4-thiadiazine 1,1-dioxide;

(5R)-5-(5-((Z)-2-(3,4-dihydro-2H-pyrano[2,3-c]pyridin-6-yl)-2-fluoroethenyl)-2-fluorophenyl)-2,5-dimethyl-5,6-dihydro-2H-1,2,4-thiadiazin-3-amine 1,1-dioxide;

(5R)-5-(2-fluoro-5-((Z)-2-fluoro-2-(5-fluoro-2-pyridinyl)ethenyl)phenyl)-2,5-dimethyl-5,6-dihydro-2H-1,2,4-thiadiazin-3-amine 1,1-dioxide;

(5R)-5-(2-fluoro-5-((Z)-2-fluoro-2-(5-methoxy-2-pyrazinyl)ethenyl)phenyl)-2,5-dimethyl-5,6-dihydro-2H-1,2,4-thiadiazin-3-amine 1,1-dioxide;

(5R)-5-(5-((Z)-2-(3-chloro-5-(trifluoromethyl)-2-pyridinyl)-2-fluoroethenyl)-2-fluorophenyl)-2,5-dimethyl-5,6-dihydro-2H-1,2,4-thiadiazin-3-amine 1,1-dioxide;

(R,Z)-ethyl 2-((5-(2-(3-(3-amino-2,5-dimethyl-1,1-dioxido-5,6-dihydro-2H-1,2,4-thiadiazin-5-yl)-4,5-difluorophenyl)-1-fluorovinyl)pyrazin-2-yl)oxy)acetate;

(5R)-5-(2-fluoro-5-((Z)-2-fluoro-2-(5-(trifluoromethyl)-2-pyridinyl)ethenyl)phenyl)-2,5-dimethyl-5,6-dihydro-2H-1,2,4-thiadiazin-3-amine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-5-methyl-3-pyridinecarbonitrile;

(R,Z)-3-amino-5-(2,3-difluoro-5-(2-fluoro-2-(5-((5-methyloxazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(5-(2-(5-(cyclopropylethynyl)pyrazin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((1-methyl-1H-imidazol-2-yl)methoxy)pyrazin-2-yl)vinyl)phenyl)-2,5-dimethyl-5,6-dihydro-2H-1,2,4-thiadiazine 1,1-dioxide;

(5R)-5-(2-fluoro-5-((Z)-2-fluoro-2-(pyrido[3,4-b]pyrazin-7-yl)ethenyl)phenyl)-2,5-dimethyl-5,6-dihydro-2H-1,2,4-thiadiazin-3-amine 1,1-dioxide;

(R,Z)-3-amino-5-(5-(2-(5-(cyclopropylethynyl)pyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2-fluoro-5-(2-fluoro-2-(5-((4-hydroxybut-2-yn-1-yl)oxy)pyrazin-2-yl)vinyl)phenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-5-carbonitrile;

(R,Z)-3-amino-5-(2-fluoro-5-(2-fluoro-2-(5-((4-fluorobut-2-yn-1-yl)oxy)pyrazin-2-yl)vinyl)phenyl)-2,5-dimethyl-5,6-dihydro-2H-1,2,4-thiadiazine 1,1-dioxide;

(5R)-5-(5-((Z)-2-(2,3-dihydro[1,4]dioxino[2,3-b]pyridin-6-yl)-2-fluoroethenyl)-2-fluorophenyl)-2,5-dimethyl-5,6-dihydro-2H-1,2,4-thiadiazin-3-amine 1,1-dioxide;

5-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-2-thiophenecarbonitrile;

(5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide;

(R,Z)-3-amino-5-(2-fluoro-5-(2-fluoro-2-(5-(trifluoromethoxy)pyridin-2-yl)vinyl)phenyl)-2,5-dimethyl-5,6-dihydro-2H-1,2,4-thiadiazine 1,1-dioxide;

(5R)-5-(2-fluoro-5-((Z)-2-fluoro-2-(3-isoquinolinyl)ethenyl)phenyl)-2,5-dimethyl-5,6-dihydro-2H-1,2,4-thiadiazin-3-amine 1,1-dioxide;

(5R)-5-(5-((Z)-2-(6-chloro-3-isoquinolinyl)-2-fluoroethenyl)-2-fluorophenyl)-2,5-dimethyl-5,6-dihydro-2H-1,2,4-thiadiazin-3-amine 1,1-dioxide;

6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile;

(R,Z)-5-amino-3-(2-fluoro-5-(2-fluoro-2-(5-fluoropyridin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-methoxypyrazin-2-yl)vinyl)phenyl)-3,6,6-trimethyl-3,6-dihydro-2H-1,4-thiazine 1,1-dioxide;

(R,Z)-5-amino-3-(5-(2-(3-chloro-5-(trifluoromethyl)pyridin-2-yl)-2-fluorovinyl)-2-fluorophenyl)-3,6,6-trimethyl-3,6-dihydro-2H-1,4-thiazine 1,1-dioxide;

(R,Z)-5-amino-3-(2-fluoro-5-(2-fluoro-2-(5-(trifluoromethyl)pyridin-2-yl)vinyl)phenyl)-3,6,6-trimethyl-3,6-dihydro-2H-1,4-thiazine 1,1-dioxide;

(R,Z)-3-amino-5-(5-(2-(5-cyclopropylpyrazin-2-yl)-2-fluorovinyl)-2-fluorophenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-4-carbonitrile;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-chloronicotinonitrile;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-5-chloronicotinonitrile;
(R,Z)-3-amino-5-(2,3-difluoro-5-(2-fluoro-2-(5-fluoropyridin-2-yl)vinyl)phenyl)-2,5-dimethyl-5,6-dihydro-2H-1,2,4-thiadiazine 1,1-dioxide;
(R,Z)-3-amino-5-(2,3-difluoro-5-(2-fluoro-2-(5-methoxypyrazin-2-yl)vinyl)phenyl)-2,5-dimethyl-5,6-dihydro-2H-1,2,4-thiadiazine 1,1-dioxide;
(R,Z)-3-amino-5-(5-(2-(3-chloro-5-(trifluoromethyl)pyridin-2-yl)-2-fluorovinyl)-2,3-difluorophenyl)-2,5-dimethyl-5,6-dihydro-2H-1,2,4-thiadiazine 1,1-dioxide;
(R,Z)-3-amino-5-(2,3-difluoro-5-(2-fluoro-2-(5-(trifluoromethyl)pyridin-2-yl)vinyl)phenyl)-2,5-dimethyl-5,6-dihydro-2H-1,2,4-thiadiazine 1,1-dioxide;
(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-methylnicotinonitrile;
(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-methylnicotinonitrile;
(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-chloronicotinonitrile;
(1R,4R,5S)-2-amino-4-(2-fluoro-5-((Z)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((E)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide; or
(R,E)-5-amino-3-(5-(4-chlorostyryl)-2-fluorophenyl)-3,6,6-trimethyl-3,6-dihydro-2H-1,4-thiazine 1,1-dioxide.

Provided herein as Embodiment 37 is the compound of Embodiment 1, or a tautomer, or a pharmaceutically acceptable salt of said compound or tautomer, selected from (1R,4R,5S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide;
6-((Z)-2-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-1-fluorovinyl)nicotinonitrile;
(R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile;
(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)nicotinonitrile;
(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)nicotinonitrile;
(1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-(2,2,2-trifluoroethoxy)pyrazin-2-yl)vinyl)phenyl)-1-(fluoromethyl)-4-methyl-8-thia-3-azabicyclo[3.2.1]oct-2-ene 8,8-dioxide;
(R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide;
(R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;
(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile;
(1R,4R,5S)-2-amino-4-(2-fluoro-5-((Z)-2-fluoro-2-(5-((3-methyl-1,2,4-oxadiazol-5-yl)methoxy)pyrazin-2-yl)vinyl)phenyl)-1-(fluoromethyl)-4-methyl-8-thia-3-azabicyclo[3.2.1]oct-2-ene 8,8-dioxide;
(R,Z)-3-amino-5-(2-fluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;
(R,Z)-3-amino-5-(2-fluoro-5-(2-fluoro-2-(5-(2,2,2-trifluoroethoxy)pyrazin-2-yl)vinyl)phenyl)-2,5-dimethyl-5,6-dihydro-2H-1,2,4-thiadiazine 1,1-dioxide;
(1R,4R,5S)-2-amino-4-(5-((Z)-2-(5-(cyclopropylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-((5-methyl-1,3,4-oxadiazol-2-yl)methoxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-(2,2,3,3-tetrafluoropropoxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-methoxypyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(5-((Z)-2-(5-ethoxypyrazin-2-yl)-2-fluorovinyl)-2-fluorophenyl)-1-(fluoromethyl)-4-methyl-8-thia-3-azabicyclo[3.2.1]oct-2-ene 8,8-dioxide;
(R,Z)-5-amino-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
(R,Z)-5-amino-3-(2-fluoro-5-(2-fluoro-2-(5-(2,2,2-trifluoroethoxy)pyrazin-2-yl)vinyl)phenyl)-3,6,6-trimethyl-3,6-dihydro-2H-1,4-thiazine 1,1-dioxide;
(1R,4R,5S)-4-(5-((Z)-2-(5-(allyloxy)pyrazin-2-yl)-2-fluorovinyl)-2-fluorophenyl)-2-amino-1-(fluoromethyl)-4-methyl-8-thia-3-azabicyclo[3.2.1]oct-2-ene 8,8-dioxide;
(R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile;
(1R,4R,5S)-2-amino-4-(5-((Z)-2-(5-((S)-but-3-yn-2-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;
(R,Z)-5-amino-3-(2-fluoro-5-(2-fluoro-2-(5-(oxazol-2-ylmethoxy)pyrazin-2-yl)vinyl)phenyl)-3,6,6-trimethyl-3,6-dihydro-2H-1,4-thiazine 1,1-dioxide;
(1R,4R,5S)-2-amino-4-(2-fluoro-5-((Z)-2-fluoro-2-(5-(2-methoxyethoxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-(((S)-1-methoxypropan-2-yl)oxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(5-((Z)-2-(5-(cyclobutylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;
(1R,4R,5S)-2-amino-4-(2-fluoro-5-((Z)-2-fluoro-2-(5-(2-fluoroethoxy)pyrazin-2-yl)vinyl)phenyl)-1-(fluoromethyl)-4-methyl-8-thia-3-azabicyclo[3.2.1]oct-2-ene 8,8-dioxide;
(1R,4R,5S)-2-amino-4-(5-((Z)-2-(5-(2,2-difluoroethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-propoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-methoxypropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(but-2-yn-1-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(8R)-8-(2-fluoro-5-((Z)-2-fluoro-2-(5-(2-propyn-1-yloxy)-2-pyrazinyl)ethenyl)phenyl)-5,8-dimethyl-4-thia-5,7-diazaspiro[2.5]oct-6-en-6-amine 4,4-dioxide;

(8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide;

(R,Z)-5-amino-3-(2-fluoro-5-(2-fluoro-2-(5-hydroxypyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,3,3-tetrafluoropropoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(3,3,3-trifluoropropoxy)pyrazin-2-yl)vinyl)phenyl)-3,6,6-trimethyl-3,6-dihydro-2H-1,4-thiazine 1,1-dioxide;

(R,Z)-3-amino-5-(5-(2-(5-(cyclopropylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(cyclobutylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-amino-5-(2-fluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-5-(2-(3-(6-amino-5,8-dimethyl-4,4-dioxido-4-thia-5,7-diazaspiro[2.5]oct-6-en-8-yl)-4-fluorophenyl)-1-fluorovinyl)pyrazine-2-carbonitrile;

(R,Z)-3-amino-5-(2-fluoro-5-(2-fluoro-2-(5-(2,2,3,3-tetrafluoropropoxy)pyrazin-2-yl)vinyl)phenyl)-2,5-dimethyl-5,6-dihydro-2H-1,2,4-thiadiazine 1,1-dioxide;

(R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide;

(R,Z)-5-amino-3-(5-(2-(5-(cyclohexylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-((5-(2-(3-(5-amino-3,6,6-trimethyl-1,1-dioxido-3,6-dihydro-2H-1,4-thiazin-3-yl)-4-fluorophenyl)-1-fluorovinyl)pyrazin-2-yl)oxy)-2,2-dimethylpropanenitrile;

(R,Z)-5-amino-3-(5-(2-(5-(but-2-yn-1-yloxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-pyrazol-1-yl)ethoxy)pyrazin-2-yl)-2-fluorovinyl)-5-amino-3,6,6-trimethyl-3,6-dihydro-2H-1,4-thiazine 1,1-dioxide;

(R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R)-5-amino-3-(5-((Z)-2-(5-((S)-but-3-yn-2-yloxy)pyrazin-2-yl)-2-fluorovinyl)-2-fluorophenyl)-3,6,6-trimethyl-3,6-dihydro-2H-1,4-thiazine 1,1-dioxide;

(8R)-8-(2-fluoro-5-((Z)-2-fluoro-2-(5-((3-methyl-1,2,4-oxadiazol-5-yl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-((5-methyl-3-isoxazolyl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(2,2,2-trifluoroethoxy)-2-pyrazinyl)ethenyl)phenyl)-5,8-dimethyl-4-thia-5,7-diazaspiro[2.5]oct-6-en-6-amine 4,4-dioxide;

(R)-3-amino-5-(2-fluoro-5-((Z)-2-fluoro-2-(5-(((S)-1-methoxypropan-2-yl)oxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(but-2-yn-1-yloxy)pyrazin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2,3-difluorophenyl)-2,5-dimethyl-5,6-dihydro-2H-1,2,4-thiadiazine 1,1-dioxide hydrochloride;

(R,Z)-3-amino-5-(5-(2-(5-(but-2-yn-1-yloxy)pyrazin-2-yl)-2-fluorovinyl)-2-fluorophenyl)-2,5-dimethyl-5,6-dihydro-2H-1,2,4-thiadiazine 1,1-dioxide;

(8R)-8-(2-fluoro-5-((Z)-2-fluoro-2-(5-((5-methyl-1,3-oxazol-2-yl)methoxy)-2-pyrazinyl)ethenyl)phenyl)-5,8-dimethyl-4-thia-5,7-diazaspiro[2.5]oct-6-en-6-amine 4,4-dioxide;

(R,Z)-5-(2-(3-(5-amino-3,6,6-trimethyl-1,1-dioxido-3,6-dihydro-2H-1,4-thiazin-3-yl)-4-fluorophenyl)-1-fluorovinyl)pyrazine-2-carbonitrile;

(R)-3-amino-5-(5-((Z)-2-(5-((S)-but-3-yn-2-yloxy)pyrazin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-(5-(2-methoxypropoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-5-amino-3-(2-fluoro-5-(2-fluoro-2-(5-((3-methyl-1,2,4-oxadiazol-5-yl)methoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-((5-methyl-1,3,4-oxadiazol-2-yl)methoxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide;

(R,Z)-3-amino-5-(2-fluoro-5-(2-fluoro-2-(5-(oxetan-3-ylmethoxy)pyrazin-2-yl)vinyl)phenyl)-2,5-dimethyl-5,6-dihydro-2H-1,2,4-thiadiazine 1,1-dioxide;

(R,Z)-6-(2-(3-(3-amino-2,5,6,6-tetramethyl-1,1-dioxido-5,6-dihydro-2H-1,2,4-thiadiazin-5-yl)-4-fluorophenyl)-1-fluorovinyl)nicotinonitrile;

(R,Z)-5-(2-(3-(3-amino-2,5,6,6-tetramethyl-1,1-dioxido-5,6-dihydro-2H-1,2,4-thiadiazin-5-yl)-4-fluorophenyl)-1-fluorovinyl)pyrazine-2-carbonitrile;

(R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5,6,6-tetramethyl-5,6-dihydro-2H-1,2,4-thiadiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-3,6,6-trimethyl-3,6-dihydro-2H-1,4-thiazine 1,1-dioxide;

(R,Z)-3-amino-5-(5-(2-(5-(but-2-yn-1-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile;

(S,Z)-5-amino-3-(2-fluoro-5-(2-fluoro-2-(5-(prop-2-yn-1-yloxy)pyrazin-2-yl)vinyl)phenyl)-3-(fluoromethyl)-6,6-dimethyl-3,6-dihydro-2H-1,4-thiazine 1,1-dioxide;

(R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile;

(S,Z)-5-amino-3-(5-(2-(5-(but-2-yn-1-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(S)-5-amino-3-(5-((Z)-2-(5-((S)-but-3-yn-2-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile;

(R)-5-amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide;

(2R,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(2S,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2,3-difluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(prop-2-yn-1-yloxy)pyrazin-2-yl)vinyl)pyridin-3-yl)-3,6,6-trimethyl-3,6-dihydro-2H-1,4-thiazine 1,1-dioxide;

(R,Z)-5-amino-3-(5-(2-(5-(cyclopropylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(benzyloxy)pyrazin-2-yl)-2-fluorovinyl)-2-fluoropyridin-3-yl)-3,6,6-trimethyl-3,6-dihydro-2H-1,4-thiazine 1,1-dioxide;

(R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile;

(2S,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide(2R,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide;

(R)-5-amino-3-(2-fluoro-5-((Z)-2-fluoro-2-(5-(((S)-1-hydroxypropan-2-yl)oxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide;

(R,Z)-3-amino-5-(2,3-difluoro-5-(2-fluoro-2-(5-(thiazol-4-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methylisoxazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methylisoxazol-3-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-4-ylmethoxy)pyrazin-2-yl)vinyl)phenyl)-2,5-dimethyl-5,6-dihydro-2H-1,2,4-thiadiazine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-4-fluoro-3-pyridinecarbonitrile;

(R,Z)-5-(5-(2-(5-(allyloxy)pyrazin-2-yl)-2-fluorovinyl)-2,3-difluorophenyl)-3-amino-2,5-dimethyl-5,6-dihydro-2H-1,2,4-thiadiazine 1,1-dioxide;

(R,Z)-3-amino-5-(2,3-difluoro-5-(2-fluoro-2-(5-(pyrimidin-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,2,4-oxadiazol-3-yl)methoxy)pyrazin-2-yl)vinyl)phenyl)-2,5-dimethyl-5,6-dihydro-2H-1,2,4-thiadiazine 1,1-dioxide;

(R,Z)-2-(2-(3-(3-amino-2,5-dimethyl-1,1-dioxido-5,6-dihydro-2H-1,2,4-thiadiazin-5-yl)-4-fluorophenyl)-1-fluorovinyl)-5-chloroisonicotinonitrile;

(R,Z)-3-amino-5-(2,3-difluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-Amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R)-3-amino-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((4-methylthiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-((2,5-dimethyloxazol-4-yl)methoxy)pyrazin-2-yl)-2-fluorovinyl)-2,3-difluorophenyl)-2,5-dimethyl-5,6-dihydro-2H-1,2,4-thiadiazine 1,1-dioxide;

(5R)-5-(5-((Z)-2-(3-chloro-5-(trifluoromethyl)-2-pyridinyl)-2-fluoroethenyl)-2-fluorophenyl)-2,5-dimethyl-5,6-dihydro-2H-1,2,4-thiadiazin-3-amine 1,1-dioxide;

(R,Z)-ethyl 2-((5-(2-(3-(3-amino-2,5-dimethyl-1,1-dioxido-5,6-dihydro-2H-1,2,4-thiadiazin-5-yl)-4,5-difluorophenyl)-1-fluorovinyl)pyrazin-2-yl)oxy)acetate;

(5R)-5-(2-fluoro-5-((Z)-2-fluoro-2-(5-(trifluoromethyl)-2-pyridinyl)ethenyl)phenyl)-2,5-dimethyl-5,6-dihydro-2H-1,2,4-thiadiazin-3-amine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-5-methyl-3-pyridinecarbonitrile;

(R,Z)-3-amino-5-(2,3-difluoro-5-(2-fluoro-2-(5-((5-methyloxazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(5-(2-(5-(cyclopropylethynyl)pyrazin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((1-methyl-1H-imidazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(cyclopropylethynyl)pyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2-fluoro-5-(2-fluoro-2-(5-((4-hydroxybut-2-yn-1-yl)oxy)pyrazin-2-yl)vinyl)phenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-5-carbonitrile;

(R,Z)-3-amino-5-(2-fluoro-5-(2-fluoro-2-(5-((4-fluorobut-2-yn-1-yl)oxy)pyrazin-2-yl)vinyl)phenyl)-2,5-dimethyl-5,6-dihydro-2H-1,2,4-thiadiazine 1,1-dioxide;

(5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide;

(R,Z)-3-amino-5-(2-fluoro-5-(2-fluoro-2-(5-(trifluoromethoxy)pyridin-2-yl)vinyl)phenyl)-2,5-dimethyl-5,6-dihydro-2H-1,2,4-thiadiazine 1,1-dioxide;

6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile;

(R,Z)-5-amino-3-(5-(2-(3-chloro-5-(trifluoromethyl)pyridin-2-yl)-2-fluorovinyl)-2-fluorophenyl)-3,6,6-trimethyl-3,6-dihydro-2H-1,4-thiazine 1,1-dioxide;

(R,Z)-5-amino-3-(2-fluoro-5-(2-fluoro-2-(5-(trifluoromethyl)pyridin-2-yl)vinyl)phenyl)-3,6,6-trimethyl-3,6-dihydro-2H-1,4-thiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-chloronicotinonitrile;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-5-chloronicotinonitrile;

(R,Z)-3-amino-5-(2,3-difluoro-5-(2-fluoro-2-(5-methoxypyrazin-2-yl)vinyl)phenyl)-2,5-dimethyl-5,6-dihydro-2H-1,2,4-thiadiazine 1,1-dioxide;

(R,Z)-3-amino-5-(5-(2-(3-chloro-5-(trifluoromethyl)pyridin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(trifluoromethyl)pyridin-2-yl)vinyl)phenyl)-2,5-dimethyl-5,6-dihydro-2H-1,2,4-thiadiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-methylnicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-methylnicotinonitrile; or (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-chloronicotinonitrile.

Provided herein as Embodiment 38 is the compound of Embodiment 1, or a tautomer, or a pharmaceutically acceptable salt of said compound or tautomer, selected from

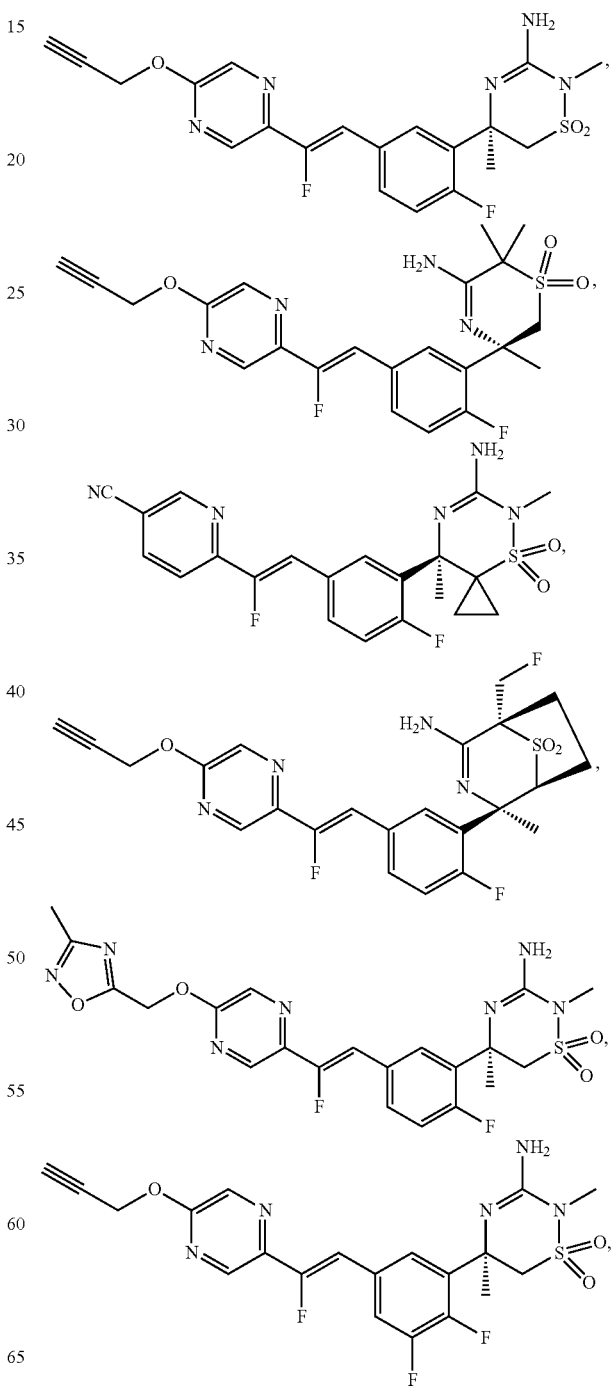

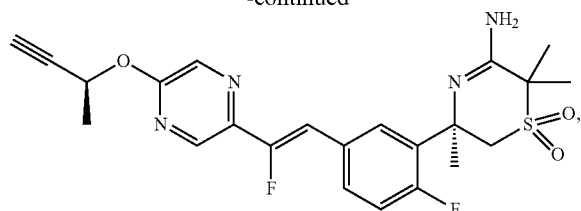

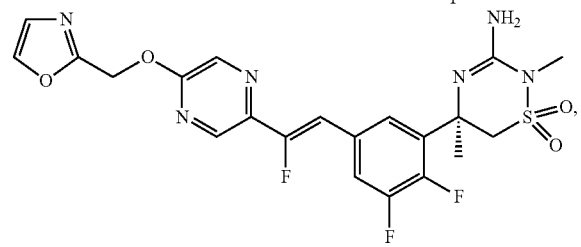

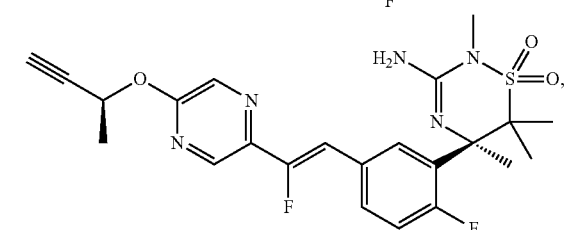

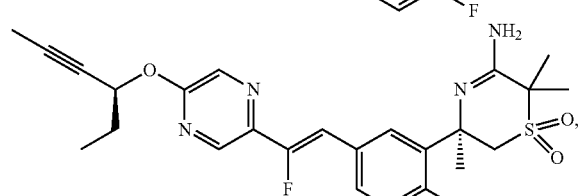

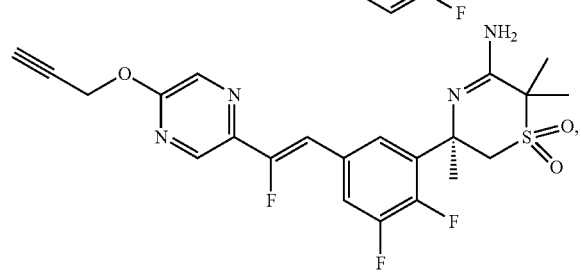

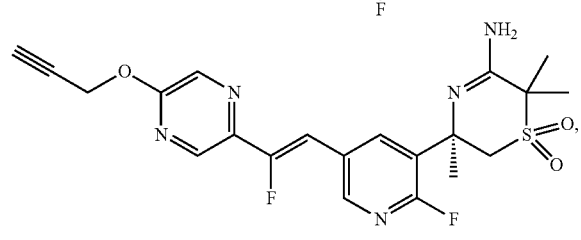

or

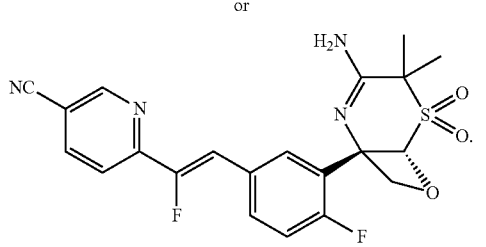

Provided herein as Embodiment 39 is the compound of Embodiment 38, or a tautomer, or a pharmaceutically acceptable salt of said compound or tautomer, wherein the compound is

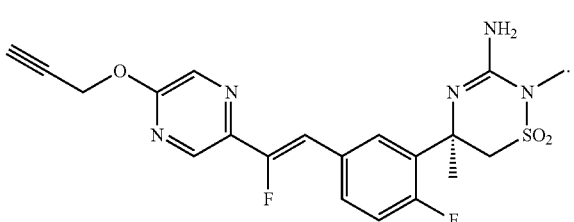

Provided herein as Embodiment 40 is the compound of Embodiment 38, or a tautomer, or a pharmaceutically acceptable salt of said compound or tautomer, wherein the compound is

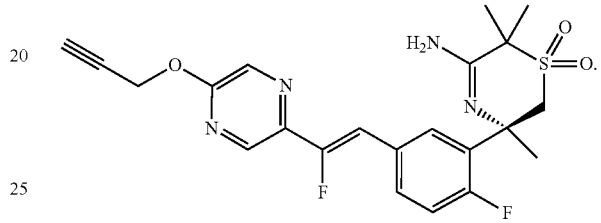

Provided herein as Embodiment 41 is the compound of Embodiment 38, or a tautomer, or a pharmaceutically acceptable salt of said compound or tautomer, wherein the compound is

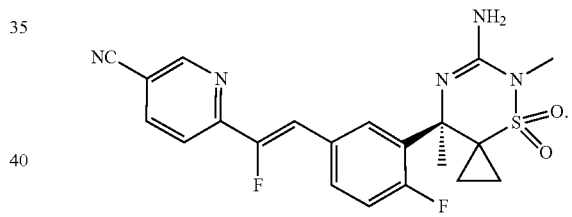

Provided herein as Embodiment 42 is the compound of Embodiment 38, or a tautomer, or a pharmaceutically acceptable salt of said compound or tautomer, wherein the compound is

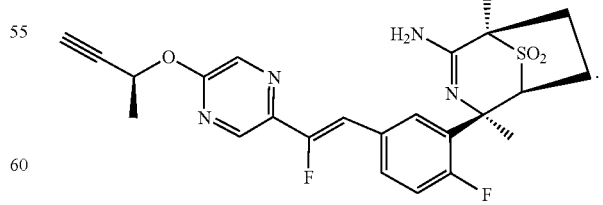

Provided herein as Embodiment 43 is the compound of Embodiment 38, or a tautomer, or a pharmaceutically acceptable salt of said compound or tautomer, wherein the compound is

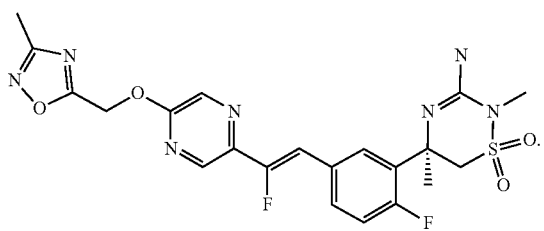 [SMILES: Cc1noc(COc2cnc(/C(F)=C/c3ccc(F)c([C@]4(C)CS(=O)(=O)N(C)C(N)=N4)c3)cn2)n1]

Provided herein as Embodiment 44 is the compound of Embodiment 38, or a tautomer, or a pharmaceutically acceptable salt of said compound or tautomer, wherein the compound is

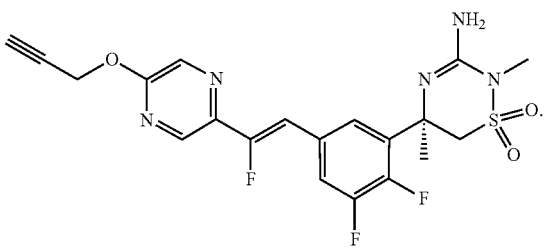 [SMILES: C#CCOc1cnc(/C(F)=C/c2cc(F)c(F)c([C@]3(C)CS(=O)(=O)N(C)C(N)=N3)c2)cn1]

Provided herein as Embodiment 45 is the compound of Embodiment 38, or a tautomer, or a pharmaceutically acceptable salt of said compound or tautomer, wherein the compound is

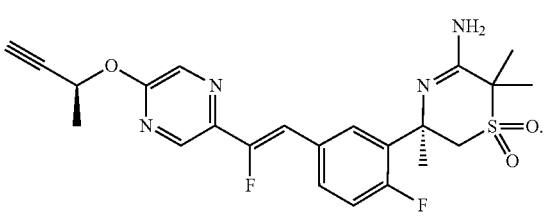 [SMILES: C#C[C@H](C)Oc1cnc(/C(F)=C/c2ccc(F)c([C@]3(C)CS(=O)(=O)C(C)(C)C(N)=N3)c2)cn1]

Provided herein as Embodiment 46 is the compound of Embodiment 38, or a tautomer, or a pharmaceutically acceptable salt of said compound or tautomer, wherein the compound is

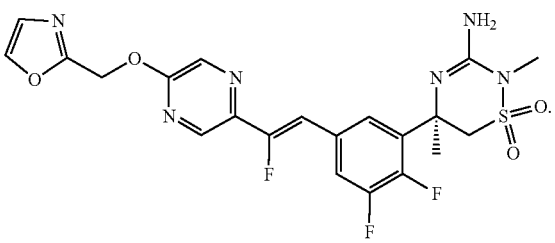

Provided herein as Embodiment 47 is the compound of Embodiment 38, or a tautomer, or a pharmaceutically acceptable salt of said compound or tautomer, wherein the compound is

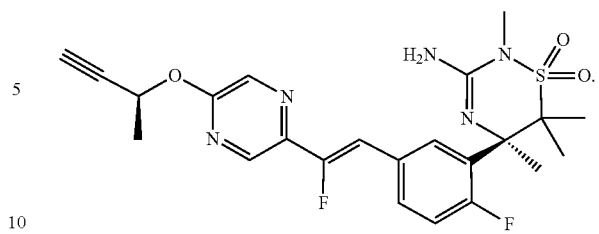

Provided herein as Embodiment 48 is the compound of Embodiment 38, or a tautomer, or a pharmaceutically acceptable salt of said compound or tautomer, wherein the compound is

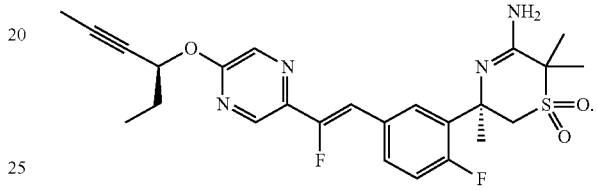

Provided herein as Embodiment 49 is the compound of Embodiment 38, or a tautomer, or a pharmaceutically acceptable salt of said compound or tautomer, wherein the compound is

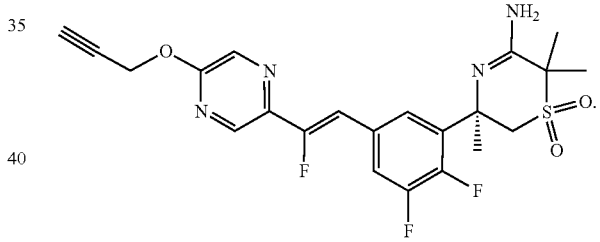

Provided herein as Embodiment 50 is the compound of Embodiment 38, or a tautomer, or a pharmaceutically acceptable salt of said compound or tautomer, wherein the compound is

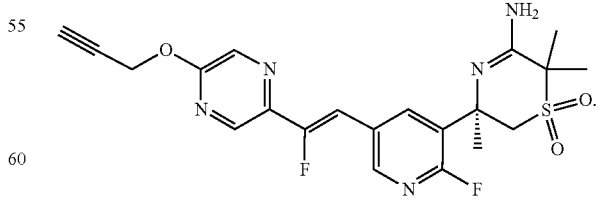

Provided herein as Embodiment 51 is the compound of Embodiment 38, or a tautomer, or a pharmaceutically acceptable salt of said compound or tautomer, wherein the compound is

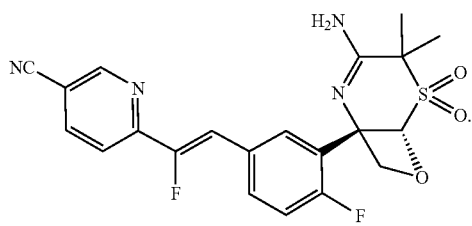 [SMILES: CC1(C)C(N)=N[C@@]2(c3cc(/C=C(\F)c4ccc(C#N)cn4)ccc3F)CO[C@H]2S1(=O)=O]

Provided herein as Embodiment 52 is the compound of Embodiment 1, or a tautomer, or a pharmaceutically acceptable salt of said compound or tautomer, wherein the compound is

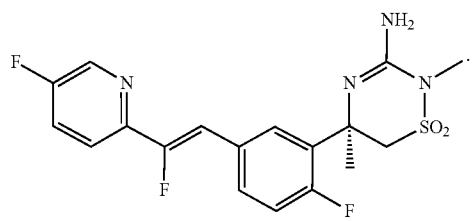 [SMILES: CN1C(N)=N[C@](C)(c2cc(/C=C(\F)c3ccc(F)cn3)ccc2F)CS1(=O)=O]

Provided herein as Embodiment 53 is a pharmaceutical composition comprising the compound according to any of Embodiments 1 to 52, or a tautomer, or a pharmaceutically acceptable salt of said compound or tautomer, and a pharmaceutically acceptable excipient.

Provided herein as Embodiment 54 is a compound according to any one of Embodiments 1 to 52, or a tautomer, or a pharmaceutically acceptable salt of said compound or tautomer, or the pharmaceutical composition according to Embodiment 53 for use as a medicament.

Provided herein as Embodiment 55 is a compound according to any one of Embodiments 1 to 52, or a tautomer, or a pharmaceutically acceptable salt of said compound or tautomer, or the pharmaceutical composition according to Embodiment 53 for use in reducing beta amyloid peptide levels in the cerebral spinal fluid of a subject.

Provided herein as Embodiment 56 is a compound according to any one of Embodiments 1 to 52, or a tautomer, or a pharmaceutically acceptable salt of said compound or tautomer, or the pharmaceutical composition according to Embodiment 53 for use in treating Alzheimer's disease, cognitive impairment, or a combination thereof in a subject.

Provided herein as Embodiment 57 is a compound according to any one of Embodiments 1 to 52, or a tautomer, or a pharmaceutically acceptable salt of said compound or tautomer, or the pharmaceutical composition according to Embodiment 53 for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 58 is a compound according to any one of Embodiments 1 to 52, or a tautomer, or a pharmaceutically acceptable salt of said compound or tautomer, or the pharmaceutical composition according to Embodiment 53 for use in reducing formation of plaque on the brain of a subject.

Provided herein as Embodiment 59 is a use of the compound according to any one of Embodiments 1 to 52, or a tautomer, or a pharmaceutically acceptable salt of said compound or tautomer, or the pharmaceutical composition according to Embodiment 53 in the preparation of a medicament for reducing beta amyloid peptide levels in the cerebral spinal fluid of a subject.

Provided herein as Embodiment 60 is a use of the compound according to any one of Embodiments 1 to 52, or a tautomer, or a pharmaceutically acceptable salt of said compound or tautomer, or the pharmaceutical composition according to Embodiment 53 for the preparation of a medicament for treating Alzheimer's disease, cognitive impairment, or a combination thereof in a subject.

Provided herein as Embodiment 61 is a use of the compound according to any one of Embodiments 1 to 52, or a tautomer, or a pharmaceutically acceptable salt of said compound or tautomer, or the pharmaceutical composition according to Embodiment 53 in the preparation of a medicament for the treatment of a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject.

Provided herein as Embodiment 62 is a use of the compound according to any one of Embodiments 1 to 52, or a tautomer, or a pharmaceutically acceptable salt of said compound or tautomer, or the pharmaceutical composition according to Embodiment 53 in the preparation of a medicament for the reduction of formation of plaque on the brain of a subject.

Provided herein as Embodiment 63 is a method of reducing beta amyloid peptide levels in the cerebral spinal fluid of a subject in need thereof, the method comprising administering to the subject a therapeutically effective amount of the compound according to any one of Embodiments 1 to 52, or a tautomer, or a pharmaceutically acceptable salt of said compound or tautomer.

Provided herein as Embodiment 64 is a method of treating Alzheimer's disease, cognitive impairment or a combination thereof in a subject in need thereof, the method comprising administering to the subject a therapeutically effective amount of the compound according to any one of Embodiments 1 to 52, or a tautomer, or a pharmaceutically acceptable salt of said compound or tautomer.

Provided herein as Embodiment 65 is a method of treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject in need thereof, the method comprising administering to the subject a therapeutically effective amount of the compound according to any one of Embodiments 1 to 52, or a tautomer, or a pharmaceutically acceptable salt of said compound or tautomer.

Provided herein as Embodiment 66 is a method of reducing the formation of plaque on the brain of a subject in need thereof, the method comprising administering to the subject a therapeutically effective amount of the compound according to any one of Embodiments 1 to 52, or a tautomer, or a pharmaceutically acceptable salt of said compound or tautomer.

The foregoing merely summarizes certain aspects of this disclosure and is not intended, nor should it be construed, as limiting the disclosure in any way.

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, or atropoisomers. Accordingly, the scope of the instant disclosure is to be understood to encompass all possible stereoisomers of the illustrated compounds including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers) of any chemical structures disclosed herein (in whole or in part). This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, Ind., 1972).

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I:

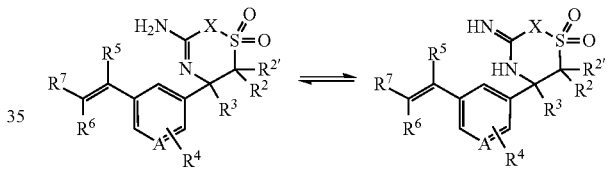

Accordingly, the scope of the instant disclosure is to be understood to encompass all tautomeric forms of the compounds disclosed herein.

Isotopically-Labelled Compounds

Further, the scope of present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I, for example, those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with isotopes such as deuterium ($^2$H) may afford certain therapeutic advantages resulting from greater metabolic stability, for example, increased in vivo half-life or reduced dosage requirements, and hence may be advantageous in some circumstances. Substitution with positron emitting isotopes, such as $^{11}$C, $^{18}$F, $^{15}$O and $^{13}$N, can be useful in Positron Emission Topography (PET)

studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagents in place of the non-labelled reagent previously employed.

Solvates

As discussed above, the compounds disclosed herein and the stereoisomers, tautomers and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Amorphous and Crystalline Forms

In certain embodiments, the compounds described herein and the stereoisomers, tautomers, isotopically-labelled forms thereof or pharmaceutically acceptable salts of any of the foregoing or solvates of any of the foregoing may exist in different forms, such as amorphous forms and crystalline forms (polymorphs). Accordingly, the scope of the instant disclosure is to be understood to encompass all such forms.

Miscellaneous Definitions

This section will define additional terms used to describe the scope of the compounds, compositions and uses disclosed herein.

The terms as "$C_{1-4}$alkyl" and "$C_{1-6}$alkyl" as used herein refers to a straight or branched chain hydrocarbon containing from 1 to 4 and 1 to 6 carbon atoms, respectively. Representative examples of $C_{1-4}$alkyl or $C_{1-6}$alkyl include, but are not limited to, methyl, ethyl, n-propyl, iso-propyl, n-butyl, sec-butyl iso-butyl, tert-butyl, pentyl and hexyl.

The term "$C_{3-6}$alkenyl" as used herein refers to a saturated hydrocarbon radical containing two to six carbon atoms having at least one carbon-carbon double bond. Alkenyl radicals include both straight and branched moieties. Representative examples of $C_{3-6}$alkenyl include, but are not limited to, 1-propenyl, 2-propenyl, 2-methyl-2-propenyl, butenyl, pentenyl and 3-hexenyl.

The term "$C_{3-6}$alkynyl" as used herein refers to a saturated hydrocarbon radical containing two to six carbon atoms having at least one carbon-carbon triple bond. Alkynyl radicals include both straight and branched moieties. Representative examples of $C_{3-6}$alkynyl include, but are not limited to, 1-propynyl, 2-propynyl 2-methyl-2-propynyl butynyl, pentynyl and 3-hexynyl.

The term "$C_{1-6}$alkoxy" as used herein refers to a radical —OR where R represents an $C_{1-6}$alkyl group as defined herein. Representative examples of $C_{1-6}$alkoxy include, but are not limited to, methoxy, ethoxy, propoxy, and butoxy.

The term "$C_{3-6}$alkenyloxy" as used herein refers to a radical —OR where R represents an $C_{3-6}$alkenyl group as defined herein. Representative examples of $C_{3-6}$alkenyl include, but are not limited to, allyloxy, 2-butenyloxy, 4-pentenyloxy and 5-hexenyloxy.

The term "$C_{3-6}$alkynyloxy" as used herein refers to a radical —OR where R represents an $C_{3-6}$alkynyl group as defined herein. Representative examples of $C_{3-6}$alkynyl include, but are not limited to, 2-propynyloxy, 3-butynyloxy, 4-pentynyloxy and 5-hexynyloxy.

The term "$C_{3-6}$carbocycle" as used herein refers to a saturated carbocyclic molecule wherein the cyclic framework has 3 to 6 carbons. Representative examples of $C_{3-6}$carbocycle include, but are not limited to, cyclopropan, cyclobutan, cyclopentan, and cyclohexan. One carbon of the $C_{3-6}$carbocycle may be of a spirocyclic structure, for example, forming a 9-amino-5-thia-8-azaspiro[3.5]non-8-ene 5,5-dioxide.

The term "$C_{3-6}$cycloalkyl" as used herein refers to a saturated carbocyclic molecule wherein the cyclic framework has 3 to 6 carbons. Representative examples of $C_{3-6}$cycloalkyl include, but are not limited to, cyclopropyl, cyclobutyl, cyclopentyl, and cyclohexyl.

The term "halogen" as used herein means —F, —Cl, —Br, or —I.

The term "heteroaryl" as used herein refers to an 5 or 6 membered heteroaryl. The 5 membered heteroaryl ring consists of two double bonds and one, two, three or four nitrogen atoms and/or optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl.

The term "heterocycloalkane" or "heterocycloalkanyl" as used herein refers to a 5 or 6 membered heterocycloalkane or a radical thereof, respectively. The heterocycloalkane or heterocycloalkanyl consists of a saturated carbocycle or a radical thereof, wherein one or two carbon atoms are substituted with an atom independently selected from N, O, or S. Representative examples of heterocycloalkanes include, but are not limited to, pyrrolidine, tetrahydrofuran, tetrahydrothiophene, piperidine, tetrahydro-2H-pyran, tetrahydro-2H-thiopyran, piperazin, morpholine, and thiomorpholine. Representative examples of heterocycloalkanyls include, but are not limited to, pyrrolidinyl, tetrahydrofuranyl, tetrahydrothiophenyl, piperidinyl, tetrahydro-2H-pyranyl, tetrahydro-2H-thiopyranyl, piperazinyl, morpholinyl, and thiomorpholinyl. In one embodiment of Formula I, wherein one of $R^2$ and $R^{2'}$ together with $R^3$ and the two carbon atoms to which $R^2$, $R^{2'}$, and $R^3$ are attached form a 5 or 6 membered heterocycloalkane, Formula I comprises, for example, the following bicyclic ring system

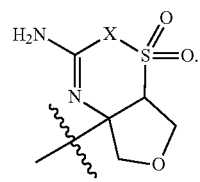

The term "5 to 10 membered heterocycle" as used herein refers to mono or bicyclic heterocycles. The 5 to 10 membered heterocycle is a heteroaryl as defined herein or a heterocycloalkanyl as defined herein, wherein the heteroaryl may be optionally fused to another heteroaryl or a heterocycloalkane as defined herein. Representative examples of 5 to 10 membered heterocycles include, but are not limited to, tetrahydropyranyl, tetrahydofuranyl, thiophenyl, thiazolyl, phenyl, pyridyl, pyrazinyl, 2,3-dihydrobenzo[b][1,4]dioxinyl, 2,3-dihydro-[1,4]dioxino[2,3-c]pyridyl, [1,3]dioxolo[4,5-c]pyridyl, 3,4-dihydro-2H-pyrano[2,3-c]pyridyl, 2,3-dihydro-[1,4]dioxino[2,3-b]pyridyl, 6,7-dihydro-[1,4]dioxino[2,3-d]pyrimidinyl, isoquinolinyl, and pyrido[3,4-b]pyrazinyl.

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1): 1-19 (1977). See also Stahl et al., Pharmaceutical Salts: Properties, Selection, and Use, $2^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "treating" as used herein refers not only to treating a subject to relieve the subject of one or more signs and symptoms of a disease or condition or to eliminate one or more such signs and symptoms, but also to prophylactically treating an asymptomatic subject to prevent the onset of the disease or condition or preventing, slowing or reversing the progression of the disease or condition.

The term "therapeutically effective amount" as used herein refers to that amount of a compound disclosed herein that will elicit the biological or medical response of a tissue, a system, or subject that is being sought by a researcher, veterinarian, medical doctor or other clinician. The term also encompasses the amount of compound disclosed herein that will prevent or reduce the risk of occurrence of the biological or medical event that is sought to be prevented in a tissue, a system, or subject by a researcher, veterinarian, medical doctor or other clinician.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. All starting materials are either commercially available, for example, from Sigma-Aldrich Chemical Company, Inc., St. Louis, Mo., USA, or known in the art and may be synthesized by employing known procedures using ordinary skill. Starting material may also be synthesized via the procedures disclosed herein.

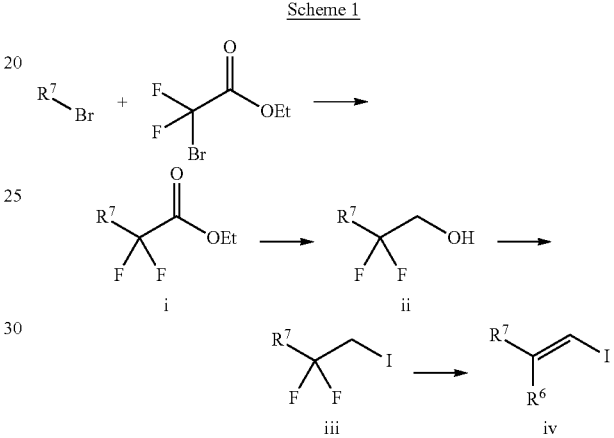

Scheme 1

The alkene iv, wherein $R^6$ is F, may be synthesized as shown in Scheme 1. The starting material $R^7$—Br is reacted with ethyl 2-bromo-2,2-difluoroacetate to give ester i. Ester i is then reduced, for example, with sodium borohydride, to give alcohol ii. The OH group of alcohol ii is then transformed into an iodo group yielding compound iii by transforming the OH group in a leaving group followed by a nucleophilic substitution, for example, by reacting alcohol ii with triflic anhydride in presence of a base, such as pyridine, followed by reaction with I⁻, sourced from, for example, sodium iodide. Alkene iv is then obtained by reacting compound iii with a base, such as potassium tert-butoxide.

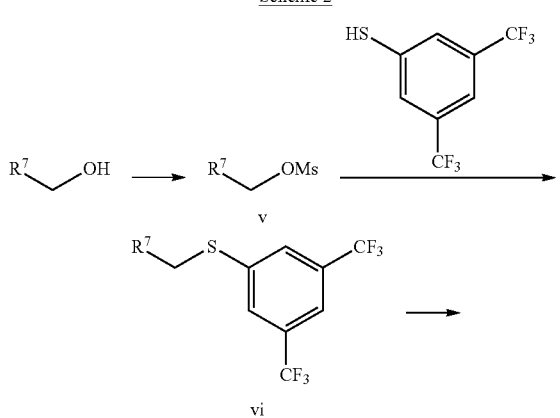

Scheme 2

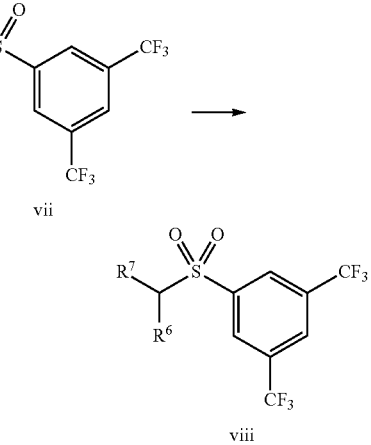

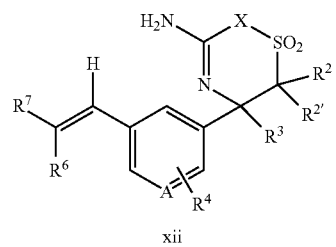

Sulfone viii, wherein $R^6$ is F, may be synthesized as shown in Scheme 2. First, the OH group of $R^7CH_2OH$ is transformed into a leaving group, for example by reacting $R^7CH_2OH$ with methane sulfonyl chloride in presence of a base, such as trimethylamine, to give compound v. Then, compound v is reacted with 3,5-bis(trifluoromethyl)benzenethiol in presence of a base, such as sodium hydroxide, to give compound vi. Alternatively, $R^7CH_2X$, wherein X is Cl, Br, or I, may be directly reacted with 3,5-bis(trifluoromethyl)benzenethiol in presence of a base, such as potassium carbonate, to give compound vi. The sulfone vii is obtained by reacting compound vi under oxidizing conditions using, for example, hydrogen peroxide. Sulfone viii, wherein $R^6$ is F, was obtained reacting sulfone vii with an electrophilic fluorination agent, such as N-fluorodibenzenesulfonimide, in presence of a base, such as lithium diisopropylamide.

The final compound xii, wherein $R^6$ is H or F, may be synthesized as shown in Scheme 3. First, the free amino group of compound ix, wherein Z is Cl, Br or I, is suitably protected, for example by reaction with di-tert-butyl dicarbonate in presence of a base, such as N,N-diisopropylethylamine (Hünig's base). The suitably protected compound x is then transformed into boronic acid xi, for example by reacting bis(pinacolato)diboron in presence of a base, such as potassium acetate, and a suitable palladium catalyst, such [1,1'-bis(diphenylphosphino)ferrocene]-dichloropalladium (II). The final compound xii is obtained by reacting boronic acid xi with compound iv, wherein $R^6$ is H or F, under Suzuki conditions, in presence of, for example, bis(di-tert-butyl(4-dimethylaminophenyl)phosphine)-dichloropalladium(II) and a base, such as potassium phosphate, followed by a deprotection of the amino group by reacting the Suzuki product with, for example, trifluoroacetic acid, if a di-BOC protecting strategy was employed.

Scheme 3

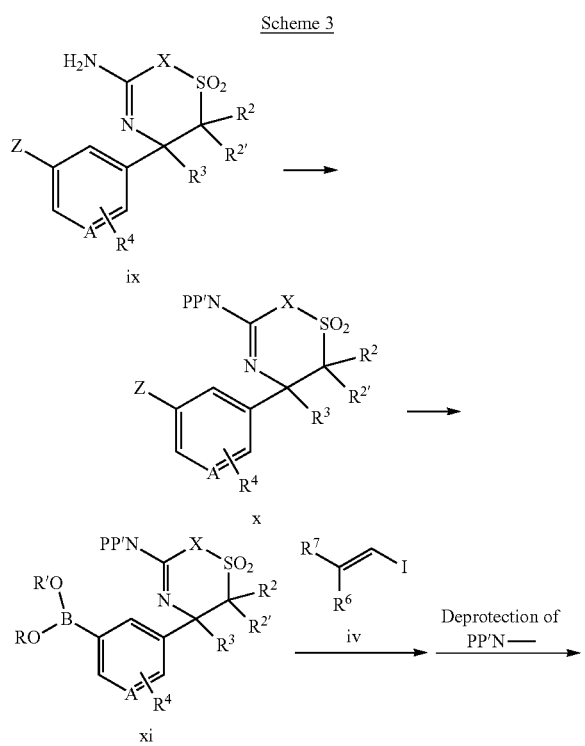

Scheme 4

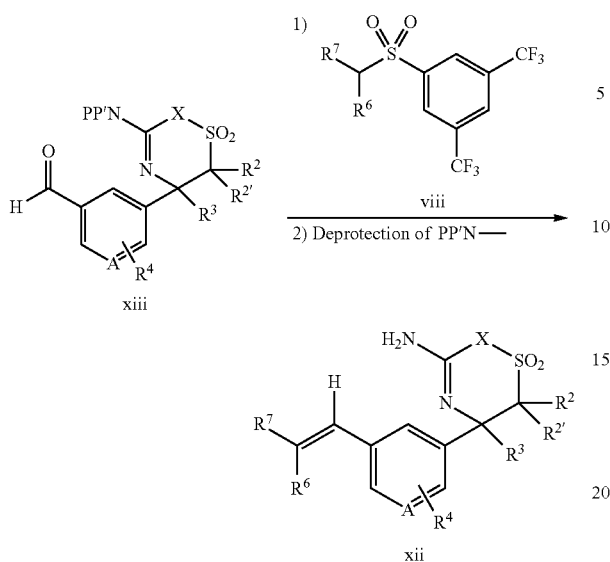

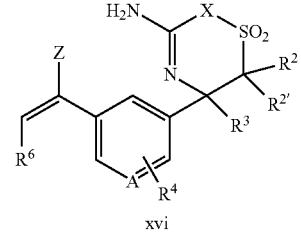

The final compound xii, wherein one of $R^6$ and $R^7$ is either H or F, may be synthesized as shown in Scheme 4. First, the free amino group of compound ix, wherein X is Cl, Br, or I, is suitably protected, for example by reaction with benzoic anhydride in presence of a base, such as trimethylamine. The suitably protected bromide x is then transformed into alkene xiii by reacting compound x with, for example, potassium vinyltrifluoroborate in presence of a base, such as potassium acetate, and a suitable palladium catalyst, such as bis(di-tert-butyl(4-dimethylaminophenyl)phosphine)-dichloropalladium(II). Aldehyde xiv is obtained by subjecting alkene xiii to oxidizing conditions using, for example osmiumtetroxide, 4-methylmorpholine-N-oxide, and potassium periodate. Aldehyde xiv is then reacted with compound viii in presence of a base, such as lithium bis(trimethylsilyl)amide, followed by conditions removing the protecting group(s) from the amino group using, for example, 1,8-diazabicyclo[5.4.0]undec-7-ene (DBU), if a benzoyl protecting strategy was employed, giving final compound xii.

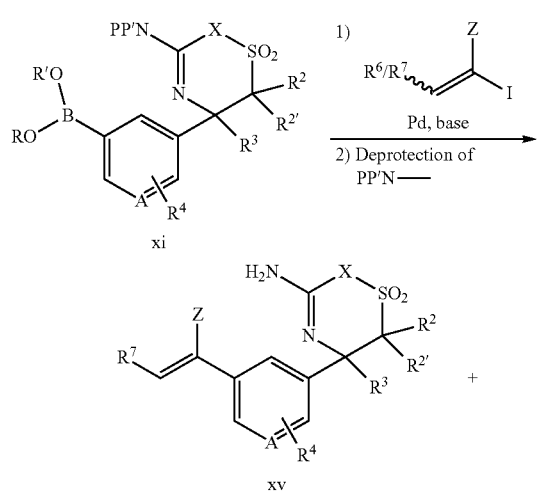

The final compounds xv and xvi, wherein Z is H or F, may be synthesized as shown in Scheme 5. The suitably protected compound xi is the coupled to a suitable vinyl iodide, wherein Z is F or H, for example, in presence of a base, such as potassium acetate, and a suitable palladium catalyst, such as bis(di-tert-butyl(4-dimethylaminophenyl)phosphine)-dichloropalladium(II). Following conditions removing the protecting group(s) from the amino group using, for example, 1,8-diazabicyclo[5.4.0]undec-7-ene (DBU), if a benzoyl protecting strategy was employed, final compound(s) xv and/or xvi may be obtained.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds disclosed herein, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependent on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize the compounds provided herein include, but are not limited to, water; esters, including lower alkyl-lower alkanoates, for example, EtOAc; ethers including aliphatic ethers, for example, Et$_2$O and ethylene glycol dimethylether or cyclic ethers, for example, THF; liquid aromatic hydrocarbons, for example, benzene, toluene and xylene; alcohols, for example, MeOH, EtOH, 1-propanol, iPrOH, n- and t-butanol; nitriles, for example, CH$_3$CN; halogenated hydrocarbons, for example, CH$_2$Cl$_2$, CHCl$_3$ and CCl$_4$; acid amides, for example, DMF; sulfoxides, for example, DMSO; bases, including heterocyclic nitrogen bases, for example, pyridine; carboxylic acids, for example, lower alkanecarboxylic acids, for example, AcOH; inorganic acids, for example, HCl, HBr, HF, and H$_2$SO$_4$; carboxylic acid anhydrides, for example, lower alkane acid anhydrides, for example, acetic anhydride; cyclic, linear, or branched hydrocarbons, for example, cyclohexane, hexane, pentane, and isopentane; and mixtures of any of these solvents, such as purely organic solvent combinations, or water-containing solvent combinations, for example, aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (for example, liquid and gas phase), extraction, distillation, trituration, and reverse phase HPLC. Reactions conditions such as temperature, duration, pressure, and atmosphere (inert gas, ambient) are known in the art and may be adjusted as appropriate for the reaction.

The disclosure further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the scope of this disclosure.

Further, processes for making and further reacting these intermediates are also understood to be encompassed in the scope of this disclosure.

Also provided herein are new starting materials and/or intermediates, as well as processes for the preparation thereof. In select embodiments, such starting materials are used and reaction conditions so selected as to obtain the desired compound(s). Starting materials are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

EXAMPLES

This section provides specific examples of compounds of Formula I and methods of making the same.

LIST OF ABBREVIATIONS

TABLE 1

| | |
|---|---|
| ACN | acetonitrile |
| AIBN | azobisisobutyronitrile |
| Boc | tert-butoxycarbonyl |
| (BOC)$_2$O | di-tert-butyl dicarbonate |
| (Bpin)$_2$ | bis(pinacolato)diboron |
| DAST | diethylaminosulfur trifluoride |
| DCE | dichloroethane |
| DCM | dichloromethane |
| DEAD | diethyl azodicarboxylate |
| DIPEA | N,N-diisopropylethylamine |
| DMA | dimethylacetamide |
| DMAP | 4-Dimethylaminopyridine |
| DMF | dimethylformamide |
| DMSO | dimethylsulfoxide |
| dppf | 1,1'-ferrocenediyl-bis(diphenylphosphine) |
| LDA | lithium diisopropylamide |
| LiHMDS | lithium bis(trimethylsilyl)amide |
| mCPBA | 3-chloroperoxybenzoic acid |
| MSA | methanesulfonic acid |
| MsCl | methanesulfonyl chloride |
| MTBE | methyl tert-butyl ether |
| NCS | n-chlorosuccinimide |
| NFSI | N-fluorodi(benzenesulfonyl)amine |
| NMO | N-methylmorpholine-N-Oxide |
| Pd(Amphos)Cl$_2$ | Bis(di-tert-butyl(4-dimethylaminophenyl)phosphine)dichloropalladium(II) |
| Pd$_2$(dba)$_3$ | Palladium(0) bis(dibenzylideneacetone) |
| Pd(dppf)Cl$_2$ | [1,1'-Bis(diphenylphosphino)ferrocene]dichloropalladium(II) |
| PMB | p-methoxybenzyl |
| pTSA | p-toluenesulfonic acid |
| pyr | pyridine |

TABLE 1-continued

| | |
|---|---|
| RT | room temperature |
| SEM | 2-(Trimethylsilyl)ethoxymethyl |
| SFC | supercritical fluid chromatography |
| s-Phos | 2-Dicyclohexylphosphino-2',6'-dimethoxybiphenyl |
| TBDMS | tert-butyldimethylsilyl |
| TEA | triethylamine |
| TFA | trifluoroacetic acid |
| TFAA | trifluoroacetic anhydride |
| Tf2O | trifluoromethanesulfonic anhydride |
| THF | tetrahydrofuran |
| TLC | thin layer chromatography |
| TMPH | 3,4,7,8-tetramethyl-1,10-phenanthroline |
| TMSCl | trimethylsilylchloride |
| x-phos | 2-Dicyclohexylphosphino-2',4',6'-triisopropylbiphenyl |

General Analytical and Purification Methods

Provided in this section are descriptions of the general analytical and purification methods used to prepare the specific compounds provided herein.

Chromatography:

Unless otherwise indicated, crude product-containing residues were purified by passing the crude material or concentrate through either a Biotage or Isco brand silica gel column (pre-packed or individually packed with $SiO_2$) and eluting the product off the column with a solvent gradient as indicated. For example a description of (330 g $SiO_2$, 0-40% EtOAc/hexane) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 mL/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were collected on a Bruker NMR instrument at 300 MHz or 400 MHz. Where so characterized, all observed protons are reported as parts-per-million (ppm) downfield from tetramethylsilane (TMS) or other internal reference in the appropriate solvent indicated.

$^{19}$F NMR Spectra:

Unless otherwise indicated, all $^{19}$F NMR spectra were collected on a Bruker NMR instrument at 376 MHz. All observed protons are reported as parts-per-million (ppm) downfield.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

Compound Names

The compounds disclosed and described herein have been named using either (1) the naming convention provided with Chem-Draw Ultra 12.0.3. software, available in Chem Office, or (2) by the ISIS database software (Advanced Chemistry Design Labs or ACD software).

Specific Examples

Provided in this section are the procedures to synthesize specific examples of the compounds provided herein. All starting materials are either commercially available from Sigma-Aldrich Chemical Company, Inc., St. Louis, Mo., USA, unless otherwise noted, or known in the art and may be synthesized by employing known procedures using ordinary skill.

Intermediates

Intermediate 1:
(Z)-6-(1-fluoro-2-iodovinyl)nicotinonitrile

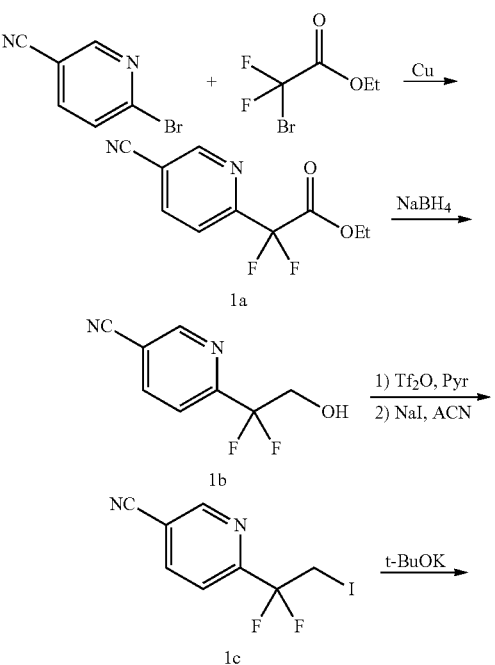

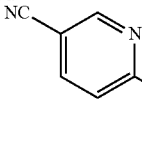

1

Preparation of ethyl 2-(5-cyanopyridin-2-yl)-2,2-difluoroacetate (1a)

To a suspension of copper (0) powder (Spectrochem PVT. LTD., Mumbai, India) (413 g, 6557 mmol) in dimethyl sulfoxide (6 L) was added ethyl 2-bromo-2,2-difluoroacetate (Matrix Scientific, Columbia, S.C., USA) (665 g, 3279 mmol) dropwise under nitrogen atmosphere at RT. The reaction mixture was stirred at RT for 1 h and 2-bromo-5-cyanopyridine (Sigma-Aldrich, St. Louis, Mo., USA) (300 g, 1639 mmol) was added portion-wise. The reaction mixture was stirred at RT for 12 h. It was filtered through a pad of celite and the filtrate was partitioned between ethyl acetate (3 L) and sat'd aqueous ammonium chloride (2.5 mL) solution. The organic layer was separated and the aqueous layer was extracted with ethyl acetate (2×2 L). The combined organic layers were washed with water (2×2 L), dried over $Na_2SO_4$ and concentrated under reduced pressure. The residue was purified by silica gel column chromatography (0-10% ethyl acetate in hexanes) to give 1a (320 g, 86% yield) as a colorless oil. MS (ESI +ve ion) m/z: [M+1]=227.1. $^1$H NMR (400 MHz, CDCl$_3$) δ 8.93 (d, J=2.0 Hz, 1H), 8.18 (dd, J=8.2, 2.1 Hz, 1H), 7.90 (dd, J=8.1, 1.0 Hz, 1H), 4.39 (q, J=7.1 Hz, 2H), 1.34 (t, J=7.1 Hz, 3H).

Preparation of 6-(1,1-difluoro-2-hydroxyethyl)nicotinonitrile (1b)

To a solution of 1a (105 g, 464 mmol) in THF (1.5 L) was added sodium borohydride (10.5 g, 279 mmol) portion-wise at −20° C. The reaction mixture was stirred at −20° C. for 30 min and methanol (525 mL) was added dropwise at −20° C. The reaction mixture was stirred at −20° C. for 1 h, then quenched with water (500 mL). It was concentrated under reduced pressure. The residue was diluted with water (0.5 L) and extracted with ethyl acetate (2×1 L). The combined organic solution was dried over $Na_2SO_4$ and concentrated. The residue was purified by silica gel column chromatography (0-25% ethyl acetate in hexanes) to provide 1b (43.0 g, 50% yield) as a light-yellow solid. MS (ESI +ve ion) m/z: [M+1]=185.1. $^1$H NMR (400 MHz, CDCl$_3$) δ 8.97-8.90 (m, 1H), 8.18 (dd, J=8.2, 2.1 Hz, 1H), 7.89 (dd, J=8.3, 0.9 Hz, 1H), 4.29 (t, J=12.4 Hz, 2H). Note: OH proton was not observed.

Preparation of 6-(1,1-difluoro-2-iodoethyl)nicotinonitrile (1c)

To a solution of 1b (87 g, 472 mmol) in acetonitrile (1.3 L) was added pyridine (74.7 g, 945 mmol) followed by dropwise addition of trifluoromethanesulfonic anhydride (Sigma-Aldrich, St. Louis, Mo., USA) (240 g, 850 mmol) at −10° C. under nitrogen atmosphere. The reaction mixture was stirred at RT for 5 h. It was cooled to 0° C. and sodium iodide (354 g, 2362 mmol) was added portion-wise. The reaction mixture was heated at 60° C. for 2 h. It was cooled to RT, diluted with water (2 L) and extracted with ethyl acetate (3×3 L). The combined organic solution was dried over $Na_2SO_4$ and concentrated under reduced pressure. The crude material was purified on a silica gel column (0-10% ethyl acetate in hexanes) to afford 1c (107 g, 77% yield) as a light-yellow solid. MS (ESI +ve ion) m/z: [M+1]=295.0. $^1$H NMR (400 MHz, CDCl$_3$) δ 8.95 (s, 1H), 8.17-8.14 (m, 1H), 7.87-7.85 (d, J=8.0 Hz, 1H), 3.97 (t, J=14.4 Hz, 2H).

Preparation of (Z)-6-(1-fluoro-2-iodovinyl)nicotinonitrile (1)

To a solution of 1c (58 g, 197 mmol) in THF (580 mL) was added potassium t-butoxide (26.6 g, 237 mmol) portion-wise at 0° C. The reaction mixture was stirred at 0° C. for 2 h, and quenched with sat'd aqueous NH$_4$Cl (100 mL) and water (100 mL). It was extracted with ethyl acetate (3×700 mL). The combined organic extracts were dried over $Na_2SO_4$ and concentrated. Purification of the residue by silica gel chromatography (1 to 5% ethyl acetate in hexanes) gave (Z)-6-(1-fluoro-2-iodovinyl)nicotinonitrile (1) (33 g, 61% yield) as a light yellow solid. MS (ESI +ve ion) m/z: [M+1]=274.9. $^1$H NMR (400 MHz, DMSO-d$_6$) δ 9.04 (dd, J=2.1, 1.0 Hz, 1H), 8.45 (dd, J=8.3, 2.1 Hz, 1H), 7.81 (dt, J=8.3, 1.1 Hz, 1H), 7.42 (d, J=36.4 Hz, 1H).

Intermediate 2: (Z)-5-fluoro-2-(1-fluoro-2-iodovinyl)pyridine

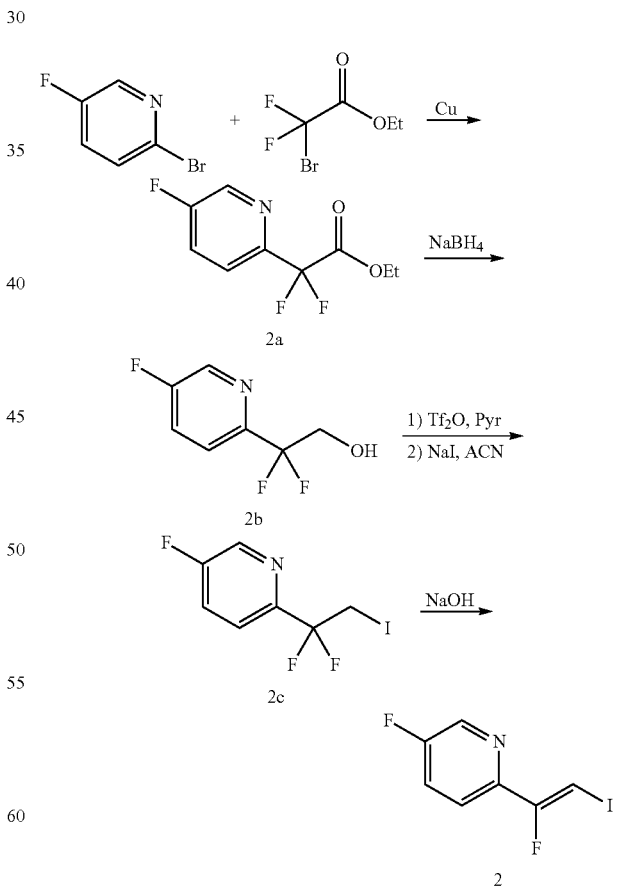

Ethyl 2,2-difluoro-2-(5-fluoropyridin-2-yl)acetate (2a, 44.8 g, 80% yield) as a viscous colorless liquid was prepared in a fashion similar to that described for 1a, starting from ethyl 2-bromo-2,2-difluoroacetate (104 g, 511 mmol) and 2-bromo-5-fluoropyridine (Shanghai Fchemicals Technology Co., Ltd., Shanghai, China) (45 g, 256 mmol). MS (ESI +ve ion) m/z: [M+1]=220.2. $^1$H NMR (400 MHz, DMSO-d$_6$) δ 8.73 (d, J=2.5 Hz, 1H), 8.05-7.95 (m, 2H), 4.34 (dd, J=7.2, 5.2 Hz, 2H), 1.23 (t, J=7.2 Hz, 3H).

2,2-Difluoro-2-(5-fluoropyridin-2-yl)ethanol (2b) (25 g, 69% yield) as a colorless liquid was prepared in a fashion similar to that described for 1b, starting from 2a (45 g, 205 mmol). MS (ESI +ve ion) m/z: [M+1]=178.2. $^1$H NMR (400 MHz, DMSO-d$_6$) δ 8.69 (d, J=2.8 Hz, 1H), 7.90 (td, J=8.7, 2.8 Hz, 1H), 7.78 (dd, J=8.7, 4.3 Hz, 1H), 5.56 (td, J=6.4, 1.3 Hz, 1H), 4.03-3.96 (m, 2H).

2-(1,1-difluoro-2-iodoethyl)-5-fluoropyridine (2c, 25 g, 62% yield) as a yellow solid was prepared in a fashion similar to that described for 1c, starting from 2b (25 g, 141 mmol). MS (ESI +ve ion) m/z: [M+1]=288.0. $^1$H NMR (400 MHz, DMSO-d$_6$) δ 8.73 (d, J=2.7 Hz, 1H), 7.96 (td, J=8.7, 2.8 Hz, 1H), 7.88-7.82 (m, 1H), 4.08-3.98 (m, 2H).

To a solution of 2-(1,1-difluoro-2-iodoethyl)-5-fluoropyridine (2c, 25 g, 87 mmol) in DMSO (200 mL) was added 5.0 M aqueous NaOH solution (30 mL, 150 mmol) dropwise at 0° C. The reaction mixture was stirred at 0° C. for 2 h, and quenched with water (100 mL). It was extracted with ethyl acetate (2×200 mL). The combined organic layers were washed with brine (200 mL), dried over Na$_2$SO$_4$ and concentrated. Purification of the residue by silica gel chromatography (0-5% ethyl acetate in hexanes) provided (Z)-5-fluoro-2-(1-fluoro-2-iodovinyl)pyridine (2) (18 g, 77% yield) as a clear oil. MS (ESI +ve ion) m/z: [M+1]=268.0. $^1$H NMR (400 MHz, DMSO-d$_6$) δ 8.64 (d, J=2.9 Hz, 1H), 7.86 (m, 1H), 7.72 (ddt, J=8.4, 3.8, 1.9 Hz, 1H), 7.02 (dd, J=36.7, 1.9 Hz, 1H).

Intermediate 3: (Z)-5-chloro-2-(1-fluoro-2-iodovinyl)pyridine

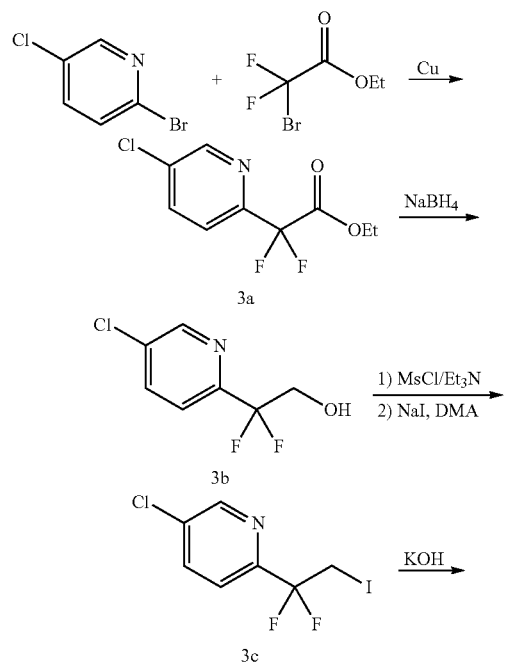

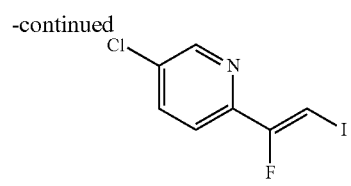

Preparation of ethyl 2-(5-chloropyridin-2-yl)-2,2-difluoroacetate (3a)

Ethyl 2-bromo-2,2-difluoroacetate (105 g, 520 mmol) was added slowly to a suspension of copper (0) powder (66.0 g, 1039 mmol) in DMSO (1.2 L) under nitrogen atmosphere at RT. The reaction mixture was stirred at RT for 1 h and 2-bromo-5-chloropyridine (Shanghai Fchemicals Technology Co., Ltd., Shanghai, China) (50.0 g, 260 mmol) was added in one portion. The reaction mixture was stirred at RT for 12 h. It was filtered through a pad of celite and the filtrate was partitioned between ethyl acetate (1 L) and sat'd aqueous ammonium chloride (100 mL) and water (100 mL). The organic layer was separated and the aqueous layer was extracted with ethyl acetate (2×100 mL). The combined organic solution was washed with water (2×100 mL), dried over Na$_2$SO$_4$ and concentrated. Purification of the residue by silica gel chromatography (0-10% ethyl acetate in hexanes) gave 3a (60 g, 64% yield) as a clear liquid. MS (ESI +ve ion) m/z: [M+1]=236.0. $^1$H NMR (400 MHz, Chloroform-d) δ 8.63-8.59 (m, 1H), 7.85 (dt, J=8.4, 1.6 Hz, 1H), 7.70 (dt, J=8.4, 0.9 Hz, 1H), 4.11 (q, J=7.1, 1.0 Hz, 2H), 1.26 (t, J=7.1, 1.0 Hz, 3H).

Preparation of 2-(5-chloropyridin-2-yl)-2,2-difluoroethan-1-ol (3b)

To a solution of 3a (47.0 g, 199 mmol) in ethanol (600 mL) at 0° C. was added sodium borohydride (7.5 g, 199 mmol) portion-wise. The reaction mixture was stirred at RT for 1 h. It was quenched with water (500 mL) and concentrated under reduced pressure. The crude material was diluted with water (500 mL) and extracted with ethyl acetate (2×500 mL). The combined organic extracts were dried over Na$_2$SO$_4$ and concentrated. Purification of the residue by silica gel chromatography (0-10% ethyl acetate in hexanes) gave 3b (35 g, 91% yield) as a light yellow solid. MS (ESI +ve ion) m/z: [M+1]=194.2. $^1$H NMR (400 MHz, Chloroform-d) δ 8.64-8.58 (m, 1H), 7.86 (dd, J=8.4, 2.4 Hz, 1H), 7.70 (dt, J=8.5, 1.5 Hz, 1H), 4.24 (t, J=12.4 Hz, 2H). Note: OH proton not observed.

Preparation of 5-chloro-2-(1,1-difluoro-2-iodoethyl)pyridine (3c)

To a solution of 3b (31 g, 160 mmol) in DCM (500 mL) at 0° C. was added triethylamine (49.1 mL, 352 mmol) followed by dropwise addition of methanesulfonyl chloride (23.7 mL, 304 mmol). The reaction mixture was stirred at RT for 1 h. The reaction mixture was diluted with water (500 mL) and extracted with DCM (2×500 mL). The combined organic extracts were washed with brine (250 mL), dried over Na$_2$SO$_4$ and concentrated under reduced pressure. The residue was dissolved in N,N-dimethyl acetamide (600 mL) and sodium iodide (96 g, 641 mol) was added in portion-wise. The reaction mixture was heated at 110° C. for 36 h.

It was cooled to RT, diluted with water (500 mL), and extracted with ethyl acetate (2×500 mL). The combined organic layers were washed with brine (500 mL), dried over $Na_2SO_4$ and concentrated under reduced pressure. The residue was purified by silica gel chromatography (0-10% ethyl acetate in hexanes) to give 3c (30 g, 60% yield) as a brown solid. MS (ESI +ve ion) m/z: [M+1]=303.9. $^1$H NMR (400 MHz, Chloroform-d) δ 8.59 (s, 1H), 7.87-7.84 (m, 1H), 7.27 (d, J=2.0 Hz, 1H), 4.27 (t, J=12.4 Hz, 2H).

Preparation of (Z)-5-chloro-2-(1-fluoro-2-iodovinyl)pyridine (3)

To a solution of 3c (30 g, 99 mmol) in DMSO (50 mL, 1.66 mL/g) was added a solution of KOH (19.4 g, 346 mmol) in water (50 mL) dropwise at 0° C. The reaction mixture was stirred at RT for 10 h. It was diluted with water (150 mL) and stirred for 15 min. The precipitated solids were collected by filtration, washed with water (2×100 mL), and dried to afford (Z)-5-chloro-2-(1-fluoro-2-iodovinyl)pyridine (24.7 g, 87% yield) as a white crystalline solid. MS (ESI +ve ion) m/z: [M+1]=284.0. $^1$H NMR (400 MHz, Chloroform-d) δ 8.54-8.51 (m, 1H), 7.74 (dd, J=8.5, 2.4 Hz, 1H), 7.50 (ddd, J=8.5, 1.8, 0.8 Hz, 1H), 6.94 (d, J=34.3 Hz, 1H).

Intermediate 4: (Z)-5-bromo-2-(1-fluoro-2-iodovinyl)pyridine (Shanghai Fchemicals Technology Co., Ltd., Shanghai, China) (100 g, 422 mmol) and ethyl bromodifluoroacetate (171 g, 844 mmol). MS (ESI +ve ion) m/z: [M+1]=280/282. $^1$H NMR (400 MHz, Chloroform-d) δ 8.73-8.72 (d, J=2.4 Hz, 1H), 8.40-8.00 (q, J=2.4 Hz, 1H), 7.67-7.65 (d, J=8.4 Hz, 1H), 4.42 (q, J=5.2 Hz, 2H), 1.39-1.33 (t, J=7.2 Hz, 3H).

Compounds 4b, 4c, and 4 were synthesized in a fashion similar to that described for 5b, 5c, and 5, respectively. 2-(5-Bromopyridin-2-yl)-2,2-difluoroethanol (4b): MS (ESI +ve ion) m/z: [M+1]=238/240. $^1$H NMR (400 MHz, Chloroform-d) δ 8.71 (q, J=1.1 Hz, 1H), 8.02 (dt, J=8.4, 1.8 Hz, 1H), 7.65 (dt, J=8.6, 1.0 Hz, 1H), 4.25 (td, J=12.4, 1.4 Hz, 2H). —OH proton was not observed. 5-Bromo-2-(1,1-difluoro-2-iodoethyl)pyridine (4c): MS (ESI +ve ion) m/z: [M+1]=348/350. $^1$H NMR (400 MHz, Chloroform-d) δ 8.76-8.72 (m, 1H), 7.99 (dd, J=8.4, 2.3 Hz, 1H), 7.61 (dd, J=8.4, 0.8 Hz, 1H), 3.92 (t, J=14.6 Hz, 2H). (Z)-5-Bromo-2-(1-fluoro-2-iodovinyl)pyridine (4): MS (ESI +ve ion) m/z: [M+1]=328/330. $^1$H NMR (400 MHz, Chloroform-d) δ 8.62 (dd, J=2.1, 1.1 Hz, 1H), 7.88 (dd, J=8.4, 2.3 Hz, 1H), 7.43 (m, 1H), 6.95 (d, J=34.2 Hz, 1H).

Intermediate 5: (Z)-2-(1-fluoro-2-iodovinyl)-5-(trifluoromethyl)pyridine

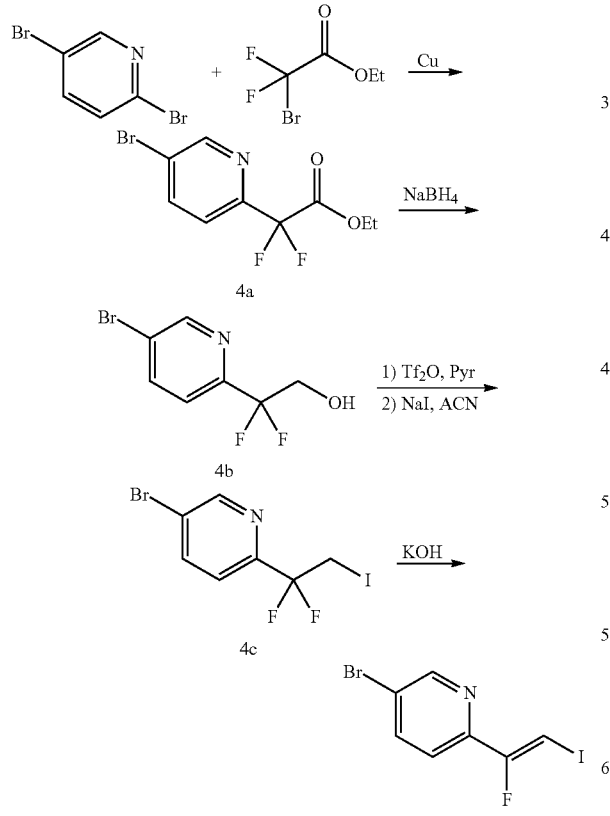

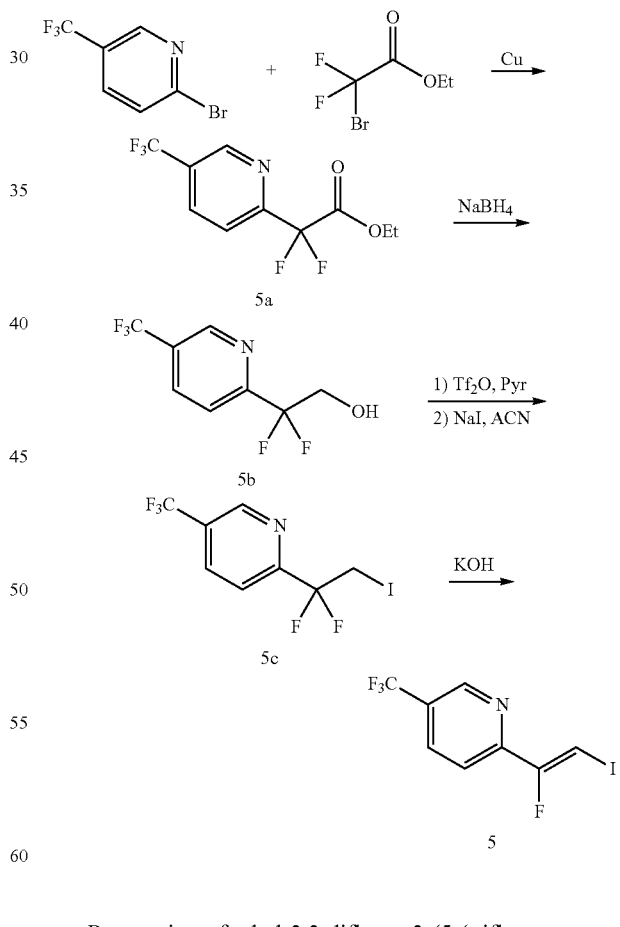

Ethyl 2-(5-bromopyridin-2-yl)-2,2-difluoroacetate (4a, 80 g, 68% yield) as a colorless oil was synthesized using the protocol described for 5a, starting from 2,5-dibromopyridine Preparation of ethyl 2,2-difluoro-2-(5-(trifluoromethyl)pyridin-2-yl)acetate (5a)

To a suspension of copper (0) powder (229 g, 1128 mmol) in DMSO (1.7 L) was added ethyl 2-bromo-2,2-difluoroacetate (47.9 g, 752 mmol) at RT. The reaction mixture was stirred at RT for 1 h and 2-bromo-5-(trifluoromethyl)pyridine (Arborchem, Mechanicsburg, Pa., USA) (85 g, 376 mmol) was added in portion-wise manner. The reaction mixture was stirred at RT for 12 h, then quenched with sat'd ammonium chloride (250 mL). The reaction mixture was filtered through a celite pad and the filtrate was extracted with ethyl acetate (3×350 mL). The combined organic solution was dried over $Na_2SO_4$ and concentrated under reduced pressure. The crude residue was purified by silica gel chromatography (0-2% ethyl acetate in hexanes) to provide 5a (65 g, 64% yield). MS (ESI, positive ion) m/z: 270.1 (M+1). $^1$H NMR (400 MHz, Chloroform-d) δ 8.94 (d, J=1.7 Hz, 1H), 8.14 (dd, J=8.2, 2.2 Hz, 1H), 7.91 (d, J=8.3 Hz, 1H), 4.46-4.33 (m, 2H), 1.45-1.26 (m, 3H).

Preparation of 2,2-difluoro-2-(5-(trifluoromethyl)pyridin-2-yl)ethanol (5b)

To a solution of 5a (62 g, 230 mmol) in ethanol (620 mL) at 0° C. was added sodium borohydride (8.7 g, 230 mmol) portion-wise. The reaction mixture was stirred for 30 minutes at 0° C., then quenched with water (100 mL) and extracted with ethyl acetate (3×250 mL). The combined organic solution was dried over $Na_2SO_4$ and concentrated under reduced pressure. The crude residue was purified by silica gel chromatography (2-10% ethyl acetate in hexanes) to provide 5b (45 g, 86% yield) as a colorless liquid. MS (ESI, positive ion) m/z: 228.1 (M+1). $^1$H NMR (400 MHz, Chloroform-d) δ 9.01-8.88 (m, 1H), 8.15 (dd, J=8.3, 2.2 Hz, 1H), 7.90 (d, J=8.2 Hz, 1H), 4.30 (td, J=12.4, 7.2 Hz, 2H), 2.81 (t, J=7.2 Hz, 1H).

Preparation of 2-(1,1-difluoro-2-iodoethyl)-5-(trifluoromethyl)pyridine (5c)

To a solution of 5b (45 g, 198 mmol) in acetonitrile (450 mL) at 0° C. was added pyridine (32.0 mL, 396 mmol) followed by drop-wise addition of trifluoromethane sulfonic anhydride (50.2 mL, 297 mmol). The reaction mixture was stirred at 0° C. for 30 min. Sodium iodide (89 g, 594 mmol) was added portion-wise to the reaction mixture at RT. The reaction mixture was stirred at 70° C. for 2 h. After the completion of the reaction (monitored by TLC), the reaction mixture was quenched with saturated sodium thiosulfate solution (250 mL) and extracted with ethyl acetate (3×250 mL). The combined organic layer was washed with brine, dried over $Na_2SO_4$ and concentrated under reduced pressure. The crude residue was purified by silica gel chromatography (0-2% ethyl acetate in hexanes) to afford 5c (45 g, 67% yield). MS (ESI, positive ion) m/z: 338.1 (M+1). $^1$H NMR (400 MHz, DMSO-$d_6$) δ 9.15 (s, 1H), 8.60-8.39 (m, 1H), 8.00 (d, J=8.2 Hz, 1H), 4.07 (t, J=16.2 Hz, 2H).

Preparation of (Z)-2-(1-fluoro-2-iodovinyl)-5-(trifluoromethyl)pyridine (5)

To a solution of 5c (50 g, 148 mmol) in DMSO (500 mL) was added dropwise a solution of sodium hydroxide (44.5 mL of 5 N solution, 223 mmol) at 0° C. The reaction mixture was stirred at 0° C. for 5 h, then quenched with water (100 mL) and extracted with ethyl acetate (3×250 mL). The combined organic layers were washed with brine (150 mL), dried over $Na_2SO_4$ and concentrated under reduced pressure. The crude residue was purified by silica gel chromatography (2-10% ethyl acetate in hexanes) to afford Intermediate 5 (40 g, 85% yield) as an off-white solid. MS (ESI, positive ion) m/z: 318.1 (M+1). $^1$H NMR (400 MHz, DMSO-$d_6$) δ 9.07-8.91 (m, 1H), 8.34 (dd, J=8.5, 2.3 Hz, 1H), 7.83 (d, J=8.3 Hz, 1H), 7.36 (d, J=36.5 Hz, 1H).

Intermediate 6: (Z)-2-(1-fluoro-2-iodovinyl)-5-(trifluoromethyl)pyridine

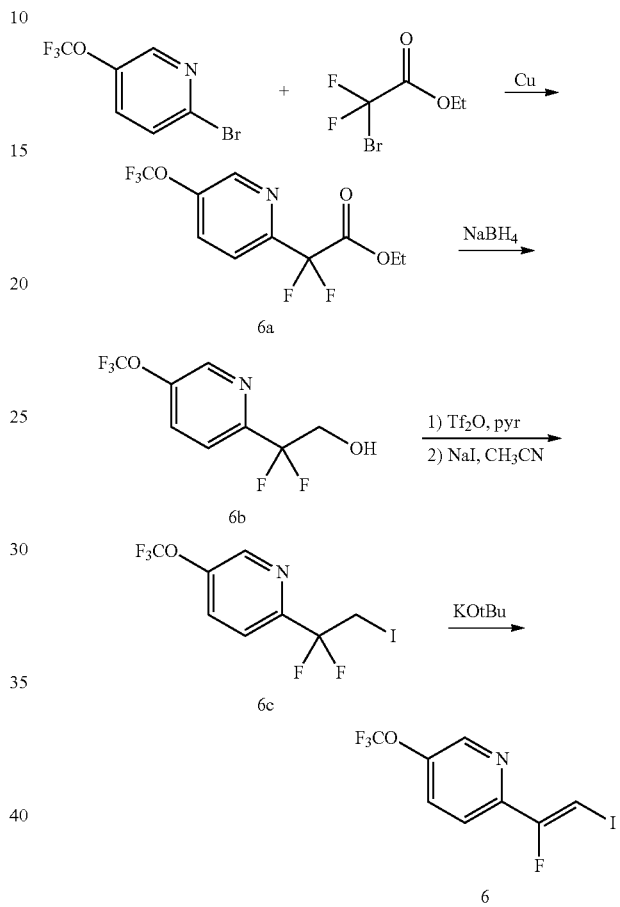

Ethyl 2,2-difluoro-2-(5-(trifluoromethoxy)pyridin-2-yl)acetate (6a, 2.61 g, 9.15 mmol, 87% yield) as a colorless oil was synthesized using the protocol described for 1a, starting from 2-bromo-5-(trifluoromethoxy)pyridine (Shanghai Fchemicals Technology Co., Ltd., Shanghai, China) (2.54 mL, 10.50 mmol) and ethyl bromodifluoroacetate (1.48 mL, 11.55 mmol). MS (ESI +ve ion) m/z: [M+1]=286.2.

Compounds 6b, 6c, and 6 were synthesized in a fashion similar to that described for 1b, 1c, and 1, respectively. 2,2-Difluoro-2-(5-(trifluoromethoxy)pyridin-2-yl)ethanol (6b): MS (ESI +ve ion) m/z: [M+1]=244.1. 2-(1,1-Difluoro-2-iodoethyl)-5-(trifluoromethoxy)pyridine (6c): MS (ESI +ve ion) m/z: [M+1]=353.9. $^1$H NMR (400 MHz, DMSO-$d_6$) δ 8.82 (d, J=2.15 Hz, 1H), 8.13 (m, 1H), 7.92 (d, J=8.80 Hz, 1H), 4.04 (t, J=16.14 Hz, 2H). (Z)-2-(1-Fluoro-2-iodovinyl)-5-(trifluoromethoxy)pyridine (6): MS (ESI +ve ion) m/z: [M+1]=334.0. $^1$H NMR (400 MHz, DMSO-$d_6$) δ 8.71 (s, 1H), 8.02 (m, 1H), 7.78 (d, J=8.61 Hz, 1H), 7.16 (d, J=37.44 Hz, 1H). $^{19}$F NMR (376 MHz, DMSO-$d_6$) δ −57.16 (s, 3F), −99.23 (s, 1F).

Intermediate 7: (Z)-6-(1-fluoro-2-iodovinyl)-5-methylnicotinonitrile

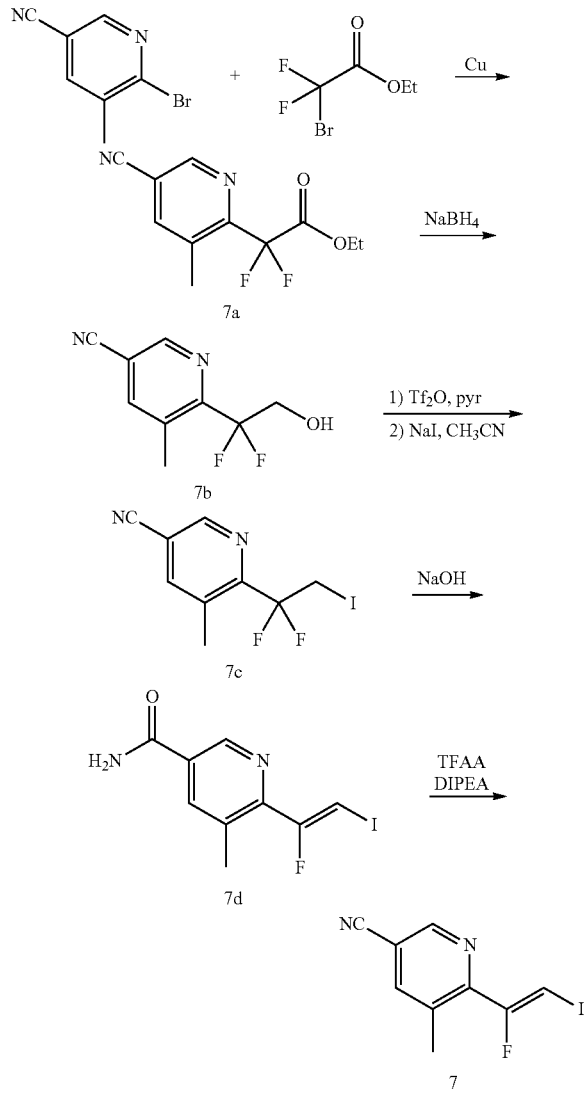

Ethyl 2-(5-cyano-3-methylpyridin-2-yl)-2,2-difluoroacetate (7a, 58 g, 59% yield) as a transparent oil was synthesized using the protocol described for 5a, starting from 2,5-dibromopyridine (Shanghai Fchemicals Technology Co., Ltd., Shanghai, China) (80 g, 406 mmol) and ethyl bromodifluoroacetate (165 g, 812 mmol). MS (ESI +ve ion) m/z: [M+1]=241.0. $^1$H NMR (400 MHz, Chloroform-d) δ 8.68 (d, J=4.1 Hz, 1H), 7.93 (d, J=2.1 Hz, 1H), 4.46 (q, J=7.1 Hz, 2H), 2.63 (q, J=2.5 Hz, 3H), 1.41-1.34 (m, 3H).

Compounds 7b and 7c were synthesized in a fashion similar to that described for 5b and 5c, respectively. 6-(1,1-Difluoro-2-hydroxyethyl)-5-methylnicotinonitrile (7b): MS (ESI +ve ion) m/z: [M+1]=199.1. $^1$H NMR (400 MHz, Chloroform-d) δ 8.68 (dd, J=2.1, 1.0 Hz, 1H), 7.95 (dd, J=1.8, 0.9 Hz, 1H), 4.31 (td, J=12.4, 7.5 Hz, 2H), 3.24 (t, J=7.6 Hz, 1H), 2.64 (t, J=2.6 Hz, 3H). —OH proton was not observed. 6-(1,1-Difluoro-2-iodoethyl)-5-methylnicotinonitrile (7c): MS (ESI +ve ion) m/z: [M+1]=309.2. $^1$H NMR (400 MHz, Chloroform-d) δ 8.70 (dd, J=1.8, 1.0 Hz, 1H), 7.90 (dd, J=1.9, 0.9 Hz, 1H), 4.06 (t, J=15.3 Hz, 2H), 2.62 (t, J=3.2 Hz, 3H).

Preparation of (Z)-6-(1-fluoro-2-iodovinyl)-5-methylnicotinamide (7d)

To a solution of 7c (25 g, 81 mmol) in DMSO (250 mL) at 0° C. was added NaOH (32.5 mL of 5 N solution, 162 mmol). The reaction mixture was stirred at 0° C. for 10 h, then quenched with water (250 mL) and extracted with ethyl acetate (2×500 mL). The combined organic solution was washed with brine (500 mL), dried over Na$_2$SO$_4$ and concentrated under reduced pressure. The crude residue was purified by silica gel chromatography (20-50% ethyl acetate in hexanes) to afford 7d (12 g, 48% yield) as an off-white solid. MS (ESI +ve ion) m/z: [M+1]=307.2. $^1$H NMR (300 MHz, DMSO-d$_6$) δ 8.85 (d, J=2.2 Hz, 1H), 8.22-8.13 (m, 2H), 7.67 (s, 1H), 6.87 (dd, J=36.4, 2.5 Hz, 1H), 2.43 (t, J=3.9 Hz, 3H).

Preparation of (Z)-6-(1-fluoro-2-iodovinyl)-5-methylnicotinonitrile (7)

To a solution of (Z)-6-(1-fluoro-2-iodovinyl)-5-methylnicotinonitrile (7) (12.0 g, 39.2 mmol) in THF (120 mL) at 0° C. was added DIPEA (34.2 mL, 196 mmol) followed by TFAA (27.7 mL, 196 mmol). The reaction mixture was stirred at 0° C. for 2 h, then quenched with water (500 mL) and extracted with ethyl acetate (2×500 mL). The combined organic solution was washed with brine (20 mL), dried over Na$_2$SO$_4$ and concentrated under reduced pressure. The crude residue was purified by silica gel chromatography (10% ethyl acetate in hexanes) to afford Intermediate 7 (10.5 g, 93% yield) as an off-white solid. MS (ESI +ve ion) m/z: [M+1]=No ionization. $^1$H NMR (400 MHz, DMSO-d$_6$) δ 8.87 (d, J=2.0 Hz, 1H), 8.31 (d, J=2.2 Hz, 1H), 7.13-6.93 (m, 1H), 2.42 (d, J=5.2 Hz, 3H).

Intermediate 8: (Z)-5-chloro-6-(1-fluoro-2-iodovinyl)nicotinonitrile

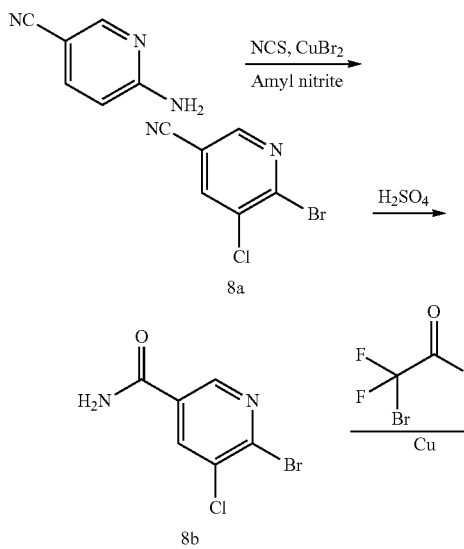

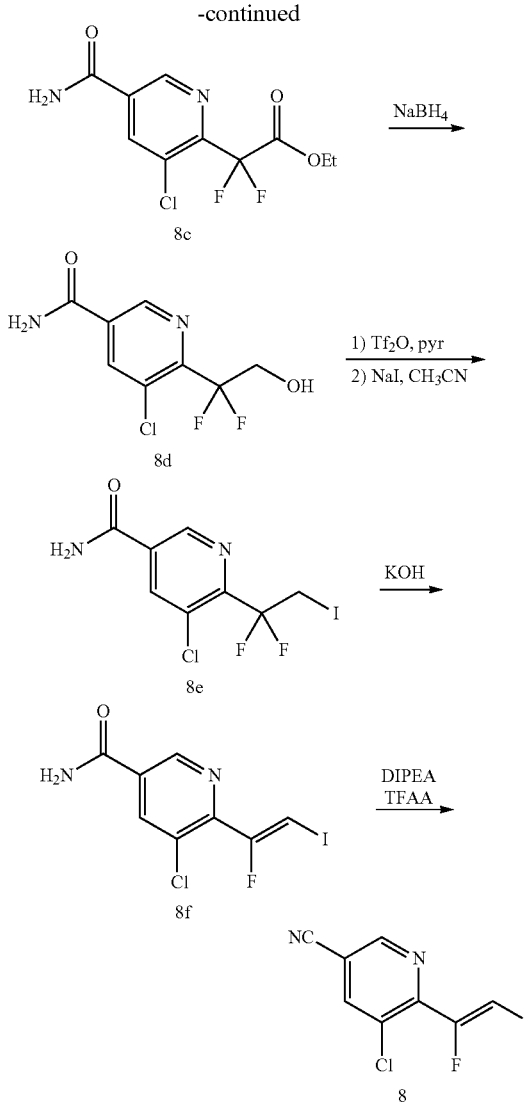

Preparation of 6-bromo-5-chloronicotinonitrile (8a)

A round bottom flask was charged with 6-aminonicotinonitrile (Arborchem, Mechanicsburg, Pa., USA) (100 g, 839 mmol), N-chlorosuccinimide (Sigma-Aldrich, St. Louis, Mo., USA) (123 g, 923 mmol), and acetonitrile (2 L). The reaction mixture was heated at 60° C. for 2 h. After cooling to RT, copper (II) bromide (Sigma-Aldrich, St. Louis, Mo., USA) (375 g, 1678 mmol) and isoamyl nitrite (Arborchem, Mechanicsburg, Pa., USA) (230 mL, 1678 mmol) were added and the mixture was heated to 65° C. for 2 h. It was cooled to RT and quenched with sat'd aqueous ammonium chloride solution (200 mL), extracted with DCM (3×500 mL). The combined organic solution was dried over $MgSO_4$ and concentrated. The crude material was purified by silica gel chromatography (10% EtOAc in hexanes) to provide 8a (63 g, 34% yield). MS (ESI, positive ion) m/z: no ionization. $^1$H NMR (400 MHz, Chloroform-d) δ 8.68-8.49 (m, 1H), 8.19-7.84 (m, 1H).

Preparation of 6-bromo-5-chloronicotinamide (8b)

A solution of 8a (63 g, 290 mmol) in sulfuric acid (154 mL) was stirred for 12 h at RT. The reaction mixture was cooled to 0° C. and quenched by the addition of ice water (500 mL). The mixture was stirred for 10 min and the solid thus obtained was filtered and dried under reduced pressure to 8b (60 g, 88% yield). MS (ESI, positive ion) m/z: 235.2 (M+1).

Preparation of ethyl 2-(5-carbamoyl-3-chloropyridin-2-yl)-2,2-difluoroacetate (8c)

To a solution of copper (0) powder (27.0 g, 425 mmol) in DMSO (250 mL) at RT was added ethyl 2-bromo-2,2-difluoroacetate (64.7 g, 319 mmol). The reaction mixture was stirred at RT for 1 h and treated with 8b (25 g, 106 mmol) was added portion-wise. The reaction mixture was stirred at RT for 12 h, and quenched with sat'd ammonium chloride (100 mL). The reaction mixture was filtered through a pad of celite. The filtrate was extracted with ethyl acetate (2×350 mL). The organic solution was dried over $Na_2SO_4$ and concentrated under reduced pressure. The crude residue was purified by silica gel chromatography (10-50% ethyl acetate in hexanes) to afford 8c (21 g, 71% yield). MS (ESI, positive ion) m/z: 279.4 (M+1). $^1$H NMR (400 MHz, Chloroform-d) δ 8.89 (d, J=1.9 Hz, 1H), 8.32 (d, J=1.9 Hz, 1H), 6.39 (d, J=72.1 Hz, 2H), 4.45 (q, J=7.1 Hz, 2H), 1.38 (t, J=7.2 Hz, 3H).

Preparation of 5-chloro-6-(1,1-difluoro-2-hydroxyethyl) nicotinamide (8d)

To a solution of 8c (21.00 g, 75 mmol) in THF (210 mL) at 0° C. was added sodium borohydride (2.85 g, 75 mmol) portion-wise followed by methanol (15.25 mL) dropwise. After completion of reaction (monitored by TLC), the reaction mixture was quenched with water (100 mL) and extracted with ethyl acetate. The combined organic extracts were dried over $Na_2SO_4$ and concentrated under reduced pressure. The crude residue was purified by silica gel chromatography (50% ethyl acetate in hexanes) to afford 8d (16 g, 90% yield). MS (ESI, positive ion) m/z: 237.0 (M+1). $^1$H NMR (300 MHz, DMSO-$d_6$) δ 8.99 (d, J=2.0 Hz, 1H), 8.43 (d, J=2.0 Hz, 1H), 8.35 (s, 1H), 7.89 (s, 1H), 5.62 (s, 1H), 4.12 (t, J=14.6 Hz, 2H).

Preparation of 5-chloro-6-(1,1-difluoro-2-iodoethyl) nicotinamide (8e)

To a solution of 8d (16.0 g, 67.6 mmol) in acetonitrile (160 mL) at −10° C. was added pyridine (10.9 mL, 135 mmol) followed by dropwise addition of trifluoromethane sulphonic anhydride (28.6 g, 101 mmol). The reaction mixture was stirred at 0° C. for 30 min then warmed to RT and sodium iodide (30.4 g, 203 mmol) was added in portion-wise manner. The reaction mixture was stirred at 70° C. for 2 h. After cooling to RT, it was quenched with sat'd aqueous sodium thiosulfate solution (300 mL) and extracted with ethyl acetate (2×350 mL). The combined organic solution was washed with brine (250 mL), dried over $Na_2SO_4$ and concentrated under reduced pressure. The crude residue was purified by silica gel chromatography (20-50% ethyl acetate in hexanes) to afford 8e (12. g, 51% yield). MS (ESI, positive ion) m/z: 347.1 (M+1). $^1$H NMR (400 MHz, DMSO-$d_6$) δ 9.00 (d, J=1.8 Hz, 1H), 8.47 (d, J=1.8 Hz, 1H), 8.37 (s, 1H), 7.91 (s, 1H), 4.14 (t, J=16.4 Hz, 2H).

Preparation of (Z)-5-chloro-6-(1-fluoro-2-iodovinyl) nicotinamide (8f)

To the solution of 8e (12 g, 34.6 mmol) in DMSO (120 mL) at 0° C. was added potassium hydroxide (10.39 mL of 5 M solution, 51.9 mmol). The reaction mixture was stirred at 0° C. for 5 h. The reaction mixture was quenched with water and extracted with ethyl acetate (3×250 mL). The combined organic solution was washed with brine (250 mL), dried over $Na_2SO_4$ and concentrated under reduced pressure. The crude residue was purified by silica gel chromatography (50% ethyl acetate in hexanes) to afford 8f (8.0 g, 71% yield). MS (ESI, positive ion) m/z: 327.2 (M+1). $^1$H NMR (300 MHz, DMSO-$d_6$) δ 8.97 (s, 1H), 8.41 (s, 1H), 8.32 (s, 1H), 7.85 (s, 1H), 7.05 (d, J=36.0 Hz, 1H).

Preparation of (Z)-5-chloro-6-(1-fluoro-2-iodovinyl)nicotinonitrile (8)

To a solution of 8f (8.0 g, 24.5 mmol) in THF (80 mL) at 0° C. was added drop N,N-diisopropylethylamine (15.8 g, 123 mmol) followed by trifluoroacetic anhydride (17.3 mL, 123 mmol). The reaction mixture was stirred at 0° C. for 2 h, then quenched with water (250 mL) and extracted with ethyl acetate (3×250 mL). The combined organic solution was washed with brine (250 mL), dried over $Na_2SO_4$ and concentrated under reduced pressure. The crude residue was purified by silica gel chromatography (2-10% ethyl acetate in hexanes) to afford intermediate 8 (6.0 g, 79% yield) as an off-white solid. MS (ESI, positive ion) m/z: no ionization. $^1$H NMR (400 MHz, Chloroform-d) δ 8.84-8.67 (m, 1H), 8.15-8.00 (m, 1H), 7.21-6.99 (m, 1H).

Intermediate 9: (Z)-3-chloro-2-(1-fluoro-2-iodovinyl)-5-(trifluoromethyl)pyridine Ethyl 2-(3-chloro-5-(trifluoromethyl)pyridin-2-yl)-2,2-difluoroacetate (9a, 90 g, 86% yield) as a colorless oil was synthesized using the protocol described for 5a, here starting from 2-bromo-3-chloro-5-(trifluoromethyl)pyridine (ChemPure Chemicals, Plymouth, Mich., USA) (90 g, 346 mmol) and ethyl bromodifluoroacetate (140 g, 691 mmol). MS (ESI +ve ion) m/z: [M+1]=304.1. $^1$H NMR (400 MHz, Chloroform-d) δ 8.80 (s, 1H), 8.09 (d, J=2.0 Hz, 1H), 4.47-4.41 (m, 2H), 1.39 (t, J=7.1 Hz, 3H).

Compounds 9b, 9c, and 9 were synthesized in a fashion similar to that described for 5b, 5c, and 5, respectively. 2-(3-Chloro-5-(trifluoromethyl)pyridin-2-yl)-2,2-difluoroethanol (9b): MS (ESI +ve ion) m/z: [M+1]=262.3. $^1$H NMR (400 MHz, Chloroform-d) δ 8.77 (d, J=2.0 Hz, 1H), 8.13 (d, J=2.0 Hz, 1H), 4.34 (m, 2H), 2.97 (t, J=7.7 Hz, 1H). 3-Chloro-2-(1,1-difluoro-2-iodoethyl)-5-(trifluoromethyl)pyridine (9c): MS (ESI +ve ion) m/z: [M+1]=372.0. $^1$H NMR (400 MHz, Chloroform-d) δ 8.80 (d, J=6.1 Hz, 1H), 8.10 (s, 1H), 4.05 (tdd, J=15.1, 4.2, 2.6 Hz, 2H). (Z)-3-chloro-2-(1-fluoro-2-iodovinyl)-5-(trifluoromethyl)pyridine (9): MS (ESI +ve ion) m/z: [M+1]=352.2. $^1$H NMR (400 MHz, DMSO-$d_6$) δ 9.00 (d, J=2.0 Hz, 1H), 8.62 (d, J=2.1 Hz, 1H), 7.22-7.05 (m, 1H).

Intermediate 10: (Z)-7-(1-fluoro-2-iodovinyl)-2,3-dihydro-[1,4]dioxino[2,3-c]pyridine

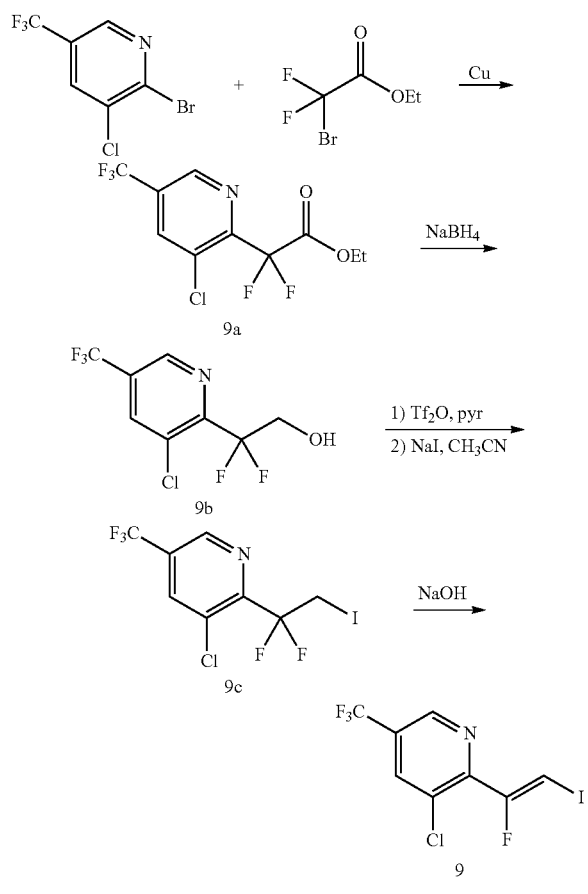

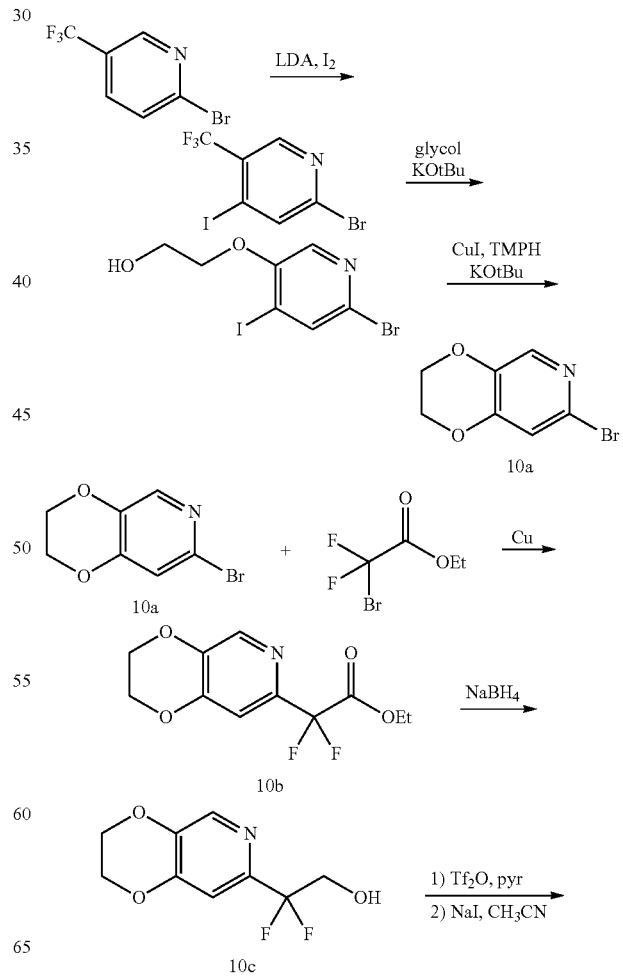

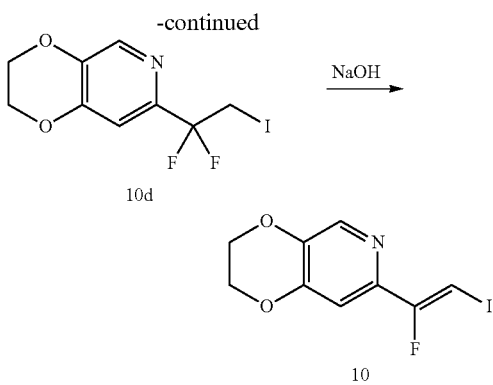

Preparation of 7-bromo-2,3-dihydro-[1,4]dioxino[2,3-c]pyridine (10a)

Diisopropylamine (3.5 mL, 24.9 mmol) was dissolved in tetrahydrofuran (50 mL) under nitrogen and cooled in a dry ice bath. n-Butyllithium solution (1.6 M in hexanes, 15 mL, 24.0 mmol) was added and the solution stirred for 10 min. A solution of 2-bromo-5-fluoropyridine (Matrix Scientific, Columbia, S.C., USA) (4.0 g, 22.7 mmol) in tetrahydrofuran (20 mL) was cooled in a −40° C. bath and slowly added to the LDA solution via cannula over 5 min, keeping the internal temperature below −65° C. The clear solution was stirred for another 75 min. A solution of iodine (Sigma-Aldrich, St. Louis, Mo., USA) (6.0 g, 23.6 mmol) in tetrahydrofuran (15 mL) was added slowly over 2 min keeping the internal temperature below −50° C. and the mixture stirred for another 5 min. Sat'd aqueous ammonium chloride (40 mL), water (100 mL) and ethyl acetate (200 mL) were added and the phases mixed and separated. The organic phase was washed with aq. sodium sulfite (100 mL) then brine (75 mL) and evaporated to dryness under reduced pressure to afford 2-bromo-5-fluoro-4-iodopyridine (6.6 g, 21.8 mmol, 96% yield) which was used without further purification. MS (ESI +ve ion) m/z: [M+1]=301.8/303.8.

A mixture of 2-bromo-5-fluoro-4-iodopyridine (6.8 g, 22.5 mmol), ethylene glycol (Sigma-Aldrich, St. Louis, USA) (6.0 mL, 108.0 mmol), and potassium t-butoxide (Sigma-Aldrich, St. Louis, Mo., USA) (2.5 g, 22.7 mmol) in N-methylpyrrolidinone (10 mL) and THF (20 mL) was heated in a 60° C. bath. After 40 min, the mixture was removed from the oil bath and allowed to stir at RT for 14 h. The mixture was concentrated under reduced pressure. Additional potassium t-butoxide (0.5 g) and ethylene glycol (1.0 mL) were added and the reaction heated in an 80° C. bath for another 3 h then cooled to RT. Ethyl acetate (200 mL) and water (150 mL) were added and the phases mixed and separated. The organic phase was washed with brine (75 mL) then evaporated to dryness under reduced pressure. Purification of the residue using silica gel chromatography (0-50% ethyl acetate in DCM) gave 2-((6-bromo-4-iodopyridin-3-yl)oxy)ethanol (3.1 g, 9.0 mmol, 40% yield). MS (ESI +ve ion) m/z: [M+1]=343.8/345.8. $^1$H NMR (400 MHz, CHLOROFORM-d) δ 7.89 (s, 1H), 7.88 (s, 1H), 4.22 (td, J=4.55, 6.36 Hz, 2H), 3.99-4.07 (m, 2H).

2-((6-Bromo-4-iodopyridin-3-yl)oxy)ethanol (3.1 g, 9.0 mmol), potassium t-butoxide (Sigma-Aldrich, St. Louis, Mo., USA) (1.1 g, 9.8 mmol), 3,4,7,8-tetramethyl-1,10-phenanthroline (Alfa Aesar, Ward Hill, Mass., USA) (0.15 g, 0.63 mmol) and copper(I) iodide (Sigma-Aldrich, St. Louis, Mo., USA) (0.09 g, 0.45 mmol) were dissolved in isopropanol (75 mL) under nitrogen. The orange solution was heated in an 80° C. bath for 35 min. The reaction mixture was evaporated to dryness under reduced pressure. The residue was partitioned between sat'd aqueous ammonium chloride (75 mL), ammonium hydroxide (10 mL), water (100 mL) and ethyl acetate (200 mL). The organic layer was washed with brine (50 mL) and evaporated to dryness under reduced pressure. Purification using silica gel chromatography (ethyl acetate/heptane) gave 7-bromo-2,3-dihydro-[1,4]dioxino[2,3-c]pyridine (10a, 1.4 g, 6.6 mmol, 74% yield) as an oil. MS (ESI +ve ion) m/z: [M+1]=216.0/218.0. $^1$H NMR (400 MHz, CHLOROFORM-d) δ 7.94 (s, 1H), 6.99 (s, 1H), 4.32-4.40 (m, 2H), 4.24-4.32 (m, 2H).

Preparation of ethyl 2-(2,3-dihydro-[1,4]dioxino[2,3-c]pyridin-7-yl)-2,2-difluoroacetate (10b)

A mixture of 7-bromo-2,3-dihydro-[1,4]dioxino[2,3-c]pyridine (10a, 2.4 g, 11.1 mmol), copper (0) powder (4.0 g, 62.9 mmol), and ethyl bromodifluoroacetate (1.6 mL, 12.5 mmol) in 15 mL of DMSO was heated in a 60° C. bath overnight. The mixture was diluted with water (100 mL) and ethyl acetate (150 mL) and filtered through a sintered glass frit. The solids were washed with ethyl acetate (50 mL) and the combined filtrate transferred to a separatory funnel. The phases were mixed and separated and the organic phase washed with a mixture of sat'd aqueous ammonium chloride (50 mL), ammonium hydroxide (10 ml), and water (100 mL) before evaporating to dryness under reduced pressure. Purification of the residue using the ISCO (ethyl acetate/heptane) gave ethyl 2-(2,3-dihydro-[1,4]dioxino[2,3-c]pyridin-7-yl)-2,2-difluoroacetate (10b, 2.2 g, 8.49 mmol, 76% yield). MS (ESI +ve ion) m/z: [M+1]=260.0.

Compounds 10c, 10d, and 10 were synthesized in a fashion similar to that described for 5b, 5c, and 5, respectively. 2-(2,3-Dihydro-[1,4]dioxino[2,3-c]pyridin-7-yl)-2,2-difluoroethanol (10c): MS (ESI +ve ion) m/z: [M+1]=218.0. 7-(1,1-Difluoro-2-iodoethyl)-2,3-dihydro-[1,4]dioxino[2,3-c]pyridine (10d): MS (ESI +ve ion) m/z: [M+1]=327.8. (Z)-7-(1-Fluoro-2-iodovinyl)-2,3-dihydro-[1,4]dioxino[2,3-c]pyridine (10): MS (ESI +ve ion) m/z: [M+1]=307.9. $^1$H NMR (400 MHz, DMSO-d$_6$) δ 8.16 (s, 1H), 7.14 (s, 1H), 6.83 (s, 0.5H), 6.74 (s, 0.5H), 4.33-4.43 (m, 4H).

Intermediate 11: (Z)-2-chloro-5-(1-fluoro-2-iodovinyl)pyrazine

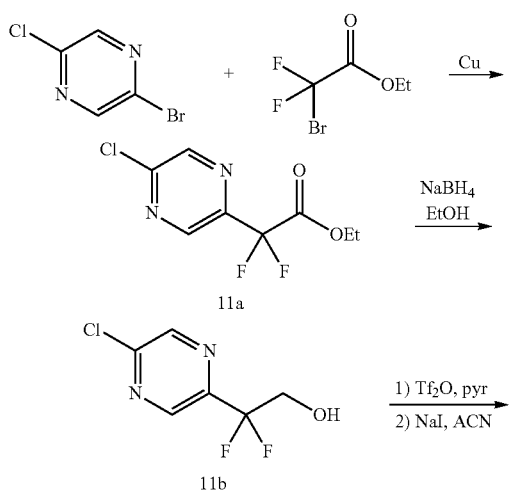

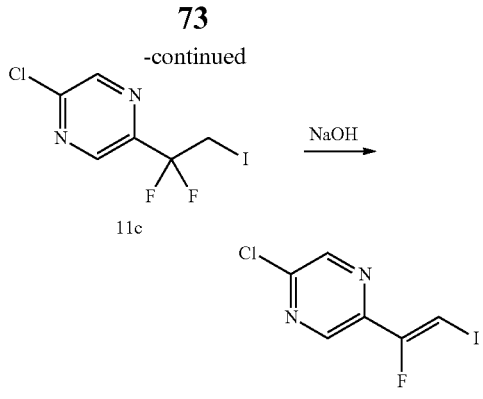

Preparation of ethyl 2-(5-chloropyrazin-2-yl)-2,2-difluoroacetate (1a)

To a suspension of copper (0) powder (244 g, 3877 mmol) in DMSO (5 L) was added ethyl 2-bromo-2,2-difluoroacetate (394 g, 1939 mmol) at RT. The reaction mixture was stirred at RT for 1 h and 2-bromo-5-chloropyrazine (Shanghai Fchemicals Technology Co., Ltd., Shanghai, China) (250 g, 1292 mmol) was added in portion-wise manner. The reaction mixture was stirred at RT for 3 h, and quenched with sat'd solution of ammonium chloride (2.0 L). The mixture was filtered through a celite pad and the filtrate was extracted with ethyl acetate (2×2 L). The combined organic layers were dried over $Na_2SO_4$ and concentrated under reduced pressure. The residue was purified by silica gel chromatography (0-2% ethyl acetate in hexanes) to afford 11a (215 g, 70% yield) as a viscous colorless liquid. $^1$H NMR (400 MHz, DMSO-$d_6$) δ 9.05 (d, J=1.4 Hz, 1H), 8.98 (dd, J=1.4, 0.7 Hz, 1H), 4.39-4.34 (m, 2H), 1.24 (t, J=7.1 Hz, 3H).

Preparation of 2-(5-chloropyrazin-2-yl)-2,2-difluoroethanol (11b)

To a solution of 11a (215 g, 909 mmol) in ethanol (400 mL) was added sodium borohydride (34.4 g, 909 mmol) portion-wise at 0° C. The reaction mixture was stirred for 30 min at 0° C. After completion of reaction (monitored by TLC), the reaction mixture was quenched with water (200 mL) and concentrated under reduced pressure to give the crude residue. The crude material was diluted with water (750 mL) and extracted with ethyl acetate (2×1.0 L). The combined organic solution was dried over $Na_2SO_4$ and concentrated under reduced pressure. The residue was purified by silica gel chromatography (0-10% ethyl acetate in hexanes) to afford 11b (130 g, 73% yield) as a colorless liquid. MS (ESI +ve ion) m/z: [M+1]=195.0. $^1$H NMR (300 MHz, DMSO-$d_6$) δ 8.97 (dt, J=1.4, 0.7 Hz, 1H), 8.82 (d, J=1.4 Hz, 1H), 5.70 (t, J=6.4 Hz, 1H), 4.01 (td, J=13.8, 6.4 Hz, 2H).

Preparation of 2-chloro-5-(1,1-difluoro-2-iodoethyl)pyrazine (11c)

To a solution of 11b (130 g, 668 mmol) in acetonitrile (1.3 L) at 0° C. was added pyridine (54.0 mL, 668 mmol) followed by the dropwise addition of triflic anhydride (147 mL, 869 mmol). The reaction mixture was stirred at 0° C. for 30 min, and RT for 10 min. It was treated with sodium iodide (300 g, 2004 mmol) portion-wise at RT. The reaction mixture was stirred at 70° C. for 2 h. It was cooled to RT and quenched with sat'd aqueous sodium thiosulfate solution (2.0 L) and extracted with ethyl acetate (2×2.0 L). The combined organic layers were washed with brine (2.0 L), dried over $Na_2SO_4$ and concentrated under reduced pressure. The residue was purified by silica gel chromatography (0-2% ethyl acetate in hexanes) to afford 11c (150.0 g, 71% yield) as a yellow solid. $^1$H NMR (300 MHz, DMSO-$d_6$) δ 8.96 (s, 1H), 8.89 (s, 1H), 4.07 (t, J=16.4 Hz, 2H).

Preparation of (Z)-2-chloro-5-(1-fluoro-2-iodovinyl)pyrazine (11)

To a solution of 11c (150 g, 493 mmol) in DMSO (900 mL) was added 5.0 M aqueous NaOH solution (148 mL, 740 mmol). The reaction mixture was stirred at 0° C. for 2 h, and quenched with water (100 mL). It was extracted with EtOAc (2×200 mL). The combined organic layers were washed with brine (300 mL), dried over $Na_2SO_4$ and concentrated under reduced pressure. The residue was purified by silica gel chromatography (0-5% ethyl acetate in hexanes) to afford 11 (78 g, 54% yield) as a white solid. $^1$H NMR (400 MHz, Chloroform-d) δ 8.59 (q, J=1.4 Hz, 1H), 8.54 (q, J=1.4 Hz, 1H), 7.05 (dd, J=34.1, 1.3 Hz, 1H).

Intermediate 12: (Z)-5-(1-fluoro-2-iodovinyl)pyrazine-2-carbonitrile

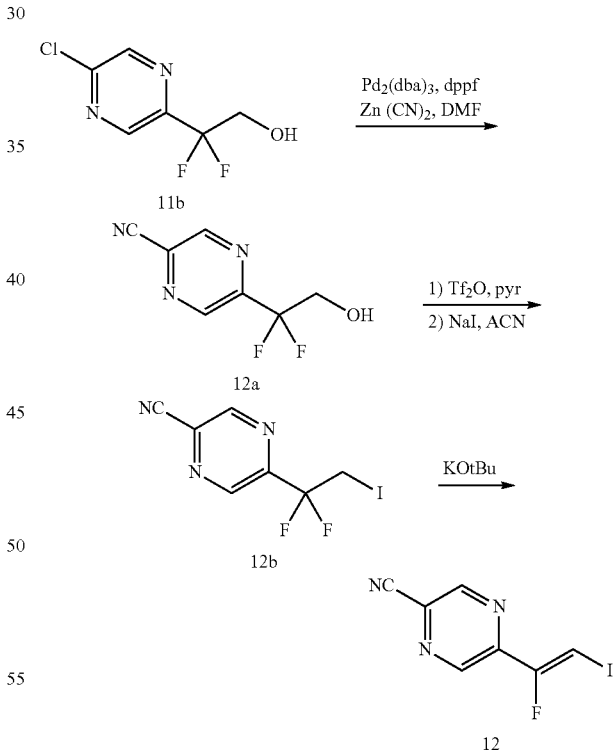

Preparation of 5-(1,1-difluoro-2-hydroxyethyl)pyrazine-2-carbonitrile (12a)

A solution of 2-(5-chloropyrazin-2-yl)-2,2-difluoroethanol (11b, 30.0 g, 154 mmol) in DMF (300 mL) was degassed with nitrogen for 10 min. To the solution was sequentially added dppf (Strem Chemicals, Inc., Newburyport, Mass., USA) (4.2 g, 7.7 mmol), Pd$_2$(dba)$_3$ (Strem Chemicals, Inc., Newburyport, Mass., USA) (7.1 g, 7.7 mmol), and Zn(CN)$_2$ (36.2 g, 308 mmol). The reaction mixture was heated at 80° C. for 5 h. It was cooled to RT and partitioned between water (200 mL) and EtOAc (200 mL). The reaction mixture was filtered through a pad of celite. The filtrate was transferred to a separatory funnel. The layers were separated. The aqueous layer was extracted with ethyl acetate (2×500 mL). The combined organic solution was washed with brine (300 mL), dried over Na$_2$SO$_4$ and concentrated under reduced pressure. The residue was purified by silica gel chromatography (0-20% ethyl acetate in hexanes) to obtain 12a (18 g, 96 mmol, 62% yield) as a clear oil. MS (ESI +ve ion) m/z: [M+1]=no ionisation. $^1$H NMR (400 MHz, DMSO-d$_6$) δ 9.39 (d, J=1.5 Hz, 1H), 9.16 (d, J=1.5 Hz, 1H), 5.77 (t, J=6.4 Hz, 1H), 4.04 (td, J=13.8, 6.4 Hz, 2H).

Preparation of 5-(1,1-difluoro-2-iodoethyl)pyrazine-2-carbonitrile (12b)

To a solution of 5-(1,1-difluoro-2-hydroxyethyl)pyrazine-2-carbonitrile (12a, 18 g, 97 mmol) in acetonitrile (180 mL) at 0° C. was added pyridine (15.7 mL, 194 mmol) followed by the dropwise addition of triflic anhydride (65.7 mL, 389 mmol). The reaction mixture was stirred at 0° C. for 30 min, and treated with sodium iodide (72.9 g, 486 mmol) in portion-wise manner. It was stirred at 70° C. for 3 h. The reaction mixture was cooled to RT and quenched with sat'd aqueous sodium thiosulfate solution (100 mL) and extracted with ethyl acetate (2×200 mL). The combined organic solution was washed with brine (200 mL), dried over Na$_2$SO$_4$ and concentrated under reduced pressure. Purification of the residue by silica gel chromatography (0-2% ethyl acetate in hexanes) afforded 12b (10.0 g, 35% yield) as a yellow solid. MS (ESI +ve ion) m/z: [M+1]=no ionisation. $^1$H NMR (400 MHz, Chloroform-d) δ 9.10 (t, J=1.2 Hz, 1H), 8.98 (dd, J=1.6, 0.8 Hz, 1H), 3.91 (td, J=14.3, 1.0 Hz, 2H).

Preparation of (Z)-5-(1-fluoro-2-iodovinyl)pyrazine-2-carbonitrile (12)

To a solution of 12b (1.00 g, 3.39 mmol) in THF (10 mL) was added potassium t-butoxide (0.76 g, 6.78 mmol) at −75° C. The reaction mixture was stirred at −75° C. for 30 min. The reaction mixture was quenched with water (10 mL) and extracted with ethyl acetate (2×25 mL). The combined organic extracts were dried over Na$_2$SO$_4$ and concentrated under reduced pressure. Purification of the residue by silica gel chromatography (0-5% ethyl acetate in hexanes) afforded 12 (0.34 g, 36% yield) as an off-white solid. MS (ESI +ve ion) m/z: [M+1]=no ionisation. $^1$H NMR (400 MHz, Chloroform-d) δ 8.92 (t, J=1.4 Hz, 1H), 8.84 (t, J=1.2 Hz, 1H), 7.38 (d, J=33.5 Hz, 1H).

Intermediate 13: (Z)-5-cyclopropyl-2-(1-fluoro-2-iodovinyl)pyrazine

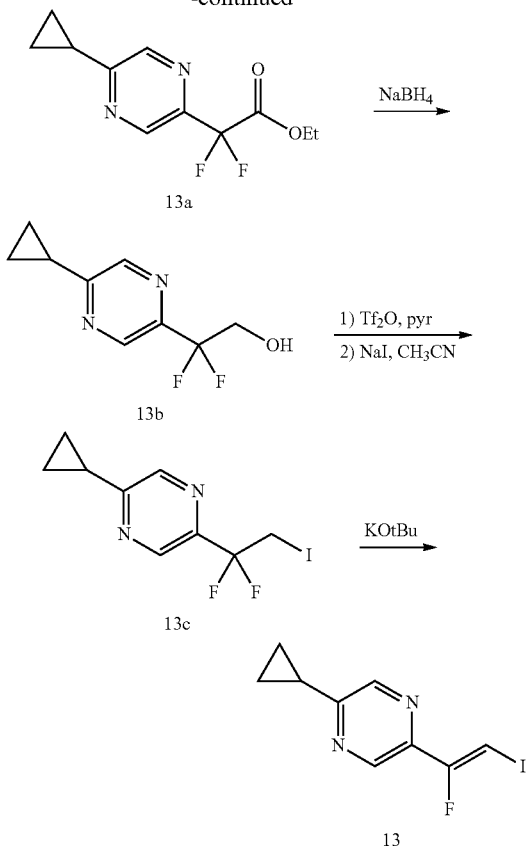

Ethyl 2-(5-cyclopropylpyrazin-2-yl)-2,2-difluoroacetate (13a, 1.8 g, 75% yield) as a colorless oil was synthesized using the protocol described for 1a, starting from 2-bromo-5-(cyclopropyl)pyrazine (CombiPhos Catalysts Inc., Princeton, N.J., USA) (1.9 g, 9.9 mmol) and ethyl bromodifluoroacetate (2.2 mL, 10.9 mmol). MS (ESI +ve ion) m/z: [M+1]=243.2.

Compounds 13b, 13c, and 13 were synthesized in a fashion similar to that described for 1b, 1c, and 1, respectively. 2-(5-Cyclopropylpyrazin-2-yl)-2,2-difluoroethanol (13b): MS (ESI +ve ion) m/z: [M+1]=201.1. 2-Cyclopropyl-5-(1,1-difluoro-2-iodoethyl)pyrazine (13c): MS (ESI +ve ion) m/z: [M+1]=311.2. $^1$H NMR (400 MHz, DMSO-d$_6$) δ 8.82 (d, J=2.15 Hz, 1H), 8.13 (m, 1H), 7.92 (d, J=8.80 Hz, 1H), 4.04 (t, J=16.14 Hz, 2H). (Z)-5-Cyclopropyl-2-(1-fluoro-2-iodovinyl)pyrazine (13): MS (ESI +ve ion) m/z: [M+1]=291.0. $^1$H NMR (400 MHz, DMSO-d$_6$) δ 8.68 (s, 1H), 8.64 (s, 1H), 7.08 (d, J=2.74 Hz, 1H), 2.27 (m, 1H), 1.10 (m, 2H), 1.00 (m, 2H). $^{19}$F NMR (376 MHz, DMSO-d$_6$) δ −100.98 (s).

Intermediate 14: (Z)-2-(1-fluoro-2-iodovinyl)-5-methoxypyrazine

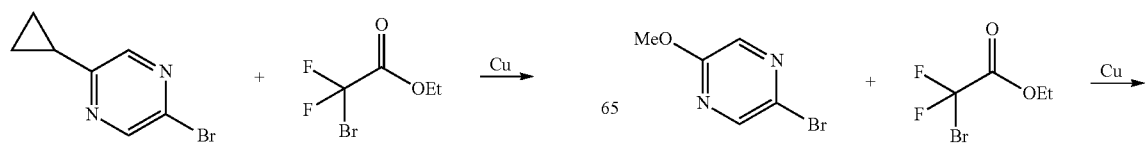

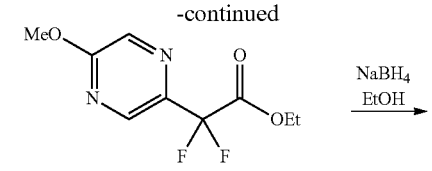
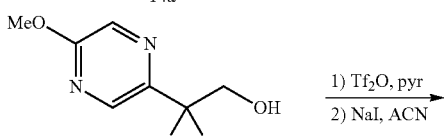
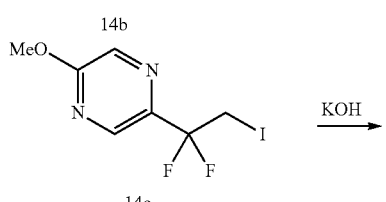
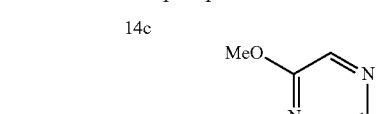
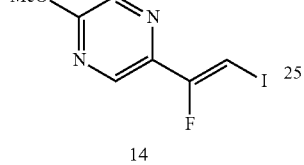

Ethyl 2-(3-chloro-5-(trifluoromethyl)pyridin-2-yl)-2,2-difluoroacetate (14a, 80 g, 65% yield) as a yellow liquid was synthesized using the protocol described for 11a, starting from 2-bromo-5-methoxypyrazine (Shanghai Fchemicals Technology Co., Ltd., Shanghai, China) (100 g, 529 mmol) and ethyl bromodifluoroacetate (215 g, 1058 mmol). MS (ESI +ve ion) m/z: [M+1]=233.0. $^1$H NMR (400 MHz, Chloroform-d) δ 8.51 (s, 1H), 8.22 (s, 1H), 4.43-4.35 (m, 2H), 4.03 (m, 3H), 1.40-1.32 (m, 3H).

Compounds 14b, 14c, and 14 were synthesized in a fashion similar to that described for 11b, 11c, and 11, respectively. 2,2-Difluoro-2-(5-methoxypyrazin-2-yl)ethanol (14b): MS (ESI +ve ion) m/z: [M+1]=191.0. $^1$H NMR (400 MHz, Chloroform-d) δ 8.51 (d, J=2.0 Hz, 1H), 8.21 (d, J=2.0 Hz, 1H), 4.27-4.17 (m, 2H), 4.07-4.00 (m, 3H). 2-(1,1-Difluoro-2-iodoethyl)-5-methoxypyrazine (14c): MS (ESI +ve ion) m/z: [M+1]=301.0. $^1$H NMR (400 MHz, Chloroform-d) δ 8.46 (s, 1H), 8.22 (s, 1H), 4.03 (s, 3H), 3.93-3.86 (m, 2H). (Z)-2-(1-Fluoro-2-iodovinyl)-5-methoxypyrazine (14): MS (ESI +ve ion) m/z: [M+1]=281.0. $^1$H NMR (400 MHz, DMSO-$d_6$) δ 8.43 (t, J=1.3 Hz, 1H), 8.34 (t, J=1.2 Hz, 1H), 6.86 (d, J=37.2 Hz, 1H), 4.01 (s, 3H).

(R)-5-(5-bromo-2-fluorophenyl)-3-(bisBocamino)-2,5-dimethyl-5,6-dihydro-2H-1,2,4-thiadiazine 1,1-dioxide (Intermediate 20)

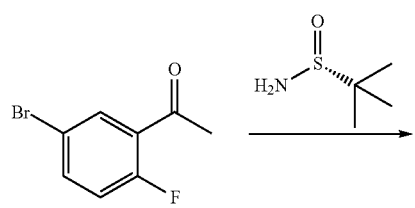

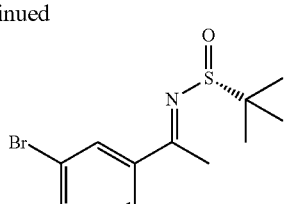
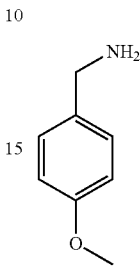
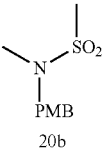
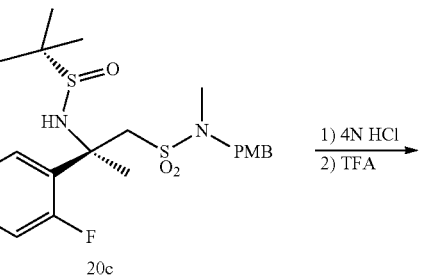
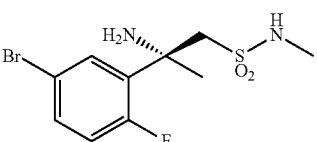
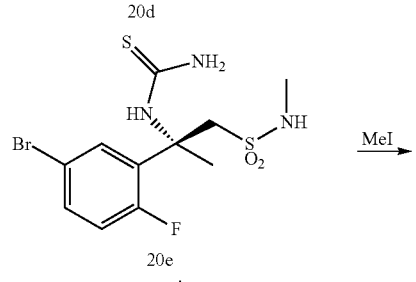
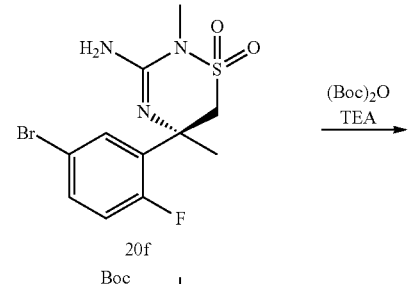
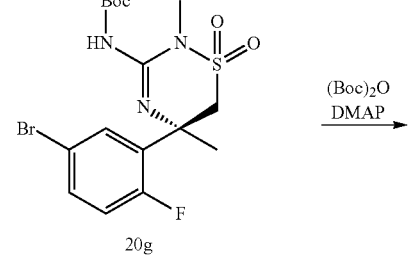

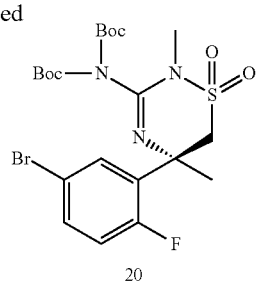
20

Preparation of (R,E)-N-(1-(5-bromo-2-fluorophenyl) ethylidene)-2-methylpropane-2-sulfinamide (20a)

To a solution of 1-(5-bromo-2-fluorophenyl)ethanone (2.5 kg, 11.5 mol) in THF (25.0 L) was added (R)-2-methylpropane-2-sulfinamide (Arborchem, Mechanicsburg, Pa., USA) (2.1 kg, 17.3 mol) and titanium (IV) ethoxide (7.9 L, 34.6 mol) at RT under nitrogen atmosphere. The reaction mixture was refluxed at 65° C. for 12 h. It was quenched with brine (5.0 L) and diluted with ethyl acetate (5.0 L). The mixture was stirred for 30 min. The thick suspension was filtered through a bed of celite and the filtered cake was washed with ethyl acetate (3×2 L). The filtrate was dried over $Na_2SO_4$ and concentrated under reduced pressure to give crude residue which was purified by column chromatography (0-15% ethyl acetate in hexanes) to afford 20a (3.0 kg, 88% yield) as a light yellow solid. MS (ESI +ve ion) m/z: [M+1]=320/322. $^1$H NMR (400 MHz, Chloroform-d) δ 7.78 (dd, J=6.6, 2.6 Hz, 1H), 7.54 (ddd, J=8.9, 4.3, 2.5 Hz, 1H), 7.03 (dd, J=10.6, 8.7 Hz, 1H), 2.77 (d, J=3.6 Hz, 3H), 1.33 (s, 9H).

Preparation of N-(4-methoxybenzyl)-N-methylmethanesulfonamide (20b)

To a solution of (4-methoxyphenyl)methanamine (500 g, 3.6 mol) in pyridine (2.5 L) at 0° C. was added MsCl (284 mL, 3.6 mol) dropwise. The reaction mixture was stirred at RT for 12 h. It was concentrated under reduced pressure. The residue was diluted with DCM (5.0 L) and washed sequentially with 1 N HCl (2×5.0 L), sat'd aqueous sodium bicarbonate (2×5.0 L) and brine (5.0 L), dried over anhydrous sodium sulphate, and concentrated under reduced pressure to afford N-(4-methoxybenzyl)methanesulfonamide (756 g, 96%) as an off-white solid which was carried forward to the next step without further purification. MS (ESI −ve ion) m/z: [M−1]=214.2. $^1$H NMR (400 MHz, Chloroform-d) δ 7.30-7.26 (m, 2H), 6.95-6.89 (m, 2H), 4.77 (s, 1H), 4.25 (d, J=3.2 Hz, 2H), 3.81 (d, J=1.8 Hz, 3H), 2.85 (d, J=2.0 Hz, 3H).

To a solution of crude N-(4-methoxybenzyl)methanesulfonamide (756 g, 3.5 mol) in DMF (5.3 L) was added sodium hydride (169 g, 4.2 mol) portion-wise at 0° C. The reaction mixture was stirred at 0° C. for 30 min and iodomethane (340 mL, 5.3 mol) was added dropwise at 0° C. The reaction mixture was stirred at RT for 12 h. After the completion of the reaction (monitored by TLC), the reaction mass was quenched with water (2.5 L) and concentrated under reduced pressure to get the crude compound. The crude residue was dissolved in water (5.0 L) and extracted with ethyl acetate (2×5.0 L). The combined organic solution was washed with brine (5.0 L), dried over Na2SO4 and concentrated under reduced pressure to afford a crude material. The crude material was stirred with diethyl ether (2.0 L) for 10 min and filtered to provide N-(4-methoxybenzyl)-N-methylmethanesulfonamide (20b, 735 g, 91%) as a light brown solid. MS (ESI −ve ion) m/z: [M−1]=228.0. $^1$H NMR (400 MHz, Chloroform-d) δ 7.33-7.26 (m, 2H), 6.92-6.87 (m, 2H), 4.26 (s, 2H), 3.82 (s, 3H), 2.82 (s, 3H), 2.77 (d, J=4.7 Hz, 3H).

Preparation of (R)-2-(5-bromo-2-fluorophenyl)-2-(((R)-tert-butylsulfinyl)amino)-N-(4-methoxybenzyl)-N-methylpropane-1-sulfonamide (20c)

Flask A: To the solution of 20b (1053 g, 4.6 mol) in THF (7350 mL) was added n-butyllithium (1.6 M in hexane, 4304 mL, 6.9 mol) dropwise at −78° C. under a nitrogen atmosphere. The reaction mixture was stirred at −78° C. for 1 h. Flask B: a solution of 20a (735 g, 2.3 mol) in THF (7350 mL) was cooled to −78° C. The contents in Flask A were cannulated dropwise into the solution in Flask B and the resulting mixture was stirred at −78° C. for 3 h. The mixture was quenched with water (5.0 L) and extracted with ethyl acetate (2×5.0 L). The organic layers were combined and washed with brine (3.0 L), dried over $Na_2SO_4$ and concentrated under reduced pressure to provide 935 g of material that was passed through a short silica gel column (eluted with ethyl acetate) to afford 20c which was used in next step without further purification. MS (ESI +ve ion) m/z: [M+1]=549/551

Preparation of (R)-2-amino-2-(5-bromo-2-fluorophenyl)-N-methylpropane-1-sulfonamide (20d)

To a solution of 20c (950 g, 1.7 mol) in DCM (9.5 L) and methanol (4.7 L) at 0° C. was added HCl (4.0 M in 1,4-dioxane, 807 mL, 3.6 mol). The reaction mixture was stirred at RT for 2 h. It was concentrated to dryness and azeotroped with toluene (500 mL). The crude material was dissolved in chloroform (9.5 L) and treated with TFA (280 mL, 3.6 mol) followed by 1,3-dimethoxybenzene (502 g, 3.6 mol). The reaction mixture was stirred at RT for 12 h. After completion of the reaction (monitored by TLC), the reaction mixture was concentrated under reduced pressure to dryness. The crude material was partitioned between diethyl ether (2.5 L) and 1 M aqueous HCl solution (2.5 L). The aqueous layer was extracted with diethyl ether (2×2.5 L). The organic extracts were discarded. The aqueous layer was then adjusted to pH=10 with addition of saturated sodium carbonate solution (800 mL), and extracted with DCM (3×2.5 L). The combined DCM extracts were dried over Na2SO4 and concentrated under reduced pressure to afford 20d (210 g, 89% yield). MS (ESI +ve ion) m/z: [M+1]=325/327. $^1$H NMR (400 MHz, Chloroform-d) δ 7.79 (ddd, J=7.4, 2.5, 1.0 Hz, 1H), 7.41 (m, 1H), 7.03-6.89 (m, 1H), 4.41 (s, 1H), 4.12 (qd, J=7.2, 1.1 Hz, 1H), 3.88-3.79 (m, 1H), 3.43 (dd, J=14.7, 0.9 Hz, 2H), 2.95 (d, J=0.9 Hz, 3H), 2.82 (dd, J=8.6, 4.5 Hz, 3H).

Preparation of (R)-2-(5-bromo-2-fluorophenyl)-N-methyl-2-thioureidopropane-1-sulfonamide (20e)

To a solution of 20d (194 g, 0.6 mol) DCM (2.9 L) was added benzoyl isothiocyanate (107 g, 0.6 mol) dropwise at 0° C. The reaction mixture was stirred at RT for 12 h. After completion of the reaction (monitored by TLC), the reaction mixture was concentrated under reduced pressure and residue was dissolved in methanol (2.0 L) and sodium methanolate (32.2 g, 0.6 mol) was added. The reaction mixture was stirred for 2 h, and concentrated to dryness. The residue was diluted with DCM (2.0 L) and water (1.0 L), the pH was adjusted to 7-8 by addition of sat'd aqueous NaHCO$_3$ solution. The layers were separated and the aqueous layer was extracted with DCM (2×1000 mL). The combined organic extracts were washed with brine (2500 mL), dried over Na$_2$SO$_4$, and concentrated under reduced pressure. The crude material was adsorbed onto a plug of silica gel and purified by column chromatography (0-40% ethyl acetate in hexanes) to provide 20e (180 g, 468 mmol, 79% yield). MS (ESI +ve ion) m/z: [M+1]=384/386. $^1$H NMR (400 MHz, Chloroform-d) δ 7.63 (s, 1H), 7.50 (dd, J=7.2, 2.5 Hz, 1H), 7.46-7.42 (m, 1H), 6.99 (dd, J=11.9, 8.7 Hz, 1H), 5.10 (s, 1H), 4.69 (s, 1H), 4.14 (q, J=7.2 Hz, 1H), 3.68 (d, J=14.4 Hz, 1H), 2.85 (d, J=4.3 Hz, 3H), 2.05 (s, 3H).

Preparation of (R)-3-amino-5-(5-bromo-2-fluorophenyl)-2,5-dimethyl-5,6-dihydro-2H-1,2,4-thiadiazine 1,1-dioxide (20f)

To a solution of 20e (180 g, 0.46 mol) in ethanol (1.8 L) was added MeI (35.1 mL, 0.56 mol) dropwise at RT. The reaction mixture was heated at 75° C. for 12 h, and concentrated under reduced pressure. The residue was diluted with ethyl acetate (1.0 L) and washed with sat'd aqueous Na$_2$CO$_3$ solution (2×500 mL). The organic layer was washed with brine (2×500 mL), dried over sodium sulfate, and concentrated under reduced pressure. The crude material was purified by crystallization in EtOH to give 20f (105 g, 64% yield) as an off white solid. MS (ESI +ve ion) m/z: [M+1]=350/352. $^1$H NMR (400 MHz, DMSO-d$_6$) δ 7.77-7.67 (m, 1H), 7.47 (dt, J=7.9, 3.3 Hz, 1H), 7.15 (dd, J=11.8, 8.5 Hz, 1H), 6.10 (s, 2H), 3.78 (d, J=3.0 Hz, 2H), 3.05 (s, 3H), 1.56 (s, 3H).

Preparation of (R)-(5-(5-bromo-2-fluorophenyl)-2,5-dimethyl-1,1-dioxido-5,6-dihydro-2H-1,2,4-thiadiazin-3-yl)carbamate (20 g)

To a solution of 20f (105 g, 0.3 mol) in DCM (1.0 L) was added TEA (41.8 mL, 0.3 mol) followed by dropwise addition of Boc-anhydride (69.6 mL, 0.3 mol) at RT. The reaction mixture was stirred for 12 h, diluted with water (1.0 L) and extracted with DCM (2×1 L). The combined organic solution was dried over sodium sulfate and concentrated under reduced pressure. The residue was purified by silica gel column chromatography (2-5% ethyl acetate in hexanes) to give 20 g (110.0 g, 81%). MS (ESI +ve ion) m/z: [M+1]=450/452. $^1$H NMR (400 MHz, Chloroform-d) δ 10.67 (s, 1H), 7.49-7.42 (m, 2H), 7.02 (ddd, J=11.7, 8.6, 1.2 Hz, 1H), 3.81 (d, J=1.2 Hz, 1H), 3.68 (dd, J=14.2, 1.2 Hz, 1H), 3.27 (d, J=1.2 Hz, 3H), 1.89 (t, J=1.0 Hz, 3H), 1.57 (d, J=1.2 Hz, 9H).

Preparation of Bis (tert-butyl)(R)-(5-(5-bromo-2-fluorophenyl)-2,5-dimethyl-1,1-dioxido-5,6-dihydro-2H-1,2l4,4-thiadiazin-3-yl)carbamate (20)

To a solution of 20 g (110 g, 240 mmol) in DCM (1.1 L) was added DMAP (35.8 g, 0.3 mol) followed by Boc-anhydride (85 mL, 360 mol). The reaction mixture was stirred at RT for 16 h. It was diluted with water and extracted with DCM (2×1 L). The combined organic solution was dried over sodium sulfate and concentrated under reduced pressure. The crude residue was purified on a silica gel column (2-5% ethyl acetate in hexanes) to provide intermediate 20 (101.2 g, 75%) as an off-white solid. MS (ESI +ve ion) m/z: [M+1]=550/552. $^1$H NMR (400 MHz, Chloroform-d) δ 7.79 (dd, J=7.2, 2.6 Hz, 1H), 7.43-7.39 (m, 1H), 7.02-6.94 (m, 1H), 3.85 (d, J=14.1 Hz, 1H), 3.60 (s, 1H), 3.17 (d, J=0.8 Hz, 3H), 1.83 (s, 3H), 1.56 (s, 18H).

Intermediate 21: (R)-3-(di-Boc-amino)-5-(2-fluoro-5-(4,4,5,5-tetramethyl-1,3,2-dioxaborolan-2-yl)phenyl)-2,5-dimethyl-5,6-dihydro-2H-1,2,4-thiadiazine 1,1-dioxide

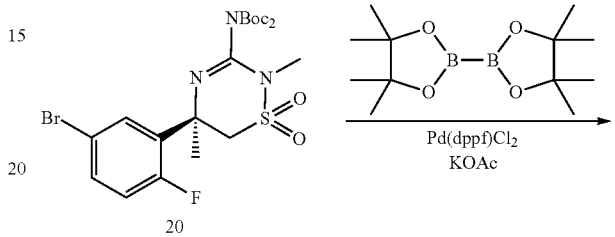

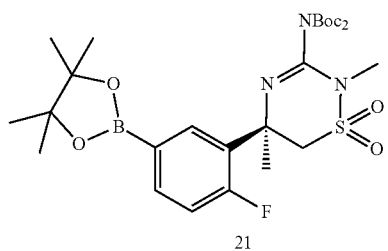

A mixture of compound 20 (5.0 g, 9.1 mmol), 4,4,4',4',5,5,5',5'-octamethyl-2,2'-bi(1,3,2-dioxaborolane) (2.8 g, 10.9 mmol), potassium acetate (2.1 g, 27.3 mmol), and [1,1'-bis(diphenylphosphino)ferrocene]-dichloropalladium (II) complex with dichloromethane (Sigma-Aldrich, St. Louis, Mo., USA) (0.7 g, 0.9 mmol) in dioxane (40 mL) was evacuated and backfilled with argon 3 times, then heated at 100° C. for 4 h. The mixture was cooled to RT, treated with EtOAc (100 mL) and water (15 mL). The layers were separated. The organic layer was dried (MgSO$_4$), filtered, and concentrated in vacuo to give an oil. The oil was purified by silica gel chromatography (0-40% EtOAc/heptane) to give boronic ester 21 (5.1 g, 94% yield) as an off-white amorphous solid. LCMS (ESI$^+$) m/z=598.2 (M+H).

Intermediate 22: (R)-8-(5-Bromo-2-fluorophenyl)-6-(bisBoclamino)-5,8-dimethyl-4-thia-5,7-diazaspiro[2.5]oct-6-ene 4,4-dioxide

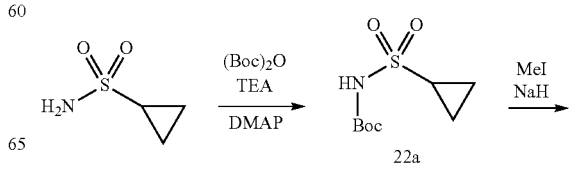

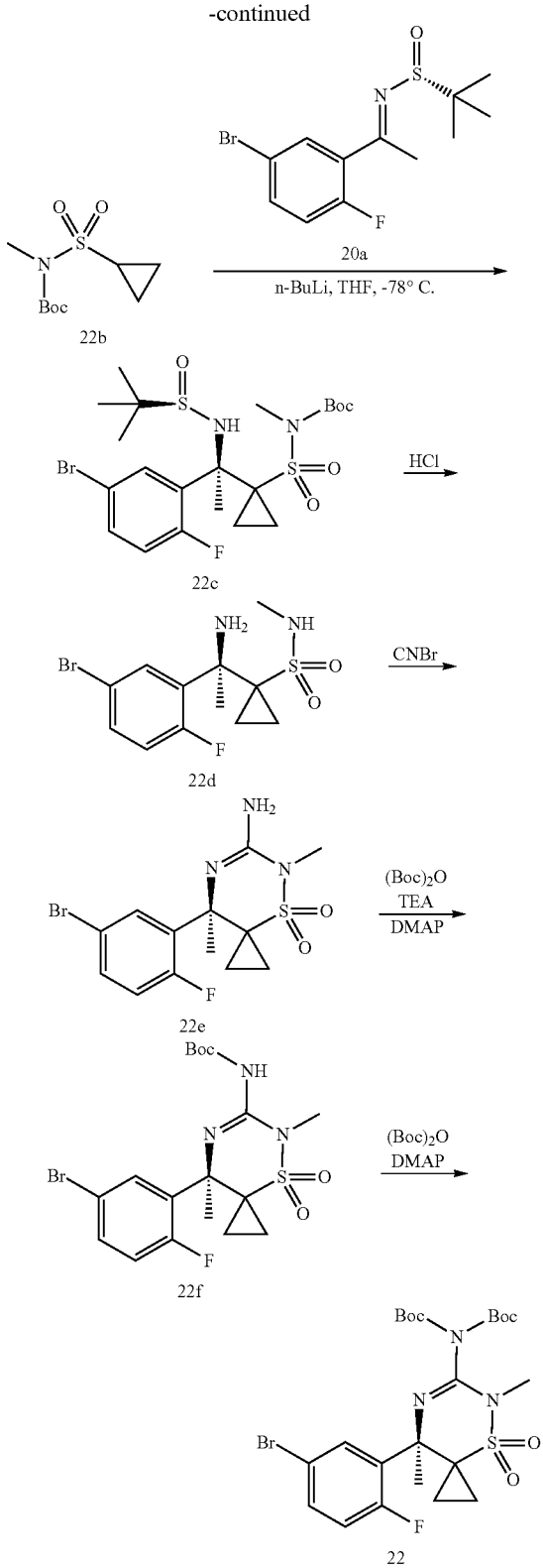

Preparation of tert-butyl (cyclopropylsulfonyl)carbamate (22a)

To a solution of cyclopropanesulfonamide (100 g, 825 mmol) in DCM (1 L) at 0° C. was sequentially added DMAP (5.0 g, 41.3 mmol), TEA (173 mL, 1238 mmol), and Boc-anhydride (216 g, 813 mmol). The reaction mixture was allowed to warm to RT and stirred for 12 h. After the completion of reaction (monitored by TLC), it was concentrated under reduced pressure. The crude residue was taken in EtOAc (2000 mL) and washed with aqueous 1.5 N HCl (2×1000 mL). The organic layer was washed with water (1000 mL), brine (1000 mL) and dried over $Na_2SO_4$. The organic layer was concentrated under reduced pressure to afford 22a (180 g, 99%) as a transparent liquid, which was used in next step without purification. MS (ESI −ve ion) m/z: [M−1]=220.2. $^1$H NMR (400 MHz, Chloroform-d) δ 7.36 (s, 1H), 2.93-2.88 (m, 1H), 1.53 (d, J=0.6 Hz, 9H), 1.39-1.36 (m, 2H), 1.15-1.10 (m, 2H).

Preparation of tert-butyl (cyclopropylsulfonyl)(methyl)carbamate (22b)

To a solution of 22a (180 g, 813 mmol) in DMF (900 mL) at 0° C. was added sodium hydride (23.43 g, 976 mmol) portion-wise. The reaction mixture was stirred at 0° C. for 10 min and methyl iodide (61.0 mL, 976 mmol) was added dropwise. The reaction mixture was stirred for an additional 2 h at RT. After the completion of reaction (monitored by TLC), the reaction mixture was quenched with ice cold water and extracted with EtOAc (2×1000 mL). The combined organic layers was washed with brine (2×1000 mL), dried over $Na_2SO_4$ and concentrated under reduced pressure. The crude residue was purified by flash chromatography (0-10% ethyl acetate in hexanes) to give 22b (154 g, 654 mmol, 80%) as transparent liquid. MS (ESI +ve ion) m/z: [M+1]=236.2. $^1$H NMR (400 MHz, Chloroform-d) δ 3.19 (d, J=3.4 Hz, 3H), 3.08 (ddd, J=8.2, 4.8, 3.2 Hz, 1H), 1.56 (d, J=2.6 Hz, 9H), 1.31 (dt, J=4.8, 1.7 Hz, 2H), 1.10-1.03 (m, 2H).

Preparation of tert-butyl (1-((R)-1-(5-bromo-2-fluorophenyl)-1-((R)-1,1-dimethylethylsulfinamido)ethyl)cyclopropyl)sulfonyl(methyl)carbamate (22c)

To a solution of 22b (90 g, 382 mmol) in tetrahydrofuran (1200 mL) at −78° C. was added n-BuLi (1.6 M in hexane, 287 mL, 459 mmol). The reaction mixture was stirred at −78° C. for 1 h. then treated with a solution of (R,E)-N-(1-(5-bromo-2-fluorophenyl)ethylidene)-2-methylpropane-2-sulfinamide (20a) (122 g, 382 mmol) in THF (500 mL) drop wise. The resulting mixture was stirred at −78° C. for 3 h. After the completion of the reaction (monitored by TLC), the reaction mixture was quenched with $NH_4Cl$ (500 mL) and extracted with EtOAc (2×1000 mL). The combined organic layers were dried over $Na_2SO_4$ and concentration under reduced pressure. The residue was purified by column chromatography (1-30% EtOAc in hexanes) to give 22c (105 g, 49%) as a yellow viscous liquid. MS (ESI +ve ion) m/z: [M+1]=555/557. $^1$H NMR (400 MHz, Chloroform-d) δ 7.94 (dd, J=7.0, 2.6 Hz, 1H), 7.43 (ddd, J=8.6, 4.2, 2.6 Hz, 1H), 6.96-6.89 (m, 1H), 5.82 (s, 1H), 2.32 (d, J=5.5 Hz, 3H), 1.62 (s, 3H), 1.87-1.70 (m, 4H), 1.52 (s, 9H), 1.40 (s, 9H).

Preparation of (R)-1-(1-amino-1-(5-bromo-2-fluorophenyl)ethyl)-N-methylcyclopropane-1-sulfonamide (22d)

To a solution of 22c (105 g, 189 mmol) in DCM (735 mL) and methanol (315 mL) at 0° C. was added a solution of HCl (4.5 M in 1,4-Dioxane, 420 mL, 1890 mmol) dropwise. The reaction mixture was allowed to warm to RT and stirred for

Preparation of (R)-tert-butyl (8-(5-bromo-2-fluorophenyl)-5,8-dimethyl-4,4-dioxido-4-thia-5,7-diazaspiro[2.5]oct-6-en-6-yl)carbamate (22f)

To a solution of 22d (60.0 g, 171.0 mmol) in acetonitrile (600 mL) was added cyanic bromide (90.0 g, 854 mmol) portion-wise. The reaction mixture was heated at 60° C. for 48 h. After the completion of reaction (monitored by TLC), the reaction mixture was concentrated under reduced pressure to afford (R)-6-amino-8-(5-bromo-2-fluorophenyl)-5,8-dimethyl-4-thia-5,7-diazaspiro[2.5]oct-6-ene 4,4-dioxide (22e) (60.0 g) as a yellow solid, which was used in next step without purification. MS m/z=376/378 [M+H]$^+$.

To a solution of the above obtained 22e (60.0 g) in DCM (600 mL) was added N,N-dimethylpyridin-4-amine (1.0 g, 8.0 mmol), TEA (26.7 mL, 191 mmol) and Boc-anhydride (44.4 mL, 191 mmol) at 0° C. The reaction mixture was stirred at RT for 12 h. It was concentrated under reduced pressure to give the crude product which was purified by silica gel column chromatography (0-15% EtOAc in hexanes) to give 22f (30.0 g, 37% over two steps) as a white solid. MS m/z=477.2 [M+H]$^+$. $^1$H NMR (400 MHz, Chloroform-d) δ 10.58 (s, 1H), 7.51-7.41 (m, 2H), 6.98 (dd, J=11.6, 8.5 Hz, 1H), 3.28 (d, J=0.9 Hz, 3H), 1.92-1.84 (m, 1H), 1.74 (d, J=1.0 Hz, 3H), 1.66-1.61 (m, 1H), 1.55 (s, 9H), 1.45 (ddd, J=10.1, 5.5, 2.1 Hz, 1H), 1.33-1.26 (m, 1H).

Preparation of di-Boc-(R)-6-amino-8-(5-bromo-2-fluorophenyl)-5,8-dimethyl-4-thia-5,7-diazaspiro[2.5]oct-6-ene 4,4-dioxide (22)

To a 2-L round bottom flask with an overhead stirrer, N$_2$ inlet, and thermol couple, was added (R)-tert-butyl (8-(5-bromo-2-fluorophenyl)-5,8-dimethyl-4,4-dioxido-4-thia-5,7-diazaspiro[2.5]oct-6-en-6-yl)carbamate (22f, 67.0 g, 141.0 mmol), 4-dimethylaminopyridine (8.6 mL, 70.3 mmol), and toluene (350 mL). The reaction mixture was cooled to 5-10° C. with an ice/water bath, and a solution of di-tert-butyl dicarbonate (39.9 mL, 183.0 mmol) in toluene (300 mL) was added dropwise in 10 min. The reaction was then warmed to RT and stirred for 1 h. The reaction mixture was washed sequentially with 1 M aqueous NaHSO$_4$ (300 mL), sat'd aqueous NaHCO$_3$ (300 mL), and brine (300 mL). The organic solution was concentrated, polish filtered to remove inorganic salt, and concentrated to dryness to afford di-Boc-(R)-6-amino-8-(5-bromo-2-fluorophenyl)-5,8-dimethyl-4-thia-5,7-diazaspiro[2.5]oct-6-ene 4,4-dioxide (22) (88 g) as a light yellow oil. MS m/z=576/578 [M+H]$^+$.

Intermediate 23: di-Boc-(R)-6-amino-8-(2-fluoro-5-(4,4,5,5-tetramethyl-1,3,2-dioxaborolan-2-yl)phenyl)-5,8-dimethyl-4-thia-5,7-diazaspiro[2.5]oct-6-ene 4,4-dioxide

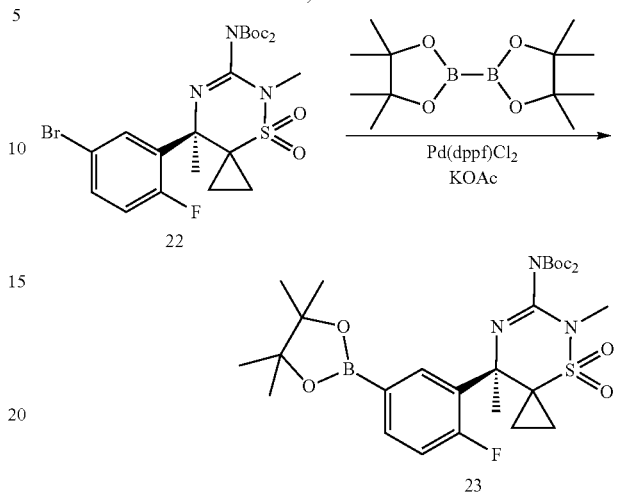

To a 2-L round bottom flask with an overhead stirrer, a N$_2$ inlet, and a thermol couple, was added di-Boc-(R)-6-amino-8-(5-bromo-2-fluorophenyl)-5,8-dimethyl-4-thia-5,7-diazaspiro[2.5]oct-6-ene 4,4-dioxide (22) (81 g, 141 mmol), potassium acetate (41 g, 422 mmol), bis(pinacolato) diboron (43 g, 169 mmol), 1,1'-bis(diphenylphosphino)ferrocene palladium(II)dichloride dichloromethane adduct (5.7 g, 7.0 mmol), and 1,4-dioxane (810 mL). The reaction mixture was purged with N$_2$ and heated to 78° C. for 20 h till full conversion. The reaction was cooled to RT, filtered through a fritted funnel to remove salt, and concentrated to remove most dioxane. The crude was dissolved in EtOAc (500 mL), washed with water (100 mL), and concentrated. The reside was loaded on a silica gel column and eluted with a gradient of heptane:EtOAc=9:1 to 4:6 affording di-Boc-(R)-6-amino-8-(2-fluoro-5-(4,4,5,5-tetramethyl-1,3,2-dioxaborolan-2-yl)phenyl)-5,8-dimethyl-4-thia-5,7-diazaspiro[2.5]oct-6-ene 4,4-dioxide (23) (72 g, 115 mmol, 82% yield) as a light yellow solid. MS m/z=624.1 [M+H]$^+$. $^1$H NMR (500 MHz, DMSO-d$_6$) δ 7.85 (dd, J=1.49, 8.63 Hz, 1H), 7.67 (t, J=6.64 Hz, 1H), 7.19 (dd, J=8.17, 12.98 Hz, 1H), 3.07 (s, 3H), 1.81 (d, J=2.72 Hz, 3H), 1.43-1.51 (m, 18H), 1.30-1.40 (m, 1H), 1.28 (s, 12H), 1.08-1.23 (m, 2H), 0.68-0.75 (m, 1H).

Intermediate 24: (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate

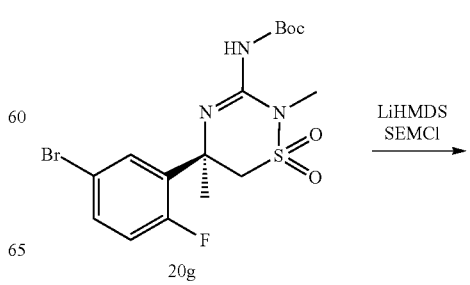

-continued

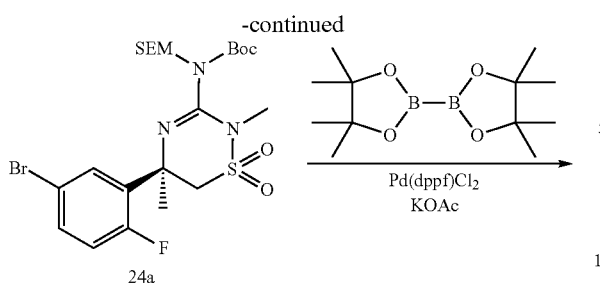

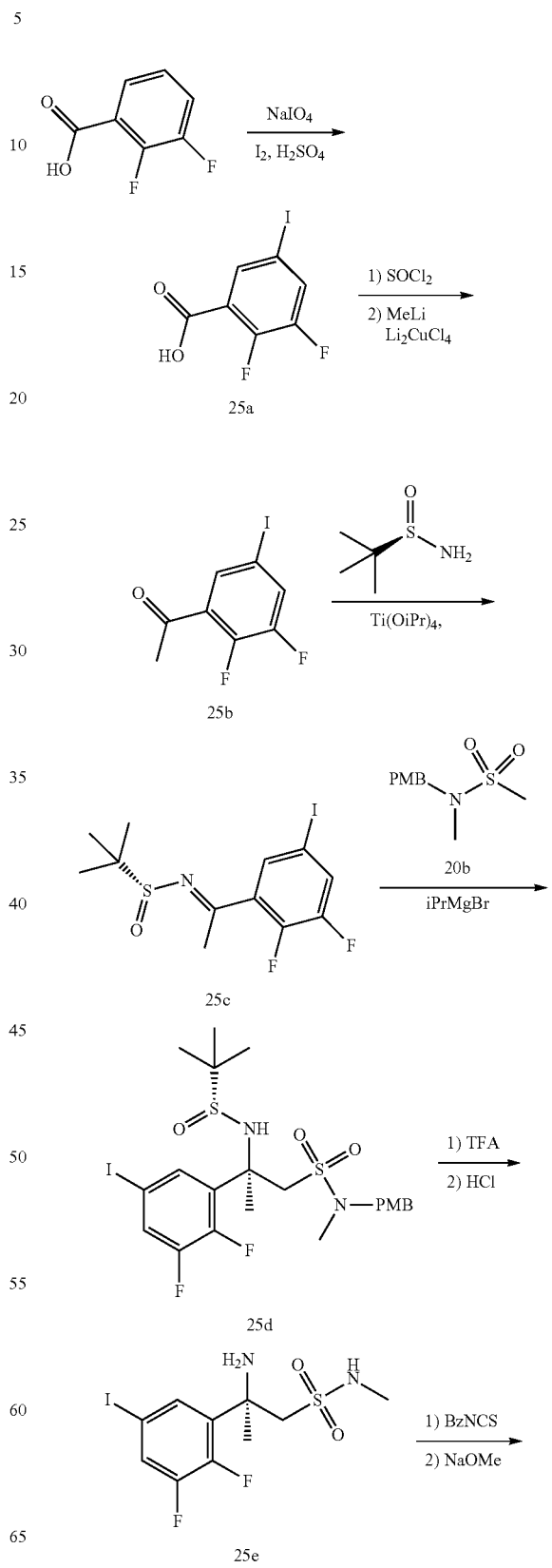

Lithium bis(trimethylsilyl)amide solution (1.0 M in THF, 12.21 mL) was added over 8 min to a solution of (R)-tert-butyl (5-(5-bromo-2-fluorophenyl)-2,5-dimethyl-1,1-dioxido-5,6-dihydro-2H-1,2,4-thiadiazin-3-yl)carbamate (20 g, 5.00 g, 11.10 mmol) in THF (30 mL) at 0° C. under argon. This mixture was stirred for 10 min before 2-(trimethylsilyl)-ethoxymethyl chloride (2.51 mL, 12.77 mmol) was added dropwise (internal temperature did not rise above 2° C.). This mixture was stirred for 10 min then warmed to RT and stirred for 1 h. EtOAc and sat'd aqueous NH$_4$Cl were added, the layers were separated and the aqueous layer was extracted with EtOAc (1×). The combined extracts were dried (MgSO$_4$), filtered, and concentrated to give an oil. The oil was purified by silica gel chromatography (0 to 20% EtOAc/heptane gradient) to give 24a (4.97 g, 77% yield) as a colorless oil. MS m/z=580/582 [M+H]$^+$. 1H NMR (400 MHz, CHLOROFORM-d) ppm 7.73 (d, J=6.87 Hz, 1H) 7.40 (ddd, J=8.66, 4.25, 2.54 Hz, 1H) 6.96 (t, J=10.08 Hz, 1H) 5.16 (d, J=10.37 Hz, 1H) 5.04 (d, J=10.37 Hz, 1H) 3.64-3.77 (m, 4H) 3.21 (s, 3H) 1.80 (s, 3H) 1.54 (s, 9H) 0.99 (t, J=8.31 Hz, 2H) 0.03 (s, 9H).

To a 100-mL round-bottomed flask was added potassium acetate (0.61 g, 6.20 mmol), bis(pinacolato) diboron (1.05 g, 4.13 mmol), (R)-tert-butyl (5-(5-bromo-2-fluorophenyl)-2,5-dimethyl-1,1-dioxido-5,6-dihydro-2H-1,2,4-thiadiazin-3-yl)((2-(trimethylsilyl)ethoxy)methyl)carbamate (24a, 1.20 g, 2.06 mmol), and 1,1'-bis(diphenylphosphino)ferrocene palladium(II)dichloride dichloromethane adduct (0.08 g, 0.10 mmol). The flask was evacuated and backfilled with argon (3×), 1,4-dioxane (26 mL) was added, and the mixture was heated to 80° C. for 6 h. The reaction mixture was cooled, diluted with EtOAc/Heptane (1:1, 20 mL), and the solid was removed by filtration. The filtrate was concentrated and the residue was purified via silica gel chromatography using a gradient of EtOAc in heptane (0-20%) to afford boronic ester 24 (0.97 g, 75% yield) as a colorless oil. MS m/z=628.3 [M+H]$^+$.

Intermediate 25: (R)-5-(5-iodo-2,3-difluorophenyl)-3-(bisBoc-amino)-2,5-dimethyl-5,6-dihydro-2H-1,2,4-thiadiazine 1,1-dioxide

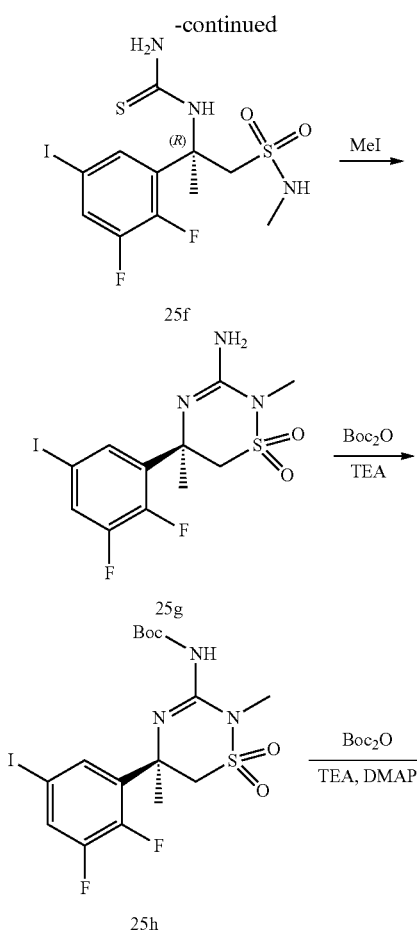

Preparation of 2,3-difluoro-5-iodobenzoic acid (25a)

Sodium periodate (193.0 g, 901.0 mmol) and iodine (602.0 g, 2371.0 mmol) were suspended in conc. sulfuric acid (2500 mL) and heated in a 40° C. bath for 20 min. The mixture was cooled to RT and 2,3-difluorobenzoic acid (ChemPure Chemicals, Plymouth, Mich., USA) (750.0 g, 4744.0 mmol) was added in one portion and additional conc. sulfuric acid (100 mL) was added. The reaction mixture was stirred for 40 min at RT. The reaction was poured into a rapidly stirred mixture of water (5000 mL), ice (~3000 g) and ethyl acetate (5000 mL). Sodium sulfite (500 g) was added and layers were separated. The organic layer was washed with hydrochloric acid (500 mL of 0.5 N aqueous solution) followed by brine (500 mL). The organic layer was dried over sodium sulfate and concentrated under reduced pressure to give 25a (1020.0 g, 76% yield). The crude solid was used without further purification. MS (ESI, positive ion) m/z: no ionization. $^1$H NMR (400 MHz, DMSO-$d_6$) δ 8.06-8.00 (m, 1H), 7.80 (d, J=5.7 Hz, 1H).

Preparation of 1-(2,3-difluoro-5-iodophenyl)ethanone (25b)

Compound 25a (400.0 g, 1352.0 mmol) was suspended in thionyl chloride (600 mL) under nitrogen atmosphere and heated to reflux for 90 min. The reaction mixture was evaporated to dryness under reduced pressure. The crude oil was dissolved in heptane (1000 mL) and evaporated to dryness under reduced pressure. The crude acid chloride was dissolved in THF (600 mL) under nitrogen atmosphere and cooled to 0° C. Dilithium tetrachlorocuprate(II) solution (Sigma-Aldrich Chemical Company, Inc., St. Louis, Mo., USA) (141.0 mL of 0.1 M in THF, 14.08 mmol) was added followed by dropwise addition of methyl magnesium chloride (3.0 M solution in THF, 497.0 mL, 1490.0 mmol) and THF (150 mL) over ~20 min. During the first portion of the addition, the orange color faded to light yellow. By the end of the addition, the solution turned from reddish-brown to dark brown color. The ice-bath was removed and sat'd ammonium chloride solution (500 mL), water (100 mL) and ethyl acetate (1000 mL) were added. The layers were separated and the organic layer was washed with a solution of ammonium hydroxide (200 mL). The organic layer was dried over sodium sulfate, filtered and concentrated under reduced pressure to afford 25b (400.0 g). The crude material was taken for next step without further purification. MS (ESI, positive ion) m/z: 283.2 (M+1).

Preparation of (Z)—N-(1-(2,3-difluoro-5-iodophenyl)ethylidene)-2-methylpropane-2-sulfinamide (25c)

To a solution of 25b (400.0 g, 1418 mmol) and (R)-2-methylpropane-2-sulfinamide (Arborchem, Mechanicsburg, Pa., USA) (241.0 g, 1986.0 mmol), and titanium (IV) ethoxide (1087.0 g, 4766.0 mmol) were dissolved in dioxane (1000 mL) under nitrogen atmosphere. The solution was heated to reflux for 2 h. The reaction mixture was cooled to RT and poured into a rapidly stirring mixture of brine (500 mL) and ethyl acetate (5000 mL). The mixture was stirred for 15 min and filtered through a pad of celite (200 g). The precipitates were washed with ethyl acetate (2×5000 mL). Layers were separated from the combined filtrate and organic layer was dried and concentrated under reduced pressure. The residue was purified by silica gel chromatography (0 to 5% EtOAc in hexanes) to give 25c (200.0 g, 37% yield over two steps) as an orange oil. MS (ESI, positive ion) m/z: 386.2 (M+1). $^1$H NMR (400 MHz, DMSO-$d_6$) δ 8.04 (t, J=8.2 Hz, 1H), 7.87-7.71 (m, 1H), 2.68 (s, 3H), 1.21 (d, J=3.9 Hz, 9H).

Preparation of (R)-2-(2,3-difluoro-5-iodophenyl)-2-((R)-1,1-dimethylethylsulfinamido)-N-(4-methoxybenzyl)-N-methylpropane-1-sulfonamide (25d)

A solution of N-(4-methoxybenzyl)-N-methylmethanesulfonamide (20b, 236.0 g, 1028.0 mmol) in THF (1200 mL) under nitrogen atmosphere was cooled to 0° C. Isopropyl magnesium chloride (2.0 M solution in THF, 544.0 mL, 1087.0 mmol) was added slowly and the reaction mixture was stirred for 15 min at 0° C. The reaction mixture was allowed to stir at RT for 30 min and the cooled to −78° C.

A solution of compound 25c (120.0 g, 312.0 mmol) in THF (300 mL) was added dropwise and the mixture was allowed to stir at same temperature for 4 h. Sat'd aqueous ammonium chloride solution (500 mL) followed by water (500 mL) and ethyl acetate (2000 mL) were added to the reaction mixture. The layers were separated and the organic layer was concentrated under reduced pressure. Purification of the residue by silica gel chromatography (35% EtOAc in hexanes) gave 25d (120.0 g, 62% yield) as a brown oil which contained a small amount of 20b. The mixture was taken as such to next step. MS (ESI, positive ion) m/z: 615.2 (M+1).

Preparation of (R)-2-amino-2-(2,3-difluoro-5-iodo-phenyl)-N-methylpropane-1-sulfonamide (25e)

To a solution of 25d (30.0 g, 48.8 mmol) was dissolved in dichloromethane (350 mL) and treated with trifluoroacetic acid (180.0 mL, 47.9 mmol). The solution was stirred at 40° C. for 1 h. The mixture was poured into water (200 mL) and the layers were separated. The organic layer was concentrated under reduced pressure to give a dark oil. Methanol (170 mL) and THF (170 mL) was added to the crude material followed by the addition of HCl solution (4 M in 1,4-dioxane, 50.0 mL, 33.7 mmol). The reaction mixture was heated at 40° C. for 30 min. The reaction mixture was concentrated under reduced pressure. The residue was dissolved in ethyl acetate (500 mL) and water (250 mL). The pH of the mixture was adjusted to ~10 with 5 N aqueous sodium hydroxide. The layers were separated and the organic layer was evaporated to dryness under reduced pressure to give 25e (12.0 g, 63% yield, 84% ee) as a light-yellow oil. It was used without further purification. MS (ESI, positive ion) m/z: 390.9 (M+1). $^1$H NMR (400 MHz, DMSO-$d_6$) δ 7.87-7.71 (m, 2H), 6.94 (t, J=4.8 Hz, 1H), 3.62 (dd, J=14.5, 2.4 Hz, 1H), 3.44-3.36 (m, 1H), 2.90-2.80 (m, 2H), 2.60-2.53 (m, 3H), 1.44 (d, J=2.4 Hz, 3H).

Preparation of (R)-2-(2,3-difluoro-5-iodophenyl)-N-methyl-2-thioureidopropane-1-sulfonamide (25f)

A solution 25e (30.0 g, 77.0 mmol) was dissolved in dichloromethane (300 mL) and treated with benzoyl isothiocyanate (1.46 g, 9.84 mmol) dropwise. The reaction mixture was stirred at RT for 16 h. It was concentrated under reduced pressure. The residue was dissolved in MeOH (250 mL) and treated with sodium methoxide (25 wt % solution in methanol, 36.4 g, 168.0 mmol) dropwise. The reaction mixture was stirred at RT for 2 h. It was concentrated under reduced pressure and the residue was partitioned between EtOAc (500 mL) and sat'd aqueous NaHCO$_3$ (200 mL). The aqueous layer was extracted with EtOAc (3×500 mL) and the combined organic solution was dried over sodium sulfate, filtered and concentrated. The crude material was purified by silica gel chromatography (35% EtOAc in hexanes) to afford 25f (27.0 g, 78% yield). MS (ESI, positive ion) m/z: 449.9 (M+1). $^1$H NMR (300 MHz, DMSO-$d_6$) δ 7.97 (s, 1H), 7.83-7.68 (m, 1H), 7.44 (d, J=6.4 Hz, 1H), 7.16-6.95 (m, 2H), 4.64 (s, 1H), 4.03 (q, J=7.2 Hz, 1H), 3.76 (t, J=15.4 Hz, 1H), 2.64-2.56 (m, 3H), 1.89 (s, 3H).

Preparation of (R)-3-amino-5-(2,3-difluoro-5-iodo-phenyl)-2,5-dimethyl-5,6-dihydro-2H-1,2,4-thiadiazine 1,1-dioxide (25 g)

To a solution of 25f (44.0 g, 98.0 mmol) in ethanol (1000 mL) was added iodomethane (7.35 mL, 118.0 mmol). The solution was heated at 50° C. for 4 h and at 70° C. bath for 24 h. The reaction mixture was cooled to RT and concentrated under reduced pressure. The residue was partitioned between EtOAc (500 mL) and sat'd aqueous NaHCO$_3$ (200 mL). The aqueous layer was extracted with EtOAc (3×500 mL) and the combined organic solution was dried over sodium sulfate and concentrated under reduced pressure to afford 40 g of crude material which was purified by chiral SFC to provide 25 g (18.5 g, 45% yield, 100% ee). MS (ESI, positive ion) m/z: 416.1 (M+1). $^1$H NMR (400 MHz, DMSO-$d_6$) δ 7.82-7.65 (m, 2H), 6.16 (s, 2H), 3.82 (s, 2H), 3.06 (s, 3H), 1.57 (s, 3H). Preparative SFC method: column (YMC Amylose SA (250×50 mm, 5 μm)); mobile phase (60:40 (A:B), A=liquid CO$_2$, B=20 mM ammonia in IPA); flow rate 150 mL/min; wave length 225 nm; sample load 75 mg/injection; cycle time 3 min; run time 6 min).

Preparation of (R)-tert-butyl(5-(2,3-difluoro-5-iodo-phenyl)-2,5-dimethyl-1,1-dioxido-5,6-dihydro-2H-1,2,4-thiadiazin-3-yl)carbamate (25h)

A solution of 25 g (23.0 g, 55.4 mmol), triethylamine (11.58 mL, 83.0 mmol) and di-tert-butyl dicarbonate (15.43 mL, 66.5 mmol) in DCM (500 mL) was stirred at RT for 12 h. The reaction mixture was concentrated under reduced pressure and the crude material thus obtained was purified by silica gel chromatography (35% EtOAc in hexanes) to provide 25h (20.0 g, 70% yield) as a white solid. MS (ESI, positive ion) m/z: 516.2 (M+1). $^1$H NMR (400 MHz, Chloroform-d) δ 10.69 (s, 1H), 7.54 (tdd, J=7.2, 2.2, 1.0 Hz, 1H), 7.45-7.33 (m, 1H), 4.23 (d, J=14.2 Hz, 1H), 3.69 (d, J=14.2 Hz, 1H), 3.33-3.22 (m, 3H), 1.90 (s, 3H), 1.58 (d, J=1.1 Hz, 9H).

Preparation of (R)-5-(5-iodo-2,3-difluorophenyl)-3-(bisBoc-amino)-2,5-dimethyl-5,6-dihydro-2H-1,2,4-thiadiazine 1,1-dioxide (25)

To a stirred solution of (R)-tert-butyl(5-(2,3-difluoro-5-iodophenyl)-2,5-dimethyl-1,1-dioxido-5,6-dihydro-2H-1,2,4-thiadiazin-3-yl)carbamate (25h, 5.0 g, 10.7 mmol) in DCM (50 mL) was added DIPEA (2.8 mL, 16.0 mmol), DMAP (0.6 g, 5.3 mmol) and Boc-anhydride (3.7 mL, 16.1 mmol). The reaction mixture was stirred at RT for 2 h. It was washed with sat'd aqueous NaHCO$_3$ solution and extracted with DCM. The organic layer was washed with brine and dried over Na$_2$SO$_4$. The organic layer was filtered and concentrated under reduced pressure. The resulting gummy oil was adsorbed onto a plug of silica gel and purified by chromatography through a Redi-Sep pre-packed silica gel column (0-50% EtOAc in hexanes) to provide intermediate 25 (5 g, 8.1 mmol, 76% yield) as a sticky yellow oil. MS (ESI, positive ion) m/z: 616.2 (M+1).

93

Intermediate 26: (R)-5-(2,3-difluoro-5-(4,4,5,5-tetramethyl-1,3,2-dioxaborolan-2-yl)phenyl)-3-(bis-Boc-amino)-2,5-dimethyl-5,6-dihydro-2H-1,2,4-thiadiazine 1,1-dioxide

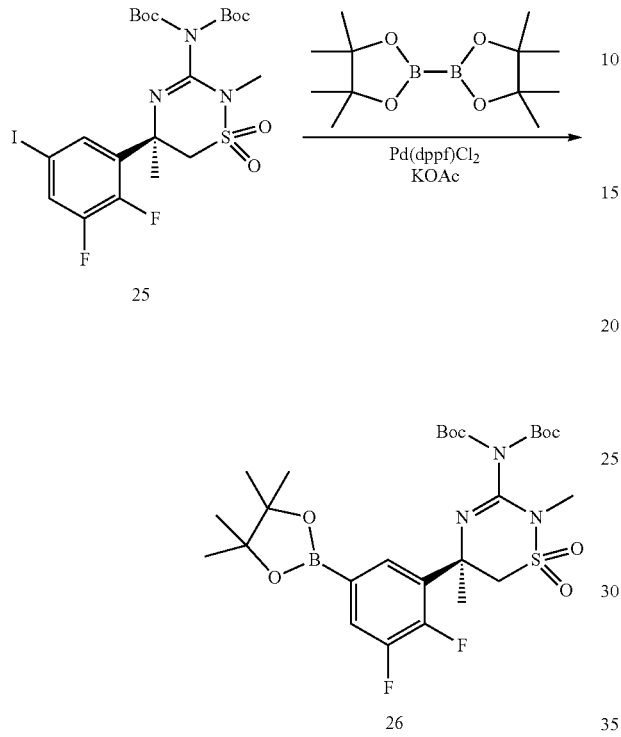

To a stirred solution of compound 25 (2.20 g, 3.57 mmol) in 1,4-dioxane (22 mL) was added (BPin)$_2$ (1.09 g, 4.29 mmol) and KOAc (0.88 g, 8.94 mmol) under N$_2$ atmosphere. N$_2$ was purged to the reaction mixture for 10 min. Pd(dppf)Cl$_2$ (0.26 g, 0.36 mmol) was added. The reaction mixture was heated at 90° C. for 3 h. It was cooled to RT and filtered through celite and washed with ethyl acetate. The filtrate was concentrated under reduced pressure to afford a gummy oil. The oil was adsorbed onto a plug of silica gel and purified by chromatography through a Redi-Sep pre-packed silica gel column (0 to 50% Et$_2$O in hexanes) to provide boronic ester 26 (3.20 g, 5.20 mmol, 145% yield) as yellow oil which contained residual 2,3-dimethylbutane-2,3-diol. The material was used without further purification. MS m/z=616.3 [M+H]$^+$.

Intermediate 27: (1R,4R,5S)-2-amino-4-(5-bromo-2-fluorophenyl)-1-(fluoromethyl)-4-methyl-8-thia-3-azabicyclo[3.2.1]oct-2-ene 8,8-dioxide

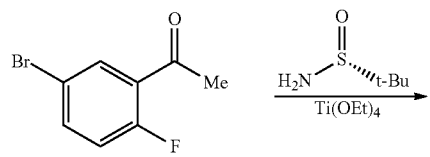

94

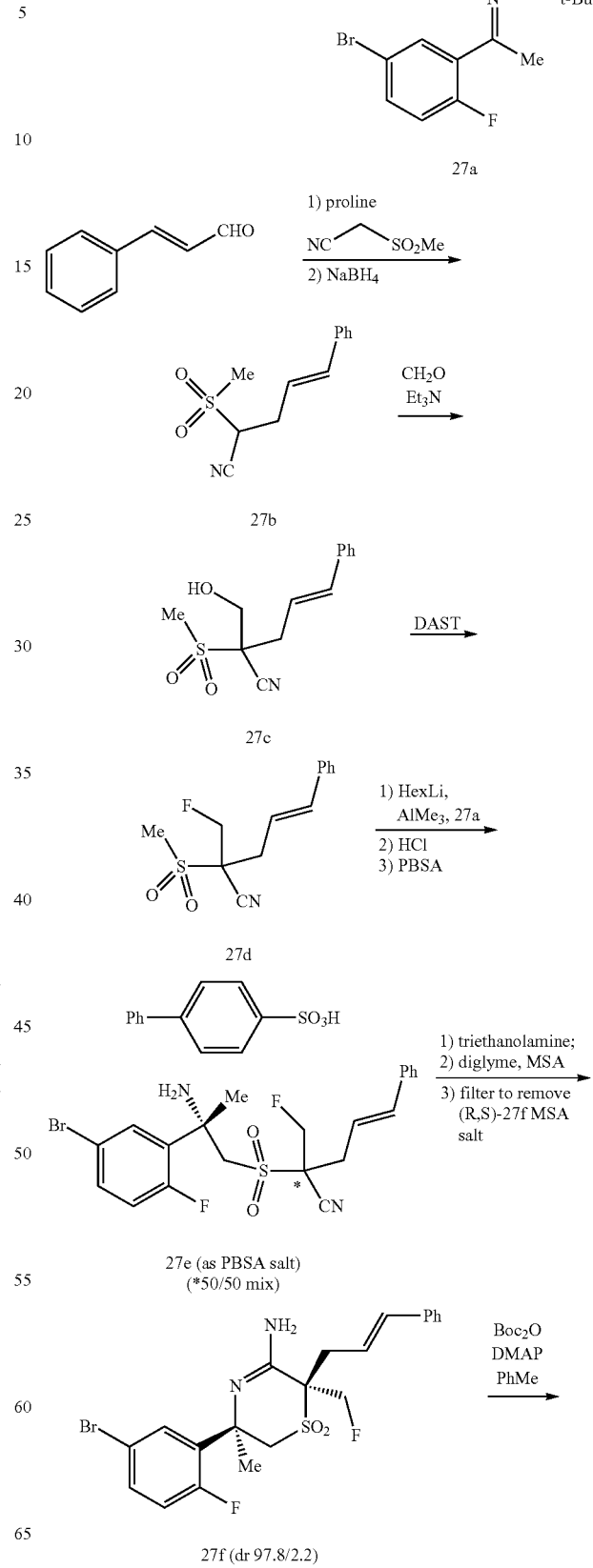

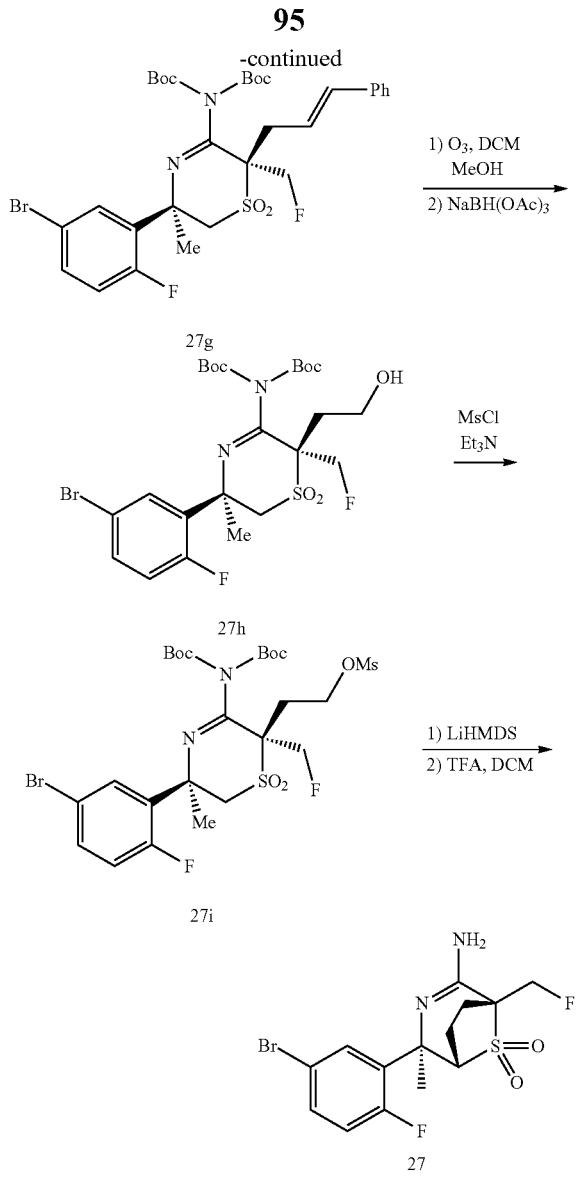

Preparation of (R,E)-N-(1-(5-bromo-2-fluorophenyl) ethylidene)-2-methylpropane-2-sulfinamide (27a)

Note: For smaller scale synthesis of this compound, please see the preparation of 20a.

To a clean and dry glass lined reactor under a nitrogen atmosphere were added 2-Methyl tetrahydrofuran (400 L), 1-(5-bromo-2-fluorophenyl)ethan-1-one (40.0 kg, 184.3 mol) and R-(+)-2-methylpropane-2-sulfinamide (22.4 kg, 184.8 mol). The reaction was maintained at 24° C. under constant agitation whereupon titanium (IV) tetraethoxide (52.4 kg, 229.7 mol) was slowly added to the reaction over a period of 1 h. The reaction mass was gradually heated to 65° C. and heating continued for 24 h at 65° C. under nitrogen atmosphere. Analysis of the reaction mass after 24 h showed 91 LCAP of product and 6 LCAP starting material. The reaction was cooled to 25° C. and quenched by the addition of 20% aqueous sodium potassium tartrate solution (480.0 L) which resulted in a milky aqueous layer. The reaction was partitioned by the addition of ethyl acetate (480 L). The organic layer was collected and the aqueous layer was further extracted with additional ethyl acetate (2×480 L). Combined ethyl acetate layers were washed with water (5×160 L) and then dried over anhydrous magnesium sulfate (20.0 kg) and filtered. The organic portion was passed through a bed of silica gel (20.0 kg) and rinsed with ethyl acetate (120 L). The combined organic solution was concentrated under reduced pressure at temperature 35-40° C. to afford a red colored thick mass. n-Heptane (80 L) was added to the solid mass in the reactor at 25° C. The contents were stirred over a period of 1 h. A clear red solution was obtained which upon cooling to 0-5° C. for 2 h resulted in crystallization of the product. The resulting slurry was filtered and the solids were washed with n-heptane (4 L). The solids were collected and dried under vacuum at 30-35° C. to obtain (R,E)-N-(1-(5-bromo-2-fluorophenyl)ethylidene)-2-methylpropane-2-sulfinamide as a yellow crystalline solid (27a, 46.2 kg, 78% yield). MS (ESI +ve ion) m/z: [M+1]=320/322. $^1$H NMR (400 MHz, Chloroform-d) δ 7.78 (dd, J=6.6, 2.6 Hz, 1H), 7.54 (ddd, J=8.9, 4.3, 2.5 Hz, 1H), 7.03 (dd, J=10.6, 8.7 Hz, 1H), 2.77 (d, J=3.6 Hz, 3H), 1.33 (s, 9H).

Preparation of (E)-2-(hydroxymethyl)-2-(methylsulfonyl)-5-phenylpent-4-enenitrile (27c)

To a 4-necked 5 L round bottomed flask equipped with a mechanical stirrer, internal thermocouple, and air condenser was charged methanol (740 mL), methane sulphonyl acetonitrile (74.0 g, 0.6 mol) and L-proline (15.9 g, 140 mmol). The contents were agitated for 15 min which resulted in a clear solution. Cinnamaldehyde (86.3 g, 652 mmol) was added to the reaction at 25-35° C. which resulted in the slow rise of reaction temperature to 30-35° C. The reaction was stirred for 3 h at 25-35° C. and the solution slowly became a slurry over the course of the reaction. The reaction was cooled to −5° C. and sodium borohydride (12.9 g, 340 mmol) was added in 5 equal portions which resulted in an exotherm to approximately 10° C. Following the complete addition of sodium borohydride, the reaction mixture was maintained at 5° C. and monitored by GC until <1% methane sulphonyl acetonitrile remained. Water (740 mL) was slowly added at a rate to control the temperature below 10° C. and then stirred for an additional 30 min at 5-10° C. The resulting slurry was isolated by filtration and washed with a 10° C. mixture of 1:1 methanol:water (148 mL) followed by 25° C. water (148 mL). The crude cake was dried by pulling air through the filter cake for 6 h until KF analysis was <25% w/w. The crude material was transferred to a 4-necked 5 L round bottomed flask equipped with a mechanical stirrer, internal thermocouple, and water condenser. Methanol (5.0 V, with respect to crude solid dry basis) was charged and the slurry was heated to 60-65° C. for 30 min. The slurry was then gradually cooled to 5-10° C. whereupon the solid was isolated by filtration and rinsed with 10° C. MeOH (2 V). The solid was dried for 4-5 h by pulling air through the cake to provide (E)-2-(methylsulfonyl)-5-phenylpent-4-enenitrile (27b).

To a 4-necked 2 L round bottomed flask equipped with a mechanical stirrer, internal thermocouple, and air condenser was charged THF (516 mL), 27b (129 g, 548 mmol) and triethylamine (2.77 g, 270 mol). The resulting clear solution was cooled to approximately 15° C. where upon 37% aqueous formaldehyde (53.9 g, 657 mol) added over 20 min while maintaining the temperature below 20° C. After a 2 h reaction time, analysis by HPLC showed <2% remaining 27b. The reaction was concentrated to approximately 2 V under reduced pressure (500-50 torr) while maintaining the internal temperature below 40° C. Charged water (516 mL, 4.0V) to reaction mass and continued to distill until THF was removed and approximately 3 V of water remained. The vessel was brought back to ambient pressure whereupon toluene (387 mL) was added and stirred for 10 min at 25-35° C. Stirring was ceased and the aqueous layer was removed. The organic layer was washed with brine (258 mL) and was concentrated to approximately 2 V under reduced pressure (500-50 torr) while maintaining the internal temperature below 40° C. until product assay is approximately 50% w/w. Slowly added heptane (258 mL), pausing to add 1 g seed after approximately 30% of the heptane was added. Continued to stir reaction mixture for 1.0 h at 25-30° C. and then cooled to 10° C. and continued to agitate for 30 min. The slurry was filtered by vacuum and the resulting cake was washed with heptane (129 mL) and dried on the filter for 2 h. The resulting solid was dried in a rotary vacuum dryer for 2 h at 40-45° C. until moisture was less than 0.5% w/w to provide (E)-2-(hydroxymethyl)-2-(methylsulfonyl)-5-phenylpent-4-enenitrile (27c, 137.0 g, 93% yield).

Preparation of (E)-2-(fluoromethyl)-2-(methylsulfonyl)-5-phenylpent-4-enenitrile (27d)

To a 4-necked 2 L round bottomed flask equipped with a mechanical stirrer, internal thermocouple, and water condenser was charged DCM (150 mL), 27c (50.0 g, 188 mmol). The flask was stirred at 25-30° C. under a nitrogen atmosphere until the solid completely dissolved whereupon the reaction was cooled to 0-5° C. DAST (45.6 g, 282 mmol) was added via dropping funnel over 1 h while maintaining the internal temperature between below 10° C. Following the complete addition of DAST, the reaction was allowed to warm to 25-30° C. and react for 36 h until <1% 27c remained. Equipped a 4-necked 5 L round bottomed flask equipped with a mechanical stirrer, internal thermocouple, and water condenser and charged saturate aqueous sodium bicarbonate solution (500 mL) and cooled to 0-5° C. Slowly transferred the contents of the DAST reactor into the aqueous sodium bicarbonate solution at a rate to maintain the internal temperature below 10° C. (note: $CO_2$ off-gassing). Continued to stir for 30 min and adjusted as necessary to pH 7 with additional bicarbonate solution. Allowed the reaction to warm to 25-35° C. and allowed the organic and aqueous layers to separate. Removed the organic layer and extracted the remaining aqueous layer with DCM (100 mL). The two organic layers were combined and washed with brine (100 mL). The resulting organic layer was concentrated under vacuum (500-5 tor) below 40° C. Methanol (75 mL) was added to the concentrate and then heated to 60-65° C. until the residue completely dissolved. Cooled the solution to 25-35° C. and seeded with 1 g of seed. Maintained the temperature for 30 min and then slowly cooled to 0-5° C. and maintained for 30 min. The resulting slurry was filtered and the wet cake was washed with methanol (50 mL) and dried on the filter for 2 h. The solids were transferred to a vacuum oven and dried for 5-6 h at 40° C. and 10-15 torr until <0.5% w/w volatiles remained to afford (E)-2-(fluoromethyl)-2-(methylsulfonyl)-5-phenylpent-4-enenitrile (27d, 44.0 g, 87% yield).

Preparation of Salt 27e

A 1200 L stainless steel reactor was flushed with nitrogen then 2-methyltetrahydrofuran (25 L) and toluene (210 L) were charged into the reactor. The water content of the solution was checked by KF (result=0.021% w/w). 27d (13.5 kg) was added and agitated until the solid was totally dissolved whereupon the solution was cooled to −60° C. to −70° C. under nitrogen flow. A solution of 33% w/w n-hexyllithium in hexane (15.1 kg) was added over 32 min while maintaining the internal temperature between −62° C. to −73° C. After 17 min of stirring at below −60° C., a sample was analyzed by $^1$H-NMR which showed incomplete lithiation (quench w/ AcOD-d4). Additional 33% w/w n-hexyllithium in hexane (0.6 kg) was added and after 10 min analysis by $^1$H-NMR and showed complete lithiation (quench w/ AcOD-d4). A solution of 16.5% w/w trimethylaluminium in toluene (21. kg) was added to the reactor over 21 min at below −60° C. The media was stirred for 50 min between −60° C. to −70° C. A solution of 27a (14.5 kg) in toluene (48 L) was added to the reactor over 24 min while maintaining −60° C. to −70° C. The addition funnel was washed with toluene (5 L). The reaction was stirred for 15 min at −60° C. to −70° C. whereupon analysis by HPLC indicated the conversion about 93.4%.

A 1000 L enameled reactor was flushed with nitrogen then charged with deionized water (150 L) and citric acid monohydrate (21.8 kg). After dissolution, the reactor was cooled to 0-5° C. then the content of 1200 L reactor were transferred into 1000 L reactor at −5/+10° C. over 35 min. During addition, the 1000 L reactor was maintained under nitrogen flux to remove methane formed during the quench. The 1200 L reactor was washed with toluene (13 L), and then added to the 1000 L reactor. pH of the 1000 L reactor was checked: pH=3 (norm: 2<pH<5). After 30 min of stirring at <25° C., the mixture was allowed to settle for 30 min. The aqueous layer was removed and deionized water (67 L) was added into the 1000 L reactor and the media was stirred 20 min at 11-12° C., then the mixture was allowed to settle for 25 min. The aqueous layer was removed then a solution of sodium chloride (16.6 kg) in deionized water (50 L) was added into reactor, the mixture was stirred 15 min and then allowed to settle for 25 min upon which the aqueous layer was removed. Organic layer was concentrated under vacuum while maintaining the internal temperature <40° C. for 2.3 h then transferred into a 250 L reactor. The 1000 L reactor was washed with toluene (5 L), this washing was added into the 250 L reactor. The solution was concentrated under vacuum while maintaining the internal temperature below 40° C. until no additional solvent was removed. The concentrated media was removed from the 250 L reactor and rinsed with THF (5 L) to afford 41.2 kg of an orange oil that contained 26.6 kg of product according to HPLC weight assay and quantitative yield.

A 1000 L enameled reactor was charged with THF (500 L) and orange oil (144.3 kg of 81.42 kg pure). The drums used for the above obtained orange oil storage were rinsed with THF (65 L) and the rinse was added into the 1000 L reactor. Concentrated hydrochloric acid solution (44.3 kg) was diluted with deionized water (32 L) and this solution was added to the 1000 L reactor over 30 min while maintaining the internal temperature below 30° C. The reaction was stirred at 20-25° C. for 4 h until HPLC analysis indicated complete conversion.

A solution of sodium carbonate (45.1 kg) in deionized water (180 L) was slowly added over approximately 50 min to the 1000 L reactor while maintaining a temperature between 15-30° C. After the mixture was agitated for 20 min a pH check indicated neutral whereupon MTBE (330 L) was added. The mixture was stirred 15 min and then allowed to settle upon which the aqueous layer was removed. A solution of sodium chloride (31.4 kg) in deionized water (95 L) was added and the mixture was stirred 15 min and then allowed to settle upon which the aqueous layer was removed. The remaining organic layer was partially concentrated under vacuum while maintaining the internal temperature below 40° C., collecting 650 L distillate. The remaining organic layer was transferred to a 250 L enameled reactor along with a rinse of isopropanol (5 L). The solution was concentrated under vacuum while maintaining the internal temperature <40° C. until no additional solvent was removed. Isopropanol (430 L) was added in 2 portions of 215 L and concentrated under vacuum while maintaining the internal temperature <40° C. until no additional solvent was removed (distillate removed: 500 L). MTBE (250 L) was added and the resulting solution was filtered through an 850 mm stainless steel filter under nitrogen pressure while collecting the filtrate in a clean 1000 L enameled reactor. The 250 L reactor was rinsed twice with MTBE (240 L) then (215 L), sending each rinse through the 850 mm stainless steel filter and collecting in the 1000 L reactor removing a total of 700 g of solids. The solution was partially concentrated under vacuum at <40° C. until 165 L of distillate was collected. MTBE (200 L) was added and again concentrated under vacuum at <40° C. until 150 L of distillate was condensed. Analysis of the resulting 226.8 kg of solution indicated 3.8% isopropanol remained (norm: <10%) and (E)-2-(((S)-2-amino-2-(5-bromo-2-fluorophenyl)propyl)sulfonyl)-2-(fluoromethyl)-5-phenylpent-4-enenitrile (66.6 kg, quantitative yield) which was used directly in the next step for slat formation.

Charged MTBE (255 L) and (E)-2-(((S)-2-amino-2-(5-bromo-2-fluorophenyl)propyl)sulfonyl)-2-(fluoromethyl)-5-phenylpent-4-enenitrile (226.8 kg solution in MTBE containing 75.1 kg of pure) to the 1000 L reactor and heated to 40° C. To a 500 L enameled reactor flushed with nitrogen was charged isopropanol (135 L) and (1,1'-biphenyl)-4-sulfonic acid (38.0 kg). The contents were stirred for 50 min at 5-10° C. until the solids totally dissolved. The contents of the 500 L reactor were slowly added to the 1000 L reactor over 20 min while maintaining the temperature of the 1000 L reactor between 40-45° C. Seed was charged and the continued to stir between 45-47° C. for 2 h and then cooled to 15-25° and held for 13 h. (1,1'-biphenyl)-4-sulfonic acid (7.5 kg) was added and the 1000 L reactor and stirred for 23 h at 15-25° C. upon which HPLC showed 9.6% (E)-2-(((S)-2-amino-2-(5-bromo-2-fluorophenyl)propyl)sulfonyl)-2-(fluoromethyl)-5-phenylpent-4-enenitrile remaining in supernatant (norm: <15%). The content of 1000 L reactor was filtered on 1200 mm polypropylene filter. The reactor was washed with MTBE (110 L) sending the wash to rinse the solid on the filter. The wet solid (109.8 kg) was dried under industrial vacuum at RT for 12 h to give salt 27e (109.4 kg) as a white powder with 98.5% yield. MS (ESI +ve ion) m/z: [M+1]=483.0/485.0.

Preparation of (3R,6R)-5-amino-3-(5-bromo-2-fluorophenyl)-6-cinnamyl-6-(fluoromethyl)-3-methyl-3,6-dihydro-2H-1,4-thiazine 1,1-dioxide (27f)

A 1000 L enameled reactor was flushed with nitrogen then MTBE (490 L) and salt 27e (107.8 kg) were charged, the media was stirred at 15-20° C. A 600 L enameled reactor was flushed with nitrogen then charged with deionized water (240 L) and triethanolamine (116.9 kg) via an addition funnel. The addition funnel was washed with deionized water (228 L), this washing was added to the 600 L reactor and the media was stirred at 20-25° C. The content of the 600 L reactor was added into the 1000 L reactor over 55 min while maintaining the temperature below <25° C. The pH was checked: pH=8.52 (norm: pH ≥8). The media was stirred for 30 min then decanted. Aqueous layer 1 was removed: (HPLC assay) showed only 0.02% of (E)-2-(((S)-2-amino-2-(5-bromo-2-fluorophenyl)propyl)sulfonyl)-2-(fluoromethyl)-5-phenylpent-4-enenitrile (% mass).

The 600 L reactor was charged with deionized water (120 L) and triethanolamine (29.2 kg) via addition funnel. The addition funnel was washed with deionized water (143 L), this washing was added into the 600 L reactor, and the media was stirred at 20-25° C. The content of the 600 L reactor was added into the 1000 L reactor over 30 min while maintaining the temperature below 25° C. The media was stirred for 30 min then decanted:aqueous layer 2 was extracted (see below), organic layer 1 was kept.

Aqueous layers 1 and 2 were mixed in R7 reactor and extracted with MTBE (200 L) at 10-15° C. for 40 min then the media was decanted. Dry extract showed no (E)-2-(((S)-2-amino-2-(5-bromo-2-fluorophenyl)propyl)sulfonyl)-2-(fluoromethyl)-5-phenylpent-4-enenitrile in organic layer. The mixed aqueous layers and organic layer 2 (200 L MTBE) were discarded.

Organic layer 1 was charged into R7 reactor. R15 reactor was charged with deionized water (292 L) and sodium chloride (73 kg); the media was stirred at 20° C. until dissolution of the salt. This solution was added into R7 reactor; the media was stirred for 15 min at 15-20° C. and decanted for 30 min. Aqueous layer 3 was removed.

R15 reactor was charged with deionized water (292 L) and sodium chloride (73 kg), the media was stirred at 20° C. until dissolution of the salt. This solution was added into R7 reactor; the media was stirred for 15 min at 15-20° C. and decanted for 15 min. Aqueous layer 4 was removed. Organic layer in R7 reactor was partially concentrated under industrial vacuum at T<40° C. for 120 min (volume of distillate: 210 L).

R15 reactor was washed with deionized water then charged with the content of R7 reactor. R7 reactor was washed with MTBE (100 L); this washing was added into R15 reactor. The media was concentrated under industrial vacuum at T<40° C. for 95 min (limit of stirring). MTBE (2×100 L) was added and concentration was pursued until limit of stirring (V=80 L) was reached then the media was cooled to T<25° C.

The content of R15 reactor was filtered on F5 filter under nitrogen pressure. R15 reactor was washed twice with MTBE (2×50 L); those washings were used to rinse the solid on F5 filter. The filtrate was charged into R15 reactor. Water content was checked: 0.03% (norm: ≤0.1%). The media was concentrated under industrial vacuum at T<40° C. for 2 h (limit of stirring) then cooled to 20-25° C. under nitrogen. IPC 2 by $^1$H NMR: MTBE content=5.45% (norm: <6%). Diglyme (195 L) was added to the media, after 15 min of stirring water content was checked: 0.021% (norm: ≤0.1%). Methanesulfonic acid (15.65 kg) was added into the reactor without cooling (exotherm from 13.6° C. to 25.5° C.) in 40 min then the media was heated to 105-115° C. for 12 h. IPC by HPLC showed 98.6% conversion (norm: >99.5%). The media was heated for 7 more hours: 99.5% conversion (see IPC 3).

The media was cooled to 15-25° C., MTBE (200 L) was added to fluidify the media. After overnight stirring, HPLC of supernatant (IPC 4) showed 0.79 ratio 27f/(R,S)-27f. The suspension was centrifuged in C4 centrifuge under nitrogen at RT. R15 reactor was washed twice with MTBE (2×70 L); the washings were used to rinse the solid in the centrifuge. The content of mother liquors and MTBE washings were checked by HPLC (IPC 5, 6 and 7). Analysis of the wet solid by HPLC (IPC 8) showed ratio 27f/(R,S)-27f ratio=1.8.

The wet solid (85.4 kg) was charged into R15 reactor with dichloromethane (200 L), the media was heated to reflux temperature for 2 h. The ratio 27f/(R,S)-27f of the suspension was checked by HPLC (IPC 9 and 10): 3.59/96.41 for the solid, 96.8/3.2 for the supernatant. The media was cooled down to T<20° C. and filtered on F2 filter. The ratio 27f/(R,S)-27f of mother liquors was checked by HPLC (IPC 11): 96.72/3.28 (norm: 95/5). R15 reactor was washed twice with dichloromethane (2×70 L); those washings were used to rinse the solid on the filter. (R,S)-27f was obtained as a wet solid (102.3 kg, see analysis in IPC 12). The 27f/(R,S)-27f ratio of washings were checked by HPLC: 96.19/3.81 and 98.27/1.73 (IPC 13 and 14).

Mother liquors containing MTBE and diglyme were charged into R7 reactor, MTBE (128 L) and a solution of sodium bicarbonate (6.7 kg) in deionized water (75 L) were added. After 15 min of stirring, the pH was checked: pH=8.43 (norm: >8). The media was stirred for 1 more hour and decanted, aqueous layer was removed. Organic layer was washed by deionized water (6×164 L), aqueous layers were removed. The media was concentrated under industrial vacuum at T<40° C. to give 27f lot 01-2 (3056 g) as a brown solution (see IPC 15).

Mother liquors containing DCM were charged into R15 reactor and stirred 1.5 h with a solution of sodium bicarbonate (10.1 kg) in deionized water (112 L) at T<25° C. (pH=8.30). The media was decanted overnight, aqueous layer was discarded. Organic layer was charged into R15 reactor and stirred 4×15 min with deionized water (4×164 L). The media was decanted, aqueous layers were discarded and organic layer was checked by $^1$H NMR (IPC 16): 0.8% diglyme detected on dried basis (norm: <5%). Organic layer was concentrated under industrial vacuum at T<40° C. Toluene (2×65 L) was added and the media was concentrated under industrial vacuum at T<40° C. The media was cooled to T<25° C. and checked by $^1$H NMR (IPC 17): 0.06% diglyme (norm: <5%), 0.20% DCM (norm: <5%), no MTBE detected (norm: <12%). R15 reactor was washed with toluene (3 L), the washing was added to the solution to give 27f lot 01-1 (94.4 kg) as a brown solution. 27f lot 01-1 and 27f lot 01-2 were mixed to give 27f lot 01 (97.0 kg containing 30.9 kg of pure product) as a brown solution in 47% yield, with chiral purity of 27f/(R,S)-27f ratio=97.8/2.2.

Preparation of Intermediate 27 g

A reactor was flushed with nitrogen then charged with 27f (97.0 kg) and toluene (135 L), cooled to −5° C. then treated with DMAP (3.0 kg). A solution of di-tert-butyl dicarbonate (33.8 kg) in toluene (80 L) was added at −5/+5° C. in 30 min then the media was stirred at RT for 1.5 h. A solution of sodium bisulfate (11.2 kg) in deionized water (93 L) was added to the media at RT in 15 min. After 20 min of stirring (pH=1), the media was decanted:aqueous layer was removed. A solution of sodium bicarbonate (8.4 kg) in deionized water (93 L) was added to the media. After 15 min of stirring (pH=8-9), the media was decanted:aqueous layer was removed. A solution of sodium chloride (31.8 kg) in deionized water (93 L) was added to the media. After 15 min of stirring, the media was decanted:aqueous layer was removed. Organic layer was evaporated under industrial vacuum at T<45° C. for 1.7 h (270 L of distillate condensed) then cooled to 15-25° C. DCM (180 L) was added and the media was evaporated under industrial vacuum at T<45° C. for 1.5 h. DCM (30 L) was added and the media was filtered on F3 filter under nitrogen pressure. The reactor was washed twice with DCM (2×20 L); those washings were used to rinse the solid on the filter. DCM filtrate and washings were mixed to give Intermediate 27 g lot 01 as a limpid dark brown solution (142.8 kg containing 41.93 kg of pure product) in 96% yield.

Preparation of (3R,6R)-3-(5-bromo-2-fluorophenyl)-5-(bisBoc-amino)-6-(fluoromethyl)-6-(2-hydroxyethyl)-3-methyl-3,6-dihydro-2H-1,4-thiazine 1,1-dioxide (27h)

R6 reactor was flushed with nitrogen and charged with DCM (40 L) and 27 g (71.4 kg). The drum used for storing 27f was washed with DCM (130 L), this washing was added into the reactor then methanol (10 L) was added. The media was cooled to −30/−35° C. under strong nitrogen flow (25 m$^3$/h) then ozone was bubbled into the media for 3 h. IPC by HPLC showed 91.2% conversion (norm: ≥98.0%). Ozone addition was pursued for 2 more h then the media was flushed with nitrogen. IPC 1 by HPLC showed 99.7% conversion. The media was transferred into R15 reactor, R6 reactor was washed with DCM (15 L), and this washing was added into R15 reactor. The media was warmed to 20° C. Sodium triacetoxyborohydride was added by portions (2×1.8 kg+1.6 kg+1.4 kg+5×3.9 kg) at T<28° C. in 2 h. After 10 min of stirring at 20-25° C., IPC 2 by HPLC showed 99.3% conversion (norm: ≥97%). The media was kept overnight at 15-20° C. Deionized water (125 L) was added at T<25° C. in 15 min, the media was stirred for 15 min and decanted. Organic layer was charged into R15 reactor, aqueous layer was discarded (pH=5). Deionized water (125 L) was added, the media was stirred 15 for min and decanted. Organic layer was charged into R15 reactor, aqueous layer was discarded (pH=5). R5 reactor was charged with deionized water (120 L), sodium phosphate monobasic dihydrate (9.4 kg) and sodium phosphate dibasic dihydrate (10.7 kg). The media was stirred until full dissolution and warmed to 20-25° C. A portion (62.2 kg) of this phosphate buffer solution was added into R15 reactor, the media was stirred for 15 min (pH=7) and decanted. Organic layer was charged into R15 reactor, aqueous layer was discarded. A second portion of phosphate solution (62.2 kg) was charged into R15 reactor, the media was stirred for 20 min and decanted (pH=7). Aqueous layer was discarded, organic layer was transferred into R14 reactor and checked by HPLC (IPC 3): concentration=6.57% mass. DCM layer was concentrated under industrial vacuum at T<40° C. for 2.7 h until minimum stirring volume was reached then heptane (2×75 L) was added. The media was concentrated under vacuum at T<40° C. until minimum stirring volume was reached and then cooled to T<25° C. IPC 4 by $^1$H NMR showed 0.8% remaining DCM (norm: <3%). Heptane (125 L) and isopropanol (10 L) were added into R14 reactor. The media was heated to 40-45° C. for 1 h and slowly cooled overnight to 20-25° C. The resulting suspension was filtered on B5 filter. R14 reactor was washed twice with heptane (2×20 L); those washings were used to rinse the solid on the filter. The mixed mother liquors and washings were analyzed by HPLC weight assay (IPC 5): 0.71% Intermediate 27h content. The wet solid (19.8 kg) was dried under industrial vacuum at 30° C. for 20 h to give 27h (17.0 kg containing 16.65 kg of pure product) as a white solid in 79% yield. MS (ESI +ve ion) m/z: [M+Na]=633.0/635.0. $^1$H NMR (400 MHz, DMSO-d$_6$) δ 7.56 (m, 1H), 7.49 (m, 1H), 7.21-7.36 (m, 2H), 5.10-5.16 (m, 0.5H), 5.01 (d, J=10.56 Hz, 1H), 4.87

(m, 1.5H), 4.03 (d, J=16.24 Hz, 1H), 3.66 (m, 2H), 2.31 (m, 1H), 2.15 (m, 1H), 1.66 (s, 3H), 1.50 (s, 18H). $^{19}$F NMR (376 MHz, DMSO-$d_6$) δ −113.56 (s, 1F), −215.24 (s, 1F).

Preparation of (1R,4R,5S)-2-amino-4-(5-bromo-2-fluorophenyl)-1-(fluoromethyl)-4-methyl-8-thia-3-azabicyclo[3.2.1]oct-2-ene 8,8-dioxide (27)

R5 reactor was flushed with nitrogen then charged with DCM (110 L) and 27h (16.96 kg). Water content was checked: 0.018% (norm: <0.05%). The media was cooled to 0° C. then triethylamine (8.27 kg) was added in 13 min at T<5° C. Addition funnel was washed with DCM (15 L); this washing was added to the media. Methanesulfonyl chloride (6.24 kg) was added to the media in 1 h at T<5° C. The bottles that contained methanesulfonyl chloride were washed with DCM (8 L); the washings were added to the media. The media was stirred for 1 h at T<5° C. IPC 1 by HPLC showed 100% conversion (norm: ≥99.5%). A solution of ammonium chloride (37.5 kg) in deionized water (150 L) was added to the media at T<5° C. in 26 min. The media was warmed to 10-15° C. and stirred for 34 min then decanted. Organic layer was transferred into R14 reactor (flushed with nitrogen) and concentrated under industrial vacuum at T<35° C. until minimum stirring volume was reached. The concentrated media that contained 2-((2R,5R)-5-(5-bromo-2-fluorophenyl)-3-(bisBoc-amino)-2-(fluoromethyl)-5-methyl-1,1-dioxido-5,6-dihydro-2H-1,4-thiazin-2-yl)ethyl methanesulfonate (27i) was kept overnight at T<5° C. under nitrogen. Water content was checked: 0.007% (norm: <0.1%). The layers were checked by HPLC (IPC 2): minimal losses in aqueous layer.

The media that contained 27i was diluted with THF (67 L) and transferred into cleaned R5 reactor. R14 reactor was washed with THF (40 L); this washing was charged into R5 reactor. Water content was checked: 0.012% (norm: <0.1%). The media was cooled to T<−5° C. then LiHMDS (35.3 kg sol. 20.7% in THF containing 7.31 kg pure) was added in 1.3 h period at T<5° C. After 32 min of stirring at T<5° C., IPC 3 by HPLC showed 98.3% conversion (norm: ≥95%). A solution of ammonium chloride (6.66 kg) in deionized water (26.6 L) was added to the media in 9 min at T<10° C. The media was warmed to 10° C. then ethyl acetate (50 L) was added. The media was stirred for 20 min at 15-25° C. and decanted for 2.5 h. Organic layer was kept apart; aqueous layer and interlayer were recharged into R5 reactor. Ethyl acetate (35 L) was charged into R5 reactor; the media was stirred for 15 min and decanted. Aqueous layer was removed, organic layer was kept in the reactor, organic layer from previous decantation was charged into reactor. A solution of ammonium chloride (13.3 kg) in deionized water (53 L) was prepared. Half of this solution was charged into R5 reactor; the media was stirred for 15 min and decanted overnight. Aqueous layer was removed (pH=9) then the second half of ammonium chloride solution was charged, the media was stirred for 10 min and decanted. Aqueous layer was removed and pH was checked: pH=7 (norm: pH=7). A solution of sodium chloride (5 kg) in deionized water (15 L) was charged; the media was stirred for 10 min and decanted. The layers were checked by HPLC (IPC 4): very limited losses in aqueous layers. Organic layer was charged into cleaned R14 reactor and concentrated under industrial vacuum at T<40° C. The partially concentrated media was checked by HPLC (IPC 5) and added to the media and the resulting mixture was concentrated until V=50 L. Water content was checked: 0.36%, $^1$H NMR (IPC 6) showed 5.5% ethyl acetate. The concentrated solution was filtered on F3 filter. R14 reactor was washed twice with DCM (2×10 L); the washings were used to rinse the solid on the filter. Mother liquors and washings were mixed (127.9 kg, the yield was considered quantitative) then charged into a 500 L enameled reactor (R5) under nitrogen followed by DCM (10 L). Trifluoroacetic acid (16.19 kg) was added in 30 min period, maintaining the temperature below 20° C. Addition funnel and pump were washed with DCM (2 L) and the resulting mixture was warmed to 35±5° C. (slight reflux). Stirring was maintained at that temperature for 9 h then the mixture was allowed to cool to 15±5° C. overnight and warmed again to 35±5° C. for 1 h. Heating was stopped because monitoring of the reaction by HPLC showed no further evolution of the conversion (97.5% see IPC 1). The resulting solution was concentrated under reduced pressure, maintaining the temperature below 20° C. until 40 L of residual volume. A 250 L enameled reactor (R14) under nitrogen was charged with a 20% w/w filtered solution of potassium carbonate (17.3 kg) in deionized water (69 L). After cooling below 0° C., the concentrated reaction mixture was transferred from R5 to R14 reactor, maintaining the temperature below 10° C., in 35 min period. R5 reactor was rinsed with DCM (12 L) and the rinse was transferred to R14 reactor. The resulting suspension was cooled at −5±5° C. overnight then filtered under vacuum. Reactor and filter cake were washed successively with deionized water (2×58 L) and isopropanol (2×60 L). A sample of the wet solid was analyzed by HPLC (IPC 2) showing the presence of an impurity.

The wet solid was removed from the filter and reworked according to the following procedure: R14 reactor under nitrogen was charged with a mixture of isopropanol (67 L), deionized water (42 L) and potassium carbonate (10.5 kg). Crude wet Intermediate 27 (16.94 kg) was added and the resulting suspension was allowed to stir for 45 min. A sample was taken for HPLC control (solid+mother liquors, IPC 3) showing good impurity rejection. Thus, the suspension was filtered under vacuum and solid was washed successively with deionized water (2×34 L) and isopropanol (2×34 L). After 24 h of drying under vacuum at 40° C., (1R,4R,5 S)-2-amino-4-(5-bromo-2-fluorophenyl)-1-(fluoromethyl)-4-methyl-8-thia-3-azabicyclo[3.2.1]oct-2-ene 8,8-dioxide (27 lot 01R, 13.76 kg, 99.1% a/a, 96.8% w/w on dry basis) was obtained as a light beige powder in 70% overall yield from Intermediate 27h. MS (ESI +ve ion) m/z: [M+1]=393.0/395.0. $^1$H NMR (400 MHz, DMSO-$d_6$) δ 7.72 (m, 1H), 7.60 (m, 1H), 7.25 (m, 1H), 5.84 (br., 2H), 5.24 (m, 0.5H), 5.10 (br, 1H), 4.98 (m, 0.5H), 3.50 (br. s., 2H), 2.06 (m, 1H), 1.89 (br., 1H), 1.81 (m, 2H), 1.33-1.50 (m, 2H).

Intermediate 28: tert-butyl ((1R,4R,5S)-4-(2-fluoro-5-(4,4,5,5-tetramethyl-1,3,2-dioxaborolan-2-yl)phenyl)-1-(fluoromethyl)-4-methyl-8,8-dioxido-8-thia-3-azabicyclo[3.2.1]oct-2-en-2-yl) carbamate

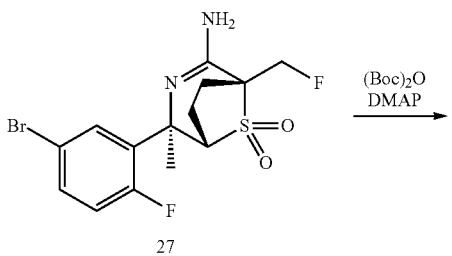

27

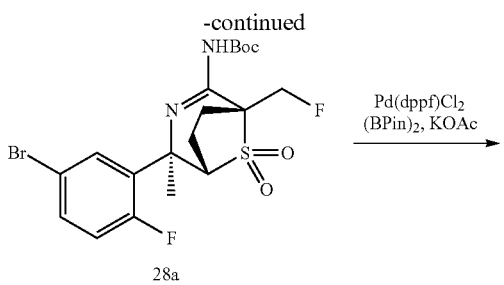

28a

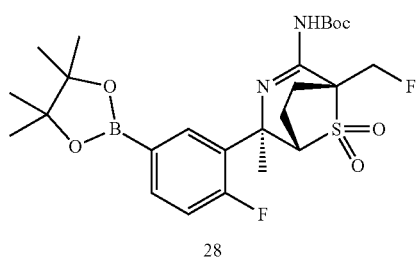

28

A mixture of (1R,4R,5 S)-2-amino-4-(5-bromo-2-fluorophenyl)-1-(fluoromethyl)-4-methyl-8-thia-3-azabicyclo[3.2.1]oct-2-ene 8,8-dioxide (27, 4.0 g, 10.2 mmol), di-tert-butyl dicarbonate (2.8 mL, 12.2 mmol), 4-dimethylaminopyridine (0.06 g, 0.51 mmol) in DCM (25 mL) was stirred for 18 h at 20° C. The reaction mixture was concentrated and the residue was purified by silica gel chromatography (0-20% (3:1 EtOAc/EtOH)/heptane) to afford intermediate 28a (2.0 g, 4.1 mmol, 40% yield) as a white solid. MS m/z=493/495 [M+H]$^+$. $^{19}$F NMR (376 MHz, CHLOROFORM-d) δ –112.91 (s, 1F), –114.95 (s, 1F).

A suspension of 28a (1.40 g, 2.84 mmol), bis(pinacolato)diboron (1.44 g, 5.68 mmol), 1,1'-bis(diphenylphosphino)ferrocene palladium(II)dichloride dichloromethane adduct (0.12 g, 0.14 mmol), potassium acetate (0.83 g, 8.51 mmol) in 1,4-dioxane (15 mL) was purged with argon for 5 min the heated in a 100° C. sand bath for 5 h. The reaction was partitioned between EtOAc (100 mL) and 5% NaHCO$_3$ (50 mL). The organic layer was washed with brine, dried over MgSO$_4$, concentrated under reduced pressure, then purified via silica gel chromatography (0-15% gradient of (3:1 EtOAc/EtOH)/heptane) to afford boronic ester 28 (0.45 g, 0.83 mmol, 29% yield) as a white foam. MS m/z=541.2 [M+H]$^+$.

Intermediate 29: (R)-3-(5-bromo-2-fluorophenyl)-5-(bisBoc-amino)-3,6,6-trimethyl-3,6-dihydro-2H-1,4-thiazine 1,1-dioxide

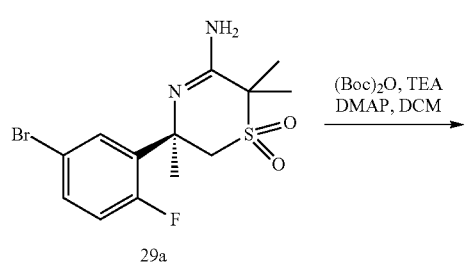

29a

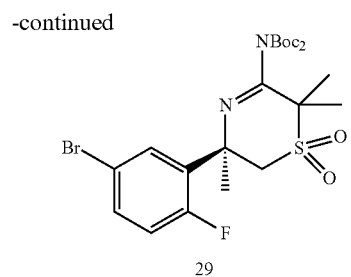

29

At RT, to a mixture of (R)-5-amino-3-(5-bromo-2-fluorophenyl)-3,6,6-trimethyl-3,6-dihydro-2H-1,4-thiazine 1,1-dioxide (29a, prepared according to the procedures described in WO 2014059185A1) (5.00 g, 13.76 mmol), DMAP (0.84 g, 6.88 mmol), and TEA (7.18 mL, 41.30 mmol) in DCM (46 mL) was added di-tert-butyl dicarbonate (7.89 mL, 34.4 mmol). The resulting mixture was allowed to stir at RT for 18 h. It was concentrated and the residue was purified by Isco CombiFlash on a Redi 330 g silica gel column (0-80% EtOAc/heptane) to give Intermediate 29 (6.68 g, 86% yield) as an off-white amorphous solid. MS m/z=463.3/465.3 [M+H]$^+$.

Intermediate 30: (R)-5-(bisBoc-amino)-3-(2-fluoro-5-(4,4,5,5-tetramethyl-1,3,2-dioxaborolan-2-yl)phenyl)-3,6,6-trimethyl-3,6-dihydro-2H-1,4-thiazine 1,1-dioxide

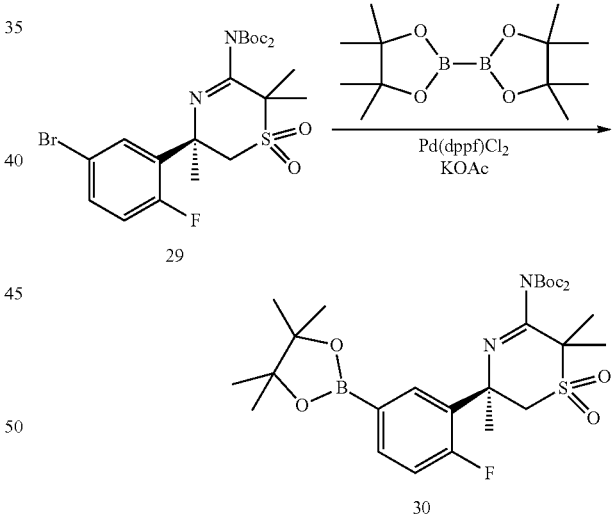

To a stirred solution of 29 (2.50 g, 4.44 mmol) in 1,4-dioxane was added (BPin)$_2$ (1.35 g, 5.32 mmol) and KOAc (1.09 g, 11.09 mmol) under N$_2$ atmosphere. N$_2$ was purged to the reaction mixture for 10 min. Pd(dppf) Cl$_2$ (0.32 g, 0.44 mmol) was added to the reaction mixture which was then heated at 90° C. for 3 h. After cooling to RT, the reaction mixture was filtered through celite and the filter cake was washed with ethyl acetate. The filtrate was concentrated under reduced pressure. The residue was adsorbed onto silica gel and purified by silica gel chromatography (0 to 50% Et$_2$O in hexanes) to provide boronic ester 30 (2.0 g, 74% yield) as a yellow oil. MS m/z=611.3 [M+H]$^+$.

Intermediate 32

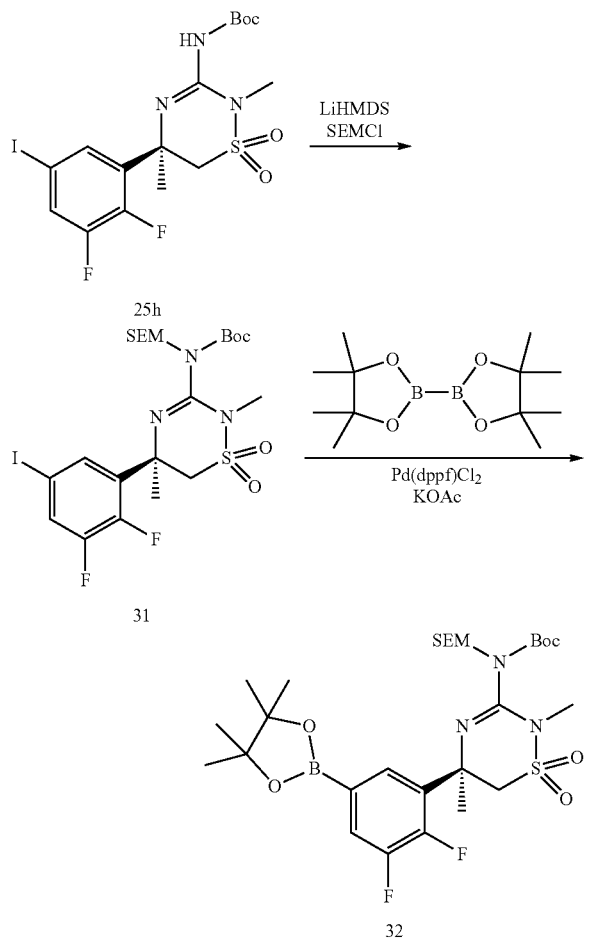

Lithium bis(trimethylsilyl)amide solution (7.62 mL of 1.0 M in THF, 7.62 mmol) was added over 3 min to a solution of (R)-tert-butyl (5-(2,3-difluoro-5-iodophenyl)-2,5-dimethyl-1,1-dioxido-5,6-dihydro-2H-1,2,4-thiadiazin-3-yl)carbamate (25h, 3.57 g, 6.93 mmol) in THF (27 mL) under nitrogen at 0° C. This mixture was stirred for 10 min before 2-(trimethylsilyl)ethoxymethyl chloride (1.41 mL, 7.97 mmol) was added dropwise. This mixture was stirred for 30 min at 0° C. then warmed to RT and stirred for 3.5 h. EtOAc and sat'd aqueous NH$_4$Cl were added, the layers were separated and the aqueous layer was extracted with EtOAc (2×). The combined extracts were dried (Na$_2$SO$_4$), filtered, and concentrated to give an oil. The oil was purified by silica gel chromatography (0 to 20% EtOAc/heptane) to give (R)-tert-butyl (5-(2,3-difluoro-5-iodophenyl)-2,5-dimethyl-1,1-dioxido-5,6-dihydro-2H-1,2,4-thiadiazin-3-yl)((2-(trimethylsilyl)ethoxy)methyl)carbamate (31) (3.32 g, 5.14 mmol, 74% yield) as a colorless oil. MS m/z=646.3 [M+H]$^+$.

A mixture of (R)-tert-butyl (5-(2,3-difluoro-5-iodophenyl)-2,5-dimethyl-1,1-dioxido-5,6-dihydro-2H-1,2,4-thiadiazin-3-yl)((2-(trimethylsilyl)ethoxy)methyl)carbamate (31) (3.32 g, 5.14 mmol), 4,4,4',4',5,5,5',5'-octamethyl-2,2'-bi(1,3,2-dioxaborolane) (1.91 g, 7.71 mmol), Pd(dppf)Cl$_2$ (0.38 g, 0.51 mmol), and potassium acetate (1.51 g, 15.43 mmol) was evacuated and backfilled with nitrogen 3 times, and then DMSO (26 mL) was added. The reaction mixture was heated at 90° C. for 2 h. The mixture was partitioned between EtOAc and water. The aqueous layer was extracted with EtOAc (3×) and the combined organic solution was dried over Na$_2$SO$_4$ and concentrated to give an oil which was purified by silica gel chromatography (0 to 20% EtOAc/heptane) to give boronic ester (32) (2.62 g, 79% yield) as off-white foam. MS m/z=646.3 [M+H]$^+$. $^1$H NMR (CHLOROFORM-d) δ: 7.74 (d, J=7.2 Hz, 1H), 7.50-7.63 (m, 1H), 5.02-5.17 (m, 2H), 3.61-3.77 (m, 4H), 3.25 (s, 3H), 1.86 (s, 3H), 1.53 (s, 9H), 1.32 (s, 12H), 1.25-1.29 (m, 9H), 0.92-0.99 (m, 2H). $^{19}$F NMR (CHLOROFORM-d) δ: −134.91 (br dd, J=5.2, 2.6 Hz, 1F), −139.22 (br d, J=13.9 Hz, 1F).

Intermediate 33: 2-(((3,5-bis(trifluoromethyl)phenyl)sulfonyl)fluoromethyl)-5-chloropyridine

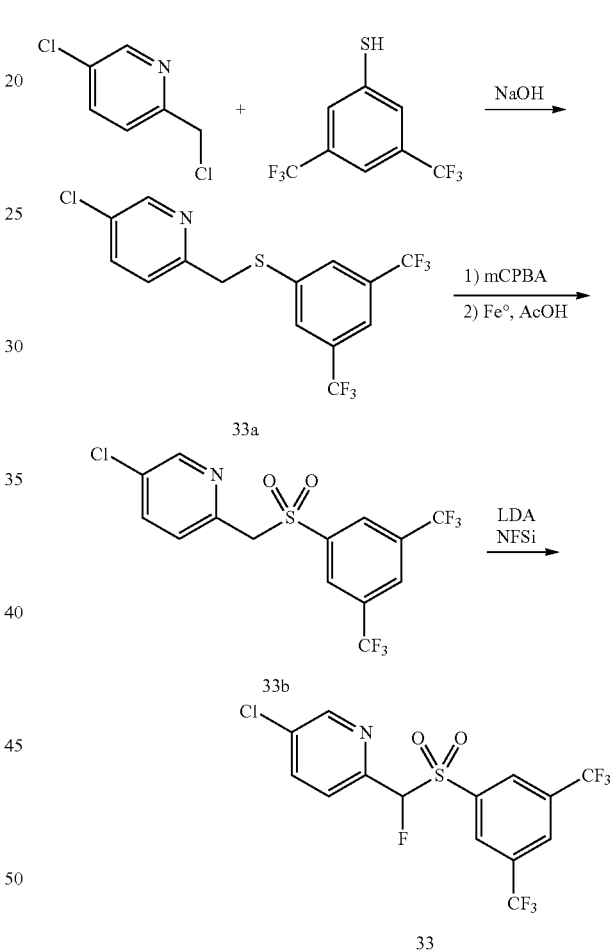

Preparation of 2-(((3,5-bis(trifluoromethyl)phenyl)thio)methyl)-5-chloropyridine (33a)

Sodium hydroxide (2 N, aqueous, 5.4 mL, 10.8 mmol) was added dropwise to a solution of 3,5-bis-trifluoromethyl benzenethiol (Sigma-Aldrich Chemical Company, Inc., St. Louis, Mo., USA) (1.8 mL, 10.9 mmol) in MeOH (3 mL). This mixture was stirred for 5 min and then 5-chloro-2-(chloromethyl)pyridine (Sigma-Aldrich Chemical Company, Inc., St. Louis, Mo., USA) (1.77 g, 10.9 mmol) was added as a solution in MeOH (10 mL). This mixture was stirred for 2 h at RT and then it was concentrated to about half volume in vacuo. EtOAc and half saturated aqueous ammonium chloride were added, the layers were separated, and the aqueous layer was extracted with EtOAc (1×). The combined organic layers were dried over anhydrous MgSO$_4$, filtered, and concentrated in vacuo to give 2-(((3,5-bis(trifluoromethyl)phenyl)thio)methyl)-5-chloropyridine (33a) as a solid (4.1 g, 101% yield). MS m/z=372 [M+H]$^+$. $^1$H NMR (400 MHz, CDCl$_3$) δ ppm 8.49 (d, J=2.35 Hz, 1H) 7.75 (s, 2H) 7.61-7.65 (m, 2H) 7.32 (d, J=8.08 Hz, 1H) 4.32 (s, 2H).

Preparation of 2-(((3,5-bis(trifluoromethyl)phenyl)sulfonyl)methyl)-5-chloropyridine (33b)

mCPBA (Sigma-Aldrich Chemical Company, Inc., St. Louis, Mo., USA) (6.2 g, 27.6 mmol) was added to a solution of 2-(((3,5-bis(trifluoromethyl)phenyl)thio)methyl)-5-chloropyridine (33a) (4.1 g, 11 mmol) in DCM (40 mL) and the mixture was stirred for 2 h. Saturated aqueous sodium bicarbonate solution and DCM were added and the biphasic mixture was stirred vigorously until all solids dissolved. The layers were separated and the organic layer was washed with saturated aqueous sodium bicarbonate solution, dried over anhydrous MgSO$_4$, filtered, and concentrated in vacuo to give a mixture of 2-(((3,5-bis(trifluoromethyl)phenyl)sulfonyl)methyl)-5-chloropyridine (33b) and 2-(((3,5-bis(trifluoromethyl)phenyl)sulfonyl)methyl)-5-chloropyridine-N-oxide as a white solid, that was taken directly to the next step without further characterization.

Iron powder (1.55 g, 27.9 mmol) and glacial acetic acid (5.4 mL, 93 mmol) were added to a suspension of 2-(((3,5-bis(trifluoromethyl)phenyl)sulfonyl)methyl)-5-chloropyridine (33a) and 2-(((3,5-bis(trifluoromethyl)phenyl)sulfonyl)methyl)-5-chloropyridine-N-oxide in EtOH (50 mL). This mixture was heated to 75° C. and then the iron was removed by filtering through a pad of celite while still hot. The filtrate was concentrated in vacuo and then suspended in 1:1 EtOAc/heptane (15 mL). After cooling to 0° C. for 1 h, the suspension was filtered and the collected solid was air dried to give 2-(((3,5-bis(trifluoromethyl)phenyl)sulfonyl)methyl)-5-chloropyridine (33b) (2.9 g, 78% yield for 2 steps) as a white solid. MS m/z=404 [M+H]$^+$. $^1$H NMR (400 MHz, CDCl$_3$) δ ppm 8.31 (d, J=2.35 Hz, 1H) 8.12 (s, 1H) 8.05 (s, 2H) 7.76 (d, J=8.02 Hz, 1H) 7.50 (d, J=8.41 Hz, 1H) 4.58 (s, 2H).

Preparation of 2-(((3,5-bis(trifluoromethyl)phenyl)sulfonyl)fluoromethyl)-5-chloropyridine (33)

LDA (Sigma-Aldrich Chemical Company, Inc., St. Louis, Mo., USA) (2.0 M solution in THF/heptane/ethylbenzene, 3.78 mL, 7.57 mmol) was added dropwise to a −78° C. solution of 2-(((3,5-bis(trifluoromethyl)phenyl)sulfonyl)methyl)-5-chloropyridine (33b) (2.91 g, 7.21 mmol) in THF (25 mL). This mixture was stirred for 15 min before NFSI (Sigma-Aldrich Chemical Company, Inc., St. Louis, Mo., USA) (2.39 g, 7.57 mmol) was added as a solid. This mixture was stirred at −78° C. for 30 min, then at RT for 30 min. The resulting suspension was partitioned between water and EtOAc. The layers were separated and the organic layer was dried over anhydrous MgSO$_4$, filtered, and concentrated in vacuo to give a solid. The solid was fused to silica gel and the product was purified by silica gel chromatography (0 to 20% EtOAc/heptane gradient) to give 2-(((3,5-bis(trifluoromethyl)phenyl)sulfonyl)fluoromethyl)-5-chloropyridine (33) (2.3 g, 76% yield) as a white solid.

MS m/z=422 [M+H]$^+$. $^1$H NMR (400 MHz, CDCl$_3$) δ ppm 8.60-8.66 (m, 1H) 8.34 (s, 2H) 8.23 (s, 1H) 7.84 (d, J=8.30 Hz, 1H) 7.56 (d, J=8.22 Hz, 1H) 6.24 (d, J=45.97 Hz, 1H).

Intermediate 34: 2-(((3,5-bis(trifluoromethyl)phenyl)sulfonyl)fluoromethyl)-5-bromopyridine

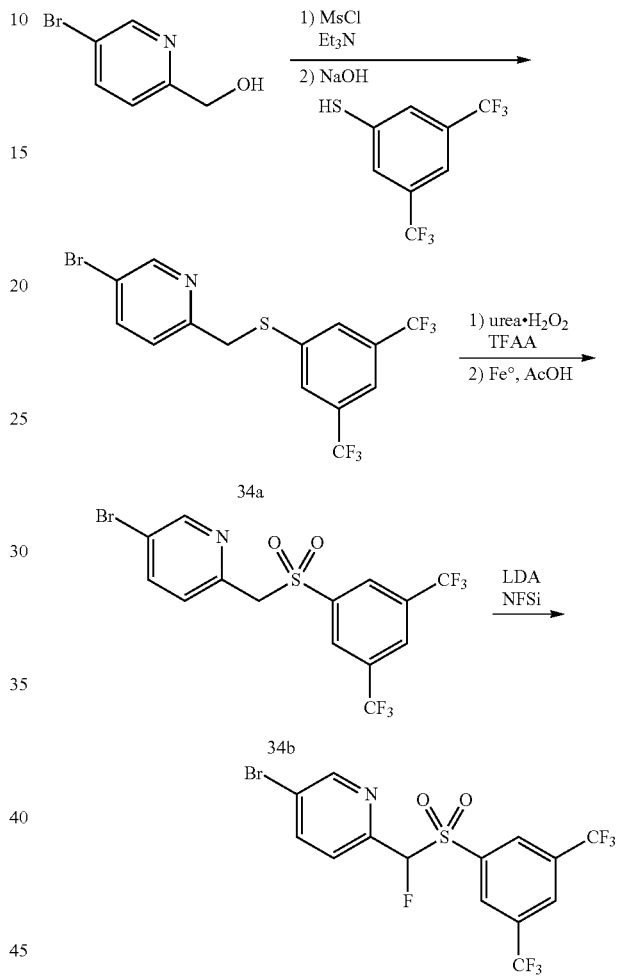

Preparation of 2-(((3,5-bis(trifluoromethyl)phenyl)thio)methyl)-5-bromopyridine (34a)

Methanesulfonyl chloride (5.3 mL, 69.1 mmol) was added dropwise to a solution of 5-bromo-2-hydroxymethylpyridine (Sigma-Aldrich Chemical Company, Inc., St. Louis, Mo., USA) (10.0 g, 53.2 mmol) and TEA (11.1 mL, 80.0 mmol) in THF (150 mL) at 0° C. The mixture was stirred for 1 h. Water was then added and the mixture was extracted with EtOAc (2×). The combined organic layers were dried over anhydrous MgSO$_4$, filtered, and concentrated in vacuo to give the mesylate as an oil. 3,5-Bis-trifluoromethyl benzenethiol (8.9 mL, 53.2 mmol) was dissolved in MeOH (150 mL). Aqueous sodium hydroxide (2 N, 31.9 mL, 63.8 mmol) was added and then the mixture was stirred for 5 min. The mesylate was added as a suspension in MeOH (40 mL) and the mixture was stirred for 1 h at RT before the MeOH was removed in vacuo. The resulting residue was partitioned between water and EtOAc, the layers were separated, and the aqueous layer was extracted with EtOAc (1×). The combined extracts were dried over anhydrous MgSO$_4$, filtered, and concentrated in vacuo to give 2-(((3,5-bis(trifluoromethyl)phenyl)thio)methyl)-5-bromopyridine (34a) (22.3 g, 101% yield) as an oil. MS m/z=416/418 [M+H]$^+$. $^1$H NMR (400 MHz, CDCl$_3$) δ ppm 8.59 (s, 1H) 7.73-7.79 (m, 3H) 7.63 (s, 1H) 7.26 (d, J=8.02 Hz, 1H) 4.29 (s, 2H).

Preparation of 2-(((3,5-bis(trifluoromethyl)phenyl)sulfonyl)methyl)-5-bromopyridine (34b)

A 100 mL 2-necked flask was charged with 2-(((3,5-bis(trifluoromethyl)phenyl)thio)methyl)-5-bromopyridine (34a) (1.8 g, 4.3 mmol), placed under argon atmosphere, and dissolved in CH$_3$CN (20 mL). The mixture was cooled to 4° C. internal temperature using an ice water bath, and then hydrogen peroxide urea adduct (1.0 g, 10.8 mmol) and TFAA (2.3 g, 10.8 mmol) were added. This mixture was stirred with warming to RT for 3 h. In a separate flask, hydrogen peroxide urea adduct (1.0 g) was suspended in CN$_3$CN (20 mL) and TFAA (2.3 g) was added. This mixture was stirred until all the peroxide complex went into solution (about 30 min) at which point the solution was added to the reaction mixture. The reaction was stirred for 1 h and then transferred to a separatory funnel. EtOAc and sat'd aqueous sodium bicarbonate solution were added. The layers were mixed and then separated. The organic layer was washed with saturated aqueous sodium thiosulfate until peroxide test strips tested negative for peroxide. The organic solution was then dried over MgSO$_4$, filtered, and then concentrated in vacuo to give a mixture of desired sulfone product and the corresponding N-oxide, which was taken directly to the next step.

A mixture of iron powder (0.96 g, 17.0 mmol), acetic acid (2.49 mL, 43.1 mmol), and the material generated in the first step in EtOH (25 mL) was heated to 80° C. for 3 h. The solution was then filtered through a pad of celite while hot and the filtrate was concentrated in vacuo. The residue was partitioned between EtOAc and saturated aqueous sodium bicarbonate solution, the layers were separated, and the organic layer was washed with saturated aqueous sodium bicarbonate solution (2×), dried over MgSO$_4$, filtered, and concentrated in vacuo. The resulting solid was recrystallized from 1:1 EtOAc/heptane to give 2-(((3,5-bis(trifluoromethyl)phenyl)sulfonyl)methyl)-5-bromopyridine (34b) (1.11 g, 58% yield for 2 steps) as a white solid. MS m/z=448/450 [M+H]$^+$. $^1$H NMR (400 MHz, CDCl$_3$) δ ppm 8.61 (s, 1H) 8.54 (d, J=2.15 Hz, 1H) 8.26 (s, 2H) 8.14 (dd, J=8.50, 2.35 Hz, 1H) 7.46 (d, J=8.41 Hz, 1H) 5.14 (s, 2H).

Preparation of 2-(((3,5-bis(trifluoromethyl)phenyl)sulfonyl)fluoromethyl)-5-bromopyridine (34)

LDA (2.0M solution in THF/heptane/ethylbenzene, 4.44 mL, 8.88 mmol) was added dropwise to a solution of 2-(((3,5-bis(trifluoromethyl)phenyl)sulfonyl)methyl)-5-bromopyridine (34b) (3.79 g, 8.46 mmol) in THF (30 mL) at −78° C. This mixture was then stirred for 15 min before N-fluorobenzenesulfonimide (2.80 g, 8.88 mmol) was added in one portion. The ice bath was removed and the mixture was allowed to warm to RT and stir for 30 min. Water was added and the product was extracted into DCM. The resulting solid was recrystallized once from DCM to give 2.0 g product, and then the remaining material was recrystallized from 1:1 EtOAc/heptane to give an additional 0.6 g of product. Together, the recrystallizations gave 2.6 g (65% yield) of 2-(((3,5-bis(trifluoromethyl)phenyl)sulfonyl)fluoromethyl)-5-bromopyridine (34) as a white solid. MS m/z=466/468 [M+H]$^+$. $^1$H NMR (400 MHz, CDCl$_3$) δ ppm 8.73 (d, J=2.15 Hz, 1H) 8.34 (s, 2H) 8.23 (s, 1H) 7.99 (dd, J=8.16, 2.35 Hz, 1H) 7.50 (d, J=8.22 Hz, 1H) 6.22 (d, J=45.97 Hz, 1H).

Intermediate 35: 6-(((3,5-bis(trifluoromethyl)phenyl)sulfonyl)fluoromethyl)nicotinonitrile

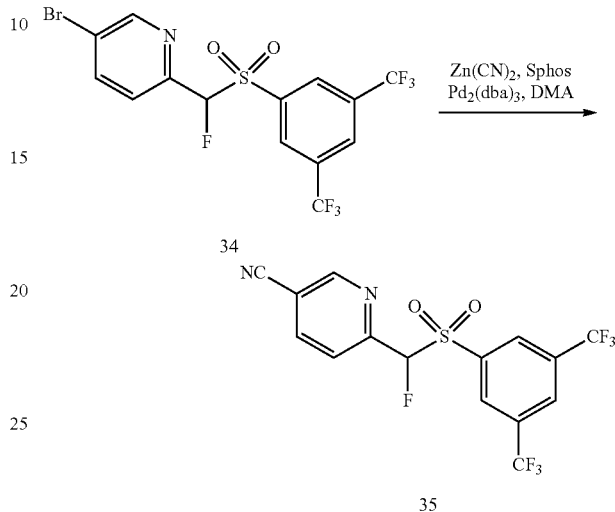

2-(Dicyclohexylphosphino)-2',6'-dimethoxy-1,1'-biphenyl (Strem Chemicals, Inc., Newburyport, Mass., USA) (44 mg, 1.07 mmol) and tris(dibenzylideneacetone)dipalladium (0) (Strem Chemicals, Inc., Newburyport, Mass., USA) (0.49 g, 0.53 mmol) were mixed in DMA (7 mL) and then argon was bubbled through the solution for 5 min at 50° C. This solution was added to a solution of 2-(((3,5-bis(trifluoromethyl)phenyl)sulfonyl)fluoromethyl)-5-bromopyridine (34) (5.00 g, 10.73 mmol) and zinc cyanide (0.88 g, 7.51 mmol) in DMA (20 mL) under argon, and then this mixture was heated to 110° C. for 16 h, at which time LCMS showed clean conversion to desired product. The reaction was cooled to RT, diluted with EtOAc, and washed with sat'd aqueous NaHCO$_3$ (2×), and dried (MgSO$_4$), filtered and concentrated to give an oil. The oil was purified by silica gel chromatography (20% EtOAc/heptane) to afford the title compound (35) (3.8 g, 86% yield) as a yellow solid. MS m/z=413.0 [M+H]$^+$.

Intermediate 36: di-Boc-(R)-3-amino-5-(2-fluoro-5-(4,4,5,5-tetramethyl-1,3,2-dioxaborolan-2-yl)phenyl)-2,5,6,6-tetramethyl-5,6-dihydro-2H-1,2,4-thiadiazine 1,1-dioxide

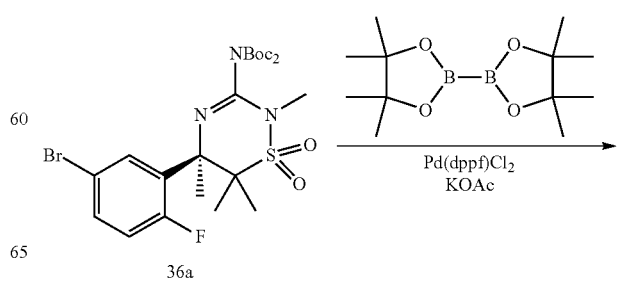

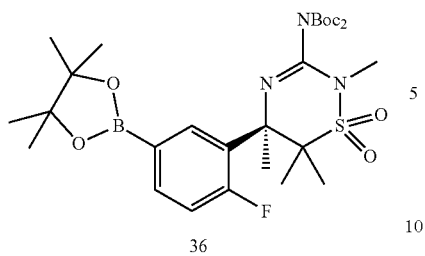

36

Compound 36a was prepared in a fashion similar to that described for Intermediate 22, using propane-2-sulfonamide as starting material. MS m/z=577.2 [M+H]⁺. Compound 36 was prepared in a fashion similar to that described for boronic ester 23, using 36a as starting material. MS m/z=577.2 [M+H]⁺.

Intermediate 37: (R)-tert-butyl (5-(2,3-difluoro-5-formylphenyl)-2,5-dimethyl-1,1-dioxido-5,6-dihydro-2H-1,2,4-thiadiazin-3-yl)carbamate

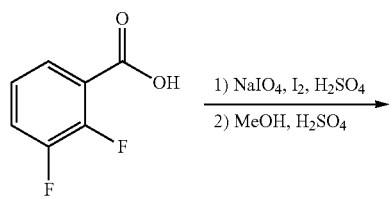

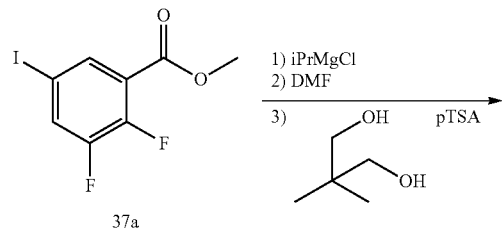

37a

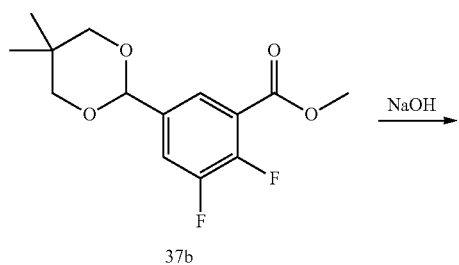

37b

37c

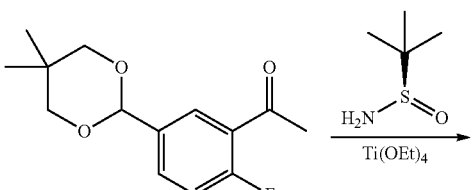

37d

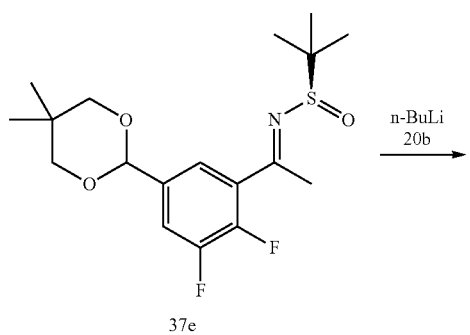

37e

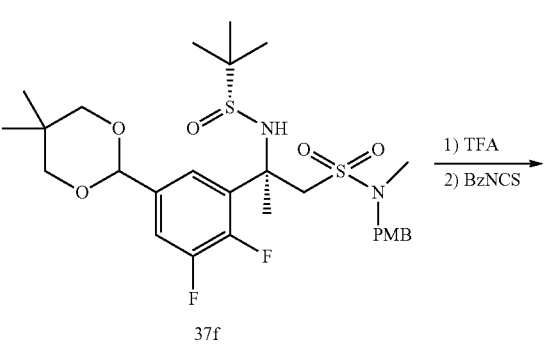

37f

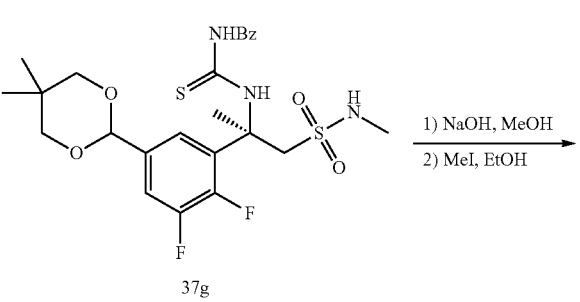

37g

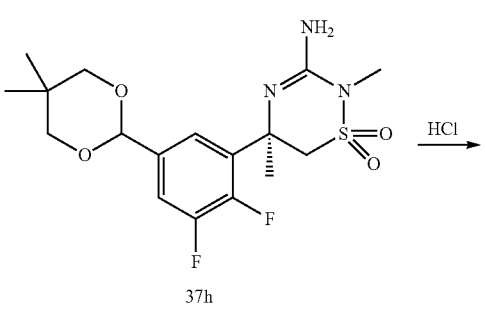

37h

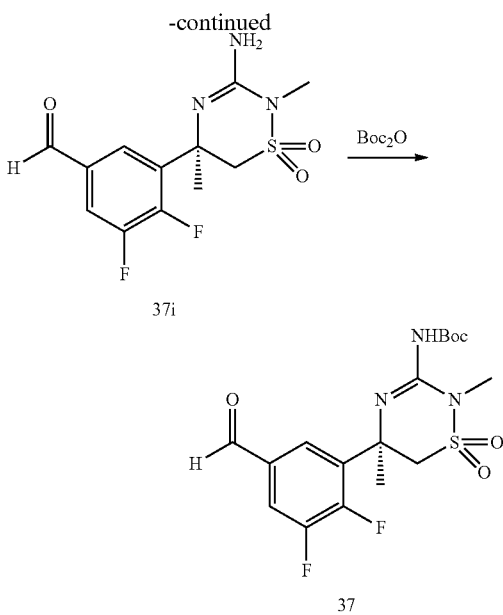

Preparation of methyl 2,3-difluoro-5-iodobenzoate (37a)

Iodine (Sigma-Aldrich, St. Louis, Mo., USA) (38.5 g, 152.0 mmol) and sodium periodate (Sigma-Aldrich, St. Louis, Mo., USA) (10.9, 51.0 mmol) were combined with conc. sulfuric acid (100 mL) and heated in a 40° C. bath with strong stirring for 40 min. 2,3-Difluorobenzoic acid (Combi-Blocks, San Diego, Calif., USA) (50 g, 316.0 mmol) was added in one portion. Additional conc. sulfuric acid (50 mL) was added to help with stirring. The dark viscous mixture was stirred for an additional hour. The reaction was poured over a mixture of ethyl acetate (300 mL) and ice (~500 mL). The flask was rinsed with additional ethyl acetate (100 mL). The mixture was stirred rapidly and decolorized with sat'd aqueous sodium sulfite. The phases were separated and the organic phase evaporated to dryness under reduced pressure. The crude acid was dissolved in methanol (300 mL) and treated with conc. sulfuric acid (50 mL). The solution was heated to reflux for 4.5 h. The mixture was concentrated to half volume under reduced pressure. Water (200 mL) and heptane (300 mL) were added and the phases mixed and separated. The organic phase was washed with brine (100 mL) and evaporated to dryness under reduced pressure. The crude off-white methyl 2,3-difluoro-5-iodobenzoate (37a, 78.0 g, 262 mmol, 83% yield) was used without further purification. MS (ESI +ve ion) m/z: [M+1]=299.0.

Preparation of methyl 5-(5,5-dimethyl-1,3-dioxan-2-yl)-2,3-difluorobenzoate (37b)

Isopropylmagnesium chloride (Sigma-Aldrich, St. Louis, Mo., USA) (2.0 M solution in THF, 150 ml, 300 mmol) was cooled in a −40° C. bath under nitrogen. A solution of methyl 2,3-difluoro-5-iodobenzoate (37a) (43 g, 144 mmol) in THF (100 mL) was added slowly over 30 min. The mixture was stirred for 10 min then a solution of DMF (30 mL, 387 mmol) in THF (30 mL) was added over 5 min. The solution was stirred for another 5 min then removed from the cold bath and allowed to warm to RT. It was poured into a rapidly stirring mixture of water (200 mL), sat'd aqueous ammonium chloride (100 mL) and ethyl acetate (200 mL). After 5 min the phases were separated and the organic phase washed with brine (100 mL). Toluene (100 mL), 2,2-dimethyl-1,3-propanediol (Sigma-Aldrich, St. Louis, Mo., USA) (20 g, 192 mmol), and p-toluenesulfonic acid monohydrate (Sigma-Aldrich, St. Louis, Mo., USA) (2.0 g, 10.5 mmol) were added and the mixture concentrated under reduced pressure to remove the ethyl acetate. The toluene solution was heated in a 60° C. bath for 90 mins then cooled to RT. Ethyl acetate (200 mL) and 50% saturated sodium bicarbonate (100 mL) were added and the phases mixed and separated. The organic phase was washed with brine (75 mL) and evaporated to dryness under reduced pressure. The crude methyl 5-(5,5-dimethyl-1,3-dioxan-2-yl)-2,3-difluorobenzoate (37b, 41.8 g) was used without further purification. MS (ESI +ve ion) m/z: [M+Na$^+$]=309.2.

Preparation of 5-(5,5-dimethyl-1,3-dioxan-2-yl)-2,3-difluorobenzoic acid (37c)

Methyl 5-(5,5-dimethyl-1,3-dioxan-2-yl)-2,3-difluorobenzoate (37b) (41.8 g, 146 mmol) was dissolved in methanol (150 mL) and treated with aqueous sodium hydroxide (10 N, 25 mL, 250 mmol). The solution was heated in a 50° C. bath for 15 min. The mixture was concentrated under reduced pressure to half volume. Water (50 mL) was added and the mixture washed with heptane (75 mL). The heptane layer was discarded. The aqueous methanol layer was diluted with water (150 mL), acidified with 5 N HCl (60 mL) and extracted with ethyl acetate (2×200 mL). The combined ethyl acetate layers were evaporated to dryness under reduced pressure to give 5-(5,5-dimethyl-1,3-dioxan-2-yl)-2,3-difluorobenzoic acid (31.6 g, 116 mmol, 79% yield). MS (ESI +ve ion) m/z: [M+Na$^+$]=295.2.

Preparation of 1-(5-(5,5-dimethyl-1,3-dioxan-2-yl)-2,3-difluorophenyl)ethanone (37d)

5-(5,5-Dimethyl-1,3-dioxan-2-yl)-2,3-difluorobenzoic acid (37c) (31.6 g, 116 mmol) was suspended in acetonitrile (200 mL) under nitrogen. 1,1'-Carbonyldiimidazole (Sigma-Aldrich, St. Louis, Mo., USA) (20 g, 123 mmol) was added and the reaction stirred at RT for 20 min. N,O-Dimethyl hydroxylamine hydrochloride (Sigma-Aldrich, St. Louis, Mo., USA) (15 g, 154 mmol) and triethylamine (20 mL, 144 mmol) were added and the reaction stirred for another 25 min. The mixture was concentrated to half volume under reduced pressure then ethyl acetate (300 mL) and HCl (300 mL of 0.5 N) were added. The phases were mixed and separated and the organic phase washed with brine (100 mL) before evaporating to dryness under reduced pressure. The crude amide was dissolved in THF (150 mL) under nitrogen and cooled in an ice bath. A solution of methylmagnesium chloride (Sigma-Aldrich, St. Louis, Mo., USA) (3.0 M solution in THF, 80 mL, 240 mmol) diluted in THF (120 mL) was added slowly over 20 min. Once the addition was complete, the reaction was carefully quenched by adding to a stirring mixture of ice (~200 mL), 1 N hydrochloric acid (250 mL) and ethyl acetate (350 mL). The mixture was stirred for 15 min then the phases were separated. The organic solution was washed with brine (100 mL) and evaporated to dryness under reduced pressure. The crude acetophenone 37d was used without further purification. MS (ESI +ve ion) m/z: [M+Na$^+$]=293.2.

Preparation of (R,E)-N-(1-(5-(5,5-dimethyl-1,3-dioxan-2-yl)-2,3-difluorophenyl)ethylidene)-2-methylpropane-2-sulfinamide (37e)

A suspension of crude 37d (31.8 g, 118 mmol) and (R)-2-methylpropane-2-sulfinamide (Asta Tech, Bristol, Pa., USA) (17.5 g, 144 mmol) in dioxane (20 mL) under nitrogen at RT was treated with titanium (IV) ethoxide (Sigma-Aldrich, St. Louis, Mo., USA) (30 mL, 145 mmol) heated in a 100° C. bath for 40 min. The reaction was cooled and poured into a rapidly stirring mixture of brine (100 mL) and heptane (200 mL). The mixture was stirred for 10 min then the phases were separated. The clear aqueous phase was discarded and the organic phase filtered through a pad of celite. The filtrate was returned to the separatory funnel and washed with brine (75 mL) before evaporating to dryness under reduced pressure. Purification using silica gel chromatography (0-40% ethyl acetate in heptane) gave (R,E)-N-(1-(5-(5,5-dimethyl-1,3-dioxan-2-yl)-2,3-difluorophenyl)ethylidene)-2-methylpropane-2-sulfinamide (37e, 12.8 g, 34.3 mmol, 29% yield) as a light yellow oil. MS (ESI +ve ion) m/z: [M+Na$^+$]=293.2. $^1$H NMR (400 MHz, CHLOROFORM-d) δ 7.40-7.55 (m, 2H), 5.34 (s, 1H), 3.76 (d, J=11.15 Hz, 2H), 3.63 (d, J=11.15 Hz, 2H), 2.76 (d, J=1.57 Hz, 3H), 1.23-1.36 (m, 12H), 0.80 (s, 3H).

Preparation of (R)-2-(5-(5,5-dimethyl-1,3-dioxan-2-yl)-2,3-difluorophenyl)-2-((R)-1,1-dimethylethylsulfinamido)-N-(4-methoxybenzyl)-N-methylpropane-1-sulfonamide (37f)

A solution of N-(4-Methoxybenzyl)-N-methylmethanesulfonamide (20b) (17 g, 74.1 mmol) in THF (50 mL) at 0° C. under nitrogen was treated with n-butyllithium (Sigma-Aldrich, St. Louis, Mo., USA) (2.5 M in hexanes, 27 mL, 67.5 mmol) dropwise and the mixture stirred for 20 min. A solution of (R,E)-N-(1-(5-(5,5-dimethyl-1,3-dioxan-2-yl)-2,3-difluorophenyl)ethylidene)-2-methylpropane-2-sulfinamide (37e) (12.8 g, 34.3 mmol) in toluene (10 mL) was added in one portion and the mixture stirred for 10 min. Sat'd aqueous ammonium chloride (30 mL) was added followed by water (100 mL) and ethyl acetate (150 mL). The phases were mixed and separated and the organic phase washed with brine (75 mL) before evaporating to dryness under reduced pressure. The crude was purified using silica gel chromatography (0-50% ethyl acetate in heptane, then purified again the mixed product/N-(4-methoxybenzyl)-N-methylmethanesulfonamide fractions with 0-50% ethyl acetate in DCM) to give (R)-2-(5-(5,5-dimethyl-1,3-dioxan-2-yl)-2,3-difluorophenyl)-2-((R)-1,1-dimethylethylsulfinamido)-N-(4-methoxybenzyl)-N-methylpropane-1-sulfonamide (37f, 5.8 g, 9.62 mmol, 28% yield). MS (ESI +ve ion) m/z: [M+H]=603.2.

Preparation of (R)—N-((2-(5-(5,5-dimethyl-1,3-dioxan-2-yl)-2,3-difluorophenyl)-1-(N-methylsulfamoyl)propan-2-yl)carbamothioyl)benzamide (37 g)

(R)-2-(5-(5,5-dimethyl-1,3-dioxan-2-yl)-2,3-difluorophenyl)-2-((R)-1,1-dimethylethylsulfinamido)-N-(4-methoxybenzyl)-N-methylpropane-1-sulfonamide (37f, 7.7 g, 12.8 mmol) was dissolved in DCM (50 mL) under nitrogen and treated with TFA (100 mL). The solution was stirred for 75 min. The red solution was evaporated to dryness under reduced pressure. The crude was redissolved in toluene (100 mL) and treated with 2,2-dimethyl-1,3-propanediol (Sigma-Aldrich, St. Louis, Mo., USA) (2.0 g, 19.2 mmol) and p-toluenesulfonic acid monohydrate (0.122 g), and the mixture heated in a 70° C. bath for 10 min. The mixture was evaporated to dryness under reduced pressure and the crude partitioned between ethyl acetate (350 mL) and 50% saturated aqueous sodium bicarbonate (100 mL). The organic layer was washed with brine (75 mL) and evaporated to dryness under reduced pressure. The crude was dissolved in DCM (50 mL) and treated with a solution of benzoyl isothiocyanate (Sigma-Aldrich, St. Louis, Mo., USA) (1.7 mL, 12.6 mmol) in DCM (10 mL). The mixture was stirred for 5 min. Methanol (10 mL) was added and the mixture evaporated to dryness under reduced pressure. The crude was partitioned between ethyl acetate (250 mL) and water (100 mL). The organic phase was evaporated to dryness under reduced pressure and the crude (R)—N-((2-(5-(5,5-dimethyl-1,3-dioxan-2-yl)-2,3-difluorophenyl)-1-(N-methylsulfamoyl)propan-2-yl)carbamothioyl)benzamide (37 g) (6.92 g, 12.78 mmol) used without purification. MS (ESI +ve ion) m/z: [M+H]=438.2.

Preparation of (R)-3-amino-5-(5-(5,5-dimethyl-1,3-dioxan-2-yl)-2,3-difluorophenyl)-2,5-dimethyl-5,6-dihydro-2H-1,2,4-thiadiazine 1,1-dioxide (37h)

A mixture of crude 37 g (6.92 g, 12.78 mmol) and 5 N sodium hydroxide (5 mL) in methanol (150 mL) was heated in a 50° C. bath for 40 min. The solution was concentrated to ~30 mL under reduced pressure then diluted with water (200 mL) and neutralized with 5 N HCl (5 mL). Ethyl acetate (250 mL) was added and the phases mixed and separated. The organic layer was washed with brine (50 mL) and evaporated to dryness under reduced pressure. The crude was dissolved in ethanol (50 mL) and treated with iodomethane (Sigma-Aldrich, St. Louis, Mo., USA) (1.5 mL, 24.15 mmol). The solution was heated in a 40° C. bath for 20 min then the bath temperature was increased to 70° C. The reaction was stirred for another 90 min then evaporated to dryness under reduced pressure. The crude was purified using silica gel chromatography (0-10% methanol in DCM) to give (R)-3-amino-5-(5-(5,5-dimethyl-1,3-dioxan-2-yl)-2,3-difluorophenyl)-2,5-dimethyl-5,6-dihydro-2H-1,2,4-thiadiazine 1,1-dioxide (37h, 2.44 g, 6.05 mmol, 47% yield). MS (ESI +ve ion) m/z: [M+H]=404.2.

Preparation of (R)-3-(3-amino-2,5-dimethyl-1,1-dioxido-5,6-dihydro-2H-1,2,4-thiadiazin-5-yl)-4,5-difluorobenzaldehyde (37i)

(R)-3-Amino-5-(5-(5,5-dimethyl-1,3-dioxan-2-yl)-2,3-difluorophenyl)-2,5-dimethyl-5,6-dihydro-2H-1,2,4-thiadiazine 1,1-dioxide (37h)(2.44 g, 6.05 mmol) was dissolved in acetone (75 mL) and treated with 5 N hydrochloric acid (20 mL). The solution was stirred at RT for 48 h. The mixture was concentrated to half volume under reduced pressure. Ethyl acetate (250 mL), water (100 mL), and 10 N NaOH (12 mL) were added and the phases mixed and separated. The organic phase was washed with brine (75 mL) and evaporated to dryness under reduced pressure to provide (R)-3-(3-amino-2,5-dimethyl-1,1-dioxido-5,6-dihydro-2H-1,2,4-thiadiazin-5-yl)-4,5-difluorobenzaldehyde (37i, 1.87 g, 5.89 mmol, 46% yield) which was used without further manipulation. MS (ESI +ve ion) m/z: [M+H]=318.0.

Preparation of (R)-tert-butyl (5-(2,3-difluoro-5-formylphenyl)-2,5-dimethyl-1,1-dioxido-5,6-dihydro-2H-1,2,4-thiadiazin-3-yl)carbamate (37)

A mixture of (R)-3-(3-amino-2,5-dimethyl-1,1-dioxido-5,6-dihydro-2H-1,2,4-thiadiazin-5-yl)-4,5-difluorobenzaldehyde (37i) (1.87 g, 5.89 mmol) and di-tert-butyl dicarbonate (Sigma-Aldrich, St. Louis, Mo., USA) (2.0 g, 9.16 mmol) in THF (10 mL) was heated in a 50° C. bath under nitrogen for 45 min. Ethyl acetate (200 mL) and 0.5 N HCl (75 mL) were added and the phases mixed and separated. The organic layer was washed with brine (75 mL) and evaporated to dryness under reduced pressure. Purification using silica gel chromatography (0-10% ethyl acetate in heptane) gave (R)-tert-butyl (5-(2,3-difluoro-5-formylphenyl)-2,5-dimethyl-1,1-dioxido-5,6-dihydro-2H-1,2,4-thiadiazin-3-yl)carbamate (37) (1.15 g, 2.75 mmol, 47% yield) as a white solid. MS (ESI +ve ion) m/z: [M+Na]=440.0.

EXAMPLES

Example 100: (R,Z)-9-amino-7-(5-(2-(5-chloropyridin-2-yl)-2-fluorovinyl)-2-fluorophenyl)-7-methyl-5-thia-8-azaspiro[3.5]non-8-ene 5,5-dioxide

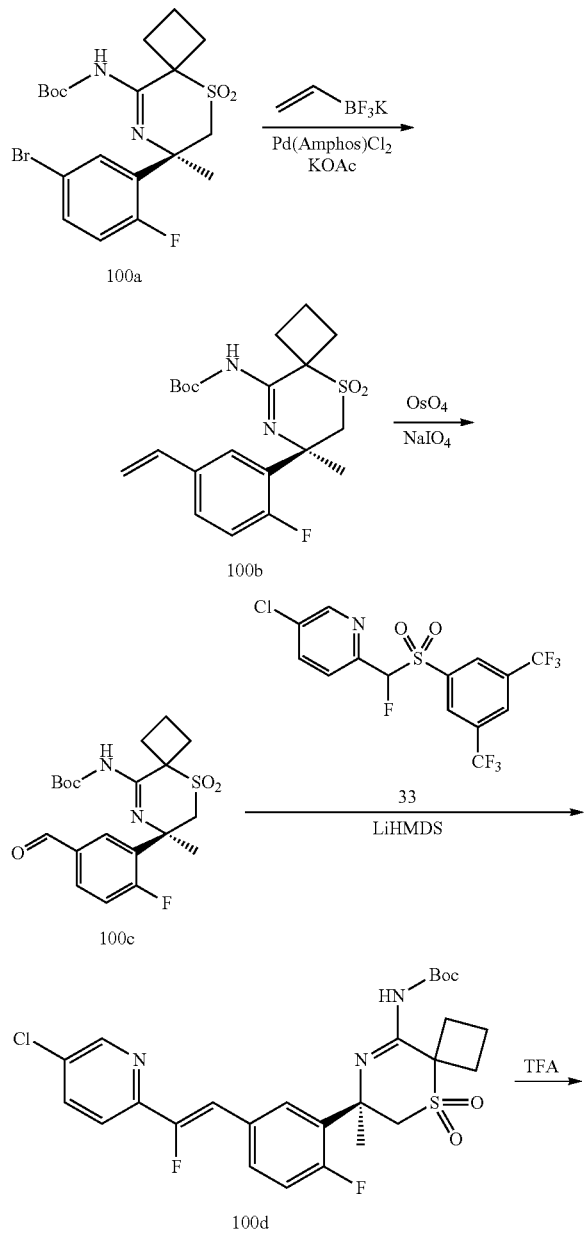

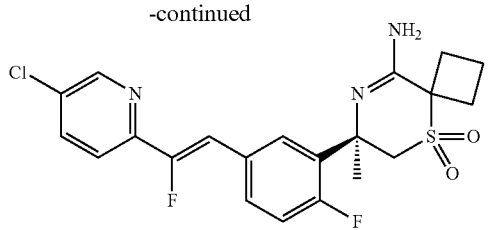

Preparation of (R)-tert-butyl (7-(2-fluoro-5-vinylphenyl)-7-methyl-5,5-dioxido-5-thia-8-azaspiro[3.5]non-8-en-9-yl)carbamate (100b)

(R)-tert-Butyl (7-(5-bromo-2-fluorophenyl)-7-methyl-5,5-dioxido-5-thia-8-azaspiro[3.5]non-8-en-9-yl)carbamate (100a, prepared according to the procedures described in WO 2014059185A1) (1.0 g, 2.1 mmol), potassium acetate (Sigma-Aldrich Chemical Company, Inc., St. Louis, Mo., USA) (0.62 g, 6.31 mmol), potassium vinyltrifluoroborate (Sigma-Aldrich Chemical Company, Inc., St. Louis, Mo., USA) (0.36 g, 2.73 mmol), and 1,1-bis[(di-t-butyl-p-methylaminophenyl]palladium(II) chloride (Sigma-Aldrich Chemical Company, Inc., St. Louis, Mo., USA) (0.15 g, 0.21 mmol) were taken up in 10 mL of 3:1 MeCN:water and heated at 75° C. for 5 h. The reaction was cooled to RT and diluted with 250 mL of EtOAc. The mixture was washed with 10 mL of water followed by 10 mL of brine, then dried over $MgSO_4$. Filtration and concentration under reduced pressure followed by flash chromatography on silica gel (1-25% EtOAc/heptane) afforded (R)-tert-butyl (7-(2-fluoro-5-vinylphenyl)-7-methyl-5,5-dioxido-5-thia-8-azaspiro[3.5]non-8-en-9-yl)carbamate (100b) (0.35 g, 39% yield) as a white solid. MS (ESI, positive ion) m/z: 423. $^1$H NMR (400 MHz, CHLOROFORM-d) δ 10.88 (br s, 1H), 7.31-7.39 (m, 2H), 7.01-7.10 (m, 1H), 6.53-6.73 (m, 1H), 5.63-5.76 (m, 1H), 5.26 (d, J=10.95 Hz, 1H), 3.87 (d, J=14.87 Hz, 1H), 3.50 (d, J=15.06 Hz, 1H), 3.09 (td, J=8.75, 12.42 Hz, 1H), 2.67-2.80 (m, 2H), 2.53-2.64 (m, 1H), 2.11-2.17 (m, 2H), 1.90 (s, 3H), 1.54 (s, 9H).

Preparation of (R)-tert-butyl (7-(2-fluoro-5-formylphenyl)-7-methyl-5,5-dioxido-5-thia-8-azaspiro[3.5]non-8-en-9-yl)carbamate (100c)

(R)-tert-Butyl (7-(2-fluoro-5-vinylphenyl)-7-methyl-5,5-dioxido-5-thia-8-azaspiro[3.5]non-8-en-9-yl)carbamate (100b) (0.36 g, 0.86 mmol) was taken up in 10 mL of 3:1 THF:water. Osmium tetroxide (Sigma-Aldrich Chemical Company, Inc., St. Louis, Mo., USA, 2.5 wt. % solution in 2-methyl-2-propanol, 0.253 mL, 0.026 mmol) and sodium periodate (Sigma-Aldrich Chemical Company, Inc., St. Louis, Mo., USA, 0.55 g, 2.59 mmol) were added. The mixture was stirred for 15 h. It was quenched with 20 mL of aq. $NaS_2O_3$ and stirred for 15 min. The mixture, which tested negative for peroxide content, was extracted with 25 mL of EtOAc. The organic portion was washed with 10 mL of brine and dried over $MgSO_4$. Filtration and concentration under reduced pressure, followed by flash chromatography on silica gel (1-25% EtOAc/heptane) afforded (R)-tert-butyl (7-(2-fluoro-5-formylphenyl)-7-methyl-5,5-dioxido-5-thia-8-azaspiro[3.5]non-8-en-9-yl)carbamate (100c) (0.25 g, 68% yield) as a white solid. MS (ESI, positive ion) m/z: 447. $^1$H NMR (400 MHz, CHLOROFORM-d) δ 10.79-11.02 (m, 1H), 9.74-9.98 (m, 1H), 7.88-7.94 (m, 1H), 7.82-7.87 (m, 1H), 7.26-7.33 (m, 1H), 3.91 (d, J=15.06 Hz, 1H), 3.48 (d, J=15.06 Hz, 1H), 2.84-3.09 (m, 2H), 2.69-2.81 (m, 1H), 2.54-2.64 (m, 1H), 2.11-2.24 (m, 2H), 1.92 (s, 3H), 1.55 (s, 9H).

Preparation of (R,Z)-tert-butyl (7-(5-(2-(5-chloropyridin-2-yl)-2-fluorovinyl)-2-fluorophenyl)-7-methyl-5,5-dioxido-5-thia-8-azaspiro[3.5]non-8-en-9-yl)carbamate (100d)

(R)-tert-butyl (7-(2-fluoro-5-formylphenyl)-7-methyl-5,5-dioxido-5-thia-8-azaspiro[3.5]non-8-en-9-yl)carbamate (100c) (0.05 g, 0.11 mmol) and 2-(((3,5-bis(trifluoromethyl)phenyl)sulfonyl)fluoromethyl)-5-chloropyridine (33) (0.07 g, 0.17 mmol) were taken up in 0.5 mL of THF. Lithium bis(trimethylsilyl)amide (Sigma-Aldrich Chemical Company, Inc., St. Louis, Mo., USA, 1.0 M solution in THF, 0.28 mL, 0.28 mmol) was added to the mixture, followed by 0.15 mL of DMSO. The mixture was stirred for 15 min. The reaction was quenched with 5 mL of sat'd aqueous NH₄Cl and extracted with 15 mL of EtOAc. The organic extracts were washed with 5 mL of brine and dried over MgSO₄. Filtration and concentration under reduced pressure, followed by flash chromatography on silica gel (10-25% EtOAc/heptane) afforded (R,Z)-tert-butyl (7-(5-(2-(5-chloropyridin-2-yl)-2-fluorovinyl)-2-fluorophenyl)-7-methyl-5,5-dioxido-5-thia-8-azaspiro[3.5]non-8-en-9-yl)carbamate (100d) (55 mg, 88% yield) as a yellow solid. ¹H NMR (400 MHz, CHLOROFORM-d) δ 10.79-10.99 (m, 1H), 8.54 (s, 1H), 7.74 (dd, J=2.15, 8.61 Hz, 1H), 7.65 (br d, J=7.24 Hz, 2H), 7.53 (d, J=8.61 Hz, 1H), 7.08-7.17 (m, 1H), 7.02 (d, J=38.73 Hz, 1H), 3.79-3.96 (m, 1H), 3.46-3.57 (m, 1H), 2.98-3.18 (m, 1H), 2.68-2.84 (m, 2H), 2.51-2.65 (m, 1H), 2.10-2.23 (m, 2H), 1.91-1.98 (m, 3H), 1.58 (s, 9H).

Preparation of (R,Z)-9-amino-7-(5-(2-(5-chloropyridin-2-yl)-2-fluorovinyl)-2-fluorophenyl)-7-methyl-5-thia-8-azaspiro[3.5]non-8-ene 5,5-dioxide (Example 100)

A mixture of (R,Z)-tert-Butyl (7-(5-(2-(5-chloropyridin-2-yl)-2-fluorovinyl)-2-fluorophenyl)-7-methyl-5,5-dioxido-5-thia-8-azaspiro[3.5]non-8-en-9-yl)carbamate (100d) (55 mg, 0.10 mmol) in 2 mL of DCM and 0.5 mL of TFA was stirred at RT for 30 min, then concentrated under reduced pressure. The residue was taken up in 25 mL of EtOAc and washed with 15 mL of sat'd aqueous NaHCO₃ and 15 mL of brine, then dried over MgSO₄. Filtration and concentration under reduced pressure followed by flash chromatography on silica gel (5-70% EtOAc/heptane) afforded (R,Z)-9-amino-7-(5-(2-(5-chloropyridin-2-yl)-2-fluorovinyl)-2-fluorophenyl)-7-methyl-5-thia-8-azaspiro[3.5]non-8-ene 5,5-dioxide (100) (36 mg, 80% yield) as a white solid. MS (ESI, positive ion) m/z: 452. ¹H NMR (400 MHz, CHLOROFORM-d) δ 8.52-8.57 (m, 1H), 7.73 (dd, J=2.35, 8.61 Hz, 2H), 7.64-7.70 (m, 1H), 7.51-7.58 (m, 1H), 6.97-7.13 (m, 2H), 3.39-3.65 (m, 2H), 2.97-3.16 (m, 1H), 2.77-2.89 (m, 1H), 2.42-2.61 (m, 2H), 2.17-2.32 (m, 2H), 1.81 (s, 3H). NH₂ peak was not observed.

Example 101: (1R,4R,5S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide

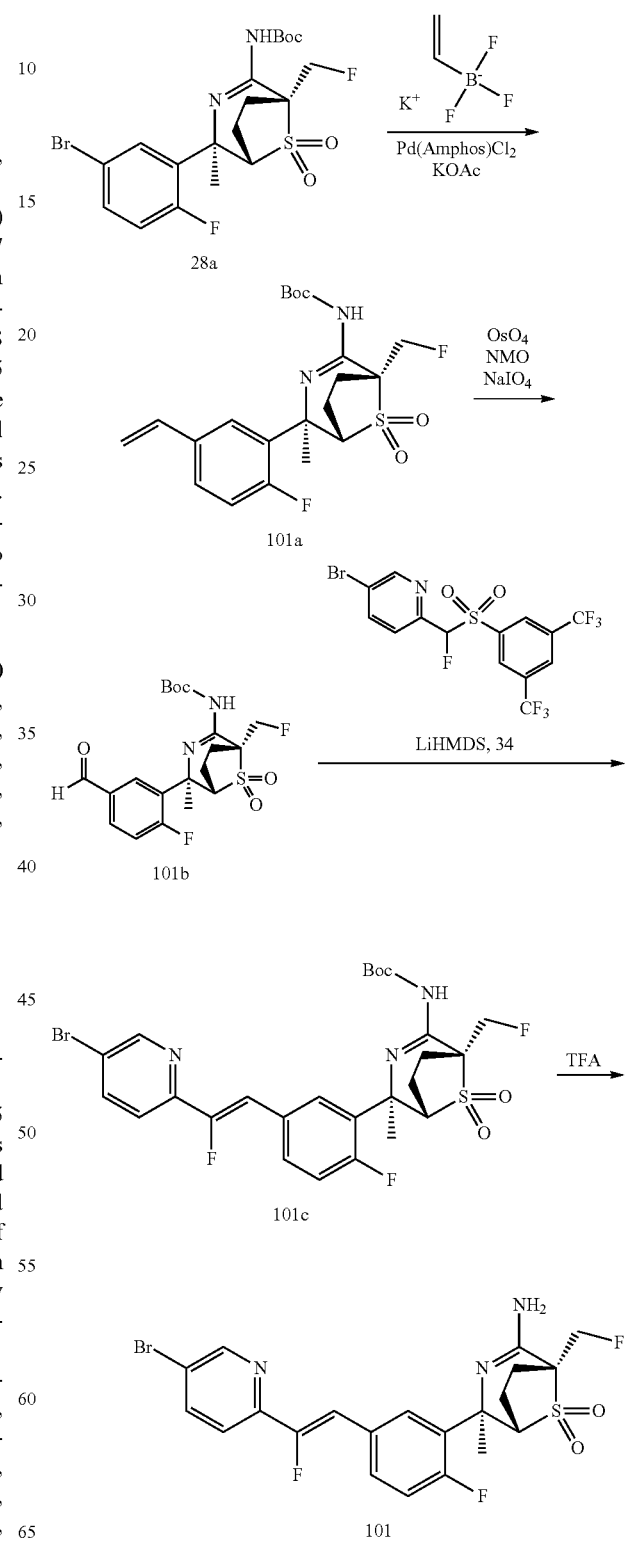

Preparation of tert-butyl ((1R,4R,5S)-4-(2-fluoro-5-vinylphenyl)-1-(fluoromethyl)-4-methyl-8,8-dioxido-8-thia-3-azabicyclo[3.2.1]oct-2-en-2-yl)carbamate (101a)

Tert-butyl ((1R,4R,5S)-4-(5-bromo-2-fluorophenyl)-1-(fluoromethyl)-4-methyl-8,8-dioxido-8-thia-3-azabicyclo[3.2.1]oct-2-en-2-yl)carbamate (28a) (1.38 g, 2.80 mmol), potassium vinyltrifluoroborate (0.47 g, 3.50 mmol), 1,1-bis[(di-t-butyl-p-methylaminophenyl]palladium(II) chloride (99 mg, 0.14 mmol), and potassium acetate (0.83 g, 8.39 mmol) were mixed in CH$_3$CN/H$_2$O (3:1, 12 mL, v/v) and argon was bubbled through the mixture for 3 min. The mixture was heated to 75° C. for 3 h, then cooled to RT. EtOAc and sat'd aqueous ammonium chloride solution were added, the layers were separated, and the aqueous layer was extracted with EtOAc (2×). The combined extracts were dried over anhydrous magnesium sulfate, filtered, and concentrated in vacuo to give an oil. The oil was purified by silica gel chromatography (0 to 50% EtOAc/heptane) to give 101a (534 mg, 1.21 mmol, 43% yield) as a yellow solid. MS m/z=441.1 [M+H]$^+$.

Preparation of tert-butyl ((1R,4R,5S)-4-(2-fluoro-5-formylphenyl)-1-(fluoromethyl)-4-methyl-8,8-dioxido-8-thia-3-azabicyclo[3.2.1]oct-2-en-2-yl)carbamate (101b)

4-Methylmorpholine-4-oxide (27 mg, 0.23 mmol) and osmium tetroxide (2.5 wt. %, solution in 2-methyl-2-propanol, 12 µL, 1.14 µmol) were added to a mixture of tert-butyl ((1R,4R,5S)-4-(2-fluoro-5-vinylphenyl)-1-(fluoromethyl)-4-methyl-8,8-dioxido-8-thia-3-azabicyclo[3.2.1]oct-2-en-2-yl)carbamate (101a) (50 mg, 0.11 mmol) in THF (0.6 mL) and water (0.4 mL). The mixture was stirred at RT for 24 h, then sodium meta-periodate (73 mg, 0.34 mmol) was added. This mixture was stirred overnight and then EtOAc and sat'd aqueous sodium thiosulfate was added. This biphasic mixture was stirred until the layers became clear and then they were separated. The aqueous layer was extracted with EtOAc and the extracts were combined, dried over anhydrous magnesium sulfate, filtered, and concentrated in vacuo to give an oil that was purified by silica gel chromatography (0 to 50% EtOAc/heptane) to give tert-butyl ((1R,4R,5S)-4-(2-fluoro-5-formylphenyl)-1-(fluoromethyl)-4-methyl-8,8-dioxido-8-thia-3-azabicyclo[3.2.1]oct-2-en-2-yl)carbamate (101b) (46 mg, 0.10 mmol, 92% yield) as a white solid. MS m/z=465.0 [M+Na]$^+$. $^1$H NMR (400 MHz, CHLOROFORM-d) δ 10.85 (br. s., 1H) 9.97 (s, 1H) 7.93-8.01 (m, 2H) 7.33 (dd, J=11.35, 8.22 Hz, 1H) 5.00-5.33 (m, 2H) 3.92 (d, J=3.13 Hz, 1H) 2.31-2.43 (m, 2H) 2.02-2.15 (m, 5H) 1.57 (s, 9H).

Preparation of tert-butyl ((1R,4R,5S)-4-(5-((Z)-2-(5-bromopyridin-2-yl)-2-fluorovinyl)-2-fluorophenyl)-1-(fluoromethyl)-4-methyl-8,8-dioxido-8-thia-3-azabicyclo[3.2.1]oct-2-en-2-yl)carbamate (101c)

LiHMDS (0.26 mL of 1.0 M solution in THF, 0.26 mmol) was added to a solution of tert-butyl ((1R,4R,5S)-4-(2-fluoro-5-formylphenyl)-1-(fluoromethyl)-4-methyl-8,8-dioxido-8-thia-3-azabicyclo[3.2.1]oct-2-en-2-yl)carbamate (101b) (46 mg, 0.10 mmol) and 2-(((3,5-bis(trifluoromethyl)phenyl)sulfonyl)fluoromethyl)-5-bromopyridine (34) (73 mg, 0.16 mmol) in THF (0.5 mL). The mixture was stirred for 5 min before DMSO (0.2 mL) was added. This mixture was stirred for 3 h at RT, EtOAc and saturated aqueous ammonium chloride were added, the layers were separated, and the organic layer was washed with water (2×), dried over anhydrous magnesium sulfate, filtered, and concentrated in vacuo to give an oil. The oil was purified by silica gel chromatography (0 to 30% EtOAc/heptane) to give tert-butyl ((1R,4R,5S)-4-(5-((Z)-2-(5-bromopyridin-2-yl)-2-fluorovinyl)-2-fluorophenyl)-1-(fluoromethyl)-4-methyl-8,8-dioxido-8-thia-3-azabicyclo[3.2.1]oct-2-en-2-yl)carbamate (101c) as a white solid. MS m/z=614.0 [M+H]$^+$. $^1$H NMR (400 MHz, CHLOROFORM-d) δ 10.88 (s, 1H), 8.62-8.67 (m, 1H), 7.90 (d, J=8.50 Hz, 1H), 7.82 (d, J=7.63 Hz, 1H), 7.58-7.69 (m, 1H), 7.43 (dd, J=8.41, 1.37 Hz, 1H), 7.16 (dd, J=11.74, 8.41 Hz, 1H), 7.05 (d, J=38.54 Hz, 1H), 5.00-5.35 (m, 2H), 3.92 (d, J=4.30 Hz, 1H), 2.27-2.44 (m, 2H), 2.00-2.17 (m, 5H), 1.59 (s, 9H). $^{19}$F NMR (376 MHz, CHLOROFORM-d) δ -110.63 (s, 1F), -122.13 (s, 1F), -228.68 (s, 1F).

Preparation of Example 101 tert-Butyl ((1R,4R,5 S)-4-(5-((Z)-2-(5-bromopyridin-2-yl)-2-fluorovinyl)-2-fluorophenyl)-1-(fluoromethyl)-4-methyl-8,8-dioxido-8-thia-3-azabicyclo[3.2.1]oct-2-en-2-yl)carbamate (101c) (19 mg, 0.031 mmol) was dissolved in DCM/TFA (1:1, v/v, 3 mL) and stirred at RT for 2 h. The solvent was removed in vacuo and the residue was dissolved in DCM. This solution was washed with 2 N aqueous sodium carbonate solution (3×), brine (1×), dried over anhydrous magnesium sulfate, filtered, and concentrated in vacuo to give an oil that was purified by silica gel chromatography (0 to 100% EtOAc/heptane) to give (1R,4R,5 S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide (101) (13 mg, 0.025 mmol, 82% yield) as a white solid. MS m/z=514.0 [M+H]$^+$. $^1$H NMR (400 MHz, CHLOROFORM-d) δ 8.61-8.65 (m, 1H), 7.86-7.92 (m, 1H), 7.79-7.86 (m, 1H), 7.66-7.74 (m, 1H), 7.50 (dd, J=8.41, 1.37 Hz, 1H), 6.95-7.14 (m, 2H), 4.86-5.28 (m, 2H), 3.84 (br d, J=5.87 Hz, 1H), 1.99-2.26 (m, 3H), 1.91-1.96 (m, 3H), 1.54-1.68 (m, 1H). Note: NH$_2$ peak was not observed. $^{19}$F NMR (376 MHz, CHLOROFORM-d) δ -111.66 (s, 1F), -123.58 (s, 1F), -227.81 (s, 1F).

Example 102: 6-((Z)-2-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-1-fluorovinyl)nicotinonitrile

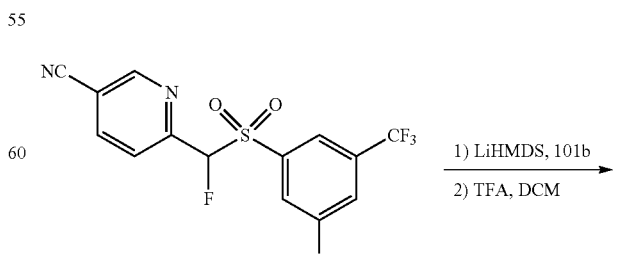

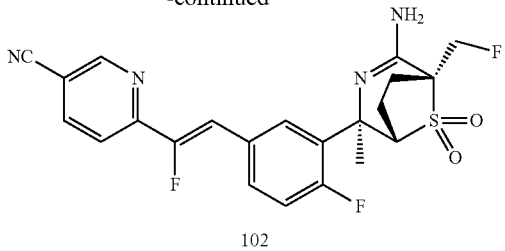

102

This compound (37 mg, 0.08 mmol, 37% overall yield) as a white solid was prepared in a fashion similar to that described for Example 101, here starting with aldehyde 101b (100 mg, 0.23 mmol) and sulfone 35 (121 mg, 0.29 mmol). MS m/z=461.1 [M+H]$^+$. $^1$H NMR (400 MHz, CHLOROFORM-d) δ 8.82 (br. s., 1H), 8.03 (d, J=7.82 Hz, 1H), 7.88 (d, J=6.46 Hz, 1H), 7.65-7.79 (m, 2H), 7.19 (br. s., 1H), 7.11 (t, J=9.78 Hz, 1H), 4.69-5.43 (m, 4H), 3.85 (br. s., 1H), 2.22 (br. s., 1H), 2.00-2.15 (m, 2H), 1.93 (br. s., 3H), 1.60 (t, J=11.15 Hz, 1H). $^{19}$F NMR (376 MHz, CHLOROFORM-d) δ −110.27 (s, 1F), −124.89 (s, 1F), −227.80.

Example 103: (R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile

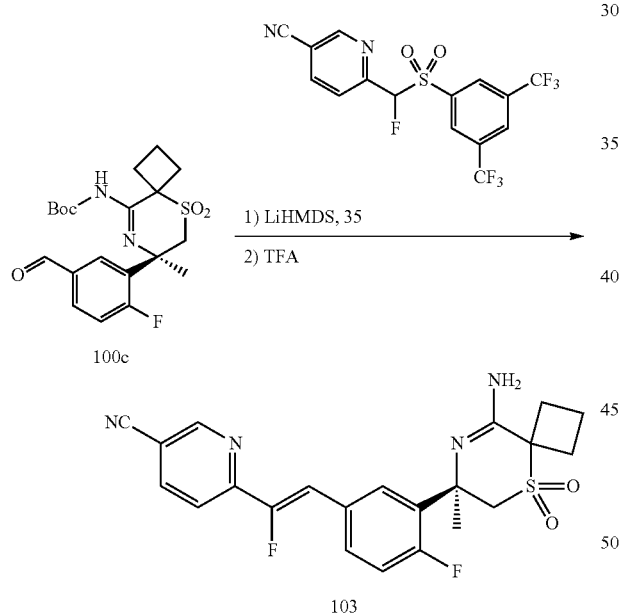

A mixture of (R)-tert-Butyl (7-(2-fluoro-5-formylphenyl)-7-methyl-5,5-dioxido-5-thia-8-azaspiro[3.5]non-8-en-9-yl)carbamate (100c) (80 mg, 0.19 mmol) and 6-(((3,5-bis(trifluoromethyl)phenyl)sulfonyl)fluoromethyl)nicotinonitrile (35) (39 mg, 0.09 mmol) in 1 mL of THF was treated with lithium bis(trimethylsilyl)amide (1.0 M solution in THF, 0.23 mL, 0.23 mmol) followed by 0.15 mL of DMSO. The mixture was stirred for 1 h, quenched with 5 mL of sat'd aqueous NH$_4$Cl, and extracted with 15 mL of EtOAc. The organic extracts were washed with 5 mL of brine and dried over MgSO$_4$. Filtration and concentration under reduced pressure, followed by flash chromatography on silica gel (10-25% EtOAc/heptane) afforded (R,Z)-tert-butyl (7-(5-(2-(5-cyanopyridin-2-yl)-2-fluorovinyl)-2-fluorophenyl)-7-methyl-5,5-dioxido-5-thia-8-azaspiro[3.5]non-8-en-9-yl)carbamate (10 mg, 19% yield) as a white solid. The white solid (10 mg, 0.018 mmol) was taken up in 1 mL of DCM and treated with 0.1 mL of TFA. The mixture was stirred for 30 min. The reaction was quenched with 10 mL of sat'd aqueous NaHCO$_3$ and was extracted with 15 mL of DCM. The organic extracts were dried over MgSO$_4$. Filtration and concentration under reduced pressure afforded (R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile (103) (7 mg, 82% yield) as a white solid. MS (ESI, positive ion) m/z: 443. $^1$H NMR (400 MHz, CHLOROFORM-d) δ 8.77-8.84 (m, 1H), 7.98-8.05 (m, 1H), 7.74-7.79 (m, 1H), 7.64-7.72 (m, 2H), 7.04-7.20 (m, 2H), 3.40-3.73 (m, 2H), 3.00-3.16 (m, 1H), 2.78-2.94 (m, 1H), 2.48-2.65 (m, 2H), 2.15-2.33 (m, 2H), 1.86 (s, 3H). NH$_2$ peak was not observed.

Example 104: (R,Z)-3-amino-5-(5-(2-(5-chloropyridin-2-yl)-2-fluorovinyl)-2-fluorophenyl)-2,5-dimethyl-5,6-dihydro-2H-1,2,4-thiadiazine 1,1-dioxide

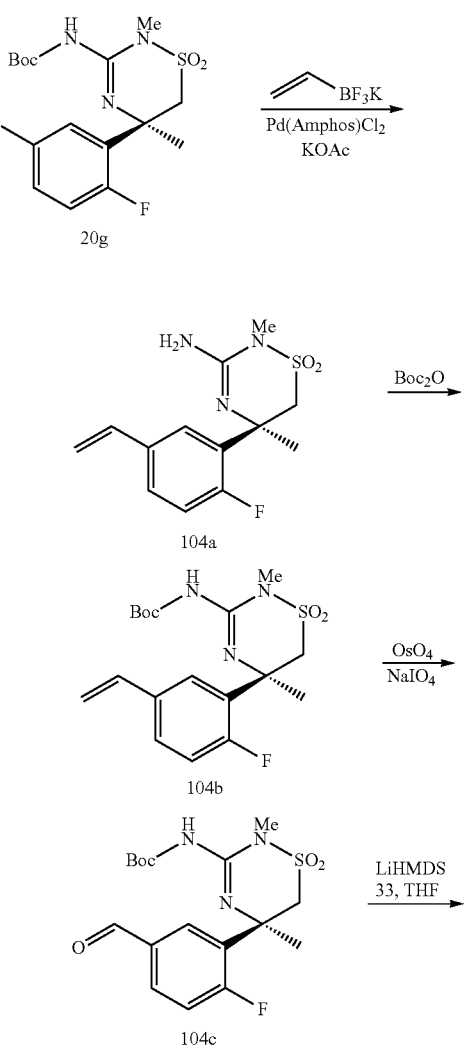

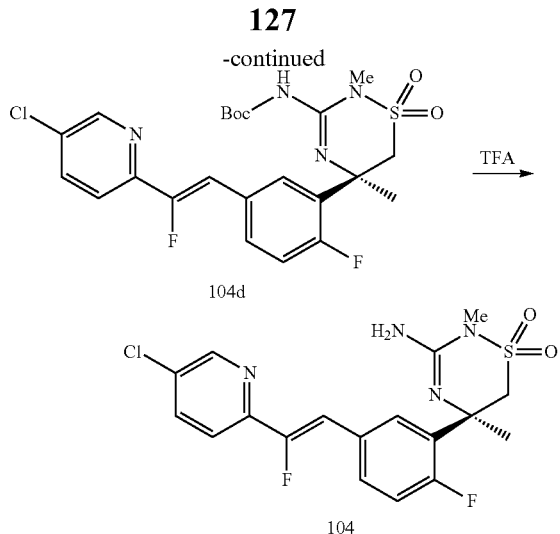

104d

104

Preparation of (R)-3-amino-5-(2-fluoro-5-vinylphenyl)-2,5-dimethyl-5,6-dihydro-2H-1,2,4-thiadiazine 1,1-dioxide (104a)

(R)-tert-Butyl (5-(5-bromo-2-fluorophenyl)-2,5-dimethyl-1,1-dioxido-5,6-dihydro-2H-1,2,4-thiadiazin-3-yl)carbamate (20 g) (1.15 g, 2.55 mmol), 1,1-bis[(di-t-butyl-p-methylaminophenyl]palladium(II) chloride (0.14 g, 0.19 mmol), potassium vinyltrifluoroborate (0.44 g, 3.32 mmol), and potassium acetate (0.75 g, 7.66 mmol, Sigma-Aldrich) were taken up in 20 mL of 3:1 MeCN:water and heated at 75° C. for 15 h. The mixture was cooled to RT and diluted with 50 mL of EtOAc. The mixture was washed with 20 mL of water and 20 mL of brine, then dried over $MgSO_4$. Filtration and concentration under reduced pressure, followed by flash chromatography on silica gel (5-25% EtOAc/heptane) afforded (R)-3-amino-5-(2-fluoro-5-vinylphenyl)-2,5-dimethyl-5,6-dihydro-2H-1,2,4-thiadiazine 1,1-dioxide (104a) (0.30 g, 40% yield) as a solid. MS (ESI, positive ion) m/z: 298.

Preparation of (R)-tert-butyl (5-(2-fluoro-5-vinylphenyl)-2,5-dimethyl-1,1-dioxido-5,6-dihydro-2H-1,2,4-thiadiazin-3-yl)carbamate (104b)

(R)-3-Amino-5-(2-fluoro-5-vinylphenyl)-2,5-dimethyl-5,6-dihydro-2H-1,2,4-thiadiazine 1,1-dioxide (104a) (0.30 g, 1.0 mmol) was taken up in 10 mL of dioxane. Di-tert-butyl dicarbonate (0.22 g, 1.01 mmol) was added. The mixture was stirred for 15 h. The mixture was diluted with 30 mL of EtOAc and washed with 10 mL of water and 10 mL of brine, then dried over $MgSO_4$. Filtration and concentration under reduced pressure afforded (R)-tert-butyl (5-(2-fluoro-5-vinylphenyl)-2,5-dimethyl-1,1-dioxido-5,6-dihydro-2H-1,2,4-thiadiazin-3-yl)carbamate (104b) (33 mg, 82% yield) as a clear oil. MS (ESI, positive ion) m/z: 398. $^1$H NMR (400 MHz, CHLOROFORM-d) δ 10.55-10.69 (m, 1H), 7.33-7.42 (m, 2H), 7.02-7.12 (m, 1H), 6.64 (dd, J=10.86, 17.51 Hz, 1H), 5.66 (d, J=17.41 Hz, 1H), 5.26 (d, J=10.95 Hz, 1H), 4.24 (d, J=13.89 Hz, 1H), 3.74 (d, J=14.08 Hz, 1H), 3.20-3.26 (m, 3H), 1.89 (s, 3H), 1.56 (s, 9H).

Preparation of (R)-tert-butyl (5-(2-fluoro-5-formylphenyl)-2,5-dimethyl-1,1-dioxido-5,6-dihydro-2H-1,2,4-thiadiazin-3-yl)carbamate (104c)

(R)-tert-Butyl (5-(2-fluoro-5-vinylphenyl)-2,5-dimethyl-1,1-dioxido-5,6-dihydro-2H-1,2,4-thiadiazin-3-yl)carbamate (104b) (0.43 g, 1.1 mmol), osmium tetroxide (2.5 wt. % solution in 2-methyl-2-propanol, 0.32 mL, 0.032 mmol) and sodium periodate (0.69 g, 3.25 mmol) were taken up in 10 mL of 3:1 THF:water. The mixture was stirred for 15 h. The reaction was diluted with 15 mL of EtOAc and quenched with 15 mL of aq. $Na_2S_2O_3$. The mixture was stirred for 15 min and tested negative for peroxides. The mixture was diluted with 10 mL of water and extracted with 20 mL of EtOAc. The organic extracts were washed with 15 mL of brine and dried over $MgSO_4$. Filtration and concentration under reduced pressure afforded (R)-tert-butyl (5-(2-fluoro-5-formylphenyl)-2,5-dimethyl-1,1-dioxido-5,6-dihydro-2H-1,2,4-thiadiazin-3-yl)carbamate (104c) (0.39 g, 90% yield) as a sticky solid. MS (ESI, positive ion) m/z: 400. $^1$H NMR (400 MHz, CHLOROFORM-d) δ 10.58-10.80 (m, 1H), 9.84-9.92 (m, 1H), 7.83-7.90 (m, 1H), 7.80 (dd, J=1.96, 8.02 Hz, 1H), 7.20-7.25 (m, 1H), 4.23 (dd, J=1.17, 14.08 Hz, 1H), 3.63 (d, J=14.08 Hz, 1H), 3.18 (s, 3H), 1.83-1.86 (m, 3H), 1.50 (s, 9H).

Preparation of (R,Z)-tert-butyl (5-(5-(2-(5-chloropyridin-2-yl)-2-fluorovinyl)-2-fluorophenyl)-2,5-dimethyl-1,1-dioxido-5,6-dihydro-2H-1,2,4-thiadiazin-3-yl)carbamate (104d)

(R)-tert-Butyl (5-(2-fluoro-5-formylphenyl)-2,5-dimethyl-1,1-dioxido-5,6-dihydro-2H-1,2,4-thiadiazin-3-yl)carbamate (104c, 72 mg, 0.18 mmol) was taken up in 2 mL of THF. 2-(((3,5-bis(trifluoromethyl)phenyl)sulfonyl)fluoromethyl)-5-chloropyridine (33, 114 mg, 0.27 mmol) and lithium bis(trimethylsilyl)amide (1.0 M solution in THF, 0.45 mL, 0.45 mmol) were added. 0.5 mL of DMSO was then added to the mixture. The mixture was stirred for 1 h. The reaction was quenched with 10 mL of sat'd aqueous $NH_4Cl$ and diluted with 10 mL of water. The mixture was extracted with 20 mL of EtOAc and the organic extracts were washed with 10 mL of brine and dried over $MgSO_4$. Filtration and concentration under reduced pressure, followed by flash chromatography on silica gel (5 to 30% EtOAc/heptane) afforded (R,Z)-tert-butyl (5-(5-(2-(5-chloropyridin-2-yl)-2-fluorovinyl)-2-fluorophenyl)-2,5-dimethyl-1,1-dioxido-5,6-dihydro-2H-1,2,4-thiadiazin-3-yl)carbamate (104d) (49 mg, 52% yield) as a white solid. MS (ESI, positive ion) m/z: 527.

Preparation of (R,Z)-3-amino-5-(5-(2-(5-chloropyridin-2-yl)-2-fluorovinyl)-2-fluorophenyl)-2,5-dimethyl-5,6-dihydro-2H-1,2,4-thiadiazine 1,1-dioxide (104)

(R,Z)-tert-Butyl (5-(5-(2-(5-chloropyridin-2-yl)-2-fluorovinyl)-2-fluorophenyl)-2,5-dimethyl-1,1-dioxido-5,6-dihydro-2H-1,2,4-thiadiazin-3-yl)carbamate (104d) (49 mg, 0.09 mmol) was taken up in 3 mL of DCM and 0.5 mL of TFA. After 30 min, the mixture was concentrated under reduced pressure. The residue was taken up in 20 mL of EtOAc and washed with 10 mL of water and 10 mL of brine, then dried over $MgSO_4$. Filtration and concentration under reduced pressure, followed by flash chromatography on silica gel (25 to 100% EtOAc/heptane) afforded (R,Z)-3-amino-5-(5-(2-(5-chloropyridin-2-yl)-2-fluorovinyl)-2-fluorophenyl)-2,5-dimethyl-5,6-dihydro-2H-1,2,4-thiadiazine 1,1-dioxide (104) (25 mg, 63% yield) as a white solid. MS (ESI, positive ion) m/z: 427. $^1$H NMR (400 MHz, CHLOROFORM-d) δ 8.51-8.61 (m, 1H), 7.84-7.92 (m, 1H), 7.72-7.79 (m, 1H), 7.65-7.71 (m, 1H), 7.54-7.62 (m, 1H), 6.97-7.14 (m, 2H), 3.82-3.92 (m, 1H), 3.70-3.78 (m, 1H), 3.23-3.27 (m, 3H), 1.82 (s, 3H). $NH_2$ peak was not observed.

Example 105: (R,Z)-3-amino-5-(5-(2-(5-bromopyridin-2-yl)-2-fluorovinyl)-2,3-difluorophenyl)-2,5-dimethyl-5,6-dihydro-2H-1,2,4-thiadiazine 1,1-dioxide

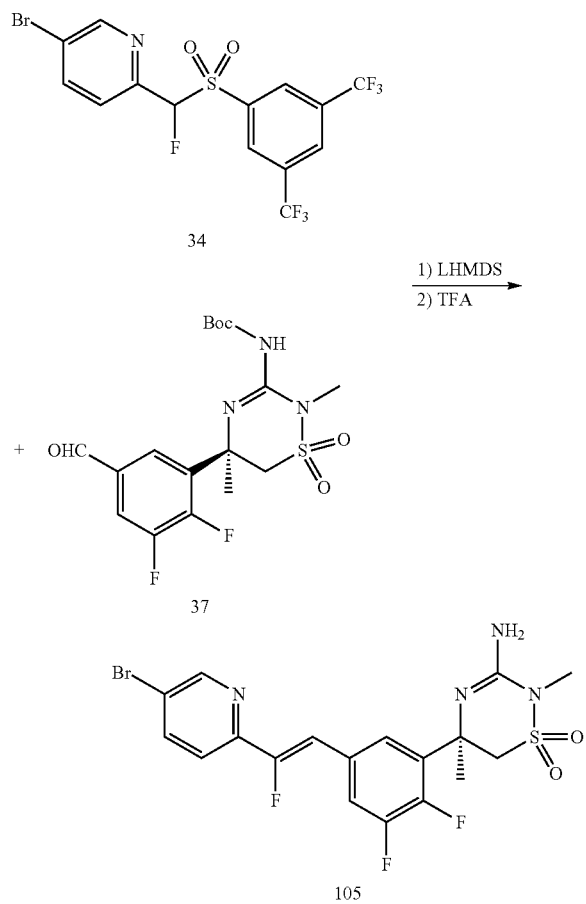

This compound (32 mg, 0.065 mmol, 22% yield for 2 steps) as a white solid was prepared in a fashion similar to that described for Example 101, here starting with aldehyde 37 (122 mg, 0.29 mmol) and sulfone 34 (204 mg, 0.44 mmol). MS m/z=489.0 [M+H]$^+$. $^1$H NMR (400 MHz, CDCl$_3$) δ 8.80 (d, J=1.96 Hz, 1H), 8.21 (d, J=8.63 Hz, 1H), 7.62-7.75 (m, 3H), 7.09 (d, J=39.32 Hz, 1H), 6.09 (s, 2H), 3.84 (d, J=4.50 Hz, 2H), 3.06 (s, 3H), 1.63 (s, 3H). $^{19}$F NMR (376 MHz, CDCl$_3$) δ −122.02 (s, 1F), −137.65 (s, 1F), −138.90 (s, 1F).

Example 106: (R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)nicotinonitrile

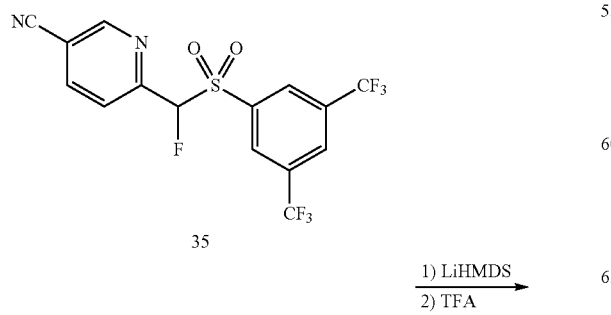

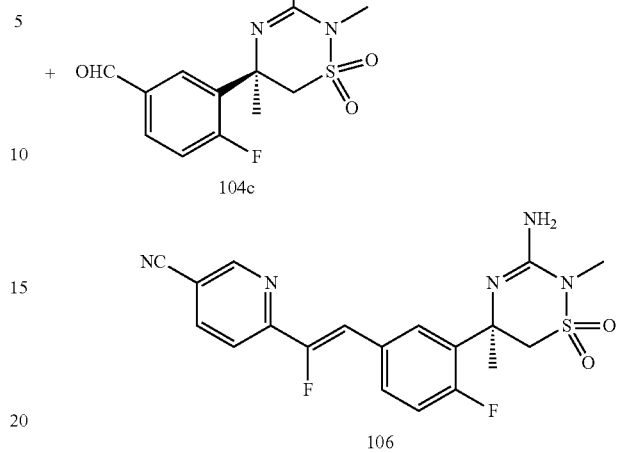

This compound (9 mg, 0.022 mmol, 10% yield for 2 steps) as a white solid was prepared in a fashion similar to that described for Example 101, here starting with aldehyde 104c (84 mg, 0.21 mmol) and sulfone 35 (113 mg, 0.27 mmol). MS m/z=418.1 [M+H]$^+$. $^1$H NMR (400 MHz, CHLOROFORM-d) δ 8.80 (d, J=0.98 Hz, 1H), 7.97-8.03 (m, 1H), 7.88-7.94 (m, 1H), 7.63-7.71 (m, 2H), 7.20 (d, J=38.54 Hz, 1H), 7.09 (dd, J=11.93, 8.61 Hz, 1H), 3.87 (d, J=13.89 Hz, 1H), 3.72 (d, J=13.89 Hz, 1H), 3.22 (s, 3H), 1.79 (s, 3H). NH$_2$ peak was not observed. $^{19}$F NMR (376 MHz, CHLOROFORM-d) δ −110.86 (s, 1F), −125.30 (s, 1F).

Example 107: (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)nicotinonitrile

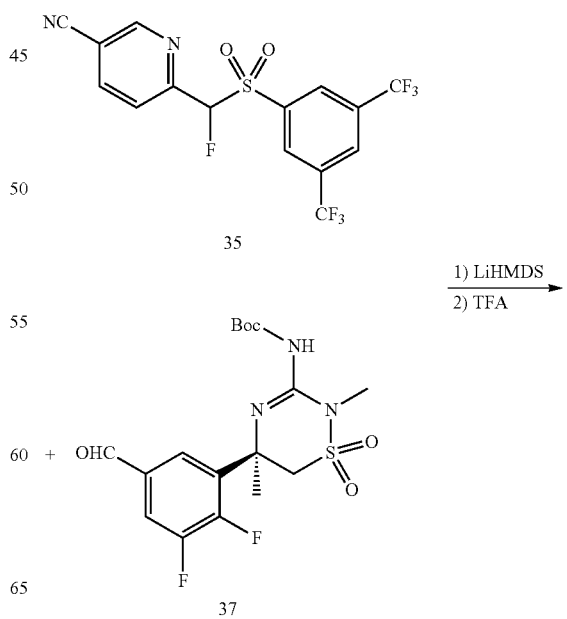

131

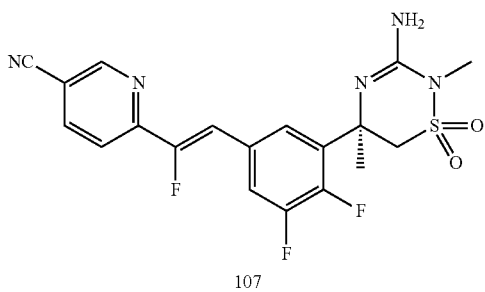

107

132

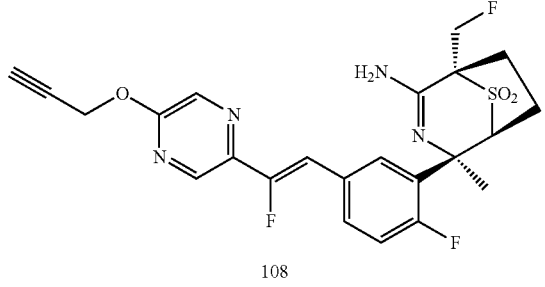

108

This compound (14 mg, 0.032 mmol, 13% yield for 2 steps) as a white solid was prepared in a fashion similar to that described for Example 101, here starting with aldehyde 37 (102 mg, 0.24 mmol) and sulfone 35 (151 mg, 0.37 mmol). MS m/z=436.1 [M+H]+. $^1$H NMR (400 MHz, CHLOROFORM-d) δ 8.82 (s, 1H), 8.02 (d, J=8.11 Hz, 1H), 7.55-7.71 (m, 3H), 7.16 (d, J=38.54 Hz, 1H), 4.41 (br. s, 2H), 3.85 (d, J=14.08 Hz, 1H), 3.67 (d, J=14.08 Hz, 1H), 3.23 (s, 3H), 1.79 (s, 3H). $^{19}$F NMR (376 MHz, CHLOROFORM-d) δ −124.11 (s, 1F), −136.75 (s, 1F), −136.99 (s, 1F).

Example 108: (1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide. (Method A)

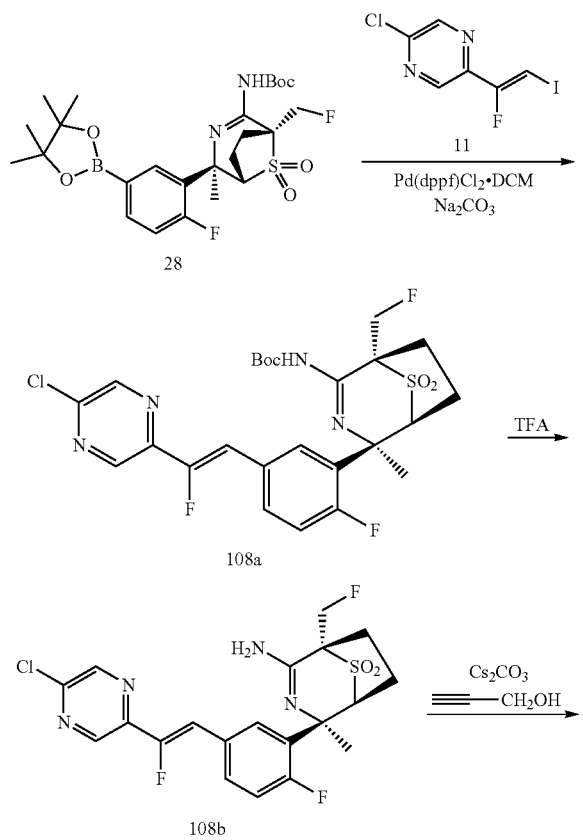

Preparation of (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b)

A suspension of boronic ester 28 (7.00 g, 12.95 mmol), (Z)-2-chloro-5-(1-fluoro-2-iodovinyl)pyrazine (5.53 g, 19.43 mmol), 1,1'-bis(diphenylphosphino)ferrocene palladium(II) dichloride dichloromethane adduct (0.26 g, 0.32 mmol), sodium carbonate (38.9 mL of 1 N solution, 38.9 mmol) in THF (50 mL) was purged with argon then heated to 75° C. for 4 h. The reaction was then partitioned between EtOAc (200 mL) and 5% aqueous NaHCO$_3$ (200 mL). The organic layer was dried over MgSO$_4$, and concentrated under reduced pressure. The resulting residue contained crude 108a was dissolved in CH$_2$Cl$_2$ (50 mL) and TFA (25 mL). This dark solution was stirred for 15 min. The solvents were removed under reduced pressure and the residue was partitioned between EtOAc (200 mL) and 1 M NaOH (50 mL). The separated organic layer was dried over MgSO$_4$, concentrated under reduced pressure, and purified by silica gel chromatography (0-30% (3:1 EtOAc/EtOH)/heptane) to afford (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 2.8 g, 5.95 mmol, 46% yield) as a white solid. MS m/z=471.0 [M+H]$^+$. $^1$H NMR (400 MHz, DMSO-d$_6$) δ ppm 8.87 (s, 1H) 8.80 (s, 1H) 7.97 (br d, J=7.63 Hz, 1H) 7.75 (br s, 1H) 7.30 (dd, J=11.74, 8.61 Hz, 1H) 7.16 (d, J=39.12 Hz, 1H) 6.30 (brs, 2H) 4.86-5.26 (m, 2H) 3.82 (br d, J=5.67 Hz, 1H) 1.95-2.09 (m, 1H) 1.76-1.86 (m, 5H) 1.34 (br t, J=12.13 Hz, 1H).

Preparation of Example 108

A suspension of (1R,4R,5 S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 100 mg, 0.21 mmol), propargyl alcohol (126 μL, 2.12 mmol), cesium carbonate (277 mg, 0.85 mmol) in THF (1.5 mL) was heated to 95° C. for 4 h. The reaction was partitioned between EtOAc (10 mL) and 5% aqueous NaHCO$_3$ (10 mL). The layers were separated. The aqueous was extracted with EtOAc (5 mL). The combined organic solution was dried over MgSO$_4$, concentrated under reduced pressure, then purified by silica gel chromatography (0-20% ((3:1 EtOAc/EtOH blend)/heptane) to afford (1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide (108) (80 mg, 0.16 mmol, 77% yield) as white solid. MS m/z=491.2 [M+H]$^+$. $^1$H NMR (400 MHz, DMSO-d$_6$) δ ppm 8.51 (s, 1H) 8.47 (s, 1H) 7.91 (br d, J=7.43 Hz, 1H) 7.70 (br s, 1H) 7.21-7.32 (m, 1H) 6.94 (d, J=40.49 Hz, 1H) 6.29 (brs, 2H) 4.87-5.27 (m, 4H) 3.81 (brd, J=5.87 Hz, 1H) 3.63 (s, 1H) 1.93-2.07 (m, 1H) 1.74-1.88 (m, 5H) 1.29-1.43 (m, 1H).

Example 109: (1R,4R,5S)-2-amino-4-(2-fluoro-5-((Z)-2-fluoro-2-(5-(2,2,2-trifluoroethoxy)pyrazin-2-yl)vinyl)phenyl)-1-(fluoromethyl)-4-methyl-8-thia-3-azabicyclo[3.2.1]oct-2-ene 8,8-dioxide

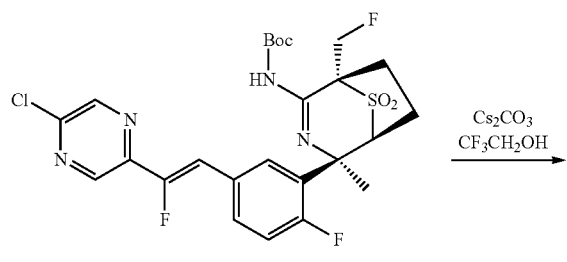

108a

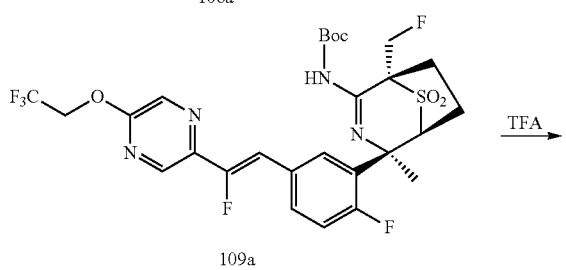

109a

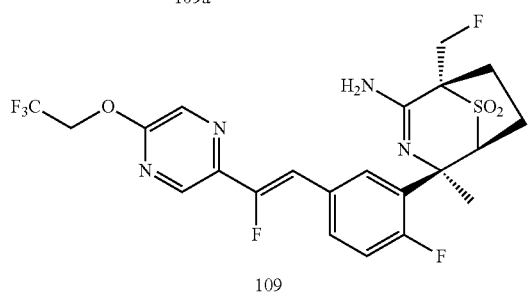

109

A suspension of tert-butyl ((1R,4R,5S)-4-(5-((Z)-2-(5-chloropyrazin-2-yl)-2-fluorovinyl)-2-fluorophenyl)-1-(fluoromethyl)-4-methyl-8,8-dioxido-8-thia-3-azabicyclo[3.2.1]oct-2-ean-2-yl)carbamate (108a, 100 mg, 0.17 mmol), 2,2,2-trifluoroethanol (Sigma-Aldrich Chemical Company, Inc., St. Louis, Mo., USA) (128 µL, 1.75 mmol), cesium carbonate (171 mg, 0.52 mmol) in THF (0.8 mL) was heated to 50° C. for 7 h. The reaction mixture was then partitioned between EtOAc (10 mL) and 5% NaHCO₃ (10 mL). The organic layer was dried over MgSO₄, concentrated under reduced pressure, then purified by silica gel chromatography (0 to 10% gradient of (3:1 blend of EtOAc/EtOH) in heptane) to afford 109a (20 mg) as a white solid. MS m/z=635.1 [M+H]⁺.

A solution of 109a (20 mg, 0.032 mmol) in DCM (1 mL) and TFA (1 mL) was stirred for 15 min at 20° C. The reaction mixture was then partitioned between EtOAc (10 mL) and 1 M NaOH (5 mL). The organic was dried over MgSO₄, concentrated under reduced pressure, then purified by silica gel chromatography (0 to 15% gradient of (3:1 blend EtOAc/EtOH) in heptane) to afford (1R,4R,5 S)-2-amino-4-(2-fluoro-5-((Z)-2-fluoro-2-(5-(2,2,2-trifluoroethoxy)

pyrazin-2-yl)vinyl)phenyl)-1-(fluoromethyl)-4-methyl-8-thia-3-azabicyclo[3.2.1]oct-2-ene 8,8-dioxide (109) (8 mg, 0.015 mmol, 47% yield) as a white solid. MS m/z=535.0 [M+H]⁺. ¹H NMR (400 MHz, CHLOROFORM-d) δ ppm 8.37 (s, 1H) 8.33 (s, 1H) 7.81 (dd, J=7.82, 1.76 Hz, 1H) 7.69 (td, J=5.38, 2.35 Hz, 1H) 7.09 (dd, J=11.74, 8.61 Hz, 1H) 6.89 (d, J=39.52 Hz, 1H) 5.11-5.35 (m, 1H) 4.87-5.07 (m, 1H) 4.82 (q, J=8.41 Hz, 2H) 3.86 (br d, J=5.48 Hz, 1H) 1.98-2.28 (m, 4H) 1.94 (s, 3H). ¹⁹F NMR (376 MHz, CHLOROFORM-d) δ ppm −73.66 (s, 3F) −111.80 (s, 1F) −125.33 (s, 1F). NH₂ peak was not observed.

Example 110: (R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide

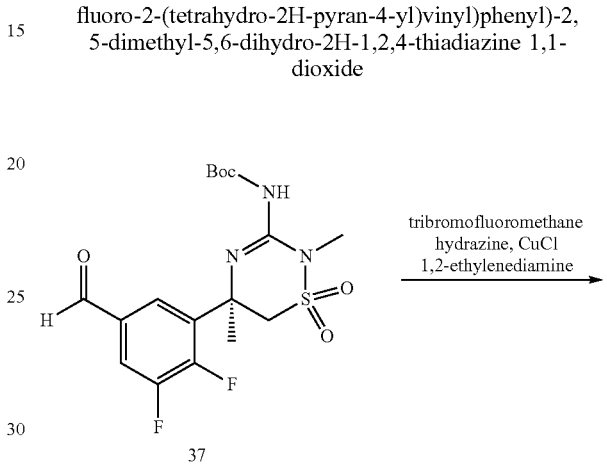

37

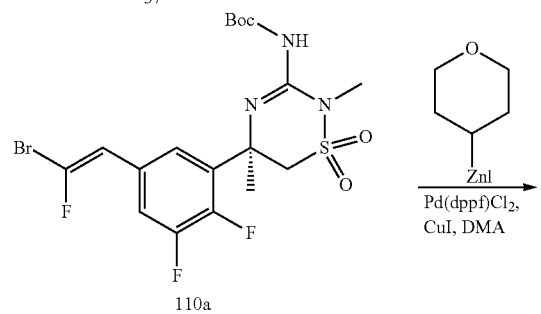

110a

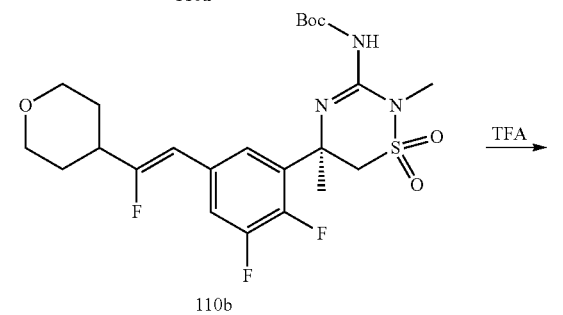

110b

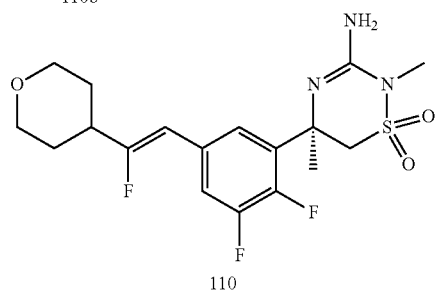

110

Preparation of 110a

A solution of aldehyde 37 (861 mg, 2.06 mmol) in MeOH (3 mL) was added dropwise to a solution of anhydrous hydrazine (189 μL, 8.25 mmol) in MeOH (2.5 mL). The mixture was stirred for 20 min and cooled to 0° C. 1,2-Ethylenediamine (345 μL, 5.16 mmol) and copper chloride (20 mg, 0.21 mmol) were added, at which time the solution turned a pale brown color. Tribromofluoromethane (303 μL, 3.09 mmol) was then added dropwise and the solution was warmed to RT and stirred for 2 h. EtOAc and aqueous ammonium chloride solution/aqueous ammonium hydroxide solution (9:1, v/v) were added, the layers were separated, and the organic layer was dried over anhydrous magnesium sulfate, filtered, and concentrated in vacuo to give an oil. The oil was purified by silica gel chromatography (0 to 30% EtOAc/heptane) to give a 7:3 ratio of (R,E)-tert-butyl (5-(5-(2-bromo-2-fluorovinyl)-2,3-difluorophenyl)-2,5-dimethyl-1,1-dioxido-5,6-dihydro-2H-1,2,4-thiadiazin-3-yl)carbamate: (R,Z)-tert-butyl (5-(5-(2-bromo-2-fluorovinyl)-2,3-difluorophenyl)-2,5-dimethyl-1,1-dioxido-5,6-dihydro-2H-1,2,4-thiadiazin-3-yl)carbamate (110a) (520 mg, 1.02 mmol, 49% yield) as a white solid. MS m/z=512.0 [M+H]$^+$.

Preparation of 110b

A premixed mixture of TMSCl and 1,2-dibromoethane (7:5, v/v, 0.04 mL) was added dropwise over 5 min to a suspension of zinc dust (78 mg, 1.20 mmol) in DMA (0.75 mL) under argon atmosphere. The mixture was stirred for 15 min before 4-iodotetrahydro-2H-pyran (Maybridge Chemical Co., Ltd.) (212 mg, 1.00 mmol) was added dropwise over 15 min as a solution in DMA (0.25 mL). This mixture was stirred for an additional 15 min and then it was added via syringe to a mixture of 110a (100 mg, 0.20 mmol), copper(I) iodide (Sigma-Aldrich Chemical Company, Inc., St. Louis, Mo., USA) (4 mg, 0.020 mmol), and (1,1'-bis(diphenylphosphino)ferrocene)dichloropalladium(II) (7 mg, 10 μmol) in DMA (0.25 mL). The mixture was heated to 70° C. for 3 h, cooled to RT, and diluted with EtOAc. The solution was washed with aqueous ammonium chloride solution/aqueous ammonium hydroxide solution (9:1, v/v), then water, dried over anhydrous magnesium sulfate, filtered, and concentrated in vacuo to give an oil. The oil was purified by silica gel chromatography (0 to 20% EtOAc/heptane) to give (R,Z)-tert-butyl (5-(2,3-difluoro-5-(2-fluoro-2-(tetrahydro-2H-pyran-4-yl)vinyl)phenyl)-2,5-dimethyl-1,1-dioxido-5,6-dihydro-2H-1,2,4-thiadiazin-3-yl)carbamate (110b) (23 mg, 0.044 mmol, 23% yield) as a white solid. MS m/z=518.2 [M+H]$^+$. $^1$H NMR (400 MHz, CHLOROFORM-d) δ 10.68 (br. s., 1H), 7.33-7.42 (m, 1H), 7.12 (d, J=6.46 Hz, 1H), 5.36 (d, J=38.34 Hz, 1H), 4.21-4.29 (m, 1H), 4.04 (dd, J=11.35, 2.93 Hz, 2H), 3.70 (d, J=14.28 Hz, 1H), 3.44 (td, J=11.74, 2.15 Hz, 2H), 3.25 (s, 3H), 2.48 (d, J=13.69 Hz, 1H), 1.89 (s, 3H), 1.59-1.83 (m, 4H), 1.56 (s, 9H). $^{19}$F NMR (376 MHz, CHLOROFORM-d) δ −104.48 (s, 1F), −136.79 (s, 1F), −140.22 (s, 1F).

Preparation of Example 110

(R,Z)-tert-butyl (5-(2,3-difluoro-5-(2-fluoro-2-(tetrahydro-2H-pyran-4-yl)vinyl)phenyl)-2,5-dimethyl-1,1-dioxido-5,6-dihydro-2H-1,2,4-thiadiazin-3-yl)carbamate (110b) (23 mg, 0.044 mmol) was dissolved in 1:1 DCM/TFA (2 mL total volume). The mixture was stirred for 1 h, then the solvent was removed in vacuo. The resulting oil was dissolved in DCM and washed with 2 N aqueous sodium carbonate solution (3×). The organic solution was then dried over anhydrous magnesium sulfate, filtered, and concentrated in vacuo to give (R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide (110) (17 mg, 0.041 mmol, 92% yield) as a white solid. MS m/z=418.1 [M+H]$^+$. $^1$H NMR (400 MHz, CDCl$_3$) δ 7.30-7.39 (m, 2H), 5.40 (d, J=39.12 Hz, 1H), 4.04 (dd, J=11.54, 2.93 Hz, 2H), 3.81 (d, J=14.08 Hz, 1H), 3.69 (d, J=14.48 Hz, 1H), 3.39-3.49 (m, 2H), 3.21 (s, 3H), 2.48 (d, J=13.30 Hz, 1H), 1.66-1.83 (m, 7H). NH$_2$ peak was not observed. $^{19}$F NMR (376 MHz, CDCl$_3$) δ −105.88 (s, 1F), −138.05 (s, 1F), −140.32 (s, 1F).

Example 111: (R,Z)-3-amino-5-(5-(2-(5-chloropyrazin-2-yl)-2-fluorovinyl)-2-fluorophenyl)-2,5-dimethyl-5,6-dihydro-2H-1,2,4-thiadiazine 1,1-dioxide. (Method C)

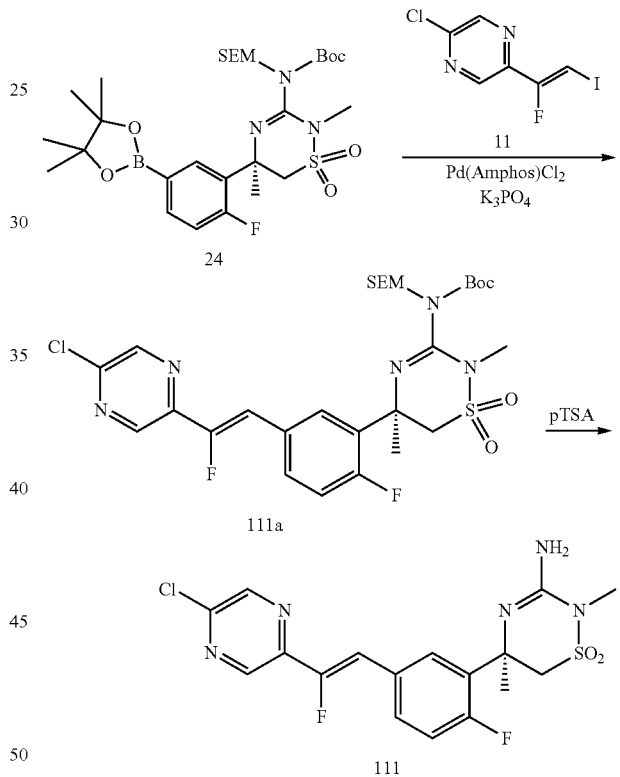

Preparation of (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (111a)

A mixture of (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate (Intermediate 24) (5.16 g, 8.22 mmol), (Z)-2-chloro-5-(1-fluoro-2-iodovinyl)pyrazine (2.81 g, 9.87 mmol), potassium phosphate tribasic (4.36 g, 20.6 mmol), and 1,1-bis[(di-t-butyl-p-methylaminophenyl]palladium(II) chloride (0.47 g, 0.66 mmol) was placed under argon atmosphere using 3 evacuation/backfill cycles. Dioxane (40 mL) and water (8 mL) were added and the mixture was evacuated/backfilled once more before it was heated to 80° C. for 7 h. The mixture was cooled to RT and partitioned between ethyl acetate and water. The layers were separated and the organic layer was dried over anhydrous magnesium sulfate, filtered, and concentrated in vacuo. The residue was fused to silica gel and purified by silica gel chromatography (0 to 30% ethyl acetate/heptane gradient, then 0 to 100% DCM/heptane gradient) to give (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl) carbamate (111a, 3.61 g, 67% yield) as a white foam. MS m/z=658 [M+H]$^+$. $^1$H NMR (400 MHz, CHLOROFORM-d) δ ppm 8.62 (s, 1H), 8.53 (s, 1H), 7.90 (dd, J=7.92, 2.05 Hz, 1H), 7.66-7.75 (m, 1H), 7.00-7.16 (m, 2H), 5.20 (d, J=10.37 Hz, 1H), 5.11 (d, J=10.56 Hz, 1H), 3.63-3.82 (m, 4H), 3.22 (s, 3H), 1.85 (s, 3H), 1.53 (s, 9H), 0.92-1.01 (m, 2H), 0.00 (s, 9H).

Preparation of (R,Z)-3-amino-5-(5-(2-(5-chloropyrazin-2-yl)-2-fluorovinyl)-2-fluorophenyl)-2,5-dimethyl-5,6-dihydro-2H-1,2,4-thiadiazine 1,1-dioxide (111)

A mixture of (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (111a, 3.61 g, 5.48 mmol) and p-toluenesulfonic acid monohydrate (1.57 g, 8.23 mmol) in dioxane (25 mL) was heated to 80° C. for 2.5 h. The mixture was cooled to RT, ethyl acetate was added, and the mixture was then washed with water (1×), brine (1×), dried over MgCl$_2$, filtered, and concentrated in vacuo to give a solid. The solid was suspended in DCM, cooled to 0° C. for 30 min, and the solid was collected by filtration to give an off-white solid (1.80 g). The filtrate was concentrated, suspended in DCM, and filtered to give another 0.15 g. The solids were combined to give a total of 1.95 g, (83% yield) of Example 111 as an off white solid. MS m/z=428 [M+H]$^+$. $^1$H NMR (400 MHz, DMSO-d6) δ ppm 8.85 (s, 1H), 8.79 (s, 1H), 7.93 (br d, J=7.63 Hz, 1H), 7.64-7.71 (m, 1H), 7.21-7.31 (m, 1H), 7.10 (d, J=40.10 Hz, 1H), 5.88-6.30 (m, 2H), 3.83 (s, 2H), 3.05 (s, 3H), 1.62 (s, 3H).

Example 112: (R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide. (Method D)

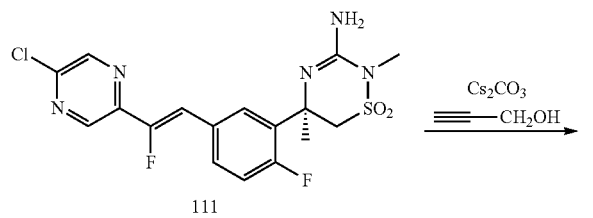

111

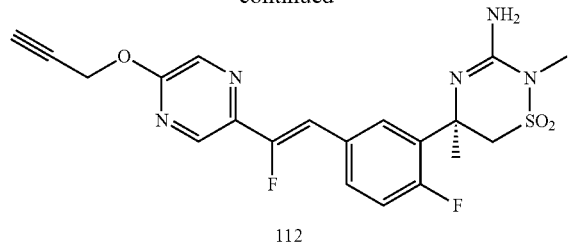

112

A mixture of (R,Z)-3-amino-5-(5-(2-(5-chloropyrazin-2-yl)-2-fluorovinyl)-2-fluorophenyl)-2,5-dimethyl-5,6-dihydro-2H-1,2,4-thiadiazine 1,1-dioxide (111) (1.80 g, 4.21 mmol), propargyl alcohol (1.99 mL, 33.7 mmol), and cesium carbonate (4.11 g, 12.6 mmol) in THF (20 mL) was heated to 50° C. for 2 h. The mixture was cooled to room temperature, ethyl acetate was added, and the mixture was then washed with water (1×), brine (1×), dried over MgCl$_2$, filtered, and concentrated in vacuo to give a viscous oil. The oil was purified by silica gel chromatography (0 to 100% EtOAc/heptane gradient) to give (R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide as an off white solid. A second compound was isolated, dissolved in EtOH (5 mL) and heated to 70° C. overnight, during which time it converted to the desired product. The solvent was removed and the residue was purified by silica gel chromatography (0 to 100% ethyl acetate/heptane gradient) to give additional material as an off-white solid. The combined material gave a total of Example 112 (1.44 g, 76% yield). MS m/z=448 [M+H]$^+$. $^1$H NMR (400 MHz, DMSO-d6) δ ppm 8.51 (s, 1H), 8.46 (s, 1H), 7.89 (br d, J=7.24 Hz, 1H), 7.59-7.67 (m, 1H), 7.15-7.28 (m, 1H), 6.89 (d, J=40.69 Hz, 1H), 6.05 (br., 2H), 5.09 (d, J=2.35 Hz, 2H), 3.79 (s, 2H), 3.61 (t, J=2.35 Hz, 1H), 3.06 (s, 3H), 1.62 (s, 3H).

Example 113: (R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile

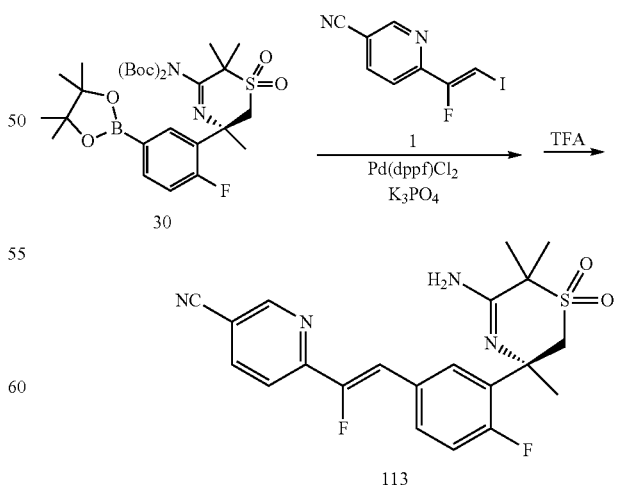

A stream of argon was bubbling through a mixture of 1,1'-bis(diphenylphosphino)ferrocene-palladium dichloride (0.018 g, 0.025 mmol), (Z)-6-(1-fluoro-2-iodovinyl)nicotinonitrile (0.088 g, 0.319 mmol), dioxaborolane (0.150 g, 0.246 mmol), sodium carbonate (0.35 mL of 2 N solution) and water (0.20) in 1,4-dioxane (2.0 mL) for 5 min. The resulting mixture was then allowed to stir at 85° C. for 18 h. The mixture was cooled to RT, filtered, and washed with ethyl acetate. The filtrate was concentrated and the residue was dissolved in 1 mL of DCM and treated with 0.5 mL of TFA. The mixture was stirred at RT for 1 h and concentrated to dryness. The brown residue was purified on a silica gel column using 0-100% ethyl acetate gradient in heptane as the eluent to give a material was impure. Further purification by Isco CombiFlash on a 12 g silica gel column using 0-5% (2 M $NH_3$/methanol) in DCM afforded (R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile (113) (36 mg, 34% yield). MS m/z=431.1 [M+H]$^+$. $^1$H NMR (400 MHz, CHLOROFORM-d) δ 8.84 (s, 1H), 8.03 (dd, J=2.05, 8.31 Hz, 1H), 7.80 (dd, J=2.25, 7.92 Hz, 1H), 7.68-7.75 (m, 2H), 7.24 (d, J=40 Hz, 1H), 7.12 (dd, J=8.51, 12.03 Hz, 1H), 3.50-3.65 (m, 2H), 1.82 (s, 4H), 1.82 (s, 3H), 1.72 (s, 3H) 1.62 (s, 3H). $NH_2$ peak was not observed.

Example 114: (R,Z)-5-amino-3-(5-(2-(5-chloropyridin-2-yl)-2-fluorovinyl)-2-fluorophenyl)-3,6,6-trimethyl-3,6-dihydro-2H-1,4-thiazine 1,1-dioxide

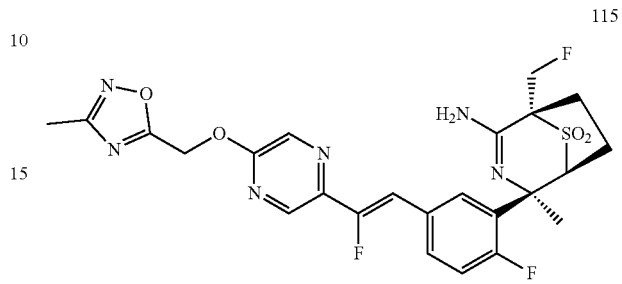

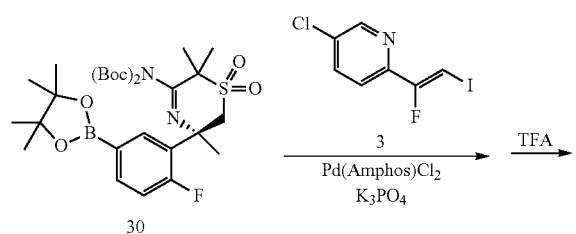

This compound (50 mg, 45% yield) as a gray solid was prepared in a fashion similar to that described in Method E for Example 258, here starting with (Z)-5-chloro-2-(1-fluoro-2-iodovinyl)pyridine (3, 91 mg, 0.32 mmol) and boronic ester 30 (150 mg, 0.25 mmol). MS m/z=440.0 [M+H]$^+$. $^1$H NMR (400 MHz, CHLOROFORM-d) δ 11.55 (br s, 1H), 8.55 (br s, 1H), 8.49 (d, J=2.35 Hz, 1H), 7.62-7.71 (m, 3H), 7.50-7.56 (m, 1H), 7.13-7.23 (m, 1H), 6.98 (d, J=40 Hz, 1H), 4.02 (d, J=15.45 Hz, 1H), 3.71 (d, J=15.45 Hz, 1H), 2.07 (s, 3H), 1.92 (s, 3H), 1.81 (s, 3H).

Example 115: (1R,4R,5S)-2-amino-4-(2-fluoro-5-((Z)-2-fluoro-2-(5-((3-methyl-1,2,4-oxadiazazol-5-yl)methoxy)pyrazin-2-yl)vinyl)phenyl)-1-(fluoromethyl)-4-methyl-8-thia-3-azabicyclo[3.2.1]oct-2-ene 8,8-dioxide

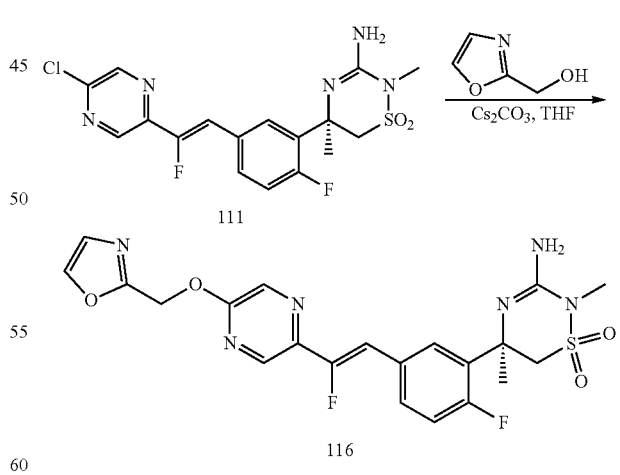

This compound (28 mg, 60% yield) as a white solid was prepared in a fashion similar to that described in Method A for Example 108, here using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 40.0 mg, 0.085 mmol) and (3-methyl-1,2,4-oxadiazol-5-yl)methanol (Enamine LLC, Monmouth Jct., N.J., USA) (9.7 mg, 0.085 mmol) as starting materials. MS m/z=549.0 [M+H]$^+$. $^1$H NMR (400 MHz, DMSO-$d_6$) δ ppm 8.59 (s, 1H) 8.48 (s, 1H) 7.90 (br d, J=7.82 Hz, 1H) 7.70 (br s, 1H) 7.27 (dd, J=11.93, 8.80 Hz, 1H) 6.96 (d, J=40.49 Hz, 1H) 6.29 (br s, 2H) 5.77 (s, 2H) 4.89-5.24 (m, 2H) 3.81 (br d, J=5.67 Hz, 1H) 2.36 (s, 3H) 1.99 (br d, J=7.82 Hz, 1H) 1.72-1.86 (m, 5H) 1.35 (brt, J=11.05 Hz, 1H).

Example 116: (R,Z)-3-amino-5-(2-fluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide This compound (37 mg, 0.075 mmol, 43% yield) as a light yellow solid was prepared in a fashion similar to that described in Method D for Example 112, using 2-oxazol-methanol (AstaTech, Inc., Bristol, Pa., USA) (176 mg, 1.78 mmol) and 111 (76 mg, 0.18 mmol) as starting materials. MS m/z=491.1 [M+H]$^+$. $^1$H NMR (400 MHz, DMSO-$d_6$) δ 8.51

(d, J=7.04 Hz, 2H) 8.19 (s, 1H) 7.89 (d, J=6.65 Hz, 1H) 7.60-7.67 (m, 1H) 7.29 (s, 1H) 7.19-7.26 (m, 1H) 6.90 (d, J=40.69 Hz, 1H) 5.57 (s, 2H) 3.82 (br. s., 2H) 3.18 (d, J=5.28 Hz, 2H) 3.05 (s, 3H) 1.62 (s, 3H). $^{19}$F NMR (376 MHz, DMSO-$d_6$) δ −111.98 (s, 1F), −124.75 (s, 1F).

Example 117: (R,Z)-3-amino-5-(2-fluoro-5-(2-fluoro-2-(5-(2,2,2-trifluoroethoxy)pyrazin-2-yl)vinyl)phenyl)-2,5-dimethyl-5,6-dihydro-2H-1,2,4-thiadiazine 1,1-dioxide

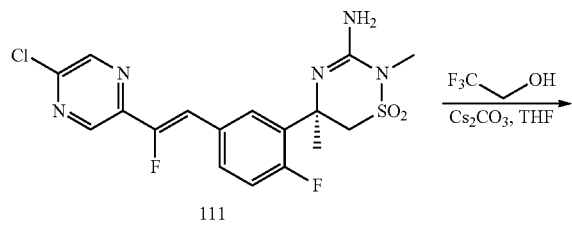

This compound (36 mg, 0.073 mmol, 31% yield) as a white solid was prepared in a fashion similar to that described in Method D for Example 112, here using 2,2,2-trifluoroethan-1-ol (234 mg, 2.34 mmol) and 111 (100 mg, 0.23 mmol) as starting materials. MS m/z=492.0 [M+H]$^+$. $^1$H NMR (400 MHz, CHLOROFORM-d) δ 8.32 (d, J=8.22 Hz, 2 H) 7.87 (dd, J=8.02, 2.15 Hz, 1H) 7.62 (ddd, J=8.51, 4.79, 2.35 Hz, 1H) 7.01-7.10 (m, 1H) 6.86 (dd, J=39.71, 1.00 Hz, 1H) 4.81 (q, J=8.41 Hz, 2H) 3.84 (d, J=13.89 Hz, 1H) 3.71 (d, J=14.09 Hz, 1H) 3.21 (s, 3H) 1.79 (s, 3H). Note: NH$_2$ peak was not observed. $^{19}$F NMR (376 MHz, CHLOROFORM-d) δ −73.68 (s, 3F), −112.31 (s, 1F), −125.82 (s, 1F).

Example 118: (1R,4R,5S)-2-amino-4-(5-((Z)-2-(5-(cyclopropylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide

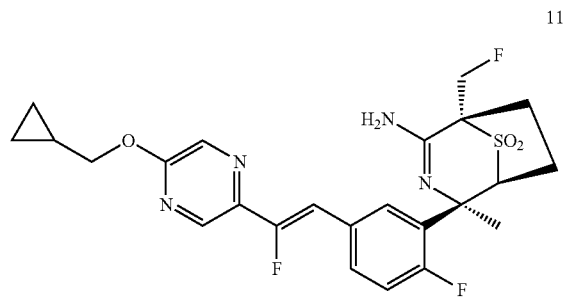

This compound (12 mg, 14% yield) as a white fluffy powder was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 80 mg, 0.17 mmol) and cyclopropylmethanol (Sigma-Aldrich Chemical Company, Inc., St. Louis, Mo., USA) (61 mg, 0.85 mmol) as starting materials. MS m/z=507.0 [M+H]$^+$. $^1$H NMR (400 MHz, DMSO-$d_6$) δ ppm 8.45 (s, 1H) 8.41 (s, 1H) 7.90 (br d, J=7.82 Hz, 1H) 7.68 (br s, 1H) 7.20-7.32 (m, 1H) 6.91 (d, J=40.88 Hz, 1H) 6.29 (br s, 2H) 4.88-5.29 (m, 2H) 4.21 (d, J=7.24 Hz, 2H) 3.81 (brs, 1H) 1.89-2.13 (m, 1H) 1.78 (s, 5H) 1.29 (br s, 2H) 0.54-0.65 (m, 2H) 0.31-0.44 (m, 2H). $^{19}$F NMR (376 MHz, DMSO-$d_6$) δ ppm −111.53 (s, 1F), −124.71 (s, 1F), −220.80 (s, 1F).

Example 119: (1R,4R,5S)-2-amino-4-(2-fluoro-5-((Z)-2-fluoro-2-(5-((5-methyl-1,3,4-oxadiazol-2-yl)methoxy)pyrazin-2-yl)vinyl)phenyl)-1-(fluoromethyl)-4-methyl-8-thia-3-azabicyclo[3.2.1]oct-2-ene 8,8-dioxide

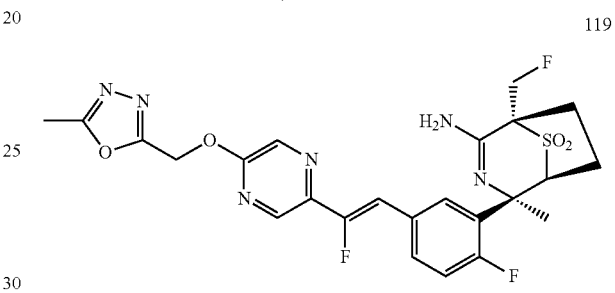

This compound (38 mg, 43% yield) as a white fluffy powder was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 75 mg, 0.16 mmol) and (5-methyl-1,3,4-oxadiazol-2-yl)methanol (ChemBridge Corporation, San Diego, Calif., USA) (136 mg, 1.19 mmol) as starting materials. MS m/z=549.1 [M+H]$^+$. $^1$H NMR (400 MHz, CHLOROFORM-d) δ ppm 8.53 (s, 1H) 8.50 (s, 1H) 7.90 (br d, J=7.63 Hz, 1H) 7.69 (br s, 1H) 7.27 (dd, J=11.64, 8.71 Hz, 1H) 6.95 (d, J=40.69 Hz, 1H) 6.28 (br s, 2H) 5.67 (s, 2H) 4.89-5.24 (m, 2H) 3.79 (br s, 1H) 2.53 (s, 3H) 1.93-2.07 (m, 1H) 1.71-1.87 (m, 5H) 1.14-1.20 (m, 1H). $^{19}$F NMR (376 MHz, CHLOROFORM-d) δ ppm −216.05 (s, 1F), −119.97 (s, 1F), 106.50 (s, 1F).

Example 120: (1R,4R,5S)-2-amino-4-(2-fluoro-5-((Z)-2-fluoro-2-(5-(2,2,3,3-tetrafluoropropoxy)pyrazin-2-yl)vinyl)phenyl)-1-(fluoromethyl)-4-methyl-8-thia-3-azabicyclo[3.2.1]oct-2-ene 8,8-dioxide

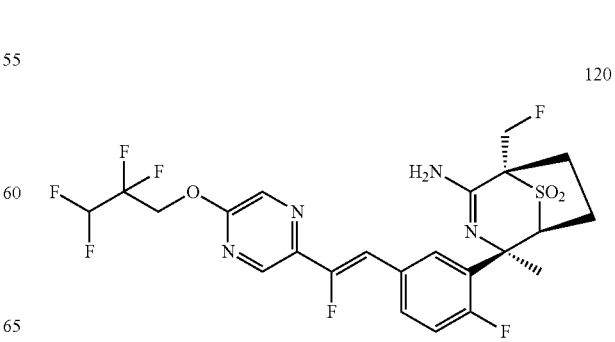

This compound (90 mg, 53% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 75 mg, 0.16 mmol) and 2,2,3,3-tetrafluoro-1-propanol (Sigma-Aldrich Chemical Company, Inc., St. Louis, Mo., USA) (113 µL, 1.19 mmol) as starting materials. MS m/z=567.0 [M+H]$^+$. $^1$H NMR (400 MHz, CHLOROFORM-d) δ ppm 8.54 (s, 1H) 8.52 (s, 1H) 7.87-7.95 (m, 1H) 7.64-7.74 (m, 1H) 7.27 (dd, J=11.83, 8.51 Hz, 1H) 6.96 (d, J=40.69 Hz, 1H) 6.54-6.87 (m, 1H) 6.28 (br s, 2H) 4.85-5.25 (m, 4H) 3.80 (br d, J=5.67 Hz, 1H) 1.91-2.07 (m, 1H) 1.69-1.88 (m, 5H) 1.34 (br t, J=10.37 Hz, 1H).

Example 121: (1R,4R,5S)-2-amino-4-(2-fluoro-5-((Z)-2-fluoro-2-(5-methoxypyrazin-2-yl)vinyl)phenyl)-1-(fluoromethyl)-4-methyl-8-thia-3-azabicyclo[3.2.1]oct-2-ene 8,8-dioxide

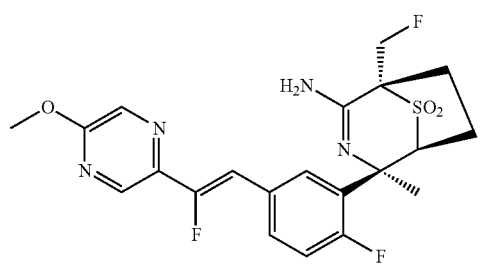

121

This compound (65 mg, 65% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108b, 100 mg, 0.21 mmol) and methanol (34 mg, 1.06 mmol) as starting materials. MS m/z=467.2 [M+H]$^+$. $^1$H NMR (400 MHz, DMSO-d$_6$) δ ppm 8.48 (s, 1H) 8.41 (s, 1H) 7.90 (br d, J=7.82 Hz, 1H) 7.69 (br s, 1H) 7.27 (dd, J=11.64, 8.51 Hz, 1H) 6.91 (d, J=40.69 Hz, 1H) 6.29 (br s, 2H) 4.86-5.27 (m, 2H) 3.99 (s, 3H) 3.80 (br d, J=5.48 Hz, 1H) 1.95-2.06 (m, 1H) 1.71-1.89 (m, 5H) 1.27-1.42 (m, 1H).

Example 122: (1R,4R,5S)-2-amino-4-(5-((Z)-2-(5-ethoxypyrazin-2-yl)-2-fluorovinyl)-2-fluorophenyl)-1-(fluoromethyl)-4-methyl-8-thia-3-azabicyclo[3.2.1]oct-2-ene 8,8-dioxide

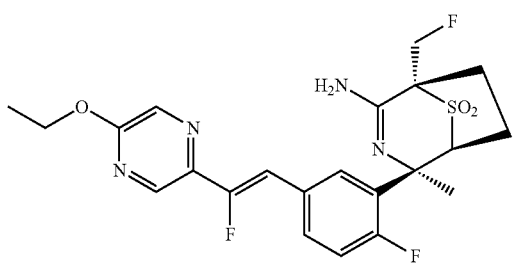

122

This compound (80 mg, 78% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and ethanol (Sigma-Aldrich Chemical Company, Inc., St. Louis, Mo., USA) (49 mg, 1.06 mmol) as starting materials. MS m/z=481.2 [M+H]$^+$. $^1$H NMR (400 MHz, DMSO-d$_6$) δ ppm 8.46 (s, 1H) 8.38 (s, 1H) 7.90 (br d, J=8.41 Hz, 1H) 7.68 (br s, 1H) 7.26 (dd, J=11.74, 8.61 Hz, 1H) 6.90 (d, J=41.08 Hz, 1H) 6.29 (br s, 2H) 4.89-5.25 (m, 2H) 4.42 (q, J=6.91 Hz, 2H) 3.80 (br d, J=5.87 Hz, 1H) 1.93-2.07 (m, 1H) 1.71-1.86 (m, 5H) 1.38 (t, J=7.04 Hz, 4H). $^{19}$F NMR (376 MHz, DMSO-d$_6$) δ ppm −111.49 (s, 1F) −124.69 (s, 1F) −220.80 (s, 1F).

Example 123: (R,Z)-5-amino-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide A mixture of (R,Z)-5-(di-Boc-amino)-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a, 0.126 g, 0.197 mmol), propargyl alcohol (0.035 mL, 0.590 mmol) and cesium carbonate (0.192 g, 0.590 mmol) in THF (2.0 mL) was stirred at RT for 24 h. The mixture was filtered and washed with ethyl acetate. The filtrate was concentrated and the residue was purified on a silica gel column using 0-100% ethyl acetate gradient in heptane as the eluent to give 123a as an amorphous solid. MS m/z=561.2 [M+H]$^+$. 123a was dissolved in 4 mL of DCM and treated with TFA (1 mL) at RT. The mixture was stirred at RT and monitored by LCMS. Upon completion, the mixture was concentrated and the residue was purified on a silica gel column using 0-3% (2 M NH$_3$/methanol) in DCM as the eluent to give Example 123

(57 mg, 63% yield) as a yellow solid. MS m/z=461.1 [M+H]. ¹H NMR (400 MHz, CHLOROFORM-d) δ 12.42 (br s, 1H), 11.37 (br s, 1H), 8.65 (br s, 1H), 8.38 (s, 1H), 8.23 (s, 1H), 7.69 (ddd, J=1.96, 4.79, 8.51 Hz, 1H), 7.59 (br d, J=7.82 Hz, 1H), 7.13-7.19 (m, 1H), 6.82 (d, J=40 Hz, 1H), 5.0 (d, J=2.35 Hz, 2H), 4.00 (d, J=15.26 Hz, 1H), 3.71 (d, J=15.65 Hz, 1H), 2.07 (s, 3H), 1.92 (s, 3H), 1.82 (s, 3H).

Example 124: (R,Z)-5-amino-3-(2-fluoro-5-(2-fluoro-2-(5-(2,2,2-trifluoroethoxy)pyrazin-2-yl)vinyl)phenyl)-3,6,6-trimethyl-3,6-dihydro-2H-1,4-thiazine 1,1-dioxide

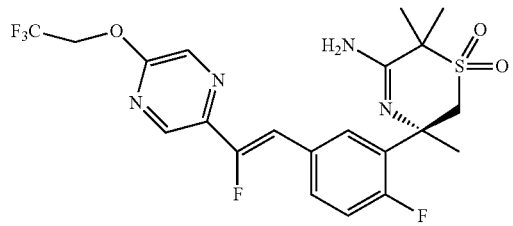

124

This compound (35 mg, 59% yield) as a yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 91 mg, 0.32 mmol) and 2,2,2-trifluoroethan-1-ol (59 mg, 0.59 mmol). MS m/z=505.1 [M+H]⁺. ¹H NMR (400 MHz, CDCl₃) δ 8.37 (s, 1H), 8.33 (s, 1H), 7.75 (dd, J=2.15, 8.02 Hz, 1H), 7.67 (ddd, J=2.25, 4.74, 8.46 Hz, 1H), 7.03-7.26 (m, 1H), 6.88 (d, J=40 Hz, 1H), 4.82 (q, J=8.41 Hz, 2H), 3.58-3.64 (m, 2H), 1.83 (s, 3H), 1.72 (s, 3H), 1.63 (s, 3H). NH₂ peak was not observed.

Example 125: (1R,4R,5S)-4-(5-((Z)-2-(5-(allyloxy)pyrazin-2-yl)-2-fluorovinyl)-2-fluorophenyl)-2-amino-1-(fluoromethyl)-4-methyl-8-thia-3-azabicyclo[3.2.1]oct-2-ene 8,8-dioxide

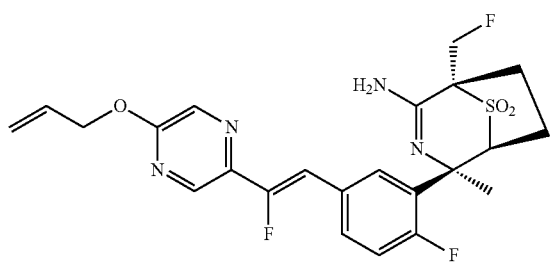

125

This compound (31 mg, 80% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 30 mg, 0.06 mmol) and allyl alcohol (Sigma-Aldrich Chemical Company, Inc., St. Louis, Mo., USA) (22 μL, 0.32 mmol) as starting materials. MS m/z=493.2 [M+H]⁺. ¹H NMR (400 MHz, DMSO-d₆) δ ppm 8.47 (s, 1H) 8.44 (s, 1H) 7.90 (br d, J=6.26 Hz, 1H) 7.69 (br s, 1H) 7.27 (dd, J=11.44, 8.71 Hz, 1H) 6.92 (d, J=40.69 Hz, 1H) 6.29 (br s, 2H) 6.02-6.18 (m, 1H) 4.87-5.50 (m, 6H) 3.80 (br d, J=5.48 Hz, 1H) 1.92-2.08 (m, 1H) 1.74-1.86 (m, 5H) 1.28-1.43 (m, 1H). ¹⁹F NMR (376 MHz, DMSO-d₆) δ ppm −112.52−−110.99 (m, 1F) −124.68 (s, 1F) −220.80 (s, 1F).

Example 126: (1R,4R,5S)-2-amino-4-(2-fluoro-5-((Z)-2-fluoro-2-(5-(oxetan-3-ylmethoxy)pyrazin-2-yl)vinyl)phenyl)-1-(fluoromethyl)-4-methyl-8-thia-3-azabicyclo[3.2.1]oct-2-ene 8,8-dioxide

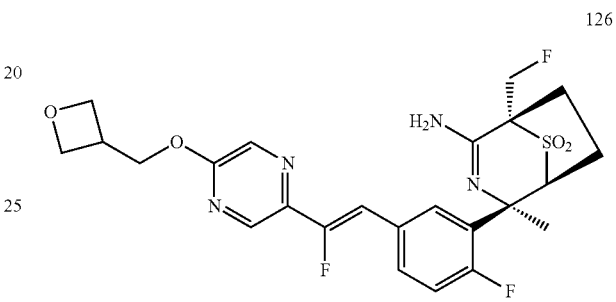

126

This compound (53 mg, 80% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 60 mg, 0.13 mmol) and 3-oxetanemethanol (Ark Pharm Inc., Libertyville Ill., USA) (51 μL, 0.637 mmol) as starting materials. MS m/z=523.2 [M+H]⁺. ¹H NMR (400 MHz, DMSO-d₆) δ ppm 8.48 (s, 1H) 8.42 (s, 1H) 7.90 (br d, J=7.43 Hz, 1H) 7.69 (br s, 1H) 7.27 (br dd, J=11.54, 8.61 Hz, 1H) 6.92 (d, J=40.88 Hz, 1H) 6.30 (br s, 2H) 4.89-5.25 (m, 2H) 4.69-4.77 (m, 2H) 4.56-4.62 (m, 2H) 4.47 (t, J=6.06 Hz, 2H) 3.81 (br d, J=5.48 Hz, 1H) 3.40-3.50 (m, 1H) 1.90-2.07 (m, 1H) 1.73-1.86 (m, 5H) 1.37 (br d, J=10.37 Hz, 1H) ¹⁹F NMR (376 MHz, DMSO-d₆) δ ppm −111.46 (s, 1F) −124.71 (s, 1F) −220.83−−220.75 (m, 1F).

Example 127: (R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile. (Method B)

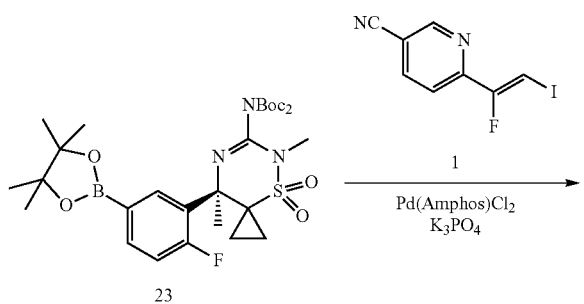

23

-continued

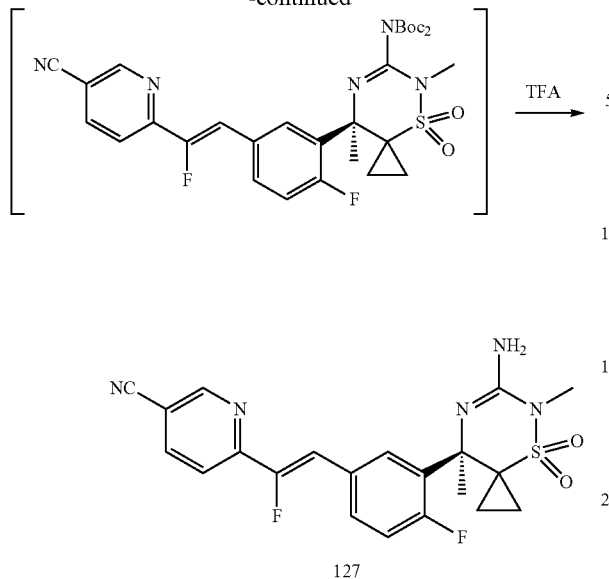

127

To a 2-L round bottom flask with an overhead stirrer, a N₂ inlet, and a thermol couple, was added di-Boc-(R)-6-amino-8-(2-fluoro-5-(4,4,5,5-tetramethyl-1,3,2-dioxaborolan-2-yl)phenyl)-5,8-dimethyl-4-thia-5,7-diazaspiro[2.5]oct-6-ene 4,4-dioxide (23) (40.0 g, 64.1 mmol), (Z)-6-(1-fluoro-2-iodovinyl)nicotinonitrile (1) (17.6 g, 64.1 mmol), potassium phosphate tribasic (33.9 g, 160 mmol), bis-(di-tert-butyl(4-dimethylaminophenyl)phosphine)dichloropalladium(II) (Sigma-Aldrich, St. Louis, Mo., USA) (2.3 g, 3.2 mmol), 1,4-dioxane (320 mL), and water (80 mL). The reaction mixture was purged with N₂ and heated to 75° C. for 20 h. The mixture was cooled to RT, and extracted with EtOAc (300 mL). The organic solution was washed with brine (100 mL) followed by water (100 mL), and concentrated. The resulting dark oil was dissolved in DCM (410 mL), cooled to 5-10° C. with an ice/water bath, and treated with trifluoroacetic acid (28.5 mL, 382 mmol) dropwise. The reaction was stirred at RT for 3 days till full conversion. The solution was cooled to 5° C., treated with brine (200 mL) and stirred at RT for 10 min. The aqueous layer was removed. The organic layer was added sat'd aqueous Na₂CO₃ solution slowly till pH=7 to 8. The organic layer was separated and concentrated. The residue was then stirred in 5 wt. % aqueous K₂CO₃ solution (500 mL) for 1 h, filtered, washed with water, and dried overnight to afford the crude as a yellow solid (35.5 g). The crude material was loaded on a silica gel column and eluted with heptane:EtOAc/EtOH[3:1]=9:1 to 0:10 to afford the crude product as a yellow solid (30 g). The crude product was stirred in MTBE (300 mL) at RT for 18 h, filtered, washed with MTBE (50 mL), and dried overnight to afford (R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile (127) (20.9 g, 47.3 mmol, 74% yield) as a crystalline solid. MS m/z=444.1 [M+H]⁺. ¹H NMR (600 MHz, DMSO-d₆) δ 9.06-9.09 (m, 1H), 8.44 (dd, J=2.10, 8.35 Hz, 1H), 7.84 (d, J=8.16 Hz, 1H), 7.80 (dd, J=1.98, 7.86 Hz, 1H), 7.71 (ddd, J=2.14, 4.39, 8.43 Hz, 1H), 7.24-7.33 (m, 1H), 7.21 (dd, J=8.51, 11.86 Hz, 1H), 5.81-6.25 (m, 2H), 3.06 (s, 3H), 1.59 (s, 4H), 1.47 (td, J=6.57, 10.74 Hz, 1H), 1.24-1.29 (m, 1H), 1.14-1.20 (m, 1H).

Example 128: (1R,4R,5S)-2-amino-4-(5-((Z)-2-(5-((S)-but-3-yn-2-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide

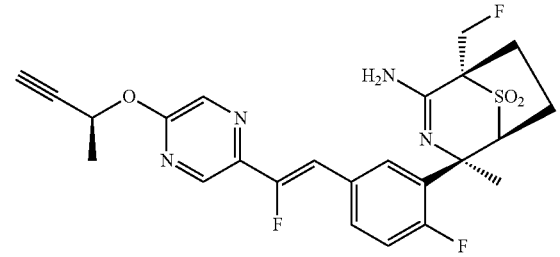

128

This compound (50 mg, 37% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 125 mg, 0.26 mmol) and (S)-(−)-3-butyn-2-ol (Alfa Aesar, Ward Hill, Mass., USA) (105 μL, 1.32 mmol) as starting materials. MS m/z=505.2 [M+H]⁺. ¹H NMR (400 MHz, DMSO-d₆) δ ppm 8.51 (s, 1H) 8.43 (s, 1H) 7.90 (br d, J=7.43 Hz, 1H) 7.70 (br s, 1H) 7.27 (dd, J=11.64, 8.70 Hz, 1H) 6.93 (d, J=40.69 Hz, 1H) 6.30 (br s, 2H) 5.75 (q, J=6.46 Hz, 1H) 4.89-5.26 (m, 2H) 3.81 (br d, J=5.87 Hz, 1H) 3.58 (s, 1H) 1.94-2.05 (m, 1H) 1.74-1.86 (m, 5H) 1.62 (d, J=6.65 Hz, 3H) 1.30-1.41 (m, 1H).

Example 129: (R,Z)-5-amino-3-(2-fluoro-5-(2-fluoro-2-(5-(oxazol-2-ylmethoxy)pyrazin-2-yl)vinyl)phenyl)-3,6,6-trimethyl-3,6-dihydro-2H-1,4-thiazine 1,1-dioxide

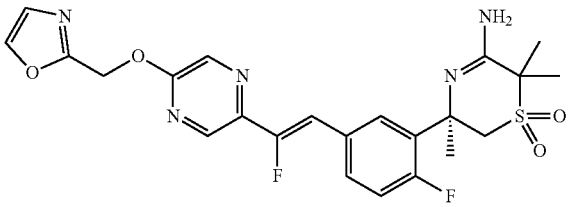

129

This compound (53 mg, 59% yield) as a white solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 80 mg, 0.125 mmol) and 2-hydroxymethyl-oxazole (62 mg, 0.624 mmol). MS m/z=504.1 [M+H]⁺. ¹H NMR (400 MHz, CDCl₃) δ 12.43 (br s, 1H), 11.37 (br s, 1H), 8.70 (br s, 1H), 8.35 (s, 1H), 8.26 (s, 1H), 7.65-7.71 (m, 2H), 7.60 (br d, J=7.63 Hz, 1H), 7.12-7.18 (m, 2H), 6.81 (d, J=40 Hz, 1H), 5.47 (s, 2H), 4.01 (d, J=15.45 Hz, 1H), 3.71 (d, J=15.65 Hz, 1H), 2.07 (s, 3H), 1.91 (s, 3H), 1.81 (s, 3H). NH₂ peak was not observed.

Example 130: (1R,4R,5S)-2-amino-4-(2-fluoro-5-((Z)-2-fluoro-2-(5-(2-methoxyethoxy)pyrazin-2-yl)vinyl)phenyl)-1-(fluoromethyl)-4-methyl-8-thia-3-azabicyclo[3.2.1]oct-2-ene 8,8-dioxide

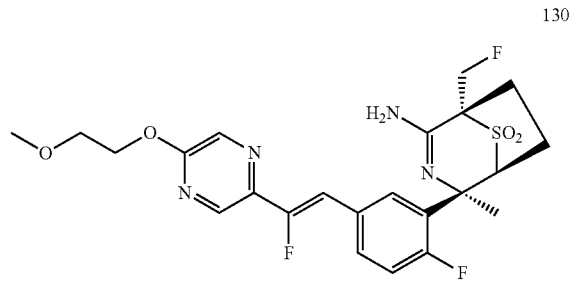 [SMILES: COCCOc1cnc(/C(F)=C/c2ccc(F)c([C@@]3(C)N=C(N)[C@@]4(CF)CC[C@@H]3S4(=O)=O)c2)cn1]

This compound (81 mg, 92% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 75 mg, 0.16 mmol) and 2-methoxyethanol (Alfa Aesar, Ward Hill, Mass., USA) (63 µL, 0.80 mmol) as starting materials. MS m/z=511.2 [M+H]+. 1H NMR (400 MHz, DMSO-d6) δ ppm 8.45 (s, 1H) 8.41 (s, 1H) 7.90 (br d, J=7.82 Hz, 1H) 7.68 (br s, 1H) 7.26 (br dd, J=11.64, 8.71 Hz, 1H) 6.90 (d, J=40.10 Hz, 1H) 6.32 (br s, 2H) 4.89-5.26 (m, 2H) 4.45-4.52 (m, 2H) 3.81 (br d, J=5.09 Hz, 1H) 3.66-3.74 (m, 2H) 3.32 (s, 3H) 1.91-2.07 (m, 1H) 1.78 (s, 5H) 1.29-1.43 (m, 1H).

Example 131: (1R,4R,5S)-2-amino-4-(2-fluoro-5-((Z)-2-fluoro-2-(5-(((S)-1-methoxypropan-2-yl)oxy)pyrazin-2-yl)vinyl)phenyl)-1-(fluoromethyl)-4-methyl-8-thia-3-azabicyclo[3.2.1]oct-2-ene 8,8-dioxide

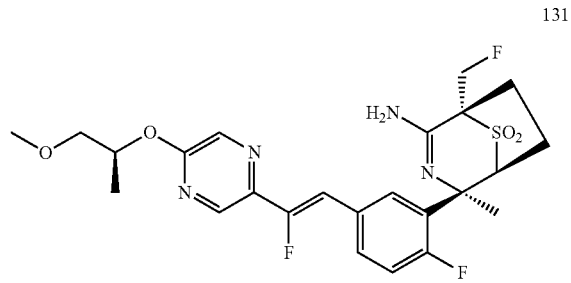 [SMILES: COC[C@H](C)Oc1cnc(/C(F)=C/c2ccc(F)c([C@@]3(C)N=C(N)[C@@]4(CF)CC[C@@H]3S4(=O)=O)c2)cn1]

This compound (120 mg, 86% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 125 mg, 0.26 mmol) and (S)-(+)-1-methoxy-2-propanol (Sigma-Aldrich Chemical Company, Inc., St. Louis, Mo., USA) (182 µL, 1.86 mmol) as starting materials. MS m/z=525.2 [M+H]+. 1H NMR (400 MHz, DMSO-d6) δ ppm 8.45 (s, 1H) 8.41 (s, 1H) 7.89 (dd, J=7.82, 2.35 Hz, 1H) 7.64-7.71 (m, 1H) 7.25 (dd, J=11.93, 8.61 Hz, 1H) 6.90 (d, J=40.88 Hz, 1H) 6.29 (br s, 2H) 4.87-5.25 (m, 2H) 4.24-4.41 (m, 2H) 3.79 (br d, J=6.06 Hz, 1H) 3.72 (td, J=6.16, 3.91 Hz, 1H) 3.21-3.39 (m, 3H) 1.91-2.06 (m, 1H) 1.73-1.85 (m, 5H) 1.35 (brt, J=9.88 Hz, 1H) 1.18 (d, J=6.46 Hz, 3H).

Example 132: (1R,4R,5S)-2-amino-4-(5-((Z)-2-(5-(cyclobutylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide

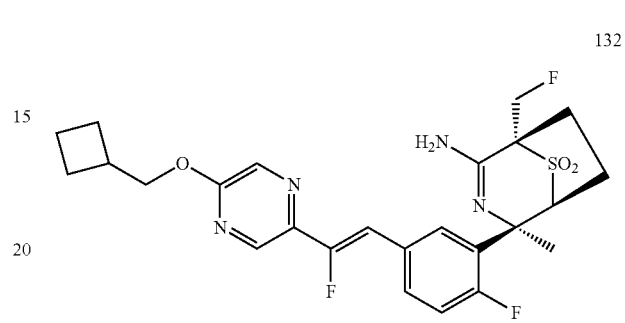

This compound (105 mg, 95% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and cyclobutanemethanol (Sigma-Aldrich Chemical Company, Inc., St. Louis, Mo., USA) (141 µL, 1.49 mmol) as starting materials. MS m/z=521.2 [M+H]+. 1H NMR (400 MHz, DMSO-d6) δ ppm 8.45 (s, 1H), 8.39 (s, 1H), 7.90 (br d, J=7.24 Hz, 1H), 7.68 (br s, 1H), 7.26 (dd, J=11.64, 8.51 Hz, 1H), 6.90 (d, J=41.08 Hz, 1H), 6.30 (br s, 2H), 4.87-5.27 (m, 2H), 4.35 (d, J=6.85 Hz, 2H), 3.80 (br d, J=5.87 Hz, 1H), 3.35 (d, J=6.65 Hz, 1H), 2.78 (dt, J=14.62, 7.26 Hz, 1H), 2.25-2.41 (m, 1H), 1.61-2.17 (m, 10H), 1.29-1.43 (m, 1H).

Example 133: (1R,4R,5S)-2-amino-4-(2-fluoro-5-((Z)-2-fluoro-2-(5-(2-fluoroethoxy)pyrazin-2-yl)vinyl)phenyl)-1-(fluoromethyl)-4-methyl-8-thia-3-azabicyclo[3.2.1]oct-2-ene 8,8-dioxide

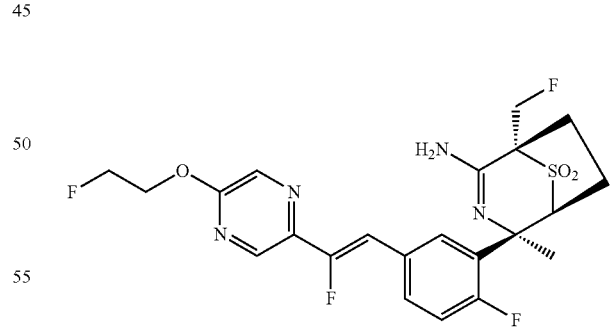

This compound (92 mg, 87% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and 2-fluoroethanol (Sigma-Aldrich Chemical Company, Inc., St. Louis, Mo., USA) (87 µL, 1.49 mmol) as starting materials. MS m/z=499.2 [M+H]+. 1H NMR (400 MHz, DMSO-d6) δ ppm 8.46 (d, J=2.74 Hz, 2H) 7.91 (br d, J=6.65 Hz, 1H) 7.63-7.73 (m, 1H) 7.26 (dd, J=11.93, 8.61 Hz, 1H) 6.92 (d, J=40.69 Hz, 1H) 6.32 (br s, 2H) 4.90-5.26 (m, 2H) 4.56-4.89 (m, 4H) 3.81 (br d, J=5.67 Hz, 1H) 1.94-2.07 (m, 1H) 1.74-1.87 (m, 5H) 1.29-1.43 (m, 1H).

Example 134: (1R,4R,5S)-2-amino-4-(5-((Z)-2-(5-(2,2-difluoroethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide

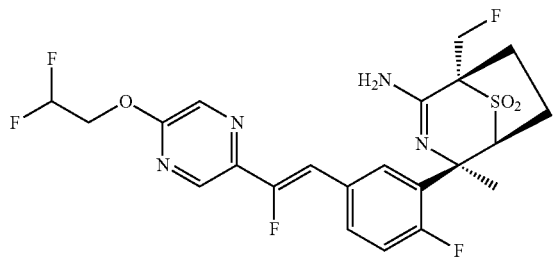 [SMILES: C[C@]1(c2cc(/C=C(\F)c3cnc(OCC(F)F)cn3)ccc2F)N=C(N)[C@@]2(CF)CC[C@@H]1S2(=O)=O]

This compound (92 mg, 87% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and 2,2-difluoroethanol (Accela ChemBio Inc., San Diego, Calif., USA) (122 µL, 1.49 mmol) as starting materials. MS m/z=517.0 [M+H]$^+$. $^1$H NMR (400 MHz, DMSO-d$_6$) δ ppm 8.52 (s, 1H) 8.50 (s, 1H) 7.91 (br d, J=7.43 Hz, 1H) 7.65-7.73 (m, 1H) 7.27 (dd, J=11.64, 8.71 Hz, 1H) 6.95 (d, J=40.30 Hz, 1H) 6.43-6.63 (m, 1H) 6.25-6.36 (m, 2H) 4.89-5.25 (m, 2H) 4.70 (td, J=15.06, 3.13 Hz, 2H) 3.81 (br d, J=5.87 Hz, 1H) 1.93-2.07 (m, 1H) 1.70-1.89 (m, 5H) 1.36 (brt, J=10.56 Hz, 1H).

Example 135: (1R,4R,5S)-2-amino-4-(2-fluoro-5-((Z)-2-fluoro-2-(5-propoxypyrazin-2-yl)vinyl)phenyl)-1-(fluoromethyl)-4-methyl-8-thia-3-azabicyclo[3.2.1]oct-2-ene 8,8-dioxide

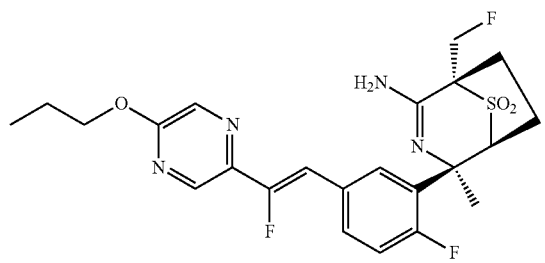

This compound (90 mg, 86% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and 1-propanol (Sigma-Aldrich Chemical Company, Inc., St. Louis, Mo., USA) (111 µL, 1.487 mmol) as starting materials. MS m/z=495.2 [M+H]$^+$. $^1$H NMR (400 MHz, DMSO-d$_6$) δ ppm 8.44 (s, 1H) 8.37 (s, 1H) 7.90 (br d, J=6.46 Hz, 1H) 7.68 (br dd, J=5.97, 2.45 Hz, 1H) 7.26 (dd, J=11.74, 8.61 Hz, 1H) 6.89 (d, J=40.69 Hz, 1H) 6.20-6.45 (m, 2H) 4.89-5.26 (m, 2H) 4.32 (t, J=6.65 Hz, 2H) 3.80 (br d, J=5.67 Hz, 1H) 1.89-2.08 (m, 1H) 1.72-1.89 (m, 7H) 1.30-1.42 (m, 1H) 0.99 (t, J=7.43 Hz, 3H).

Example 136: (1R,4R,5S)-2-amino-4-(2-fluoro-5-((Z)-2-fluoro-2-(5-(2-methoxypropoxy)pyrazin-2-yl)vinyl)phenyl)-1-(fluoromethyl)-4-methyl-8-thia-3-azabicyclo[3.2.1]oct-2-ene 8,8-dioxide

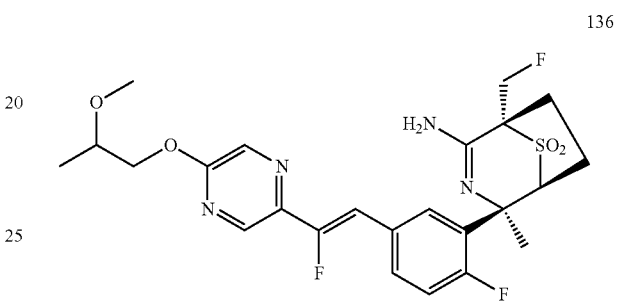

This compound (90 mg, 86% yield) as a white solid was prepared in a fashion similar to that described in Method A for Example 108, using (1R,4R,5S)-2-amino-4-(5-((Z)-2-(5-chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and 2-methoxypropan-1-ol (Ark Pharm Inc., Libertyville Ill. USA) (134 µL, 1.487 mmol) as starting materials. MS m/z=525.2 [M+H]$^+$. $^1$H NMR (400 MHz, DMSO-d$_6$) δ ppm 8.44 (s, 1H) 8.34 (s, 1H) 7.89 (dd, J=7.92, 2.25 Hz, 1H) 7.67 (ddd, J=8.41, 4.69, 2.35 Hz, 1H) 7.25 (dd, J=11.84, 8.51 Hz, 1H) 6.88 (d, J=40.88 Hz, 1H) 6.29 (brs, 2H) 5.30-5.42 (m, 1H) 4.88-5.25 (m, 2H) 3.48-3.61 (m, 2H) 3.29 (s, 3H) 3.06-3.26 (m, 1H) 1.93-2.06 (m, 1H) 1.72-1.85 (m, 5H) 1.32-1.41 (m, 1H) 1.30 (d, J=6.46 Hz, 3H).

Example 137: (1R,4R,5S)-2-amino-4-(5-((Z)-2-(5-(but-2-yn-1-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide

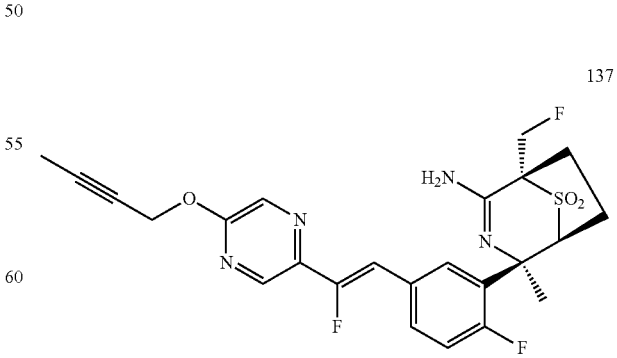

This compound (100 mg, 93% yield) as a white solid was prepared in a fashion similar to that described in Method A for Example 108, using (1R,4R,5S)-2-amino-4-(5-((Z)-2-(5- chloropyrazin-2-yl)-2-fluorovinyl)-2-fluorophenyl)-1-(fluoromethyl)-4-methyl-8-thia-3-azabicyclo[3.2.1]oct-2-ene 8,8-dioxide (108a, 100 mg, 0.21 mmol) and 2-butyn-1-ol (Sigma-Aldrich Chemical Company, Inc., St. Louis, Mo., USA) (104 µL, 1.487 mmol) as starting materials. MS m/z=505.2 [M+H]$^+$. $^1$H NMR (400 MHz, DMSO-d$_6$) δ ppm 8.49 (s, 1H) 8.43 (s, 1H) 7.91 (br d, J=6.65 Hz, 1H) 7.69 (br d, J=2.74 Hz, 1H) 7.27 (dd, J=11.64, 8.70 Hz, 1H) 6.92 (d, J=40.69 Hz, 1H) 6.32 (br s, 2H) 4.89-5.25 (m, 4H) 3.81 (br d, J=5.28 Hz, 1H) 1.94-2.08 (m, 1H) 1.74-1.90 (m, 8H) 1.29-1.42 (m, 1H). $^{19}$F NMR (376 MHz, DMSO-d$_6$) δ ppm −111.40 (s, 1F) −124.66 (s, 1F) −220.80 (s, 1F).

Example 138: (8R)-8-(2-fluoro-5-((Z)-2-fluoro-2-(5-(2-propyn-1-yloxy)-2-pyrazinyl)ethenyl)phenyl)-5,8-dimethyl-4-thia-5,7-diazaspiro[2.5]oct-6-en-6-amine 4,4-dioxide

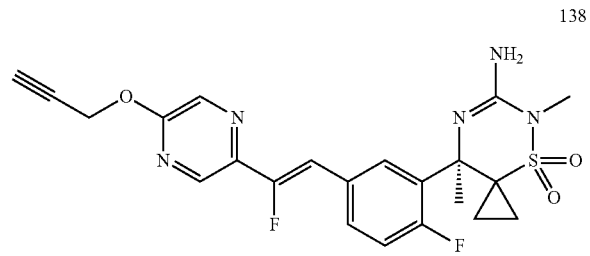 [SMILES: C#CCOc1cnc(/C(F)=C/c2ccc(F)c([C@@]3(C)N=C(N)N(C)S(=O)(=O)C34CC4)c2)cn1]

138

This compound (12 mg, 23% yield) was prepared as a white solid in a fashion similar to that described in Method D for Example 112, using intermediate 139 (0.05 g, 0.11 mmol) and propargyl alcohol (Sigma-Aldrich Chemical Company, Inc., St. Louis, Mo., USA) (0.03 g, 0.55 mmol) as starting materials. MS m/z=474.1 [M+H]$^+$. $^1$H NMR (400 MHz, CHLOROFORM-d) δ ppm 11.68 (br. s., 1H) 8.10-8.47 (m, 2H) 7.47-7.74 (m, 2H) 7.12 (dd, J=11.44, 9.10 Hz, 1H)) 6.67-6.91 (m, 1H) 4.92-5.12 (m, 2H) 3.18-3.47 (m, 3H) 2.53 (s, 1H) 1.82-1.96 (m, 3H) 1.47 (br. s., 1H) 1.33-1.43 (m, 1H) 1.16-1.33 (m, 2H) 0.88 (t, J=6.46 Hz, 1H). $^{19}$F NMR (376 MHz, CHLOROFORM-d) δ −109.66 (br s, 1F) −124.55 (s, 1F).

Example 139: (8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide

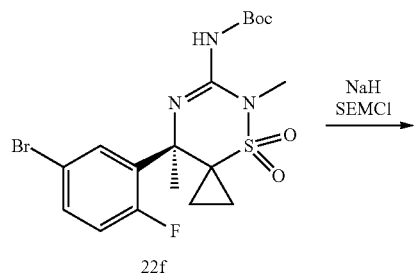

22f

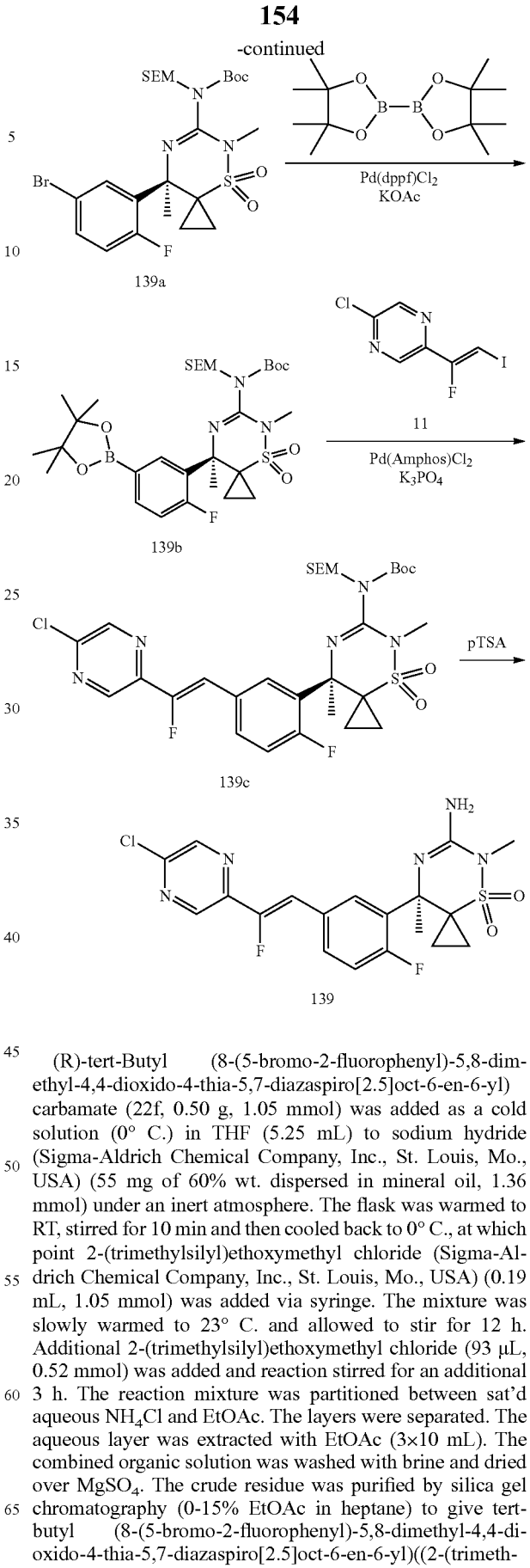

(R)-tert-Butyl (8-(5-bromo-2-fluorophenyl)-5,8-dimethyl-4,4-dioxido-4-thia-5,7-diazaspiro[2.5]oct-6-en-6-yl)carbamate (22f, 0.50 g, 1.05 mmol) was added as a cold solution (0° C.) in THF (5.25 mL) to sodium hydride (Sigma-Aldrich Chemical Company, Inc., St. Louis, Mo., USA) (55 mg of 60% wt. dispersed in mineral oil, 1.36 mmol) under an inert atmosphere. The flask was warmed to RT, stirred for 10 min and then cooled back to 0° C., at which point 2-(trimethylsilyl)ethoxymethyl chloride (Sigma-Aldrich Chemical Company, Inc., St. Louis, Mo., USA) (0.19 mL, 1.05 mmol) was added via syringe. The mixture was slowly warmed to 23° C. and allowed to stir for 12 h. Additional 2-(trimethylsilyl)ethoxymethyl chloride (93 µL, 0.52 mmol) was added and reaction stirred for an additional 3 h. The reaction mixture was partitioned between sat'd aqueous NH$_4$Cl and EtOAc. The layers were separated. The aqueous layer was extracted with EtOAc (3×10 mL). The combined organic solution was washed with brine and dried over MgSO$_4$. The crude residue was purified by silica gel chromatography (0-15% EtOAc in heptane) to give tert-butyl (8-(5-bromo-2-fluorophenyl)-5,8-dimethyl-4,4-dioxido-4-thia-5,7-diazaspiro[2.5]oct-6-en-6-yl)((2-(trimethylsilyl)ethoxy)methyl)carbamate 139a (0.61 g, 1.00 mmol, 96% yield). MS m/z=608.2 [M+H]+. 1H NMR (400 MHz, CHLOROFORM-d) δ ppm 7.47-7.61 (m, 1H) 7.33-7.42 (m, 1H) 6.86-7.01 (m, 1H) 5.71 (d, J=12.13 Hz, 1H), 4.94-5.14 (m, 2H) 4.51 (d, J=12.13 Hz, 1H) 2.84-2.97 (m, 3H) 1.80-1.89 (m, 2H) 1.76 (s, 3H) 1.43-1.49 (m, 9H) 0.81-1.04 (m, 4H) 0.00 (d, J=1.76 Hz, 9H).

tert-Butyl (8-(2-fluoro-5-(4,4,5,5-tetramethyl-1,3,2-dioxaborolan-2-yl)phenyl)-5,8-dimethyl-4,4-dioxido-4-thia-5,7-diazaspiro[2.5]oct-6-en-6-yl)((2-(trimethylsilyl)ethoxy)methyl) 139b (0.20 g, 0.30 mmol, 68% yield) as a colorless oil was prepared employing a procedure analogous to that used for the preparation of intermediate 23, here using carbamate 139a (0.27 g, 0.45 mmol), potassium acetate (0.13 g, 1.36 mmol), bis(pinacolato) diboron (Sigma-Aldrich Chemical Company, Inc., St. Louis, Mo., USA) (0.23 g, 0.91 mmol) and 1,1'-bis(diphenylphosphino)ferrocene palladium(II) dichloride dichloromethane adduct (0.26 g, 0.32 mmol) (Strem Chemicals, Inc., Newburyport, Mass., USA) (0.019 g, 0.023 mmol). MS m/z=654.4 [M+H]+.

Finally, compound 139 (59 mg, 43% yield overall) was prepared as an off white solid in a fashion similar to that described in Method C for Example 111, using intermediate 139b (0.20 g, 0.31 mmol), (Z)-2-chloro-5-(1-fluoro-2-iodovinyl)pyrazine (11, 96 mg, 0.33 mmol), potassium phosphate tribasic (Strem Chemicals, Inc., Newburyport, Mass., USA) (0.10 g, 0.76 mmol), and 1,1-bis[(di-t-butyl-p-methylaminophenyl]palladium(II) chloride (Sigma-Aldrich Chemical Company, Inc., St. Louis, Mo., USA) (22 mg, 0.03 mmol) as starting materials. The subsequent deprotection step on 139c was carried out using p-toluenesulfonic acid monohydrate (1.57 g, 8.23 mmol) to give (8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide (139). MS m/z=454.1 [M+H]+. 1H NMR (400 MHz, CHLOROFORM-d) δ ppm 8.61 (s, 1H) 8.51 (s, 1H) 7.54-7.79 (m, 2H)) 7.15 (s, 1H) 6.85-7.05 (m, 1H) 3.36 (s, 3H) 1.91-1.98 (m, 1H) 1.86-1.89 (m, 5H) 1.43-1.84 (m, 2H) 1.30-1.48 (m, 1H). 19F NMR (376 MHz, CHLOROFORM-d) δ ppm −111.16--106.94 (m, 1F) −127.26--120.85 (m, 1F).

Example 140: (R,Z)-5-amino-3-(2-fluoro-5-(2-fluoro-2-(5-hydroxypyrazin-2-yl)vinyl)phenyl)-3,6,6-trimethyl-3,6-dihydro-2H-1,4-thiazine 1,1-dioxide

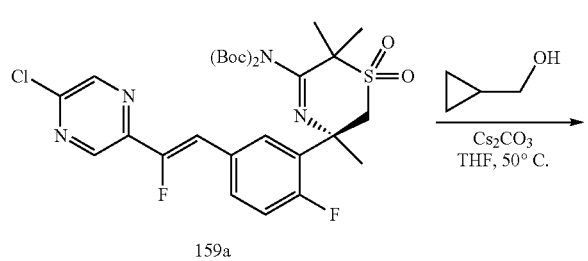

159a

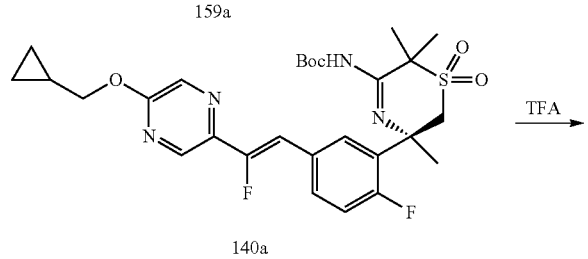

140a

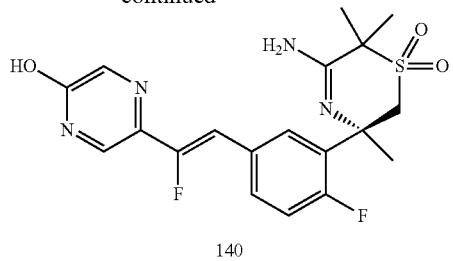

140

A mixture of cyclopropylmethanol (45 mg, 0.62 mmol), bisBoc-protected-(R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a, 80 mg, 0.125 mmol) and cesium carbonate (122 mg, 0.374 mmol) in THF (1.5 mL) was allowed to stir at 50° C. and monitored by LCMS. Upon completion, the mixture was cooled to RT, filtered and washed with ethyl acetate. The filtrate was concentrated and the residue was purified by silica gel chromatography (0-100% ethyl acetate in heptane) to give 140a. MS m/z=577.3 [M+H]+. 140a was dissolved in 4 mL of DCM and treated with TFA (1 mL) at RT. The mixture was stirred at RT and monitored by LCMS. Upon completion, the mixture was concentrated and the residue was purified on a silica gel column (0-10% methanol in DCM) to give Example 140 (25 mg, 74% yield) as a yellow solid. MS m/z=423.0 [M+H]+. 1H NMR (400 MHz, CHLOROFORM-d) δ 8.04 (s, 1H), 7.69 (br d, J=7.82 Hz, 1H), 7.32-7.40 (m, 2H), 7.06-7.11 (m, 1H), 6.48 (d, J=40 Hz, 1H), 3.92 (br d, J=15.06 Hz, 2H), 3.70 (br d, J=15.26 Hz, 2H), 1.99 (s, 3H), 1.86 (s, 3H), 1.71 (s, 3H). OH peak was not observed.

Example 141: (R,Z)-5-amino-3-(2-fluoro-5-(2-fluoro-2-(5-(2,2,3,3-tetrafluoropropoxy)pyrazin-2-yl)vinyl)phenyl)-3,6,6-trimethyl-3,6-dihydro-2H-1,4-thiazine 1,1-dioxide

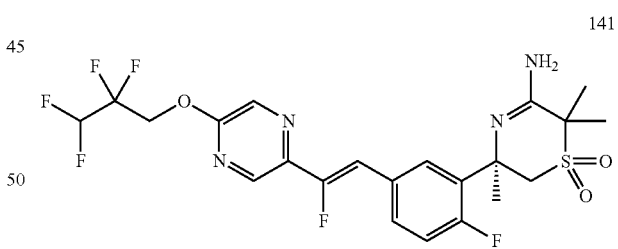

141

This compound (33 mg, 49% yield) as a yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 80 mg, 0.12 mmol and 2,2,3,3-tetrafluoropropanol (82 mg, 0.62 mmol). MS m/z=537.2 [M+H]+. 1H NMR (400 MHz, CHLOROFORM-d) δ 8.36 (s, 1H), 8.27 (s, 1H), 7.69 (dd, J=8.51, 4.79, 1.96, 1H), 7.62 (br d, J=8.02 Hz, 1H), 7.12-7.18 (m, 1H), 6.85 (d, J=40 Hz, 1H), 5.99 (tt, J=52, 4.11, 1H), 4.77 (t, J=12.62 Hz, 2H), 3.95 (d, J=15.45 Hz, 3H), 3.69 (d, J=15.45 Hz, 3H), 2.03 (s, 3H), 1.89 (s, 3H), 1.78 (s, 3H). NH2 peak was not observed.

Example 142: (R,Z)-5-amino-3-(2-fluoro-5-(2-fluoro-2-(5-(3,3,3-trifluoropropoxy)pyrazin-2-yl)vinyl)phenyl)-3,6,6-trimethyl-3,6-dihydro-2H-1,4-thiazine 1,1-dioxide

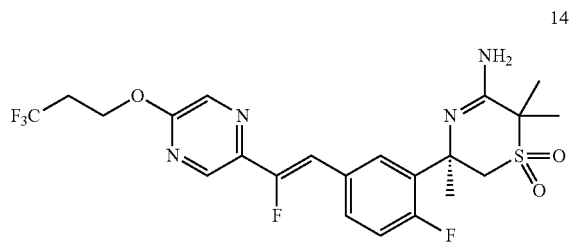

142

This compound (27 mg, 41% yield) as a yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 80 mg, 0.12 mmol) and 3,3,3-trifluoropropan-1-ol (71 mg, 0.62 mmol). MS m/z=519.2 [M+H]$^+$. $^1$H NMR (400 MHz, CHLOROFORM-d) δ 8.35 (s, 1H), 8.19 (s, 1H), 7.69 (ddd, J=1.96, 4.79, 8.51 Hz, 1H), 7.61 (br d, J=7.82 Hz, 1H), 7.12-7.17 (m, 1H), 6.85 (d, J=40 Hz, 1H), 4.60 (t, J=6.46 Hz, 2H), 3.95 (d, J=15.45 Hz, 1H), 3.69 (d, J=15.45 Hz, 1H), 2.59-2.71 (m, 2H), 2.04 (s, 3H), 1.89 (m, 3H), 1.79 (s, 3H). NH$_2$ peak was not observed.

Example 143: (R,Z)-3-amino-5-(5-(2-(5-(cyclopropylmethoxy)pyrazin-2-yl)-2-fluorovinyl)-2-fluorophenyl)-2,5-dimethyl-5,6-dihydro-2H-1,2,4-thiadiazine 1,1-dioxide

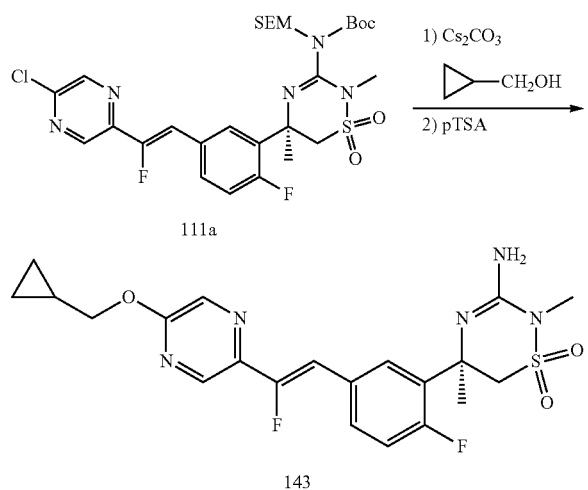

143

This compound (37 mg, 22% yield for 2 steps) as a light yellow solid was prepared in a fashion similar to that described for Example 174, here using cyclopropylmethanol (263 mg, 3.65 mmol) and 111a (240 mg, 0.37 mmol) as starting materials. MS m/z=464.2 [M+H]$^+$. $^1$H NMR (400 MHz, DMSO-d$_6$) δ 8.44 (s, 1H), 8.40 (s, 1H), 7.87 (d, J=6.26 Hz, 1H), 7.57-7.66 (m, 1H), 7.21 (dd, J=12.03, 8.51 Hz, 1H), 6.85 (d, J=40.88 Hz, 1H), 6.07 (br. s, 2H), 4.21 (d, J=7.24 Hz, 2H), 3.80 (s, 2H), 3.05 (s, 3H), 2.09 (s, 1H), 1.62 (s, 3H), 0.55-0.63 (m, 2H), 0.34-0.42 (m, 2H). $^{19}$F NMR (376 MHz, DMSO-d$_6$) δ −112.22 (s, 1F), −124.76 (s, 1F).

Example 144: (R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide

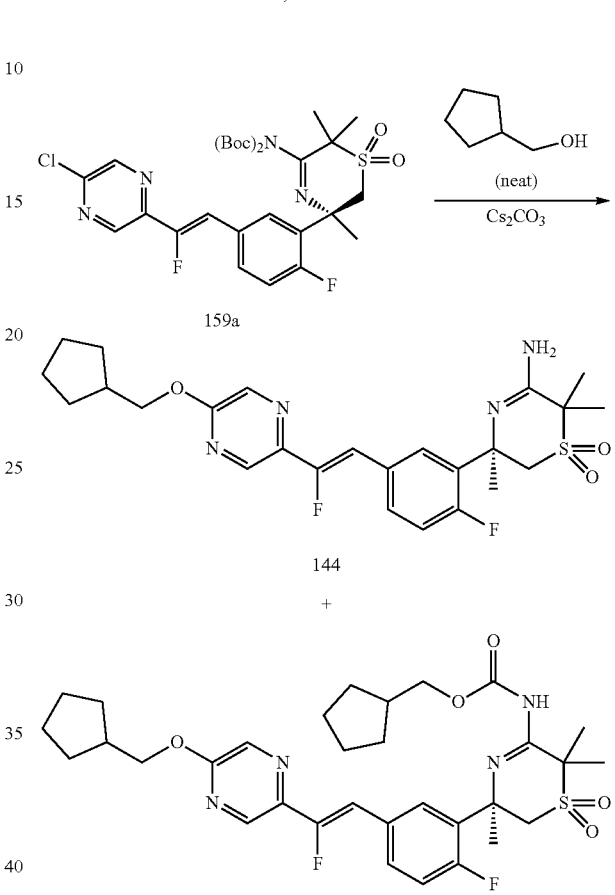

A mixture of (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 0.08 g, 0.12 mmol) and cesium carbonate (0.12 g, 0.37 mmol) in cyclopentylmethanol (0.43 mL, 3.99 mmol) was stirred at 50° C. for 24 h. The mixture was cooled to RT, diluted with ethyl acetate, and filtered. The filtrate was concentrated and the residue was purified on a silica gel column (0-10% (2 M NH$_3$/methanol) in DCM) to give two products. The first eluent was (R,Z)-cyclopentylmethyl (5-(5-(2-(5-(cyclopentylmethoxy)pyrazin-2-yl)-2-fluorovinyl)-2-fluorophenyl)-2,2,5-trimethyl-1,1-dioxido-5,6-dihydro-2H-1,4-thiazin-3-yl)carbamate (MS m/z=631.2 [M+H]$^+$). The second eluent was (R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide (144) (24 mg, 38% yield). MS m/z=505.2 [M+H]$^+$. $^1$H NMR (400 MHz, CHLOROFORM-d) δ 8.35 (s, 1H), 8.19 (s, 1H), 7.74 (dd, J=2.15, 8.02 Hz, 1H), 7.66 (ddd, J=2.25, 4.70, 8.51 Hz, 1H), 7.05-7.10 (m, 1H), 6.80 (d, J=40 Hz, 1H), 4.25 (d, J=7.24 Hz, 2H), 3.53-3.65 (m, 2H), 2.25-2.46 (m, 1H), 1.78-1.89 (m, 2H), 1.82 (s, 3H), 1.71 (s, 3H), 1.54-1.73 (m, 4H), 1.62 (s, 3H), 1.34-1.44 (m, 2H). NH$_2$ peak was not observed.

Example 145: (R,Z)-5-amino-3-(5-(2-(5-(cyclobutylmethoxy)pyrazin-2-yl)-2-fluorovinyl)-2-fluorophenyl)-3,6,6-trimethyl-3,6-dihydro-2H-1,4-thiazine 1,1-dioxide

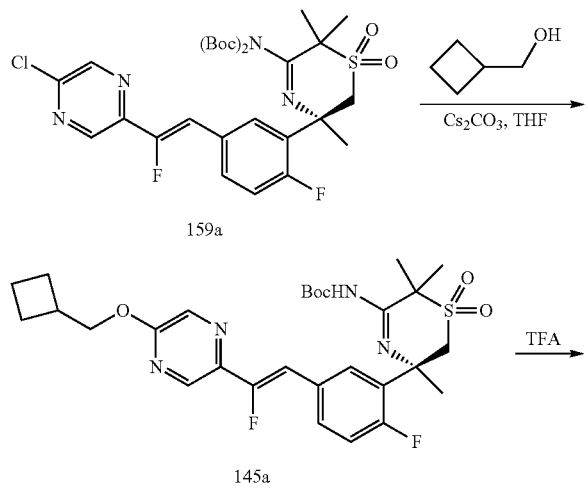

159a

145a

A mixture of cyclobutanemethanol (0.054 mL, 0.624 mmol), bisBoc-protected-(R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a, 80 mg, 0.125 mmol) and cesium carbonate (0.030 mL, 0.374 mmol) in THF (1.5 mL) was stirred at 50° C. and monitored by LCMS. Upon completion, the mixture was cooled to RT, filtered and washed with ethyl acetate. The filtrate was concentrated and the residue was purified by silica gel chromatography (0-100% ethyl acetate in heptane) to give 145a. MS m/z=591.2 [M+H]$^+$. 145a was dissolved in 4 mL of DCM and treated with TFA (1 mL) at RT. The mixture was stirred at RT and monitored by LCMS. Upon completion, the mixture was concentrated and the residue was purified on a silica gel column (0-10% methanol in DCM) to give Example 145 (10 mg, 26% yield) of as a yellow solid. MS m/z=491.1 [M+H]$^+$. $^1$H NMR (400 MHz, CHLOROFORM-d) δ 8.35 (s, 1H), 8.19 (s, 1H), 8.19 (s, 1H), 7.74 (dd, J=8.02, 2.15 Hz, 1H), 7.66 (ddd, J=8.51, 4.69, 2.25 Hz, 1H), 7.05-7.10 (m, 1H), 6.80 (d, J=40 Hz, 1H), 4.35 (d, J=6.85 Hz, 2H), 3.54-3.64 (m, 2H), 2.75-2.86 (m, 1H), 2.14-2.18 (m, 2H), 1.84-2.03 (m, 4H), 1.82 (s, 3H), 1.71 (s, 3H), 1.62 (s, 3H). NH$_2$ peak was not observed.

Example 146: (R,Z)-3-amino-5-(2-fluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide

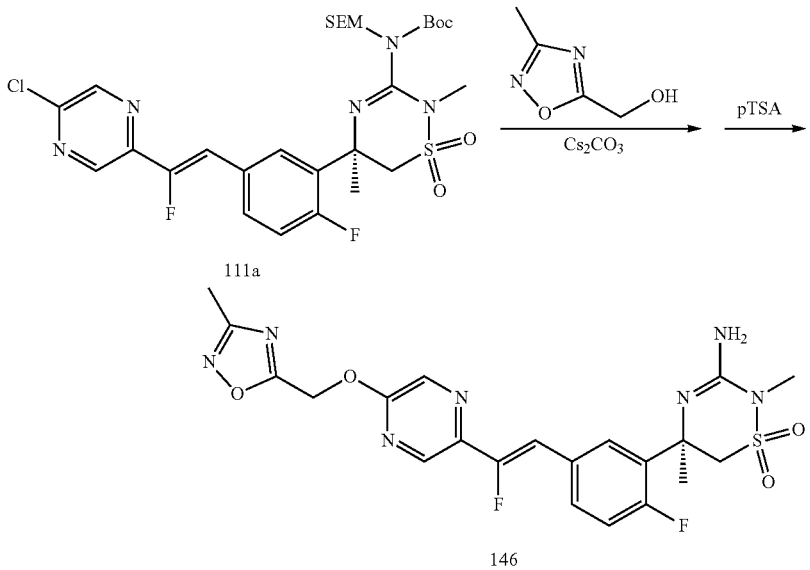

111a

146

-continued

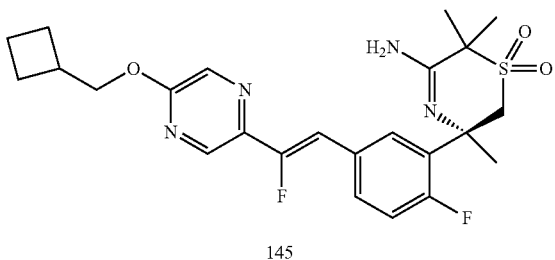

145

This compound (65 mg, 42% yield for 2 steps) as a light yellow solid was prepared in a fashion similar to that described for Example 174, here using (2-methyl-1,2,4-oxadiozol-5-yl)methanol (Enamine LLC, Monmouth Ject., N.J., USA) (173 mg, 1.52 mmol) and 111a (200 mg, 0.31 mmol) as starting materials. MS m/z=506.1 [M+H]$^+$. $^1$H NMR (400 MHz, CDCl$_3$) δ 8.33 (s, 1H) 8.28 (s, 1H) 7.87 (dd, J=8.02, 1.96 Hz, 1H) 7.56-7.62 (m, 1H) 6.98-7.12 (m, 1H) 6.80 (d, J=40.69 Hz, 1H) 5.62 (s, 2H) 3.85 (d, J=13.69 Hz, 1H) 3.71 (d, J=14.08 Hz, 1H) 3.20 (s, 3H) 2.43 (s, 3H) 1.78 (s, 3H). NH$_2$ peak was not observed. $^{19}$F NMR (376 MHz, CDCl$_3$) δ −112.35 (s, 1F), −125.79 (s, 1F).

Example 147: (R,Z)-5-(2-(3-(6-amino-5,8-dimethyl-4,4-dioxido-4-thia-5,7-diazaspiro[2.5]oct-6-en-8-yl)-4-fluorophenyl)-1-fluorovinyl)pyrazine-2-carbonitrile

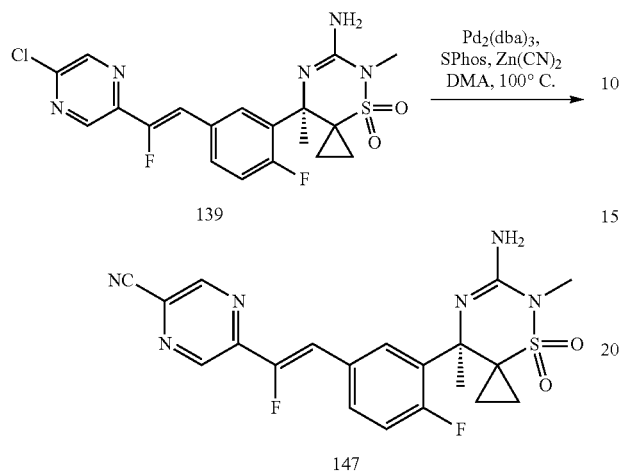

A vial was charged with (R,Z)-6-amino-8-(5-(2-(5-chloropyrazin-2-yl)-2-fluorovinyl)-2-fluorophenyl)-5,8-dimethyl-4-thia-5,7-diazaspiro[2.5]oct-6-ene 4,4-dioxide (139, 59 mg, 0.130 mmol), zinc (II) cyanide (Sigma-Aldrich Chemical Company, Inc., St. Louis, Mo., USA) (46 mg, 0.390 mmol), 2-(dicyclohexylphosphino)-2',6'-dimethoxy-1,1'-biphenyl (Strem Chemicals, Inc., Newburyport, Mass., USA) (0.016 g, 0.039 mmol), and tris(dibenzylideneacetone)dipalladium(0) (Sigma-Aldrich Chemical Company, Inc., St. Louis, Mo., USA) (18 mg, 0.019 mmol). The vial was evacuated and backfilled with $N_2$, and N, N-dimethylacetamide (1.3 mL) was added. The mixture was heated at 100° C. for 1 h at which point the reaction was determined to be complete by LCMS analysis. The mixture was filtered through celite and the cake was washed with EtOAc. The filtrate was washed with water and brine, dried over $Na_2SO_4$ and concentrated in vacuo. The crude residue was purified by silica gel chromatography (0-15% EtOAc in heptane) to give the title compound 147 (22 mg, 0.049 mmol, 38% yield) as a yellow solid. MS m/z=445.1 [M+H]$^+$. $^1$H NMR (400 MHz, CHLOROFORM-d) δ 8.95 (s, 1H), 8.83 (s, 1H), 7.73-7.80 (m, 1H), 7.70 (br. s., 1H), 7.16-7.31 (m, 2H), 7.04-7.14 (m, 1H), 3.26 (s, 3H), 1.75-1.83 (m, 3H), 1.65-1.73 (m, 1H), 1.48-1.57 (m, 1H), 1.13-1.30 (m, 2H), 1.10 (br. s., 1H), $^{19}$F NMR (376 MHz, CHLOROFORM-d) δ ppm −98.16 (s, 1F) −104.88 (br s, 1F).

Example 148: (R,Z)-3-amino-5-(2-fluoro-5-(2-fluoro-2-(5-(2,2,3,3-tetrafluoropropoxy)pyrazin-2-yl)vinyl)phenyl)-2,5-dimethyl-5,6-dihydro-2H-1,2,4-thiadiazine 1,1-dioxide

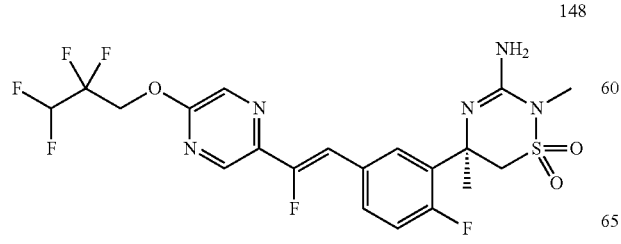

This compound (32 mg, 13% yield) was prepared as a white solid in a fashion similar to that described in Method D for Example 112, using 2,2,3,3-tetrafluoro-1-propanol (Sigma-Aldrich, St. Louis, Mo., USA) (0.31 g, 2.34 mmol) and thiadiazine 111 (0.20 g, 0.47 mmol) as starting materials. MS m/z=523.8 [M+H]$^+$. $^1$H NMR (400 MHz, CDCl$_3$) δ 8.32-8.40 (m, 1H), 8.21-8.32 (m, 1H), 7.81 (d, J=7.43 Hz, 1H), 7.64 (td, J=2.69, 5.58 Hz, 1H), 7.08 (dd, J=8.51, 12.03 Hz, 1H), 6.75-6.94 (m, 1H), 6.75-6.94 (m, 1H), 5.78-6.23 (m, 1H), 4.70-4.91 (m, 2H), 3.84-4.03 (m, 1H), 3.72 (d, J=14.08 Hz, 1H), 3.11-3.34 (m, 3H), 1.73-1.88 (m, 4H). $^{19}$F NMR (376 MHz, CDCl$_3$) δ −113.13 (br. s., 1F), −125.10-122.92 (m, 4F), −137.88 (d, J=52.45 Hz, 1F).

Example 149: (R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide

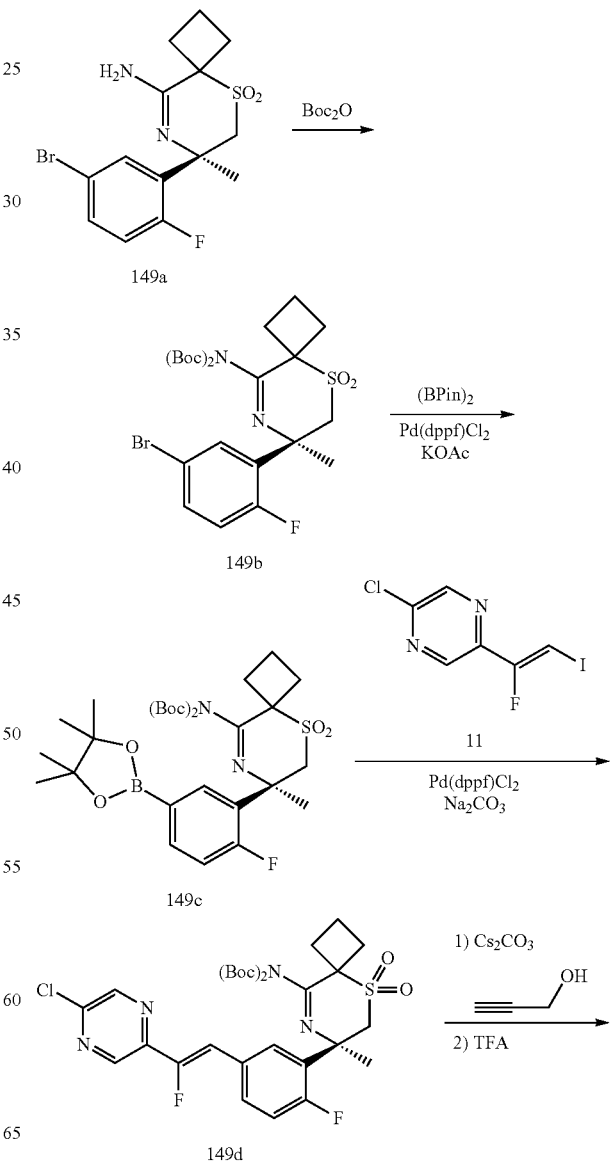

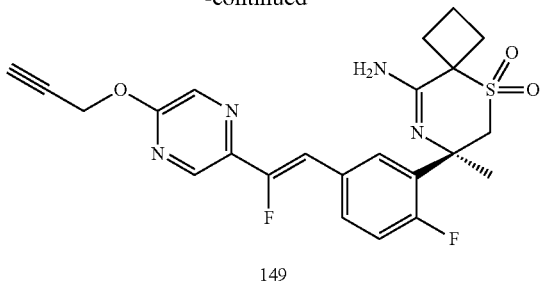

149

Preparation of bis-Boc (R)-9-amino-7-(5-bromo-2-fluorophenyl)-7-methyl-5-thia-8-azaspiro[3.5]non-8-ene 5,5-dioxide (149b)

(R)-9-amino-7-(5-bromo-2-fluorophenyl)-7-methyl-5-thia-8-azaspiro[3.5]non-8-ene 5,5-dioxide (149a, prepared according to the procedures described in WO 2014059185A1) (1.00 g, 2.66 mmol) was taken up in 15 mL of THF. N,N-Diisopropylethylamine (1.39 mL, 7.99 mmol), 4-(dimethylamino)pyridine (Sigma-Aldrich Chemical Company, Inc., St. Louis, Mo., USA) (33 mg, 2.66 mmol), and di-tert-butyl dicarbonate (Sigma-Aldrich Chemical Company, Inc., St. Louis, Mo., USA) (1.28 g, 5.86 mmol) were added. After 18 h, the solvent was removed under reduced pressure and the residue was purified by flash chromatography on silica gel (1 to 40% EtOAc/heptane) affording 149b (1.35 g, 88% yield) as a white solid. MS (ESI, positive ion) m/z: 597.2.

Preparation of bis-Boc (R)-9-amino-7-(2-fluoro-5-(4,4,5,5-tetramethyl-1,3,2-dioxaborolan-2-yl)phenyl)-7-methyl-5-thia-8-azaspiro[3.5]non-8-ene 5,5-dioxide (149c)

bis-Boc (R)-9-amino-7-(5-bromo-2-fluorophenyl)-7-methyl-5-thia-8-azaspiro[3.5]non-8-ene 5,5-dioxide (149b, 1.35 g, 2.346 mmol), bis(pinacolato)diboron (1.19 g, 4.69 mmol), potassium acetate (0.806 g, 8.21 mmol, Sigma-Aldrich), and 1,1'-bis(diphenylphosphino)ferrocene palladium(II)dichloride dichloromethane adduct (192 mg, 0.23 mmol) were taken up in 20 mL of dioxane. The mixture was purged with nitrogen and heated at 90° C. After 5 h, the mixture was cooled to RT. The mixture was partitioned between 200 mL of EtOAc and 200 mL of water, and the organic portion was washed with 100 mL of brine and dried over MgSO$_4$. Filtration and concentration under reduced pressure, followed by flash chromatography on silica gel (1 to 30% EtOAc/heptane) afforded 149c (0.98 g, 67% yield) as a white solid. MS (ESI, positive ion) m/z: 623.2.

Preparation of bis-Boc (R,Z)-9-amino-7-(5-(2-(5-chloropyrazin-2-yl)-2-fluorovinyl)-2-fluorophenyl)-7-methyl-5-thia-8-azaspiro[3.5]non-8-ene 5,5-dioxide (149d)

(Z)-2-Chloro-5-(1-fluoro-2-iodovinyl)pyrazine (11) (0.27 g, 0.96 mmol), bis-Boc (R)-9-amino-7-(2-fluoro-5-(4,4,5,5-tetramethyl-1,3,2-dioxaborolan-2-yl)phenyl)-7-methyl-5-thia-8-azaspiro[3.5]non-8-ene 5,5-dioxide (149c) (0.60 g, 0.96 mmol), sodium carbonate (0.31 g, 2.89 mmol), and 1,1'-bis(diphenylphosphino)ferrocene palladium(II)dichloride dichloromethane adduct (79 mg, 0.09 mmol) were taken up in 10 mL of 9:1 dioxane:water and heated at 75° C. for 15 h. Additional 1,1'-bis(diphenylphosphino)ferrocene palladium(II)dichloride dichloromethane adduct (79 mg, 0.09 mmol) was added. The mixture was heated at 75° C. for 5 h, then cooled to RT. It was diluted with 30 mL of EtOAc and washed with 10 mL of water and 10 mL of brine, then dried over MgSO$_4$. Filtration and concentration under reduced pressure afforded bis-Boc (R,Z)-9-amino-7-(5-(2-(5-chloropyrazin-2-yl)-2-fluorovinyl)-2-fluorophenyl)-7-methyl-5-thia-8-azaspiro[3.5]non-8-ene 5,5-dioxide (149d) (0.24 g, 38% yield) as a sticky yellow solid.

Preparation of (7R)-7-(2-fluoro-5-((Z)-2-fluoro-2-(5-(2-propyn-1-yloxy)-2-pyrazinyl)ethenyl)phenyl)-7-methyl-5-thia-8-azaspiro[3.5]non-8-en-9-amine 5,5-dioxide (149)

A solution of Intermediate 149d (0.24 g, 0.37 mmol) in 5 mL of THF was treated with cesium carbonate (0.36 g, 1.10 mmol) and propargyl alcohol (66 µL, 1.10 mmol). The mixture was heated at 50° C. for 15 h, and then cooled to RT. It was diluted with 25 mL of EtOAc and washed with 10 mL of water and 10 mL of brine, then dried over MgSO$_4$. Filtration and concentration under reduced pressure afforded a yellow oil that was taken up in 5 mL of DCM. Trifluoroacetic acid (1.0 mL) was added to the mixture, and the reaction was stirred for 1 h. The solvent was removed under reduced pressure and the residue was purified by supercritical fluid chromatography SFC (Chiralcel OX-H (250×21 mm, 5 µM: Mobile Phase: 55:45 (A:B) A: Liquid CO$_2$ B: Methanol (20 mM NH$_3$) Flow Rate: 70 g/min 22.5 mg/injection) afforded (R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide (Example 149) (40 mg, 0.085 mmol, 23% yield) as a white solid. MS (ESI, positive ion) m/z: 473. $^1$H NMR (400 MHz, CHLOROFORM-d) δ 8.36-8.44 (m, 1H), 8.18-8.30 (m, 1H), 7.69-7.74 (m, 1H), 7.61-7.67 (m, 1H), 7.06 (dd, J=8.80, 11.93 Hz, 1H), 6.84 (d, J=39.71 Hz, 1H), 4.99-5.11 (m, 2H), 3.39-3.54 (m, 2H), 2.97-3.11 (m, 1H), 2.77-2.92 (m, 1H), 2.53 (br s, 3H), 2.14-2.33 (m, 2H), 1.79 (s, 3H). NH$_2$ peak was not observed.

Example 150: (R,Z)-5-amino-3-(5-(2-(5-(cyclohexylmethoxy)pyrazin-2-yl)-2-fluorovinyl)-2-fluorophenyl)-3,6,6-trimethyl-3,6-dihydro-2H-1,4-thiazine 1,1-dioxide

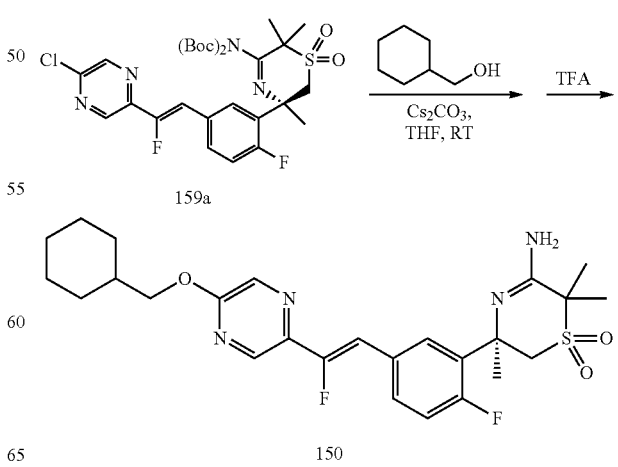

150

This compound (22 mg, 34% yield) as a yellow solid was prepared in a fashion similar to that described for Example 123, here starting with R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 80 mg, 0.12 mmol) and cyclohexylmethanol (450 mg, 3.95 mmol). MS m/z=519.2 [M+H]$^+$. $^1$H NMR (400 MHz, CHLOROFORM-d) δ 8.33 (s, 1H), 8.15 (s, 1H), 7.69 (ddd, J=1.76, 4.84, 8.46 Hz, 1H), 7.59 (br d, J=7.04 Hz, 1H), 7.12-7.17 (m, 1H), 6.78 (d, J=40 Hz, 1H), 4.15 (d, J=6.06 Hz, 2H), 3.96 (d, J=15.45 Hz, 1H), 3.70 (d, J=15.45 Hz, 1H), 2.06 (s, 3H), 1.90 (s, 3H), 1.81 (s, 3H), 1.68-1.92 (m, 5H), 1.15-1.36 (m, 4H), 0.94-1.14 (m, 2H). NH$_2$ peak was not observed.

Example 151: (R,E)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide; and Example 152: (R,Z)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide phenyl)sulfonyl)fluoromethyl)-5-chloropyridine (33) (155 mg, 0.36 mmol) and (R)-tert-butyl (5-(2,3-difluoro-5-formylphenyl)-2,5-dimethyl-1,1-dioxido-5,6-dihydro-2H-1,2,4-thiadiazin-3-yl)carbamate (37) (102 mg, 0.24 mmol) in THF (0.5 mL) and the mixture was stirred for 5 min before DMSO (1 mL) was added. This mixture was stirred for 1.5 h. Sat'd aqueous NH$_4$Cl and EtOAc were added. The layers were separated and the organic layer was washed with water (2×), and concentrated in vacuo. The crude product was purified by silica gel chromatography (0-20% EtOAc/heptane) to give the product (94 mg, 0.172 mmol) as a white solid. It was a mixture of cis- and trans-isomers (~3:2). MS (ESI, positive ion) m/z: 545.0 (M+1). The white solid (94 mg, 0.172 mmol) in DCM (0.6 ml) was added trifluoroacetic acid (0.19 mL, 2.56 mmol) dropwise. The reaction mixture was stirred at RT for 1 h. The solvent was evaporated in vacuo and to the residue was added DCM and evaporated again. The residue was dissolved in MeOH and purified by reverse-phase preparative HPLC (using a Phenomenex Gemini column, 10 micron, C18, 110 Å, 150×30 mm, 0.1% TFA in CH$_3$CN/H$_2$O, gradient 10% to 70% over 15 min) to provide the TFA salt of (R,E)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide (151)

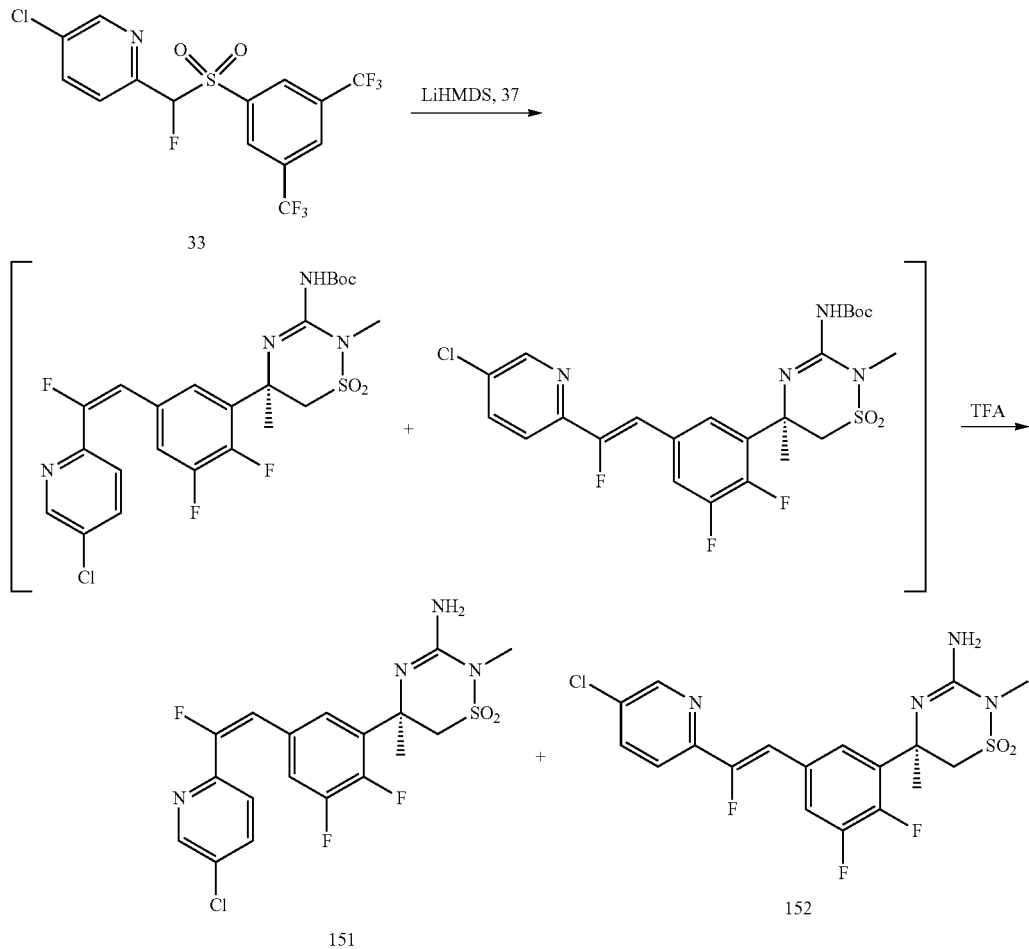

LiHMDS (0.36 mL of 1 M in solution in THF, 0.36 mmol) was added to a mixture of 2-(((3,5-bis(trifluoromethyl)

(35 mg, 0.08 mmol, 46% yield) as a white solid, and the TFA salt of (R,Z)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide (152) (24 mg, 0.05 mmol, 31% yield) as a white solid.

Example 151

MS (ESI, positive ion) m/z: 445.1 (M+1). $^1$H NMR (CHLOROFORM-d) δ 12.17 (br. s., 1H), 8.51 (s, 1H), 7.69 (d, J=8.4 Hz, 1H), 7.29-7.46 (m, 2H), 7.04 (d, J=6.5 Hz, 1H), 6.54-6.59 (d, 1H), 4.37 (d, J=14.7 Hz, 1H), 3.72 (d, J=14.7 Hz, 1H), 3.31 (s, 3H), 1.95 (s, 3H). NH$_2$ peak was not observed. $^{19}$F NMR (CHLOROFORM-d) δ −75.55 (s, 3F), −103.50 (s, 1F), −136.12 (d, J=20.9 Hz, 1F), −139.78 (d, J=20.9 Hz, 1F).

Example 152

MS (ESI, positive ion) m/z: 445.1 (M+1). $^1$H NMR (CHLOROFORM-d) δ 12.22 (br. s., 1H), 8.43 (s, 1H), 7.65 (d, J=8.2 Hz, 1H), 7.40-7.60 (m, 2H), 7.34 (d, J=4.5 Hz, 1H), 6.80-6.89 (d, 1H), 4.50 (d, J=14.1 Hz, 1H), 3.80 (d, J=14.7 Hz, 1H), 3.36 (s, 3H), 2.00 (s, 3H). NH$_2$ peak was not observed. $^{19}$F NMR (CHLOROFORM-d) Shift: −75.69 (s, 6F), −121.08 (br. s., 1F), −135.50 (d, J=20.9 Hz, 1F), −138.40 (d, J=20.9 Hz, 1F).

Example 153: (R,Z)-3-((5-(2-(3-(5-amino-3,6,6-trimethyl-1,1-dioxido-3,6-dihydro-2H-1,4-thiazin-3-yl)-4-fluorophenyl)-1-fluorovinyl)pyrazin-2-yl)oxy)-2,2-dimethylpropanenitrile

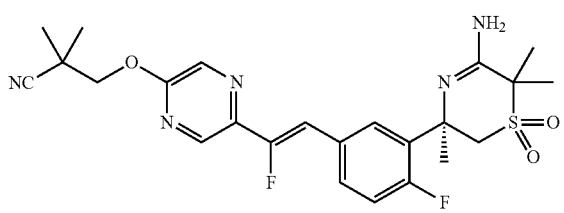

153

This compound (22 mg, 67% yield) as a white solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 80 mg, 0.12 mmol) and 3-hydroxy-22,-dimethylpropanenitrile (200 mg, 2.02 mmol). MS m/z=504.2 [M+H]$^+$. $^1$H NMR (400 MHz, CHLOROFORM-d) δ 11.51 (br s, 1H), 8.46 (br s, 1H), 8.33 (s, 1H), 8.26 (s, 1H), 7.68 (ddd, J=8.51, 4.79, 1.96, 1H), 7.62 (br d, J=7.82 Hz, 1H), 7.16 (dd, J=8.61, 12.13 Hz, 1H), 6.82 (d, J=40 Hz, 1H), 4.01 (d, J=15.45 Hz, 1H), 3.71 (d, J=15.45 Hz, 1H), 3.58 (s, 2H), 2.07 (s, 3H), 1.91 (s, 3H), 1.81 (s, 3H), 1.36 (s, 6H).

Example 154: (R,Z)-5-amino-3-(5-(2-(5-(but-2-yn-1-yloxy)pyrazin-2-yl)-2-fluorovinyl)-2-fluorophenyl)-3,6,6-trimethyl-3,6-dihydro-2H-1,4-thiazine 1,1-dioxide

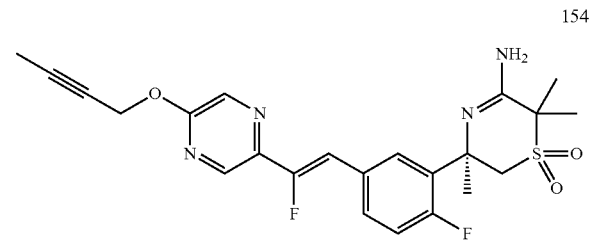 [SMILES: CC#CCOc1cnc(/C(F)=C/c2ccc(F)c([C@]3(C)CS(=O)(=O)C(C)(C)C(N)=N3)c2)cn1]

154

This compound (6.2 mg, 20% yield) as a light yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl) vinyl)phenyl)-2,2,5-trimethyl-1,1-dioxido-5,6-dihydro-2H-1,4-thiazin-3-yl)carbamate (159a, 42 mg, 0.06 mmol) and 2-butyn-1-ol (14 mg, 0.19 mmol). MS m/z=475.1 [M+H]$^+$. $^1$H NMR (400 MHz, CHLOROFORM-d) δ 8.39 (s, 1H), 8.25 (s, 1H), 7.73 (dd, J=1.96, 8.02 Hz, 1H), 7.61-7.70 (m, 1H), 7.06-7.11 (m, 1H), 6.84 (d, J=40 Hz, 1H), 5.00 (q, J=2.35 Hz, 2H), 3.52-3.66 (m, 2H), 1.90 (t, J=2.25 Hz, 3H), 1.84 (s, 3H), 1.72 (s, 3H), 1.64 (s, 3H). NH$_2$ peak was not observed.

Example 155: (R,Z)-3-(5-(2-(5-(2-(1H-imidazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide

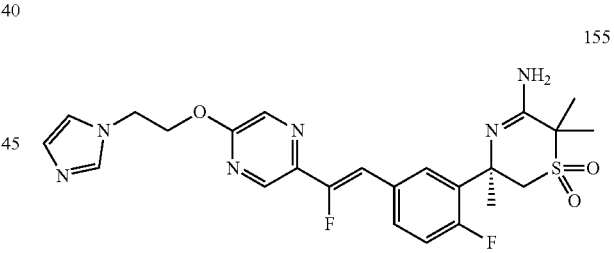

155

This compound (21 mg, 65% yield) as a light yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl) vinyl)phenyl)-2,2,5-trimethyl-1,1-dioxido-5,6-dihydro-2H-1,4-thiazin-3-yl)carbamate (159a, 42 mg, 0.06 mmol) and 1-(2-hydroxyethyl)-imidazole (37 mg, 0.33 mmol). MS m/z=517.2 [M+H]$^+$. $^1$H NMR (400 MHz, CHLOROFORM-d) δ 8.32 (s, 1H), 8.20 (s, 1H), 7.74 (dd, J=2.25, 7.92 Hz, 1H), 7.65 (ddd, J=2.25, 4.74, 8.46 Hz, 1H), 7.58 (s, 1H), 7.00-7.12 (m, 3H), 6.83 (d, J=40 Hz, 1H), 4.65 (t, J=5.28 Hz, 2H), 4.38 (t, J=5.28 Hz, 2H), 3.55-3.66 (m, 2H), 1.83 (s, 3H), 1.71 (s, 3H), 1.62 (s, 3H). NH$_2$ peak was not observed.

Example 156: (R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide

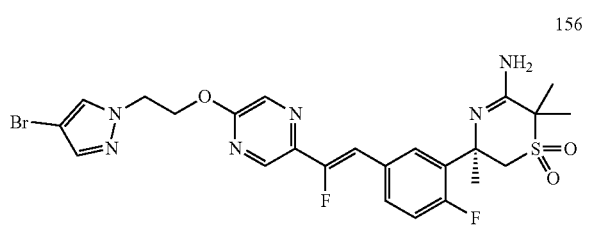 [SMILES: CC1(C)C(N)=N[C@](C)(c2cc(/C=C(\F)c3cnc(OCCn4cc(Br)cn4)cn3)ccc2F)CS1(=O)=O]

156

This compound (21 mg, 65% yield) as a light yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 85 mg, 0.13 mmol) and 4-bromo-1-(2-hydroxyethyl)pyrazole (76 mg, 0.40 mmol). MS m/z=595.1 [M+H]+. 1H NMR (400 MHz, CHLOROFORM-d) δ 8.33 (s, 1H), 8.19 (s, 1H), 7.72 (br d, J=8.02 Hz, 1H), 7.64-7.67 (m, 1H), 7.52 (s, 1H), 7.50 (s, 1H), 7.06-7.11 (m, 1H), 6.82 (d, J=40 Hz, 1H), 4.74 (t, J=5.18 Hz, 2H), 4.53 (t, J=5.18 Hz, 2H), 3.61 (s, 2H), 1.84 (s, 3H), 1.71 (s, 3H), 1.63 (s, 3H).

Example 157: (R,Z)-3-(5-(2-(5-(2-(1H-pyrazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide

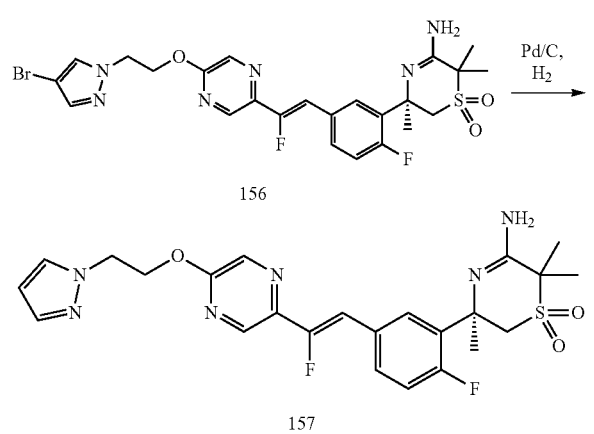

A mixture of (R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide (156, 0.020 g, 0.034 mmol) and palladium in 50% water (3.57 mg, 0.017 mmol) in methanol (5 mL, 124 mmol) under 20 psi of hydrogen was allowed to stir at RT for 48 h. The mixture was filtered and washed with methanol. The filtrate was concentrated and purified by silica gel chromatography (0-10% methanol in DCM) to give (2.0 mg, 11% yield) of Example 157 as a white solid. MS m/z=517.1 [M+H]+. 1H NMR (400 MHz, CHLOROFORM-d) δ 8.34 (s, 1H), 8.17 (s, 1H), 7.62-7.72 (m, 2H), 7.55 (d, J=1.76 Hz, 1H), 7.48 (d, J=4.0 Hz, 1H), 7.10-7.15 (m, 1H), 6.82 (d, J=40 Hz, 1H), 6.27 (t, J=2.05 Hz, 1H), 4.76 (t, J=5.38 Hz, 2H), 4.56 (t, J=5.38 Hz, 2H), 3.82 (d, J=15.65 Hz, 1H), 3.67 (br d, J=15.65 Hz, 1H), 1.98 (s, 3H), 1.83 (s, 3H), 1.74 (s, 3H).

Example 158: (R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide

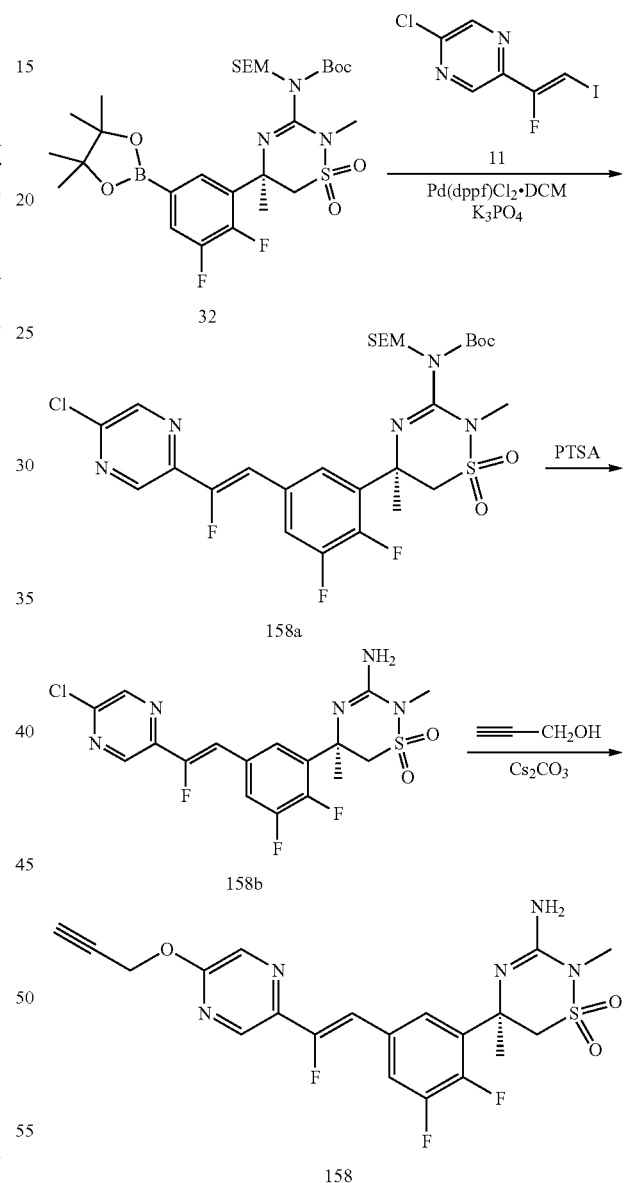

Preparation of (R,Z)-tert-butyl (5-(5-(2-(5-chloropyrazin-2-yl)-2-fluorovinyl)-2,3-difluorophenyl)-2,5-dimethyl-1,1-dioxido-5,6-dihydro-2H-1,2,4-thiadiazin-3-yl)((2-(trimethylsilyl)ethoxy)methyl)carbamate (158a)

A mixture of boronic ester 32 (77 mg, 0.12 mmol), (Z)-2-chloro-5-(1-fluoro-2-iodovinyl)pyrazine (11) (41 mg, 0.14 mmol), potassium phosphate tribasic (63 mg, 0.30 mmol), and 1,1-bis[(di-t-butyl-p-methylaminophenyl]palladium(II) chloride (8.4 mg, 0.012 mmol) was placed under nitrogen atmosphere using 3 evacuation/backfill cycles. Dioxane (0.60 mL) and water (0.12 mL) were added and the mixture was heated to 80° C. for 2.5 h. The mixture was cooled to RT and partitioned between EtOAc and water. The layers were separated and the organic layer was dried (Na₂SO₄), filtered, and concentrated in vacuo. The crude product was fused to silica gel and purified by silica gel chromatography (0 to 20% EtOAc/heptane) to give 158a (0.062 g, 0.092 mmol, 77% yield) as white foam. MS (ESI, positive ion) m/z: =676.4 (M+1).

Preparation of (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b)

A mixture of (R,Z)-tert-butyl (5-(5-(2-(5-chloropyrazin-2-yl)-2-fluorovinyl)-2,3-difluorophenyl)-2,5-dimethyl-1,1-dioxido-5,6-dihydro-2H-1,2,4-thiadiazin-3-yl)((2-(trimethylsilyl)ethoxy)methyl)carbamate (158a, 55 mg, 0.08 mmol) and p-toluenesulfonic acid monohydrate (23 mg, 0.12 mmol) in dioxane (0.4 mL) was heated to 80° C. for 2.5 h. The mixture was cooled to RT, EtOAc was added, and then the mixture was washed with water followed by brine, and concentrated in vacuo to give (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (36 mg) as a solid which was used as crude. MS (ESI, positive ion) m/z: =446.0 (M+1).

Preparation of Example 158

A mixture of (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (36 mg, 0.081 mmol), 3-propynol (Aldrich, 38.2 μL, 0.65 mmol), and cesium carbonate (92 mg, 0.28 mmol) in THF (0.8 mL) was heated to 60° C. for 8 h. The mixture was cooled to RT, EtOAc was added, and the mixture was then washed with water followed by brine, and concentrated in vacuo. The crude product was purified by silica gel chromatography (0 to 85% EtOAc/heptane) to give (R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide (158) (12 mg, 0.026 mmol, 32% yield) as an off white solid. MS (ESI, positive ion) m/z: =466.1 (M+1). ¹H NMR (CHLOROFORM-d) δ: 8.40 (s, 1H), 8.26 (s, 1H), 7.46-7.65 (m, 2H), 6.80 (d, J=36 Hz, 1H), 5.05 (d, J=2.3 Hz, 2H), 3.91 (d, J=13.9 Hz, 1H), 3.74 (d, J=14.1 Hz, 1H), 3.26 (s, 2H), 2.54 (s, 1H), 1.83 (s, 3H). NH₂ peak was not observed. ¹⁹F NMR (CHLOROFORM-d) δ: −124.05 (br s, 1F), −137.25 (br d, J=20.8 Hz, 1F), −138.55 (br d, J=20.8 Hz, 1F).

Example 159: (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide

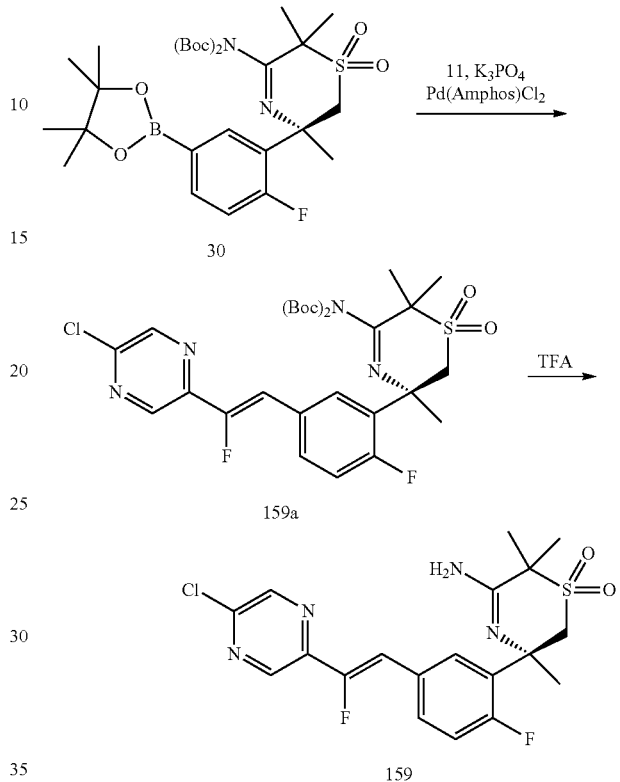

Preparation of (R,Z)-5-(di-Boc-amino)-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a)

A stream of argon was bubbling through a mixture of dioxaborolane (1.90 g, 3.11 mmol), (Z)-2-chloro-5-(1-fluoro-2-iodovinyl)pyrazine (11) (1.06 g, 3.73 mmol), bis(di-tert-butyl(4-dimethylaminophenyl)phosphine)-dichloropalladium(II) (0.22 g, 0.31 mmol), potassium phosphate tribasic (2.15 g, 9.34 mmol) and water (3.0 mL) in 1,4-dioxane (15.6 mL) for 10 min. The resulting mixture was heated at 85° C. for 20 h. The mixture was cooled to RT, filtered, and washed with ethyl acetate. The filtrate was concentrated and the residue was purified on a 80 g silica gel column (0 to 100% ethyl acetate in heptane) to give 159a (1.48 g, 74%) a brown amorphous solid. MS m/z=663.2 [M+23]⁺.

To a solution of 159a (0.018 g, 0.028 mmol) in DCM (5 mL) was added TFA (1 mL) at 0° C. The resulting mixture was allowed to stir at RT, and monitored by LCMS. Upon completion, the mixture was concentrated and the residue was purified by Isco CombiFlash on a 12 g silica gel column using 0-10% (2% NH₃/methanol solution) in DCM to give Example 159 (10 mg, 94% yield) as a yellow solid. MS m/z=441.0 [M+H]⁺. ¹H NMR (400 MHz, CHLOROFORM-d) δ 8.63 (t, J=1.27 Hz, 1H), 8.54 (br s, 1H), 7.79 (dd, J=2.15, 8.02 Hz, 1H), 7.68 (ddd, J=2.35, 4.79, 8.51 Hz, 1H), 7.08-7.14 (m, 1H), 7.03 (d, J=40 Hz, 1H), 3.56-3.64 (m, 2H), 1.82 (s, 3H), 1.72 (s, 3H), 1.63 (s, 3H). NH₂ peak was not observed.

Example 160: (R)-5-amino-3-(5-((Z)-2-(5-((S)-but-3-yn-2-yloxy)pyrazin-2-yl)-2-fluorovinyl)-2-fluorophenyl)-3,6,6-trimethyl-3,6-dihydro-2H-1,4-thiazine 1,1-dioxide

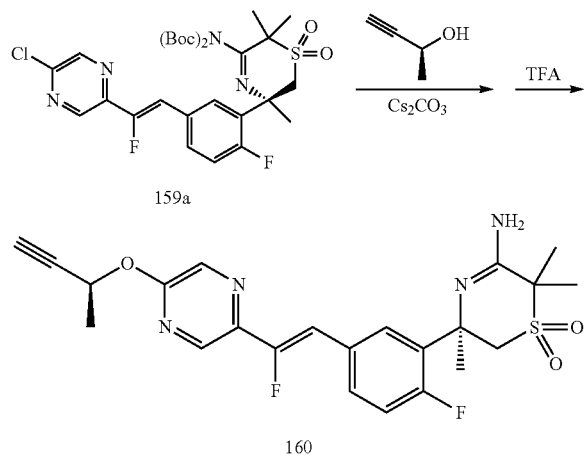

This compound (6.0 mg, 25% yield) as a yellow solid was prepared in a fashion similar to that described in Method H for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 32 mg, 0.05 mmol) and (S)-(−)-3-butyn-2-ol (35 mg, 0.50 mmol). MS m/z=475.1 [M+H]$^+$. $^1$H NMR (400 MHz, CHLOROFORM-d) δ 8.41 (s, 1H), 8.23 (br s, 1H), 7.73 (dd, J=8.02, 2.15 Hz, 1H), 7.67 (ddd, J=8.41, 4.79, 2.45 Hz, 1H), 7.06-7.11 (m, 1H), 6.84 (d, J=40 Hz, 1H), 5.75-5.80 (m, 1H), 3.55-3.65 (m, 2H), 2.48 (d, J=1.96 Hz, 1H), 1.84 (s, 3H), 1.72 (s, 3H), 1.70 (d, J=6.65 Hz, 3H), 1.64 (s, 3H). NH$_2$ peak was not observed.

Example 161: (8R)-8-(2-fluoro-5-((Z)-2-fluoro-2-(5-((3-methyl-1,2,4-oxadiazol-5-yl)methoxy)-2-pyrazinyl)ethenyl)phenyl)-5,8-dimethyl-4-thia-5,7-diazaspiro[2.5]oct-6-en-6-amine 4,4-dioxide

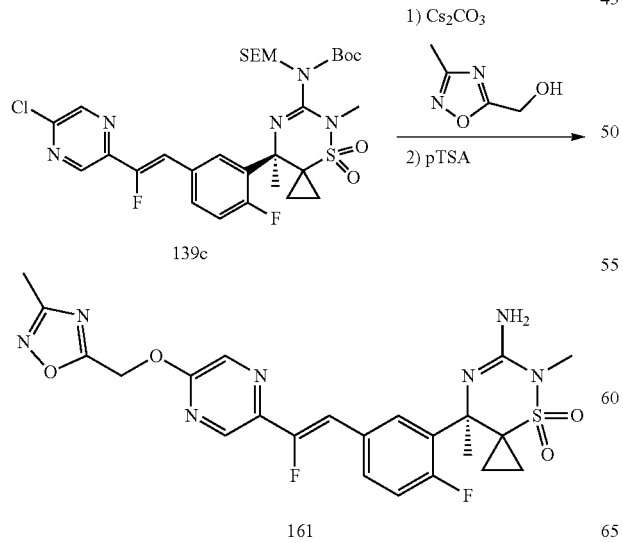

A mixture of (R,Z)-tert-butyl (8-(5-(2-(5-chloropyrazin-2-yl)-2-fluorovinyl)-2-fluorophenyl)-5,8-dimethyl-4,4-dioxido-4-thia-5,7-diazaspiro[2.5]oct-6-en-6-yl)((2-(trimethylsilyl)ethoxy)methyl)carbamate (139c, 200 mg, 0.29 mmol), cesium carbonate (286 mg, 0.87 mmol), and (2-methyl-1,2,4-oxadiozol-5-yl)methanol (Enamine LLC, Monmouth Ject., N.J., USA) (100 mg, 0.87 mmol) in THF (2.92 mL) was heated at 60° C. for 12 h. After cooling to RT, the reaction mixture was filtered through a pad of celite and the filter cake was rinsed with EtOAc. The filtrate was concentrated. The residue was dissolved in 1,4-dioxane (2.92 mL), treated with p-toluenesulfonic acid monohydrate (56 mg, 0.29 mmol), and heated at 60° C. for 1 h, at which point the reaction was determined to be complete by LCMS analysis. The mixture was diluted with EtOAc, filtered through a pad of celite and concentrated in vacuo. The crude residue was purified via silica gel chromatography (0-25% EtOAc in heptane) to afford (R,Z)-6-amino-8-(2-fluoro-5-(2-fluoro-2-(5-((3-methyl-1,2,4-oxadiazol-5-yl)methoxy)pyrazin-2-yl)vinyl)phenyl)-5,8-dimethyl-4-thia-5,7-diazaspiro[2.5]oct-6-ene 4,4-dioxide (161, 68 mg, 0.13 mmol, 44% yield) as a light yellow solid. MS m/z=532.1 [M+H]$^+$. $^1$H NMR (400 MHz, CHLOROFORM-d) δ 8.37 (s, 1H), 8.35 (s, 1H), 7.60-7.71 (m, 2H), 6.99-7.14 (m, 1H), 6.75-6.95 (m, 1H), 5.63 (s, 2H), 3.18-3.31 (m, 3H), 2.43 (s, 3H), 1.79-1.86 (m, 3H), 1.58-1.69 (m, 2H), 1.44-1.55 (m, 2H), 1.03-1.15 (m, 1H), 0.89-0.99 (m, 1H). $^{19}$F NMR (376 MHz, CHLOROFORM-d) Shift −107.79 (br. s., 1F), −125.68 (br. s., 1F).

Example 162: (8R)-8-(2-fluoro-5-((Z)-2-fluoro-2-(5-((5-methyl-3-isoxazolyl)methoxy)-2-pyrazinyl)ethenyl)phenyl)-5,8-dimethyl-4-thia-5,7-diazaspiro[2.5]oct-6-en-6-amine 4,4-dioxide

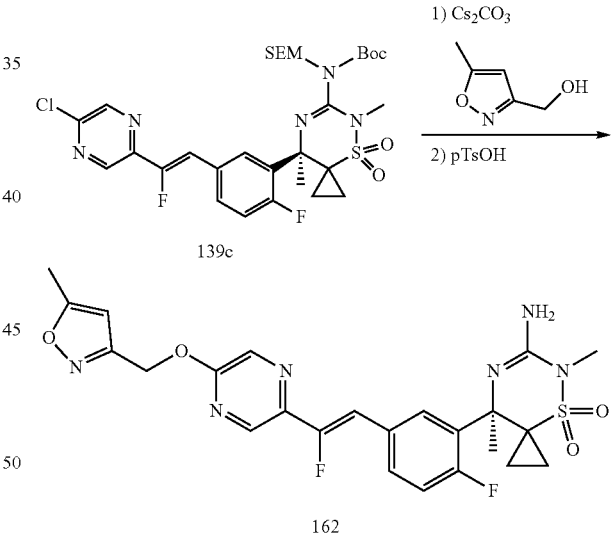

This compound (85 mg, 55% yield) as a light yellow solid was prepared in a fashion similar to that described for Example 161, here starting with intermediate 139c (0.20 g, 0.29 mmol) and (5-methylisoxazol-3-yl)methanol (Sigma-Aldrich Chemical Company, Inc., St. Louis, Mo., USA) (0.16 g, 1.46 mmol). MS m/z=532.1 [M+H]$^+$. $^1$H NMR (400 MHz, CHLOROFORM-d) δ 8.39 (s, 1H), 8.34-8.46 (m, 1H), 8.26 (s, 1H), 7.59-7.72 (m, 2H), 6.98-7.11 (m, 1H), 6.72-6.90 (m, 1H), 6.10 (s, 1H), 5.47 (s, 2H), 3.21-3.33 (m, 3H), 2.45 (s, 3H), 1.83 (s, 3H), 1.58-1.68 (m, 2H), 1.46-1.54 (m, 1H), 1.04-1.15 (m, 1H), 0.93-1.03 (m, 1H). $^{19}$F NMR (376 MHz, CHLOROFORM-d) δ −108.08 (br. s., 1F), −125.44 (br. s., 1F).

Example 163: (8R)-8-(2-fluoro-5-((Z)-2-fluoro-2-(5-(2,2,2-trifluoroethoxy)-2-pyrazinyl)ethenyl)phenyl)-5,8-dimethyl-4-thia-5,7-diazaspiro[2.5]oct-6-en-6-amine 4,4-dioxide

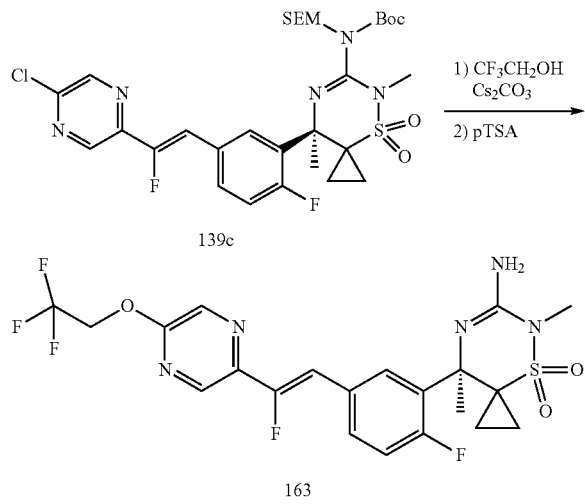

This compound (35 mg, 23% yield) as a light yellow solid was prepared in a fashion similar to that described for Example 161, here starting with intermediate 139c (0.20 g, 0.29 mmol) and 2,2,2-trifluoroethanol (Sigma-Aldrich Chemical Company, Inc., St. Louis, Mo., USA) (0.15 g, 1.46 mmol). MS m/z=518.0 [M+H]$^+$. $^1$H NMR (400 MHz, CHLOROFORM-d) δ ppm 8.36 (s, 1H), 8.33 (s, 1H), 7.68 (br d, J=7.82 Hz, 1H), 7.59-7.65 (m, 1H), 7.05 (dd, J=11.74, 8.61 Hz, 1H), 6.76-6.96 (m, 1H), 4.81 (q, J=8.41 Hz, 2H), 3.25 (s, 3H), 0.88-1.01 (m, 1H), 1.71-1.87 (m, 3H), 1.46-1.55 (m, 2H), 1.22-1.34 (m, 1H), 1.10 (dt, J=9.44, 6.63 Hz, 1H). $^{19}$F NMR (376 MHz, CHLOROFORM-d) −125.78 (s, 1F), −111.48−−104.63 (m, 1F), −73.67 (s, 1F).

Example 164: (R)-3-amino-5-(2-fluoro-5-((Z)-2-fluoro-2-(5-(((S)-1-methoxypropan-2-yl)oxy)pyrazin-2-yl)vinyl)phenyl)-2,5-dimethyl-5,6-dihydro-2H-1,2,4-thiadiazine 1,1-dioxide This compound (11 mg, 15% yield for 2 steps) as a white solid was prepared in a fashion similar to that described in for Example 174, here using (S)-(+)-1-methoxy-2-propanol (120 mg, 1.33 mmol) and 111a (175 mg, 0.27 mmol) as starting materials. MS m/z=482.1 [M+H]$^+$. $^1$H NMR (400 MHz, CHLOROFORM-d) δ 8.31 (s, 1H) 8.17 (s, 1H) 7.85 (dd, J=8.12, 2.05 Hz, 1H) 7.58-7.64 (m, 1H) 7.05 (dd, J=11.74, 8.41 Hz, 1H) 6.76 (d, J=39.91 Hz, 1H) 5.43 (td, J=6.26, 3.91 Hz, 1H) 3.82 (d, J=13.89 Hz, 1H) 3.72 (d, J=13.89 Hz, 1H) 3.54-3.65 (m, 2H) 3.41 (s, 3H) 3.21 (s, 3H) 1.79 (s, 3H) 1.38 (d, J=6.46 Hz, 3H).

Example 165: (R,Z)-3-amino-5-(5-(2-(5-(but-2-yn-1-yloxy)pyrazin-2-yl)-2-fluorovinyl)-2,3-difluorophenyl)-2,5-dimethyl-5,6-dihydro-2H-1,2,4-thiadiazine 1,1-dioxide

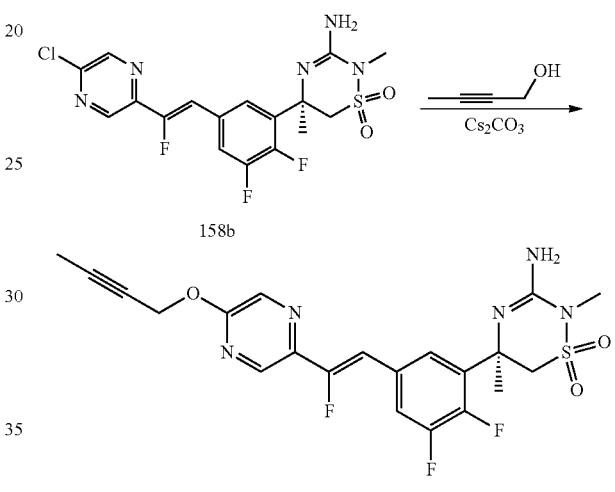

This compound (16 mg, 41% yield) as a light-yellow solid was prepared in a fashion similar to that described for Example 158, here starting with 158b (36 mg, 0.08 mmol), cesium carbonate (118 mg, 0.36 mmol), and 2-butyn-1-ol

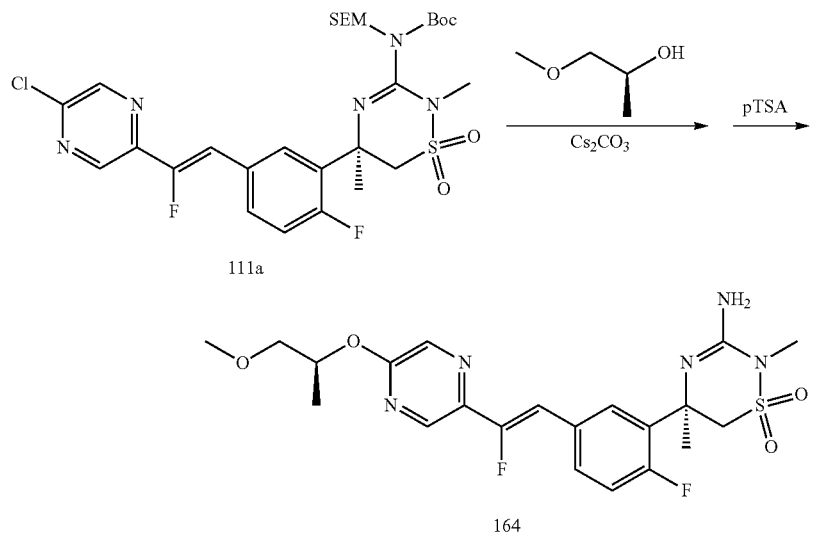

(Aldrich-sigma, 45 mg, 0.65 mmol). MS (ESI, positive ion) m/z: =480.0 (M+1). $^1$H NMR (400 MHz, CHLOROFORM-d) δ ppm 8.40 (s, 1H), 8.25 (s, 1H), 7.52-7.61 (m, 2H), 6.68-6.91 (d, 1H, J=40 Hz), 4.98-5.03 (m, 2H), 3.83 (d, J=14.09 Hz, 1H), 3.70 (d, J=14.08 Hz, 1H), 3.24 (s, 3H), 1.90 (t, J=2.25 Hz, 3H), 1.80 (s, 3H). $^{19}$F NMR (CHLOROFORM-d) δ −124.17 (br. s., 1F), −137.53 (d, J=20.8 Hz, 1F), −138.61 (d, J=19.9 Hz, 1F).

Example 166: (R,Z)-3-amino-5-(2,3-difluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide

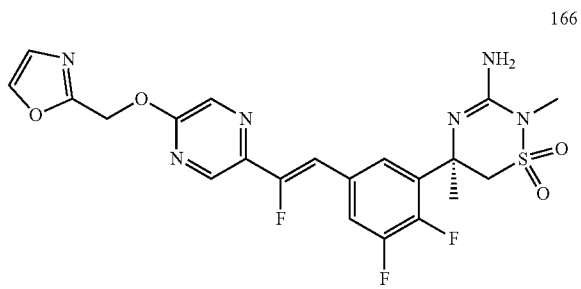 [SMILES: CN1C(N)=N[C@](C)(c2cc(/C=C(\F)c3cnc(OCc4ncco4)cn3)cc(F)c2F)CS1(=O)=O]

166

This compound (20 mg, 49% yield) as an off-white solid was prepared in a fashion similar to that described for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide 158b (36 mg, 0.08 mmol), 2-hydroxymethyl-oxazole (AstaTech, 64 mg, 0.646 mmol), and cesium carbonate (118 mg, 0.363 mmol) as starting materials. MS (ESI, positive ion) m/z: =509.1 (M+1). $^1$H NMR (400 MHz, CHLOROFORM-d) δ ppm 8.40 (s, 1H), 8.31 (s, 1H), 7.71 (s, 1H), 7.48-7.62 (m, 2H), 7.18 (s, 1H), 6.82 (d, 1H, J=40.0 Hz), 5.54 (s, 2H), 3.89 (br d, J=13.9 Hz, 1H), 3.70 (d, J=14.1 Hz, 1H), 3.24 (s, 3H), 1.81 (s, 3H). $^{19}$F NMR (376 MHz, CHLOROFORM-d) δ ppm −124.18 (br. s., 1F), −137.36 (d, J=19.94 Hz, 1F), −138.49 (d, J=21.67 Hz, 1F).

Example 167: (R)-3-amino-5-(5-((Z)-2-(5-((S)-but-3-yn-2-yloxy)pyrazin-2-yl)-2-fluorovinyl)-2,3-difluorophenyl)-2,5-dimethyl-5,6-dihydro-2H-1,2,4-thiadiazine 1,1-dioxide hydrochloride

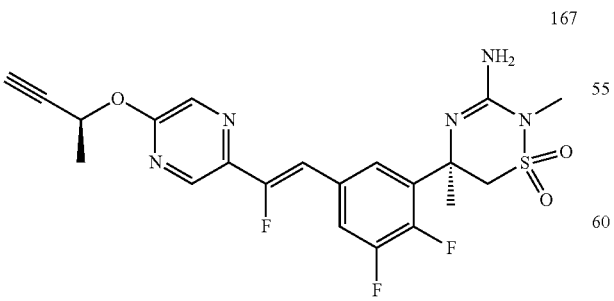

167

This compound (2 mg, 5% yield) as a light-yellow oil was prepared in a fashion similar to that described for Example 158, using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide 158b (36 mg, 0.08 mmol), (S)-(−)-3-butyn-2-ol (Alfa Aesar, 45 mg, 0.646 mmol), and cesium carbonate (118 mg, 0.363 mmol) as starting materials. MS (ESI, positive ion) m/z: =480.1 (M+1). $^1$H NMR (CHLOROFORM-d) δ 8.37 (s, 1H), 8.15 (s, 1H), 7.55-7.63 (m, 1H), 7.31 (br d, J=5.9 Hz, 1H), 6.74 (d, 1H, J=40 Hz), 5.69-5.78 (m, 1H), 4.44-4.52 (m, 1H), 3.80 (d, J=14.0 Hz, 1H), 3.35 (s, 3H), 2.47 (d, J=2.0 Hz, 1H), 1.97-2.03 (m, 3H), 1.70 (s, 3H).

Example 168: (R,Z)-3-amino-5-(5-(2-(5-(but-2-yn-1-yloxy)pyrazin-2-yl)-2-fluorovinyl)-2-fluorophenyl)-2,5-dimethyl-5,6-dihydro-2H-1,2,4-thiadiazine 1,1-dioxide

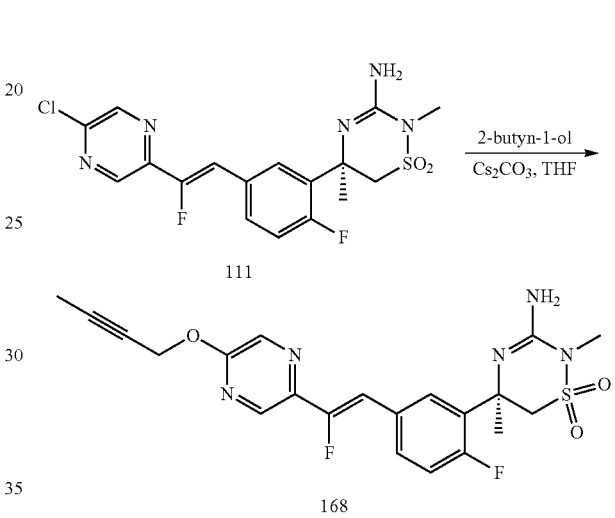

111

168

This compound (50 mg, 0.11 mmol, 46% yield) as a yellow solid was prepared in a fashion similar to that described in Method D for Example 112, using 2-butyn-1-ol (Aldrich-Sigma, 164 mg, 2.34 mmol) and 111 (100 mg, 0.23 mmol) as starting materials. MS m/z=462.2 [M+H]$^+$. $^1$H NMR (400 MHz, CHLOROFORM-d) δ 8.37 (s, 1H) 8.24 (s, 1H) 7.84 (dd, J=7.92, 2.05 Hz, 1H) 7.60-7.66 (m, 1H) 7.06 (dd, J=12.03, 8.51 Hz, 1H) 6.82 (d, J=39.71 Hz, 1H) 4.97-5.02 (m, 2H) 3.81 (d, J=13.89 Hz, 1H) 3.72 (d, J=13.89 Hz, 1H) 3.22 (s, 3H) 1.89 (t, J=2.25 Hz, 3H) 1.79 (s, 3H). Note: NH$_2$ peak was not observed. $^{19}$F NMR (376 MHz, CHLOROFORM-d) δ −112.68 (s, 1F), −125.47 (s, 1F).

Example 169: (8R)-8-(2-fluoro-5-((Z)-2-fluoro-2-(5-((5-methyl-1,3-oxazol-2-yl)methoxy)-2-pyrazinyl)ethenyl)phenyl)-5,8-dimethyl-4-thia-5,7-diazaspiro[2.5]oct-6-en-6-amine 4,4-dioxide

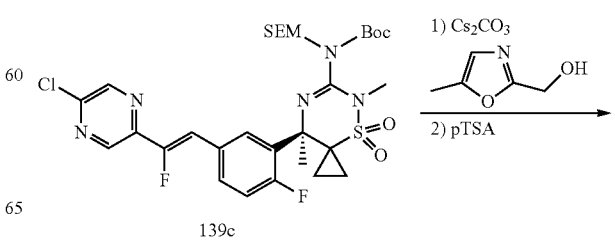

139c

-continued

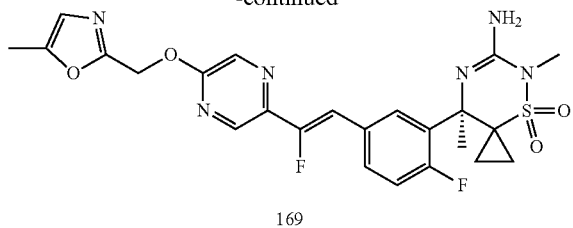

169

This compound (35 mg, 23% yield) as a light yellow solid was prepared in a fashion similar to that described for Example 161, here starting with intermediate 139c (0.20 g, 0.29 mmol) and (5-methyloxazol-2-yl)methanol (Sigma-Aldrich Chemical Company, Inc., St. Louis, Mo., USA) (0.16 g, 1.46 mmol). MS m/z=531.1 [M+H]$^+$. $^1$H NMR (400 MHz, CHLOROFORM-d) δ ppm 8.39 (s, 1H), 8.29 (s, 1H), 7.55-7.68 (m, 1H), 7.43-7.52 (m, 1H), 6.98-7.10 (m, 2H), 6.87 (s, 1H), 6.77 (s, 1H), 5.45 (s, 2H), 3.29 (s, 3H), 2.35 (s, 3H), 2.26 (s, 3H), 1.84 (s, 3H), 1.60-1.72 (m, 1H), 1.47-1.59 (m, 1H), 1.06-1.20 (m, 1H), 1.03 (br s, 1H). $^{19}$F NMR (376 MHz, CHLOROFORM-d) δ ppm −125.25 (br s, 1F), −108.36 (br s, 1F).

Example 170: (R,Z)-5-(2-(3-(5-amino-3,6,6-trimethyl-1,1-dioxido-3,6-dihydro-2H-1,4-thiazin-3-yl)-4-fluorophenyl)-1-fluorovinyl)pyrazine-2-carbonitrile

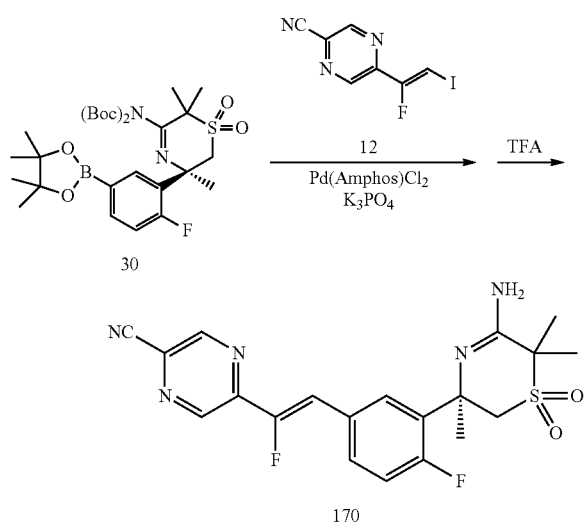

170

This compound (20 mg, 37% yield) as a yellow solid was prepared in a fashion similar to that described in Method E for Example 258, here starting with (Z)-5-(1-fluoro-2-iodovinyl)pyrazine-2-carbonitrile (12) (43 mg, 0.16 mmol) and boronic ester 30 (80 mg, 0.13 mmol). MS m/z=432.0 [M+H]$^+$. $^1$H NMR (400 MHz, CHLOROFORM-d) δ 8.96 (t, J=1.37 Hz, 1H), 8.83 (t, J=1.17 Hz, 1H), 7.84 (dd, J=2.25, 7.92 Hz, 1H), 7.72 (ddd, J=2.25, 4.70, 8.51 Hz, 1H), 7.24 (d, J=40 Hz, 1H), 7.14 (dd, J=11.93, 8.41 Hz, 1H), 3.60 (s, 2H), 2.05 (s, 1H), 1.81 (s, 3H), 1.73 (s, 3H), 1.62 (s, 3H). NH$_2$ peak was not observed.

Example 171: (R)-3-amino-5-(5-((Z)-2-(5-((S)-but-3-yn-2-yloxy)pyrazin-2-yl)-2-fluorovinyl)-2-fluorophenyl)-2,5-dimethyl-5,6-dihydro-2H-1,2,4-thiadiazine 1,1-dioxide

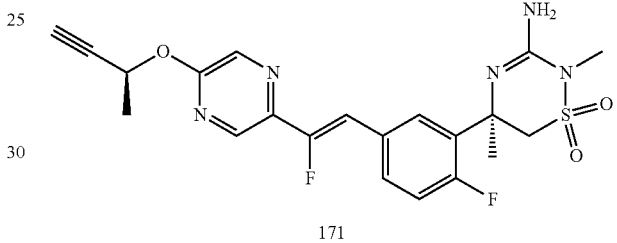

111

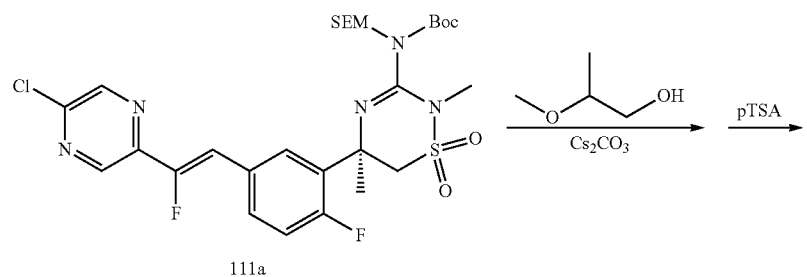

171

This compound (32 mg, 0.069 mmol, 32% yield) as a yellow solid was prepared in a fashion similar to that described in Method D for Example 112, using (S)-(−)-3-butyne-2-ol (77 mg, 1.10 mmol) and 111 (94 mg, 0.22 mmol) as starting materials. MS m/z=462.0 [M+H]$^+$. $^1$H NMR (400 MHz, CHLOROFORM-d) δ 8.38 (s, 1H) 8.21 (s, 1H) 7.78-7.90 (m, 1H) 7.56-7.68 (m, 1H) 7.00-7.15 (m, 1H) 6.82 (d, J=39.71 Hz, 1H) 5.68-5.86 (m, 1H) 3.74 (m, 2H) 3.22 (s, 3H) 2.48 (d, J=2.15 Hz, 1H) 1.80 (s, 3H) 1.69 (d, J=6.65 Hz, 3H). Note: NH$_2$ peak was not observed.

Example 172: (R)-3-amino-5-(2-fluoro-5-((Z)-2-fluoro-2-(5-(2-methoxypropoxy)pyrazin-2-yl)vinyl)phenyl)-2,5-dimethyl-5,6-dihydro-2H-1,2,4-thiadiazine 1,1-dioxide 111a

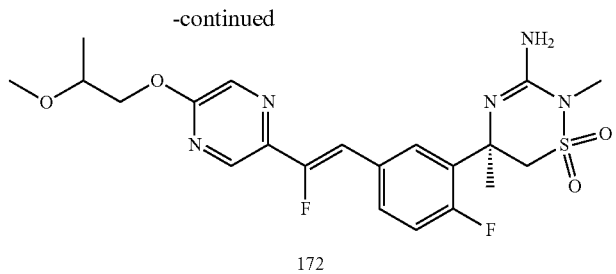

172

This compound (52 mg, 54% yield for 2 steps) as a white solid was prepared in a fashion similar to that described for Example 174, here using 2-methoxy-1-propanol (143 mg, 1.59 mmol) and 111a (131 mg, 0.20 mmol) as starting materials. MS m/z=482.1 [M+H]$^+$. $^1$H NMR (400 MHz, CHLOROFORM-d) δ 8.31 (s, 1H) 8.19-8.27 (m, 1H) 7.83-7.90 (m, 1H) 7.57-7.67 (m, 1H) 7.01-7.10 (m, 1H) 6.78 (d, J=39.91 Hz, 1H) 4.31-4.45 (m, 2H) 3.66-3.88 (m, 3H) 3.45 (s, 3H) 3.21 (s, 3H) 1.79 (s, 3H) 1.28 (d, J=6.26 Hz, 3H). NH$_2$ peak was not observed.

Example 173: (R,Z)-3-amino-5-(2-fluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide

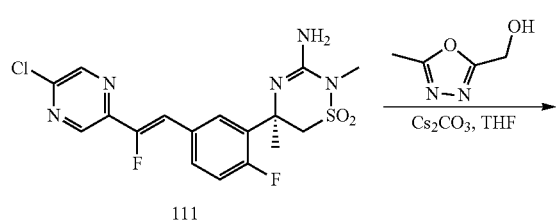

111

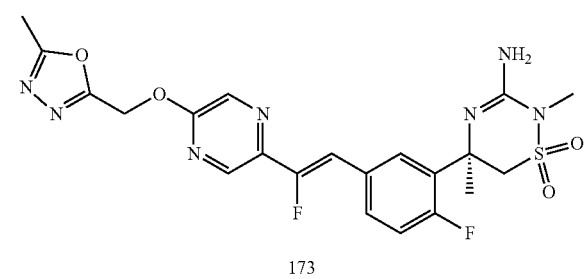

173

This compound (24 mg, 0.047 mmol, 30% yield) as a yellow solid was prepared in a fashion similar to that described in Method D for Example 112, here using (5-methyl-1,3,4-oxadiazol-2-yl)methanol (Enamine LLC, Monmouth Ject., N.J., USA) (145 mg, 1.27 mmol) and 111 (68 mg, 0.16 mmol) as starting materials. MS m/z=506.1 [M+H]$^+$. $^1$H NMR (400 MHz, CDCl$_3$) δ 8.37 (s, 1H) 8.30 (s, 1H) 7.84-7.89 (m, 1H) 7.60-7.67 (m, 1H) 7.02-7.12 (m, 1H) 6.85 (d, J=39.71 Hz, 1H) 5.61 (s, 2H) 3.83 (d, J=13.89 Hz, 1H) 3.72 (d, J=13.89 Hz, 1H) 3.22 (s, 3H) 2.58 (s, 3H) 2.18 (s, 3H). Note: NH$_2$ peak was not observed. $^{19}$F NMR (376 MHz, CDCl$_3$) δ −112.39 (s, 1F), −125.69 (s, 1F).

Example 174: (R,Z)-3-amino-5-(5-(2-(5-(cyclobutylmethoxy)pyrazin-2-yl)-2-fluorovinyl)-2-fluorophenyl)-2,5-dimethyl-5,6-dihydro-2H-1,2,4-thiadiazine 1,1-dioxide

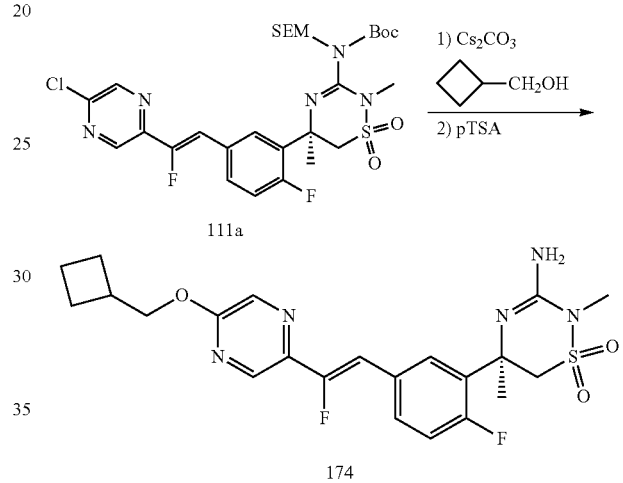

A mixture of (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate 111a (81 mg, 0.12 mmol), cesium carbonate (120 mg, 0.37 mmol), and cyclobutanemethanol (Sigma-Aldrich) (0.085 mL, 0.98 mmol) in THF (0.5 mL) was stirred under argon for 16 h. EtOAc and water were added. The layers were separated, and the organic layer was dried over anhydrous magnesium sulfate, filtered, and concentrated in vacuo to give an oil. The oil was purified by silica gel chromatography (0 to 40% EtOAc/heptane) to give (R,Z)-tert-butyl (5-(5-(2-(5-(cyclobutylmethoxy)pyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate as a yellow solid. MS m/z=708.2 [M+H]$^+$. This solid was dissolved in 1,4-dioxane (1 mL) and 4-methylbenzenesulfonic acid hydrate (35 mg, 0.19 mmol) was added. The mixture was heated to 80° C. for 3 h, then cooled to RT. The mixture was then partitioned between EtOAc and sat'd aqueous sodium bicarbonate solution, the layers were separated, and the organic layer was dried over anhydrous magnesium sulfate, filtered, and concentrated in vacuo to give an oil. The oil was purified by silica gel chromatography (EtOAc) to give (R,Z)-3-amino-5-(5-(2-(5-(cyclobutylmethoxy)pyrazin-2-yl)-2-fluorovinyl)-2-fluorophenyl)-2,5-dimethyl-5,6-dihydro-2H-1,2,4-thiadiazine 1,1-dioxide (174) (33 mg, 0.069 mmol, 56% yield for 2 steps) as a white solid. MS m/z=478.1 [M+H]⁺. ¹H NMR (400 MHz, CHLOROFORM-d) δ 8.30 (s, 1H), 8.16 (s, 1H), 7.86 (dd, J=8.12, 2.05 Hz, 1H), 7.56-7.72 (m, 1H), 6.99-7.12 (m, 1H), 6.76 (d, J=40.10 Hz, 1H), 4.27-4.39 (m, 2H), 3.84 (d, J=13.89 Hz, 1H), 3.73 (d, J=14.09 Hz, 1H), 3.21 (s, 3H), 2.73-2.86 (m, 1H), 2.10-2.20 (m, 2H), 1.83-2.05 (m, 4H), 1.79 (s, 3H). ¹⁹F NMR (376 MHz, CHLOROFORM-d) δ −112.84 (s, 1F), −125.32 (s, 1F).

Example 175: (R,Z)-5-amino-3-(2-fluoro-5-(2-fluoro-2-(5-((3-methyl-1,2,4-oxadiazol-5-yl)methoxy)pyrazin-2-yl)vinyl)phenyl)-3,6,6-trimethyl-3,6-dihydro-2H-1,4-thiazine 1,1-dioxide

175

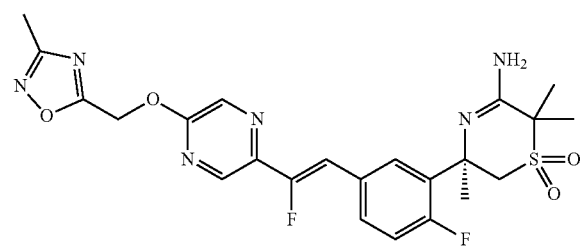

This compound (65 mg, 54% yield) as a yellow solid was prepared in a fashion similar to that described for Example 123, here staring with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 150 mg, 0.234 mmol) and (2-methyl-1,2,4-oxadiozol-5-yl)methanol (133 mg, 1.17 mmol). MS m/z=519.2 [M+H]⁺. ¹H NMR (400 MHz, CHLOROFORM-d) δ 11.31 (br s, 1H), 8.72 (br s, 1H), 8.32 (s, 2H), 7.68 (td, J=2.67, 6.02 Hz, 1H), 7.59 (br d, J=7.63 Hz, 1H), 7.14 (br d, J=8.61 Hz, 1H), 6.83 (d, J=40 Hz, 1H), 5.57 (s, 2H), 4.00 (d, J=15.45 Hz, 1H), 3.71 (d, J=15.45 Hz, 1H), 2.40 (s, 3H), 2.06 (s, 3H), 1.90 (s, 3H), 1.80 (s, 3H).

Example 176: (R,Z)-5-amino-3-(2-fluoro-5-(2-fluoro-2-(5-((5-methyl-1,3,4-oxadiazol-2-yl)methoxy)pyrazin-2-yl)vinyl)phenyl)-3,6,6-trimethyl-3,6-dihydro-2H-1,4-thiazine 1,1-dioxide

176

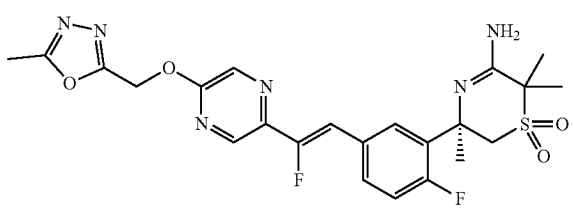

This compound (77.4 mg, 64% yield) as a white solid was prepared in a fashion similar to that described for Example 123, here using (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 150 mg, 0.234 mmol) and (5-methyl-1,3,4-oxadiazol-2-yl)methanol (133 mg, 1.17 mmol) as starting materials. MS m/z=519.1 [M+H]⁺. ¹H NMR (400 MHz, CHLOROFORM-d) δ 8.35 (s, 1H), 8.27 (s, 1H), 7.76 (dd, J=2.15, 8.02 Hz, 1H), 7.63 (ddd, J=2.25, 4.74, 8.46 Hz, 1H), 7.07 (dd, J=12.0, 8.61 Hz, 1H), 5.59 (s, 2H), 3.53-3.64 (m, 2H), 2.57 (s, 3H), 2.04 (s, 1H), 1.81 (s, 3H), 1.69 (s, 3H), 1.60 (s, 3H). NH₂ peak was not observed.

Example 177: (R)-5-amino-3-(2-fluoro-5-((Z)-2-fluoro-2-(5-((R)-pent-1-yn-3-yloxy)pyrazin-2-yl)vinyl)phenyl)-3,6,6-trimethyl-3,6-dihydro-2H-1,4-thiazine 1,1-dioxide; and Example 178: (R)-5-amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide

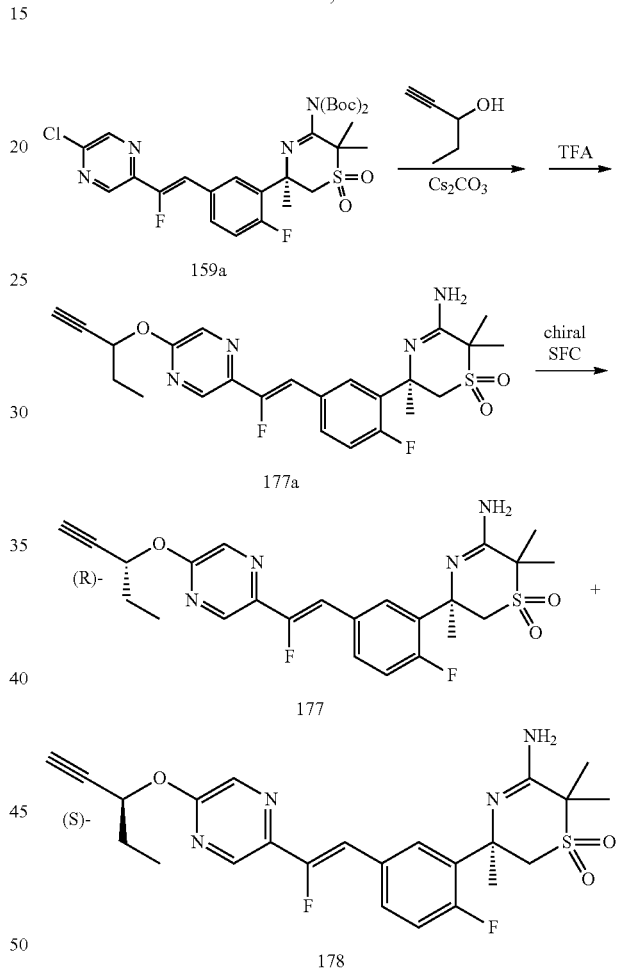

Intermediate 177a (45 mg, 37% yield) as a light yellow solid was prepared in a fashion similar to that described for Example 123, here starting with (R,Z)-tert-butyl (5-(2-fluoro-5-(2-fluoro-2-(5-(prop-2-yn-1-yloxy)pyrazin-2-yl)vinyl)phenyl)-2,2,5-trimethyl-1,1-dioxido-5,6-dihydro-2H-1,4-thiazin-3-yl)carbamate (159a, 153 mg, 0.24 mmol) and 1-pentyn-3-ol (201 mg, 2.38 mmol). 177a: MS m/z=589.3 [M+H]⁺. SFC purification of 177a gave Example 177 (5.8 mg) and Example 178 (7.6 mg). Preparative SFC purification method: OJ-H (5 µm, 21×250 mm); organic modifier: 10% Methanol with 20 mM NH₃, 90% carbon dioxide; flow rate=70 mL/min; temp=40° C.; BPR=100 bar; wave length 220 nm; pressure=176 bar; all sample was dissolved in 3 mL MeOH, 0.6 mL/injection. The relative stereochemistry was arbitrarily assigned.

(R)-5-Amino-3-(2-fluoro-5-((Z)-2-fluoro-2-(5-((R)-pent-1-yn-3-yloxy)pyrazin-2-yl)vinyl)phenyl)-3,6,6-trimethyl-3,6-dihydro-2H-1,4-thiazine 1,1-dioxide (177): MS m/z=489.2 [M+H]+. 1H NMR (400 MHz, CDCl3) δ 8.40 (s, 1H), 8.23 (s, 1H), 7.74 (dd, J=7.92, 2.25 Hz, 1H), 7.66 (ddd, J=8.46, 4.74, 2.25 Hz, 1H), 7.06-7.11 (m, 1H), 6.83 (d, J=40 Hz, 1H), 5.63 (dt, J=2.15, 6.46 Hz, 1H), 3.50-3.65 (m, 2H), 2.96-2.06 (m, 2H), 2.48 (d, J=2.15 Hz, 1H), 1.82 (s, 3H), 1.71 (s, 3H), 1.62 (s, 3H), 1.14 (t, J=7.43 Hz, 6H). NH2 peak was not observed.

(R)-5-Amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide (178): MS m/z=489.2 [M+H]+. 1H NMR (400 MHz, CDCl3) δ 8.40 (s, 1H), 8.23 (s, 1H), 7.74 (dd, J=7.92, 2.25 Hz, 1H), 7.66 (ddd, J=8.46, 4.74, 2.25 Hz, 1H), 7.06-7.11 (m, 1H), 6.83 (d, J=40 Hz, 1H), 5.63 (dt, J=2.15, 6.46 Hz, 1H), 3.53-3.64 (m, 2H), 2.48 (d, J=2.15 Hz, 1H), 2.00 (quin, J=7.19 Hz, 2H), 1.82 (s, 3H), 1.71 (s, 3H), 1.62 (s, 3H), 1.14 (t, J=7.43 Hz, 3H).

Example 179: (R,Z)-3-amino-5-(2-fluoro-5-(2-fluoro-2-(5-(oxetan-3-ylmethoxy)pyrazin-2-yl)vinyl)phenyl)-2,5-dimethyl-5,6-dihydro-2H-1,2,4-thiadiazine 1,1-dioxide

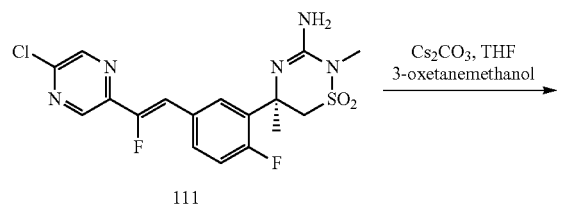

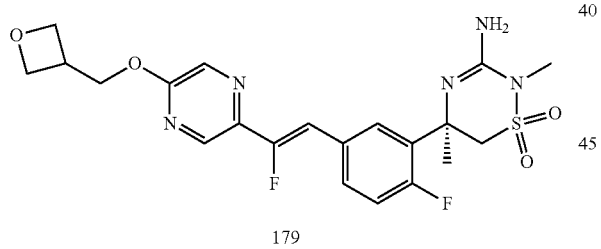

This compound (24 mg, 0.050 mmol, 36% yield) as a white solid was prepared in a fashion similar to that described in Method D for Example 112, here using 3-oxetanemethanol (Sigma-Aldrich) (99 mg, 1.12 mmol) and 111 (60 mg, 0.14 mmol) as starting materials. MS m/z=480.1 [M+H]+. 1H NMR (400 MHz, CDCl3) δ 8.34 (s, J=8.40 Hz, 1H), 8.20 (s, J=5.53 Hz, 1H), 7.86 (d, J=7.79 Hz, 1H), 7.60-7.67 (m, 1H), 7.00-7.14 (m, 1H), 6.78 (d, J=39.91 Hz, 1H), 4.90 (dd, J=7.73, 6.36 Hz, 2H), 4.56-4.66 (m, 4H), 3.84 (d, J=13.89 Hz, 1H), 3.72 (d, J=14.08 Hz, 1H), 3.48 (t, J=6.75 Hz, 1H), 3.22 (s, 3H), 1.79 (s, 3H). NH2 peak was not observed. 19F NMR (376 MHz, CDCl3) δ −112.65 (s, 1F), −125.44 (s, 1F).

Example 180: (R,Z)-6-(2-(3-(3-amino-2,5,6,6-tetramethyl-1,1-dioxido-5,6-dihydro-2H-1,2,4-thiadiazin-5-yl)-4-fluorophenyl)-1-fluorovinyl)nicotinonitrile

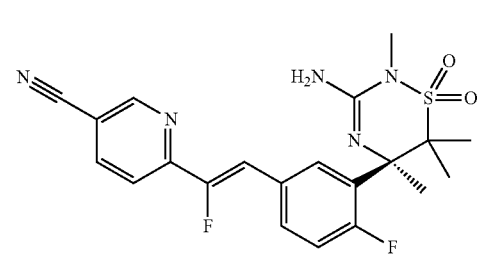

This compound (53 mg, 75% yield) as off-white solid was prepared in a fashion similar to that described in Method B for Example 127, here starting with (Z)-6-(1-fluoro-2-iodovinyl)nicotinonitrile (1) (66 mg, 0.24 mmol) and boronic ester 36 (100 mg, 0.16 mmol). MS m/z=446 [M+H]+. 1H NMR (400 MHz, CHLOROFORM-d) δ ppm 8.83 (s, 1H) 8.03 (dd, J=8.31, 2.05 Hz, 1H) 7.89 (br d, J=7.04 Hz, 1H) 7.68-7.77 (m, 2H) 7.26 (d, J=39.13 Hz, 1H) 7.09 (dd, J=12.42, 8.51 Hz, 1H) 3.31 (s, 3H) 1.96 (d, J=2.93 Hz, 3H) 1.64 (d, J=2.15 Hz, 3H) 1.18 (s, 3H). NH2 peak was not observed. 19F NMR (376 MHz, CHLOROFORM-d) δ ppm −102.93 (s, 1F) −125.57 (d, J=39.01 Hz, 1F).

Example 181: (R,Z)-5-(2-(3-(3-amino-2,5,6,6-tetramethyl-1,1-dioxido-5,6-dihydro-2H-1,2,4-thiadiazin-5-yl)-4-fluorophenyl)-1-fluorovinyl)pyrazine-2-carbonitrile

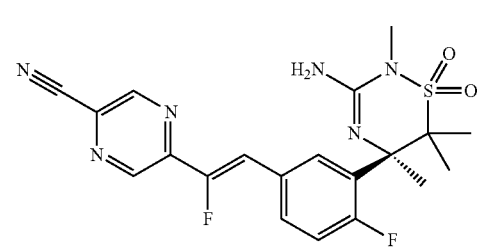

This compound (73 mg, 65% yield) as off-white solid was prepared in a fashion similar to that described in Method B for Example 127, here starting with (Z)-5-(1-fluoro-2-iodovinyl)pyrazine-2-carbonitrile (12) (104 mg, 0.38 mmol) and boronic ester 36 (158 mg, 0.25 mmol). MS m/z=447 [M+H]+. 1H NMR (400 MHz, CHLOROFORM-d) δ ppm 8.96 (s, 1H) 8.83 (s, 1H) 7.93 (br d, J=6.85 Hz, 1H) 7.73 (ddd, J=8.46, 4.25, 2.15 Hz, 1H) 7.26 (d, J=39.32 Hz, 1H) 7.11 (dd, J=12.32, 8.41 Hz, 1H) 3.32 (s, 3H) 1.95 (d, J=3.13 Hz, 3H) 1.64 (d, J=2.15 Hz, 3H) 1.19 (s, 3H). NH2 was not clear in NMR. 19F NMR (376 MHz, CHLOROFORM-d) δ ppm −102.93 (s, 1F) −125.57 (d, J=39.01 Hz, 1F).

Example 182: (R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide

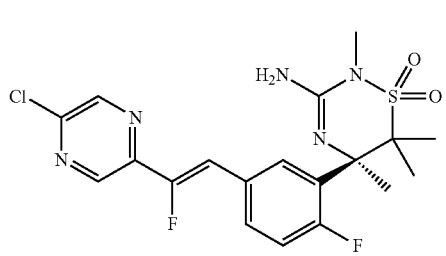

182

This compound (35 mg, 100% yield) as off-white solid was prepared in a fashion similar to that described in Method B for Example 127, here starting with (Z)-2-chloro-5-(1-fluoro-2-iodovinyl)pyrazine (11) and boronic ester 36. MS m/z=456 [M+H]$^+$. $^1$H NMR (400 MHz, CHLOROFORM-d) δ ppm 8.64 (s, 1H) 8.55 (s, 1H) 7.88 (br d, J=7.24 Hz, 1H) 7.64-7.75 (m, 1H) 6.99-7.12 (m, 2H) 3.32 (s, 3H) 1.96 (d, J=3.13 Hz, 3H) 1.64 (br d, J=1.96 Hz, 3H) 1.19 (s, 3H). NH$_2$ was not clear in NMR. $^{19}$F NMR (376 MHz, CHLOROFORM-d) δ ppm −103.31 (s, 1F) −126.78 (d, J=39.01 Hz, 1F).

Example 183: (R,Z)-3-amino-5-(2-fluoro-5-(2-fluoro-2-(5-(prop-2-yn-1-yloxy)pyrazin-2-yl)vinyl)phenyl)-2,5,6,6-tetramethyl-5,6-dihydro-2H-1,2,4-thiadiazine 1,1-dioxide

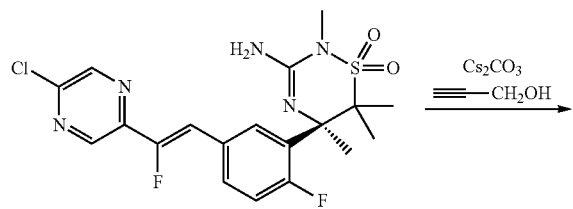

This compound (48 mg, 44% yield) as a white solid was prepared in a fashion similar to that described in Method D for Example 112, here starting with (R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide (182) and propargyl alcohol (TCI America). MS m/z=476 [M+H]$^+$. $^1$H NMR (400 MHz, CHLOROFORM-d) δ 8.40 (s, 1H), 8.27 (s, 1H), 7.82 (d, J=7.43 Hz, 1H), 7.63-7.72 (m, 1H), 7.05 (dd, J=8.61, 12.32 Hz, 1H), 6.78-6.94 (m, 1H), 5.04 (d, J=2.35 Hz, 2H), 3.31 (s, 3H), 2.53 (t, J=2.45 Hz, 1H), 1.96 (d, J=2.93 Hz, 3H), 1.64 (d, J=2.15 Hz, 3H), 1.17 (s, 3H). NH$_2$ was not clear in NMR. $^{19}$F NMR (376 MHz, CHLOROFORM-d) δ −104.81 (br. s., 1F), −125.81 (d, J=39.01 Hz, 1F).

Example 184: (R,Z)-5-amino-3-(5-(2-(2,3-dihydro-[1,4]dioxino[2,3-c]pyridin-7-yl)-2-fluorovinyl)-2-fluorophenyl)-3,6,6-trimethyl-3,6-dihydro-2H-1,4-thiazine 1,1-dioxide

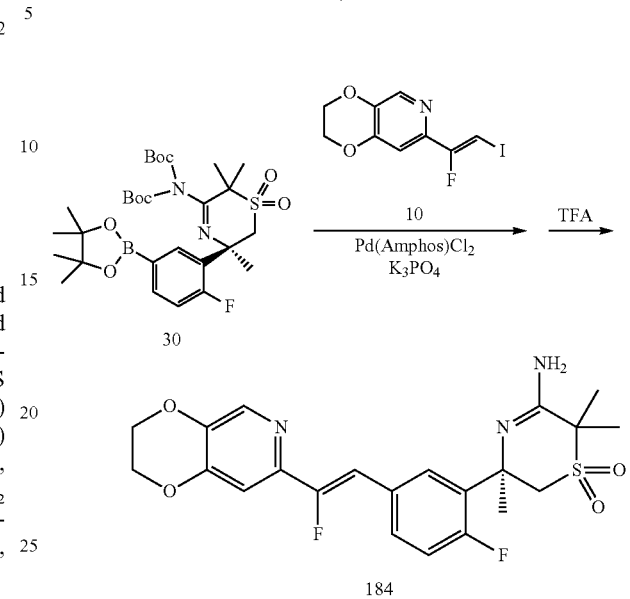

This compound (20 mg, 37% yield) as a white solid was prepared in a fashion similar to that described in Method E for Example 258, here string with (Z)-7-(1-fluoro-2-iodovinyl)-2,3-dihydro-[1,4]dioxino[2,3-c]pyridine (10, 11 mg, 0.36 mmol) and boronic ester 30 (80 mg, 0.13 mmol). MS m/z=464.1 [M+H]$^+$. $^1$H NMR (400 MHz, CHLOROFORM-d) δ 11.50 (br s, 1H), 8.70 (br s, 1H), 8.17 (s, 1H), 7.62-7.68 (m, 2H), 7.10-7.26 (m, 2H), 6.89 (d, J=40 Hz, 1H), 4.28-4.33 (m, 4H), 3.99 (d, J=15.45 Hz, 1H), 3.71 (d, J=15.45 Hz, 1H), 2.05 (s, 3H), 1.92 (s, 3H), 1.80 (s, 3H).

Example 185: (R,Z)-3-amino-5-(5-(2-(5-(but-2-yn-1-yloxy)pyrazin-2-yl)-2-fluorovinyl)-2-fluorophenyl)-2,5,6,6-tetramethyl-5,6-dihydro-2H-1,2,4-thiadiazine 1,1-dioxide

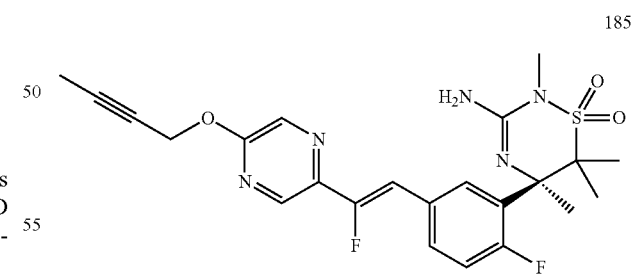

This compound (33 mg, 89% yield) as off-white solid was prepared in a fashion similar to that described in Method D for Example 112, using (R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide (182) and but-2-yn-1-ol (sigma-Aldrich) as starting materials. MS m/z=490 [M+H]$^+$. $^1$H NMR (400 MHz, CHLOROFORM-d) δ 8.39 (s, 1H), 8.25 (s, 1H), 7.82 (d, J=6.85 Hz, 1H), 7.60-7.72 (m, 1H), 7.05 (dd, J=8.51, 12.42 Hz, 1H), 6.73-

6.95 (m, 1H), 5.00 (d, J=2.35 Hz, 2H), 3.31 (s, 3H), 1.96 (d, J=2.93 Hz, 3H), 1.89 (t, J=2.25 Hz, 3H), 1.63 (d, J=1.76 Hz, 3H), 1.17 (s, 3H). NH$_2$ was not clear in NMR. $^{19}$F NMR (376 MHz, CHLOROFORM-d) δ −104.90 (br. s., 1F), −125.73 (d, J=39.88 Hz, 1F).

Example 186: (R)-3-amino-5-(5-((Z)-2-(5-((S)-but-3-yn-2-yloxy)pyrazin-2-yl)-2-fluorovinyl)-2-fluorophenyl)-2,5,6,6-tetramethyl-5,6-dihydro-2H-1,2,4-thiadiazine 1,1-dioxide

186

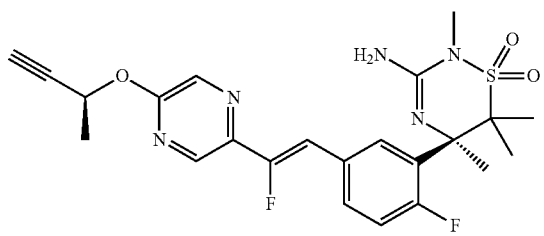

This compound (35 mg, 69% yield) as off-white solid was prepared in a fashion similar to that described in Method D for Example 112, using (R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide (182) and (S)-(−)-3-butyn-2-ol (Alfa Aesar) as starting materials. MS m/z=490 [M+H]$^+$. $^1$H NMR (400 MHz, CHLOROFORM-d) δ 8.41 (s, 1H), 8.22 (s, 1H), 7.82 (d, J=7.24 Hz, 1H), 7.68 (d, J=3.91 Hz, 1H), 7.05 (dd, J=8.41, 12.32 Hz, 1H), 6.76-6.92 (m, 1H), 5.69-5.82 (m, 1H), 3.31 (s, 3H), 2.48 (d, J=1.96 Hz, 1H), 1.96 (d, J=2.74 Hz, 3H), 1.69 (d, J=6.65 Hz, 3H), 1.63 (d, J=1.57 Hz, 3H), 1.17 (s, 3H). NH$_2$ was not clear in NMR. $^{19}$F NMR (376 MHz, CHLOROFORM-d) δ −104.90 (br. s., 1F), −125.72 (d, J=39.88 Hz, 1F).

Example 187: (R,Z)-3-amino-5-(5-(2-(2,3-dihydro-[1,4]dioxino[2,3-c]pyridin-7-yl)-2-fluorovinyl)-2-fluorophenyl)-2,5-dimethyl-5,6-dihydro-2H-1,2,4-thiadiazine 1,1-dioxide This compound (93 mg, 0.21 mmol, 52% yield for 2 steps) as a white solid was prepared in a fashion similar to that described in Method C for Example 111, here using (Z)-7-(1-fluoro-2-iodovinyl)-2,3-dihydro-[1,4]dioxino[2,3-c]pyridine 10 (141 mg, 0.46 mmol) and boronic ester 24 (250 mg, 0.40 mmol) as starting materials. MS m/z=451.1 [M+H]$^+$. $^1$H NMR (400 MHz, DMSO-d$_6$) δ 8.21 (s, 1H), 7.85 (d, J=7.04 Hz, 1H), 7.55-7.65 (m, 1H), 7.12-7.23 (m, 2H), 6.88 (d, J=40.69 Hz, 1H), 6.04 (br. s., 2H), 4.39 (dd, J=15.85, 4.70 Hz, 4H), 3.79 (br. s., 2H), 3.05 (s, 3H), 1.61 (s, 3H). $^{19}$F NMR (376 MHz, DMSO-d$_6$) δ −112.57 (s, 1F), −122.15 (s, 1F).

Example 188: (S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile

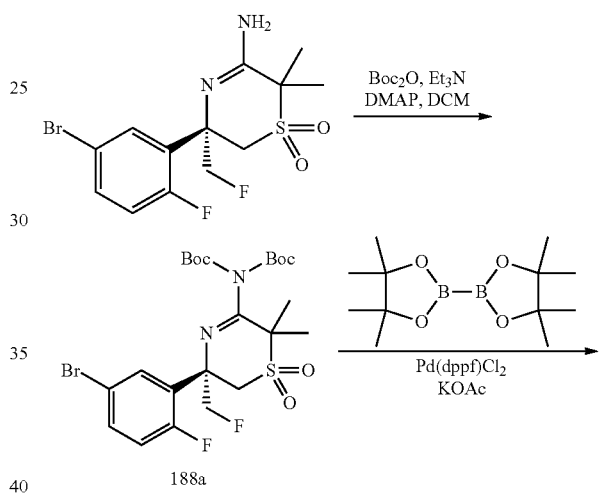

188a

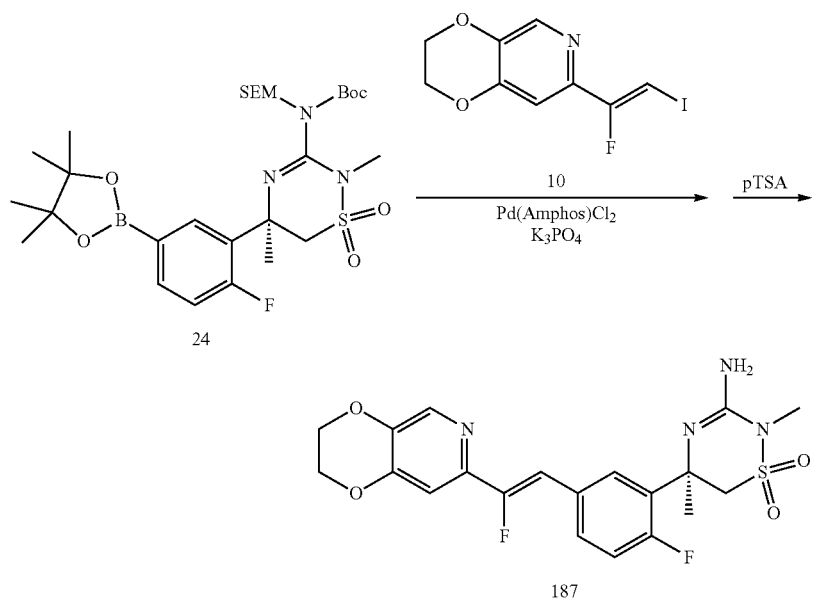

187

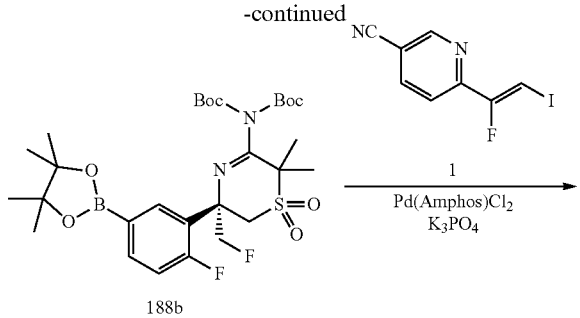

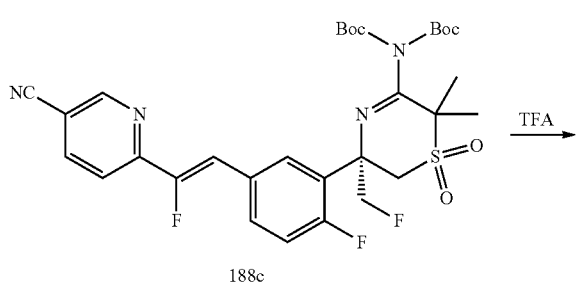

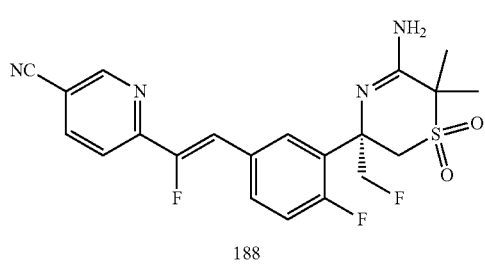

Preparation of 188a

To a mixture of (S)-5-amino-3-(5-bromo-2-fluorophenyl)-3-(fluoromethyl)-6,6-dimethyl-3,6-dihydro-2H-1,4-thiazine 1,1-dioxide (prepared according to the method described in WO 2014059185) (9.0 g, 23.6 mmol), N,N-dimethylpyridin-4-amine (1.4 g, 11.8 mmol) and N-ethyl-N-isopropylpropan-2-amine (12.3 mL, 70.8 mmol) in DCM (79 mL) was added di-tert-butyl dicarbonate (12.9 g, 59.0 mmol) at RT. The resulting mixture was allowed to stir at RT overnight. The mixture was partitioned between DCM and diluted NaHCO$_3$. The aqueous layer was back extracted with DCM (2×) and the combined organics dried (Na$_2$SO$_4$) and concentrated. The residue was purified by Biotage 340 g ultra column (0-80% ethyl acetate/heptane) to give 188a (11.7 g, 20.12 mmol, 85% yield) as off-white solid. MS (ESI, positive ion) m/z: =603.0 (M+Na)$^+$.

Preparation of 188b

A stream of argon was bubbling through a mixture of 188a (2.9 g, 5.0 mmol), 4,4,4',4',5,5,5',5'-octamethyl-2,2'-bi(1,3,2-dioxaborolane) (1.9 g, 7.4 mmol), (1,1'-bis(diphenylphosphino)ferrocene)dichloropalladium(II) (365 mg, 0.5 mmol) and potassium acetate (1.7 g, 17.5 mmol) in 1,4-dioxane (25 mL) for 10 min. The mixture was then allowed to stir at 90° C. for overnight. After cooling to RT, the mixture was filtered through a pad of celite, washed with 7/3 ethyl acetate/heptane. The filtrate was concentrated and the residue was purified by Biotage 100 g ultra column (0-60% ethyl acetate gradient in heptane) to afford 188b (2.59 g, 83% yield) as a white solid. MS (ESI, positive ion) m/z: =651.3 (M+Na)$^+$.

Preparation of 188c

A mixture of 188b (152 mg, 0.24 mmol), (Z)-6-(1-fluoro-2-iodovinyl)nicotinonitrile (80 mg, 0.29 mmol), potassium phosphate tribasic (128 mg, 0.60 mmol), and 1,1-bis[(di-t-butyl-p-methylaminophenyl]palladium(II) chloride (17 mg, 0.024 mmol) was placed under nitrogen atmosphere using 3 evacuation/backfill cycles. Dioxane (2.7 mL) and water (0.5 mL) were added and the mixture was heated to 80° C. for 1.5 h. The mixture was cooled to RT and partitioned between EtOAc and water. The layers were separated and the organic layer was concentrated in vacuo. The crude product was fused to silica gel and purified by silica gel chromatography (0 to 20% EtOAc/heptane) to give 188c (106 mg, 0.16 mmol, 68% yield) as an off-white foam. MS (ESI, positive ion) m/z: =671.4 (M+Na)$^+$.

Preparation of Example 188

A solution of 188c (106 mg, 0.16 mmol) in DCM (1.6 mL) at RT was treated with trifluoroacetic acid (0.5 mL, 6.73 mmol) dropwise and stirred for 1 h. The solvent was concentrated in vacuo and to the residue was added DCM and evaporated again. The process was repeated twice. The residue was partitioned between DCM and sat'd aqueous NaHCO$_3$. The aqueous layer was back extracted with DCM (2×) and the combined organics were dried (Na$_2$SO$_4$) and concentrated to give (S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile (188) (67 mg, 0.15 mmol, 91% yield) as a white solid. MS (ESI, positive ion) m/z: =449.0 (M+1). $^1$H NMR (CHLOROFORM-d) δ: 8.83 (s, 1H), 8.02 (dd, J=8.4, 2.0 Hz, 1H), 7.80-7.86 (m, 1H), 7.73-7.80 (m, 1H), 7.70 (d, J=8.0 Hz, 1H), 7.23 (d, J=36 Hz, 1H), 7.12 (dd, J=12.1, 8.6 Hz, 1H), 4.70-4.84 (dd, J=48, 8.6 Hz, 1H), 4.43-4.57 (dd, J=48, 8.6 Hz, 1H), 3.78-3.86 (m, 1H), 3.65-3.73 (m, 1H), 1.76 (s, 3H), 1.64 (s, 3H). $^{19}$F NMR (CHLOROFORM-d) δ: −110.17 (br d, J=6.1 Hz, 1F), −125.14 (br s, 1F), −219.22 (br s, 1F).

Example 189: (S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide

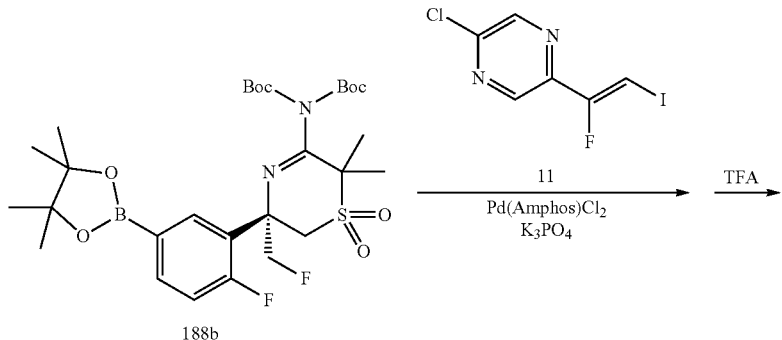

This compound (99 mg, 74% yield for 2 steps) as an off-white solid was prepared in a fashion similar to that described for Example 188, here using 188b (807 mg, 1.28 mmol), (Z)-2-chloro-5-(1-fluoro-2-iodovinyl)pyrazine (11) (438 mg, 1.54 mmol), 1,1-bis[(di-t-butyl-p-methylaminophenyl]palladium(II) chloride (91 mg, 0.128 mmol), and potassium phosphate tribasic (681 mg, 3.21 mmol) as starting materials, followed by deprotection using trifluoroacetic acid (0.71 mL) in DCM (2.4 mL). MS (ESI, positive ion) m/z: =459.1 (M+1). $^1$H NMR (DMSO-$d_6$) δ: 8.86 (s, 1H), 8.81 (s, 1H), 7.92 (dd, J=7.8, 2.2 Hz, 1H), 7.69-7.78 (m, 1H), 7.28 (dd, J=12.1, 8.6 Hz, 1H), 7.13 (d, J=40 Hz, 1H), 6.41 (s, 2H), 4.43-4.65 (m, 2H), 3.62-3.81 (m, 2H), 1.61 (s, 3H), 1.49 (s, 3H). $^{19}$F NMR (DMSO-$d_6$) δ: −109.81 (br d, J=9.5 Hz, 1F), −125.30 (s, 1F), −218.14 (d, J=8.7 Hz, 1F).

Example 190: (S,Z)-5-amino-3-(2-fluoro-5-(2-fluoro-2-(5-(prop-2-yn-1-yloxy)pyrazin-2-yl)vinyl)phenyl)-3-(fluoromethyl)-6,6-dimethyl-3,6-dihydro-2H-1,4-thiazine 1,1-dioxide

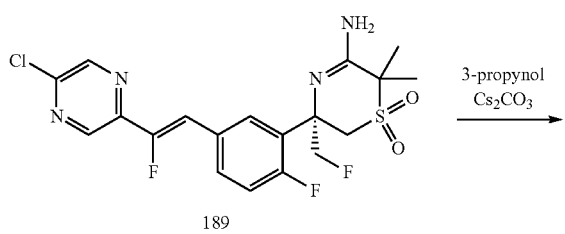

This compound (71 mg, 77% yield) as an off-white solid was prepared in a fashion similar to that described in Method A for Example 108, here using (S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide (189) (88 mg, 0.19 mmol), 3-propynol (Aldrich-Sigma, 86 mg, 1.53 mmol) and cesium carbonate (219 mg, 0.671 mmol) as starting materials. MS (ESI, positive ion) m/z: =479.1 (M+1). $^1$H NMR (CHLOROFORM-d) δ 8.39 (s, 1H), 8.26 (s, 1H), 7.69-7.79 (m, 2H), 7.09 (dd, J=12.0, 8.5 Hz, 1H), 6.85 (d, J=40 Hz, 1H), 5.04 (d, J=2.2 Hz, 2H), 4.68-4.86 (m, 1H), 4.42-4.60 (m, 1H), 3.66-3.85 (m, 2H), 2.53 (s, 1H), 1.76 (s, 3H), 1.64 (s, 3H). $^{19}$F NMR (CHLOROFORM-d) δ-111.92 (br d, J=6.9 Hz, 1F), −125.37 (br s, 1F), −219.15 (br s, 1F).

Example 191: (R,Z)-5-amino-3-(5-(2-(5-chloropyrazin-2-yl)-2-fluorovinyl)-2-fluorophenyl)-2,2-difluoro-3,6,6-trimethyl-3,6-dihydro-2H-1,4-thiazine 1,1-dioxide

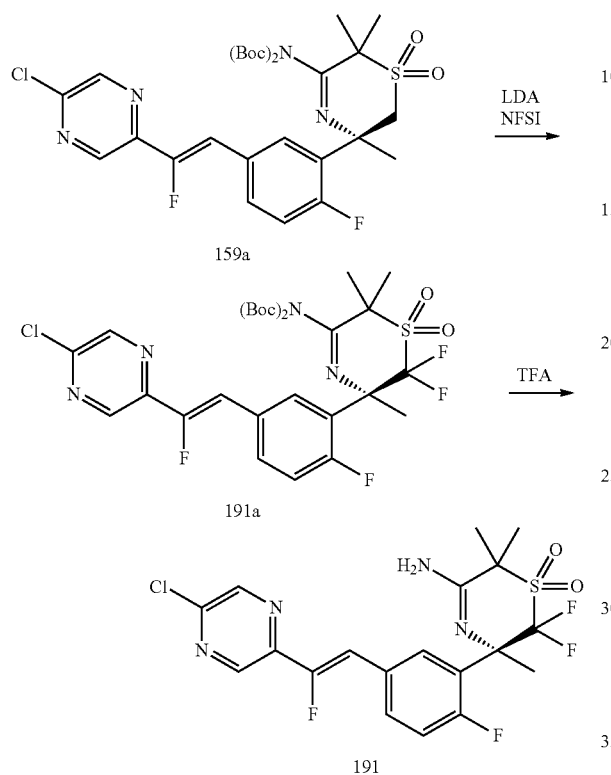

To a solution of (R,Z)-5-(di-Boc-amino)-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a, 0.50 g, 0.78 mmol) in THF (3.90 mL) was dropwise added lithium bis(trimethylsilyl)amide solution (1.0 M in THF, 1.56 mL, 1.56 mmol) at −78° C. The mixture was stirred at the same temperature for 1 h, and a solution of n-fluorobenzenesulfonimide (0.37 g, 1.17 mmol) in 2.0 mL of THF was dropwise added. The resulting mixture was allowed to stir at the same temperature and monitored by LCMS. Upon completion, the mixture was quenched with sat'd aqueous NH$_4$Cl solution, extracted with ethyl acetate (40 mL×3). The combined extracts were washed with brine, dried (Na$_2$SO$_4$) and concentrated. The residue was purified on a silica gel column using 0-60% ethyl acetate in heptane to give (75 mg, 14% yield) of (R,Z)-5-(Di-Boc-amino)-3-(5-(2-(5-chloropyrazin-2-yl)-2-fluorovinyl)-2-fluorophenyl)-2,2-difluoro-3,6,6-trimethyl-3,6-dihydro-2H-1,4-thiazine 1,1-dioxide (191a) as a brown amorphous solid. MS m/z=699.2 [M+Na]$^+$. $^1$H NMR (400 MHz, CHLOROFORM-d) δ 8.61 (s, 1H), 8.49 (s, 1H), 7.90 (ddd, J=2.15, 4.50, 8.61 Hz, 1H), 7.69 (dd, J=1.96, 7.43 Hz, 1H), 7.19 (dd, J=11.64, 8.71 Hz, 1H), 7.10 (d, J=40 Hz, 1H), 2.11 (br s, 3H), 1.76 (s, 3H), 1.74 (d, J=2.93 Hz, 3H), 1.59 (s, 18H). A solution of 191a (75 mg, 0.11 mmol) in DCM (5 mL, 0.111 mmol) and TFA (1 mL) was stirred at RT for 2 h. The mixture was concentrated and the residue was purified on a silica gel column (0-10% (2 M NH$_3$/methanol) in DCM) to give (52 mg, 98% yield) of Example 191 as a white solid. MS m/z=477.0 [M+H]$^+$. $^1$H NMR (400 MHz, CDCl$_3$) δ 11.15 (br s, 1H), 8.67 (s, 1H), 8.58 (s, 1H), 8.53 (br s, 1H), 7.82 (ddd, J=1.76, 4.40, 8.51 Hz, 1H), 7.67 (br d, J=7.43 Hz, 1H), 7.18-7.26 (m, 1H), 7.06 (d, J=40 Hz, 1H), 2.25 (d, J=2.93 Hz, 3H), 1.98 (s, 3H), 1.96 (d, J=2.35 Hz, 3H).

Example 192: (R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile

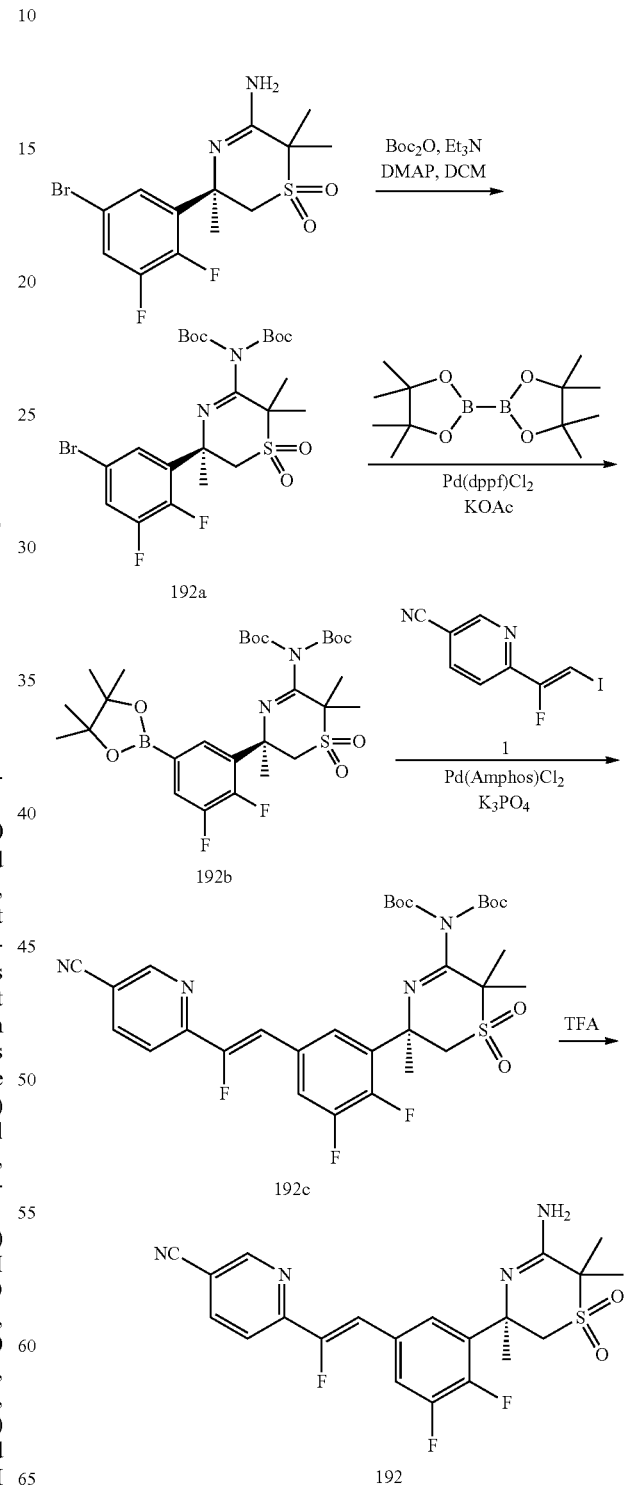

Preparation of 192a

To a mixture of (R)-tert-butyl (5-(5-bromo-2,3-difluorophenyl)-2,2,5-trimethyl-1,1-dioxido-5,6-dihydro-2H-1,4-thiazin-3-yl)carbamate (prepared according to the method described in WO 2014059185) (2.69 g, 5.59 mmol), DMAP (0.34 g, 2.79 mmol) and N-ethyl-N-isopropylpropan-2-amine (1.94 mL, 11.18 mmol) in DCM (19 mL) was added di-tert-butyl dicarbonate (1.83 g, 8.38 mmol) at RT. The resulting mixture was allowed to stir at RT overnight. Additional N-ethyl-N-isopropylpropan-2-amine (1 mL) and di-tert-butyl dicarbonate (1.2 g) were added and the mixture stirred for another 4 h. The mixture was partitioned between DCM and diluted NaHCO$_3$. The aqueous layer was back extracted with DCM (2×) and the combined organics were dried (Na$_2$SO$_4$) and concentrated. The residue was purified by Biotage 340 g ultra column (0-60% ethyl acetate/heptane) to give 192a (3.55 g, 6.11 mmol, 109% yield) as a white solid. MS (ESI, positive ion) m/z: =603.0 (M+1)$^+$.

Preparation of 192b

A stream of argon was bubbling through a mixture of 192a (3.6 g, 6.19 mmol), 4,4,4',4',5,5,5',5'-octamethyl-2,2'-bi(1,3,2-dioxaborolane) (2.36 g, 9.29 mmol), (1,1'-bis(diphenylphosphino)ferrocene)dichloropalladium(II) (0.45 g, 0.62 mmol) and potassium acetate (2.12 g, 21.67 mmol) in 1,4-dioxane (31 mL) for 10 min. The mixture was heated at 90° C. for 3 h. After cooling to RT, the mixture was filtered through a pad of celite, washed with 7/3 ethyl acetate/heptane. The filtrate was concentrated and the residue was purified by Biotage 100 g ultra column (0-60% ethyl acetate in heptane) to give 192b (3.53 g, 91% yield) as a white solid. MS (ESI, positive ion) m/z: =651.2 (M+1)$^+$.

Preparation of 192c

A mixture of 192b (154 mg, 0.24 mmol), (Z)-6-(1-fluoro-2-iodovinyl)nicotinonitrile (1) (81 mg, 0.29 mmol), potassium phosphate tribasic (130 mg, 0.61 mmol), and 1,1-bis[(di-t-butyl-p-methylaminophenyl]palladium(II) chloride (17 mg, 0.025 mmol) was placed under nitrogen atmosphere using three evacuation/backfill cycles. Dioxane (1.3 mL) and water (0.25 mL) were added and the mixture was heated to 80° C. for 1.5 h. The mixture was cooled to RT and partitioned between EtOAc and water. The layers were separated and the organic layer was concentrated in vacuo. The crude product was fused to silica gel and purified by silica gel chromatography (0 to 50% EtOAc/heptane) to give 192c (144 mg, 0.22 mmol, 91% yield) as a tan foam. MS (ESI, positive ion) m/z: =671.3 (M+1)$^+$.

Preparation of Example 192

A mixture of 192c (144 mg, 0.22 mmol) in DCM (2.2 mL) and trifluoroacetic acid (0.7 mL) was stirred at RT for 1 h. The solvent was concentrated in vacuo and to the residue was added DCM and evaporated again. The process was repeated twice. The residue was partitioned between DCM and saturated NaHCO$_3$. The aqueous layer was back extracted with DCM (2×) and the combined organics were concentrated to give (R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile (192) (86 mg, 0.192 mmol, 86% yield) as a white solid. MS (ESI, positive ion) m/z: =449.1 (M+1). $^1$H NMR (CHLOROFORM-d) δ 8.85 (s, 1H), 8.05 (dd, J=8.3, 2.1 Hz, 1H), 7.73 (d, J=8.4 Hz, 1H), 7.64 (br t, J=9.3 Hz, 1H), 7.50 (br d, J=6.5 Hz, 1H), 7.20 (d, J=40 Hz, 1H), 3.59 (s, 2H), 1.82 (s, 3H), 1.72 (s, 3H), 1.63 (s, 3H). $^{19}$F NMR (CHLOROFORM-d) δ: −124.07 (br s, 1F), −136.29 (br d, J=20.8 Hz, 1F), −136.87 (br d, J=20.8 Hz, 1F).

Example 193: (R,Z)-5-amino-3-(5-(2-(5-chloropyrazin-2-yl)-2-fluorovinyl)-2,3-difluorophenyl)-3,6,6-trimethyl-3,6-dihydro-2H-1,4-thiazine 1,1-dioxide

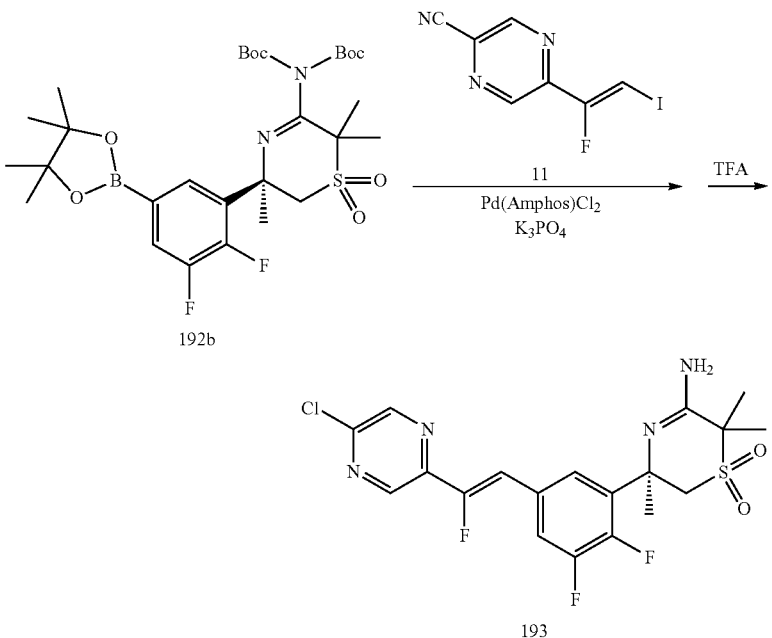

This compound (460 mg, 78% yield for 2 steps) as an off-white solid was prepared in a fashion similar to that described in Method A for Example 108, here using 192b (807 mg, 1.28 mmol), (Z)-2-chloro-5-(1-fluoro-2-iodovinyl) pyrazine (11) (438 mg, 1.54 mmol), potassium phosphate tribasic (681 mg, 3.21 mmol), and 1,1-bis[(di-t-butyl-p-methylaminophenyl]palladium(II) chloride (91 mg, 0.128 mmol) as starting materials, followed by deprotection using trifluoroacetic acid (3 mL, 40.3 mmol) in DCM (10 mL). MS (ESI, positive ion) m/z: =459.0 (M+1). $^1$H NMR (CHLOROFORM-d) δ 8.65 (s, 1H), 8.56 (s, 1H), 7.59 (br t, J=8.4 Hz, 1H), 7.49 (br d, J=6.3 Hz, 1H), 7.00 (d, J=40 Hz, 1H), 3.59 (s, 2H), 1.82 (s, 3H), 1.72 (s, 3H), 1.63 (s, 3H). Note: NH$_2$ peak was not observed. $^{19}$F NMR (CHLOROFORM-d) δ −125.28 (br s, 1F), −136.80−−136.57 (m, 1F), −136.95 (br d, J=19.9 Hz, 1F).

Example 194: (S,Z)-5-amino-3-(5-(2-(5-(but-2-yn-1-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide

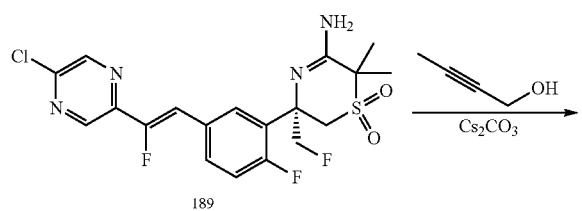

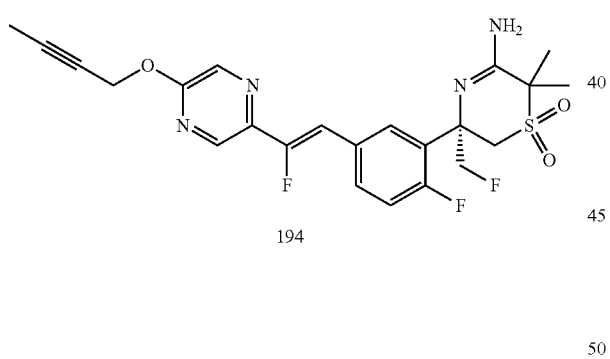

This compound (30 mg, 35% yield) as an off-white solid was prepared in a fashion similar to that described in Method A for Example 108, here using (S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide (189, 80 mg, 0.17 mmol), but-2-yn-1-ol (Aldrich-Sigma, 98 mg, 1.40 mmol) and cesium carbonate (199 mg, 0.61 mmol) as starting materials. MS (ESI, positive ion) m/z: =493.1 (M+1). $^1$H NMR (DMSO-d$_6$) δ 8.50 (s, 1H), 8.43 (s, 1H), 7.80-7.91 (m, 1H), 7.67 (br dd, J=5.7, 2.5 Hz, 1H), 7.25 (dd, J=12.1, 8.6 Hz, 1H), 6.88 (d, J=40 Hz, 1H), 6.41 (br s, 2H), 5.04 (br d, J=2.3 Hz, 2H), 4.37-4.65 (m, 2H), 3.58-3.82 (m, 2H), 1.85 (s, 3H), 1.60 (s, 3H), 1.48 (s, 3H). $^{19}$F NMR (DMSO-d$_6$) δ −111.00 (br d, J=8.7 Hz, 1F), −124.69 (br s, 1F), −219.03−−217.03 (m, 1F).

Example 195: (S)-5-amino-3-(5-((Z)-2-(5-((S)-but-3-yn-2-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide

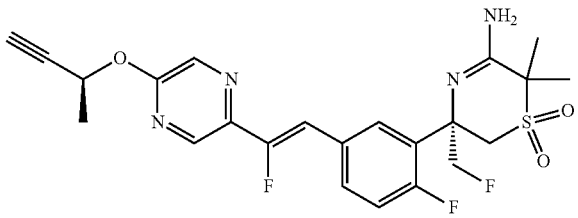

This compound (79 mg, 94% yield) as a tan solid was prepared in a fashion similar to that described in Method A for Example 108, here using (S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide (189, 78 mg, 0.17 mmol), (S)-(−)-3-butyn-2-ol (Alfa Aesar, 95 mg, 1.36 mmol) and cesium carbonate (194 mg, 0.6 mmol) as starting materials. MS (ESI, positive ion) m/z: =493.1 (M+1). $^1$H NMR (CHLOROFORM-d) δ: 8.41 (s, 1H), 8.23 (s, 1H), 7.67-7.82 (m, 2H), 7.09 (dd, J=12.1, 8.6 Hz, 1H), 6.84 (d, J=40 Hz, 1H), 5.74-5.83 (m, 1H), 4.67-4.88 (m, 1H), 4.42-4.61 (m, 1H), 3.64-3.87 (m, 2H), 2.49 (s, 1H), 1.77 (s, 3H), 1.70 (d, J=6.7 Hz, 3H), 1.65 (s, 3H). $^{19}$F NMR (CHLOROFORM-d) δ: −112.00 (br d, J=6.9 Hz, 1F), −125.30 (br s, 1F), −219.16 (br s, 1F).

Example 196: (R,Z)-3-amino-5-(5-(2-(2,3-dihydrobenzo[b][1,4]dioxin-6-yl)-2-fluorovinyl)-2-fluorophenyl)-2,5-dimethyl-5,6-dihydro-2H-1,2,4-thiadiazine 1,1-dioxide

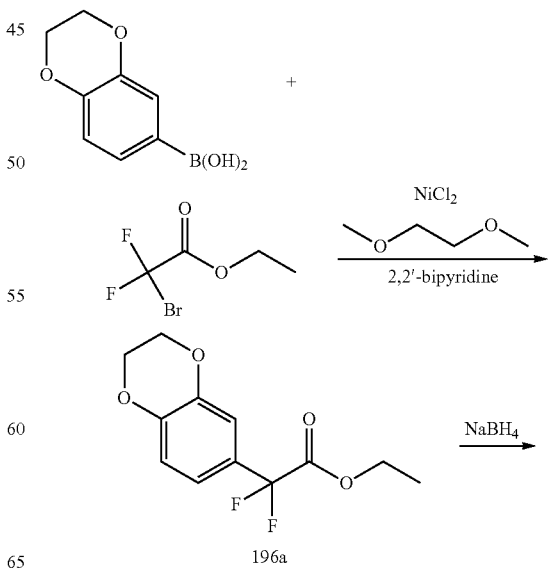

-continued

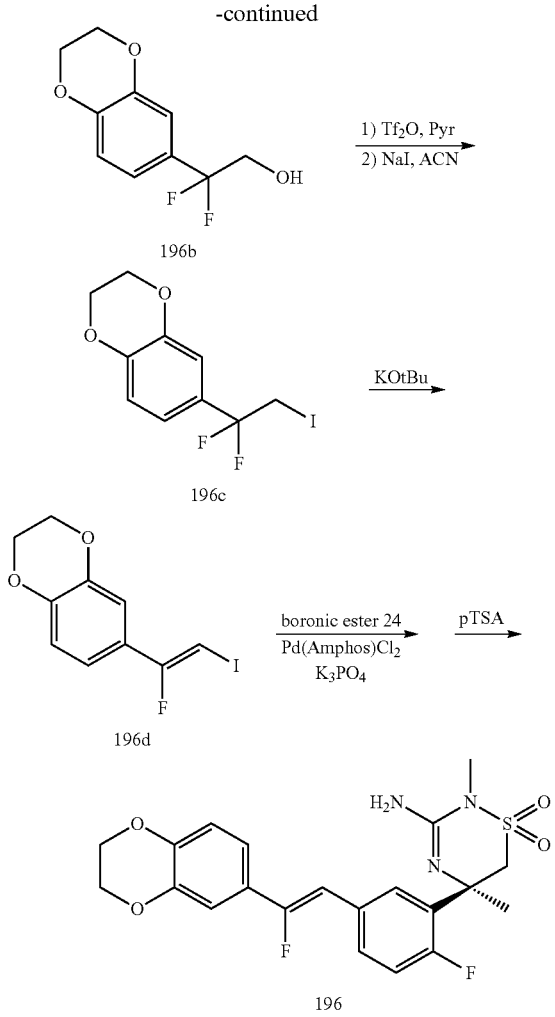

Preparation Ethyl 2-(2,3-dihydrobenzo[b][1,4]dioxin-6-yl)-2,2-difluoroacetate (196a)

The solvent 1,4-dioxane (15 mL) was sparged with a stream of argon in a 100 mL round bottom flask for 5 min. To the flask was added 1,4-benzodioxane-6-boronic acid (Frontier Scientific Inc., Logan, Utah, USA) (1.00 g, 5.56 mmol), ethyl bromodifluoroacetate (Oakwood Products, Inc., Estill, S.C., USA) (1.13 mL, 8.33 mmol), nickel (II) chloride-dimethoxyethane adduct (Strem Chemicals, Inc., Newburyport, Mass., USA) (0.09 g, 0.41 mmol), 2,2'-bipyridine (Strem Chemicals, Inc., Newburyport, Mass., USA) (65 mg, 0.42 mmol), potassium carbonate powder (1.69 g, 12.22 mmol) and the suspension was sparged with a stream of argon for 1 min. The suspension was heated at 80° C. for 18 h. The reaction was partitioned between EtOAc (60 mL) and sat'd aqueous $NaHCO_3$ (25 mL). The organic layer was washed with brine (2 mL), dried over $MgSO_4$, concentrated under reduced pressure onto dry silica (10 g), then purified via silica gel chromatography (40 g) eluting products with a gradient of 0-10% of (3:1 EtOAc/EtOH blend)/heptane to afford 196a (300 mg, 1.16 mmol, 21% yield) as a colorless oil. $^1$H NMR (400 MHz, CHLOROFORM-d) δ ppm 7.13 (s, 1H), 7.09 (d, J=8.41 Hz, 1H), 6.92 (d, J=8.41 Hz, 1H), 4.26-4.34 (m, 6H), 1.32 (t, J=7.14 Hz, 3H). $^{19}$F NMR (376 MHz, CHLOROFORM-d) δ ppm −102.61 (s).

Preparation of 2-(2,3-dihydrobenzo[b][1,4]dioxin-6-yl)-2,2-difluoroethanol (196b)

To a stirring solution of ethyl 2-(2,3-dihydrobenzo[b][1,4]dioxin-6-yl)-2,2-difluoroacetate (196a, 300 mg, 1.16 mmol) in EtOH (3 mL) at 0° C. was added sodium borohydride (Sigma-Aldrich Chemical Company, Inc., St. Louis, Mo., USA) (44.0 mg, 1.16 mmol). After 10 min the cooling bath was removed and the reaction was stirred for 30 min. The reaction was then chilled to 0° C. and hydrochloric acid 5.0 N (1.69 mL, 8.45 mmol) was added. After 10 min, the solvent was removed in half under reduced pressure. The reaction was returned to 0° C. and sodium hydroxide (0.23 mL of 5 M solution) was added. The mixture was then partitioned between EtOAc (20 mL) and water (20 mL). The aqueous was further extracted with EtOAc (5 mL). The combined organic extracts were dried over $MgSO_4$, filtered, concentrated under reduced pressure, then purified by silica gel chromatography (40 g) eluting products with a gradient of 0 to 15% (3:1 EtOAc/EtOH)/heptane to afford 2-(2,3-dihydrobenzo[b][1,4]dioxin-6-yl)-2,2-difluoroethanol (196b, 190 mg, 0.88 mmol, 76% yield) as a colorless oil. MS m/z=197.1 [M+H]$^+$ (elimination of HF). $^1$H NMR (400 MHz, DMSO-d$_6$) δ ppm 6.90-7.02 (m, 3H), 5.55 (t, J=6.46 Hz, 1H), 4.27 (s, 4H), 3.79 (td, J=14.13, 6.36 Hz, 2H). $^{19}$F NMR (376 MHz, DMSO-d$_6$) δ ppm −102.14 (s).

Preparation of 6-(1,1-difluoro-2-iodoethyl)-2,3-dihydrobenzo[b][1,4]dioxine (196c)

To a stirring solution of 2-(2,3-dihydrobenzo[b][1,4]dioxin-6-yl)-2,2-difluoroethanol (196b, 190 mg, 0.88 mmol) and pyridine (143 μL, 1.76 mmol) in MeCN (4 mL) at −10° C. was added triflic anhydride (Sigma-Aldrich Chemical Company, Inc., St. Louis, Mo., USA) (155 μL, 0.92 mmol). After 5 min the cooling bath was removed and to the reaction at 20° C. was added sodium iodide (395 mg, 2.64 mmol). The cloudy mixture was then heated to 60° C. for 2 h. It was partitioned between EtOAc (30 mL) and 5% $NaHCO_3$ (10 mL). The organic layer was further extracted with brine (2 mL) then dried over $MgSO_4$. It was filtered, concentrated under reduced pressure onto silica (5 g), then purified by silica gel chromatography eluting products with a gradient of 0-10% EtOAc/heptane to afford 6-(1,1-difluoro-2-iodoethyl)-2,3-dihydrobenzo[b][1,4]dioxine (196c, 120 mg, 0.37 mmol, 42% yield) as a colorless oil. MS m/z=307.0 [M+H]$^+$ (elimination of HF).

Preparation (Z)-6-(1-fluoro-2-iodovinyl)-2,3-dihydrobenzo[b][1,4] of (196d)

To a stirring solution of 6-(1,1-difluoro-2-iodoethyl)-2,3-dihydrobenzo[b][1,4]dioxine (196c, 120 mg, 0.36 mmol) in THF (2 mL) at 20° C. was added potassium t-butoxide (Sigma-Aldrich Chemical Company, Inc., St. Louis, Mo., USA, 50 mg, 0.44 mmol). After 20 min, another portion of potassium t-butoxide (20 mg) was added. After 20 min, the reaction was quenched with sat'd aqueous $NH_4Cl$ (0.5 mL). It was partitioned between EtOAc (15 mL) and sat'd aqueous $NaHCO_3$ (10 mL). The organic layer was washed with sat'd NaCl (2 mL), dried over $MgSO_4$, filtered, then concentrated under reduced pressure to afford (Z)-6-(1-fluoro- 2-iodovinyl)-2,3-dihydrobenzo[b][1,4]dioxine (196d, 106 mg, 0.346 mmol, 94% yield) as a colorless film.

Preparation of (R,Z)-3-amino-5-(5-(2-(2,3-dihydrobenzo[b][1,4]dioxin-6-yl)-2-fluorovinyl)-2-fluorophenyl)-2,5-dimethyl-5,6-dihydro-2H-1,2,4-thiadiazine 1,1-dioxide (196)

This compound (30 mg, 22% yield) as a white solid was prepared in a fashion similar to that described in Method C for Example 111, using (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate (205 mg, 0.327 mmol) and (Z)-6-(1-fluoro-2-iodovinyl)-2,3-dihydrobenzo[b][1,4]dioxine (Intermediate 24, 205 mg, 0.33 mmol), and 196d (100 mg, 0.33 mmol) as starting materials. MS m/z=450.1 [M+H]$^+$. $^1$H NMR (400 MHz, DMSO-d$_6$) δ ppm 7.83 (br d, J=7.43 Hz, 1H), 7.46-7.54 (m, 1H), 7.11-7.23 (m, 3H), 6.94 (d, J=9.00 Hz, 1H), 6.55 (d, J=41.86 Hz, 1H), 6.00 (br s, 2H), 4.29 (s, 4H), 3.78 (br s, 2H), 3.04 (s, 3H), 1.61 (s, 3H). $^{19}$F NMR (376 MHz, DMSO-d$_6$) δ ppm −113.44 (br s, 1F), −115.49 (br s, 1F).

Example 197: (R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile

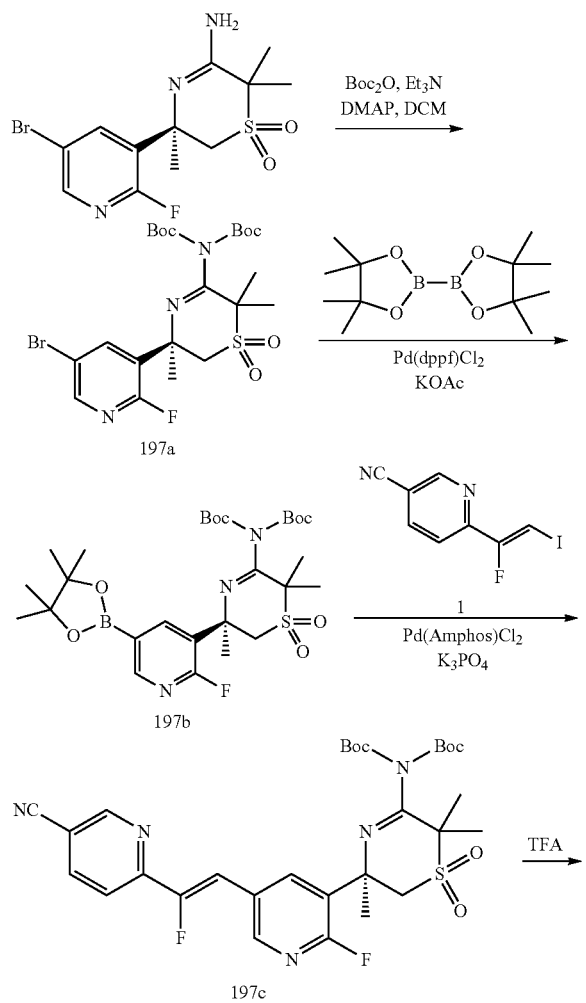

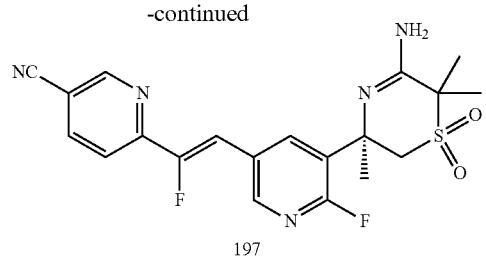

Compound 197a (5.53 g, 98% yield) as an off-white solid was prepared in a fashion similar to that described for compound 192a, here starting with (R)-5-amino-3-(5-bromo-2-fluoropyridin-3-yl)-3,6,6-trimethyl-3,6-dihydro-2H-1,4-thiazine 1,1-dioxide (prepared according to the method described in WO 2014059185) (3.63 g, 9.97 mmol), DMAP (0.61 g, 4.98 mmol), N-ethyl-N-isopropylpropan-2-amine (5.20 ml, 29.9 mmol), and di-tert-butyl dicarbonate (5.44 g, 24.9 mmol). LCMS: MS (ESI, positive ion) m/z: =586.1 (M+Na)$^+$.

Compounds 197b, 197c, and 197 were prepared in a fashion similar to that described for 192b, 192c, and 192, respectively. 197b: MS (ESI, positive ion) m/z: =612.3 (M+Na)$^+$. 197c: MS (ESI, positive ion) m/z: =632.2 (M+Na)$^+$. (R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile (197): MS (ESI, positive ion) m/z: =432.0 (M+1)$^+$. $^1$H NMR (400 MHz, CHLOROFORM-d) δ ppm 8.86 (1H, s), 8.47 (1H, s), 8.24 (1H, d, J=9.19 Hz), 8.06 (1H, d, J=8.02 Hz), 7.74 (1H, d, J=8.02 Hz), 7.25 (1H, d, J=40 Hz), 3.59 (2H, q, J=15.19 Hz), 1.79 (3H, s), 1.74 (3H, s), 1.63 (3H, s). $^{19}$F NMR (376 MHz, CHLOROFORM-d) δ ppm −64.35 (br. s., 1F), −121.90 (s, 1F).

Example 198: (R)-5-amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide; and Example 199: (R)-5-amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide

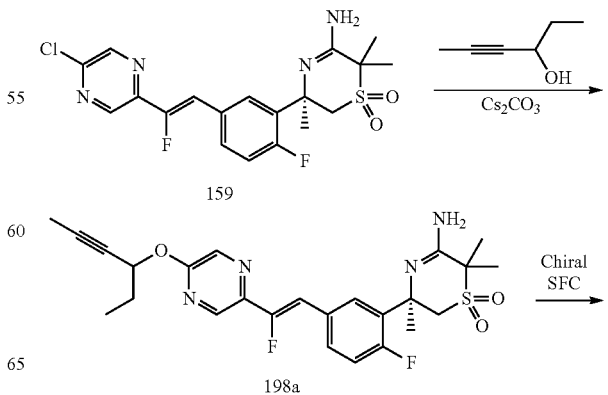

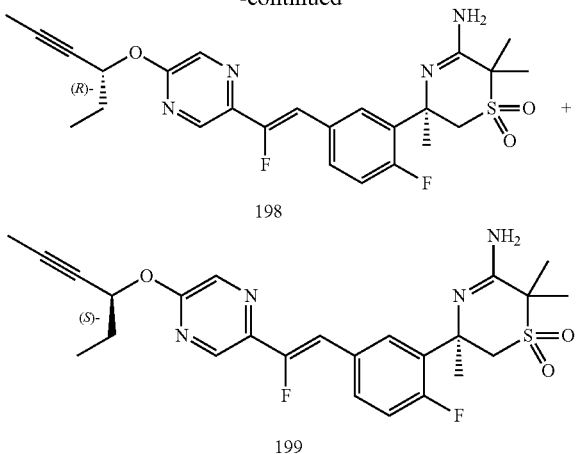

198

199

Compound 198a (122 mg, 71% yield) as a white solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 150 mg, 0.34 mmol) and 4-hexyn-3-ol (Sigma-Aldrich, 167 mg, 1.70 mmol) as starting materials. MS m/z=503.1 [M+H]$^+$. Compound 198a was subjected to chiral SFC to give (31 mg, 26% yield) of Example 198 as a white solid and (38 mg, 31% yield) of Example 199 as a white solid. Preparative SFC purification method:
column (Chiralpak IA-SFC (250×30 mm, 5 μm)); mobile phase (85:15 (A:B), A=liquid $CO_2$, B=20 mM ammonia in IPA); flow rate 120 mL/min; wave length 220 nm; BPI (Bar) 100; Sample conc. 10.2 mg/mL; Inj. Vol. 0.75 mL; run time 8 min. The relative stereochemistry was arbitrarily assigned.

(R)-5-Amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide (198): MS m/z=503.1 [M+H]$^+$. $^1$H NMR (400 MHz, CHLOROFORM-d) δ 8.39 (s, 1H), 8.20 (s, 1H), 7.62-7.77 (m, 2H), 7.08 (dd, J=8.41, 11.93 Hz, 1H), 6.81 (d, J=40 Hz, 1H), 5.56-5.62 (m, 1H), 3.52-3.68 (m, 2H), 1.90-1.99 (m, 2H), 1.86 (d, J=2.15 Hz, 3H), 1.83 (s, 3H), 1.72 (s, 3H), 1.63 (s, 3H), 1.10 (t, J=7.43 Hz, 3H).

(R)-5-Amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide (199): MS m/z=503.1 [M+H]$^+$. $^1$H NMR (400 MHz, CHLOROFORM-d) δ 8.39 (s, 1H), 8.20 (s, 1H), 7.62-7.77 (m, 2H), 7.08 (dd, J=8.41, 11.93 Hz, 1H), 6.81 (d, J=40 Hz, 1H), 5.56-5.62 (m, 1H), 3.52-3.68 (m, 2H), 1.90-1.99 (m, 2H), 1.86 (d, J=1.96 Hz, 3H), 1.83 (s, 3H), 1.72 (s, 3H), 1.63 (s, 3H), 1.10 (t, J=7.43 Hz, 3H).

Example 200: (2R,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide; and Example 201: (2S,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide; and Example 202: (R,Z)-5-amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide

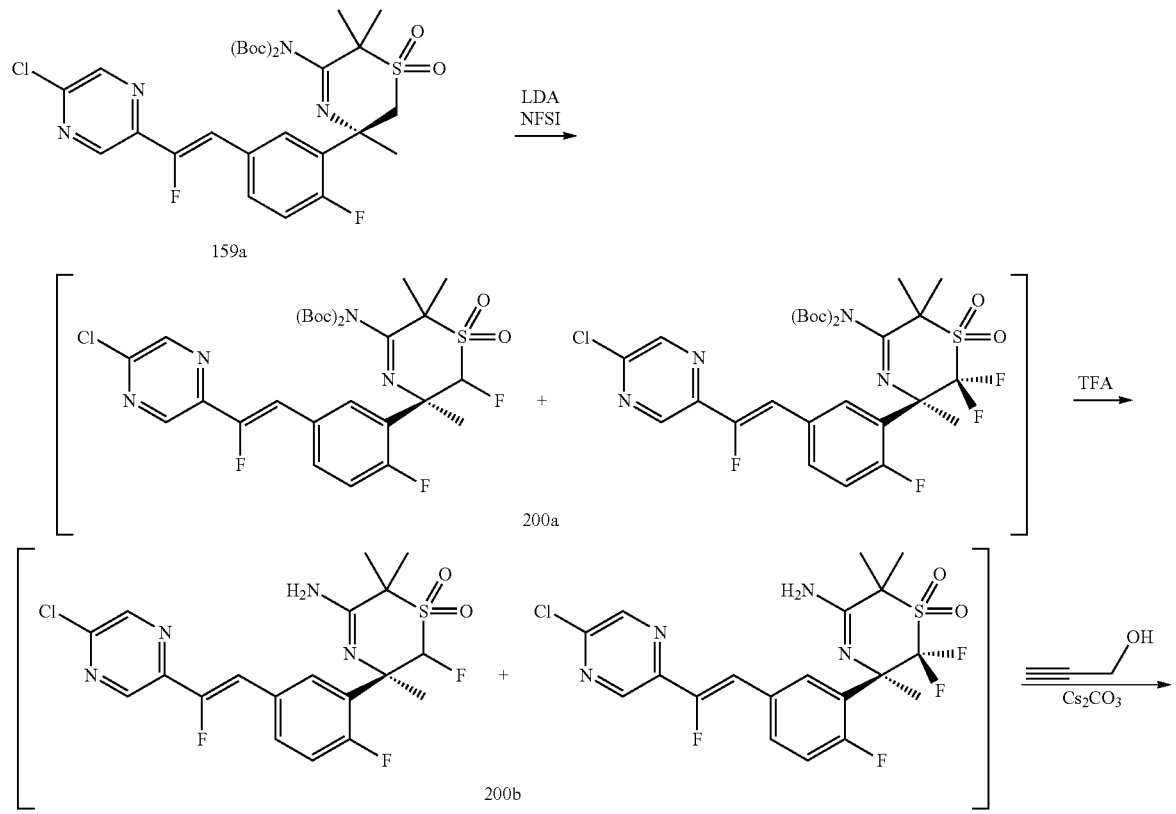

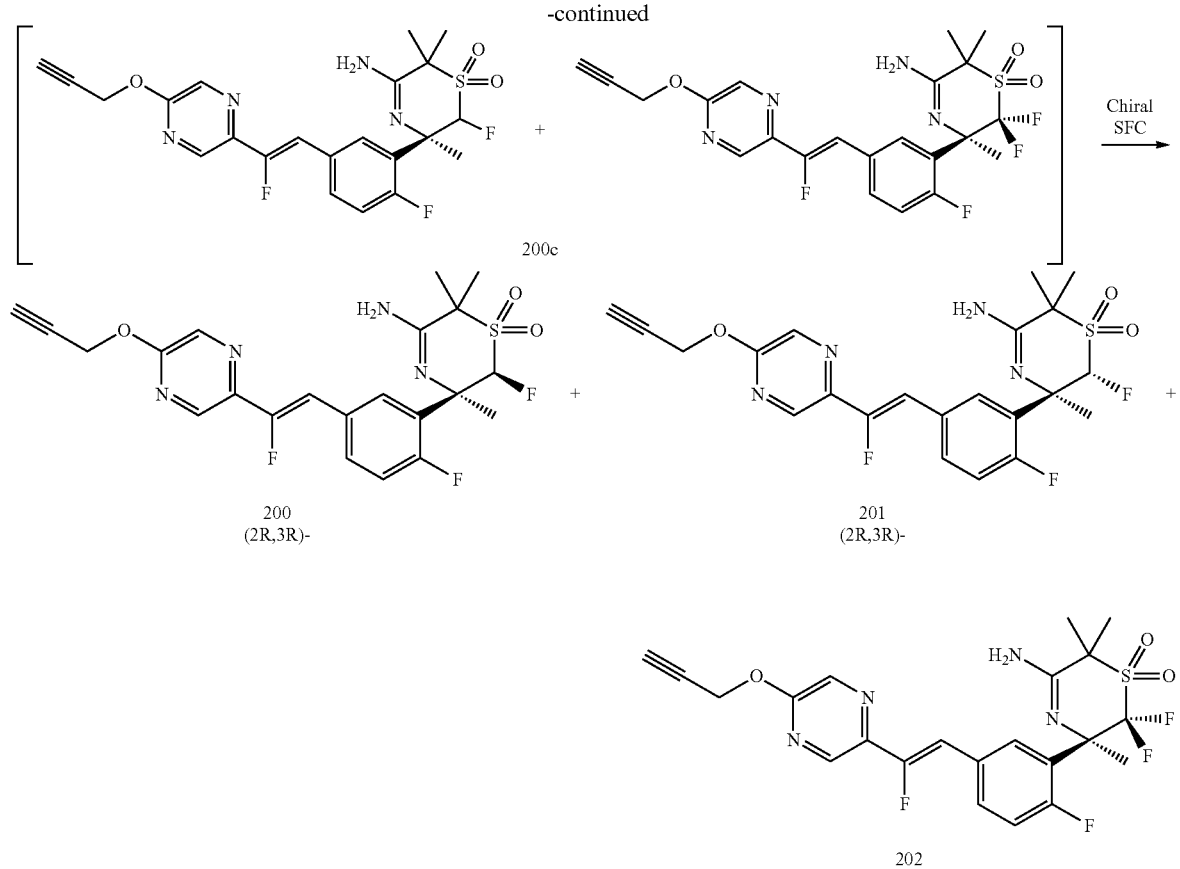

To a solution of (R,Z)-5-(di-Boc-amino)-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159a, 0.50 g, 0.78 mmol) in THF (3.90 mL, 0.78 mmol) was dropwise added lithium bis(trimethylsilyl)amide (1.0 M in THF, 1.56 mL, 1.56 mmol) at −78° C. The mixture was stirred at the same temperature for 1 h, and a solution of N-fluorobenzenesulfonimide (0.37 g, 1.17 mmol) in 2.0 mL of THF was dropwise added. The resulting mixture was allowed to stir at the same temperature and monitored by LCMS. Upon completion, the mixture was quenched with sat'd aqueous $NH_4Cl$ solution, extracted with ethyl acetate (40 mL×3). The combined extracts were washed with brine, dried ($Na_2SO_4$) and concentrated. The residue was purified on a silica gel column using 0-60% ethyl acetate in heptane as the eluent to give 200a (250 mg) as a solid. The solid of 200a was dissolved in DCM (5 mL) and TFA (1 mL) and stirred at RT for 2 h. It was concentrated and the residue was purified by Isco CombiFlash on a 12 g silica gel column using 0-10% (2 M $NH_3$/methanol) in DCM as the eluent to give 200b (205 mg) as a tan solid.

A mixture of 200b (205 mg) and cesium carbonate (437 mg, 1.34 mmol) in THF (5 mL) was added propargyl alcohol (0.13 mL, 2.23 mmol) at RT. The resulting mixture was stirred at RT for 24 h. The mixture was filtered and washed with ethyl acetate. The filtrate was concentrated and the residue was purified on a silica gel column using 0-100% (3:1 EtOAc/ethanol) in heptane as the eluent to give 200c (170 mg) as a tan solid. Chiral SFC of 200c gave Example 200 (11 mg), Example 201 (51 mg), and Example 202 (41 mg). Preparative SFC purification conditions: 2-Ethylpyridine column (5 μm, 21×250 mm); organic modifier: 10% Methanol with no $NH_3$, 90% $CO_2$; flow rate=70 mL/min; temp=40° C.; BPR=100 bar; wave length, 220 nm; pressure=144 bar, all sample was dissolved in 6 mL of MeOH, 1.0 mL/injection; run time 10 min. The relative stereochemistry was arbitrarily assigned for 200 and 201.

(2R,3R)-5-Amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide (200): MS m/z=479.1 $[M+H]^+$. $^1$H NMR (400 MHz, CHLOROFORM-d) δ 8.38 (s, 1H), 8.26 (s, 1H), 7.56-7.69 (m, 2H), 7.05-7.11 (m, 1H), 6.82 (d, J=40 Hz, 1H), 5.77 (dd, J=44, 2.15 Hz, 1H), 5.04 (d, J=2.54 Hz, 2H), 2.54 (t, J=2.45 Hz, 1H), 1.78-1.85 (m, 6H), 1.61 (s, 3H).

(2S,3R)-5-Amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide (201): MS m/z=479.1 $[M+H]^+$. $^1$H NMR (400 MHz, CHLOROFORM-d) δ 8.38 (s, 1H), 8.25 (s, 1H), 7.88-7.95 (m, 1H), 7.67-7.74 (m, 1H), 7.07-7.12 (m, 1H), 6.86 (d, J=40 Hz, 1H), 5.67 (d, J=48 Hz, 1H), 5.04 (d, J=2.35 Hz, 2H), 2.54 (t, J=2.45 Hz, 1H), 1.85 (s, 3H), 1.70 (s, 6H).

(R,Z)-5-Amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide (202): MS m/z=497.1 $[M+H]^+$. $^1$H NMR (400 MHz, CHLOROFORM-d) δ 8.41 (s, 1H), 8.27 (s, 1H), 7.63-7.76 (m, 2H), 7.09-7.14 (m, 1H), 6.86 (d, J=40 Hz, 1H), 5.05 (d, J=2.35 Hz, 2H), 2.54 (t, J=2.45 Hz, 1H), 2.0 (br s, 3H), 1.78 (d, J=2.54 Hz, 3H), 1.71 (s, 3H).

Example 203: (R,Z)-5-amino-3-(5-(2-(5-chloropyrazin-2-yl)-2-fluorovinyl)-2-fluoropyridin-3-yl)-3,6,6-trimethyl-3,6-dihydro-2H-1,4-thiazine 1,1-dioxide

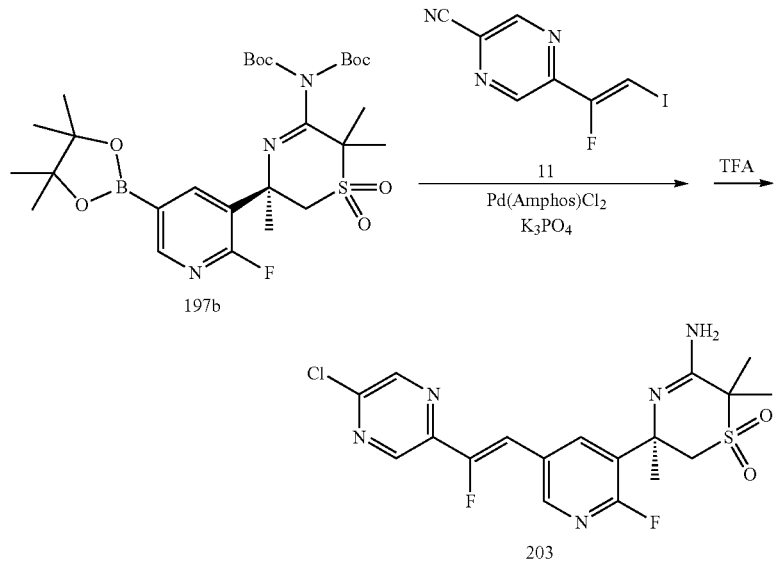

This compound (489 mg, 84% yield for 2 steps) as a tan solid was prepared in a fashion similar to that described in Method A for Example 108, here using boronic ester 197b (803 mg, 1.31 mmol), compound 11 (448 mg, 1.57 mmol), potassium phosphate tribasic (697 mg, 3.28 mmol), and 1,1-bis[(di-t-butyl-p-methylaminophenyl]palladium(II) chloride (93 mg, 0.131 mmol) as starting materials, followed by deprotection using trifluoroacetic acid (2 mL) in DCM (5.5 mL). MS (ESI, positive ion) m/z: =442.0 (M+1). $^1$H NMR (CHLOROFORM-d) δ: 8.67 (s, 1H), 8.58 (s, 1H), 8.41 (s, 1H), 8.25 (dd, J=9.7, 1.9 Hz, 1H), 7.07 (d, J=40 Hz, 1H), 3.50-3.69 (m, 2H), 1.80 (s, 3H), 1.74 (s, 3H), 1.63 (s, 3H). $^{19}$F NMR (CHLOROFORM-d) δ: −64.57 (s, 1F), −123.25 (s, 1F).

Example 204: (R,Z)-5-amino-3-(2,3-difluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide

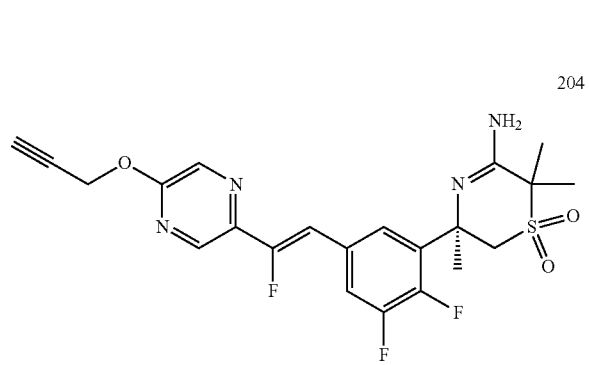 [SMILES: C#CCOc1cnc(/C(F)=C/c2cc(F)c(F)c([C@]3(C)CS(=O)(=O)C(C)(C)C(N)=N3)c2)cn1]

This compound (43 mg, 44% yield) as a tan solid was prepared in a fashion similar to that described in Method A for Example 108, here using (R,Z)-5-amino-3-(5-(2-(5-chloropyrazin-2-yl)-2-fluorovinyl)-2,3-difluorophenyl)-3,6,6-trimethyl-3,6-dihydro-2H-1,4-thiazine 1,1-dioxide (193) (93 mg, 0.20 mmol), 3-propynol (Aldrich-Sigma, 96 µL, 1.62 mmol), and cesium carbonate (231 mg, 0.71 mmol) as starting materials. MS (ESI, positive ion) m/z: =479.1 (M+1)$^+$. $^1$H NMR (DMSO-d$_6$) δ 8.42-8.55 (m, 2H), 7.60 (br d, J=6.5 Hz, 2H), 6.89 (d, 1H, J=40 Hz), 6.16 (br s, 2H), 5.09 (d, J=2.2 Hz, 2H), 3.58-3.72 (m, 2H), 2.55 (s, 1H), 1.63 (s, 3H), 1.58 (s, 3H), 1.46 (s, 3H). $^{19}$F NMR (376 MHz, DMSO-d$_6$) δ ppm −123.47 (1F, br. s.), −138.15 (1F, d, J=22.54 Hz), −139.05 (1F, d, J=21.67 Hz).

Example 205: (R,Z)-5-amino-3-(2-fluoro-5-(2-fluoro-2-(5-(prop-2-yn-1-yloxy)pyrazin-2-yl)vinyl)pyridin-3-yl)-3,6,6-trimethyl-3,6-dihydro-2H-1,4-thiazine 1,1-dioxide

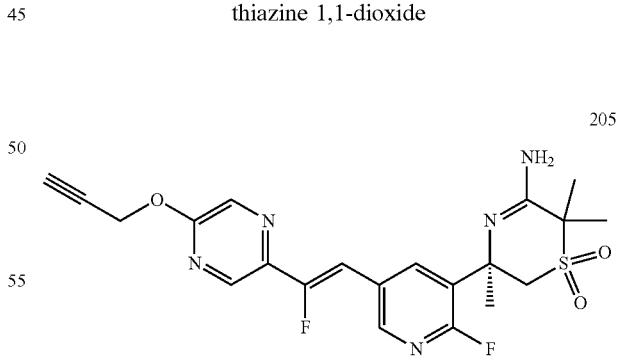

This compound (43 mg, 44% yield) as a tan solid was prepared in a fashion similar to that described in Method A for Example 108, here using (R,Z)-5-amino-3-(5-(2-(5-chloropyrazin-2-yl)-2-fluorovinyl)-2-fluoropyridin-3-yl)-3,6,6-trimethyl-3,6-dihydro-2H-1,4-thiazine 1,1-dioxide (203) (101 mg, 0.23 mmol), 3-propynol (108 µL, 1.83 mmol), and cesium carbonate (261 mg, 0.80 mmol) as starting materials. MS (ESI, positive ion) m/z: =462.2 (M+1). $^1$H NMR (400

MHz, CDCl₃) δ ppm 8.42 (2H, d, J=9.59 Hz), 8.29 (1H, s), 8.20 (1H, d, J=9.39 Hz), 6.79-6.95 (1H, d, J=40 Hz), 5.06 (2H, d, J=2.15 Hz), 3.58 (2H, d, J=4.50 Hz), 2.55 (1H, s), 1.80 (3H, s), 1.73 (3H, s), 1.63 (3H, s). ¹⁹F NMR (376 MHz, CDCl₃) δ ppm −65.81 (1F, s), −122.23 (1F, s).

Example 206: (R,Z)-5-amino-3-(5-(2-(5-(cyclopropylmethoxy)pyrazin-2-yl)-2-fluorovinyl)-2-fluorophenyl)-3,6,6-trimethyl-3,6-dihydro-2H-1,4-thiazine 1,1-dioxide

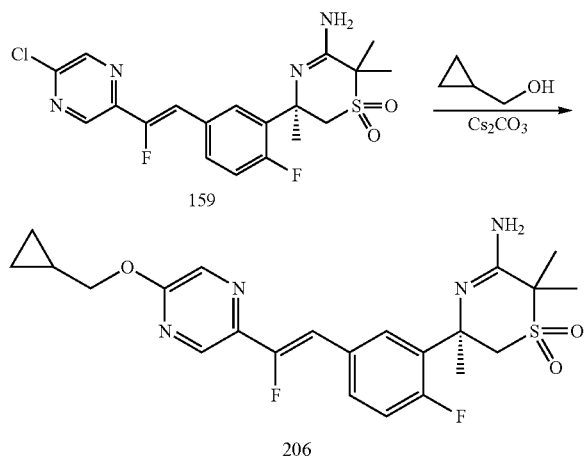

This compound (31 mg, 58% yield) as a light yellow solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159) (150 mg, 0.34 mmol) and cyclopropylmethanol (41 mg, 0.57 mmol) as starting materials. MS m/z=477.2 [M+H]⁺. ¹H NMR (400 MHz, CDCl₃) δ 8.33 (s, 1H), 8.22 (s, 1H), 7.71-7.78 (m, 1H), 7.64-7.70 (m, 1H), 7.0-7.10 (m, 1H), 6.80 (d, J=40 Hz, 1H), 4.22 (d, J=7.24 Hz, 2H), 3.59 (q, J=15.13 Hz, 2H), 1.82 (s, 3H), 1.70 (s, 3H), 1.62 (s, 3H), 1.28-1.38 (m, 1H), 0.62-0.70 (m, 2H), 0.37-0.41 (m, 2H).

Example 207: (R)-5-amino-3-(2-fluoro-5-((Z)-2-fluoro-2-(5-((R)-pent-3-yn-2-yloxy)pyrazin-2-yl)vinyl)phenyl)-3,6,6-trimethyl-3,6-dihydro-2H-1,4-thiazine 1,1-dioxide; and Example 208: (R)-5-amino-3-(2-fluoro-5-((Z)-2-fluoro-2-(5-((S)-pent-3-yn-2-yloxy)pyrazin-2-yl)vinyl)phenyl)-3,6,6-trimethyl-3,6-dihydro-2H-1,4-thiazine 1,1-dioxide

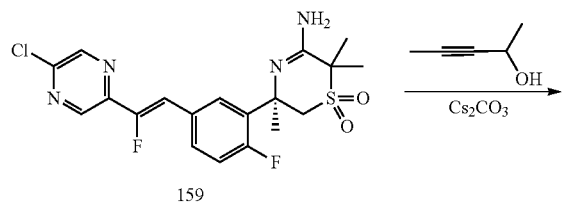

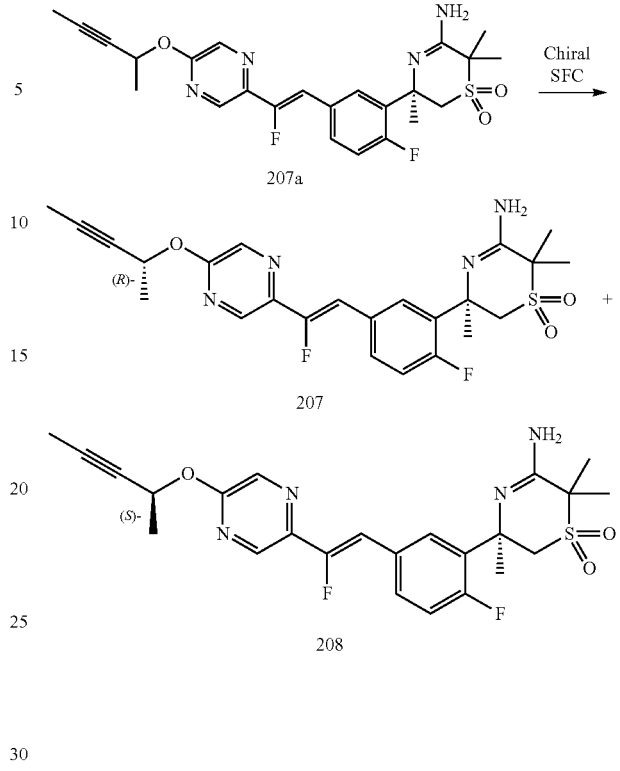

Compound 207a (106 mg, 67% yield) as a white solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 142 mg, 0.34 mmol) and 3-pentyn-2-ol (135 mg, 1.61 mmol) as starting materials. MS m/z=503.1 [M+H]⁺. Chiral SFC of 207a gave Example 207 (31 mg, 26% yield) and Example 208 (38 mg, 31% yield). Preparative Thar 200 SFC method: column: Chiralpak IA (250×30 mm, 5 μm); mobile phase: 75:25 (A:B), A: liquid CO₂, B: methanol (20 mM NH₃); flow rate: 130 g/min; column/oven temp.: ambient; wave length 285 nm; 18.17 mg/injection; 184 bar inlet pressure; BPR=102 bar. The relative stereochemistry was arbitrarily assigned.

(R)-5-Amino-3-(2-fluoro-5-((Z)-2-fluoro-2-(5-((R)-pent-3-yn-2-yloxy)pyrazin-2-yl)vinyl)phenyl)-3,6,6-trimethyl-3,6-dihydro-2H-1,4-thiazine 1,1-dioxide (207): MS m/z=489.1 [M+H]⁺. ¹H NMR (400 MHz, CHLOROFORM-d) δ 8.38 (s, 1H), 8.18 (s, 1H), 7.75 (dd, J=1.96, 8.02 Hz, 1H), 7.62-7.68 (m, 1H), 7.07 (dd, J=8.61, 11.93 Hz, 1H), 6.80 (d, J=40 Hz, 1H), 5.73 (qd, J=2.05, 6.58 Hz, 1H), 3.51-3.68 (m, 2H), 1.85 (d, I=1.96 Hz, 3H), 1.82 (s, 3H), 1.70 (s, 3H), 1.64 (d, J=6.65 Hz, 3H), 1.61 (s, 3H).

(R)-5-Amino-3-(2-fluoro-5-((Z)-2-fluoro-2-(5-((S)-pent-3-yn-2-yloxy)pyrazin-2-yl)vinyl)phenyl)-3,6,6-trimethyl-3,6-dihydro-2H-1,4-thiazine 1,1-dioxide (208): MS m/z=489.2 [M+H]⁺. ¹H NMR (400 MHz, CHLOROFORM-d) δ 8.40 (s, 1H), 8.20 (s, 1H), 7.74 (dd, J=1.86, 7.92 Hz, 1H), 7.63-7.70 (m, 1H), 7.08 (dd, J=8.61, 11.93 Hz, 1H), 6.82 (d, J=40 Hz, 1H), 5.70-5.78 (m, 1H), 3.59 (q, J=15.06 Hz, 2H), 1.85 (d, J=1.96 Hz, 3H), 1.82 (s, 3H), 1.71 (s, 3H), 1.64 (d, J=6.46 Hz, 3H), 1.62 (s, 3H).

Example 209: (R,Z)-5-amino-3-(5-(2-(5-(benzyloxy)pyrazin-2-yl)-2-fluorovinyl)-2-fluoropyridin-3-yl)-3,6,6-trimethyl-3,6-dihydro-2H-1,4-thiazine 1,1-dioxide

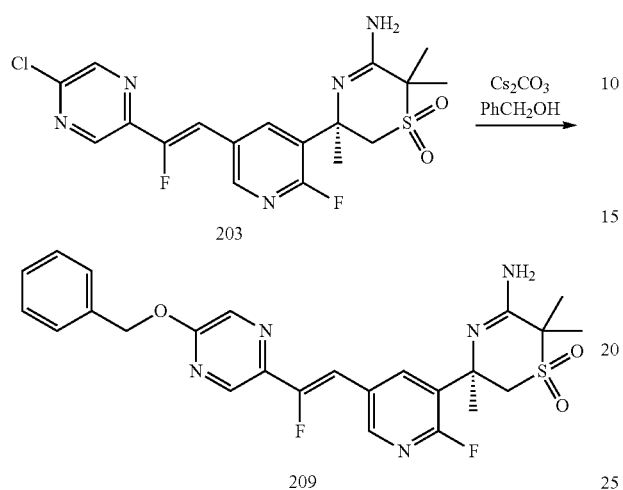

This compound (92 mg, 78% yield) as an off-white solid was prepared in a fashion similar to that described in Method A for Example 108, here using (R,Z)-5-amino-3-(5-(2-(5-chloropyrazin-2-yl)-2-fluorovinyl)-2-fluoropyridin-3-yl)-3,6,6-trimethyl-3,6-dihydro-2H-1,4-thiazine 1,1-dioxide (203) (101 mg, 0.23 mmol), benzyl alcohol (Aldrich, 118 L, 1.14 mmol), and cesium carbonate (261 mg, 0.80 mmol) as starting materials. MS (ESI, positive ion) m/z: =514.2 (M+1). $^1$H NMR (400 MHz, CHLOROFORM-d) δ ppm 8.41 (2H, d, J=7.83 Hz), 8.27 (1H, s), 8.19 (1H, dd, J=9.68, 2.25 Hz), 7.45-7.52 (2H, m), 7.33-7.45 (3H, m), 6.76-6.92 (1H, d, J=40 Hz), 5.46 (2H, s), 3.58 (2H, d, J=2.93 Hz), 1.80 (3H, s), 1.73 (3H, s), 1.63 (3H, s). $^{19}$F NMR (376 MHz, CHLOROFORM-d) δ ppm −65.98 (1F, s), −122.08 (1F, s).

Example 210: (R,Z)-5-amino-3-(2-fluoro-5-(2-fluoro-2-(5-(pyridin-4-ylmethoxy)pyrazin-2-yl)vinyl)phenyl)-3,6,6-trimethyl-3,6-dihydro-2H-1,4-thiazine 1,1-dioxide

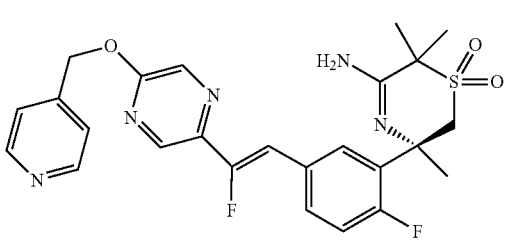

This compound (41 mg, 70% yield) as a white solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 142 mg, 0.34 mmol) and 4-pyridinemethanol (37 mg, 0.34 mmol) as starting materials. MS m/z=514.1 [M+H]$^+$. $^1$H NMR (400 MHz, CHLOROFORM-d) δ 8.64 (d, J=5.0 Hz, 2H), 8.36 (s, 1H), 8.32 (s, 1H), 7.74 (dd, J=7.92, 2.05 Hz, 1H), 7.64-7.69 (m, 1H), 7.37 (d, J=5.09 Hz, 2H), 7.04-7.12 (m, 1H), 6.85 (d, J=40 Hz, 1H), 5.47 (s, 2H), 3.55-3.66 (m, 2H), 1.83 (s, 3H), 1.72 (s, 3H), 1.63 (s, 3H).

Example 211: (R,Z)-5-amino-3-(2-fluoro-5-(2-fluoro-2-(5-phenoxypyrazin-2-yl)vinyl)phenyl)-3,6,6-trimethyl-3,6-dihydro-2H-1,4-thiazine 1,1-dioxide

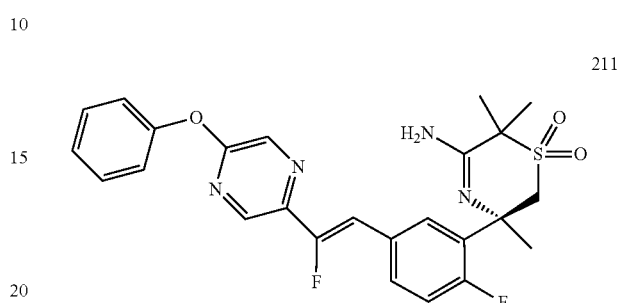

This compound (51 mg, 90% yield) as a white solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 142 mg, 0.34 mmol) and phenol (32 mg, 0.34 mmol) as starting materials. MS m/z=499.1 [M+H]$^+$. $^1$H NMR (400 MHz, CHLOROFORM-d) δ 8.39 (s, 1H), 8.36 (s, 1H), 7.74-7.79 (m, 1H), 7.63-7.70 (m, 1H), 7.45 (t, J=8.0 Hz, 2H), 7.28 (t, J=8.0 Hz, 1H), 7.19 (d, J=8.0 Hz, 2H), 7.07 (dd, J=8.41, 12.0 Hz, 1H), 6.87 (d, J=40 Hz, 1H), 3.54-3.64 (m, 2H), 1.83 (s, 3H), 1.70 (3, 3H), 1.62 (s, 3H).

Example 212: (R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile

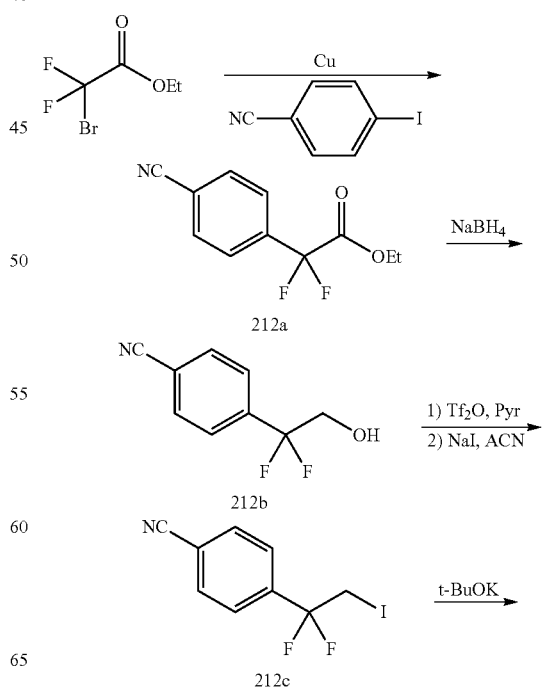

-continued

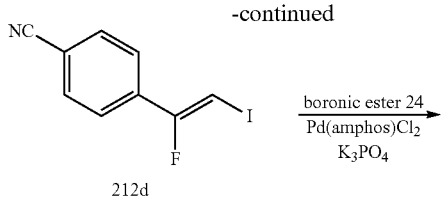

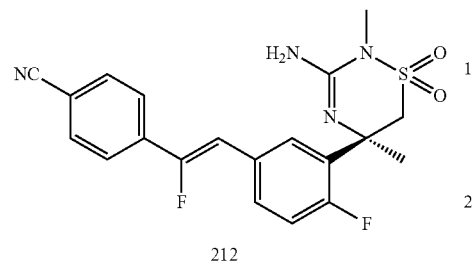

212

Preparation ethyl 2-(4-cyanophenyl)-2,2-difluoroacetate Difluoroacetate (212a)

A suspension of copper dust (Sigma-Aldrich Chemical Company, Inc., St. Louis, Mo., USA) (2.22 g, 34.90 mmol) and ethyl bromodifluoroacetate (Oakwood Products, Inc., Estill, S.C., USA) (2.36 mL, 17.47 mmol) in DMSO (10 mL) was sonicated for 20 min then stirred at 20° C. for 90 min. To the suspension was added 4-iodobenzonitrile (Combi-Blocks, San Diego, Calif., USA) (2.00 g, 8.73 mmol) in one portion. The suspension was then heated to 40° C. for 90 min. The reaction mixture was then filtered, and the solid washed with EtOAc (50 mL). The filtrate was partitioned between sat'd aqueous $NH_4Cl$ (50 mL) and water (50 mL). The organic layer was washed with sat'd NaCl (10 mL), dried over $MgSO_4$, concentrated under reduced pressure, then purified by silica gel chromatography (80 g) eluting products with a gradient of 0-15% (3:1 EtOAc/EtOH blend)/heptane to afford 212a (1.06 g, 4.71 mmol, 54% yield) as a colorless oil. MS m/z=226.1 [M+H]$^+$. $^1$H NMR (400 MHz, CDCl$_3$) δ ppm 7.73-7.80 (m, 4H), 4.32 (q, J=7.04 Hz, 2H), 1.32 (t, J=7.14 Hz, 3H). $^{19}$F NMR (376 MHz, CDCl$_3$) δ ppm −104.89 (s).

Preparation of 4-(1,1-difluoro-2-hydroxyethyl)benzonitrile (212b)

To a stirring solution of ethyl 2-(4-cyanophenyl)-2,2-difluoroacetate (212a, 1.00 g, 4.44 mmol) in EtOH (10 mL) at 0° C. was added sodium borohydride (0.16 g, 4.44 mmol). After 10 min the cooling bath was removed and the reaction mixture was stirred for 30 min. It was chilled to 0° C. and hydrochloric acid (0.89 mL of 5 M solution, 4.44 mmol) was added. The reaction mixture was then partitioned between EtOAc (20 mL) and sat'd aqueous NaHCO$_3$ (20 mL). The aqueous was further extracted with EtOAc (5 mL). The combined organic extracts were dried over MgSO$_4$, filtered, concentrated under reduced pressure, then purified by silica gel chromatography (40 g) eluting products with a gradient of 0-15% (3:1 EtOAc/EtOH)/heptane to afford 4-(1,1-difluoro-2-hydroxyethyl)benzonitrile (212b, 650 mg, 3.55 mmol, 80% yield) as a white solid. MS m/z=184.1 [M+H]$^+$. $^1$H NMR (400 MHz, CHLOROFORM-d) δ ppm 7.72-7.82 (m, 2H), 7.65-7.71 (m, 2H), 4.01 (t, J=12.81 Hz, 2H), 1.97 (br s, 1H).

Preparation of 4-(1,1-difluoro-2-iodoethyl)benzonitrile (212c)

To a solution of 4-(1,1-difluoro-2-hydroxyethyl)benzonitrile (212b, 650 mg, 3.55 mmol) and pyridine (579 μL, 7.10 mmol) in MeCN (14 mL) at −10° C. was added trifluoromethanesulfonic anhydride (630 μL, 3.73 mmol). After 5 min the cooling bath was removed and the reaction was stirred at 20° C. for 1 h. To the reaction mixture at 20° C. was added sodium iodide (1.60 g, 10.65 mmol), and the resulting cloudy mixture was then heated to 60° C. for 2 h. It was then partitioned between EtOAc (30 mL) and 5% NaHCO$_3$ (10 mL). The organic layer was further washed with brine (2 mL) then dried over MgSO$_4$. It was filtered, concentrated under reduced pressure onto dry silica (5 g), then purified by silica gel chromatography (24 g) eluting products with a gradient of 0-10% EtOAc/heptane to afford 212c (887 mg, 3.03 mmol, 85% yield) as a colorless oil. MS m/z=294.0 [M+H]$^+$.

Preparation of (Z)-4-(1-fluoro-2-iodovinyl)benzonitrile (212d)

To a stirring solution of 4-(1,1-difluoro-2-iodoethyl)benzonitrile (212c, 850 mg, 2.90 mmol) in THF (10 mL) at 20° C. was added potassium t-butoxide (391 mg, 3.48 mmol). After 20 min, the reaction was quenched with sat'd aqueous NH$_4$Cl (1 mL). The reaction mixture was then partitioned between EtOAc (60 mL) and sat'd aqueous NaHCO$_3$ (30 mL). The organic layer was washed with sat'd NaCl (2 mL), dried over MgSO$_4$, filtered, then concentrated under reduced pressure to afford 212d (712 mg, 2.61 mmol, 90% yield) as a colorless oil.

Preparation of (R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile (212)

This compound (50 mg, 25% yield) as an off-white solid was prepared in a fashion similar to that described in Method C for Example 111, using (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate (205 mg, 0.327 mmol) and (Z)-6-(1-fluoro-2-iodovinyl)-2,3-dihydrobenzo[b][1,4]dioxine (24) (320 mg, 0.33 mmol) and (Z)-4-(1-fluoro-2-iodovinyl)benzonitrile (212d) (278 mg, 1.02 mmol) as starting materials. MS m/z=417.2 [M+H]$^+$. $^1$H NMR (400 MHz, DMSO-d$_6$) δ ppm 7.88-7.97 (m, 5H), 7.55-7.63 (m, 1H), 7.22 (dd, J=12.13, 8.41 Hz, 1H), 7.00 (d, J=41.67 Hz, 1H), 6.02 (br s, 2H), 3.80 (br s, 2H), 3.05 (s, 3H), 1.62 (s, 3H). $^{19}$F NMR (376 MHz, DMSO-d$_6$) δ ppm −111.66 (br s, 1F) −118.16 (br s, 1F).

Example 213: (2S,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide; and Example 214: (2R,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide; and Example 215: (R,Z)-5-amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide

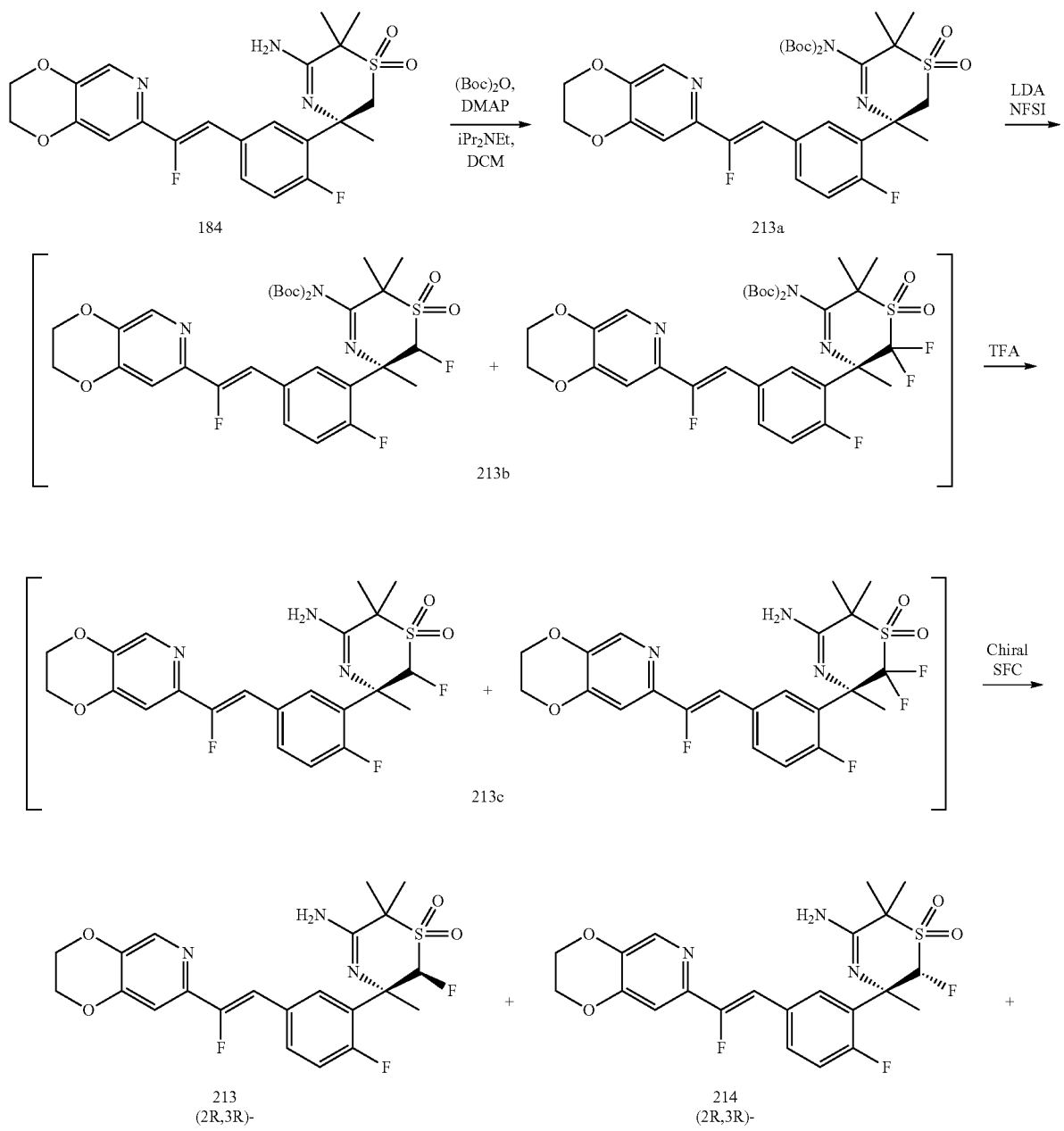

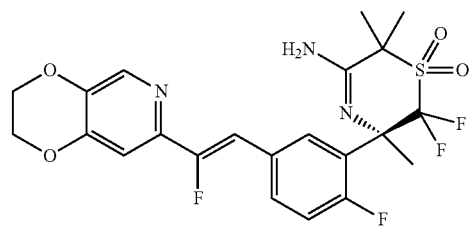

215

To a mixture of (R,Z)-5-amino-3-(5-(2-(2,3-dihydro-[1,4]dioxino[2,3-c]pyridin-7-yl)-2-fluorovinyl)-2-fluorophenyl)-3,6,6-trimethyl-3,6-dihydro-2H-1,4-thiazine 1,1-dioxide (184) (80 mg, 0.17 mmol), di-tert-butyl dicarbonate (94 mg, 0.43 mmol) and N-ethyl-N-isopropylpropan-2-amine (0.09 mL, 0.52 mmol) in DCM (1.0 mL) was added N,N-dimethylpyridin-4-amine (10 mg, 0.08 mmol) at RT. The mixture was stirred at RT and monitored by LCMS. Upon completion, the mixture was directly loaded onto a silica gel column eluting with 0-50% ethyl acetate in heptane to give 77 mg of 213a. MS m/z=664.2.2 [M+H]+. 1H NMR (400 MHz, CHLOROFORM-d) δ 8.11 (s, 1H), 7.67-7.74 (m, 2H), 7.07-7.14 (m, 2H), 6.92 (d, J=40 Hz, 1H), 4.30-4.40 (m, 4H), 3.73-3.81 (m, 1), 3.56 (d, J=15.26 Hz, 1H), 1.92 (s, 1H), 1.67 (m, 3H), 1.62 (s, 3H), 1.57 (s, 18H). NH2 peak was not observed.

To a solution of 213a (0.077 g, 0.116 mmol) in THF (1 mL) at −78° C. was added lithium bis(trimethylsilyl)amide solution (1.0 M in THF, 0.17 mL, 0.17 mmol). The resulting mixture was stirred at the same temperature for 1 h, and a solution of N-fluorobenzenesulfonimide (0.044 g, 0.139 mmol) in 1 mL of THF was added. The resulting mixture was stirred under dry-ice/acetone bath and monitored by LCMS. Upon completion, the mixture was quenched with sat'd aqueous NH4Cl solution; the mixture was extracted with ethyl acetate (20 mL×4). The combined extracts were dried (Na2SO4) and concentrated. The residue was purified on a silica gel column using 0-100% ethyl acetate in heptane as the eluent to give 70 mg of 213b.

A solution of 213b in 5 mL of DCM and 1 mL of TFA was stirred at RT for 2 h, and concentrated. The residue was purified on a silica gel column using 0-6% (2 M NH3/methanol) in DCM as the eluent to give 213c (39 mg). Chiral SFC of 213c gave 2.8 mg of Example 213, 1.0 mg of Example 214, and 1.0 mg of Example of 215. SFC conditions: column: IA-H (250×21 mm, 5 μm); mobile phase: 83:17 (A:B), A: liquid CO2, B: methanol (20 mM NH3); flow rate: 165 g/min; column/oven temp.: ambient temperature; wave length 280 nm; BPR=100 bar; run time 16 min. The relative stereochemistry of 213 and 214 was arbitrarily assigned.

(2S,3R)-5-Amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide (213): MS m/z=482.2 [M+H]+. 1H NMR (400 MHz, CDCl3) δ 8.13 (s, 1H), 7.68 (dt, J=2.05, 5.33 Hz, 1H), 7.55 (br d, J=7.82 Hz, 1H), 7.12 (d, J=1.37 Hz, 1H), 7.08 (dd, J=12.13, 8.61 Hz, 1H), 6.83 (d, J=40 Hz, 1H), 5.82 (dd, J=2.15, 44 Hz, 1H), 4.31-4.37 (m, 2H), 2.05 (s, 3H), 1.89 (br s, 3H), 1.69 (s, 3H). NH2 peak was not observed.

(2R,3R)-5-Amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide (214): MS m/z=482.2 [M+H]+. 1H NMR (400 MHz, CHLOROFORM-d) δ 8.15 (s, 1H), 7.83 (br d, J=7.43 Hz, 1H), 7.74-7.80 (m, 1H), 7.16 (d, J=1.96 Hz, 1H), 7.12 (dd, J=11.74, 8.61 Hz, 1H), 6.90 (d, J=40 Hz, 1H), 5.65 (d, J=48 Hz, 1H), 4.31-4.39 (m, 2H), 1.80 (br d, J=9.19 Hz, 3H), 1.58 (br s, 6H). NH2 peak was not observed.

(R,Z)-5-Amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide (215): MS m/z=482.2 [M+H]+. 1H NMR (400 MHz, CDCl3) δ 8.16 (s, 1H), 7.76 (ddd, J=1.96, 4.50, 8.61 Hz, 1H), 7.64 (br d, J=7.43 Hz, 1H), 7.13-7.18 (m, 2H), 6.88 (d, J=40 Hz, 1H), 4.31-4.39 (m, 2H), 2.20 (br s, 1H), 1.97 (br s, 3H), 1.94 (br d, 2.15 Hz, 3H). NH2 peak was not observed.

Example 216: (R)-5-amino-3-(2-fluoro-5-((Z)-2-fluoro-2-(5-((R)-hex-3-yn-2-yloxy)pyrazin-2-yl)vinyl)phenyl)-3,6,6-trimethyl-3,6-dihydro-2H-1,4-thiazine 1,1-dioxide; and Example 217: (R)-5-amino-3-(2-fluoro-5-((Z)-2-fluoro-2-(5-((S)-hex-3-yn-2-yloxy)pyrazin-2-yl)vinyl)phenyl)-3,6,6-trimethyl-3,6-dihydro-2H-1,4-thiazine 1,1-dioxide

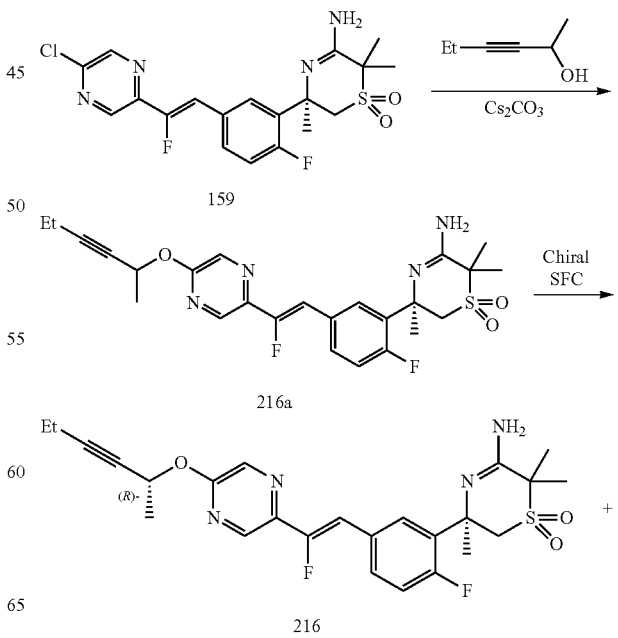

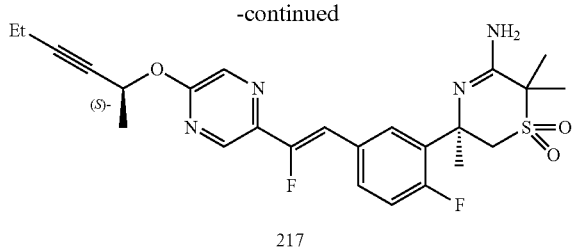

217

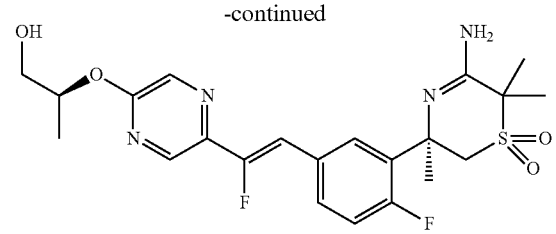

218

+

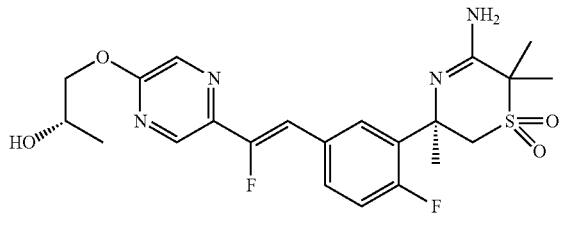

219

Compound 216a (74 mg, 65% yield) as a white solid was prepared in a fashion similar to that described in Method D for Example 112, here using (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 100 mg, 0.23 mmol) and 1-butynyl ethyl carbinol (111 mg, 1.34 mmol) as starting materials. MS m/z=503.1 [M+H]$^+$. 216a was separated by Chiral SFC to give Example 216 (21 mg, 28% yield) as a white solid and Example 217 (22 mg, 29% yield) as a white solid. SFC conditions: column IA-H (250×21 mm, 5 μm); mobile phase: 83:17 (A:B), A: liquid $CO_2$, B: methanol (20 mM $NH_3$); flow rate: 165 g/min; column/oven temp.: ambient temperature; wave length 280 nm; BPR=100 bar; run time 16 min. The relative stereochemistry of 216 and 217 was arbitrarily assigned.

(R)-5-Amino-3-(2-fluoro-5-((Z)-2-fluoro-2-(5-((R)-hex-3-yn-2-yloxy)pyrazin-2-yl)vinyl)phenyl)-3,6,6-trimethyl-3,6-dihydro-2H-1,4-thiazine 1,1-dioxide (216): MS m/z=503.1 [M+H]$^+$. $^1$H NMR (400 MHz, CDCl$_3$) δ 8.38 (s, 1H), 8.19 (s, 1H), 7.74 (dd, J=1.76, 8.02 Hz, 1H), 7.62-7.68 (m, 1H), 7.05-7.10 (m, 1H), 6.80 (d, J=40 Hz, 1H), 5.76 (td, J=1.79, 6.60 Hz, 1H), 3.50-3.69 (m, 2H), 2.22 (dq, J=1.76, 7.50 Hz, 2H), 1.82 (s, 3H), 1.70 (s, 3H), 1.64 (d, J=6.46 Hz, 3H), 1.62 (s, 3H), 1.13 (t, J=7.53 Hz, 6H). $NH_2$ peak was not observed.

(R)-5-Amino-3-(2-fluoro-5-((Z)-2-fluoro-2-(5-((S)-hex-3-yn-2-yloxy)pyrazin-2-yl)vinyl)phenyl)-3,6,6-trimethyl-3,6-dihydro-2H-1,4-thiazine 1,1-dioxide (217): MS m/z=503.1 [M+H]$^+$. $^1$H NMR (400 MHz, CDCl$_3$) δ 8.39 (s, 1H), 8.20 (s, 1H), 7.73 (br d, J=7.82 Hz, 1H), 7.62-7.68 (m, 1H), 7.05-7.10 (m, 1H), 6.82 (d, J=40 Hz, 1H), 5.73-5.80 (m, 1H), 3.53-3.66 (m, 2H), 2.22 (dq, J=1.76, 7.50 Hz, 2H), 1.83 (s, 3H), 1.71 (s, 3H), 1.64 (d, J=6.65 Hz, 3H), 1.63 (s, 3H), 1.13 (t, J=7.43 Hz, 6H). $NH_2$ peak was not observed.

Example 218: (R)-5-amino-3-(2-fluoro-5-((Z)-2-fluoro-2-(5-(((S)-1-hydroxypropan-2-yl)oxy)pyrazin-2-yl)vinyl)phenyl)-3,6,6-trimethyl-3,6-dihydro-2H-1,4-thiazine 1,1-dioxide; and Example 219: (R)-5-amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide

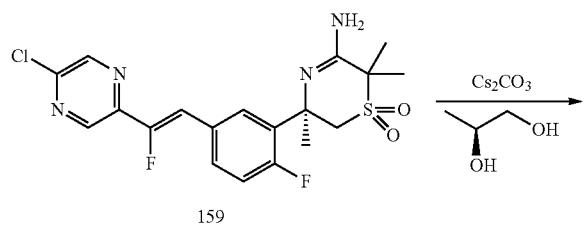

159

In a fashion similar to that described in Method D for Example 112, the reaction of (R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide (159, 120 mg, 0.27 mmol) with (S)-propane-1,2-diol (104 mg, 1.36 mmol) gave a mixture (74 mg, 65% yield) of 2 regio isomers with MS m/z=418.1 [M+H]$^+$. The mixture was subjected to SFC to provide Example 218 (18 mg, 18% yield) as a white solid and Example 219 (40 mg, 39% yield) as a white solid. Preparative Thar 200 SFC method: column: IA-H (250×21 mm, 5 μm); mobile phase: 60:40 (A:B) A: liquid $CO_2$, B: ethanol (20 mM $NH_3$); flow rate: 100 g/min; column/oven temp.: ambient temperature; wave length 280 nm; BPR=100 bar; run time 16 min.

(R)-5-Amino-3-(2-fluoro-5-((Z)-2-fluoro-2-(5-(((S)-1-hydroxypropan-2-yl)oxy)pyrazin-2-yl)vinyl)phenyl)-3,6,6-trimethyl-3,6-dihydro-2H-1,4-thiazine 1,1-dioxide (218): MS m/z=481.1 [M+H]$^+$. $^1$H NMR (400 MHz, CHLOROFORM-d) δ 8.31 (s, 1H), 8.18 (s, 1H), 7.74 (dd, J=2.25, 7.92 Hz, 1H), 7.62-7.68 (m, 1H), 7.05-7.10 (m, 1H), 6.79 (d, J=40 Hz, 1H), 5.25-5.34 (m, 1H), 3.76-3.86 (m, 2H), 3.53-3.66 (m, 2H), 1.82 (s, 3H), 1.70 (s, 3H), 1.62 (s, 3H), 1.38 (d, J=6.46 Hz, 3H).

(R)-5-Amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide (219): MS m/z=481.1 [M+H]$^+$. $^1$H NMR (400 MHz, CHLOROFORM-d) δ 8.30 (s, 1H), 8.21 (s, 1H), 7.75 (dd, J=2.15, 8.02 Hz, 1H), 7.63 (ddd, J=2.25, 4.74, 8.46 Hz, 1H), 7.03-7.10 (m, 1H), 6.79 (d, J=40 Hz, 1H), 4.34-4.42 (m, 1H), 4.19-4.27 (m, 2H), 3.54-3.65 (m, 2H), 1.82 (s, 3H), 1.69 (s, 3H), 1.61 (s, 3H), 1.30 (d, J=6.06 Hz, 3H).

Example 220: (R,Z)-3-amino-5-(2,3-difluoro-5-(2-fluoro-2-(5-(thiazol-4-ylmethoxy)pyrazin-2-yl)vinyl)phenyl)-2,5-dimethyl-5,6-dihydro-2H-1,2,4-thiadiazine 1,1-dioxide

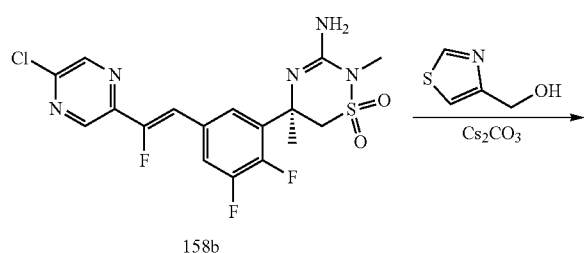

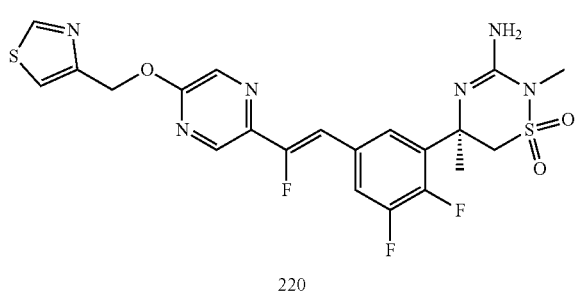

220

This compound (22 mg, 37% yield) as a white solid was prepared in a fashion similar to that described in Method D for Example 158, using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b) (50 mg, 0.11 mmol), thiazole-4-methanol (Combi-Blocks, 48.5 µL, 0.56 mmol), and cesium carbonate (110 mg, 0.336 mmol) as starting materials. MS (ESI, positive ion) m/z: =525.0 (M+1). $^1$H NMR (400 MHz, CHLOROFORM-d) δ ppm 8.87 (1H, d, J=1.96 Hz), 8.41 (1H, s), 8.29 (1H, s), 7.51-7.60 (2H, m), 7.47 (1H, d, J=1.96 Hz), 6.80 (1H, d, J=40 Hz), 5.63 (2H, s), 3.84 (1H, d, J=14.09 Hz), 3.71 (1H, d, J=13.89 Hz), 3.24 (3H, s), 1.81 (3H, s). $^{19}$F NMR (376 MHz, CHLOROFORM-d) δ ppm −124.13 (1F, br. s.), −137.52 (1F, br. s.), −138.64 (1F, d, J=20.81 Hz).

Example 221: (R,Z)-3-amino-5-(2,3-difluoro-5-(2-fluoro-2-(5-((3-methylisoxazol-5-yl)methoxy)pyrazin-2-yl)vinyl)phenyl)-2,5-dimethyl-5,6-dihydro-2H-1,2,4-thiadiazine 1,1-dioxide

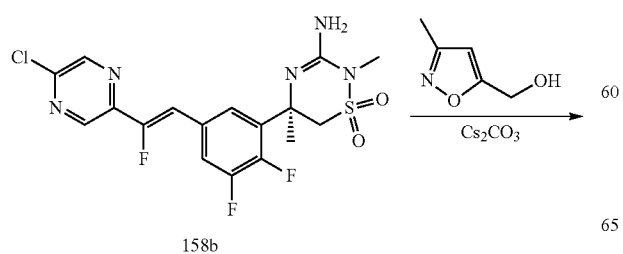

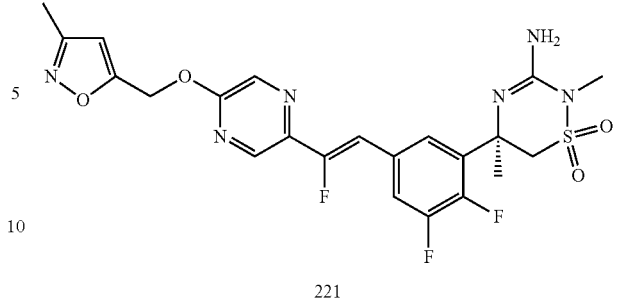

221

This compound (22 mg, 37% yield) as a white solid was prepared in a fashion similar to that described in Method D for Example 158, using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b) (50 mg, 0.11 mmol), (3-methyl-1,2-oxazol-5-yl)methanol (Maybridge, 53.6 µL, 0.56 mmol), and cesium carbonate (110 mg, 0.34 mmol) as starting materials. MS (ESI, positive ion) m/z: =523.1 (M+1). $^1$H NMR (400 MHz, CHLOROFORM-d) δ ppm 8.38 (1H, s), 8.26 (1H, s), 7.52-7.59 (2H, m), 6.80 (1H, d, J=40 Hz), 6.22 (1H, s), 5.50 (2H, s), 3.83 (1H, d, J=14.09 Hz), 3.70 (1H, d, J=14.08 Hz), 3.23 (3H, s), 2.33 (3H, s), 1.80 (3H, s). $^{19}$F NMR (376 MHz, CHLOROFORM-d) δ ppm −124.37 (1F, s), −137.50 (1F, d, J=20.81 Hz), −138.43 (1F, d, J=20.81 Hz).

Example 222: (R,Z)-3-amino-5-(5-(2-(5-chloro-4-hydroxypyridin-2-yl)-2-fluorovinyl)-2-fluorophenyl)-2,5-dimethyl-5,6-dihydro-2H-1,2,4-thiadiazine 1,1-dioxide

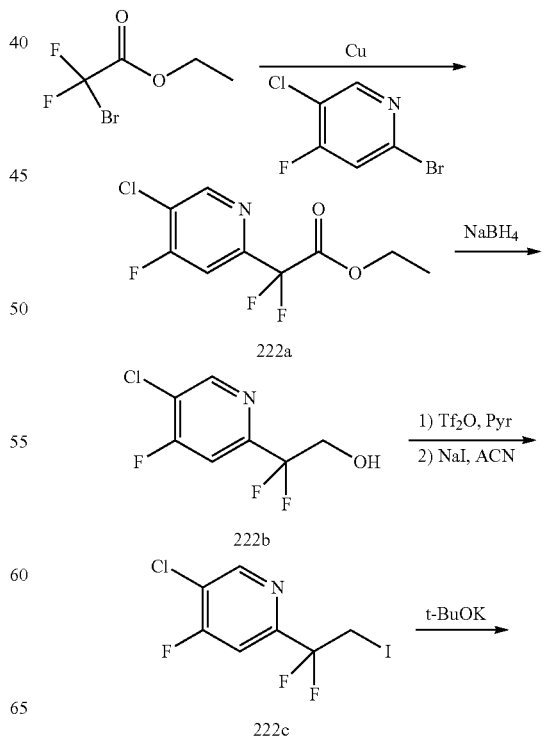

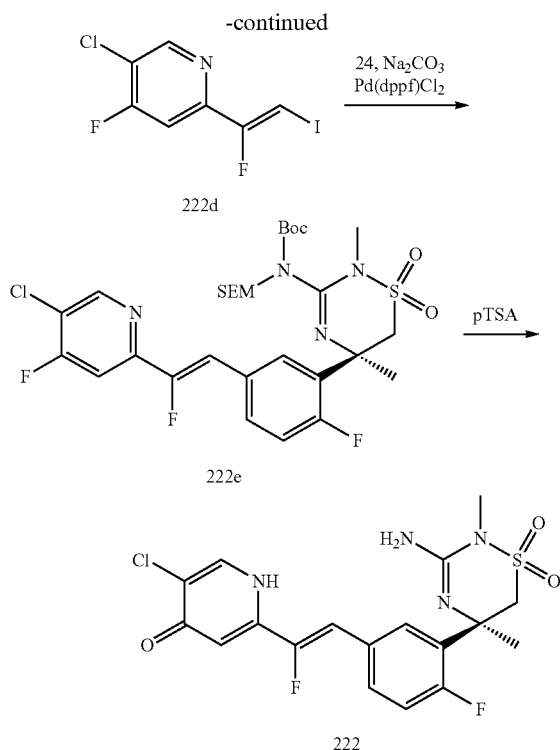

was then heated to 70° C. with rapid stirring for 45 min. The reaction mixture was then partitioned between EtOAc (60 mL) and 5% NaHCO$_3$ (40 mL). The organic layer was washed with sat'd NaCl (10 mL), dried over MgSO$_4$, concentrated under reduced pressure, then purified via silica gel chromatography (0-15% gradient of (3:1 EtOAc/EtOH)/heptane) to afford 222e (650 mg, 0.96 mmol, 47% yield) as a white solid. MS m/z=675.2 [M+H]$^+$.

Preparation of Example 222

A suspension of (R,Z)-tert-butyl (5-(5-(2-(5-chloro-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (222e, 58 mg, 0.09 mmol) and 4-methylbenzene sulfonic acid monohydrate (Sigma-Aldrich Chemical Company, Inc., St. Louis, Mo., USA) (82 mg, 0.43 mmol) in MeCN (1 mL) was heated to 70° C. for 90 min, then stirred at 20° C. for 14 h. The reaction mixture was partitioned between EtOAc (15 mL) and 5% NaHCO$_3$ (10 mL). The organic layer was dried over MgSO$_4$ then concentrated onto dry silica (3 g) under reduced pressure. The products were purified via silica gel chromatography (0-100% (3:1 EtOAc/EtOH blend)/heptane). The resulting solid was dissolved in 1:1 MeCN/water (1 mL) along with 1 drop of neat AcOH. The solution was frozen then lyophilized to afford (R,Z)-3-amino-5-(5-(2-(5-chloro-4-hydroxypyridin-2-yl)-2-fluorovinyl)-2-fluorophenyl)-2,5-dimethyl-5,6-dihydro-2H-1,2,4-thiadiazine 1,1-dioxide acetate (222) (18 mg, 0.04 mmol, 41% yield) as a white fluffy solid. MS m/z=443.0 [M+H]$^+$. $^1$H NMR (400 MHz, DMSO-d$_6$) δ ppm 8.41 (s, 1H), 7.85 (br d, J=6.46 Hz, 1H), 7.60-7.67 (m, 1H), 7.22 (dd, J=12.13, 8.41 Hz, 1H), 7.09-7.17 (m, 1H), 7.02 (d, J=40.69 Hz, 1H), 3.87 (br s, 2H), 3.06 (s, 3H), 1.91 (s, 3H), 1.63 (s, 3H). NH, NH$_2$, and acetic acid OH peaks were not observed and possibly overlapped with the water peak at 3.30 ppm.

Ethyl 2-(5-chloro-4-fluoropyridin-2-yl)-2,2-difluoroacetate (222a, 1.2 g, 32% yield) as a colorless oil was prepared in a manner similar to that described for 212a, starting from ethyl bromodifluoroacetate (6.0 g, 29 mmol) and 2-bromo-5-chloro-4-fluoropyridine (Anichem LLC, North Brunswick Township, N.J., USA) (3.1 g, 14.8 mmol). MS m/z=254.0 [M+H]$^+$. $^1$H NMR (400 MHz, CDCl$_3$) δ ppm 8.65 (d, J=9.00 Hz, 1H), 7.57 (d, J=8.61 Hz, 1H), 4.39 (q, J=7.24 Hz, 2H), 1.34 (t, J=7.14 Hz, 3H). $^{19}$F NMR (376 MHz, CDCl$_3$) δ ppm −101.55 (s, 1F), −105.26 (s, 2F).

Compounds 222b, 222c, and 222d were prepared in a manner similar to that described for 212b, 212c, and 212d, respectively. 2-(5-Chloro-4-fluoropyridin-2-yl)-2,2-difluoroethanol (222b): MS m/z=212.0 [M+H]$^+$ (elimination of HF). 5-Chloro-2-(1,1-difluoro-2-iodoethyl)-4-fluoropyridine (222c): MS m/z=322.0 [M+H]$^+$. $^1$H NMR (400 MHz, CDCl$_3$) δ 8.66 (d, J=9.00 Hz, 1H), 7.52 (d, J=8.80 Hz, 1H), 3.91 (t, J=14.48 Hz, 2H). (Z)-5-Chloro-4-fluoro-2-(1-fluoro-2-iodovinyl)pyridine (222d): MS m/z=302.2 [M+H]$^+$.

Preparation of (R,Z)-tert-butyl (5-(5-(2-(5-chloro-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl) carbamate (222e)

A suspension of (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate (24, 1.30 g, 2.07 mmol), (Z)-5-chloro-4-fluoro-2-(1-fluoro-2-iodovinyl)pyridine (222d, 0.94 g, 3.11 mmol), 1,1'-bis(diphenylphosphino)ferrocene palladium(II)dichloride dichloromethane adduct (Sigma-Aldrich Chemical Company, Inc., St. Louis, Mo., USA) (85 mg, 0.10 mmol), sodium carbonate (658 mg, 6.21 mmol) in 1,4-dioxane (10 mL) and water (5 mL) was sparged with a stream of argon for 5 min. The suspension Example 223: (R,Z)-3-amino-5-(2,3-difluoro-5-(2-fluoro-2-(5-((5-methylisoxazol-3-yl)methoxy)pyrazin-2-yl)vinyl)phenyl)-2,5-dimethyl-5,6-dihydro-2H-1,2,4-thiadiazine 1,1-dioxide

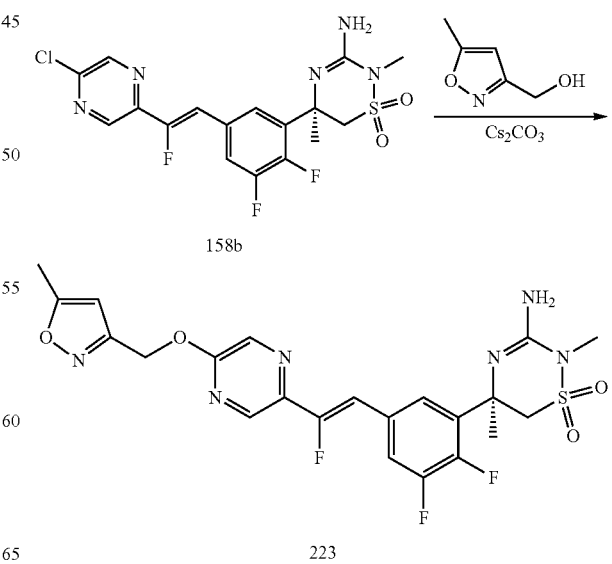

This compound (22 mg, 37% yield) as a white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (5-methyl-3-isoxazolyl)methanol (Maybridge, 53.6 μL, 0.56 mmol), and cesium carbonate (110 mg, 0.33 mmol) as starting materials. MS (ESI, positive ion) m/z: =523.1 (M+1). $^1$H NMR (400 MHz, DMSO-$d_6$) δ ppm 8.50 (2H, d, J=13.89 Hz), 7.60-7.75 (2H, m), 6.90 (1H, d, J=40 Hz), 6.36 (1H, s), 6.09 (2H, s), 5.49 (2H, s), 3.84 (2H, d, J=3.33 Hz), 3.06 (3H, s), 2.41 (3H, s), 1.63 (3H, s). $^{19}$F NMR (376 MHz, DMSO-$d_6$) δ ppm −123.27 (1F, br. s.), −138.31 (1F, d, J=22.55 Hz), −139.02 (1F, d, J=21.67 Hz).

Example 224: (R,Z)-3-amino-5-(2,3-difluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide

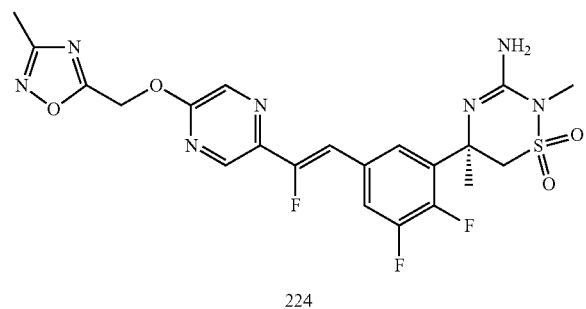

This compound (35 mg, 60% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b) (50 mg, 0.11 mmol), (3-methyl-1,2,4-oxadiazol-5-yl)methanol (Enamine, 0.05 m L, 0.56 mmol) and cesium carbonate (110 mg, 0.33 mmol) as starting materials. MS (ESI, positive ion) m/z: =524.0 (M+1). $^1$H NMR (400 MHz, DMSO-$d_6$) δ ppm 8.60 (1H, s), 8.49 (1H, s), 7.59-7.72 (2H, m), 6.91 (1H, d, J=40 Hz), 6.09 (2H, s, J=5.27 Hz), 3.78-3.89 (2H, m), 3.05 (3H, s), 2.33-2.36 (3H, m), 1.62 (3H, s). $^{19}$F NMR (376 MHz, DMSO-$d_6$) δ ppm −123.24 (1F, br. s.), −138.19 (1F, d, J=21.68 Hz), −138.99 (1F, d, J=21.68 Hz).

Example 225: (R,Z)-3-amino-5-(2,3-difluoro-5-(2-fluoro-2-(5-(oxazol-4-ylmethoxy)pyrazin-2-yl)vinyl)phenyl)-2,5-dimethyl-5,6-dihydro-2H-1,2,4-thiadiazine 1,1-dioxide

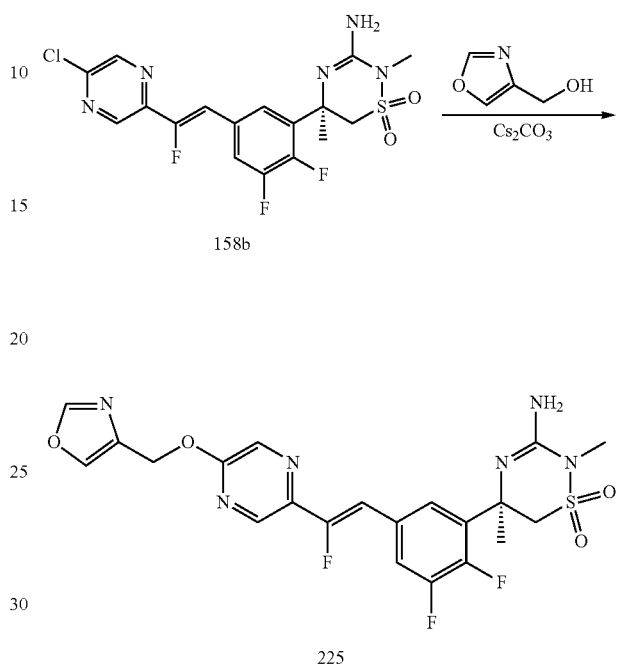

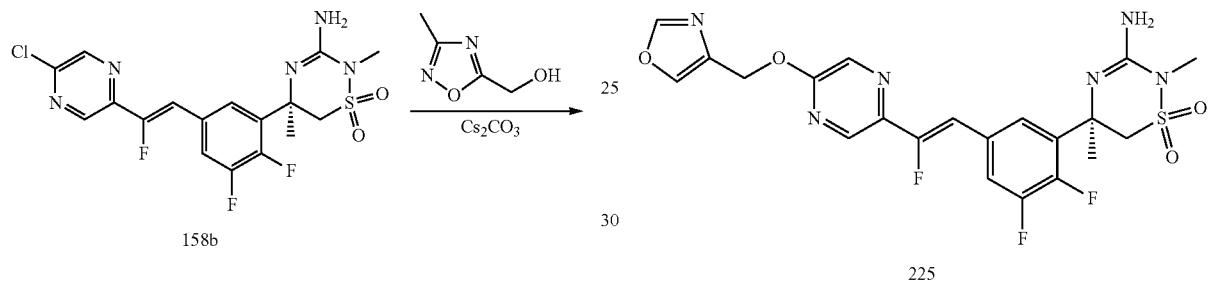

This compound (19 mg, 33% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), oxazol-4-yl-methanol (Synthonix, 44.4 μL, 0.56 mmol), and cesium carbonate (110 mg, 0.36 mmol) as starting materials. MS (ESI, positive ion) m/z: =509.1 (M+1). $^1$H NMR (400 MHz, DMSO-$d_6$) δ ppm 8.52 (1H, s), 8.43 (2H, d, J=4.30 Hz), 8.26 (1H, s), 7.59-7.72 (2H, m), 6.89 (1H, d, J=40 Hz), 6.09 (2H, s), 5.37 (2H, s), 3.83 (2H, d, J=3.33 Hz), 3.05 (3H, s), 1.62 (3H, s). $^{19}$F NMR (376 MHz, DMSO-$d_6$) δ ppm −123.31 (1F, br. s.), −138.39 (1F, d, J=21.68 Hz), −139.03 (1F, d, J=21.68 Hz).

Example 226: 6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-4-fluoro-3-pyridinecarbonitrile

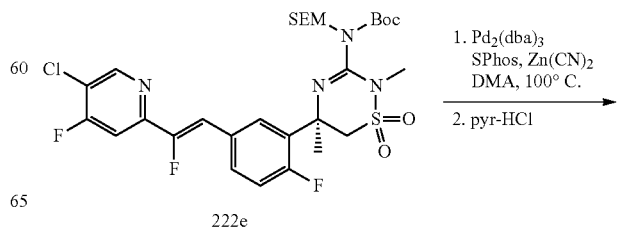

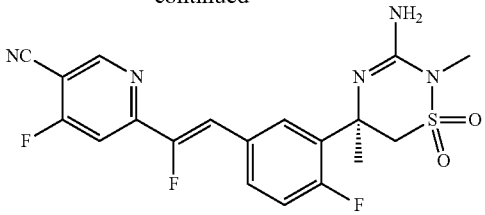

226

A 3-mL vial was charged with (R,Z)-tert-butyl (5-(5-(2-(5-chloro-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (222e, 85 mg, 0.126 mmol), zinc cyanide (Sigma-Aldrich Chemical Company, Inc., St. Louis, Mo., USA) (44 mg, 0.38 mmol), 2-(dicyclohexylphosphino)-2',6'-dimethoxy-1,1'-biphenyl (Strem Chemicals, Inc., Newburyport, Mass., USA) (16 mg, 0.04 mmol), tris(dibenzylideneacetone)dipalladium (0) (Sigma-Aldrich Chemical Company, Inc., St. Louis, Mo., USA) (18 mg, 0.02 mmol), and N, N-dimethylacetamide (1.26 mL). The vial was evacuated and backfilled with $N_2$. The mixture was heated at 100° C. for 1 h, cooled to RT, and filtered through a pad of celite. The cake was washed with EtOAc. The filtrate was washed with water and brine, dried over $Na_2SO_4$ and concentrated in vacuo. The crude was purified by silica gel chromatography (0-30% EtOAc in heptane) to afford (R,Z)-tert-butyl (5-(5-(2-(5-cyano-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (47 mg, 56% yield) as a yellow oil. The yellow oil was dissolved in acetonitrile (0.71 mL) and treated with pyridine hydrochloride (0.12 g, 1.06 mmol). The mixture was stirred with heating 70° C. for 5 h, at which point the starting material was consumed. The mixture was diluted with DCM, partitioned with sat'd aqueous $NaHCO_3$, and the aqueous layer was extracted with DCM (5 mL×3). The combined organic washings were dried over $MgSO_4$ and concentrated. The crude residue was purified via ISCO (0-80% 3:1 EtOAc/EtOH in heptane gradient) to provide (R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-4-fluoronicotinonitrile (226, 18 mg, 59% yield) as a white solid. MS m/z=436.1 [M+H]$^+$. $^1$H NMR (400 MHz, DMSO-d6) δ 9.14 (d, J=9.19 Hz, 1H), 7.92-8.00 (m, 1H), 7.88 (d, J=10.37 Hz, 1H), 7.65-7.75 (m, 1H), 7.37 (s, 1H), 7.22-7.32 (m, 1H), 6.08 (br. s., 2H), 3.81 (s, 2H), 2.99-3.07 (m, 3H), 1.61 (s, 3H). $^{19}$F NMR (376 MHz, DMSO-d6) δ −96.29 (s, 1F), −109.98 (s, 1F), −124.10 (br. s., 1F).

Example 227: (R,Z)-5-(5-(2-(5-(allyloxy)pyrazin-2-yl)-2-fluorovinyl)-2,3-difluorophenyl)-3-amino-2,5-dimethyl-5,6-dihydro-2H-1,2,4-thiadiazine 1,1-dioxide

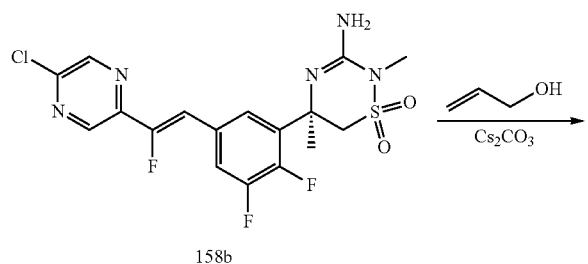

158b

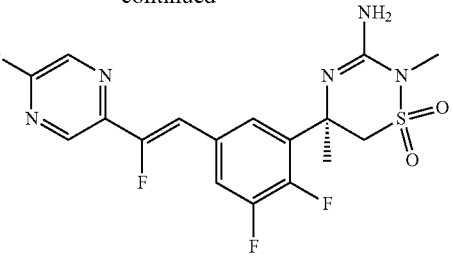

227

This compound (12 mg, 23% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), allyl alcohol (Sigma-Aldrich, 38 μL, 0.56 mmol), and cesium carbonate (110 mg, 0.336 mmol) as starting materials. MS (ESI, positive ion) m/z: =468.0 (M+1)$^+$. $^1$H NMR (400 MHz, DMSO-d$_6$) δ ppm 8.46 (2H, d, J=18.98 Hz), 7.59-7.71 (2H, m), 6.87 (1H, d, J=40 Hz), 6.02-6.16 (3H, m), 5.44 (1H, dd, J=17.31, 1.66 Hz), 5.30 (1H, dd, J=10.56, 1.37 Hz), 4.92 (2H, d, J=5.48 Hz), 3.83 (2H, br. s.), 3.05 (3H, s), 1.62 (3H, s). $^{19}$F NMR (376 MHz, DMSO-d$_6$) δ ppm −123.25 (1F, br. s.), −138.44 (1F, d, J=22.54 Hz), −139.05 (1F, d, J=22.54 Hz).

Example 228: (R,Z)-3-amino-5-(2,3-difluoro-5-(2-fluoro-2-(5-(pyrimidin-2-ylmethoxy)pyrazin-2-yl)vinyl)phenyl)-2,5-dimethyl-5,6-dihydro-2H-1,2,4-thiadiazine 1,1-dioxide

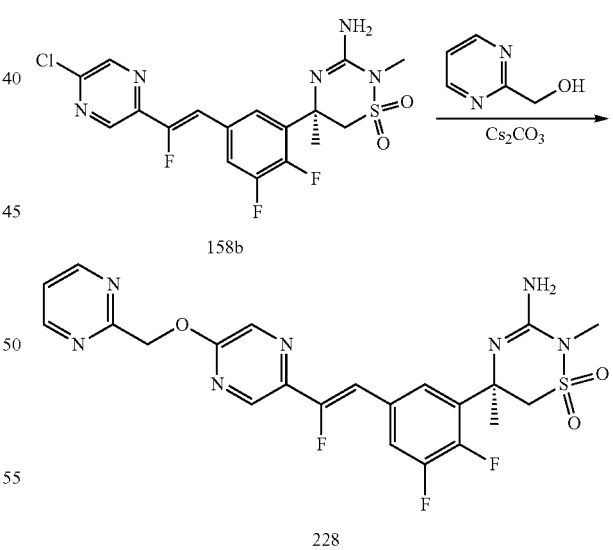

158b

228

This compound (33 mg, 57% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), 2-(hydroxymethyl)-pyrimidine (Synthonix, Wake Forest, N.C., USA) (50 μL, 0.56 mmol), and cesium carbonate (110 mg, 0.33 mmol) as starting materials. MS (ESI, positive ion) m/z: =520.1 (M+1)⁺. ¹H NMR (400 MHz, DMSO-d₆) δ ppm 8.79 (2H, d, J=4.89 Hz), 8.56 (1H, s), 8.40 (1H, s), 7.58-7.71 (2H, m), 7.44 (1H, t, J=4.89 Hz), 6.88 (1H, d, J=40 Hz), 5.65 (2H, s), 3.84 (2H, d, J=4.30 Hz), 3.04 (3H, s), 1.62 (3H, s). ¹⁹F NMR (376 MHz, DMSO-d6) −123.19 (1F, s), −138.40 (1F, d, J=18.8 Hz), −139.02 (1F, d, J=22.7 Hz).

Example 229: (R,Z)-3-amino-5-(2,3-difluoro-5-(2-fluoro-2-(5-((5-methyl-1,2,4-oxadiazol-3-yl)methoxy)pyrazin-2-yl)vinyl)phenyl)-2,5-dimethyl-5,6-dihydro-2H-1,2,4-thiadiazine 1,1-dioxide

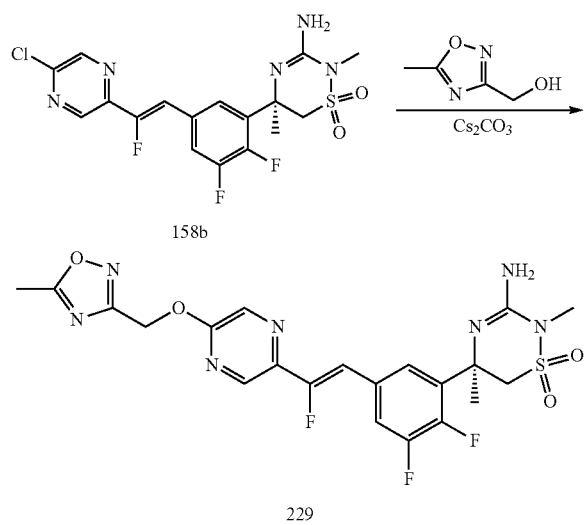

This compound (26 mg, 43% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (5-methyl-1,2,4-oxadiazol-3-yl)methanol (ChemBridge, 64 mg, 0.56 mmol), and cesium carbonate (110 mg, 0.33 mmol) as starting materials. MS (ESI, positive ion) m/z: =524.0 (M+1)⁺. ¹H NMR (400 MHz, DMSO-d₆) δ ppm 8.52 (2H, d, J=8.80 Hz), 7.59-7.74 (2H, m), 6.90 (1H, s, J=40 Hz), 6.09 (2H, s), 5.59 (2H, s), 3.83 (2H, d, J=3.52 Hz), 3.05 (3H, s), 2.61 (3H, s), 1.62 (3H, s). ¹⁹F NMR (376 MHz, DMSO-d₆) δ ppm −123.26 (1F, s), −138.26 (1F, d, J=22.54 Hz), −139.00 (1F, d, J=22.55 Hz).

Example 230: (R,Z)-3-amino-5-(5-(2-(5-chloro-4-methoxypyridin-2-yl)-2-fluorovinyl)-2-fluorophenyl)-2,5-dimethyl-5,6-dihydro-2H-1,2,4-thiadiazine 1,1-dioxide

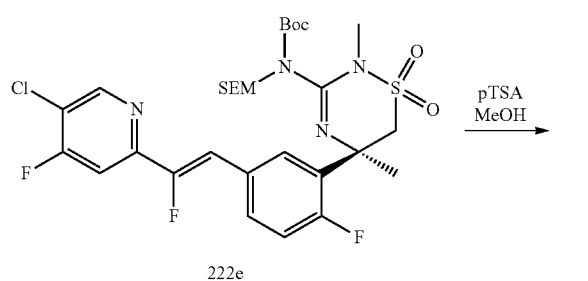

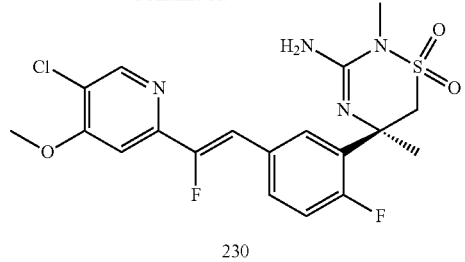

A suspension of (R,Z)-tert-butyl (5-(5-(2-(5-chloro-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (222e, 75 mg, 0.11 mmol) and 4-methylbenzene sulfonic acid monohydrate (106 mg, 0.55 mmol) in MeOH (1 mL) was heated to 70° C. for 2 h. The reaction mixture was then partitioned between EtOAc (15 mL) and 5% NaHCO₃ (10 mL). The organic layer was dried over MgSO₄ then concentrated onto dry silica (3 g) under reduced pressure. The products were purified via silica gel chromatography (0-50% (3:1 EtOAc/EtOH blend)/heptane). The resulting solid was dissolved in 1:1 MeCN/water (1 mL), frozen, and lyophilized to afford the title compound (230, 30 mg, 0.07 mmol, 59% yield) as an off-white fluffy solid. MS m/z=457.1 [M+H]⁺. ¹H NMR (400 MHz, DMSO-d₆) δ ppm 8.49-8.57 (m, 1H), 7.83-7.94 (m, 1H), 7.56-7.70 (m, 1H), 7.33-7.42 (m, 1H), 7.18-7.30 (m, 1H), 7.10 (d, J=40.30 Hz, 1H), 5.78-6.33 (m, 2H), 4.05 (s, 3H), 3.77-3.84 (m, 2H), 3.03-3.06 (m, 3H), 1.59-1.64 (m, 3H).

Example 231: (R,Z)-2-(2-(3-(3-amino-2,5-dimethyl-1,1-dioxido-5,6-dihydro-2H-1,2,4-thiadiazin-5-yl)-4-fluorophenyl)-1-fluorovinyl)-5-chloroisonicotinonitrile

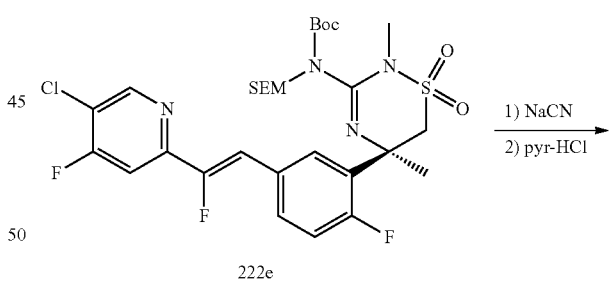

A suspension of (R,Z)-tert-butyl (5-(5-(2-(5-chloro-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (222e, 60 mg, 0.09 mmol) and sodium cyanide (Sigma-Aldrich Chemical Company, Inc., St. Louis, Mo., USA) (21 mg, 0.44 mmol) in DMF (0.4 mL) was stirred for 20 h at RT. It was partitioned between EtOAc (10 mL) and 5% NaHCO$_3$ (5 mL). The organic layer was dried over MgSO$_4$, and concentrated under reduced pressure. The residue was dissolved in MeCN (2 mL) and treated with pyridine hydrochloride (505 mg, 4.37 mmol). The mixture was heated to at 70° C. for 6 h. It was partitioned between EtOAc (10 mL) and sat'd aqueous NaHCO$_3$ (10 mL). The separated aqueous layer was further extracted with EtOAc (5 mL). The combined organic extracts were dried over MgSO$_4$, filtered, concentrated under reduced pressure, and then purified by silica gel chromatography (0-50% (3:1 EtOAc/EtOH blend)/heptane). The resulting solid was then dissolved in 1:1 MeCN/water (1 mL), frozen, then lyophilized to afford the title compound (231) (15 mg, 37% yield) as an off-white fluffy solid. MS m/z=452.0 [M+H]$^+$. $^1$H NMR (400 MHz, DMSO-d$_6$) δ ppm 8.99-9.03 (m, 1H) 8.26-8.30 (m, 1H) 7.87-7.94 (m, 1H) 7.63-7.73 (m, 1H) 7.10-7.29 (m, 2H) 5.79-6.47 (m, 2H) 3.78-3.91 (m, 2H) 3.04-3.07 (m, 3H) 1.57-1.67 (m, 3H).

Example 232: (R,Z)-3-amino-5-(5-(2-(5-chloro-4-fluoropyridin-2-yl)-2-fluorovinyl)-2-fluorophenyl)-2,5-dimethyl-5,6-dihydro-2H-1,2,4-thiadiazine 1,1-dioxide

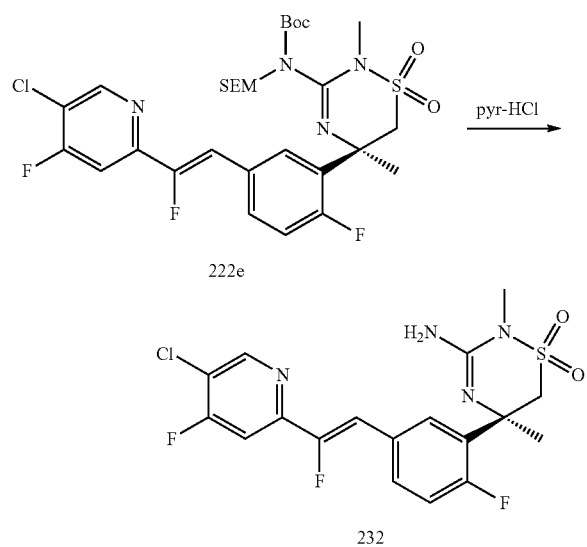

A suspension of (R,Z)-tert-butyl (5-(5-(2-(5-chloro-4-fluoropyridin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (222e, 60 mg, 0.09 mmol) and pyridine hydrochloride (Sigma-Aldrich Chemical Company, Inc., St. Louis, Mo., USA, 154 mg, 1.33 mmol) in MeCN (1 mL) was heated to 70° C. for 6 h. It was cooled to RT and partitioned between EtOAc (10 mL) and 5% NaHCO$_3$ (5 mL). The organic layer was dried over MgSO$_4$, concentrated under reduced pressure, then purified via silica gel chromatography (0-50% (3:1 EtOAc/EtOH blend)/heptane). Fractions that contained MS m/z=445.1 [M+H]$^+$ were concentrated and the resulting solid was dissolved in 1:1 MeCN/water (1 mL), frozen, and lyophilized to afford (R,Z)-3-amino-5-(5-(2-(5-chloro-4-fluoropyridin-2-yl)-2-fluorovinyl)-2-fluorophenyl)-2,5-dimethyl-5,6-dihydro-2H-1,2,4-thiadiazine 1,1-dioxide (232, 10 mg, 25% yield) as a white fluffy solid. MS m/z=445.1 [M+H]$^+$. $^1$H NMR (400 MHz, DMSO-d$_6$) δ ppm 8.80-8.86 (m, 1H), 7.87-7.95 (m, 1H), 7.77-7.84 (m, 1H), 7.63-7.71 (m, 1H), 7.07-7.29 (m, 2H), 5.96-6.16 (m, 2H), 3.74-3.86 (m, 2H), 3.00-3.10 (m, 3H), 1.58-1.64 (m, 3H).

Example 233: (R,Z)-3-amino-5-(2,3-difluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide

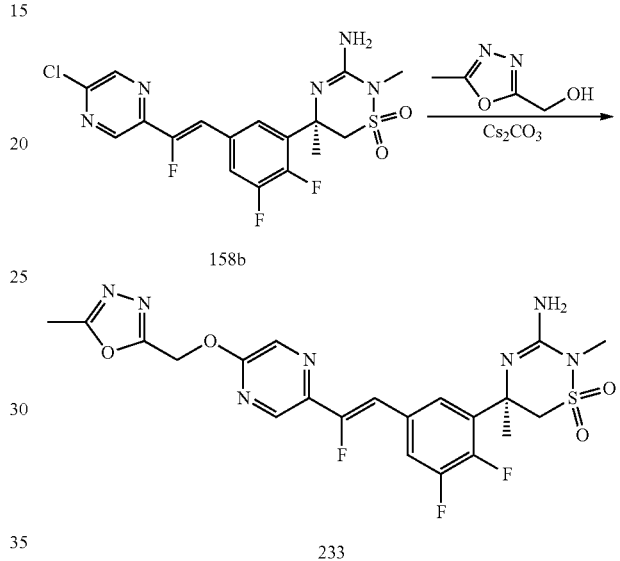

This compound (20 mg, 34% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (5-methyl-1,3,4-oxadiazol-2-yl)methanol (Enamine, 49.8 μL, 0.56 mmol), and cesium carbonate (110 mg, 0.33 mmol) as starting materials. MS (ESI, positive ion) m/z: =524.2 (M+1)$^+$. $^1$H NMR (400 MHz, DMSO-d$_6$) δ ppm 8.53 (2H, d, J=7.43 Hz), 7.60-7.72 (2H, m), 6.92 (1H, d, J=40 Hz), 6.09 (2H, br s), 5.68 (2H, s), 3.84 (2H, br s), 3.05 (3H, s), 1.62 (3H, s). $^{19}$F NMR (376 MHz, DMSO-d$_6$) δ ppm −123.24 (1F, br s), −138.19 (1F, br d, J=21.68 Hz), −138.96 (1F, br d, J=19.94 Hz).

Example 234: (R,Z)-3-Amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide

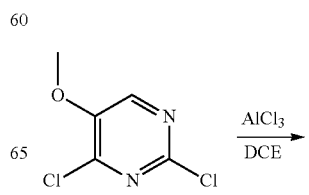

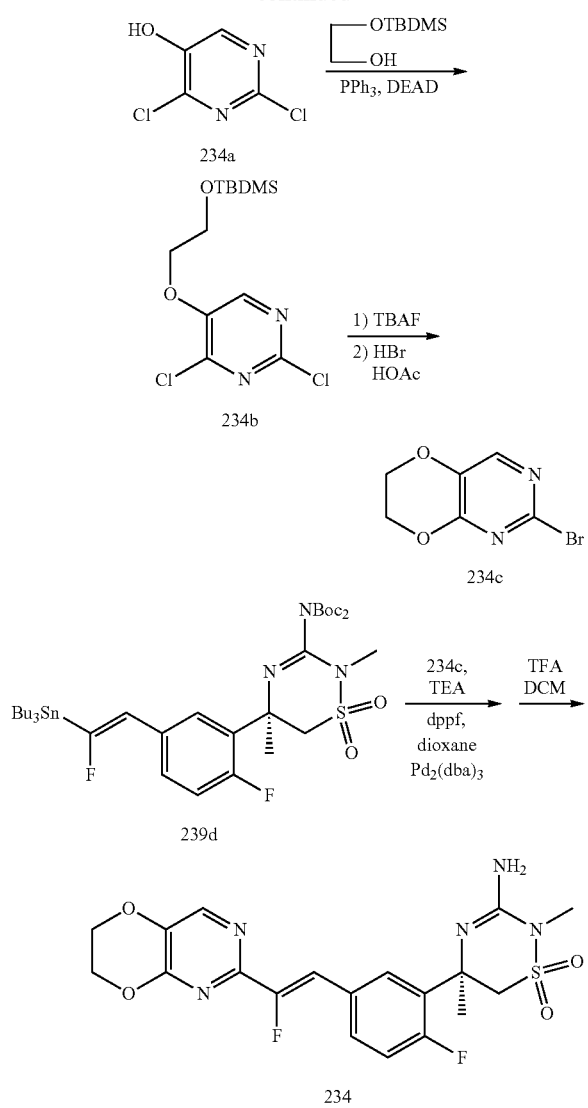

Preparation of 2,4-dichloropyrimidin-5-ol (234a)

2,4-Dichloro-5-methoxypyrimidine (Combi-Blocks, San Diego, Calif., USA) (6.0 g, 33.5 mmol) was suspended in 1,2-dichloroethane (40 mL) under nitrogen. Aluminum chloride (Sigma-Aldrich, St. Louis, Mo., USA) (13.4 g, 101.0 mmol) was added and the reaction mixture heated in a 70° C. bath for 15 min. The resulting dark brown mixture was cooled in an ice bath and ice (~20 g) and 5 N sodium hydroxide (20 mL) were added slowly. A strong exotherm was observed. The temperature was allowed to drop to <20° C. and methanol (40 mL) was added dropwise. The dark mixture was stirred for 1 h. Saturated ammonium chloride (50 mL), water (75 mL), acetic acid (3 mL) and ethyl acetate (200 mL) were added and the phases mixed and separated. The organic phase was evaporated to dryness under reduced pressure and the residue was purified using silica gel chromatography (ethyl acetate/heptane) to give 2,4-dichloropyrimidin-5-ol (234a, 1.7 g, 10.3 mmol, 31% yield). MS (ESI +ve ion) m/z: [M+1]=165.0.

Preparation of 5-(2-((tert-butyldimethylsilyl)oxy)ethoxy)-2,4-dichloropyrimidine (234b)

2,4-Dichloropyrimidin-5-ol (234a) (1.7 g, 10.3 mmol) and triphenylphosphine (Sigma-Aldrich, St. Louis, Mo., USA) (2.7 g, 10.3 mmol) were suspended in THF (40 mL) under nitrogen and cooled with an ice bath. 2-(t-Butyldimethylsiloxy)ethanol (Gelest, Morrisville, Pa., USA) (2.2 mL, 11.1 mmol) was added followed by dropwise addition of diethyl azodicarboxylate solution (Sigma-Aldrich, St. Louis, Mo., USA) (40% in toluene, 4.8 mL, 10.5 mmol). The reaction was stirred for 10 min, then evaporated to dryness under reduced pressure. The crude material was triturated in 1:2 heptane:DCM (40 mL). The solids were filtered off. The filtrate was concentrated and the residue was purified using silica gel chromatography (ethyl acetate/heptane) to give 234b (2.7 g, 8.3 mmol, 81% yield) as an oil. MS (ESI +ve ion) m/z: [M+1]=323.0.

Preparation of 2-bromo-6,7-dihydro-[1,4]dioxino[2,3-d]pyrimidine (234c)

5-(2-((tert-Butyldimethylsilyl)oxy)ethoxy)-2,4-dichloropyrimidine (234b) (2.71 g, 8.38 mmol) was dissolved in 2-methyltetrahydrofuran (50 mL). The solution was added dropwise to a rapidly stirring solution of tetra-N-butylammonium fluoride (Sigma-Aldrich, St. Louis, Mo., USA) (9.00 mL of 1 M solution in THF, 9.00 mmol) in 2-methyltetrahydrofuran (150 mL). Once the addition was complete the solution was stirred for an additional 10 min. Ethyl acetate (100 mL), water (150 mL), and brine (40 mL) were added. The phases were mixed and separated. The organic layer was washed with brine (50 mL) before evaporated to dryness under reduced pressure. Purification using silica gel chromatography (ethyl acetate/heptane) gave 2-chloro-6,7-dihydro-[1,4]dioxino[2,3-d]pyrimidine (0.43 g, 2.50 mmol, 30% yield) as an off white solid. MS (ESI +ve ion) m/z: [M+1]=173.0. 2-Chloro-6,7-dihydro-[1,4]dioxino[2,3-d]pyrimidine (0.43 g, 2.50 mmol) was dissolved in a 33 wt % solution of hydrogen bromide in acetic acid (Sigma-Aldrich, St. Louis, Mo., USA) (5 mL, 30.4 mmol) under nitrogen. The solution was heated in a 60° C. bath for 50 min then it was evaporated to dryness under reduced pressure. The crude was dissolved in DCM (150 mL) and washed with sat'd aqueous sodium bicarbonate (2×40 mL). The organic solution was evaporated to dryness under reduced pressure to give 234c which was used without further manipulation. MS (ESI +ve ion) m/z: [M+1]=217.0/219.0.

Preparation of Example 234

2-Bromo-6,7-dihydro-[1,4]dioxino[2,3-d]pyrimidine (234c) (50 mg, 0.23 mmol) and 1,1'-bis(diphenylphosphino)ferrocene (Strem Chemicals, Boston, Mass., USA) (24 mg, 0.04 mmol) were suspended in dioxane (0.5 mL) and subjected to house vac/nitrogen flush (3×). Tris(dibenzylideneacetone)dipalladium(0) (Sigma-Aldrich, St. Louis, Mo., USA) (15 mg, 0.02 mmol) was added and the mixture stirred in a 50° C. bath for 20 min. A solution of stannane (239d, see preparation of Example 239) (0.12 g, 0.15 mmol) was dissolved in dioxane (0.2 mL) and treated with triethylamine (0.10 mL, 0.72 mmol) and the solution was subjected to house vac/nitrogen flush (3×). The clear, colorless solution was added to the palladium mixture dropwise over 30 min. The reaction was stirred for 12 h. The temperature was increased to 120° C. and the reaction stirred for another 12 h. The reaction was cooled and heptane (50 mL) and methanol (50 mL) were added. The phases were mixed and separated and the heptane layer discarded. The methanol layer was evaporated to dryness under reduced pressure and the crude purified using silica gel chromatography (ethyl acetate/heptane) to give (R,Z)-3-(bisBoc amino)-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide (43 mg, 0.066 mmol, 44% yield). MS (ESI +ve ion) m/z: [M+Na$^+$]=673.8.

(R,Z)-3-(bisBoc amino)-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide (43 mg, 0.066 mmol) was dissolved in DCM (4 mL) and treated with trifluoroacetic acid (2 mL). The mixture was stirred for 1 h then evaporated to dryness under reduced pressure. The crude was partitioned between dichloromethane (10 mL) and sat'd aqueous sodium bicarbonate (10 mL). The organic layer was concentrated and the residue was purified using silica gel chromatography (10-25% (3:1 ethyl acetate:ethanol) in DCM) to give (R,Z)-3-amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide (234) (24 mg, 0.05 mmol, 81% yield) as a white solid. MS (ESI +ve ion) m/z: [M+1]=451.8. $^1$H NMR (400 MHz, CHLOROFORM-d) δ 8.15 (s, 1H), 7.80 (dd, J=1.96, 8.02 Hz, 1H), 7.51-7.58 (m, 1H), 6.90-7.05 (m, 2H), 4.45 (dd, J=2.93, 5.28 Hz, 2H), 4.25 (dd, J=3.33, 4.89 Hz, 2H), 3.82 (d, J=13.89 Hz, 1H), 3.64 (d, J=14.09 Hz, 1H), 3.13 (s, 3H), 1.95 (s, 2H), 1.71 (s, 3H).

Example 235: (R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide

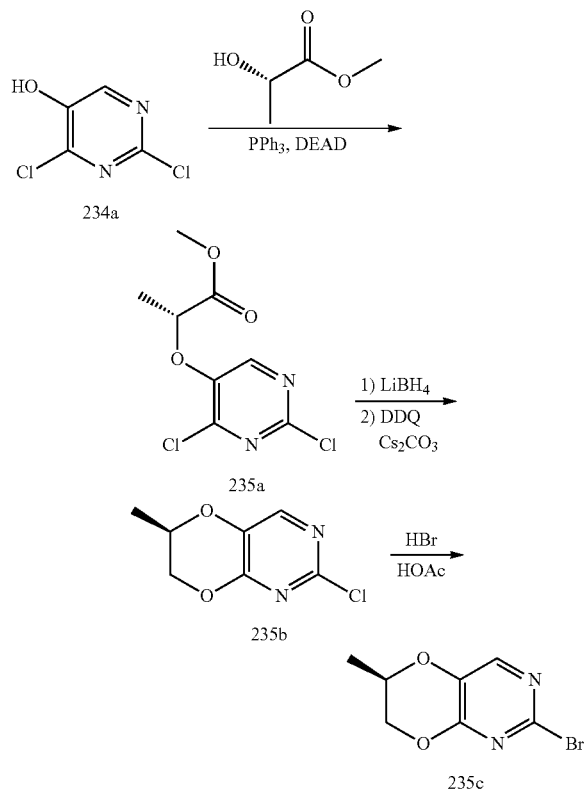

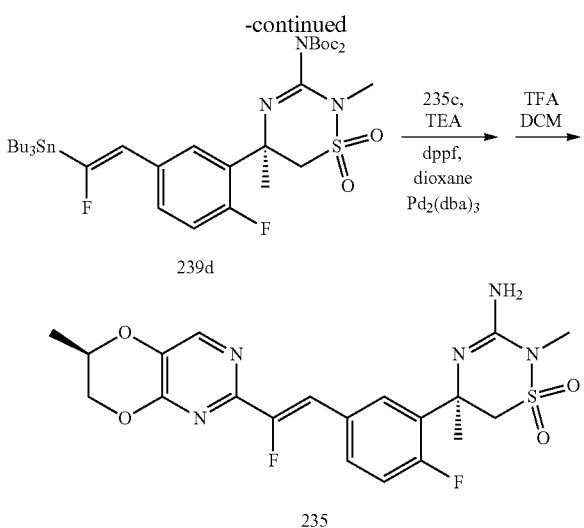

Preparation of (R)-ethyl 2-((2,4-dichloropyrimidin-5-yl)oxy)propanoate (235a)

2,4-Dichloropyrimidin-5-ol (234a) (0.75 g, 4.55 mmol) was dissolved in acetonitrile (40 mL) under nitrogen. Triphenylphosphine (Sigma-Aldrich, St. Louis, Mo., USA) (1.20 g, 4.58 mmol) and ethyl lactate (TCI Chemical, Portland Oreg., USA) (0.55 mL, 4.80 mmol) were added and the mixture stirred for 5 min. Diethyl azodicarboxylate solution (Sigma-Aldrich, St. Louis, Mo., USA) (50 wt % in toluene, 2.10 mL, 4.61 mmol) was added dropwise. The mixture was stirred at RT for 16 h then evaporated to dryness under reduced pressure. The crude was triturated with 1:1 DCM:heptane (70 mL) and filtered through a fritted funnel. The filtrate was concentrated and purified using silica gel chromatography (0-40% ethyl acetate/heptane) to give (R)-ethyl 2-((2,4-dichloropyrimidin-5-yl)oxy)propanoate (235a, 1.00 g, 3.77 mmol, 83% yield). MS (ESI +ve ion) m/z: [M+1]=265.0.

Preparation of (R)-2-chloro-6-methyl-6,7-dihydro-[1,4]dioxino[2,3-d]pyrimidine (235b)

(R)-Ethyl 2-((2,4-dichloropyrimidin-5-yl)oxy)propanoate (235a) (1.0 g, 3.77 mmol) and methanol (0.19 mL, 4.69 mmol) were dissolved in methyl tert-butyl ether (20 mL) under nitrogen and cooled in an ice bath. Lithium borohydride (Sigma-Aldrich, St. Louis, Mo., USA) (2.0 M in THF, 2.3 mL, 4.60 mmol) was added dropwise. After stirring for 5 min the solution was removed from the cold bath and stirred at RT for another 30 min. The mixture was cooled in an ice bath and water (5 mL) was added slowly. After stirring for 3 min, ethyl acetate (120 mL) and water (75 mL) were added. The mixture was stirred for 10 min then the phases were separated. The organic phase was washed with brine (75 mL) then evaporated to ~30 mL under reduced pressure. LCMS of the residue indicated the formation of a mixture of two products, MS (ESI +ve ion) m/z: [M+1]=225.8 (major), and MS (ESI +ve ion) m/z: [M+1]=223.8 (minor). The residue was dissolved in N,N-dimethylacetamide (75 mL) and treated with cesium carbonate (1.1 g) and 2,3-dichloro-5,6-dicyano-1,4-benzoquinone (Sigma-Aldrich, St. Louis, Mo., USA) (0.75 g) were added and stirred at RT for 14 h. Water (75 mL), sat'd aqueous sodium bicarbonate (75 mL)

and ethyl acetate (75 mL) were added and the phases mixed and separated. The organic phase was washed with 0.5 N sodium hydroxide (75 mL) then brine (100 mL) before evaporating to dryness under reduced pressure. The crude was purified using silica gel chromatography (ethyl acetate/ heptane) to give (R)-2-chloro-6-methyl-6,7-dihydro-[1,4]dioxino[2,3-d]pyrimidine (235b, 0.063 g, 0.34 mmol, 9% yield). MS (ESI +ve ion) m/z: [M+1]=187.0.

Preparation of (R)-2-bromo-6-methyl-6,7-dihydro-[1,4]dioxino[2,3-d]pyrimidine (235c)

(R)-2-Chloro-6-methyl-6,7-dihydro-[1,4]dioxino[2,3-d]pyrimidine (235b) (0.063 g, 0.34 mmol) was dissolved in a 33 wt % solution of hydrogen bromide in acetic acid (Sigma-Aldrich, St. Louis, Mo., USA) (5.0 mL, 0.338 mmol) under nitrogen. The solution was heated in a 60° C. bath for 1 h. The solution was evaporated to dryness under reduced pressure. The crude was dissolved in DCM (10 mL), washed with sat'd aqueous sodium bicarbonate (10 mL), and concentrated. Purification using silica gel chromatography (ethyl acetate/heptane) gave 235 (64 mg, 0.28 mmol, 82% yield). MS (ESI +ve ion) m/z: [M+1]=217.0/219.0.

Preparation of Example 235

(R)-2-Bromo-6-methyl-6,7-dihydro-[1,4]dioxino[2,3-d]pyrimidine (235c) (55 mg, 0.24 mmol), tris(dibenzylideneacetone)dipalladium(0) (Sigma-Aldrich, St. Louis, Mo., USA) (0.035 g, 0.038 mmol), and 1,1'-bis(diphenylphosphino)ferrocene (Strem Chemicals, Boston, Mass., USA) (0.050 g, 0.090 mmol) were combined and subjected to house vac/nitrogen flush (3×). Dry, degassed dioxane (0.3 mL) and triethylamine (0.1 mL) were added. The mixture was stirred at RT for 10 min then a solution of stannane 239d (0.13 g, 0.162 mmol) in degassed dioxane (0.2 mL) was added. The mixture was heated in a 90° C. bath for 3 days. DCM (5 mL) and water (5 mL) were added and the mixture stirred for 10 min. It was filtered through a pad of celite and the filtrate was concentrated. The residue was purified using silica gel chromatography (ethyl acetate/heptane) to provide (R)-3-(Bis Boc amino)-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide (0.055 g, 51% yield). MS (ESI +ve ion) m/z: [M+Na$^+$]=687.8.

(R)-3-(Bis Boc amino)-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide (0.055 g, 0.083 mmol) was dissolved in DCM (2 mL) and treated with trifluoroacetic acid (1 mL). The solution was stirred for 20 min after which the solution was evaporated to dryness under reduced pressure and the residue partitioned between DCM (5 mL) and sat'd aqueous sodium bicarbonate (5 mL). The organic solution was concentrated and the residue was purified using silica gel chromatography (0-15% ethanol in ethyl acetate) to afford (R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide (235) (18.6 mg, 0.04 mmol, 48% yield) as a white solid. MS (ESI +ve ion) m/z: [M+1]=465.8. $^1$H NMR (400 MHz, CHLOROFORM-d) δ 8.21 (s, 1H), 7.88 (d, J=8.02 Hz, 1H), 7.60-7.67 (m, 1H), 6.98-7.12 (m, 2H), 4.49 (ddd, J=2.35, 5.18, 11.64 Hz, 1H), 4.31-4.40 (m, 1H), 4.07-4.12 (m, 1H), 3.96 (d, J=13.89 Hz, 1H), 3.75 (d, J=14.09 Hz, 1H), 3.25 (s, 3H), 1.82 (s, 3H), 1.44 (d, J=6.46 Hz, 3H).

Example 236: (R)-3-amino-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide

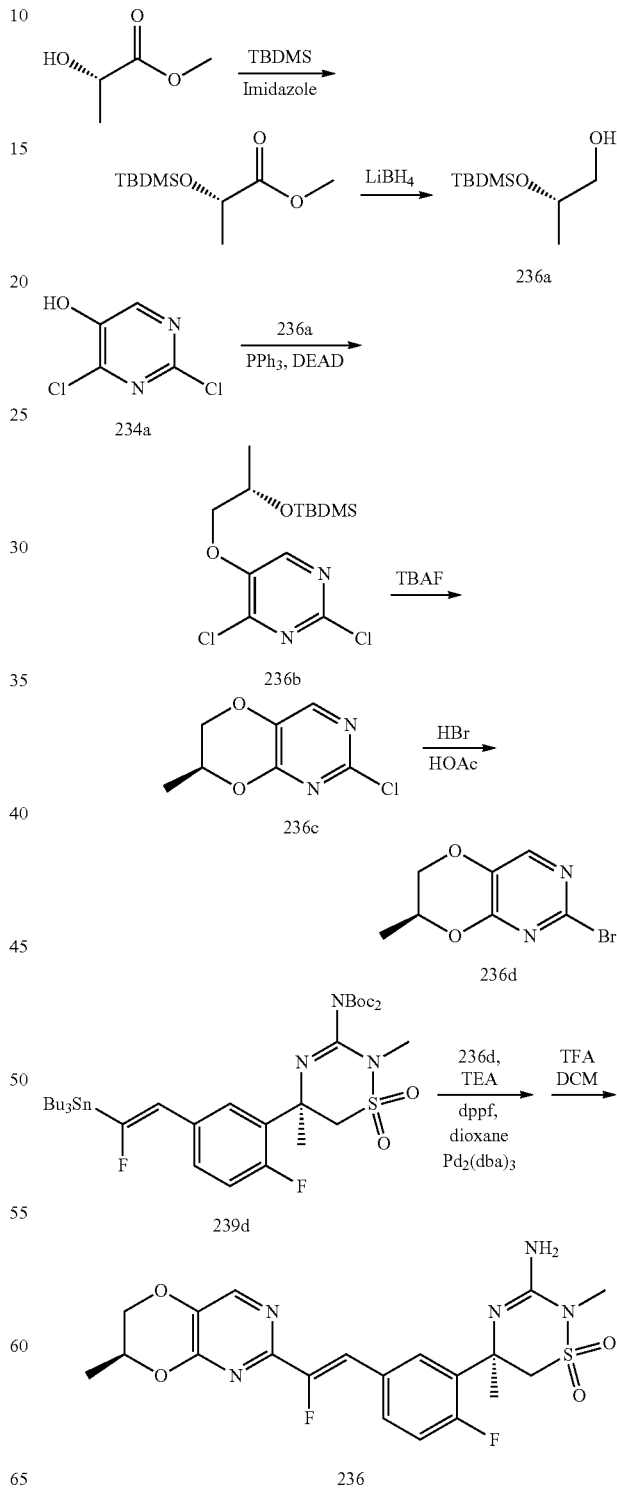

Preparation of (S)-2-((tert-butyldimethylsilyl)oxy) propan-1-ol (236a)

Ethyl lactate (TCI Chemical, Portland, Oreg., USA) (2.0 mL, 17.4 mmol) and imidazole (Sigma-Aldrich, St. Louis, Mo., USA) (1.8 g, 26.4 mmol) were dissolved in DCM (50 mL) under nitrogen. tert-Butylchlorodimethylsilane (Sigma-Aldrich, St. Louis, Mo., USA) (3.1 g, 20.9 mmol) was added and the reaction stirred at RT for 10 h. Dichloromethane (200 mL), water (100 mL) and sat'd aqueous ammonium chloride (75 mL) were added and the phases mixed and separated. The organic phase was dried with magnesium sulfate and evaporated to dryness under reduced pressure. The crude (S)-ethyl 2-((tert-butyldimethylsilyl)oxy)propanoate was used without further purification. MS (ESI +ve ion) m/z: [M+1]=233.0.

(S)-Ethyl 2-((tert-butyldimethylsilyl)oxy)propanoate (4.0 g, 17.2 mmol) and methanol (0.90 mL, 22.2 mmol) were dissolved in methyl tert-butyl ether (80 mL) under nitrogen and cooled in an ice bath. Lithium borohydride (Sigma-Aldrich, St. Louis, Mo., USA) (2.0 M in THF, 11.0 mL, 22.0 mmol) was added dropwise and the reaction stirred for 10 min. It was removed from the cold bath and stirred at RT for 2 h. The solution was recooled in an ice bath and water (5 mL) was added dropwise. A white precipitate formed. The mixture was stirred for 5 min then additional water (45 mL) was added. The phases were separated and the organic layer washed with brine (50 mL) before evaporating to dryness under reduced pressure. The crude (S)-2-((tert-butyldimethylsilyl)oxy)propan-1-ol (236a) was used without further purification. MS (ESI +ve ion) m/z: [M+1]=191.0 $^1$H NMR (400 MHz, CHLOROFORM-d) δ=3.91 (m, 1H), 3.50 (d, J=10.6 Hz, 1H), 3.37 (dd, J=6.5, 10.8 Hz, 1H), 2.02 (br. s., 1H), 1.12 (d, J=6.3 Hz, 3H), 0.90 (s, 9H), 0.09 (s, 6H).

Preparation of (S)-2-chloro-7-methyl-6,7-dihydro-[1,4]dioxino[2,3-d]pyrimidine (236b)

2,4-Dichloropyrimidin-5-ol (234a) (0.75 g, 4.55 mmol) and triphenylphosphine (Sigma-Aldrich, St. Louis, Mo., USA) (1.20 g, 4.58 mmol) were dissolved in tetrahydrofuran (5 mL) under nitrogen and cooled in an ice bath. (S)-2-((tert-Butyldimethylsilyl)oxy)propan-1-ol (236a) (0.865 g, 4.55 mmol) was added followed by dropwise addition of diethyl azodicarboxylate solution (Sigma-Aldrich, St. Louis, Mo., USA) (50 wt % in toluene, 2.10 mL, 4.61 mmol). Once the addition was complete the solution was a light yellow-orange. The reaction was stirred for 5 min then removed from the cold bath. It was stirred at RT for 4 h then evaporated to dryness under reduced pressure. The crude was purified using silica gel chromatography (0-40% ethyl acetate in heptane) to give 236b (0.93 g, 2.77 mmol, 61% yield). MS (ESI +ve ion) m/z: [M+1]=337.0.

Preparation of (S)-2-chloro-7-methyl-6,7-dihydro-[1,4]dioxino[2,3-d]pyrimidine (236c)

(S)-5-(2-((tert-Butyldimethylsilyl)oxy)propoxy)-2,4-dichloropyrimidine (236b) (0.93 g, 2.77 mmol) was dissolved in tetrahydrofuran (75 mL) and tetra-n-butylammonium fluoride (Sigma-Aldrich, St. Louis, Mo., USA) (1 M solution in THF, 2.80 mL, 2.80 mmol) was added dropwise. The solution was stirred for 30 min then water (75 mL) and ethyl acetate (75 mL) were added. The phases were mixed and separated and the organic phase washed with water (75 mL) before evaporating to dryness under reduced pressure. Purification using silica gel chromatography (ethyl acetate/ heptane) gave 236c (0.15 g, 0.81 mmol, 29% yield) as an off white solid. MS (ESI +ve ion) m/z: [M+1]=187.0.

Preparation of (S)-2-bromo-7-methyl-6,7-dihydro-[1,4]dioxino[2,3-d]pyrimidine (236d)

(S)-2-Chloro-7-methyl-6,7-dihydro-[1,4]dihydro[2,3-d] pyrimidine (236c) (0.15 g, 0.81 mmol) was dissolved in a 33 wt % solution of hydrogen bromide in acetic acid (5.00 mL, 0.81 mmol) under nitrogen and heated in a 60° C. bath for 90 min. The mixture was evaporated to dryness under reduced pressure and the crude dissolved in DCM (50 mL). It was washed with sat'd aqueous sodium bicarbonate (40 mL) then evaporated to dryness under reduced pressure. Purification using silica gel chromatography (ethyl acetate/ heptane) gave 236d (0.17 g, 0.75 mmol, 93% yield) as an off white solid. MS (ESI +ve ion) m/z: [M+1]=231.0/233.0.

Preparation of Example 236

(S)-2-Bromo-7-methyl-6,7-dihydro-[1,4]dioxino[2,3-d] pyrimidine intermediate (236d) (0.061 g, 0.264 mmol), tris(dibenzylideneacetone)dipalladium(0) (Sigma-Aldrich, St. Louis, Mo., USA (0.040 g, 0.044 mmol), and 1,1'-bis (diphenylphosphino)ferrocene (Strem Chemicals, Boston, Mass., USA) (0.060 g, 0.108 mmol) were combined then subjected to house vac/nitrogen flush (3×). Dry, degassed dioxane (0.3 mL) and triethylamine (0.10 mL, 0.72 mmol) were added. The mixture was stirred at RT for 10 min then a solution of stannane 239d (0.11 g, 0.14 mmol) in degassed dioxane (0.2 mL) was added. The mixture was heated in at 90° C. for 3 days. The mixture was evaporated to dryness under reduced pressure and purified using silica gel chromatography (0-15% (3:1=ethanol:ethyl acetate) in DCM) to give (R)-3-(bisBoc amino)-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide (0.035 g, 0.053 mmol, 37% yield). MS (ESI +ve ion) m/z: [M+Na$^+$]=687.8.

(R)-3-(bisBoc amino)-5-(2-fluoro-5-((Z)-2-fluoro-2-((S)-7-methyl-6,7-dihydro-[1,4]dioxino[2,3-d]pyrimidin-2-yl) vinyl)phenyl)-2,5-dimethyl-5,6-dihydro-2H-1,2,4-thiadiazine 1,1-dioxide (0.035 g, 0.053 mmol) was dissolved in DCM (2 mL) and treated with trifluoroacetic acid (2 mL). The solution was stirred at RT for 20 min, and evaporated to dryness under reduced pressure. The crude was partitioned between DCM (5 mL) and sat'd aqueous sodium bicarbonate (10 mL). The organic layer was purified using silica gel chromatography (0-15% ethanol in ethyl acetate) to give (R)-3-amino-5-(2-fluoro-5-((Z)-2-fluoro-2-((S)-7-methyl-6, 7-dihydro-[1,4]dioxino[2,3-d]pyrimidin-2-yl)vinyl)phenyl)-2,5-dimethyl-5,6-dihydro-2H-1,2,4-thiadiazine 1,1-dioxide (236) (0.013 g, 0.028 mmol, 53% yield) as a white solid. MS (ESI +ve ion) m/z: [M+1]=466.0. $^1$H NMR (400 MHz, CHLOROFORM-d) δ 8.26 (s, 1H), 7.90 (d, J=7.43 Hz, 1H), 7.64 (br. s., 1H), 7.02-7.14 (m, 2H), 4.54-4.64 (m, 1H), 4.34 (dd, J=1.76, 11.54 Hz, 1H), 3.81-3.95 (m, 2H), 3.67-3.79 (m, 1H), 3.22 (s, 3H), 2.04 (s, 2H), 1.79 (s, 3H), 1.50 (d, J=6.46 Hz, 3H).

Example 237: (R,Z)-3-amino-5-(2,3-difluoro-5-(2-fluoro-2-(5-((4-methylthiazol-2-yl)methoxy)pyrazin-2-yl)vinyl)phenyl)-2,5-dimethyl-5,6-dihydro-2H-1,2,4-thiadiazine 1,1-dioxide

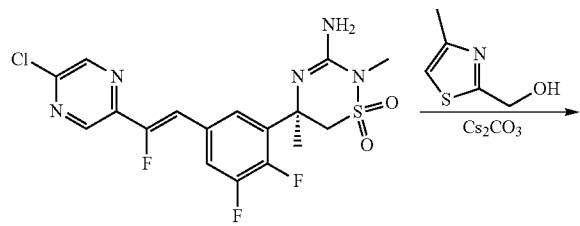

158b

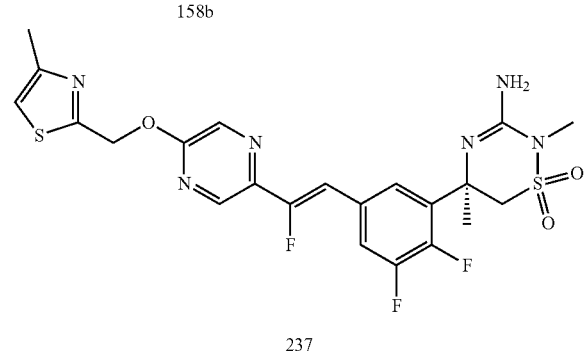

237

This compound (33 mg, 55% yield) as an off-white solid was prepared in a fashion similar to that described in Method D for Example 158, here starting with (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (4-methyl-1,3-thiazol-2-yl)methanol (Combi-Blocks, San Diego, Calif., USA) (57 μL, 0.56 mmol), and cesium carbonate (110 mg, 0.33 mmol) as starting materials. MS (ESI, positive ion) m/z: =539.2 (M+1)⁺. ¹H NMR (400 MHz, DMSO-d₆) δ ppm 8.53 (2H, s), 7.59-7.76 (2H, m), 7.33 (1H, d, J=0.98 Hz), 6.90 (1H, d, J=40 Hz), 6.09 (2H, br s), 5.69 (2H, s), 3.80-3.87 (2H, m), 3.05 (3H, s), 2.37 (3H, s), 1.62 (3H, s). ¹⁹F NMR (376 MHz, DMSO-d₆) δ ppm −123.23 (1F, br s), −138.27 (1F, br d, J=21.67 Hz), −138.99 (1F, br d, J=22.54 Hz).

Example 238: (R,Z)-3-amino-5-(5-(2-(5-((2,5-dimethyloxazol-4-yl)methoxy)pyrazin-2-yl)-2-fluorovinyl)-2,3-difluorophenyl)-2,5-dimethyl-5,6-dihydro-2H-1,2,4-thiadiazine 1,1-dioxide

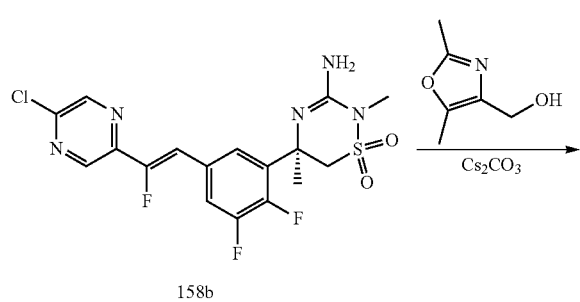

158b

-continued

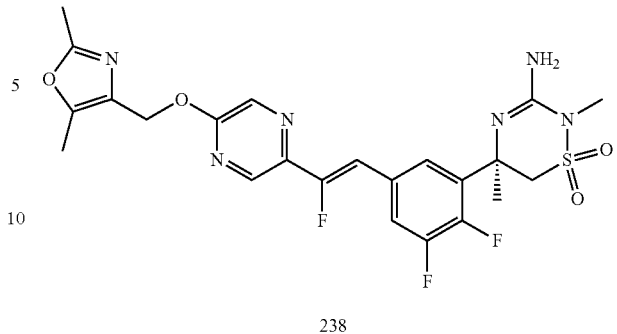

238

This compound (31 mg, 51% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (2,5-dimethyloxazol-4-yl)methanol (Frontier, Logan, Utah, USA) (71 mg, 0.56 mmol), and cesium carbonate (110 mg, 0.33 mmol) and cesium carbonate (110 mg, 0.336 mmol) as starting materials. MS (ESI, positive ion) m/z: =537.2 (M+1)⁺. ¹H NMR (400 MHz, DMSO-d₆) δ ppm 8.51 (1H, s), 8.40 (1H, s), 7.58-7.74 (2H, m), 6.97 (1H, d, J=40 Hz), 6.08 (2H, br s), 5.24 (2H, s), 3.74-3.94 (2H, m), 3.05 (3H, s), 2.34 (6H, d, J=3.72 Hz), 1.62 (3H, s). ¹⁹F NMR (376 MHz, DMSO-d₆) δ ppm −123.24 (1F, br s), −138.41 (1F, br d, J=21.68 Hz), −139.02 (1F, br d, J=21.68 Hz).

Example 239: (5R)-5-(5-((Z)-2-(3,4-dihydro-2H-pyrano[2,3-c]pyridin-6-yl)-2-fluoroethenyl)-2-fluorophenyl)-2,5-dimethyl-5,6-dihydro-2H-1,2,4-thiadiazin-3-amine 1,1-dioxide

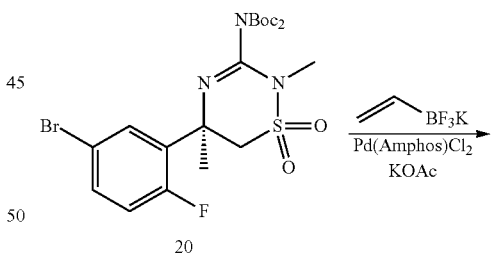

20

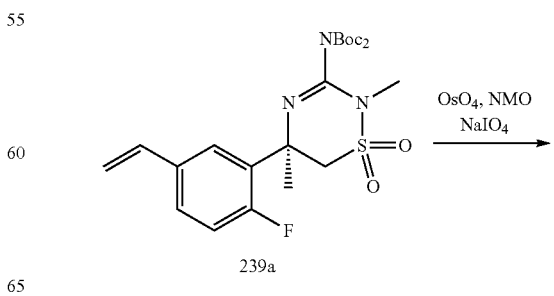

239a

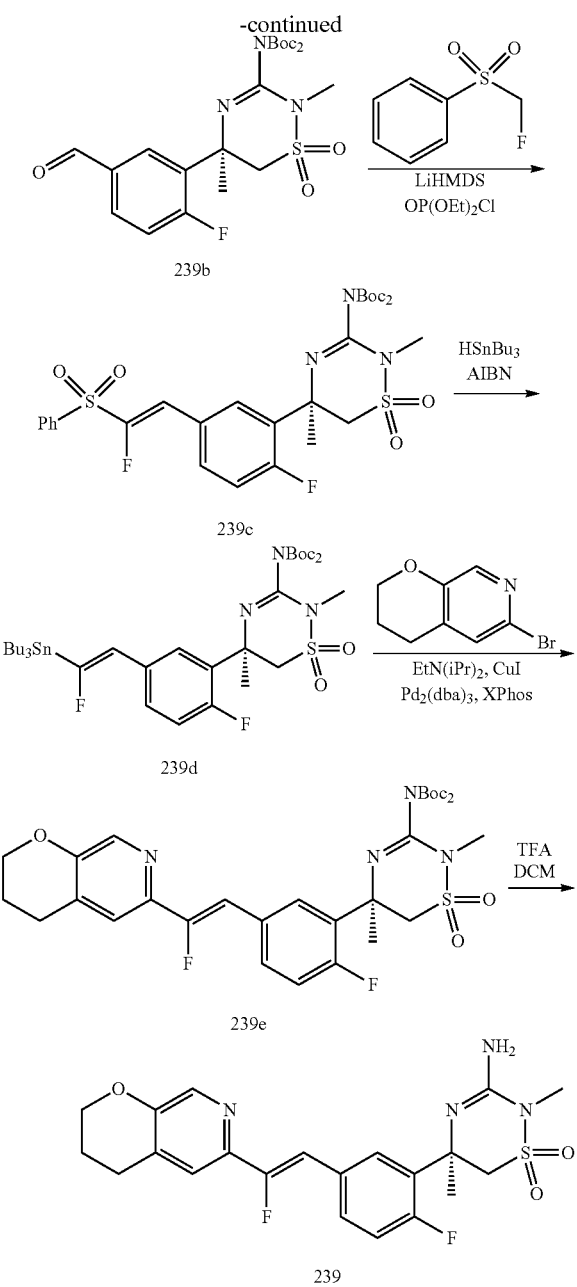

purified by flash chromatography on silica gel (0-50% EtOAc in heptane) to give the styrene product 239a as a yellow oil (6.20 g, 12.46 mmol, 69% yield). MS m/z=342.1 [M+H-Boc-tBu]$^+$.

Preparation of 239b

To a turbid solution of styrene 239a (6.2 g, 12.46 mmol) in THF (93 mL) was added 4-methylmorpholine-N-oxide (Sigma-Aldrich Chemical Company, Inc., St. Louis, Mo., USA) (2.19 g, 18.69 mmol) in water (31.2 mL)/tetrahydrofuran (93 mL) followed by osmium tetroxide (Strem Chemicals, Inc., Newburyport, Mass., USA) (7.61 mL of 4 wt. % solution in water, 1.24 mmol). The turbid solution became transparent and after stirring at 23° C. for 4 h, LCMS analysis indicated >95% conversion to the putative diol intermediate. Sodium (meta)periodate (Sigma-Aldrich Chemical Company, Inc., St. Louis, Mo., USA) (81 mg, 0.38 mmol) was added, resulting in a slurry. After 2 h, the desired aldehyde 239b was formed and reaction complete by LCMS analysis. The mixture was diluted with EtOAc (200 mL). The organic layer was washed with saturated $Na_2S_2O_3$ (5×60 mL), brine (60 mL), dried over $MgSO_4$, and concentrated. The resulting oil was purified by silica gel chromatography (0 to 50% 3:1 EtOAc/EtOH in heptane) to give the aldehyde product 239b as an off-white foam (5.03 g, 10.07 mmol, 81% yield). MS m/z=522.2 [M+Na]$^+$. $^1$H NMR (400 MHz, CHLOROFORM-d) δ ppm 9.98 (s, 1H), 8.27 (dd, J=7.83, 2.15 Hz, 1H), 7.89 (ddd, J=8.27, 4.84, 2.15 Hz, 1H), 7.20-7.27 (m, 1H), 3.65-3.88 (m, 2H), 3.14-3.21 (m, 3H), 1.87 (s, 3H), 1.55 (s, 18H).

Preparation of 239c

Fluoromethyl phenyl sulfone (Matrix Scientific, Columbia, S.C., USA) (3.40 g, 19.52 mmol) and diethyl chlorophosphate (Sigma-Aldrich Chemical Company, Inc., St. Louis, Mo., USA) (2.83 mL, 19.52 mmol) were taken up in dry THF (50 mL) under $N_2$. This mixture was cooled to −78° C. via a dry ice/acetone bath. A lithium bis(trimethylsilyl) amide 1.0 M solution in THF (Sigma-Aldrich Chemical Company, Inc., St. Louis, Mo., USA) (39.0 mL, 39.0 mmol) was added dropwise and then the reaction was stirred at −78° C. for 1 h. A solution of aldehyde 239b (3.9 g, 7.81 mmol) in 28 mL of dry THF was then added dropwise. The reaction was allowed to warm to 23° C. and stirred for 12 h, at which point the reaction was determined to be complete by LCMS analysis. The reaction was diluted with 200 mL of EtOAc, cooled to 0° C. and quenched with sat'd aqueous $NH_4Cl$ (100 mL). The aqueous layer was diluted with 100 mL of water and extracted with EtOAc (3×50 mL). The combined organic fractions were dried over $MgSO_4$, concentrated and then purified via silica gel chromatography (0-25% 3:1 Ethyl acetate/EtOH in heptane) to give vinyl sulfone 239c (3.75 g, 5.57 mmol, 74% yield) as a mixture with the corresponding mono-boc deprotection product in a 5:1 ratio. This mixture was taken on as is. MS m/z=678.2 [M+Na]$^+$.

Preparation of 239d

A mixture of vinyl sulfone 239c (2.35 g, 3.58 mmol), and 2,2'-azobis(2-methylpropionitrile) (Sigma-Aldrich Chemical Company, Inc., St. Louis, Mo., USA) (59 mg, 0.36 mmol) were combined in a sealable vial, evacuated and backfilled with $N_2$. 1,4-dioxane (7.17 mL) which had been sparged with Ar for 10 min was added, followed by the dropwise addition of tributylstannane (Sigma-Aldrich Preparation of 239a A 250 mL round bottom flask was charged with potassium acetate (Sigma-Aldrich Chemical Company, Inc., St. Louis, Mo., USA) (5.34 g, 54.5 mmol), 1,1-bis[(di-t-butyl-p-methylaminophenyl]palladium(II) chloride (Sigma-Aldrich Chemical Company, Inc., St. Louis, Mo., USA) (0.57 g, 0.80 mmol), potassium vinyltrifluoroborate (Sigma-Aldrich Chemical Company, Inc., St. Louis, Mo., USA) (3.16 g, 23.62 mmol), and aryl bromide 20 (10.00 g, 18.17 mmol) under an $N_2$ atmosphere. Acetonitrile (68.1 mL) and water (22.7 mL) were added and the mixture was heated at 75° C. for 1.5 h then at 60° C. for 12 h. The crude mixture was diluted with EtOAc (150 mL), washed with sat'd aqueous $NaHCO_3$ (60 mL), brine (60 mL), dried over $MgSO_4$ and concentration under reduced pressure. The residue was Chemical Company, Inc., St. Louis, Mo., USA) (1.93 mL, 7.17 mmol). The mixture was heated to 80° C. for 12 h (a clear solution at 80° C.). LCMS showed incomplete conversion to the desired product ([M+H-boc]$^+$=706 and [M+H-boc-tbutyl]$^+$ 650 observed), 2 additional equivalents of tributyltin hydride (1.93 mL, 7.17 mmol) were added to the reaction mixture and stirring was continued for 12 h at 80° C. The reaction mixture was concentrated, diluted with DCM (50 mL), adsorbed onto SiO$_2$ and purified via silica gel chromatography (0-15% EtOAc/EtOH in heptane) to give the desired vinyl stannane 239d as a colorless oil (0.54 g, 0.67 mmol, 19% yield). MS m/z=650.4 [M+H-boc-tBu]$^+$. $^1$H NMR (400 MHz, CHLOROFORM-d) δ ppm 7.98 (d, J=7.83 Hz, 1H), 7.69-7.80 (m, 1H), 6.94-7.09 (m, 1H), 5.49-5.75 (m, 1H), 3.96 (d, J=14.08 Hz, 1H), 3.49 (d, J=14.09 Hz, 1H), 3.10-3.21 (m, 3H), 1.79-1.92 (m, 3H), 1.51-1.58 (m, 18H), 1.28-1.40 (m, 12H), 1.01-1.11 (m, 6H), 0.91 (t, J=7.34 Hz, 9H).

Preparation of (5R)-5-(5-((Z)-2-(3,4-dihydro-2H-pyrano[2,3-c]pyridin-6-yl)-2-fluoroethenyl)-2-fluorophenyl)-2,5-dimethyl-5,6-dihydro-2H-1,2,4-thiadiazin-3-amine 1,1-dioxide (239)

2-(Dicyclohexylphosphino)-2',4',6',-tri-isopropyl-1,1'-biphenyl (Strem Chemicals, Inc., Newburyport, Mass., USA) (7.8 mg, 0.016 mmol), tris(dibenzylideneacetone)dipalladium(0) (Strem Chemicals, Inc., Newburyport, Mass., USA) (10 mg, 10.94 μmol), copper(I) iodide (Sigma-Aldrich Chemical Company, Inc., St. Louis, Mo., USA) (21 mg, 0.11 mmol) and 6-bromo-3,4-dihydro-2H-pyrano[2,3-c]pyridine (47 mg, 0.22 mmol) were combined in a vial, which was then capped with a septum, evacuated and backfilled with N$_2$ (3×). 1,4-Dioxane (1.09 mL) was added and the mixture was stirred at 23° C. for 1 h at which point Hunig's base (Sigma-Aldrich Chemical Company, Inc., St. Louis, Mo., USA) (0.057 mL, 0.33 mmol) then stannane 239d (88 mg, 0.11 mmol) were added dropwise, neat and as a solution in dioxane (0.5 mL), respectively. The mixture was stirred at 80° C. for 24 h. The reaction mixture was diluted with DCM (2 mL) and adsorbed onto SiO$_2$, then purified via silica gel chromatography using a 0-50% gradient of 3:1 EtOAc/EtOH in heptane to give thiadiazine 239e (15 mg, 0.023 mmol, 21% yield) as a white solid. MS m/z=671.1 [M+Na]$^+$. Thiadiazine 239e (0.01 g, 0.015 mmol) was immediately taken up in dichloromethane (0.15 mL) then trifluoroacetic acid (3 μL, 0.04 mmol) was added dropwise. The mixture was stirred at 40° C. for 12 h. The mixture was diluted with sat'd aqueous NaHCO$_3$ (2 mL) and extracted with EtOAc (5 mL×3). The organic solution was concentrated and the residue was purified via Gilson reverse phase preparatory HPLC (5-95% gradient of (0.1% TFA in MeCN) in (0.1% TFA in H$_2$O). The combined fractions were concentrated, basified to pH 10 with 1 N NaOH, extracted with EtOAc (3×) and DCM (2×), and the collected organic fractions concentrated in vacuo to afford Example 239 (2.2 mg, 4.91 μmol, 31% yield) as a white solid. MS m/z=449.4 [M+H]$^+$. $^1$H NMR (400 MHz, CHLOROFORM-d) δ ppm 8.11 (s, 1H), 7.82 (dd, J=8.22, 1.96 Hz, 1H), 7.55-7.65 (m, 1H), 7.27 (s, 1H), 6.96-7.08 (m, 1H), 6.71-6.88 (m, 1H), 4.18-4.29 (m, 2H), 3.63-3.87 (m, 2H), 3.19 (s, 3H), 2.78 (t, J=6.36 Hz, 2H), 1.96-2.08 (m, 2H), 1.77 (s, 3H). $^{19}$F NMR (376 MHz, CHLOROFORM-d) δ ppm -113.60 (d, J=1.73 Hz, 1F), -122.44 (br s, 1F).

Example 240: (5R)-5-(2-fluoro-5-((Z)-2-fluoro-2-(5-fluoro-2-pyridinyl)ethenyl)phenyl)-2,5-dimethyl-5,6-dihydro-2H-1,2,4-thiadiazin-3-amine 1,1-dioxide

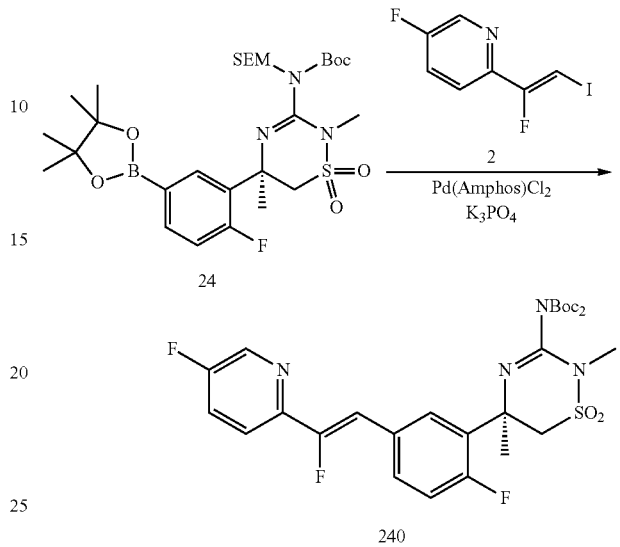

This compound (27 mg, 27% yield) as a white solid was prepared in a fashion similar to that described in Method C for Example 111, here starting with (Z)-5-fluoro-2-(1-fluoro-2-iodovinyl)pyridine 2 (70 mg, 0.26 mmol) and boronic ester 24 (0.15 g, 0.24 mmol). MS m/z=411.1 [M+H]$^+$. $^1$H NMR (400 MHz, DMSO-d6) δ 8.58-8.74 (m, 1H), 7.82-7.93 (m, 2H), 7.71-7.80 (m, 1H), 7.59-7.68 (m, 1H), 7.15-7.27 (m, 1H), 6.91-7.11 (m, 1H), 5.90-6.27 (m, 2H), 3.70-3.91 (m, 2H), 2.95-3.15 (m, 3H), 1.52-1.73 (m, 3H). $^{19}$F NMR (376 MHz, DMSO-d$_6$) δ -111.93 (s, 1F), -122.59 (br s, 1F), -126.33 (s, 1F).

Example 241: (5R)-5-(2-fluoro-5-((Z)-2-fluoro-2-(5-methoxy-2-pyrazinyl)ethenyl)phenyl)-2,5-dimethyl-5,6-dihydro-2H-1,2,4-thiadiazin-3-amine 1,1-dioxide

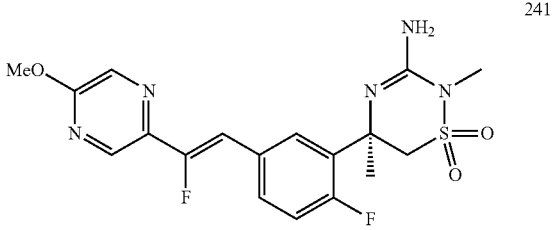 [SMILES: COc1cnc(/C(F)=C/c2ccc(F)c([C@]3(C)CS(=O)(=O)N(C)C(N)=N3)c2)cn1]

This compound (35 mg, 34% yield) as a white solid was prepared in a fashion similar to that described in Method C for Example 111, here starting (Z)-5-fluoro-2-(1-fluoro-2-iodovinyl)pyridine 14 (74 mg, 0.26 mmol) and (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate 24 (0.15 g, 0.24 mmol). MS m/z=424.1 [M+H]$^+$. $^1$H NMR (400 MHz, DMSO-d6) δ 8.47 (s, 1H), 8.29-8.43 (m, 1H), 7.87 (dd, J=1.76, 8.02 Hz, 1H), 7.55-7.75 (m, 1H), 7.21 (dd, J=8.41, 12.13 Hz, 1H), 6.76-6.98 (m, 1H), 6.09 (br s, 2H), 3.97 (s, 3H), 3.81 (s, 2H), 3.04 (s, 3H), 1.61 (s, 3H). $^{19}$F NMR (376 MHz, DMSO-d6) δ -112.16 (s, 1F), -124.71 (br s, 1F).

Example 242: (5R)-5-(5-((Z)-2-(3-chloro-5-(trifluoromethyl)-2-pyridinyl)-2-fluoroethenyl)-2-fluorophenyl)-2,5-dimethyl-5,6-dihydro-2H-1,2,4-thiadiazin-3-amine 1,1-dioxide

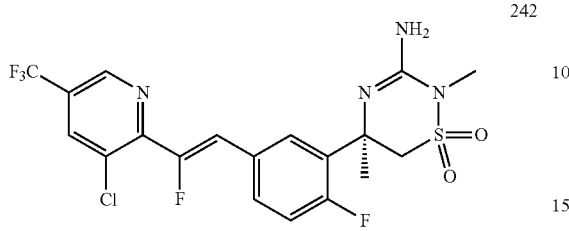

242

This compound (23 mg, 19% yield) as a white solid was prepared in a fashion similar to that described in Method C for Example 111, here starting with (Z)-5-fluoro-2-(1-fluoro-2-iodovinyl)pyridine 9 (92 mg, 0.26 mmol) and (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl)carbamate 24 (0.15 g, 0.24 mmol). MS m/z=495.2 [M+H]$^+$. $^1$H NMR (400 MHz, DMSO-d6) δ 8.96-9.08 (m, 1H), 8.52-8.65 (m, 1H), 7.84-7.95 (m, 1H), 7.61-7.70 (m, 1H), 7.16-7.30 (m, 1H), 6.82-7.02 (m, 1H), 6.02-6.23 (m, 2H), 3.73-3.91 (m, 2H), 2.97-3.14 (m, 3H), 1.50-1.76 (m, 3H). $^{19}$F NMR (376 MHz, DMSO-d6) δ −60.77 (s, 3F), −110.76 (s, 1F), −113.50 (br s, 1F).

Example 243: (R,Z)-ethyl 2-((5-(2-(3-(3-amino-2,5-dimethyl-1,1-dioxido-5,6-dihydro-2H-1,2,4-thiadiazin-5-yl)-4,5-difluorophenyl)-1-fluorovinyl)pyrazin-2-yl)oxy)acetate

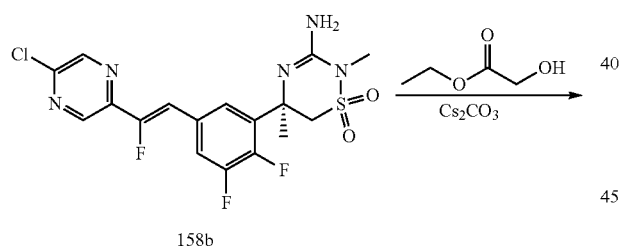

158b

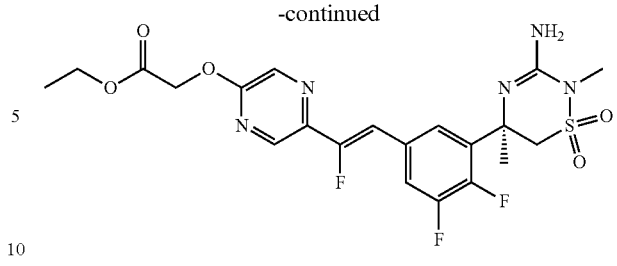

243

This compound (15 mg, 26% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), ethyl glycolate (Sigma-Aldrich, 53 µL, 0.56 mmol), and cesium carbonate (110 mg, 0.33 mmol) and cesium carbonate (110 mg, 0.33 mmol) as starting materials. MS (ESI, positive ion) m/z: =514.1 (M+1)$^+$. $^1$H NMR (400 MHz, DMSO-d$_6$) δ ppm 8.61 (2H, br s), 8.56 (1H, s), 8.49 (1H, s), 7.80 (1H, br dd, J=9.59, 7.24 Hz), 7.51 (1H, br d, J=6.26 Hz), 7.03 (1H, d, J=40 Hz), 5.06 (2H, s), 4.54-4.69 (2H, m), 4.16 (2H, q, J=7.04 Hz), 3.23 (3H, s), 1.86 (3H, s), 1.12-1.27 (3H, m). $^{19}$F NMR (376 MHz, DMSO-d$_6$) δ ppm −73.98 (1F, br d, J=177.73 Hz), −137.53 (2F, br dd, J=188.13, 21.67 Hz).

Example 244: (5R)-5-(2-fluoro-5-((Z)-2-fluoro-2-(5-(trifluoromethyl)-2-pyridinyl)ethenyl)phenyl)-2,5-dimethyl-5,6-dihydro-2H-1,2,4-thiadiazin-3-amine 1,1-dioxide

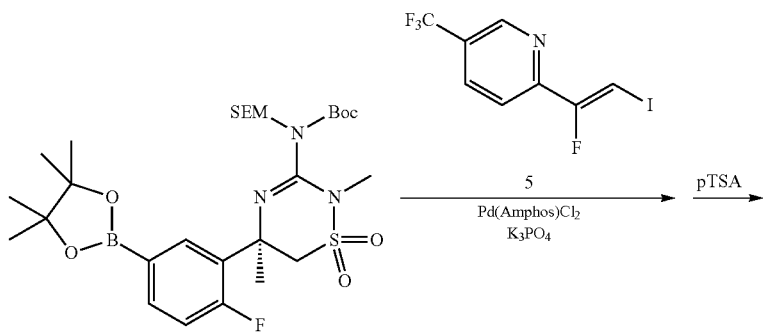

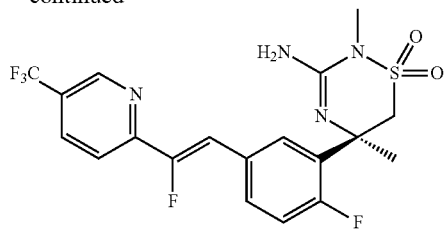

244

This compound (22 mg, 36% yield) as an off-white solid was prepared in a fashion similar to that described in Method C for Example 111, starting from boronic ester 24 (100 mg, 0.16 mmol) and (Z)-2-(1-fluoro-2-iodovinyl)-5-(trifluoromethyl)pyridine (5) (42 mg, 0.13 mmol). MS (ESI, positive ion) m/z: 461. $^1$H NMR (400 MHz, DMSO-d$_6$) δ 8.90-9.15 (m, 1H), 8.28-8.41 (m, 1H), 7.92-8.02 (m, 1H), 7.84-7.91 (m, 1H), 7.65-7.79 (m, 1H), 6.98-7.39 (m, 2H), 6.07 (br s, 2H), 3.73-3.89 (m, 2H), 3.04 (s, 3H), 1.61 (s, 3H).

Example 245: 6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-5-methyl-3-pyridinecarbonitrile

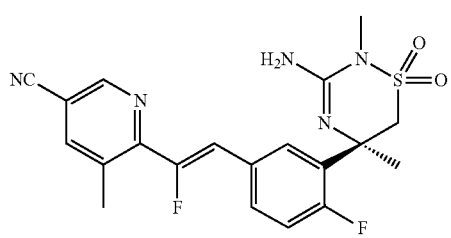

245

This compound (41 mg, 48% yield) as an off-white solid was prepared in a fashion similar to that described in Method C for Example 111, starting from boronic ester 24 (150 mg, 0.24 mmol) and (Z)-6-(1-fluoro-2-iodovinyl)-5-methylnicotinonitrile (7) (57 mg, 0.20 mmol). MS (ESI, positive ion) m/z: 432. $^1$H NMR (400 MHz, DMSO-d$_6$) δ 8.84-8.95 (m, 1H), 8.30 (d, J=1.17 Hz, 1H), 7.90 (br d, J=7.24 Hz, 1H), 7.56-7.72 (m, 1H), 7.23 (dd, J=8.51, 12.03 Hz, 1H), 6.97 (d, J=38.73 Hz, 1H), 6.05 (br s, 2H), 3.71-3.86 (m, 2H), 2.94-3.12 (m, 3H), 1.61 (s, 3H).

Example 246: (R,Z)-3-amino-5-(2,3-difluoro-5-(2-fluoro-2-(5-((5-methyloxazol-2-yl)methoxy)pyrazin-2-yl)vinyl)phenyl)-2,5-dimethyl-5,6-dihydro-2H-1,2,4-thiadiazine 1,1-dioxide

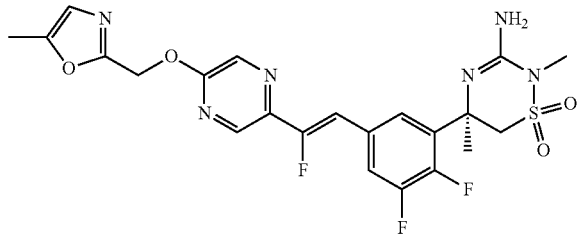

246

This compound (39 mg, 64% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), (5-methyloxazol-2-yl)methanol (Enamine, 66 mg, 0.58 mmol), and cesium carbonate (114 mg, 0.35 mmol) as starting materials. MS (ESI, positive ion) m/z: =523.1 (M+1)$^+$. $^1$H NMR (400 MHz, DMSO-d$_6$) δ ppm 8.51 (2H, s), 7.59-7.72 (2H, m), 6.90 (1H, d, J=40 Hz), 6.89 (1H, s), 6.09 (2H, br s), 5.48 (2H, s), 3.84 (2H, br s), 3.05 (3H, s), 2.31 (3H, s), 1.62 (3H, s). $^{19}$F NMR (376 MHz, DMSO-d$_6$) δ ppm −123.25 (1F, s), −138.24--138.30 (1F, s), −138.95--139.01 (1F, s).

Example 247: (R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide

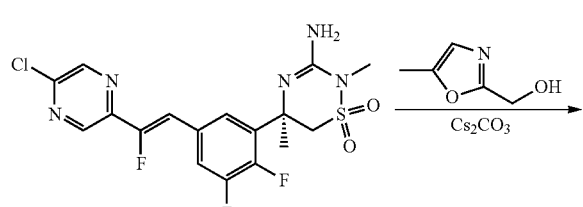

158b

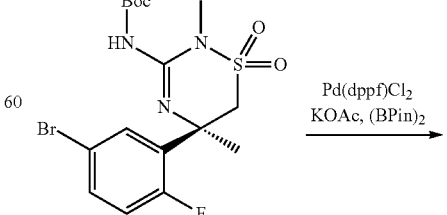

20g

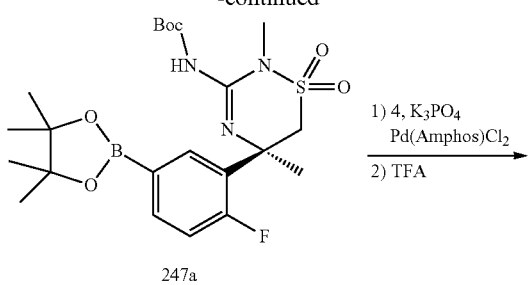

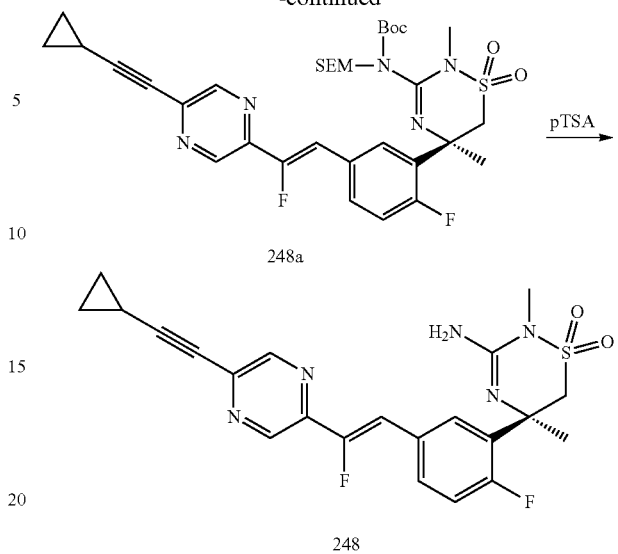

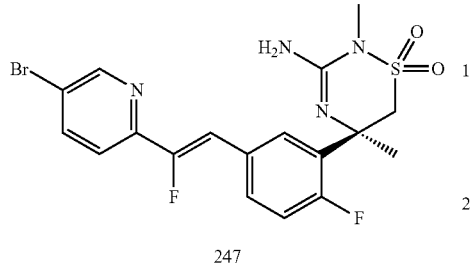

A mixture of (R)-tert-butyl (5-(5-bromo-2-fluorophenyl)-2,5-dimethyl-1,1-dioxido-5,6-dihydro-2H-1,2,4-thiadiazin-3-yl)carbamate (20 g, 1.23 g, 2.73 mmol), bis(pinacolato)diboron (0.69 g, 2.73 mmol), potassium acetate (0.80 g, 8.19 mmol) and 1,4-dioxane (15 mL) was purged with Ar, then [1,1'-bis(diphenylphosphino)ferrocene]-dichloropalladium (II) complex with dichloromethane (0.13 g, 0.16 mmol) was added. The mixture was heated to 90° C. for 2.5 h, cooled to RT, and filtered through celite. The cake was washed with EtOAc. The filtrate was concentrated in vacuo to give 247a as a dark oil which was used without purification. MS m/z=498 [M+H]+, 398 [M+H]+, and 416 [M+H]+.

Example 247 (548 mg, 42% yield) as off-white solid was prepared in a fashion similar to that described in Method E for Example 258, using (Z)-5-bromo-2-(1-fluoro-2-iodovinyl)pyridine (4, 1.34 g, 4.10 mmol) and boronic ester (247a, 1.36 g, 2.73 mmol) as starting materials. MS m/z=471.0/473.0 [M+H]+. $^1$H NMR (400 MHz, DMSO-$d_6$) δ ppm 8.78 (d, J=1.56 Hz, 1H) 8.19 (dd, J=8.41, 2.15 Hz, 1H) 7.89 (br d, J=7.04 Hz, 1H) 7.59-7.71 (m, 2H) 7.23 (dd, J=11.93, 8.61 Hz, 1H) 7.01-7.17 (m, 1H) 5.93-6.38 (m, 2H) 3.85 (br s, 2H) 3.05 (s, 3H) 1.63 (s, 3H).

Example 248: (R,Z)-3-amino-5-(5-(2-(5-(cyclopropylethynyl)pyrazin-2-yl)-2-fluorovinyl)-2-fluorophenyl)-2,5-dimethyl-5,6-dihydro-2H-1,2,4-thiadiazine 1,1-dioxide To a mixture of (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (111a, 0.15 g, 0.23 mmol), trans-dichlorobis(triphenyl-phosphine)palladium (II) (0.016 g, 0.023 mmol), copper(I) iodide (4.34 mg, 0.023 mmol), N,N-dimethylacetamide (2 mL) and N,N-diisopropylethylamine (0.40 mL, 2.28 mmol) purged with Ar was added cyclopropylacetylene (0.10 mL, 1.14 mmol). The mixture was heated at 50° C. for 3 h, diluted with EtOAc and washed with water. The organic solution was dried over Na$_2$SO$_4$, and concentrated in vacuo. The crude was purified by silica gel chromatography (0-50% EtOAc in heptane) to afford 248a (0.13 g, 84% yield) as a yellow solid. MS m/z=688 [M+H]+.

A mixture of 248a (0.13 g, 0.19 mmol), p-toluenesulfonic acid monohydrate (0.12 g, 0.61 mmol), and 1,4-dioxane (1 mL) was heated at 80° C. for 1.5 h. The mixture was diluted with saturated Na$_2$CO$_3$ and extracted with EtOAc. The organic solution was dried over Na$_2$SO$_4$ and concentrated in vacuo. The crude was purified by silica gel chromatography (0-100% EtOAc/EtOH (3/1) in heptane) to afford Example 248 (66 mg, 75% yield) as an off-white solid. MS m/z=458 [M+H]+. $^1$H NMR (400 MHz, DMSO-$d_6$) δ 8.85 (s, 1H), 8.70 (s, 1H), 7.86-7.99 (m, 1H), 7.61-7.73 (m, 1H), 7.24 (dd, J=8.51, 12.03 Hz, 1H), 7.03-7.18 (m, 1H), 5.98-6.16 (m, 2H), 3.71-3.86 (m, 2H), 3.04 (s, 3H), 1.69 (m, 1H), 1.61 (s, 3H), 0.96-1.05 (m, 2H), 0.83-0.90 (m, 2H).

Example 249: (R,Z)-3-amino-5-(2,3-difluoro-5-(2-fluoro-2-(5-((1-methyl-1H-imidazol-2-yl)methoxy)pyrazin-2-yl)vinyl)phenyl)-2,5-dimethyl-5,6-dihydro-2H-1,2,4-thiadiazine 1,1-dioxide

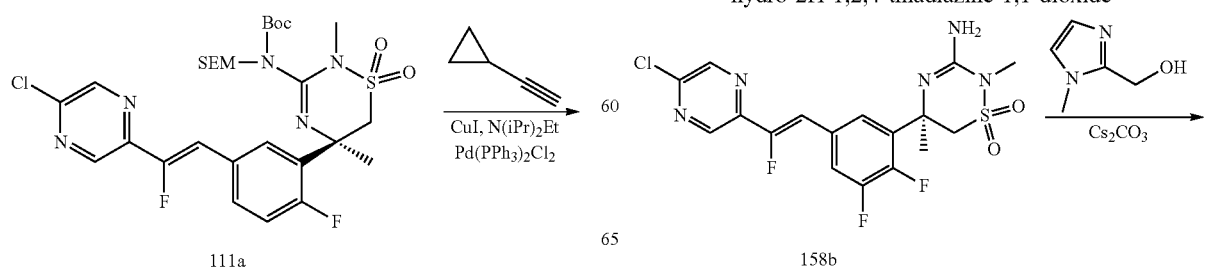

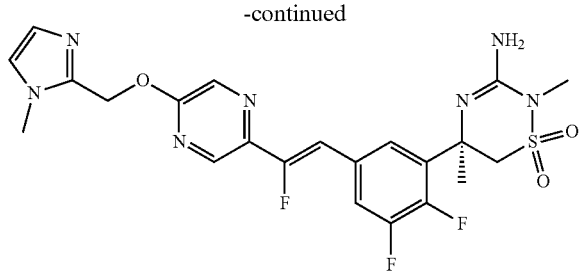

249

This compound (22 mg, 38% yield) as an off-white solid was prepared in a fashion similar to that described in Method D for Example 158, here using (R,Z)-3-amino-5-(5-(2-(5-chloropyrazin-2-yl)-2-fluorovinyl)-2,3-difluorophenyl)-2,5-dimethyl-5,6-dihydro-2H-1,2,4-thiadiazine 1,1-dioxide (158b, 50 mg, 0.11 mmol), 1-methyl-1H-imidazol-2-yl-methanol (Sigma-Aldrich, 38 mg, 0.33 mmol), and cesium carbonate (73 mg, 0.22 mmol) as starting materials. MS (ESI, positive ion) m/z: =522.0 (M+1)⁺. $^1$H NMR (400 MHz, DMSO-$d_6$) δ ppm 8.53 (1H, s), 8.45 (1H, s), 7.60-7.73 (2H, m), 7.22 (1H, s), 6.90 (1H, s), 6.89 (1H, d, J=40 Hz), 5.45 (2H, s), 3.78-3.91 (2H, m), 3.72 (3H, s), 3.05 (3H, s), 1.63 (3H, s). $^{19}$F NMR (376 MHz, DMSO-$d_6$) δ ppm −123.20 (1F, s), −138.32--138.37 (1F, d, J=20 Hz)), −138.95--139.01 (1F, d, J=24 Hz).

Example 250: (5R)-5-(2-fluoro-5-((Z)-2-fluoro-2-(pyrido[3,4-b]pyrazin-7-yl)ethenyl)phenyl)-2,5-dimethyl-5,6-dihydro-2H-1,2,4-thiadiazin-3-amine 1,1-dioxide

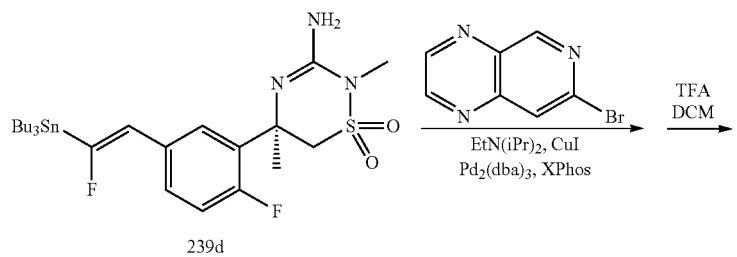

239d

This compound (38 mg, 19% yield) as a white solid was prepared in a fashion similar to that described for Example 239, here starting with 7-bromopyrido[3,4-b]pyrazine (J & W Parmlab, LLC, Levittown, Pa., USA) (69 mg, 0.33 mmol) and stannane 239d (132 mg, 0.16 mmol). MS m/z=445.1 [M+H]⁺. $^1$H NMR (400 MHz, CDCl$_3$) δ ppm 9.50 (s, 1H), 9.04 (br s, 1H), 8.92 (s, 1H), 8.14-8.24 (m, 1H), 7.91 (br s, 1H), 7.77 (br d, J=6.46 Hz, 1H), 6.96-7.15 (m, 3H), 3.92 (br d, J=13.69 Hz, 1H), 3.72 (br d, J=15.06 Hz, 1H), 1.82 (br s, 3H), 1.26 (br s, 2H). NH$_2$ peak was not observed. $^{19}$F NMR (376 MHz, CDCl$_3$) δ ppm −123.28 (br s, 1F), −111.90 (s, 1F).

Example 251: (R,Z)-3-amino-5-(5-(2-(5-(cyclopropylethynyl)pyridin-2-yl)-2-fluorovinyl)-2-fluorophenyl)-2,5-dimethyl-5,6-dihydro-2H-1,2,4-thiadiazine 1,1-dioxide

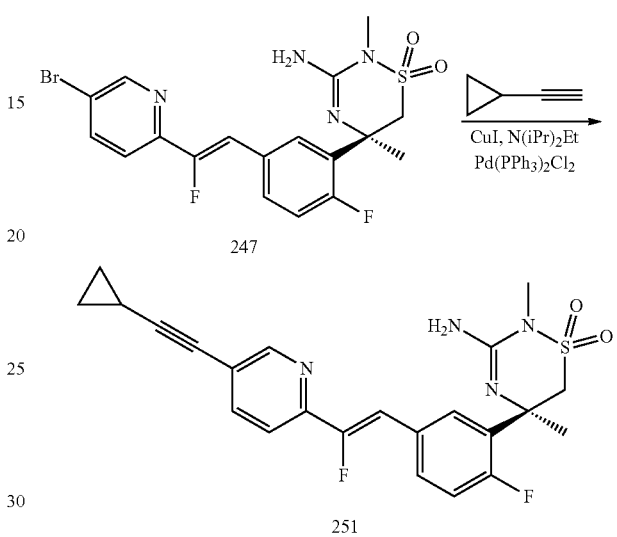

This compound (45 mg, 59% yield) as a yellow solid was prepared in a fashion similar to that described for Example 248, here using (R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide (247, 78 mg, 0.16 mmol) as starting material. MS m/z=457 [M+H]⁺. $^1$H NMR (400 MHz, DMSO-$d_6$) δ ppm 8.61 (d, J=1.37 Hz, 1H) 7.89 (dd, J=8.31, 2.05 Hz, 2H) 7.56-7.72 (m, 2H) 7.21 (dd, J=12.03, 8.51 Hz, 1H) 7.01-7.14 (m, 1H) 5.98-6.14 (m, 2H) 3.70-3.86 (m, 2H) 3.04 (s, 3H) 1.55-1.69 (m, 4H) 0.90-1.00 (m, 2H) 0.77-0.83 (m, 2H).

Example 252: (R,Z)-3-amino-5-(2-fluoro-5-(2-fluoro-2-(5-((4-hydroxybut-2-yn-1-yl)oxy)pyrazin-2-yl)vinyl)phenyl)-2,5-dimethyl-5,6-dihydro-2H-1,2,4-thiadiazine 1,1-dioxide

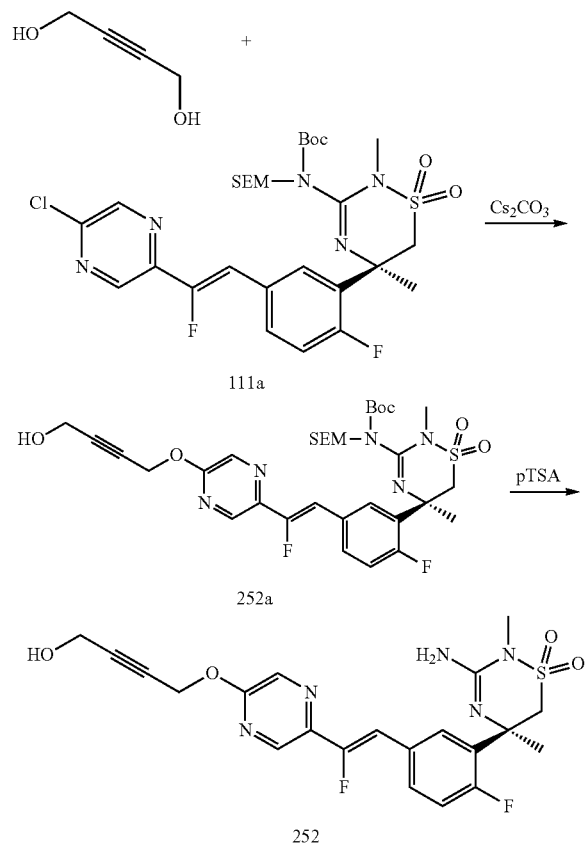

A mixture of (R,Z)-tert-butyl (5-(5-(2-(5-chloropyrazin-2-yl)-2-fluorovinyl)-2-fluorophenyl)-2,5-dimethyl-1,1-dioxido-5,6-dihydro-2H-1,2,4-thiadiazin-3-yl)((2-(trimethylsilyl)ethoxy)methyl)carbamate (111a, 0.168 g, 0.255 mmol), THF (4 mL), but-2-yne-1,4-diol (Sigma-Aldrich, 0.044 g, 0.511 mmol), and cesium carbonate (0.125 g, 0.383 mmol) was heated at 70° C. for 3 h. Additional but-2-yne-1,4-diol (0.044 g, 0.511 mmol) was added and the reaction was continued for 8 h. The mixture was diluted with EtOAc and washed with water. The organic solution was dried over Na$_2$SO$_4$, and concentrated in vacuo. The crude was purified by silica gel chromatography (0-100% EtOAc in heptane) to afford 252a as a white solid (115 mg, 64% yield). MS m/z=708 [M+H]$^+$.

A mixture of 252a (29 mg, 0.041 mmol) and p-toluenesulfonic acid monohydrate (23 mg, 0.123 mmol), and 1,4-dioxane (1 mL) was heated at 80° C. for 1.5 h. It was diluted with saturated Na$_2$CO$_3$ and extracted with EtOAc. The organic solution was dried over Na$_2$SO$_4$ and concentrated in vacuo. The crude was purified by silica gel chromatography (0-100% EtOAc/EtOH (3/1) in heptane) to give Example 252 as a white solid (12 mg, 59% yield). MS m/z=478 [M+H]$^+$. $^1$H NMR (400 MHz, DMSO-d$_6$) δ 8.50 (s, 1H), 8.45 (s, 1H), 7.84-7.92 (m, 1H), 7.63 (br dd, J=3.42, 6.55 Hz, 1H), 7.16-7.27 (m, 1H), 6.81-6.96 (m, 1H), 6.05 (br s, 2H), 5.25 (t, J=5.97 Hz, 1H), 5.13 (s, 2H), 4.12 (br d, J=6.06 Hz, 2H), 3.75-3.84 (m, 2H), 3.05 (s, 3H), 1.61 (s, 3H). $^{19}$F NMR (376 MHz, DMSO-d$_6$) δ −113.02−−110.93 (m, 1F), −125.48−−123.91 (m, 1F).

Example 253: 2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-5-carbonitrile

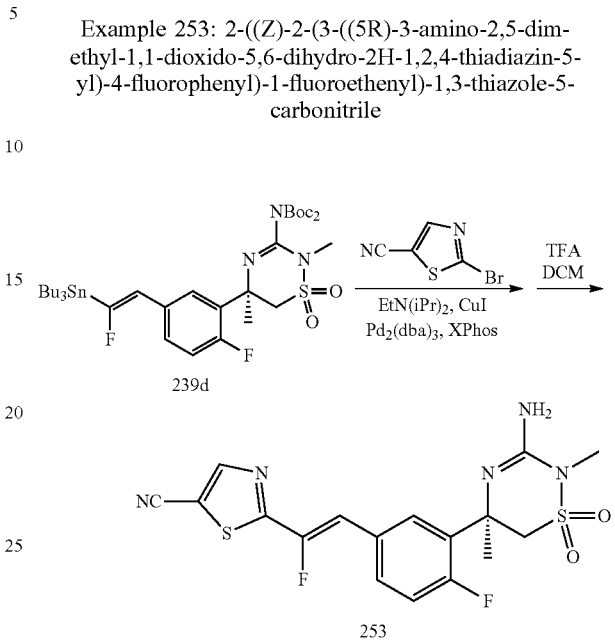

This compound (42 mg, 44% yield) as a white solid was prepared in a fashion similar to that described for Example 239, here starting with 2-bromothiazole-5-carbonitrile (Combi-Blocks, San Diego, Calif., USA) (86 mg, 0.45 mmol) and stannane 239d (182 mg, 0.23 mmol). MS m/z=445.1 [M+H]$^+$. $^1$H NMR (400 MHz, CHLOROFORM-d) δ ppm 8.06-8.17 (m, 1H), 7.81-7.93 (m, 1H), 7.73 (br s, 1H), 7.52-7.68 (m, 1H), 7.03-7.14 (m, 1H), 6.83-6.98 (m, 1H), 3.94 (br s, 1H), 3.77-3.89 (m, 1H), 3.64-3.77 (m, 1H), 3.22 (s, 3H), 1.78 (s, 3H). $^{19}$F NMR (376 MHz, CHLOROFORM-d) δ ppm −115.70 (br s, 1F) −110.74 (br s, 1F).

Example 254: (R,Z)-3-amino-5-(2-fluoro-5-(2-fluoro-2-(5-((4-fluorobut-2-yn-1-yl)oxy)pyrazin-2-yl)vinyl)phenyl)-2,5-dimethyl-5,6-dihydro-2H-1,2,4-thiadiazine 1,1-dioxide

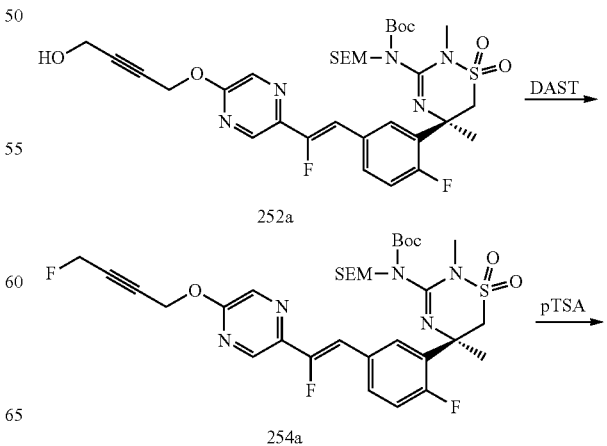

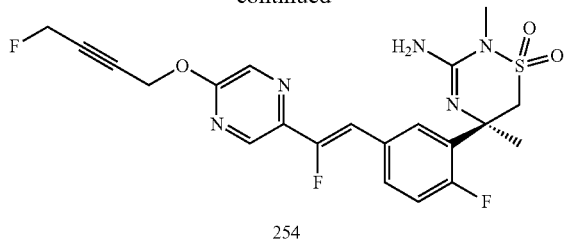

254

To a mixture of (R,Z)-tert-butyl (5-(2-fluoro-5-(2-fluoro-2-(5-((4-hydroxybut-2-yn-1-yl)oxy)pyrazin-2-yl)vinyl)phenyl)-2,5-dimethyl-1,1-dioxido-5,6-dihydro-2H-1,2,4-thiadiazin-3-yl)((2-(trimethylsilyl)ethoxy)methyl)carbamate (252a, 66 mg, 0.093 mmol) and DCM (2 mL) at 0° C. was added DAST (0.049 mL, 0.370 mmol). The mixture was stirred at 0° C. for 1.5 h, diluted with EtOAc and saturated NaHCO$_3$. The organic solution was dried over Na$_2$SO$_4$ and concentrated in vacuo. The crude was purified by silica gel chromatography (0-100% EtOAc in heptane) to provide 254a as a yellow solid (56 mg, 86% yield). MS m/z=710 [M+H]$^+$.

A mixture of 254a (56 mg, 0.079 mmol) and p-toluenesulfonic acid monohydrate (45 mg, 0.237 mmol), and 1,4-dioxane (1 mL) was heated at 80° C. for 1.5 h, diluted with saturated Na$_2$CO$_3$ and extracted with EtOAc. The organic solution was dried over Na$_2$SO$_4$ and concentrated in vacuo. The crude was purified by silica gel chromatography (0-100% EtOAc/EtOH (3/1) in heptane) to afford a material that was a mixture of the desired 254 and an impurity. The material was purified again by silica gel chromatography (0-100% EtOAc in DCM) to give Example 254 (23 mg, 60% yield) as a white solid. MS m/z=480 [M+H]$^+$. $^1$H NMR (400 MHz, DMSO-d$_6$) δ 8.52 (s, 1H), 8.47 (s, 1H), 7.82-7.91 (m, 1H), 7.58-7.68 (m, 1H), 7.28 (s, 1H), 6.80-6.99 (m, 1H), 5.91-6.20 (m, 2H), 5.23 (s, 2H), 5.21 (s, 1H), 5.12 (s, 1H), 3.69-3.91 (m, 2H), 3.06 (s, 3H), 1.63 (s, 3H). $^{19}$F NMR (376 MHz, DMSO-d$_6$) δ -111.98 (s, 1F), -125.43--124.05 (m, 1F), -216.05--215.27 (m, 1F).

Example 255: (5R)-5-(5-((Z)-2-(2,3-dihydro[1,4]dioxino[2,3-b]pyridin-6-yl)-2-fluoroethenyl)-2-fluorophenyl)-2,5-dimethyl-5,6-dihydro-2H-1,2,4-thiadiazin-3-amine 1,1-dioxide

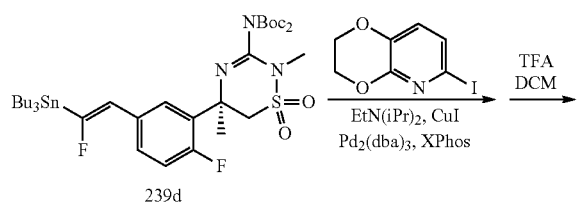

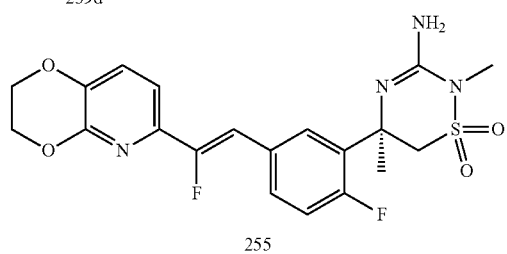

255

This compound (19 mg, 41% yield) as a white solid was prepared in a fashion similar to that described for Example 239, here starting with 6-iodo-2,3-dihydro-[1,4]dioxino[2,3-b]pyridine (Acros Organics, NJ, USA) (78 mg, 0.30 mmol) and stannane 239d (0.16 g, 0.20 mmol). MS m/z=451.1 [M+H]$^+$. $^1$H NMR (400 MHz, CHLOROFORM-d) δ 7.75-7.85 (m, 1H), 7.57-7.69 (m, 1H), 7.27 (s, 1H) 7.17-7.24 (m, 3H), 7.00-7.12 (m, 1H), 6.74-6.95 (m, 1H), 4.46-4.55 (m, 2H), 4.27-4.37 (m, 2H), 3.81-3.94 (m, 1H), 3.67-3.77 (m, 1H), 3.22 (s, 3H), 1.80 (s, 3H). $^{19}$F NMR (376 MHz, CHLOROFORM-d) δ -113.33 (s, 1F), -123.66 (br s, 1F).

Example 256: 5-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-2-thiophenecarbonitrile

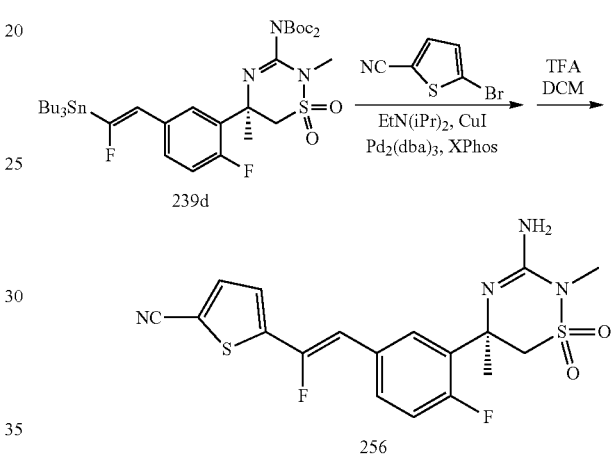

256

This compound (43 mg, 55% yield) as a white solid was prepared in a fashion similar to that described for Example 239, here using 5-bromothiophene-2-carbonitrile (Matrix Scientific, Columbia, S.C., USA) (0.049 g, 0.261 mmol) and stannane 239d (0.14 g, 0.17 mmol) as starting materials. MS m/z=423.1 [M+H]$^+$. $^1$H NMR (400 MHz, CHLOROFORM-d) δ 7.74-7.85 (m, 1H), 7.61-7.71 (m, 2H), 7.46-7.58 (m, 1H), 7.03-7.13 (m, 1H), 6.00-6.18 (m, 1H), 3.90-3.99 (m, 1H), 3.75-3.90 (m, 2H), 3.65-3.74 (m, 1H), 3.18-3.26 (m, 3H), 1.79 (s, 3H). $^{19}$F NMR (376 MHz, CHLOROFORM-d) δ -112.37 (s, 1F), -113.51 (br s, 1F).

Example 257: (5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide

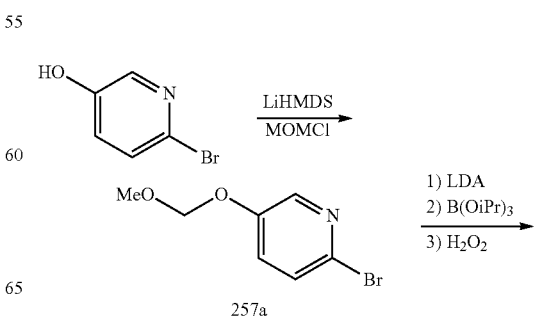

257a

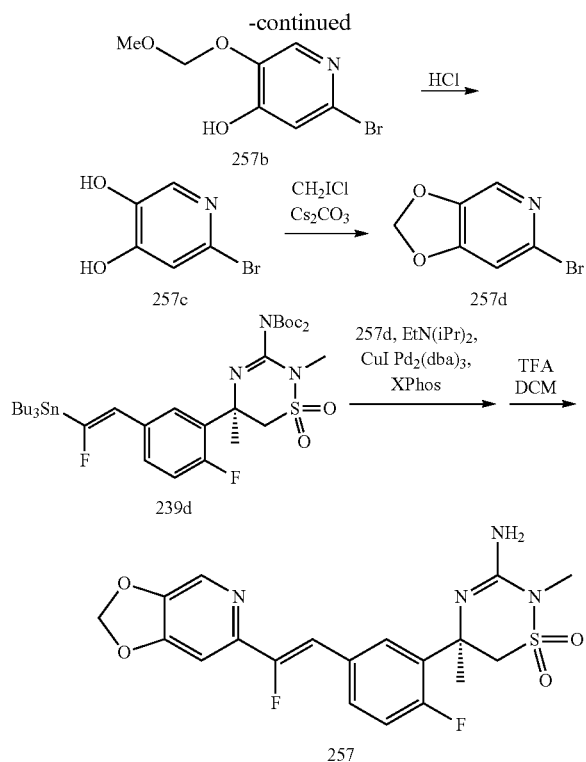

Preparation of 2-bromo-5-(methoxymethoxy)pyridine (257a)

To a solution of 6-bromopyridin-3-ol (Sigma-Aldrich Chemical Company, Inc., St. Louis, Mo., USA) (5.0 g, 28.7 mmol) in 29 mL of THF at 0° C. was added 1 M solution of lithium bis(trimethylsilyl)amide (Sigma-Aldrich Chemical Company, Inc., St. Louis, Mo., USA) (28.7 mL, 28.7 mmol) dropwise. After 10 min, chloro(methoxy)methane (Sigma-Aldrich Chemical Company, Inc., St. Louis, Mo., USA) (2.5 mL, 34.5 mmol) was added dropwise to the mixture. The mixture was gradually warmed to 23° C. and stirred for 15 h. It was quenched with 25 mL of sat'd aqueous NH$_4$Cl and diluted with 100 mL of water. The mixture was then extracted with 50 mL of EtOAc (3×) and the combined organic extracts were dried over MgSO$_4$. Filtration and concentration under reduced pressure followed by silica gel chromatography (0-30% gradient of 3:1 EtOAc/EtOH in heptane) afforded 257a (4.6 g, 21.3 mmol, 74% yield) as a light yellow oil. MS m/z=218.0/220.0 [M+H]$^+$.

Preparation of 2-bromo-5-(methoxymethoxy)pyridin-4-ol (257b)

To a 3-neck flask, fitted with a thermocouple and a magnetic stirring bar, and which had been evacuated and backfilled with N$_2$, was added diisopropylamine (Sigma-Aldrich Chemical Company, Inc., St. Louis, Mo., USA) (0.74 mL, 5.27 mmol) followed by 10 mL of THF. The mixture was cooled with a dry-ice acetone bath to −70° C. and n-butyllithium (Sigma-Aldrich Chemical Company, Inc., St. Louis, Mo., USA) (3.15 mL of 1.6 M solution in hexanes, 5.04 mmol) was added dropwise. The mixture was allowed to slowly warm to 0° C. over the course of an hour, then re-cooled to −70° C. 2-Bromo-5-(methoxymethoxy) pyridine (257a, 1.00 g, 4.59 mmol) was taken up in 10 mL of THF and added to the cold LDA mixture at a rate such that the internal temperature of the mixture did not exceed −65° C. Once the addition was complete, the reaction was stirred for an additional hour at −70° C. and then triisopropyl borate (Sigma-Aldrich Chemical Company, Inc., St. Louis, Mo., USA) (1.16 mL, 5.04 mmol) in 15 mL THF, not allowing the internal temperature of the mixture to exceed −65° C. Stirring was continued for an additional 3 h at which point the mixture was allowed to warm to −15° C. and hydrogen peroxide (Sigma-Aldrich Chemical Company, Inc., St. Louis, Mo., USA) (1.03 mL of 30% wt. solution, 9.17 mmol) was carefully added to the reaction and the mixture was warmed slowly to 23° C. After stirring for 1.5 h, the reaction was diluted with water (10 mL), extracted with EtOAc (5×) and the organic layer was tested for peroxides (none), dried over MgSO$_4$ and concentrated. The aqueous layer was sufficiently quenched with sodium thiosulfate before discarded. Alcohol 257b was concentrated (1.07 g, 3.46 mmol, 75% yield) and taken on without further purification. MS m/z=234.0/236.0 [M+H]$^+$.

Preparation of 6-bromo-[1,3]dioxolo[4,5-c]pyridine (257d)

2-Bromo-5-(methoxymethoxy)pyridin-4-ol 257b (0.4 g, 1.71 mmol) was taken up in 1,4-dioxane (17 mL) and a 4.0 M solution of hydrogen chloride in 1,4-dioxane (Sigma-Aldrich Chemical Company, Inc., St. Louis, Mo., USA) (5.13 mL, 20.51 mmol) was added dropwise. After 1 h, the reaction was filtered off any excess salts, and concentrated. The resulting diol 257c was of >90% purity by LCMS analysis and was taken into subsequent reaction as is. MS m/z=190.0/192.0 [M+H]$^+$.

To a vial containing cesium carbonate (Sigma-Aldrich Chemical Company, Inc., St. Louis, Mo., USA) (258 mg, 0.79 mmol) and 6-bromopyridine-3,4-diol (257c, 0.10 g, 0.53 mmol) in 3.1 mL of DMF was added chloroiodomethane (Sigma-Aldrich Chemical Company, Inc., St. Louis, Mo., USA) (57 µL, 0.79 mmol) and the mixture was heated to 60° C. for 2 h. The mixture was filtered through celite, washed with H$_2$O, extracted with EtOAc, dried over MgSO$_4$, and concentrated in vacuo. The resulting 6-bromo-[1,3]dioxolo[4,5-c]pyridine (257d, 41 mg, 39% yield over 2 steps), was taken on without further purification into the subsequent cross-coupling step.

Preparation of (5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide (257)

The title compound (0.007 g, 0.016 mmol, 9% yield of two steps) was prepared in a fashion similar to that described for Example 239, here using chloro(2-dicyclohexylphosphino-2',4',6'-triisopropyl-1,1'-biphenyl)[2-(2'-amino-1,1'-biphenyl)]palladium(II) (Sigma-Aldrich Chemical Company, Inc., St. Louis, Mo., USA) (0.027 g, 0.034 mmol), copper(I) iodide (Sigma-Aldrich Chemical Company, Inc., St. Louis, Mo., USA) (0.033 g, 0.171 mmol), 6-bromo-[1,3]dioxolo[4,5-c]pyridine 257d (0.045 g, 0.247 mmol), Hunig's base (Sigma-Aldrich Chemical Company, Inc., St. Louis, Mo., USA) (0.089 mL, 0.514 mmol) and stannane 239d (0.138 g, 0.171 mmol) as starting materials for the cross-coupling step. The resulting mixture was immediately subjected to deprotection conditions using trifluoroacetic acid (0.190 g, 1.66 mmol) to give the title compound 257 as a white solid. MS m/z=424.1 [M+H]+. 1H NMR (400 MHz, CHLOROFORM-d) δ 8.03-8.17 (m, 1H), 7.77-7.86 (m, 1H), 7.57-7.71 (m, 1H), 7.15-7.21 (m, 1H), 6.99-7.12 (m, 1H), 6.76-6.96 (m, 1H), 5.97-6.14 (m, 2H), 3.81-3.98 (m, 1H), 3.64-3.78 (m, 1H), 3.03-3.31 (m, 3H), 2.48-3.02 (m, 2H) 1.69-1.87 (m, 3H). 19F NMR (376 MHz, CHLOROFORM-d) δ −113.01 (s, 1F), −122.09 (br s, 1F).

Example 258: (R,Z)-3-amino-5-(2-fluoro-5-(2-fluoro-2-(5-(trifluoromethoxy)pyridin-2-yl)vinyl)phenyl)-2,5-dimethyl-5,6-dihydro-2H-1,2,4-thiadiazine 1,1-dioxide. (Method E)

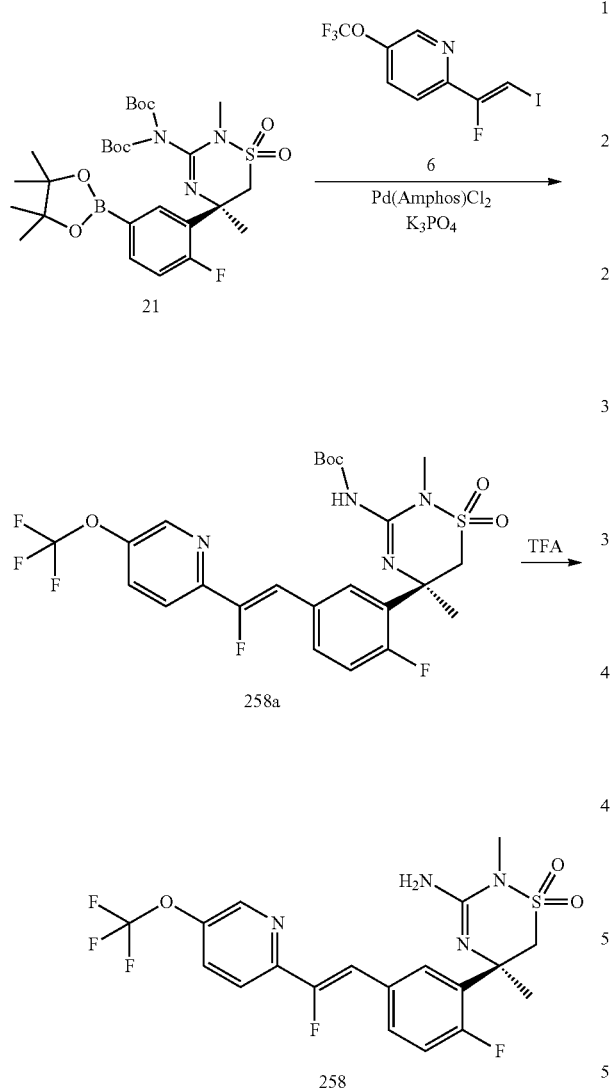

A mixture of boronic ester 21 (280 mg, 0.46 mmol), (Z)-2-(1-fluoro-2-iodovinyl)-5-(trifluoromethoxy)pyridine (6, 120 mg, 0.36 mmol), potassium phosphate (229 mg, 1.08 mmol) and bis(di-tert-butyl(4-dimethylaminophenyl)phosphine)dichloropalladium(II) (18 mg, 0.03 mmol) in 1,4-dioxane (2.5 mL) and water (0.7 mL) was purged with Ar, then the vial was sealed and heated to 90° C. for 60 min. The mixture was cooled to RT and diluted with water and extracted with EtOAc. The organic solution was dried over Na2SO4, and concentrated in vacuo. The residue was purified by silica gel chromatography (15-50% EtOAc in heptane) to give 258a as a brown solid. MS m/z=577.1 [M+H]+. The brown solid was dissolved in DCM (2 mL) and TFA (1 mL). The mixture was stirred at RT for 30 min. The mixture was concentrated in vacuo, and the residue was diluted with EtOAc (50 mL) and treated with sat'd Na2CO3 (10 mL). The organic solution was dried over Na2SO4, and concentrated in vacuo. The residue was purified by silica gel chromatography (20-80% EtOAc in DCM) to afford Example 258 (48 mg, 0.10 mmol, 28% yield) as a brown amorphous solid. MS m/z=477.1 [M+H]+. 1H NMR (400 MHz, DMSO-d6) δ 8.75 (d, J=2.35 Hz, 1H), 8.04 (dd, J=1.57, 8.80 Hz, 1H), 7.91 (d, J=6.46 Hz, 1H), 7.82 (d, J=8.41 Hz, 1H), 7.67 (m, 1H), 7.23 (m, 1H), 7.15 (s, 0.5 H), 7.05 (s, 0.5 H), 6.11 (br., 2H), 3.83 (br., 2H), 3.05 (s, 3H), 1.62 (s, 3H). 19F NMR (376 MHz, DMSO-d6) δ −57.10 (s, 3F), −111.48 (s, 1F), −123.16 (s, 1F).

Example 259: (5R)-5-(2-fluoro-5-((Z)-2-fluoro-2-(3-isoquinolinyl)ethenyl)phenyl)-2,5-dimethyl-5,6-dihydro-2H-1,2,4-thiadiazin-3-amine 1,1-dioxide

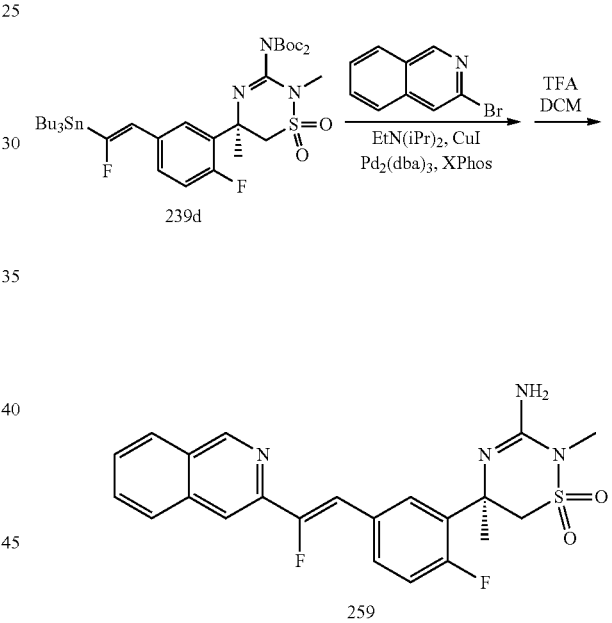

This compound (13 mg, 16% yield) as a white solid was prepared in a fashion similar to that described for Example 239, here starting with 3-bromoisoquinoline (Combi-Blocks, San Diego, Calif., USA) (56 mg, 0.27 mmol) and stannane 239d (145 mg, 0.18 mmol). MS m/z=443.1 [M+H]+. 1H NMR (400 MHz, CHLOROFORM-d) δ ppm 9.17 (s, 1H), 7.95-8.02 (m, 3H), 7.90 (s, 1H), 7.83 (d, J=8.02 Hz, 1H), 7.68-7.76 (m, 2H), 7.57-7.67 (m, 2H), 7.00-7.17 (m, 2H), 3.91 (d, J=13.89 Hz, 1H), 3.73 (d, J=13.89 Hz, 1H), 3.23 (s, 3H), 1.82 (s, 3H). 19F NMR (376 MHz, CHLOROFORM-d) δ ppm −113.00 (s, 1F), −123.47 (s, 1F).

Example 260: (5R)-5-(5-((Z)-2-(6-chloro-3-isoquinolinyl)-2-fluoroethenyl)-2-fluorophenyl)-2,5-dimethyl-5,6-dihydro-2H-1,2,4-thiadiazin-3-amine 1,1-dioxide

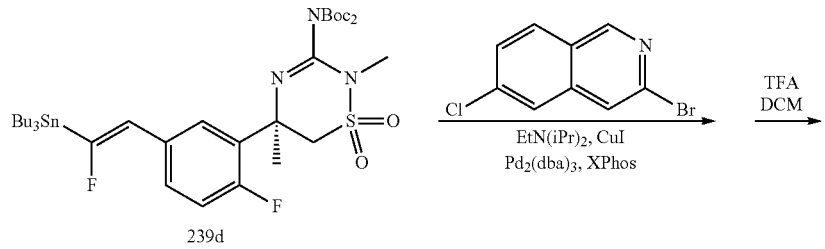

This compound (11 mg, 13% yield overall) was prepared in a fashion similar to that described for Example 239, using chloro(2-dicyclohexylphosphino-2',4',6'-triisopropyl-1,1'-biphenyl) [2-(2'-amino-1,1'-biphenyl)]palladium(II) (Sigma-Aldrich Chemical Company, Inc., St. Louis, Mo., USA) (0.027 g, 0.035 mmol), copper(I) iodide (Sigma-Aldrich Chemical Company, Inc., St. Louis, Mo., USA) (0.033 g, 0.174 mmol), 3-bromo-6-chloroisoquinoline (Oxchem, Inc., Chicago, Ill., USA) (0.063 g, 0.262 mmol), Hunig's base (Sigma-Aldrich Chemical Company, Inc., St. Louis, Mo., USA) (0.091 ml, 0.523 mmol) and stannane 239d (0.140 g, 0.174 mmol) as starting materials for the cross-coupling step. The resulting mixture was immediately subjected to deprotection conditions using trifluoroacetic acid (0.21 g, 1.83 mmol) to give the title compound 260 as a white solid. MS m/z=477.1 [M+H]$^+$. $^1$H NMR (400 MHz, CDCl$_3$) δ ppm 9.17 (s, 1H), 9.12 (s, 1H), 7.95-8.02 (m, 1H), 7.91 (d, J=8.61 Hz, 1H), 7.79 (s, 2H), 7.59-7.66 (m, 1H), 7.52-7.58 (m, 1H), 6.99-7.15 (m, 2H), 6.70-6.70 (m, 1H), 3.94 (d, J=13.89 Hz, 1H), 3.73 (d, J=13.89 Hz, 1H), 3.23 (s, 3H), 1.82 (s, 3H). $^{19}$F NMR (376 MHz, CDCl$_3$) δ ppm −112.63 (s, 1F), −123.76 (s, 1F).

Example 261: 6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile

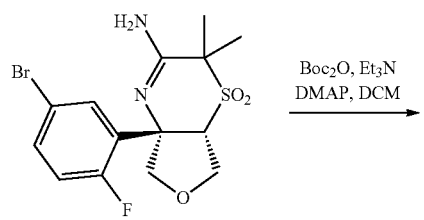

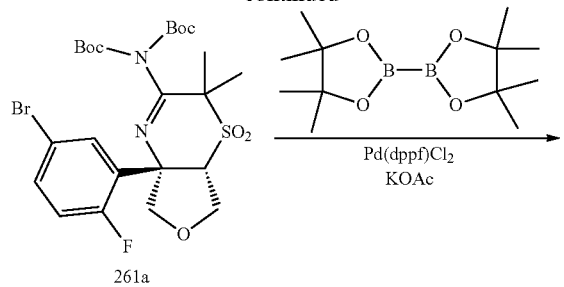

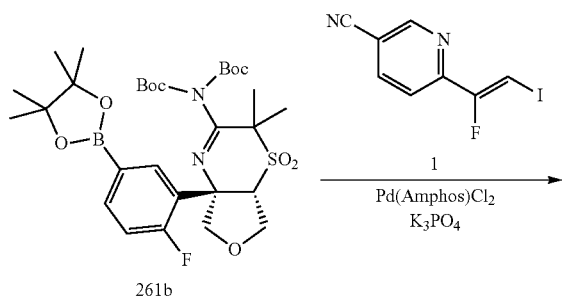

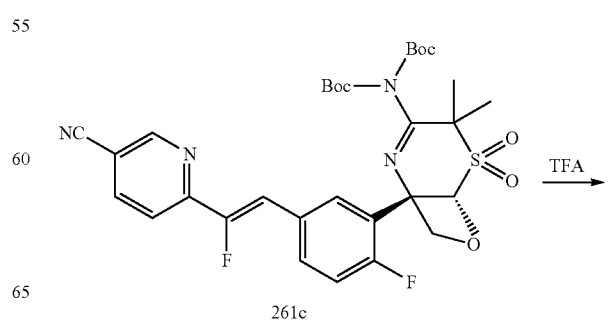

-continued

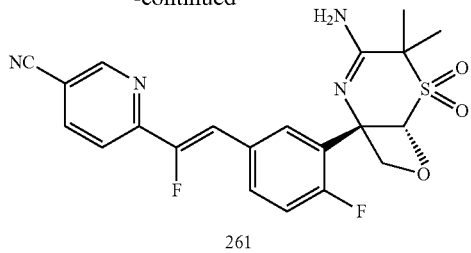

261

Preparation of 261a

To a solution of (4aS,7aS)-3-amino-4a-(5-bromo-2-fluorophenyl)-2,2-dimethyl-4a,5,7,7a-tetrahydro-2H-furo[3,4-b][1,4]thiazine 1,1-dioxide (WO 2014059185) (283 mg, 0.723 mmol) in DCM (2.5 mL) was added di-tert-butyl dicarbonate (420 µL, 1.81 mmol), N,N-diisopropylethylamine, anhydrous (379 µL, 2.17 mmol), followed by 4-dimethylaminopyridine (44 mg, 0.36 mmol). The reaction mixture was stirred at RT for 2 h. The mixture was partitioned between DCM and diluted NaHCO₃. The aqueous layer was back extracted with DCM (2×) and the combined organics was dried (Na₂SO₄) and concentrated. The residue was purified by silica gel column (0-40% ethyl acetate/heptane) to give 261a (338 mg, 0.57 mmol, 79% yield) as white solid. MS (ESI, positive ion) m/z: =613.1 (M+Na)⁺.

Preparation of 261b

A stream of argon was bubbling through a mixture of 261a (338 mg, 0.57 mmol), 4,4,4',4',5,5,5',5'-octamethyl-2,2'-bi(1,3,2-dioxaborolane) (218 mg, 0.85 mmol), (1,1'-bis(diphenylphosphino)ferrocene)dichloropalladium(II) (42 mg, 0.057 mmol) and potassium acetate (196 mg, 2.00 mmol) in 1,4-dioxane (2.9 mL) for 10 min. The mixture was heated at 90° C. for 2 h. After cooling to RT the mixture was filtered through a pad of celite, washed with ethyl acetate. The filtrate was concentrated and the residue was purified by silica gel column using 0-35% ethyl acetate gradient in heptane as the eluent to give 261b (227 mg, 0.35 mmol, 62% yield) as a white solid. MS (ESI, positive ion) m/z: =661.3 (M+Na)⁺.

Preparation of Example 261

A mixture of 261b (100 mg, 0.16 mmol), (Z)-6-(1-fluoro-2-iodovinyl)nicotinonitrile (52 mg, 0.188 mmol), potassium phosphate tribasic (83 mg, 0.39 mmol), and 1,1-bis[(di-t-butyl-p-methylaminophenyl]palladium(II) chloride (11 mg, 0.016 mmol) was placed under nitrogen atmosphere using 3 evacuation/backfill cycles. Dioxane (1.3 mL) and water (0.25 mL) were added and the mixture was heated to 80° C. for 1.5 h. The mixture was cooled to RT and partitioned between EtOAc and brine. The layers were separated and the organic layer was concentrated in vacuo. The crude product was purified by silica gel chromatography (0 to 50% EtOAc/heptane) to give 261c (73 mg, 0.11 mmol, 71% yield) as a white foam. MS (ESI, positive ion) m/z: =681.2 (M+Na)⁺. A solution of 261c (73 mg, 0.11 mmol) in dichloromethane (1 mL) and trifluoroacetic acid (0.33 mL, 4.43 mmol) was stirred at RT for 1 h. The solvent was removed in vacuo and to the residue was added DCM and evaporated again. The process was repeated twice. The residue was partitioned between DCM and sat'd aqueous NaHCO₃ solution. The aqueous layer was back extracted with DCM (2×) and the combined organic layer was dried (Na₂SO₄) and concentrated to give 6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile (261) (49 mg, 0.11 mmol, 96% yield) as white solid. MS (ESI, positive ion) m/z: =459.0 (M+1)⁺. ¹H NMR (400 MHz, CDCl₃) δ ppm 8.85 (1H, s), 8.04 (1H, dd, J=8.41, 2.15 Hz), 7.92 (1H, dd, J=8.02, 1.76 Hz), 7.68-7.78 (2H, m), 7.25 (1H, d, J=40 Hz), 7.11-7.24 (1H, m), 4.78 (1H, br d, J=10.56 Hz), 4.36-4.44 (1H, m), 4.11-4.27 (2H, m), 4.01 (1H, dd, J=7.83, 2.15 Hz), 1.80 (3H, s), 1.56 (3H, s). ¹⁹F NMR (376 MHz, CDCl₃) δ ppm −108.92 (1F, s), −124.92 (1F, br s).

Example 262: (R,Z)-5-amino-3-(2-fluoro-5-(2-fluoro-2-(5-fluoropyridin-2-yl)vinyl)phenyl)-3,6,6-trimethyl-3,6-dihydro-2H-1,4-thiazine 1,1-dioxide

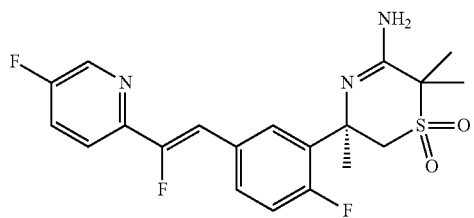

262

This compound (42 mg, 31% yield) as a white solid was prepared in a fashion similar to that described in Method E for Example 258, using (Z)-5-fluoro-2-(1-fluoro-2-iodovinyl)pyridine (2, 87 mg, 0.32 mmol) and boronic ester 30 (200 mg, 0.32 mmol) as starting materials. MS m/z=424.1 [M+H]⁺. ¹H NMR (400 MHz, DMSO-d₆) δ 8.68 (d, J=2.8 Hz, 1H), 7.89 (td, J=8.7, 2.9 Hz, 1H), 7.79 (td, J=9.7, 8.7, 3.3 Hz, 2H), 7.69-7.60 (m, 1H), 7.23 (dd, J=12.2, 8.5 Hz, 1H), 7.01 (d, J=40.3 Hz, 1H), 6.15 (s, 2H), 3.68 (d, J=15.3 Hz, 1H), 3.56 (d, J=15.2 Hz, 1H), 1.61 (d, J=15.8 Hz, 6H), 1.47 (s, 3H).

Example 263: (R,Z)-5-amino-3-(2-fluoro-5-(2-fluoro-2-(5-methoxypyrazin-2-yl)vinyl)phenyl)-3,6,6-trimethyl-3,6-dihydro-2H-1,4-thiazine 1,1-dioxide

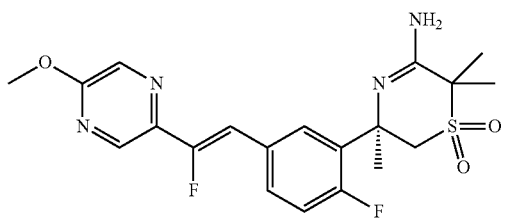

263

This compound (40 mg, 16% yield) as a white solid was prepared in a fashion similar to that described Method E for Example 258, using (Z)-2-(1-fluoro-2-iodovinyl)-5-methoxypyrazine (14, 190 mg, 0.69 mmol) and boronic ester 30 (350 mg, 0.57 mmol) as starting materials. MS m/z=437.1 [M+H]⁺. ¹H NMR (400 MHz, DMSO-d₆) δ ¹H NMR (400 MHz, DMSO-d₆) δ: 8.49 (s, 1H), 8.41 (s, 1H), 7.79 (d, J=7.9 Hz, 1H), 7.64 (s, 1H), 7.23 (dd, J=11.8, 8.9

Hz, 2H), 6.14 (d, J=4.7 Hz, 2H), 3.99 (s, 3H), 3.68 (d, J=15.2 Hz, 1H), 3.56 (d, J=15.2 Hz, 1H), 1.61 (d, J=15.7 Hz, 6H), 1.46 (s, 3H).

Example 264: (R,Z)-5-amino-3-(5-(2-(3-chloro-5-(trifluoromethyl)pyridin-2-yl)-2-fluorovinyl)-2-fluorophenyl)-3,6,6-trimethyl-3,6-dihydro-2H-1,4-thiazine 1,1-dioxide

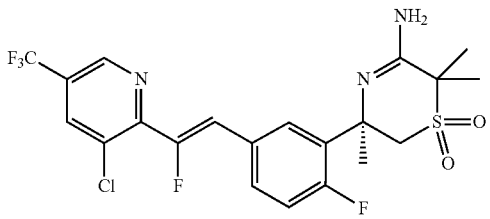

264

This compound (50 mg, 17% yield) as a white solid was prepared in a fashion similar to that described Method E for Example 258, using (Z)-3-chloro-2-(1-fluoro-2-iodovinyl)-5-(trifluoromethyl)pyridine (9) (201 mg, 0.57 mmol) and boronic ester 30 (350 mg, 0.57 mmol) as starting materials. LCMS (ESI⁺) m/z=508.4 (M+H). ¹H NMR (400 MHz, DMSO-d₆) δ 9.04 (s, 1H), 8.62 (d, J=1.9 Hz, 1H), 7.82 (dd, J=8.0, 2.4 Hz, 1H), 7.68 (dt, J=6.9, 3.3 Hz, 1H), 7.26 (dd, J=12.1, 8.4 Hz, 1H), 7.00 (s, 1H), 6.15 (s, 2H), 3.69 (d, J=15.2 Hz, 1H), 3.55 (s, 1H), 1.61 (d, J=17.4 Hz, 6H), 1.46 (s, 3H).

Example 265: (R,Z)-5-amino-3-(2-fluoro-5-(2-fluoro-2-(5-(trifluoromethyl)pyridin-2-yl)vinyl)phenyl)-3,6,6-trimethyl-3,6-dihydro-2H-1,4-thiazine 1,1-dioxide

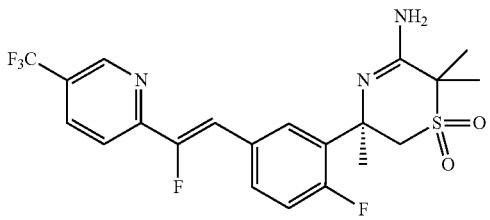

265

This compound (33 mg, 12% yield) as a white solid was prepared in a fashion similar to that described Method E for Example 258, using (Z)-2-(1-fluoro-2-iodovinyl)-5-(trifluoromethyl)pyridine (5) (182 mg, 0.57 mmol) and boronic ester 30 (350 mg, 0.57 mmol) as starting materials. LCMS (ESI⁺) m/z=474.0 (M+H). ¹H NMR (400 MHz, DMSO-d₆) δ 9.04 (s, 1H), 8.44-8.28 (m, 1H), 7.88 (dd, J=13.9, 8.2 Hz, 2H), 7.80-7.65 (m, 1H), 7.30 (d, J=4.5 Hz, 2H), 6.17 (s, 2H), 3.68 (d, J=12 Hz, 1H) 3.57 (d, J=15.3 Hz, 1H), 1.75-1.52 (m, 6H), 1.47 (d, J=2.4 Hz, 3H).

Example 266: (R,Z)-3-amino-5-(5-(2-(5-cyclopropylpyrazin-2-yl)-2-fluorovinyl)-2-fluorophenyl)-2,5-dimethyl-5,6-dihydro-2H-1,2,4-thiadiazine 1,1-dioxide

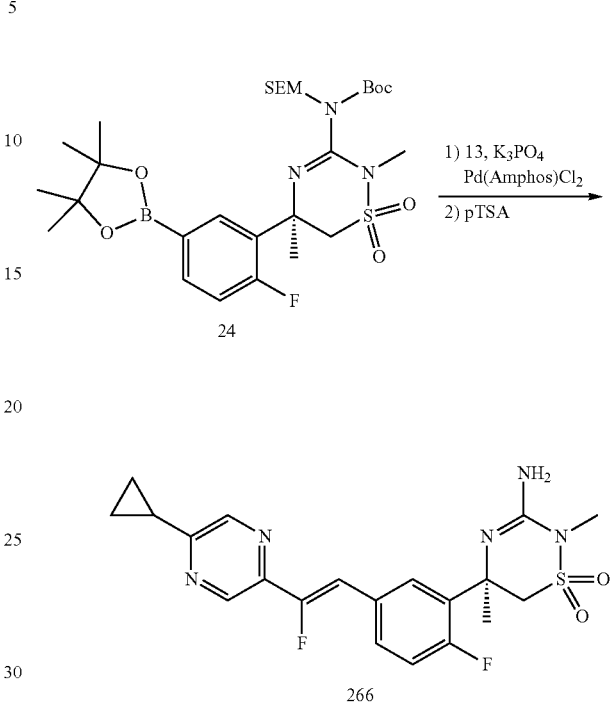

A mixture of (Z)-2-cyclopropyl-5-(1-fluoro-2-iodovinyl) pyrazine (13) (100 mg, 0.34 mmol), (R)-tert-butyl (5-(2-fluoro-5-(4,4,5,5-tetramethyl-1,3,2-dioxaborolan-2-yl)phenyl)-2,5-dimethyl-1,1-dioxido-5,6-dihydro-2H-1,2,4-thiadiazin-3-yl)((2-(trimethylsilyl)ethoxy)methyl) carbamate (24) 281 mg, 0.45 mmol), potassium phosphate tribasic (220 mg, 1.03 mmol), and bis-(di-tert-butyl(4-dimethylaminophenyl)phosphine)dichloropalladium(II) (20 mg, 0.03 mmol) in dioxane/water=2:1 (3 mL) was heated to 85° C. for 2 h. It was cooled to RT, diluted with EtOAc (35 mL) and water (10 mL). The organic layer was concentrated in vacuo to give an oil which was purified by silica gel chromatography (5-45% EtOAc in heptane) to give a brown amorphous solid. LCMS (ESI⁺) m/z=664.1 (M+H). The brown amorphous solid and 4-methylbenzenesulfonic acid hydrate (164 mg, 0.86 mmol) in 2 mL of dioxane was heated at 80° C. for 2 h. After cooling, the reaction mixture was diluted with 25 mL of EtOAc and washed with 2 mL of 1 N NaOH followed by 2 mL of brine. The organic layer was concentrated and the residue was purified on a silica gel column (2-5% MeOH in EtOAc) to give (R,Z)-3-amino-5-(5-(2-(5-cyclopropylpyrazin-2-yl)-2-fluorovinyl)-2-fluorophenyl)-2,5-dimethyl-5,6-dihydro-2H-1,2,4-thiadiazine 1,1-dioxide (Example 266, 99 mg, 66% yield) as an off-white crystalline solid. LCMS (ESI⁺) m/z=434.1 (M+H). ¹H NMR (400 MHz, DMSO-d₆) δ 8.73 (s, 1H), 8.69 (s, 1H), 7.91 (m, 1H), 7.63 (m, 1H), 7.22 (m, 1H), 7.00 (d, J=40.01 Hz, 1H), 6.04 (br., 2H), 3.79 (s, 2H), 3.05 (s, 3H), 2.29 (m, 1H), 1.61 (s, 3H), 1.13 (m, 2H), 1.02 (m, 2H). ¹⁹F NMR (376 MHz, DMSO-d₆) δ −111.67 (s, 1F), −12.31 (s, 1F).

Example 267: 2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-4-carbonitrile

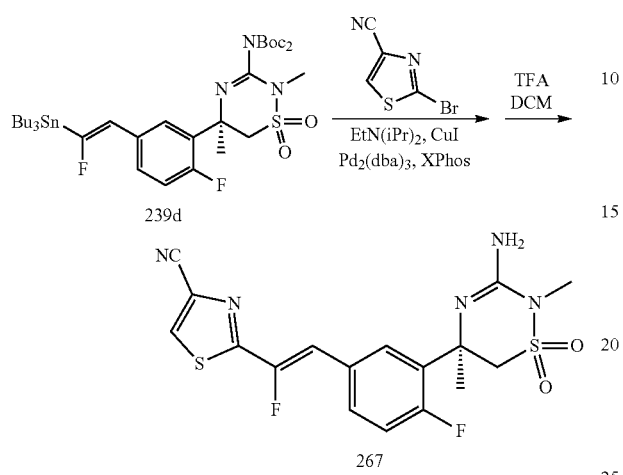

This compound (0.012 g, 17% yield overall) was prepared in a fashion similar to that described for Example 239, using chloro(2-dicyclohexylphosphino-2',4',6'-triisopropyl-1,1'-biphenyl) [2-(2'-amino-1,1'-biphenyl)]palladium(II) (Sigma-Aldrich Chemical Company, Inc., St. Louis, Mo., USA) (0.026 g, 0.033 mmol), copper(I) iodide (Sigma-Aldrich Chemical Company, Inc., St. Louis, Mo., USA) (0.031 g, 0.165 mmol), 2-bromothiazole-4-carbonitrile (Oxchem, Inc., Chicago, Ill., USA) (0.047 g, 0.247 mmol), Hunig's base (Sigma-Aldrich Chemical Company, Inc., St. Louis, Mo., USA) (0.086 ml, 0.494 mmol) and stannane 239d (0.133 g, 0.165 mmol) as starting materials for the cross-coupling step. The resulting mixture was immediately subjected to deprotection conditions using trifluoroacetic acid (0.133 g, 1.17 mmol) to give the title compound 267 as a white solid. MS m/z=424.1 [M+H]$^+$. $^1$H NMR (400 MHz, CHLOROFORM-d) δ ppm 7.97-8.05 (m, 1H), 7.81-7.89 (m, 1H), 7.61-7.71 (m, 1H), 7.06-7.16 (m, 1H), 6.89-7.04 (m, 1H), 3.91 (d, J=13.89 Hz, 1H), 3.71 (d, J=14.09 Hz, 1H), 3.24 (s, 3H), 2.02-2.83 (m, 2H), 1.74-1.85 (m, 3H). $^{19}$F NMR (376 MHz, CHLOROFORM-d) δ ppm −116.48 (br s, 1F), −110.25 (s, 1F).

Example 268: (R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-chloronicotinonitrile

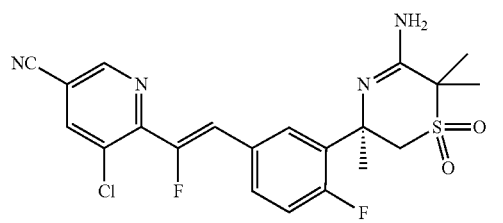

This compound (50 mg, 17% yield) as a white solid was prepared in a fashion similar to that described Method E for Example 258, using (Z)-5-chloro-6-(1-fluoro-2-iodovinyl)nicotinonitrile (8) (177 mg, 0.57 mmol) and boronic ester 30 (350 mg, 0.57 mmol) as starting materials. LCMS (ESI$^+$) m/z=465.2 (M+H). $^1$H NMR (400 MHz, DMSO-d$_6$) δ: 9.07 (d, J=1.8 Hz, 1H), 8.74 (d, J=1.9 Hz, 1H), 7.83 (d, J=7.9 Hz, 1H), 7.69 (dd, J=9.1, 4.5 Hz, 1H), 7.26 (dd, J=12.1, 8.6 Hz, 1H), 7.01 (d, J=38.2 Hz, 1H), 6.14 (s, 2H), 3.68 (d, J=15.2 Hz, 1H), 3.57 (d, J=15.1 Hz, 1H), 1.61 (d, J=17.1 Hz, 6H), 1.46 (s, 3H). $^{19}$F NMR (400 MHz, DMSO-d$_6$) δ: −111.94 (s, 1F), −115.98 (s, 1F).

Example 269: (R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-5-chloronicotinonitrile

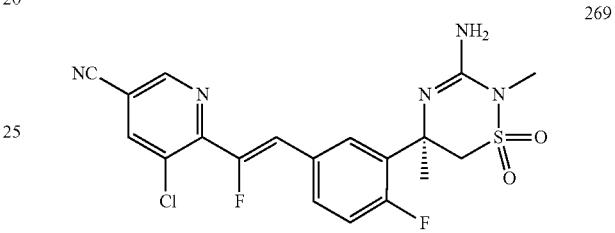

This compound (30 mg, 10% yield) as a white solid was prepared in a fashion similar to that described Method E for Example 258, using (Z)-5-chloro-6-(1-fluoro-2-iodovinyl)nicotinonitrile (8) (207 mg, 0.67 mmol) and boronic ester 21 (400 mg, 0.67 mmol) as starting materials. LCMS (ESI$^+$) m/z=452.2 (M+H). $^1$H NMR (400 MHz, DMSO-d$_6$) δ 9.07 (d, J=1.8 Hz, 1H), 8.74 (d, J=1.8 Hz, 1H), 7.99-7.89 (m, 1H), 7.67 (dd, J=8.3, 4.3 Hz, 1H), 7.26 (dd, J=12.0, 8.6 Hz, 1H), 7.02 (d, J=38.2 Hz, 1H), 6.07 (s, 2H), 3.81 (s, 2H), 3.05 (s, 3H), 1.62 (s, 3H). $^{19}$F NMR (400 MHz, DMSO-d$_6$) δ −110.48 (s, 1F), −114.37 (s, 1F).

Example 270: (R,Z)-3-amino-5-(2,3-difluoro-5-(2-fluoro-2-(5-fluoropyridin-2-yl)vinyl)phenyl)-2,5-dimethyl-5,6-dihydro-2H-1,2,4-thiadiazine 1,1-dioxide

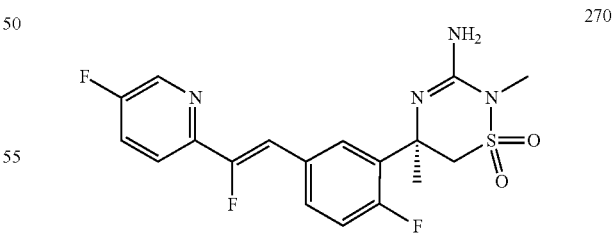

This compound (32 mg, 11% yield) as a white solid was prepared in a fashion similar to that described in Method E for Example 258, using (Z)-5-fluoro-2-(1-fluoro-2-iodovinyl)pyridine (2, 208 mg, 0.78 mmol) and boronic ester 26 (400 mg, 0.65 mmol) as starting materials. MS m/z=429.2 [M+H]$^+$. $^1$H NMR (400 MHz, DMSO-d$_6$) δ 8.69 (d, J=2.8 Hz, 1H), 7.90 (td, J=8.7, 2.9 Hz, 1H), 7.82-7.74 (m, 1H), 7.71 (d, J=6.5 Hz, 1H), 7.65 (ddd, J=9.8, 7.2, 2.2 Hz, 1H), 7.02 (d, J=39.4 Hz, 1H), 6.13 (d, J=9.7 Hz, 2H), 3.91-3.80 (m, 2H), 3.05 (s, 3H), 1.63 (s, 3H). $^{19}$F NMR (400 MHz, DMSO-d$_6$) δ −121.03 (s, 1F), −125.75 (s, 1F), −138.18 (d, 1F), −138.99 (d, 1F).

Examples 271-276 were also prepared in a fashion similar to that described in Method E for Example 258.

Example 271: (R,Z)-3-amino-5-(2,3-difluoro-5-(2-fluoro-2-(5-methoxypyrazin-2-yl)vinyl)phenyl)-2,5-dimethyl-5,6-dihydro-2H-1,2,4-thiadiazine 1,1-dioxide

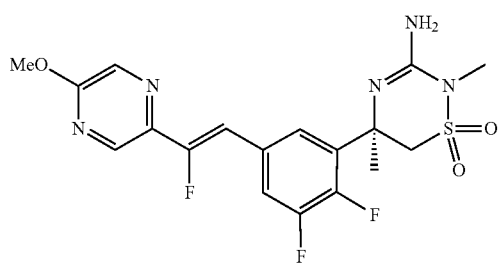

MS m/z=422.2 [M+H]$^+$. $^1$H NMR (400 MHz, DMSO-d$_6$) δ 8.50 (s, 1H), 8.42 (d, J=1.4 Hz, 1H), 7.75-7.55 (m, 2H), 6.88 (d, J=40.0 Hz, 1H), 6.11 (s, 2H), 3.99 (s, 3H), 3.85 (d, J=5.0 Hz, 2H), 3.05 (s, 3H), 1.63 (s, 3H). $^{19}$F NMR (400 MHz, DMSO-d$_6$) δ −123.21 (s, 1F), −138.43 (d, 1F), −139.02 (d, 1F).

Example 272: (R,Z)-3-amino-5-(5-(2-(3-chloro-5-(trifluoromethyl)pyridin-2-yl)-2-fluorovinyl)-2,3-difluorophenyl)-2,5-dimethyl-5,6-dihydro-2H-1,2,4-thiadiazine 1,1-dioxide

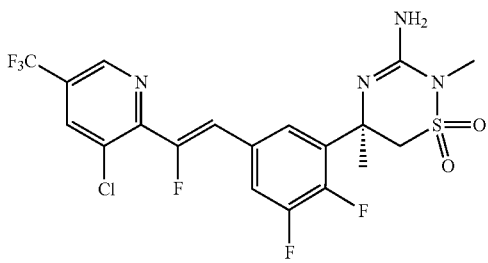

MS m/z=5120 [M+H]$^+$. $^1$H NMR (400 MHz, DMSO-d$_6$) δ 9.05 (d, J=1.8 Hz, 1H), 8.67-8.56 (m, 1H), 7.85-7.61 (m, 2H), 6.95 (d, J=37.5 Hz, 1H), 6.12 (s, 2H), 3.86 (q, J=14.1 Hz, 2H), 3.05 (s, 3H), 1.63 (s, 3H). $^{19}$F NMR (400 MHz, DMSO-d$_6$) δ −60.77 (s, 3F), −111.74 (s, 1F), −136.98 (d, 1F), −138.74 (d, 1F).

Example 273: (R,Z)-3-amino-5-(2,3-difluoro-5-(2-fluoro-2-(5-(trifluoromethyl)pyridin-2-yl)vinyl)phenyl)-2,5-dimethyl-5,6-dihydro-2H-1,2,4-thiadiazine 1,1-dioxide

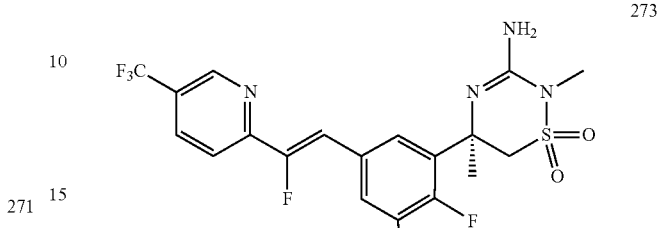

MS m/z=479.2 [M+H]$^+$. $^1$H NMR (400 MHz, DMSO-d$_6$) δ 9.06 (d, J=1.9 Hz, 1H), 8.38 (dd, J=8.4, 2.3 Hz, 1H), 7.91 (d, J=8.2 Hz, 1H), 7.83-7.59 (m, 2H), 7.26 (d, J=39.0 Hz, 1H), 6.13 (s, 2H), 4.02-3.64 (m, 2H), 3.06 (s, 3H), 1.64 (s, 3H). $^{19}$F NMR (400 MHz, DMSO-d) δ −60.84 (s, 3F), −112.50 (s, 1F), −137.16 (d, 1F), −138.77 (d, 1F).

Example 274: (R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-methylnicotinonitrile

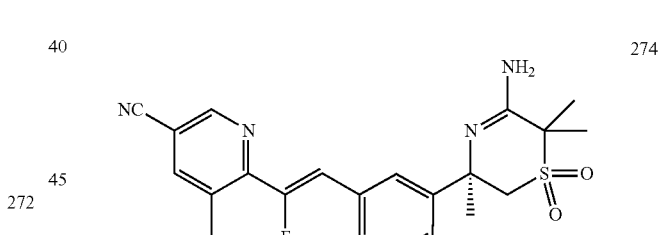

This compound (45 mg, 18% yield) as a white solid was prepared in a fashion similar to that described Method E for Example 258, using (Z)-5-methyl-6-(1-fluoro-2-iodovinyl)nicotinonitrile (7) (165 mg, 0.57 mmol) and boronic ester 30 (350 mg, 0.57 mmol) as starting materials. LCMS (ESI$^+$) m/z=445.0 (M+H). $^1$H NMR (400 MHz, DMSO-d$_6$) δ 8.91 (d, J=2.2 Hz, 1H), 8.31 (d, J=2.2 Hz, 1H), 7.80 (dd, J=8.2, 2.4 Hz, 1H), 7.68 (dq, J=8.7, 2.5 Hz, 1H), 7.24 (dd, J=12.2, 8.5 Hz, 1H), 6.97 (d, J=39.2 Hz, 1H), 6.15 (s, 2H), 3.69 (d, J=15.1 Hz, 1H), 3.56 (d, J=15.0 Hz, 1H), 2.54 (s, 3H), 1.61 (d, J=17.7 Hz, 6H), 1.46 (s, 3H). $^{19}$F NMR (400 MHz, DMSO-d$_6$) δ −111.05 (s, 1F), −114.07 (s, 1F).

Example 275: (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-methylnicotinonitrile

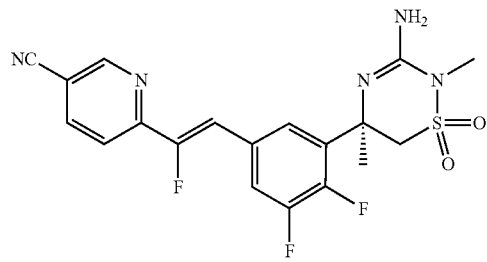

275

LCMS (ESI+) m/z=450.2 (M+H). $^1$H NMR (400 MHz, DMSO-$d_6$) δ 8.92 (s, 1H), 8.32 (dd, J=1.9, 0.9 Hz, 1H), 7.80-7.52 (m, 2H), 6.97 (d, J=38.3 Hz, 1H), 6.10 (s, 2H), 3.95-3.71 (m, 2H), 3.04 (s, 3H), 2.51 (s, 3H), 1.62 (s, 3H). $^{19}$F NMR (400 MHz, DMSO-$d_6$) δ −112.19 (s, 1F), −137.4 (d, 1F), −138.85 (d, 1F).

Example 276: (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-chloronicotinonitrile

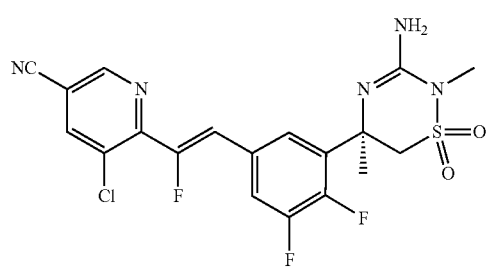

276

LCMS (ESI+) m/z=470.2 (M+H). $^1$H NMR (400 MHz, DMSO-$d_6$) δ 9.08 (d, J=1.7 Hz, 1H), 8.76 (d, J=1.8 Hz, 1H), 7.74 (d, J=6.3 Hz, 1H), 7.72-7.60 (m, 1H), 7.02 (d, J=37.4 Hz, 1H), 6.12 (s, 2H), 3.85 (t, J=12.2 Hz, 2H), 3.05 (s, 3H), 1.63 (s, 3H). $^{19}$F NMR (400 MHz, DMSO-$d_6$) δ −112.57 (d, 1F), −136.67 (d, 1F), −138.66 (s, 1F).

Example 277: (1R,4R,5S)-2-amino-4-(2-fluoro-5-((Z)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide; and Example 278: (1R,4R,5S)-2-amino-4-(2-fluoro-5-((E)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide

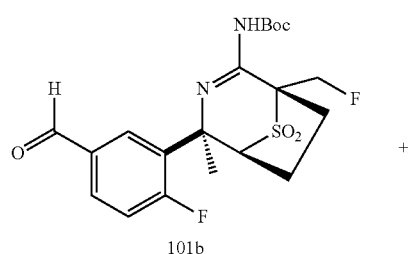

101b

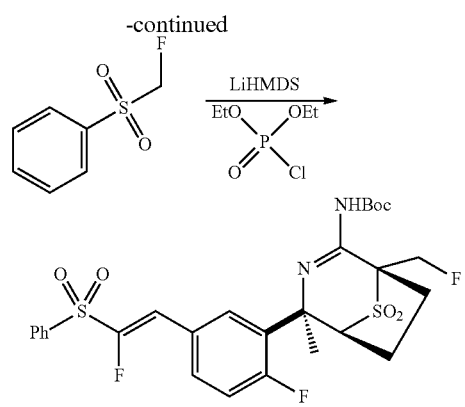

277a

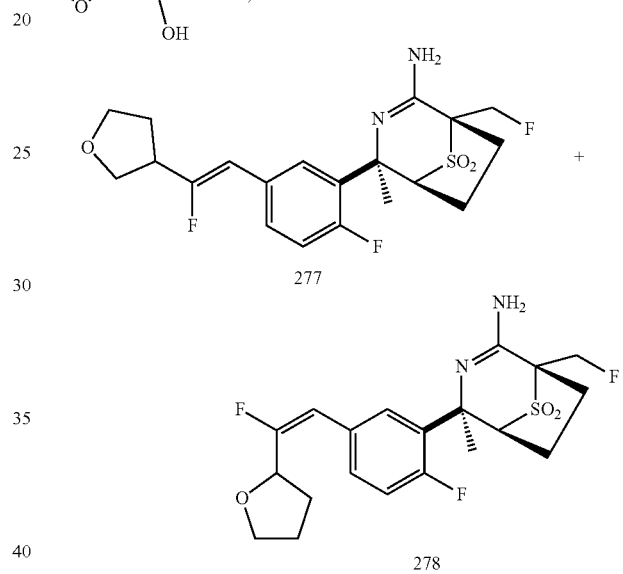

277

278

To a mixture of fluoromethyl phenyl sulfone (Matrix Scientific, Elgin, S.C., USA, 732 mg, 4.20 mmol) and diethyl chlorophosphate (Sigma-Aldrich, 0.61 mL, 4.20 mmol) in THF (30 mL) at −70° C. was added lithium bis(trimethylsilyl)amide (9.04 mL of 1.0 M solution in THF, 9.04 mmol) dropwise. The reaction was stirred at −70° C. for 1 h. A solution of tert-butyl ((1R,4R,5S)-4-(2-fluoro-5-formylphenyl)-1-(fluoromethyl)-4-methyl-8,8-dioxido-8-thia-3-azabicyclo[3.2.1]oct-2-en-2-yl)carbamate (101b, 930 mg, 2.10 mmol) in 20 mL of THF was added dropwise. The cold bath was removed and the reaction was stirred for 5 min, quenched with sat'd aqueous NH$_4$Cl, and extracted with EtOAc. The organic layer was dried over MgSO$_4$ and evaporated. The residue was purified via silica gel chromatography (2-8% EtOAc in DCM) gave tert-butyl ((1R,4R,5 S)-4-(2-fluoro-5-((E)-2-fluoro-2-(phenylsulfonyl)vinyl) phenyl)-1-(fluoromethyl)-4-methyl-8,8-dioxido-8-thia-3-azabicyclo[3.2.1]oct-2-en-2-yl)carbamate (277a, 1.17 g, 1.95 mmol, 93% yield) with the E/Z ratio>10:1. LCMS (ESI, pos.): 599.0 (M+1)+.

In a 12 mL flat-bottomed vial was charged (Ir[dF(CF$_3$)ppy]$_2$(dtbpy))PF$_6$ (3 mg, 2.67 mol), 277a (110 mg, 0.18 mmol) and (+/−)-1-tetrahydro-2-furoic acid (50 mg, 0.43 mmol). Dichloroethane (1.0 mL) was added and a stream of Ar was allowed to pass through the solvent for 5 min. The vial was sealed and the light yellow solution was placed over a blue LED lamp (Kessil H150, 1.5 A, 34 W). After 14 h, EtOAc (10 mL) was added. The mixture was washed with sat'd aqueous NaHCO$_3$ (2×3 mL), water (3 mL), and brine (3 mL). The organic layer was dried over Na$_2$SO$_4$, filtered, and concentrated. The residue was purified by chromatography on silica using EtOAc in DCM (10-25%) as eluent to give the Boc-intermediates as a white foam. MS m/z=529.1 [M+H]$^+$. The white foam was dissolved in DCM (2 mL) and treated with TFA (0.2 mL) at RT. After 20 min, EtOAc (10 mL) was added. The mixture was washed with saturated NaHCO$_3$ (2×3 mL) and brine (3 mL). The organic layer was dried over Na$_2$SO$_4$, filtered, and concentrated. The residue was purified by chromatography on silica using MeOH-EtOAc (10%) in heptane (10-50%) as eluent to give Example 277 and Example 278.

(1R,4R,5 S)-2-amino-4-(2-fluoro-5-((Z)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide (277) (21 mg, 27% yield) as a white foam. LCMS (ESI, pos.): 429.0 (M+1)$^+$. $^1$H NMR (400 MHz, CDCl$_3$) δ ppm 7.63 (ddd, J=7.6, 4.7, 2.3 Hz, 1H), 7.47 (ddt, J=8.5, 4.6, 2.1, 2.1 Hz, 1H), 6.95-7.06 (m, 1H), 5.76 (d, J=38.7 Hz, 1H), 5.10-5.32 (m, 1H), 4.87-5.08 (m, 1H), 4.42-4.58 (m, 1H), 3.93-4.06 (m, 1H), 3.85-3.92 (m, 1H), 3.83 (d, J=5.1 Hz, 1H), 1.94-2.25 (m, 7H), 1.91 (s, 3H), 1.51-1.64 (m, 1H). $^{19}$F NMR (376 MHz, CDCl$_3$) δ ppm −113.42 (1F), −117.98 (1F), −227.83 (1F).

(1R,4R,5S)-2-amino-4-(2-fluoro-5-((E)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide (278) (14 mg, 18% yield). LCMS (ESI, pos.): 429.0 (M+1)$^+$. $^1$H NMR (400 MHz, CDCl$_3$) δ ppm 7.47 (ddd, J=18.6, 7.6, 2.2 Hz, 1H), 7.13-7.23 (m, 1H), 7.02 (dd, J=11.8, 8.3 Hz, 1H), 6.32 (dd, J=19.8, 4.5 Hz, 1H), 5.11-5.33 (m, 1H), 4.85-5.08 (m, 1H), 4.58-4.82 (m, 1H), 3.98 (q, J=6.8 Hz, 1H), 3.76-3.91 (m, 2H), 1.95-2.28 (m, 7H), 1.91 (s, 3H), 1.49-1.64 (m, 1H). $^{19}$F NMR (376 MHz, CDCl$_3$) δ ppm −113.97 (1F), −118.81−−119.47 (1F), −228.04 (1F).

Example 279: (R,E)-5-amino-3-(5-(4-chlorostyryl)-2-fluorophenyl)-3,6,6-trimethyl-3,6-dihydro-2H-1,4-thiazine 1,1-dioxide

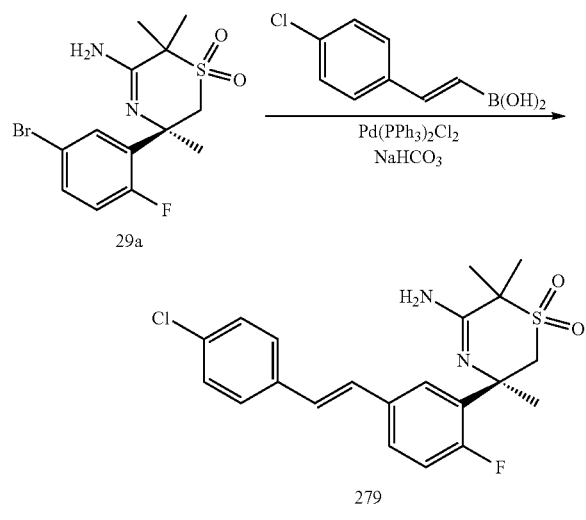

A mixture of (R)-5-amino-3-(5-bromo-2-fluorophenyl)-3,6,6-trimethyl-3,6-dihydro-2H-1,4-thiazine 1,1-dioxide (29a, 180 mg, 0.50 mmol), bis(triphenylphosphine)palladium(II) dichloride (17 mg, 0.025 mmol), trans-2-(4-chlorophenyl)vinylboronic acid (Sigma-Aldrich) (136 mg, 0.74 mmol) and sodium bicarbonate (104 mg, 1.24 mmol) in 1.5 mL of dioxane and 0.5 mL of water in a sealed glass tube was heated at 130° C. for 30 minutes in a microwave. After cooling to room temperature, the mixture was filtered through a pad of celite and the cake was rinsed with 5 mL of EtOAc. The filtrate was evaporated in vacuo and the residue was purified by silica gel chromatography (25 to 75% EtOAc in DCM) to give Example 279 (170 mg, 0.40 mmol, 82% yield) as an off-white solid. MS m/z=421.1 [M+H]$^+$. $^1$H NMR (400 MHz, CHLOROFORM-d) δ 7.61 (dd, J=2.2, 7.9 Hz, 1H), 7.42 (dd, J=3.0, 5.4 Hz, 1H), 7.39 (d, J=8.4 Hz, 2H), 7.33-7.27 (m, 2H), 7.09-6.98 (m, 2H), 6.97-6.89 (m, 1H), 3.66-3.52 (m, 2H), 1.81 (s, 3H), 1.70 (s, 3H), 1.61 (s, 3H). NH$_2$ peak was not observed.

Biological Evaluation

Provided in this section is the biological evaluation of the specific examples provided herein. In particular, Table 2 contains biological activity data. The data presented in Table 2 provides the IC$_{50}$ (μM) for the specific examples obtained in a BACE1 enzyme assay, BACE1 cell assay, BACE2 enzyme assay and CatD assay.

TABLE 2

| Ex. No. | BACE1 Enzyme IC$_{50}$ (μM) | BACE1 Cell IC$_{50}$ (μM) | BACE2 Enzyme IC$_{50}$ (μM) | Cat D Enzyme IC$_{50}$ (μM) |
|---|---|---|---|---|
| 100 | 0.010 | 0.472 | 0.007 | 91 |
| 101 | 0.005 | 0.079 | 0.013 | 211.8 |
| 102 | 0.005 | 0.017 | 0.032 | >133.0 |
| 103 | 0.003 | 0.039 | 0.050 | 94.7 |
| 104 | 0.003 | 0.024 | 0.002 | 95 |
| 105 | 0.012 | 0.023 | 0.009 | 35.8 |
| 106 | 0.001 | 0.002 | 0.031 | 182 |
| 107 | 0.003 | 0.003 | 0.025 | 81.8 |
| 108 | 0.003 | 0.006 | 0.057 | 144.6 |
| 109 | 0.028 | 0.227 | 0.167 | 135 |
| 110 | 0.709 | 0.631 | 0.963 | 194 |
| 111 | 0.007 | 0.006 | 0.005 | 86.3 |
| 112 | 0.003 | 0.008 | 0.052 | 35.8 |
| 113 | 0.002 | 0.004 | 0.009 | 100 |
| 114 | 0.009 | 0.080 | 0.003 | 115 |
| 115 | 0.022 | 0.027 | 0.192 | 101.53 |
| 116 | 0.003 | 0.001 | 0.045 | 43.8 |
| 117 | 0.023 | 0.148 | 0.186 | 29.1 |
| 118 | 0.035 | 0.706 | 0.124 | >400.0 |
| 119 | 0.021 | 0.060 | 0.182 | >400.0 |
| 120 | 0.037 | 0.542 | 0.258 | >400.0 |
| 121 | 0.098 | 0.191 | 0.180 | >400.0 |
| 122 | 0.054 | 0.527 | 0.194 | >400.0 |
| 123 | 0.001 | 0.003 | 0.051 | 230.8 |
| 124 | 0.039 | 0.134 | 0.161 | 218 |
| 125 | 0.048 | 0.446 | 0.163 | 91.2 |
| 126 | 0.138 | 0.457 | 0.141 | 100.1 |
| 127 | 0.006 | 0.008 | 0.175 | 129.4 |
| 128 | 0.004 | 0.018 | 0.147 | 124.6 |
| 129 | 0.007 | 0.005 | 0.056 | 163 |
| 130 | 0.033 | 0.060 | 0.163 | 173 |
| 131 | 0.013 | 0.097 | 0.104 | >400.0 |
| 132 | 0.038 | 1.955 | 0.217 | >400.0 |
| 133 | 0.131 | 0.339 | 0.151 | 427.5 |
| 134 | 0.101 | 0.318 | 0.123 | 196 |
| 135 | 0.086 | 0.866 | 0.120 | >400.0 |
| 136 | 0.051 | 0.218 | 0.315 | 78.2 |
| 137 | 0.001 | 0.004 | 0.044 | 65.3 |
| 138 | 0.016 | 0.078 | 0.622 | 124.6 |
| 139 | 0.049 | 0.198 | 0.070 | 428.2 |
| 140 | 0.154 | 0.241 | 0.203 | 177 |
| 141 | 0.055 | 0.229 | 0.330 | 96.2 |

TABLE 2-continued

| Ex. No. | BACE1 Enzyme IC$_{50}$ (μM) | BACE1 Cell IC$_{50}$ (μM) | BACE2 Enzyme IC$_{50}$ (μM) | Cat D Enzyme IC$_{50}$ (μM) |
|---|---|---|---|---|
| 142 | 0.193 | 0.739 | 0.425 | 90.5 |
| 143 | 0.044 | 0.380 | 0.222 | 30.5 |
| 144 | 0.030 | 1.072 | 0.143 | 17 |
| 145 | 0.058 | 0.518 | 0.107 | 27.5 |
| 146 | 0.003 | 0.006 | 0.097 | 151 |
| 147 | 0.006 | 0.015 | 0.184 | 41.1 |
| 148 | 0.018 | 0.088 | 0.217 | 25.3 |
| 149 | 0.002 | 0.003 | 0.051 | 110 |
| 150 | 0.046 | 1.615 | 0.155 | 13.8 |
| 151 | 0.240 | 1.420 | 0.121 | 40.9 |
| 152 | 0.015 | 0.047 | 0.006 | 48.8 |
| 153 | 0.636 | 2.185 | 1.060 | 249 |
| 154 | 0.001 | 0.002 | 0.034 | 109 |
| 155 | 5.135 | 0.985 | 2.390 | 439.6 |
| 156 | 0.096 | 1.315 | 0.671 | 90.5 |
| 157 | 0.187 | 0.181 | 0.478 | 57.5 |
| 158 | 0.001 | 0.002 | 0.031 | 45.9 |
| 159 | 0.004 | 0.027 | 0.003 | 143 |
| 160 | 0.001 | 0.005 | 0.120 | 206.8 |
| 161 | 0.080 | 0.048 | 2.630 | 59.6 |
| 162 | 0.065 | 0.168 | 0.732 | 15.7 |
| 163 | 0.133 | 1.117 | 2.880 | 223 |
| 164 | 0.011 | 0.011 | 0.108 | 107 |
| 165 | 0.001 | 0.001 | 0.047 | 18.2 |
| 166 | 0.004 | 0.004 | 0.090 | 40.9 |
| 167 | 0.000 | 0.011 | 0.290 | 32.5 |
| 168 | 0.000 | 0.000 | 0.010 | 25.4 |
| 169 | 0.066 | 0.124 | 0.907 | 697.8 |
| 170 | 0.002 | 0.005 | 0.017 | 644.7 |
| 171 | 0.005 | 0.006 | 0.142 | 17 |
| 172 | 0.025 | 0.023 | 0.084 | 67.6 |
| 173 | 0.007 | 0.009 | 0.103 | 78.1 |
| 174 | 0.154 | 1.405 | 0.113 | 22 |
| 175 | 0.088 | 0.053 | 0.225 | 124 |
| 176 | 0.111 | 0.056 | 0.409 | 148 |
| 177 | 0.208 | 0.600 | 0.101 | 61.4 |
| 178 | 0.003 | 0.022 | 0.232 | 77.6 |
| 179 | 0.176 | 0.120 | 0.217 | 43 |
| 180 | 0.007 | 0.026 | 0.075 | 93.7 |
| 181 | 0.007 | 0.028 | 0.087 | 178 |
| 182 | 0.039 | 0.318 | 0.076 | 217 |
| 183 | 0.013 | 0.075 | 0.678 | 261 |
| 184 | 0.296 | 0.277 | 0.790 | 335.2 |
| 185 | 0.002 | 0.005 | 0.159 | 258.8 |
| 186 | 0.005 | 0.024 | 0.451 | 375.1 |
| 187 | 0.172 | 0.108 | 0.078 | 165 |
| 188 | 0.013 | 0.222 | 0.057 | 155 |
| 189 | 0.060 | 2.220 | 0.059 | 61.8 |
| 190 | 0.006 | 0.074 | 0.274 | 104 |
| 191 | 0.128 | 5.090 | 0.052 | 62.2 |
| 192 | 0.012 | 0.035 | 0.046 | 76.1 |
| 193 | 0.121 | 0.833 | 0.104 | 82.3 |
| 194 | 0.007 | 0.055 | 0.181 | 49.4 |
| 195 | 0.011 | 0.188 | 0.523 | 64.9 |
| 196 | 0.583 | 1.082 | 0.157 | 56.1 |
| 197 | 0.033 | 0.052 | 0.087 | 81.3 |
| 198 | 0.113 | 0.173 | 0.371 | 38.25 |
| 199 | 0.004 | 0.002 | 0.102 | 51.2 |
| 200 | 0.018 | 0.206 | 0.086 | 41.6 |
| 201 | 0.006 | 0.214 | 0.082 | 55.2 |
| 202 | 0.166 | 9.570 | 0.870 | 59.3 |
| 203 | 0.125 | 0.196 | 0.056 | 85.4 |
| 204 | 0.005 | 0.009 | 0.179 | 42.7 |
| 205 | 0.005 | 0.007 | 0.129 | 244 |
| 206 | 0.069 | 0.188 | 0.139 | 74.7 |
| 207 | 0.507 | 2.530 | 0.519 | 57.5 |
| 208 | 0.001 | 0.005 | 0.107 | 79.5 |
| 209 | 0.124 | 2.525 | 0.311 | 46.5 |
| 210 | 1.720 | 2.230 | 0.476 | 467.28 |
| 211 | 0.349 | 1.825 | 0.333 | 59.5 |
| 212 | 0.015 | 0.036 | 0.132 | 60.4 |
| 213 | 0.626 | 3.585 | 0.683 | 172 |
| 214 | 0.225 | 5.940 | 0.851 | 302.69 |
| 215 | 3.135 | 28.650 | 4.025 | 91.3 |
| 216 | 0.628 | 5.365 | 0.364 | 29.9 |
| 217 | 0.009 | 0.288 | 0.233 | 26.8 |
| 218 | 0.180 | 0.529 | 0.285 | 195 |
| 219 | 0.136 | 0.142 | 0.377 | 208 |
| 220 | 0.014 | 0.047 | 0.066 | 32.2 |
| 221 | 0.038 | 0.215 | 0.197 | 28.3 |
| 222 | 1.565 | 3.110 | 0.473 | 64.7 |
| 223 | 0.061 | 0.196 | 0.210 | 22.3 |
| 224 | 0.040 | 0.042 | 0.421 | 74.8 |
| 225 | 0.008 | 0.009 | 0.084 | 69.8 |
| 226 | 0.007 | 0.341 | 0.014 | 47 |
| 227 | 0.046 | 0.427 | 0.269 | 56.2 |
| 228 | 0.028 | 0.025 | 0.266 | 39.5 |
| 229 | 0.008 | 0.010 | 0.257 | 68.2 |
| 230 | 0.179 | 0.656 | 0.024 | 111 |
| 231 | 0.084 | 0.097 | 0.094 | >4.94 |
| 232 | 0.007 | 0.029 | 0.002 | 68.8 |
| 233 | 0.060 | 0.035 | 0.621 | 51.7 |
| 234 | 0.392 | 0.099 | 0.554 | 107 |
| 235 | 0.268 | 0.128 | 0.533 | 160 |
| 236 | 1.125 | 0.410 | 2.355 | 55.2 |
| 237 | 0.004 | 0.093 | 0.103 | 25.4 |
| 238 | 0.006 | 0.042 | 0.094 | 46.8 |
| 239 | 0.530 | 1.022 | 0.143 | 328.8 |
| 240 | 0.034 | 0.067 | 0.008 | 375.4 |
| 241 | 0.107 | 0.168 | 0.075 | 91.3 |
| 242 | 0.005 | 0.026 | 0.010 | 99.9 |
| 243 | 0.113 | 0.856 | 0.398 | 90.3 |
| 244 | 0.006 | 0.008 | 0.031 | 206 |
| 245 | 0.005 | 0.004 | 0.021 | 137 |
| 246 | 0.009 | 0.036 | 0.111 | 34.9 |
| 247 | 0.006 | 0.028 | 0.007 | 11 |
| 248 | 0.003 | 0.013 | 0.016 | 12.7 |
| 249 | 0.682 | 0.085 | 1.815 | >400.0 |
| 250 | 4.000 | 5.285 | 3.945 | >400.0 |
| 251 | 0.007 | 0.110 | 0.036 | 33.8 |
| 252 | 0.010 | 0.007 | 0.056 | 47.4 |
| 253 | 0.013 | 0.028 | 0.021 | 92 |
| 254 | 0.007 | 0.021 | 0.052 | 28.3 |
| 255 | 3.835 | 3.020 | 0.458 | 122 |
| 256 | 0.035 | 0.099 | 0.014 | 15.4 |
| 257 | 0.207 | 0.102 | 0.235 | 237 |
| 258 | 0.006 | 0.033 | 0.040 | 54.4 |
| 259 | 0.272 | 1.125 | 0.041 | 116 |
| 260 | 0.552 | 4.180 | 0.112 | 72.5 |
| 261 | 0.002 | 0.034 | 0.012 | 178 |
| 262 | 0.047 | 0.180 | 0.011 | 108 |
| 263 | 0.189 | 0.133 | 0.190 | 237 |
| 264 | 0.010 | 0.075 | 0.038 | 117 |
| 265 | 0.008 | 0.010 | 0.043 | 89.4 |
| 266 | 0.750 | 0.653 | 0.078 | 69.8 |
| 267 | 0.026 | 0.038 | 0.006 | 57.5 |
| 268 | 0.007 | 0.035 | 0.012 | 136 |
| 269 | 0.002 | 0.004 | 0.003 | 119 |
| 270 | 0.075 | 0.138 | 0.028 | 265 |
| 271 | 0.170 | 0.169 | 0.398 | 42.5 |
| 272 | 0.004 | 0.018 | 0.022 | 61.5 |
| 273 | 0.007 | 0.013 | 0.046 | 76.2 |
| 274 | 0.006 | 0.051 | 0.028 | 122 |
| 275 | 0.001 | 0.014 | 0.009 | 55.9 |
| 276 | 0.002 | 0.017 | 0.006 | 58 |
| 277 | 0.251 | 0.972 | 0.139 | 213.5 |
| 278 | 1.113 | 1.977 | 0.624 | 247 |
| 279 | 0.056 | 0.442 | 0.056 | 39.3 |

The results presented in Table 2 have been generated with the in vitro assays described below. These assays may be used to test any of the compounds described herein to assess and characterize a compound's ability to modulate BACE activity and to regulate the cleavage of Aβ precursor protein, thereby reducing or inhibiting the production of Aβ protein.

In Vitro Enzymatic BACE1 and BACE2 FRET (Fluorescence Resonance Energy Transfer) Assays The cDNAs for both human recombinant BACE1 and 2 with C-terminal 6-His Tags were cloned into transient protein expression vectors, which were subsequently transfected into mammalian cell lines. These recombinant proteins were further purified using Ni-NTA affinity chromatography (Qiagen). The assay buffer used in these screens was 0.05 M acetate, pH 4.5, 8% DMSO final, 100 µM genapol (which is a nonionic detergent, below its Critical Micelle Concentration). The β-secretase enzyme (0.02 nM for BACE1 and 0.64 nM for BACE2), which was pre-incubated for one hour with the test compound, typically in about 1 uL of DMSO according to a serial dilution, was added thereto. The assay was effectively started by the addition of FRET substrate (50 nM) and the combination was incubated for one hour. The FRET assay was terminated by the addition of tris buffer, which raised the pH to neutrality, and the fluorescence was determined. The FRET substrate was a peptide with commercially available fluorophore and quencher, on opposite sides of the BACE cleavage site. The specific FRET substrate used in this assay was made by Amgen in-house. Commercially available FRET substrates, for example, the FRET substrate offered with the BACE1 FRET Assay Kit sold by ThermoFisher Scientific (Catalog Number P2985), may be used in this assay with the appropriate modifications, which are within the purview of the ability of a person with ordinary skill in the art. Proteolytic cleavage of the FRET substrate released quenching of fluorescence (excitation 488 nm and emission 590 nm).

The in vitro BACE FRET enzyme data for each of the Examples is provided in Table 2.

In Vitro BACE1 Cell-Based Assay

The cell-based assay measures inhibition or reduction of Aβ40 in conditioned medium of test compound treated cells expressing amyloid precursor protein. Cells stably expressing Amyloid Precursor Protein (APP) were plated at a density of 45K cells/well in 384 well plates (Corning/BioCoat 354663). The test compounds were then added to cells in 22-point dose response concentrations with the starting concentration being 62.5 µM. The compounds were diluted from stock solutions in DMSO and the final DMSO concentration of the test compounds on cells was 0.625%. The cells were cultivated overnight at 37° C. and 5% $CO_2$ in DMEM supplemented with 10% FBS. After 24 h of incubation with the test compounds, the conditioned media was collected and the Aβ40 levels were determined using HTRF (Homogeneous Time Resolved Fluorescence). The $IC_{50}$ of the compound was calculated from the percent of control or percent inhibition of Aβ 40 as a function of the concentration of the test compound.

The HTRF to detect Aβ40 was performed in 384 well plates (Costar 3658). The antibody pair that were used to detect Aβ 40 from cell supernatants were ConfAb40 antibody (Amgen in-house) and biotinylated 6E10 (BIOLEGEND). As an alternative to ConfAb40, a commercially available antibody, Anti-beta Amyloid 1-40 antibody [BDI350] from Abcam, Cambridge, Mass. 02139-1517 (Product code: ab20068), may be used in this assay. The concentrations were 0.35 µg/mL of ConfAb40 antibody and 1.33 µg/mL of 6E10-biotinylated antibody, as well as 4.5 µg/mL of Streptavidin Allophycocyanin Conjugate (ThermoFisher Scientific) in HTRF Buffer (1M Hepes pH 7.5, 1M NaCl, 1% BSA, 0.5% Tween 20).

The conditioned media was incubated with above antibodies and Streptavidin Allophycocyanin Conjugate for 30-60 minutes at 23° C. The final readout was performed on Envision from PerkinElmer.

The in vitro BACE cell-based data for each of the Examples is provided in Table 2.

In Vitro Enzymatic Cathepsin D (CatD) FRET Assay

Recombinant CatD was expressed in CHO cells. The assay buffer for CatD was 0.05 M citrate pH 3.5, 10% DMSO final, 5 mM CHAPS. The CatD enzyme (9 nM) was pre-incubated for one hour with inhibitors, typically in about 1 uL of DMSO according to a serial dilution, is added thereto. The assays was effectively started by the addition of different FRET substrates (20 nM for CatD) and the combination was incubated for one hour. The FRET assay was terminated with by addition of tris buffer, which raises the pH to neutrality, and the fluorescence was determined. The FRET substrate was a peptide with commercially available fluorophore and quencher, on opposite sides of the CatD cleavage site. The CatD substrate peptide sequence was based on sequence #1 of Table 1 from Gulnik et al., *FEBS Lett.* 413(2):379-384 (1997). Proteolytic cleavage of the FRET substrate released quenching of fluorescence (CatD excitation 500 nm and emission 580 nm).

Alternatively, a CatD assay may also be run according to the procedure described in Yasuda et al., *J. Biochem.* 125(6): 1137-1143 (1999). In addition, the CatD and Cathepsin E assays are described in International Patent Application Publication No. WO2011069934.

The in vitro CatD FRET assay data for each of the Examples is provided in Table 2, conducted by the first procedure described above. As shown by the high micromolar CatD data (very poorly active or inactive against CatD), the compounds disclosed herein possess the unexpected property of little to no ability to inhibit the activity of CatD. Thus, with this surprising selectivity profile, the compounds provided herein are believed to minimize, reduce or completely eliminate any risk of retinal atrophy and abnormal development of the eye and of the retinal pigmented epithelium as it relates to the normal function and activity of CatD.

In Vivo Inhibition of β-Secretase

Several animal models, including mouse, rat, dog, and monkey, may be used to screen for inhibition of β-secretase activity in vivo following administration of a test compound. This procedure may be used to show that the compounds provided herein reduce the formation and/or deposition of Aβ peptide in the cerebrospinal fluid (CSF) as well as in the brain. Animals to be used in this experiment can be wild type, transgenic, or gene knockout animals. For example, the Tg2576 mouse model, prepared and conducted as described in Hsiao et al., Science 274:99-102 (1996), and other non-transgenic or gene knockout animals are useful to analyze in vivo inhibition of Aβ peptide production in the presence of test compounds.

Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of Aβ levels and test compound concentrations (Dovey et al., *J. Neurochem.*, 76(1):173-181 (2001)) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., *J. Pharmacol. Exp. Ther.* 313(2):902-908 (2005)), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Aβ by specific sandwich ELISA assays based on ECL (Electrochemiluminescence) technology. For example, rat Aβ40 is measured using biotinylated-4G8 (Signet) as a capture antibody and Fab40 (an in-house antibody specific to the C-terminal of Aβ40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Aβ peptide levels are measured for reduction by X % and Y % in cerebrospinal fluid and brain, respectively, when compared to the levels measured in the vehicle-treated or control mice. Alternatively, the antibody sold with the V-PLEX abeta40 Peptide (4G8) Kit, commercially available from Meso Scale Diagnostics (MSD), Rockville, Md. 20850-3173 (Catalog NO. K150SJE-1) may be used in this assay.

This procedure may be used to show that the compounds provided herein reduce the formation and/or deposition of Aβ peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs.

The results presented in Table 3 were obtained using certain compounds described herein in the in vivo protocol described above.

TABLE 3

| Ex. No. | % Aβ reduction in rat CSF at 10 mpk | % Aβ reduction in rat brain at 10 mpk |
| --- | --- | --- |
| 112 | 78 | 100 |
| 127 | 64 | 70 |
| 128 | 33 | 35 |
| 146 | 12 | 16 |
| 123 | 77 | 88 |
| 158 | 72 | 71 |
| 160 | 52 | 34 |
| 166 | 45 | 26 |
| 204 | 65 | 61 |
| 186 | 19 | 43 |
| 199 | 43 | 58 |
| 205 | 68 | 65 |
| 261 | 69 | 60 |

Methods of Use

According to the amyloid cascade hypothesis, cerebral deposition of amyloid-beta (Aβ) peptide is critical for Alzheimer's disease (AD) pathogenesis. Aβ peptide generation is initiated when β-secretase (BACE1) cleaves the amyloid precursor protein. De Meyer et al. re-affirm the putative role that the accumulation of Aβ peptide in cerebral spinal fluid (CSF) in a subject plays in the progression of symptoms, initially revealed as mild cognitive impairment, which ultimately leads to AD. *Arch Neurol.* 67(8):949-956 (2010). Aβ peptides generated from amyloid precursor protein (APP) by proteolytic cleavage, such as by aspartyl protease enzymes, including β-secretase (BACE) and γ-secretase, likely play a causal role in AD pathogenesis (Tanzi et al., *Cell* 120(4):545-555 (2005); Walsh et al., *Neuron* 44(1):181-193 (2004)). Although the precise mechanisms of Aβ toxicity are unclear, oligomeric forms of Aβ may contribute to cognitive decline by altering synaptic structure and function (Palop et al., *Nat. Neurosci.* 13(7): 812-818 (2010); Selkoe, *Behav. Brain Res.* 192(1): 106-113 (2008); Shankar et al., *Nat. Med.* 14(8):837-842 (2008)). Transgenic mouse models that overexpress mutant APP and produce high levels of Aβ show amyloid plaque deposition, synaptic deficits, learning and memory impairments, and other behavioral abnormalities (Games et al., *Nature* 373: 523-527 (1995); Gotz et al., *Mol. Psychiatry* 9(7):664-683 (2004); Hsia et al., *Proc. Natl. Academy of Science USA* (96): 3228-3233, 1999; Hsiao et al., *Science* (274): 99-102, 1996, citing Harris et al, *Neuron* (68): 428-441, 2010).

For many years now, BACE1 has been a prime target for designing drugs to prevent or treat AD. Vassar et al., *Lancet Neurol.* 13:319-329 (2014). Several pharmaceutical companies are presently pursuing BACE1 inhibitors in human clinical trials. Id. at abstract.

For example, MK-8931, a small molecule inhibitor of BACE1, was the first molecule to enter phase I clinical trials. Yan, *Transl. Neurodegener.* 5(13): 1-11 (2016) at page 4. MK-8931 was shown to have an excellent safety profile with no immediately noticeable side effects. Id. Merck was able to show that MK-8931 enters the brain and blocks β-secretase by showing that MK-8931 significantly reduced CSF Aβ peptide concentrations in a sustained and dose-dependent manner. Vassar et al., *Lancet Neurol.* 13:319-329 (2014) at page 323. MK-8931 is currently evaluated in a phase II/III clinical trial to assess the efficacy and safety of the compound for the treatment of AD patients with amnestic mild cognitive impairment (prodromal AD). Yan, *Transl. Neurodegener.* 5(13):1-11 (2016) at page 4.

Further, E2609, a BACE inhibitor identified by Eisai, showed significant reduction in Aβ peptide levels in the CSF and plasma in nonhuman primates. Yan, *Transl. Neurodegener.* 5(13):1-11 (2016) at page 7. E2609 did not show clinical significant safety concerns after repeated doses up to 200 mg in a phase I clinical trial. Id. After 14 d dosing the Aβ peptide level reduction in the CSF was statistically significant compared to baseline (46.2% (25 mg), 61.9% (50 mg), 73.8% (100 mg), 79.9% (200 mg)). Id. In November 2014, Eisai stated that a phase II dose-finding study in patients with mild cognitive impairment (MCI) due to AD or prodromal AD and a positive amyloid PET-scan will be conducted in collaboration with Biogen.

Additionally, companies are also developing therapies targeting asymptomatic patients. JNJ-54861911, which was first developed by Shionogi & Co. in Japan and later in collaboration with Janssen, demonstrated an ability to cross the blood-brain barrier and to dose-dependently reduce Aβ peptide concentrations. Yan, *Transl. Neurodegener.* 5(13): 1-11 (2016) at pages 5-7. For example, an oral dose of 95 mg once daily achieved Aβ peptide reduction of up to 95% in CSF. Id. In October 2015, Janssen and Shionogi launched a phase II/III trial targeting asymptomatic subjects that are at risk for developing Alzheimer's dementia. Id.

Similarly, Amgen and Novartis announced in late 2015 a collaboration to co-develop Novartis' BACE inhibitor CNP520. Yan, *Transl. Neurodegener.* 5(13): 1-11 (2016) at page 8. The study is aimed at, inter alia, showing that CNP520 "can slow down the onset and progression of clinical symptoms associated with Alzheimer's disease (AD) in participants at the risk to develop clinical symptoms based on their age and genotype." https://clinicaltrials.gov/ct2/show/NCT02565511 (last visited Oct. 23, 2016).

The compounds disclosed herein have been shown to modulate, and specifically inhibit the activity of the β-secretase enzymes as shown in Table 2 for specific examples disclosed herein, thereby reducing the generation of Aβ peptide. Accordingly, the compounds provided herein are useful for, for example, the prevention or treatment of β-secretase related diseases, including, but not limited to, AD. The compounds provided herein have the ability to modulate the activity of the β-secretase enzyme, thereby regulating the production of Aβ peptide and reducing the formation and deposition of Aβ peptide in both the cerebral spinal fluid as well as in the brain, resulting in a decrease of Aβ plaque in the brain.

More specifically, provided are the following uses for the compounds disclosed herein:

Provided are the compounds disclosed herein for use in reducing beta amyloid peptide levels in the cerebral spinal fluid of a subject.

Provided are the compounds disclosed herein for use in treating AD, cognitive impairment, or a combination thereof in a subject. In one embodiment, the compounds provided herein are useful for treating various stages and degrees of AD, including without limitation, mild, moderate and severe AD. In another embodiment, the compounds provided herein are useful for treating preclinical AD, mild cognitive impairment (MCI) due to AD, and dementia due to AD. In yet another embodiment, the compounds provided herein may be used to treat prodromal subjects.

Provided are the compounds disclosed herein for use in treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of AD, or a combination thereof in a subject.

Provided are the compounds disclosed herein for use in reducing formation of plaque in the brain of a subject.

As previously discussed, in certain embodiments, the compounds described herein are to be understood to include all stereoisomers, tautomers, isotopically-labelled forms thereof or pharmaceutically acceptable salts of any of the foregoing or solvates of any of the foregoing or amorphous and crystalline forms (polymorphs) of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Dosage, Formulation, and Route of Administration

The amount of compound(s) which is/are administered and the dosage regimen for treating neurological disorders and β-secretase mediated diseases with the compounds and/or compositions disclosed herein depends on a variety of factors, including the age, weight, sex and medical condition of the subject, the type of disease, the severity of the disease, the route and frequency of administration, and the particular compound employed. A daily dose of about 0.01 to 500 mg/kg, or in some embodiments, between about 0.01 and about 50 mg/kg, and in still other embodiments between about 0.01 and about 30 mg/kg body weight may be appropriate. In yet other embodiments, a daily dose of between about 0.1 and about 10 mg/kg body weight may be appropriate and should be useful for all uses disclosed herein. The daily dose can be administered a number of times a day such as from one to four doses per day.

While it may be possible to administer a compound disclosed herein alone in the uses described, the compound administered normally will be present as an active ingredient in a pharmaceutical composition. Thus, in another embodiment, provided herein is a pharmaceutical composition comprising a compound disclosed herein in combination with a pharmaceutically acceptable excipient, such as diluents, carriers, adjuvants and the like, and, if desired, other active ingredients. In one embodiment, a pharmaceutical composition may comprise a therapeutically effective amount of a compound disclosed herein.

The compound(s) disclosed herein may be administered by any suitable route in the form of a pharmaceutical composition adapted to such a route and in a dose effective for the treatment intended. The compounds and compositions present herein may, for example, be administered orally, mucosally, topically, rectally, pulmonarily, such as by inhalation spray, or parentally including intravascularly, intravenously, intraperitoneally, subcutaneously, intramuscularly, intrasternally, and by infusion techniques, in dosage unit formulations containing conventional pharmaceutically acceptable excipients such as carriers, adjuvants, and vehicles.

For oral administration, the pharmaceutical composition may be in the form of, for example, a tablet, capsule, suspension or liquid. The pharmaceutical composition is typically made in the form of a dosage unit containing a particular amount of the active ingredient. Examples of such dosage units are tablets or capsules. For example, these may contain an amount of active ingredient from about 1 to 2000 mg, from about 1 to 500 mg, and from about 5 to 150 mg.

For therapeutic purposes, the compounds provided herein are ordinarily combined with one or more diluents or other "excipients" appropriate to the indicated route of administration.

If orally administered on a per dose basis, the compounds provided herein may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other excipients and modes of administration are well and widely known in the pharmaceutical art. The active ingredient may also be administered by injection as a composition with suitable excipients including saline, dextrose, or water, and optionally comprising one or more of a cosolvent such as propylene glycol or emulsifier such as, for example, Tween 80. Such formulations may also include compounds such as a cyclodextrin (for example, Captisol).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and in some embodiments may be from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional excipients, such as preservatives, stabilizers, wetting agents, emulsifiers, buffers etc. Tablets and pills can additionally be prepared with enteric coatings. Such compositions may also comprise excipients, such as wetting, sweetening, flavoring, and perfuming agents. Accordingly, in yet another embodiment of the present disclosure, there is provided a method of manufacturing a medicament, the method comprising combining an amount of a compound according to Formula I with a pharmaceutically acceptable diluent to manufacture the medicament.

In yet another embodiment, the provided herein is a method of manufacturing a medicament for the treatment of AD, the method comprising combining an amount of a compound provided herein with a pharmaceutically acceptable excipient to manufacture the medicament.

Combinations

While the compounds disclosed herein can be dosed or administered as the sole active pharmaceutical agent, they can also be used in combination with one or more compounds provided herein or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound provided herein and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds provided herein may be in conjunction with additional therapies known to those skilled in the art in the prevention or treatment of β-secretase, γ-secretase and/or other reagents known in influence the formation and/or deposition of Aβ peptide, otherwise responsible for the formation of plaque in the brain.

If formulated as a fixed dose, such combination products employ the compounds disclosed herein within the accepted dosage ranges. The compounds provided herein may also be administered sequentially with other known medicinal agents. This disclosure is not limited in the sequence of administration; compounds provided herein may be administered either prior to, simultaneous with or after administration of the known anti-inflammatory agent.

The foregoing description is merely illustrative and is not intended to limit the disclosure to the described compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions.

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:
1. A compound of Formula I

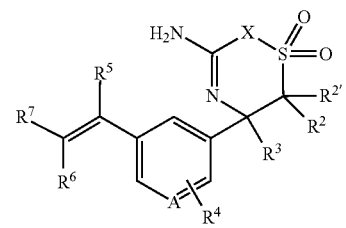

or a tautomer, or a pharmaceutically acceptable salt of said compound or tautomer, wherein A is N, CH or $CR^4$;

X is NR' or $C(R^1R^{1'})$;

$R^1$ and $R^{1'}$ independently are H or $C_{1-4}$alkyl, wherein the $C_{1-4}$alkyl is optionally substituted with 1 to 3 fluoro substituents;

provided that X is $C(R^1R^{1'})$, one of $R^1$ and $R^{1'}$ and one of $R^2$ and $R^{2'}$ together optionally form a —$CH_2CH_2$— group bridging the two carbon atoms to which R', $R^{1'}$, $R^2$, and $R^{2'}$ are attached, wherein the other of $R^1$ and $R^{1'}$ and the other of $R^2$ and $R^{2'}$ independently are H or $C_{1-4}$alkyl, wherein the $C_{1-4}$alkyl is optionally substituted with 1 to 3 fluoro substituents;

$R^1$ and $R^{1'}$ with the carbon atom to which $R^1$ and $R^{1'}$ are attached optionally form a $C_{3-6}$carbocycle;

$R^2$ and $R^{2'}$ independently are H, halogen or $C_{1-4}$alkyl;

$R^2$ and $R^{2'}$ with the carbon atom to which $R^2$ and $R^{2'}$ are attached optionally form a $C_{3-6}$carbocycle;

$R^3$ is $C_{1-4}$alkyl, wherein the $C_{1-4}$alkyl is optionally substituted with 1 to 3 fluoro substituents;

one of $R^2$ and $R^{2'}$ together with $R^3$ and the two carbon atoms to which $R^2$, $R^{2'}$, and $R^3$ are attached optionally form a 5 or 6 membered heterocycloalkane;

$R^4$ is independently at each occurrence a halogen;
$R^5$ is H or F; and
one of $R^6$ and $R^7$ is F or H and the other of $R^6$ and $R^7$ is a 5 or 6 membered heterocycloalkane, phenyl, or 5 to 10-membered heterocycle, wherein the phenyl or heterocycle is optionally substituted with 1 to 3 substituents independently selected from halogen, OH, CN, $C_{1-6}$alkyl, $C_{3-6}$cycloalkyl, cyclopropylethynyl, $C_{1-6}$alkoxy, $C_{3-6}$alkenyloxy, $C_{3-6}$alkynyloxy, —OCH$_2$C(O)OC$_{1-6}$alkyl, —OCH$_2$—C$_{3-6}$cycloalkyl, phenoxy, benzyloxy, or —O—C$_{1-4}$alkyl-heteroaryl, wherein the $C_{1-6}$alkyl, $C_{1-6}$alkoxy, or heteroaryl is optionally substituted with 1 to 5 substituents selected from F, Br, OH, methyl, methoxy, or oxetanyl.

2. The compound according to claim 1, or a tautomer, or a pharmaceutically acceptable salt of said compound or tautomer, wherein the compound of Formula I is a compound of Formula II

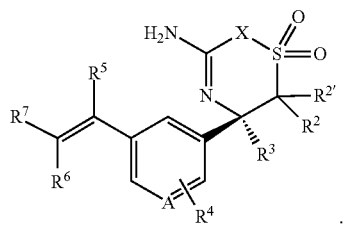

3. The compound according to claim 1, or a tautomer, or a pharmaceutically acceptable salt of said compound or tautomer, wherein the compound of Formula I is a compound of Formula III

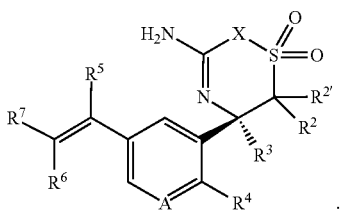

4. The compound according to claim 1, or a tautomer, or a pharmaceutically acceptable salt of said compound or tautomer, wherein A is N.

5. The compound according to claim 1, or a tautomer, or a pharmaceutically acceptable salt of said compound or tautomer, wherein A is CH.

6. The compound according to claim 1, or a tautomer, or a pharmaceutically acceptable salt of said compound or tautomer, wherein A is CR$^4$.

7. The compound according to claim 1, or a tautomer, or a pharmaceutically acceptable salt of said compound or tautomer, wherein X is NR$^1$.

8. The compound according to claim 1, or a tautomer, or a pharmaceutically acceptable salt of said compound or tautomer, wherein R$^1$ is methyl.

9. The compound according to claim 1, or a tautomer, or a pharmaceutically acceptable salt of said compound or tautomer, wherein X is C(R$^1$R$^{1'}$).

10. The compound according to claim 1, or a tautomer, or a pharmaceutically acceptable salt of said compound or tautomer, wherein R$^1$ and R$^{1'}$ independently are H or methyl.

11. The compound according to claim 1, or a tautomer, or a pharmaceutically acceptable salt of said compound or tautomer, wherein R$^1$ and R$^{1'}$ are methyl.

12. The compound according to claim 1, or a tautomer, or a pharmaceutically acceptable salt of said compound or tautomer, wherein one of R$^1$ and R$^{1'}$ and one of R$^2$ and R$^{2'}$ together optionally form a —CH$_2$CH$_2$— group bridging the two carbon atoms to which R$^1$, R$^{1'}$, R$^2$ and R$^{2'}$ are attached, wherein the other of R$^1$ and R$^{1'}$ and the other of R$^2$ and R$^{2'}$ independently are H or C$_{1-4}$alkyl, wherein the C$_{1-4}$alkyl is optionally substituted with 1 to 3 fluoro substituents.

13. The compound of claim 12, or a tautomer, or a pharmaceutically acceptable salt of said compound or tautomer, wherein the compound is a compound of Formula IV

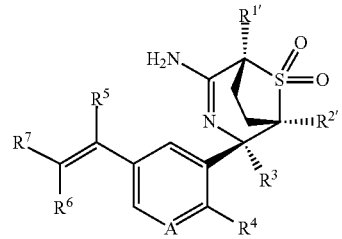

14. The compound of claim 13, or a tautomer, or a pharmaceutically acceptable salt of said compound or tautomer, wherein R$^{1'}$ is CH$_2$F and R$^{2'}$ is H.

15. The compound according to claim 1, or a tautomer, or a pharmaceutically acceptable salt of said compound or tautomer, wherein R$^2$ and R$^{2'}$ independently are H, F, or methyl.

16. The compound according to claim 1, or a tautomer, or a pharmaceutically acceptable salt of said compound or tautomer, wherein R$^2$ and R$^{2'}$ with the carbon atom to which R$^2$ and R$^{2'}$ are attached optionally form a C$_3$carbocycle.

17. The compound according to claim 1, or a tautomer, or a pharmaceutically acceptable salt of said compound or tautomer, wherein R$^3$ is methyl, CH$_2$F, or CHF$_2$.

18. The compound according to claim 1, or a tautomer, or a pharmaceutically acceptable salt of said compound or tautomer, wherein R$^4$ is F.

19. The compound according to claim 1, or a tautomer, or a pharmaceutically acceptable salt of said compound or tautomer, wherein one of R$^6$ and R$^7$ is F or H and the other of R$^6$ and R$^7$ is tetrahydropyranyl, tetrahydofuranyl, thiophenyl, thiazolyl, phenyl, pyridyl, pyrazinyl, 2,3-dihydrobenzo[b][1,4]dioxinyl, 2,3-dihydro-[1,4]dioxino[2,3-c]pyridyl, [1,3]dioxolo[4,5-c]pyridyl, 3,4-dihydro-2H-pyrano[2,3-c]pyridyl, 2,3-dihydro-[1,4]dioxino[2,3-b]pyridyl, 6,7-dihydro-[1,4]dioxino[2,3-d]pyrimidinyl, isoquinolinyl, or pyrido[3,4-b]pyrazinyl, and wherein said other of R$^6$ and R$^7$ is optionally substituted.

20. The compound according to claim 1, or a tautomer, or a pharmaceutically acceptable salt of said compound or tautomer, wherein one of R$^6$ and R$^7$ is F or H and the other of R$^6$ and R$^7$ is optionally substituted with 1 or 2 substituents independently selected from F, Cl, Br, OH, CN, methyl, trifluoromethyl, cyclopropyl, cyclopropylethynyl, methoxy, trifluoromethoxy, ethoxy, 2-fluoroethoxy, 2,2-difluoroethoxy, 2,2,2-trifluoroethoxy, 2-methoxyethoxy, propoxy, 2,2,3,3-tetrafluoropropoxy, 3,3,3-trifluoropropoxy, propan-1-ol-2-oxy, 2-propanoloxy, 2-cyano-2-methyl-propoxy, oxetan-3-ylmethoxy, (1-methoxypropan-2-yl)oxy, 2-methoxypropoxy, allyloxy, 2-propynyloxy, 2-butynyloxy, 3-butyn-2-yloxy, 2-butyn-4-ol-oxy, 4-fluoro-2-butynoxy, pent-1-yn-3-yloxy, pent-3-yn-2-yloxy, hex-4-yn-3-yloxy, hex-3-yn-2-yloxy, —OCH$_2$C(O)OC$_2$H$_5$, cyclopropylmethoxy, cyclobutylmethoxy, cyclopentylmethoxy, cyclohexylmethoxy, phenoxy, benzyloxy, or —OC$_{1-2}$alkyl-heteroaryl, wherein the heteroaryl is optionally substituted with one or two methyl groups or the heteroaryl is optionally substituted with one bromo.

21. The compound according to claim 1, or a tautomer, or a pharmaceutically acceptable salt of said compound or tautomer, wherein one of R$^6$ and R$^7$ is F or H and the other of R$^6$ and R$^7$ is

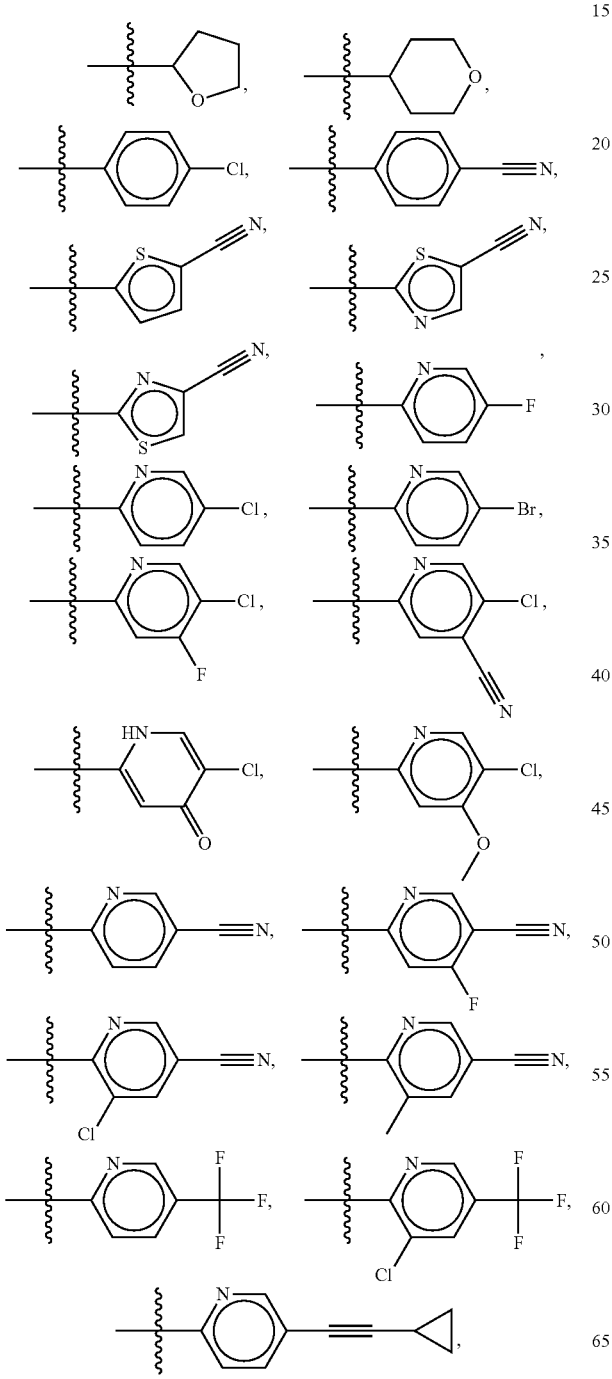

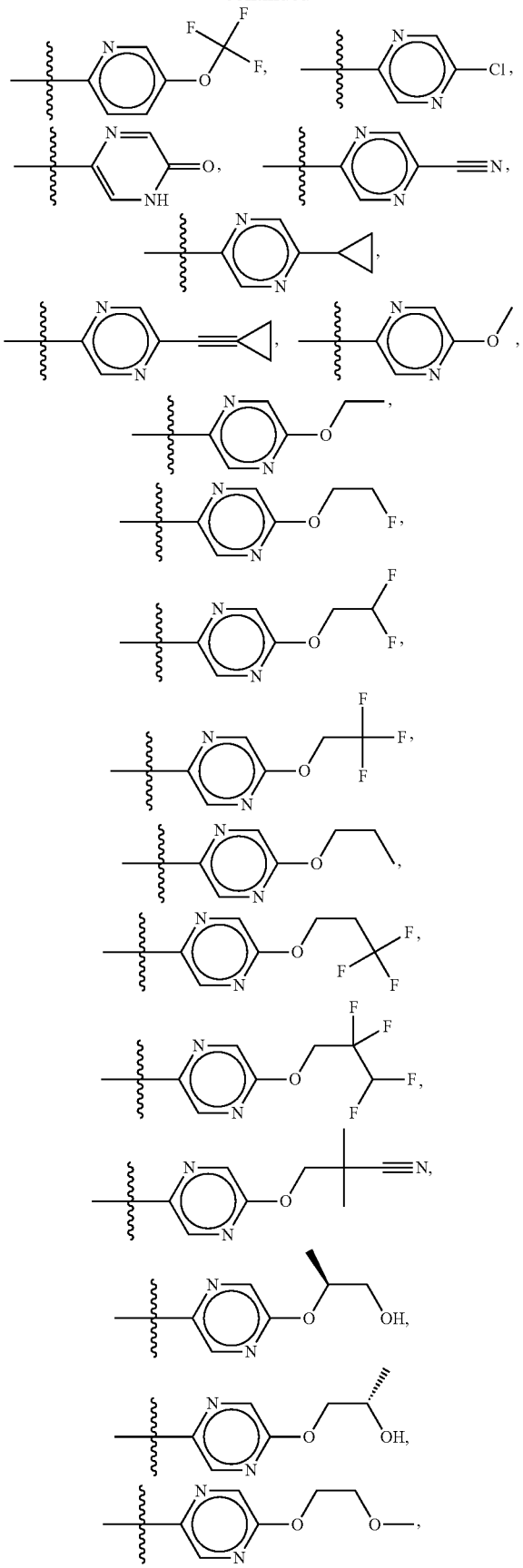

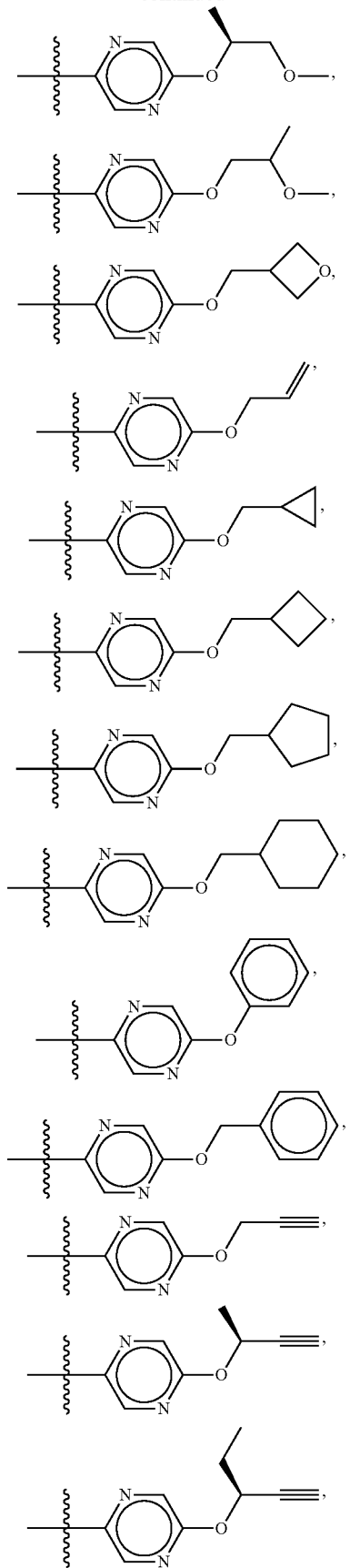
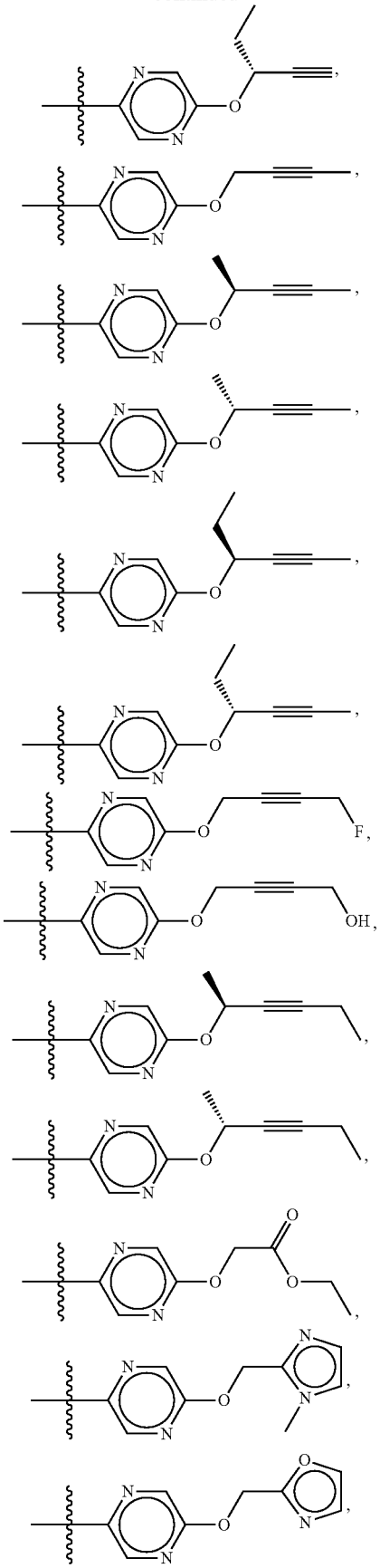

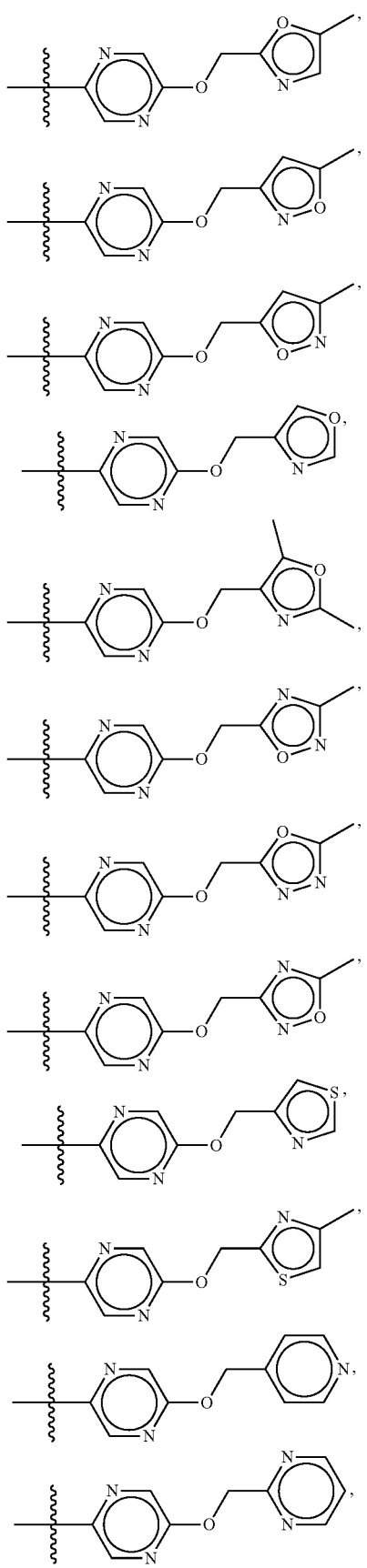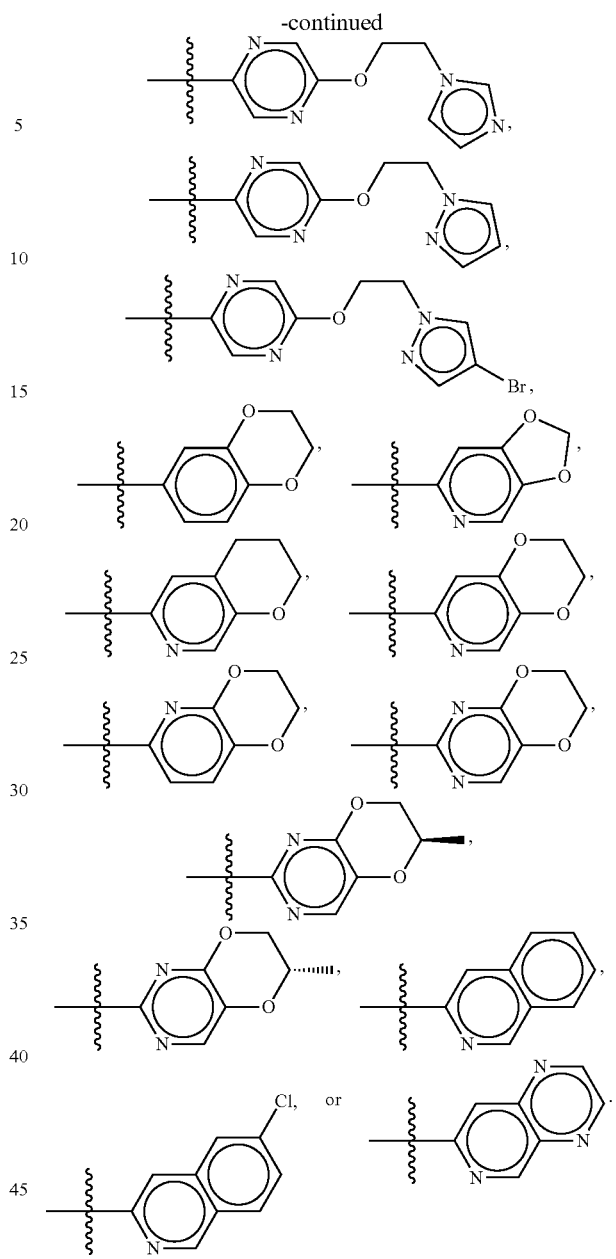

22. The compound according to claim 1, or a tautomer, or a pharmaceutically acceptable salt of said compound or tautomer, wherein one of $R^6$ and $R^7$ is F or H and the other of $R^6$ and $R^7$ is tetrahydropyranyl, phenyl, pyridyl, pyrazinyl, or 6,7-dihydro-[1,4]dioxino[2,3-d]pyrimidinyl, and wherein the other of $R^6$ and $R^7$ is optionally substituted.

23. The compound according to claim 1, or a tautomer, or a pharmaceutically acceptable salt of said compound or tautomer, wherein one of $R^6$ and $R^7$ is F or H and the other of $R^6$ and $R^7$ is optionally substituted with 1 or 2 substituents independently selected from OH, CN, methyl, trifluoromethyl, cyclopropylethynyl, trifluoromethoxy, ethoxy, 2-fluoroethoxy, 2,2-difluoroethoxy, 2,2,2-trifluoroethoxy, 2-methoxyethoxy, propoxy, 2,2,3,3-tetrafluoropropoxy, 3,3,3-trifluoropropoxy, propan-1-ol-2-oxy, 2-propanoloxy, 2-cyano-2-methyl-propoxy, (1-methoxypropan-2-yl)oxy, 2-methoxypropoxy, allyloxy, 2-propynyloxy, 2-butynyloxy, 3-butyn-2-yloxy, 2-butyn-4-ol-oxy, 4-fluoro-2-butynoxy, (S)-pent-1-yn-3-yloxy, (S)-pent-3-yn-2-yloxy, hex-4-yn-3-yloxy, —OCH$_2$C(O)OC$_2$H$_5$, cyclopropylmethoxy, cyclopentylmethoxy, cyclohexylmethoxy, benzyloxy, or —OCH$_2$-(5-membered-heteroaryl), wherein the 5-membered-heteroaryl is optionally substituted with one or two methyl groups or the heteroaryl is optionally substituted with one bromo.

24. The compound according to claim 1, or a tautomer, or a pharmaceutically acceptable salt of said compound or tautomer, wherein one of R$^6$ and R$^7$ is F or H and the other of R$^6$ and R$^7$ is

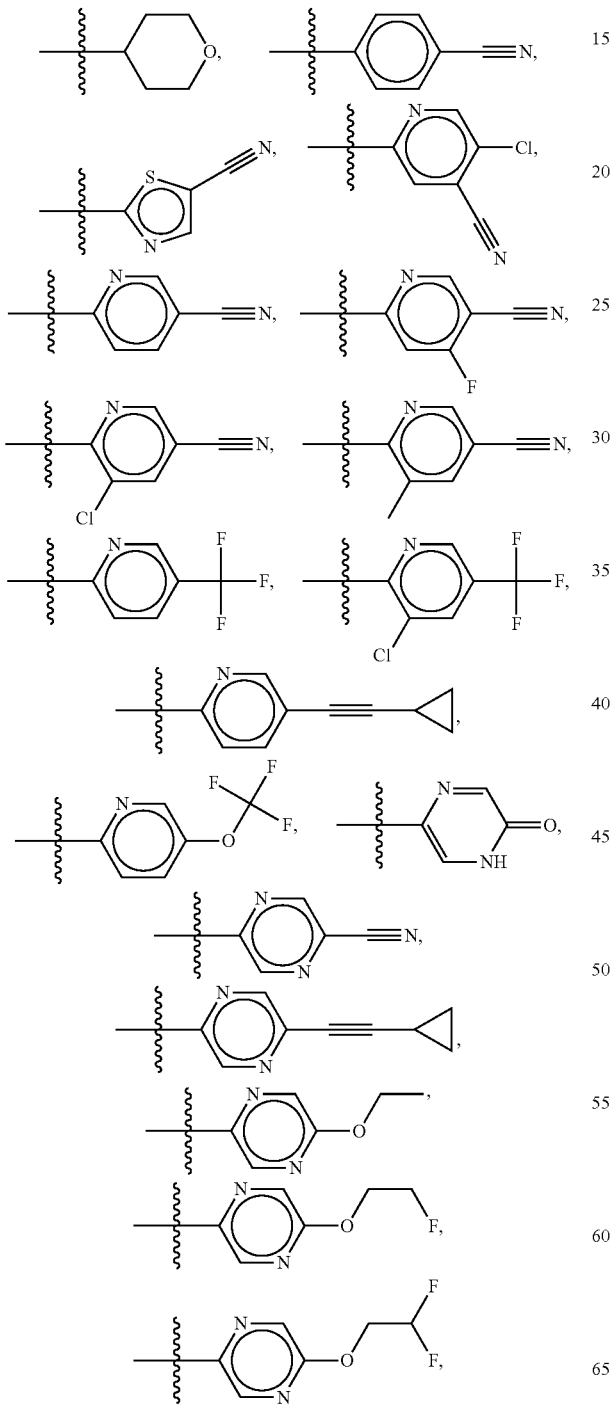
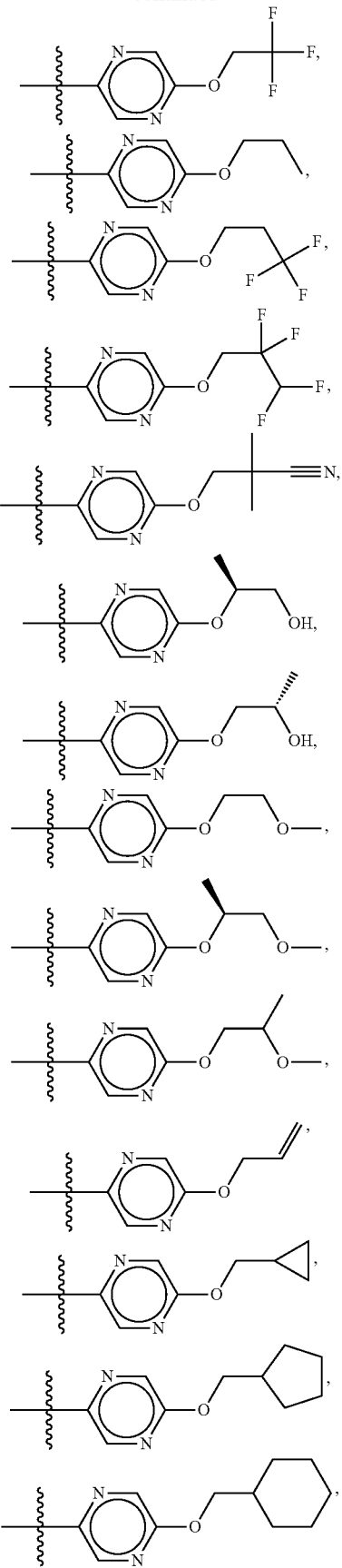

299
-continued
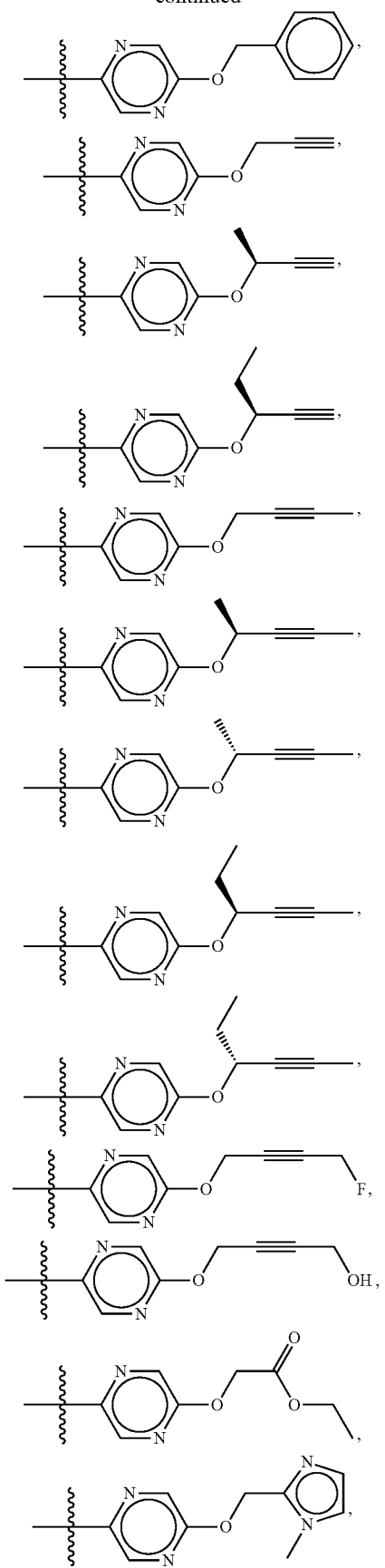
300
-continued
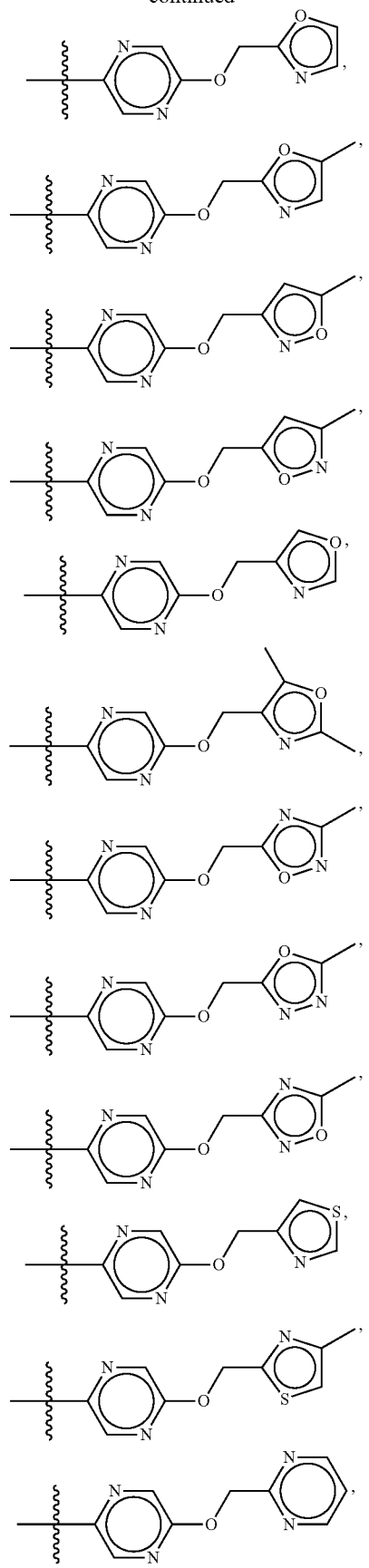

-continued

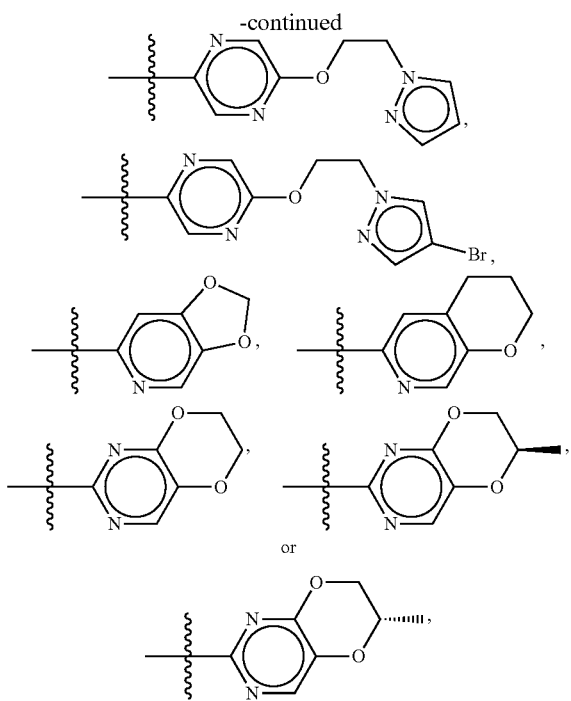

25. The compound according to claim 1, or a tautomer, or a pharmaceutically acceptable salt of said compound or tautomer, wherein
$R^5$ is H; and
$R^6$ is F.

26. The compound of claim 1, or a tautomer, or a pharmaceutically acceptable salt of said compound or tautomer, selected from
- (R,Z)-9-amino-7-(5-(2-(5-chloropyridin-2-yl)-2-fluorovinyl)-2-fluorophenyl)-7-methyl-5-thia-8-azaspiro[3.5]non-8-ene 5,5-dioxide;
- (1R,4R,5S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide;
- 6-((Z)-2-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-1-fluorovinyl)nicotinonitrile;
- (R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile;
- (R,Z)-3-amino-5-(5-(2-(5-chloropyridin-2-yl)-2-fluorovinyl)-2-fluorophenyl)-2,5-dimethyl-5,6-dihydro-2H-1,2,4-thiadiazine 1,1-dioxide;
- (R,Z)-3-amino-5-(5-(2-(5-bromopyridin-2-yl)-2-fluorovinyl)-2,3-difluorophenyl)-2,5-dimethyl-5,6-dihydro-2H-1,2,4-thiadiazine 1,1-dioxide;
- (R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)nicotinonitrile;
- (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)nicotinonitrile;
- (1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide;
- (1R,4R,5S)-2-amino-4-(2-fluoro-5-((Z)-2-fluoro-2-(5-(2,2,2-trifluoroethoxy)pyrazin-2-yl)vinyl)phenyl)-1-(fluoromethyl)-4-methyl-8-thia-3-azabicyclo[3.2.1]oct-2-ene 8,8-dioxide;
- (R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide;
- (R,Z)-3-amino-5-(5-(2-(5-chloropyrazin-2-yl)-2-fluorovinyl)-2-fluorophenyl)-2,5-dimethyl-5,6-dihydro-2H-1,2,4-thiadiazine 1,1-dioxide;
- (R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;
- (R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile;
- (R,Z)-5-amino-3-(5-(2-(5-chloropyridin-2-yl)-2-fluorovinyl)-2-fluorophenyl)-3,6,6-trimethyl-3,6-dihydro-2H-1,4-thiazine 1,1-dioxide;
- (1R,4R,5S)-2-amino-4-(2-fluoro-5-((Z)-2-fluoro-2-(5-((3-methyl-1,2,4-oxadiazol-5-yl)methoxy)pyrazin-2-yl)vinyl)phenyl)-1-(fluoromethyl)-4-methyl-8-thia-3-azabicyclo[3.2.1]oct-2-ene 8,8-dioxide;
- (R,Z)-3-amino-5-(2-fluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;
- (R,Z)-3-amino-5-(2-fluoro-5-(2-fluoro-2-(5-(2,2,2-trifluoroethoxy)pyrazin-2-yl)vinyl)phenyl)-2,5-dimethyl-5,6-dihydro-2H-1,2,4-thiadiazine 1,1-dioxide;
- (1R,4R,5S)-2-amino-4-(5-((Z)-2-(5-(cyclopropylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;
- (1R,4R,5S)-2-amino-4-(2-fluoro-5-((Z)-2-fluoro-2-(5-((5-methyl-1,3,4-oxadiazol-2-yl)methoxy)pyrazin-2-yl)vinyl)phenyl)-1-(fluoromethyl)-4-methyl-8-thia-3-azabicyclo[3.2.1]oct-2-ene 8,8-dioxide;
- (1R,4R,5S)-2-amino-4-(2-fluoro-5-((Z)-2-fluoro-2-(5-(2,2,3,3-tetrafluoropropoxy)pyrazin-2-yl)vinyl)phenyl)-1-(fluoromethyl)-4-methyl-8-thia-3-azabicyclo[3.2.1]oct-2-ene 8,8-dioxide;
- (1R,4R,5S)-2-amino-4-(2-fluoro-5-((Z)-2-fluoro-2-(5-methoxypyrazin-2-yl)vinyl)phenyl)-1-(fluoromethyl)-4-methyl-8-thia-3-azabicyclo[3.2.1]oct-2-ene 8,8-dioxide;
- (1R,4R,5S)-2-amino-4-(5-((Z)-2-(5-ethoxypyrazin-2-yl)-2-fluorovinyl)-2-fluorophenyl)-1-(fluoromethyl)-4-methyl-8-thia-3-azabicyclo[3.2.1]oct-2-ene 8,8-dioxide;
- (R,Z)-5-amino-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;
- (R,Z)-5-amino-3-(2-fluoro-5-(2-fluoro-2-(5-(2,2,2-trifluoroethoxy)pyrazin-2-yl)vinyl)phenyl)-3,6,6-trimethyl-3,6-dihydro-2H-1,4-thiazine 1,1-dioxide;
- (1R,4R,5S)-4-(5-((Z)-2-(5-(allyloxy)pyrazin-2-yl)-2-fluorovinyl)-2-fluorophenyl)-2-amino-1-(fluoromethyl)-4-methyl-8-thia-3-azabicyclo[3.2.1]oct-2-ene 8,8-dioxide;
- (1R,4R,5S)-2-amino-4-(2-fluoro-5-((Z)-2-fluoro-2-(5-(oxetan-3-ylmethoxy)pyrazin-2-yl)vinyl)phenyl)-1-(fluoromethyl)-4-methyl-8-thia-3-azabicyclo[3.2.1]oct-2-ene 8,8-dioxide;
- (R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile;
- (1R,4R,5S)-2-amino-4-(5-((Z)-2-(5-((S)-but-3-yn-2-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(R,Z)-5-amino-3-(2-fluoro-5-(2-fluoro-2-(5-(oxazol-2-ylmethoxy)pyrazin-2-yl)vinyl)phenyl)-3,6,6-trimethyl-3,6-dihydro-2H-1,4-thiazine 1,1-dioxide;

(1R,4R,5S)-2-amino-4-(2-fluoro-5-((Z)-2-fluoro-2-(5-(2-methoxyethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-((S)-1-methoxypropan-2-yl)oxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(cyclobutylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-fluoroethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(2,2-difluoroethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-propoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-((2-methoxypropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(but-2-yn-1-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(8R)-8-(2-fluoro-5-((Z)-2-fluoro-2-(5-(2-propyn-1-yloxy)-2-pyrazinyl)ethenyl)phenyl)-5,8-dimethyl-4-thia-5,7-diazaspiro[2.5]oct-6-en-6-amine 4,4-dioxide;

(8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide;

(R,Z)-5-amino-3-(2-fluoro-5-(2-fluoro-2-(5-(hydroxy-pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,3,3-tetrafluoropropoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(3,3,3-trifluoropropoxy)pyrazin-2-yl)vinyl)phenyl)-3,6,6-trimethyl-3,6-dihydro-2H-1,4-thiazine 1,1-dioxide;

(R,Z)-3-amino-5-(5-(2-(5-(cyclopropylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(cyclobutylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-amino-5-(2-fluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-5-(2-(3-(6-amino-5,8-dimethyl-4,4-dioxido-4-thia-5,7-diazaspiro[2.5]oct-6-en-8-yl)-4-fluorophenyl)-1-fluorovinyl)pyrazine-2-carbonitrile;

(R,Z)-3-amino-5-(2-fluoro-5-(2-fluoro-2-(5-(2,2,3,3-tetrafluoropropoxy)pyrazin-2-yl)vinyl)phenyl)-2,5-dimethyl-5,6-dihydro-2H-1,2,4-thiadiazine 1,1-dioxide;

(R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide;

(R,Z)-5-amino-3-(5-(2-(5-(cyclohexylmethoxy)pyrazin-2-yl)-2-fluorovinyl)-2-fluorophenyl)-3,6,6-trimethyl-3,6-dihydro-2H-1,4-thiazine 1,1-dioxide;

(R,E)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(5-(2-(5-chloropyridin-2-yl)-2-fluorovinyl)-2,3-difluorophenyl)-2,5-dimethyl-5,6-dihydro-2H-1,2,4-thiadiazine 1,1-dioxide;

(R,Z)-3-((5-(2-(3-(5-amino-3,6,6-trimethyl-1,1-dioxido-3,6-dihydro-2H-1,4-thiazin-3-yl)-4-fluorophenyl)-1-fluorovinyl)pyrazin-2-yl)oxy)-2,2-dimethylpropanenitrile;

(R,Z)-5-amino-3-(5-(2-(5-(but-2-yn-1-yloxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-imidazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide;

(R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-pyrazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide;

(R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R,Z)-5-amino-3-(5-(2-(5-chloropyrazin-2-yl)-2-fluorovinyl)-2-fluorophenyl)-3,6,6-trimethyl-3,6-dihydro-2H-1,4-thiazine 1,1-dioxide;

(R)-5-amino-3-(5-((Z)-2-(5-((S)-but-3-yn-2-yloxy)pyrazin-2-yl)-2-fluorovinyl)-2-fluorophenyl)-3,6,6-trimethyl-3,6-dihydro-2H-1,4-thiazine 1,1-dioxide;

(8R)-8-(2-fluoro-5-((Z)-2-fluoro-2-(5-(3-methyl-1,2,4-oxadiazol-5-yl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(5-methyl-3-isoxazolyl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(2,2,2-trifluoroethoxy)-2-pyrazinyl)ethenyl)phenyl)-5,8-dimethyl-4-thia-5,7-diazaspiro[2.5]oct-6-en-6-amine 4,4-dioxide;

(R)-3-amino-5-(2-fluoro-5-((Z)-2-fluoro-2-(5-((S)-1-methoxypropan-2-yl)oxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(but-2-yn-1-yloxy)pyrazin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2,3-difluorophenyl)-2,5-dimethyl-5,6-dihydro-2H-1,2,4-thiadiazine 1,1-dioxide hydrochloride;

(R,Z)-3-amino-5-(5-(2-(5-(but-2-yn-1-yloxy)pyrazin-2-yl)-2-fluorovinyl)-2-fluorophenyl)-2,5-dimethyl-5,6-dihydro-2H-1,2,4-thiadiazine 1,1-dioxide;

(8R)-8-(2-fluoro-5-((Z)-2-fluoro-2-(5-(5-methyl-1,3-oxazol-2-yl)methoxy)-2-pyrazinyl)ethenyl)phenyl)-5,8-dimethyl-4-thia-5,7-diazaspiro[2.5]oct-6-en-6-amine 4,4-dioxide;

(R,Z)-5-(2-(3-(5-amino-3,6,6-trimethyl-1,1-dioxido-3,6-dihydro-2H-1,4-thiazin-3-yl)-4-fluorophenyl)-1-fluorovinyl)pyrazine-2-carbonitrile;

(R)-3-amino-5-(5-((Z)-2-(5-((S)-but-3-yn-2-yloxy)pyrazin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-(5-(2-methoxypropoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(cyclobutylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(2-fluoro-5-(2-fluoro-2-(5-((3-methyl-1,2,4-oxadiazol-5-yl)methoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-((5-methyl-1,3,4-oxadiazol-2-yl)methoxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((R)-pent-1-yn-3-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide;

(R,Z)-3-amino-5-(2-fluoro-5-(2-fluoro-2-(5-(oxetan-3-ylmethoxy)pyrazin-2-yl)vinyl)phenyl)-2,5-dimethyl-5,6-dihydro-2H-1,2,4-thiadiazine 1,1-dioxide;

(R,Z)-6-(2-(3-(3-amino-2,5,6,6-tetramethyl-1,1-dioxido-5,6-dihydro-2H-1,2,4-thiadiazin-5-yl)-4-fluorophenyl)-1-fluorovinyl)nicotinonitrile;

(R,Z)-5-(2-(3-(3-amino-2,5,6,6-tetramethyl-1,1-dioxido-5,6-dihydro-2H-1,2,4-thiadiazin-5-yl)-4-fluorophenyl)-1-fluorovinyl)pyrazine-2-carbonitrile;

(R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5,6,6-tetramethyl-5,6-dihydro-2H-1,2,4-thiadiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-3,6,6-trimethyl-3,6-dihydro-2H-1,4-thiazine 1,1-dioxide;

(R,Z)-3-amino-5-(5-(2-(5-(but-2-yn-1-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(R,Z)-3-amino-5-(5-(2-(2,3-dihydro-[1,4]dioxino[2,3-c]pyridin-7-yl)-2-fluorovinyl)-2-fluorophenyl)-2,5-dimethyl-5,6-dihydro-2H-1,2,4-thiadiazine 1,1-dioxide;

(S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile;

(S,Z)-5-amino-3-(5-(2-(5-chloropyrazin-2-yl)-2-fluorovinyl)-2-fluorophenyl)-3-(fluoromethyl)-6,6-dimethyl-3,6-dihydro-2H-1,4-thiazine 1,1-dioxide;

(S,Z)-5-amino-3-(2-fluoro-5-(2-fluoro-2-(5-(prop-2-yn-1-yloxy)pyrazin-2-yl)vinyl)phenyl)-3-(fluoromethyl)-6,6-dimethyl-3,6-dihydro-2H-1,4-thiazine 1,1-dioxide;

(R,Z)-5-amino-3-(5-(2-(5-chloropyrazin-2-yl)-2-fluorovinyl)-2-fluorophenyl)-2,2-difluoro-3,6,6-trimethyl-3,6-dihydro-2H-1,4-thiazine 1,1-dioxide;

(R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile;

(R,Z)-5-amino-3-(5-(2-(5-chloropyrazin-2-yl)-2-fluorovinyl)-2,3-difluorophenyl)-3,6,6-trimethyl-3,6-dihydro-2H-1,4-thiazine 1,1-dioxide;

(S,Z)-5-amino-3-(5-(2-(5-(but-2-yn-1-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(S)-5-amino-3-(5-((Z)-2-(5-((S)-but-3-yn-2-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(R,Z)-3-amino-5-(5-(2-(2,3-dihydrobenzo[b][1,4]dioxin-6-yl)-2-fluorovinyl)-2-fluorophenyl)-2,5-dimethyl-5,6-dihydro-2H-1,2,4-thiadiazine 1,1-dioxide;

(R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile;

(R)-5-amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide;

(2R,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(2S,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(5-(2-(5-chloropyrazin-2-yl)-2-fluorovinyl)-2-fluoropyridin-3-yl)-3,6,6-trimethyl-3,6-dihydro-2H-1,4-thiazine 1,1-dioxide;

(R,Z)-5-amino-3-(2,3-difluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(5-fluoro-5-(2-fluoro-2-(5-(prop-2-yn-1-yloxy)pyrazin-2-yl)vinyl)pyridin-3-yl)-3,6,6-trimethyl-3,6-dihydro-2H-1,4-thiazine 1,1-dioxide;

(R,Z)-5-amino-3-(5-(2-(5-(cyclopropylmethoxy)pyrazin-2-yl)-2-fluorovinyl)-2-fluorophenyl)-3,6,6-trimethyl-3,6-dihydro-2H-1,4-thiazine 1,1-dioxide;

(R)-5-amino-3-(2-fluoro-5-((Z)-2-fluoro-2-(5-((R)-pent-3-yn-2-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-pent-3-yn-2-yloxy)pyrazin-2-yl)vinyl)phenyl)-3,6,6-trimethyl-3,6-dihydro-2H-1,4-thiazine 1,1-dioxide;

(R,Z)-5-amino-3-(5-(2-(5-(benzyloxy)pyrazin-2-yl)-2-fluorovinyl)-2-fluoropyridin-3-yl)-3,6,6-trimethyl-3,6-dihydro-2H-1,4-thiazine 1,1-dioxide;

(R,Z)-5-amino-3-(2-fluoro-5-(2-fluoro-2-(5-(pyridin-4-ylmethoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-phenoxypyrazin-2-yl)vinyl)phenyl)-3,6,6-trimethyl-3,6-dihydro-2H-1,4-thiazine 1,1-dioxide;

(R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile;

(2S,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;

(2R,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide;

(R)-5-amino-3-(2-fluoro-5-((Z)-2-fluoro-2-(5-((R)-hex-3-yn-2-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-hex-3-yn-2-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-1-hydroxypropan-2-yl)oxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide;

(R,Z)-3-amino-5-(2,3-difluoro-5-(2-fluoro-2-(5-(thiazol-4-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methylisoxazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-chloro-4-hydroxypyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methylisoxazol-3-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-4-ylmethoxy)pyrazin-2-yl)vinyl)phenyl)-2,5-dimethyl-5,6-dihydro-2H-1,2,4-thiadiazine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-4-fluoro-3-pyridinecarbonitrile;

(R,Z)-5-(5-(2-(5-(allyloxy)pyrazin-2-yl)-2-fluorovinyl)-2,3-difluorophenyl)-3-amino-2,5-dimethyl-5,6-dihydro-2H-1,2,4-thiadiazine 1,1-dioxide;

(R,Z)-3-amino-5-(2,3-difluoro-5-(2-fluoro-2-(5-(pyrimidin-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,2,4-oxadiazol-3-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-chloro-4-methoxypyridin-2-yl)-2-fluorovinyl)-2-fluorophenyl)-2,5-dimethyl-5,6-dihydro-2H-1,2,4-thiadiazine 1,1-dioxide;

(R,Z)-2-(2-(3-(3-amino-2,5-dimethyl-1,1-dioxido-5,6-dihydro-2H-1,2,4-thiadiazin-5-yl)-4-fluorophenyl)-1-fluorovinyl)-5-chloroisonicotinonitrile;

(R,Z)-3-amino-5-(5-(2-(5-chloro-4-fluoropyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-Amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R)-3-amino-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((4-methylthiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-((2,5-dimethyloxazol-4-yl)methoxy)pyrazin-2-yl)-2-fluorovinyl)-2,3-difluorophenyl)-2,5-dimethyl-5,6-dihydro-2H-1,2,4-thiadiazine 1,1-dioxide;

(5R)-5-(5-((Z)-2-(3,4-dihydro-2H-pyrano[2,3-c]pyridin-6-yl)-2-fluoroethenyl)-2-fluorophenyl)-2,5-dimethyl-5,6-dihydro-2H-1,2,4-thiadiazin-3-amine 1,1-dioxide;

(5R)-5-(2-fluoro-5-((Z)-2-fluoro-2-(5-fluoro-2-pyridinyl)ethenyl)phenyl)-2,5-dimethyl-5,6-dihydro-2H-1,2,4-thiadiazin-3-amine 1,1-dioxide;

(5R)-5-(2-fluoro-5-((Z)-2-fluoro-2-(5-methoxy-2-pyrazinyl)ethenyl)phenyl)-2,5-dimethyl-5,6-dihydro-2H-1,2,4-thiadiazin-3-amine 1,1-dioxide;

(5R)-5-(5-((Z)-2-(3-chloro-5-(trifluoromethyl)-2-pyridinyl)-2-fluoroethenyl)-2-fluorophenyl)-2,5-dimethyl-5,6-dihydro-2H-1,2,4-thiadiazin-3-amine 1,1-dioxide;

(R,Z)-ethyl 2-((5-(2-(3-(3-amino-2,5-dimethyl-1,1-dioxido-5,6-dihydro-2H-1,2,4-thiadiazin-5-yl)-4,5-difluorophenyl)-1-fluorovinyl)pyrazin-2-yl)oxy)acetate;

(5R)-5-(2-fluoro-5-((Z)-2-fluoro-2-(5-(trifluoromethyl)-2-pyridinyl)ethenyl)phenyl)-2,5-dimethyl-5,6-dihydro-2H-1,2,4-thiadiazin-3-amine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-5-methyl-3-pyridinecarbonitrile;

(R,Z)-3-amino-5-(2,3-difluoro-5-(2-fluoro-2-(5-(5-methyloxazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(5-(2-(5-(cyclopropylethynyl)pyrazin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(1-methyl-1H-imidazol-2-yl)methoxy)pyrazin-2-yl)vinyl)phenyl)-2,5-dimethyl-5,6-dihydro-2H-1,2,4-thiadiazine 1,1-dioxide;

(5R)-5-(2-fluoro-5-((Z)-2-fluoro-2-(pyrido[3,4-b]pyrazin-7-yl)ethenyl)phenyl)-2,5-dimethyl-5,6-dihydro-2H-1,2,4-thiadiazin-3-amine 1,1-dioxide;

(R,Z)-3-amino-5-(5-(2-(5-(cyclopropylethynyl)pyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2-fluoro-5-(2-fluoro-2-(5-((4-hydroxybut-2-yn-1-yl)oxy)pyrazin-2-yl)vinyl)phenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-5-carbonitrile;

(R,Z)-3-amino-5-(2-fluoro-5-(2-fluoro-2-(5-(4-fluorobut-2-yn-1-yl)oxy)pyrazin-2-yl)vinyl)phenyl)-2,5-dimethyl-5,6-dihydro-2H-1,2,4-thiadiazine 1,1-dioxide;

(5R)-5-(5-((Z)-2-(2,3-dihydro[1,4]dioxino[2,3-b]pyridin-6-yl)-2-fluoroethenyl)-2-fluorophenyl)-2,5-dimethyl-5,6-dihydro-2H-1,2,4-thiadiazin-3-amine 1,1-dioxide;

5-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-2-thiophenecarbonitrile;

(5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide;

(R,Z)-3-amino-5-(2-fluoro-5-(2-fluoro-2-(5-(trifluoromethoxy)pyridin-2-yl)vinyl)phenyl)-2,5-dimethyl-5,6-dihydro-2H-1,2,4-thiadiazine 1,1-dioxide;

(5R)-5-(2-fluoro-5-((Z)-2-fluoro-2-(3-isoquinolinyl)ethenyl)phenyl)-2,5-dimethyl-5,6-dihydro-2H-1,2,4-thiadiazin-3-amine 1,1-dioxide;

(5R)-5-(5-((Z)-2-(6-chloro-3-isoquinolinyl)-2-fluoroethenyl)-2-fluorophenyl)-2,5-dimethyl-5,6-dihydro-2H-1,2,4-thiadiazin-3-amine 1,1-dioxide;

6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile;

(R,Z)-5-amino-3-(2-fluoro-5-(2-fluoro-2-(5-fluoropyridin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-methoxypyrazin-2-yl)vinyl)phenyl)-3,6,6-trimethyl-3,6-dihydro-2H-1,4-thiazine 1,1-dioxide;

(R,Z)-5-amino-3-(5-(2-(3-chloro-5-(trifluoromethyl)pyridin-2-yl)-2-fluorovinyl)-2-fluorophenyl)-3,6,6-trimethyl-3,6-dihydro-2H-1,4-thiazine 1,1-dioxide;

(R,Z)-5-amino-3-(2-fluoro-5-(2-fluoro-2-(5-(trifluoromethyl)pyridin-2-yl)vinyl)phenyl)-3,6,6-trimethyl-3,6-dihydro-2H-1,4-thiazine 1,1-dioxide;

(R,Z)-3-amino-5-(5-(2-(5-cyclopropylpyrazin-2-yl)-2-fluorovinyl)-2-fluorophenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-4-carbonitrile;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-chloronicotinonitrile;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-5-chloronicotinonitrile;

(R,Z)-3-amino-5-(2,3-difluoro-5-(2-fluoro-2-(5-fluoropyridin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-methoxypyrazin-2-yl)vinyl)phenyl)-2,5-dimethyl-5,6-dihydro-2H-1,2,4-thiadiazine 1,1-dioxide;

(R,Z)-3-amino-5-(5-(2-(3-chloro-5-(trifluoromethyl)pyridin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(trifluoromethyl)pyridin-2-yl)vinyl)phenyl)-2,5-dimethyl-5,6-dihydro-2H-1,2,4-thiadiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-methylnicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-methylnicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-chloronicotinonitrile;

(1R,4R,5S)-2-amino-4-(2-fluoro-5-((Z)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((E)-2-fluoro-2-(tetrahydrofuran-2-yl)vinyl)phenyl)-1-(fluoromethyl)-4-methyl-8-thia-3-azabicyclo[3.2.1]oct-2-ene 8,8-dioxide; or (R,E)-5-amino-3-(5-(4-chlorostyryl)-2-fluorophenyl)-3,6,6-trimethyl-3,6-dihydro-2H-1,4-thiazine 1,1-dioxide.

27. The compound of claim 1, or a tautomer, or a pharmaceutically acceptable salt of said compound or tautomer, selected from (1R,4R,5S)-2-amino-4-(5-((Z)-2-(5-bromopyridin-2-yl)-2-fluorovinyl)-2-fluorophenyl)-1-(fluoromethyl)-4-methyl-8-thia-3-azabicyclo[3.2.1]oct-2-ene 8,8-dioxide;

6-((Z)-2-(3-((1S,2R,5R)-4-amino-5-(fluoromethyl)-2-methyl-8,8-dioxido-8-thia-3-azabicyclo[3.2.1]oct-3-en-2-yl)-4-fluorophenyl)-1-fluorovinyl)nicotinonitrile;

(R,Z)-6-(2-(3-(9-amino-7-methyl-5,5-dioxido-5-thia-8-azaspiro[3.5]non-8-en-7-yl)-4-fluorophenyl)-1-fluorovinyl)nicotinonitrile;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)nicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)nicotinonitrile;

(1R,4R,5S)-2-amino-4-(2-fluoro-5-((Z)-2-fluoro-2-(5-(prop-2-yn-1-yloxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2,2,2-trifluoroethoxy)pyrazin-2-yl)vinyl)phenyl)-1-(fluoromethyl)-4-methyl-8-thia-3-azabicyclo[3.2.1]oct-2-ene 8,8-dioxide;

(R,Z)-3-amino-5-(2,3-difluoro-5-(2-fluoro-2-(tetrahydro-2H-pyran-4-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)nicotinonitrile;

(1R,4R,5S)-2-amino-4-(2-fluoro-5-((Z)-2-fluoro-2-(5-((3-methyl-1,2,4-oxadiazol-5-yl)methoxy)pyrazin-2-yl)vinyl)phenyl)-1-(fluoromethyl)-4-methyl-8-thia-3-azabicyclo[3.2.1]oct-2-ene 8,8-dioxide;

(R,Z)-3-amino-5-(2-fluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-(2,2,2-trifluoroethoxy)pyrazin-2-yl)vinyl)phenyl)-2,5-dimethyl-5,6-dihydro-2H-1,2,4-thiadiazine 1,1-dioxide;

(1R,4R,5S)-2-amino-4-(5-((Z)-2-(5-(cyclopropylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-((5-methyl-1,3,4-oxadiazol-2-yl)methoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2,2,3,3-tetrafluoropropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-methoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-ethoxypyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(R,Z)-5-amino-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,2-trifluoroethoxy)pyrazin-2-yl)vinyl)phenyl)-3,6,6-trimethyl-3,6-dihydro-2H-1,4-thiazine 1,1-dioxide;

(1R,4R,5S)-4-(5-((Z)-2-(5-(allyloxy)pyrazin-2-yl)-2-fluorovinyl)-2-fluorophenyl)-2-amino-1-(fluoromethyl)-4-methyl-8-thia-3-azabicyclo[3.2.1]oct-2-ene 8,8-dioxide;

(R,Z)-6-(2-(3-(6-amino-5,8-dimethyl-4,4-dioxido-4-thia-5,7-diazaspiro[2.5]oct-6-en-8-yl)-4-fluorophenyl)-1-fluorovinyl)nicotinonitrile;

(1R,4R,5S)-2-amino-4-(5-((Z)-2-(5-((S)-but-3-yn-2-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(R,Z)-5-amino-3-(2-fluoro-5-(2-fluoro-2-(5-(oxazol-2-ylmethoxy)pyrazin-2-yl)vinyl)phenyl)-3,6,6-trimethyl-3,6-dihydro-2H-1,4-thiazine 1,1-dioxide;

(1R,4R,5S)-2-amino-4-(2-fluoro-5-((Z)-2-fluoro-2-(5-(2-methoxyethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-((S)-1-methoxypropan-2-yl)oxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(cyclobutylmethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-fluoroethoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(2,2-difluoroethoxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-propoxypyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(2-fluoro-5-((Z)-2-fluoro-2-(5-(2-methoxypropoxy)pyrazin-2-yl)vinyl)phenyl)-1-(fluoromethyl)-4-methyl-8-thia-3-azabicyclo[3.2.1]oct-2-ene 8,8-dioxide;

(1R,4R,5S)-2-amino-4-(5-((Z)-2-(5-(but-2-yn-1-yloxy)pyrazin-2-yl)-2-fluorovinyl)-2-fluorophenyl)-1-(fluoromethyl)-4-methyl-8-thia-3-azabicyclo[3.2.1]oct-2-ene 8,8-dioxide;

(8R)-8-(2-fluoro-5-((Z)-2-fluoro-2-(5-(2-propyn-1-yloxy)-2-pyrazinyl)ethenyl)phenyl)-5,8-dimethyl-4-thia-5,7-diazaspiro[2.5]oct-6-en-6-amine 4,4-dioxide;

(8R)-8-(5-((Z)-2-(5-chloro-2-pyrazinyl)-2-fluoroethenyl)-2-fluorophenyl)-5,8-dimethyl-4-thia-5,7-diazaspiro[2.5]oct-6-en-6-amine 4,4-dioxide;

(R,Z)-5-amino-3-(2-fluoro-5-(2-fluoro-2-(5-hydroxypyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(2,2,3,3-tetrafluoropropoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(3,3,3-trifluoropropoxy)pyrazin-2-yl)vinyl)phenyl)-3,6,6-trimethyl-3,6-dihydro-2H-1,4-thiazine 1,1-dioxide;

(R,Z)-3-amino-5-(5-(2-(5-(cyclopropylmethoxy)pyrazin-2-yl)-2-fluorovinyl)-2-fluorophenyl)-2,5-dimethyl-5,6-dihydro-2H-1,2,4-thiadiazine 1,1-dioxide;

(R,Z)-5-amino-3-(5-(2-(5-(cyclopentylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(cyclobutylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-amino-5-(2-fluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-5-(2-(3-(6-amino-5,8-dimethyl-4,4-dioxido-4-thia-5,7-diazaspiro[2.5]oct-6-en-8-yl)-4-fluorophenyl)-1-fluorovinyl)pyrazine-2-carbonitrile;

(R,Z)-3-amino-5-(2-fluoro-5-(2-fluoro-2-(5-(2,2,3,3-tetrafluoropropoxy)pyrazin-2-yl)vinyl)phenyl)-2,5-dimethyl-5,6-dihydro-2H-1,2,4-thiadiazine 1,1-dioxide;

(R,Z)-9-amino-7-(2-fluoro-5-(2-fluoro-2-(5-(prop-2-yn-1-yloxy)pyrazin-2-yl)vinyl)phenyl)-7-methyl-5-thia-8-azaspiro[3.5]non-8-ene 5,5-dioxide;

(R,Z)-5-amino-3-(5-(2-(5-(cyclohexylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-((5-(2-(3-(5-amino-3,6,6-trimethyl-1,1-dioxido-3,6-dihydro-2H-1,4-thiazin-3-yl)-4-fluorophenyl)-1-fluorovinyl)pyrazin-2-yl)oxy)-2,2-dimethylpropanenitrile;

(R,Z)-5-amino-3-(5-(2-(5-(but-2-yn-1-yloxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(2-(4-bromo-1H-pyrazol-1-yl)ethoxy)pyrazin-2-yl)-2-fluorovinyl)-2-fluorophenyl)-3,6,6-trimethyl-3,6-dihydro-2H-1,4-thiazine 1,1-dioxide;

(R,Z)-3-(5-(2-(5-(2-(1H-pyrazol-1-yl)ethoxy)pyrazin-2-yl)-2-fluorovinyl)-2-fluorophenyl)-5-amino-3,6,6-trimethyl-3,6-dihydro-2H-1,4-thiazine 1,1-dioxide;

(R,Z)-3-amino-5-(2,3-difluoro-5-(2-fluoro-2-(5-(prop-2-yn-1-yloxy)pyrazin-2-yl)vinyl)phenyl)-2,5-dimethyl-5,6-dihydro-2H-1,2,4-thiadiazine 1,1-dioxide;

(R)-5-amino-3-(5-((Z)-2-(5-((S)-but-3-yn-2-yloxy)pyrazin-2-yl)-2-fluorovinyl)-2-fluorophenyl)-3,6,6-trimethyl-3,6-dihydro-2H-1,4-thiazine 1,1-dioxide;

(8R)-8-(2-fluoro-5-((Z)-2-fluoro-2-(5-(3-methyl-1,2,4-oxadiazol-5-yl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(5-methyl-3-isoxazolyl)methoxy)-2-pyrazinyl)ethenyl)phenyl)-5,8-dimethyl-4-thia-5,7-diazaspiro[2.5]oct-6-en-6-amine 4,4-dioxide;

(8R)-8-(2-fluoro-5-((Z)-2-fluoro-2-(5-(2,2,2-trifluoroethoxy)-2-pyrazinyl)ethenyl)phenyl)-5,8-dimethyl-4-thia-5,7-diazaspiro[2.5]oct-6-en-6-amine 4,4-dioxide;

(R)-3-amino-5-(2-fluoro-5-((Z)-2-fluoro-2-(5-((S)-1-methoxypropan-2-yl)oxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(but-2-yn-1-yloxy)pyrazin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-2-ylmethoxy)pyrazin-2-yl)vinyl)phenyl)-2,5-dimethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2,3-difluorophenyl)-2,5-dimethyl-5,6-dihydro-2H-1,2,4-thiadiazine 1,1-dioxide hydrochloride;

(R,Z)-3-amino-5-(5-(2-(5-(but-2-yn-1-yloxy)pyrazin-2-yl)-2-fluorovinyl)-2-fluorophenyl)-2,5-dimethyl-5,6-dihydro-2H-1,2,4-thiadiazine 1,1-dioxide;

(8R)-8-(2-fluoro-5-((Z)-2-fluoro-2-(5-(5-methyl-1,3-oxazol-2-yl)methoxy)-2-pyrazinyl)ethenyl)phenyl)-5,8-dimethyl-4-thia-5,7-diazaspiro[2.5]oct-6-en-6-amine 4,4-dioxide;

(R,Z)-5-(2-(3-(5-amino-3,6,6-trimethyl-1,1-dioxido-3,6-dihydro-2H-1,4-thiazin-3-yl)-4-fluorophenyl)-1-fluorovinyl)pyrazine-2-carbonitrile;

(R)-3-amino-5-(5-((Z)-2-(5-((S)-but-3-yn-2-yloxy)pyrazin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-(5-(2-methoxypropoxy)pyrazin-2-yl)vinyl)phenyl)-2,5-dimethyl-5,6-dihydro-2H-1,2,4-thiadiazine 1,1-dioxide;

(R,Z)-3-amino-5-(2-fluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-5-amino-3-(2-fluoro-5-(2-fluoro-2-(5-((3-methyl-1,2,4-oxadiazol-5-yl)methoxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-((5-methyl-1,3,4-oxadiazol-2-yl)methoxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-pent-1-yn-3-yloxy)pyrazin-2-yl)vinyl)phenyl)-3,6,6-trimethyl-3,6-dihydro-2H-1,4-thiazine 1,1-dioxide;

(R,Z)-3-amino-5-(2-fluoro-5-(2-fluoro-2-(5-(oxetan-3-ylmethoxy)pyrazin-2-yl)vinyl)phenyl)-2,5-dimethyl-5,6-dihydro-2H-1,2,4-thiadiazine 1,1-dioxide;

(R,Z)-6-(2-(3-(3-amino-2,5,6,6-tetramethyl-1,1-dioxido-5,6-dihydro-2H-1,2,4-thiadiazin-5-yl)-4-fluorophenyl)-1-fluorovinyl)nicotinonitrile;

(R,Z)-5-(2-(3-(3-amino-2,5,6,6-tetramethyl-1,1-dioxido-5,6-dihydro-2H-1,2,4-thiadiazin-5-yl)-4-fluorophenyl)-1-fluorovinyl)pyrazine-2-carbonitrile;

(R,Z)-3-amino-5-(5-(2-(5-chloropyrazin-2-yl)-2-fluorovinyl)-2-fluorophenyl)-2,5,6,6-tetramethyl-5,6-dihydro-2H-1,2,4-thiadiazine 1,1-dioxide;

(R,Z)-3-amino-5-(2-fluoro-5-(2-fluoro-2-(5-(prop-2-yn-1-yloxy)pyrazin-2-yl)vinyl)phenyl)-2,5,6,6-tetramethyl-5,6-dihydro-2H-1,2,4-thiadiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-3,6,6-trimethyl-3,6-dihydro-2H-1,4-thiazine 1,1-dioxide;

(R,Z)-3-amino-5-(5-(2-(5-(but-2-yn-1-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(R)-3-amino-5-(5-((Z)-2-(5-((S)-but-3-yn-2-yloxy)pyrazin-2-yl)-2-fluorovinyl)-2-fluorophenyl)-2,5,6,6-tetramethyl-5,6-dihydro-2H-1,2,4-thiadiazine 1,1-dioxide;

(S,Z)-6-(2-(3-(5-amino-3-(fluoromethyl)-6,6-dimethyl-1,1-dioxido-3,6-dihydro-2H-1,4-thiazin-3-yl)-4-fluorophenyl)-1-fluorovinyl)nicotinonitrile;

(S,Z)-5-amino-3-(2-fluoro-5-(2-fluoro-2-(5-(prop-2-yn-1-yloxy)pyrazin-2-yl)vinyl)phenyl)-3-(fluoromethyl)-6,6-dimethyl-3,6-dihydro-2H-1,4-thiazine 1,1-dioxide;

(R,Z)-6-(2-(3-(5-amino-3,6,6-trimethyl-1,1-dioxido-3,6-dihydro-2H-1,4-thiazin-3-yl)-4,5-difluorophenyl)-1-fluorovinyl)nicotinonitrile;

(S,Z)-5-amino-3-(5-(2-(5-(but-2-yn-1-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(S)-5-amino-3-(5-((Z)-2-(5-((S)-but-3-yn-2-yloxy)pyrazin-2-yl)-2-fluorovinyl)-2-fluorophenyl)-3-(fluoromethyl)-6,6-dimethyl-3,6-dihydro-2H-1,4-thiazine 1,1-dioxide;

(R,Z)-6-(2-(5-(5-amino-3,6,6-trimethyl-1,1-dioxido-3,6-dihydro-2H-1,4-thiazin-3-yl)-6-fluoropyridin-3-yl)-1-fluorovinyl)nicotinonitrile;

(R)-5-amino-3-(2-fluoro-5-((Z)-2-fluoro-2-(5-((R)-hex-4-yn-3-yloxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-hex-4-yn-3-yloxy)pyrazin-2-yl)vinyl)phenyl)-3,6,6-trimethyl-3,6-dihydro-2H-1,4-thiazine 1,1-dioxide;

(2R,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(2S,3R)-5-amino-2-fluoro-3-(2-fluoro-5-((Z)-2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-2,2-difluoro-3-(2-fluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2,3-difluoro-5-(2-fluoro-2-(5-(prop-2-yn-1-yloxy)pyrazin-2-yl)vinyl)phenyl)-3,6,6-trimethyl-3,6-dihydro-2H-1,4-thiazine 1,1-dioxide;

(R,Z)-5-amino-3-(2-fluoro-5-(2-fluoro-2-(5-(prop-2-yn-1-yloxy)pyrazin-2-yl)vinyl)pyridin-3-yl)-3,6,6-trimethyl-3,6-dihydro-2H-1,4-thiazine 1,1-dioxide;

(R,Z)-5-amino-3-(5-(2-(5-(cyclopropylmethoxy)pyrazin-2-yl)-2-fluorovinyl)-2-fluorophenyl)-3,6,6-trimethyl-3,6-dihydro-2H-1,4-thiazine 1,1-dioxide;

(R,Z)-5-amino-3-(5-(2-(5-(benzyloxy)pyrazin-2-yl)-2-fluorovinyl)-2-fluoropyridin-3-yl)-3,6,6-trimethyl-3,6-dihydro-2H-1,4-thiazine 1,1-dioxide;

(R,Z)-4-(2-(3-(3-amino-2,5-dimethyl-1,1-dioxido-5,6-dihydro-2H-1,2,4-thiadiazin-5-yl)-4-fluorophenyl)-1-fluorovinyl)benzonitrile;

(2S,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;

(2R,3R)-5-amino-3-(5-((Z)-2-(2,3-dihydro-[1,4]dioxino[2,3-c]pyridin-7-yl)-2-fluorovinyl)-2-fluorophenyl)-2-fluoro-3,6,6-trimethyl-3,6-dihydro-2H-1,4-thiazine 1,1-dioxide;

(R,Z)-5-amino-3-(5-(2-(2,3-dihydro-[1,4]dioxino[2,3-c]pyridin-7-yl)-2-fluorovinyl)-2-fluorophenyl)-2,2-difluoro-3,6,6-trimethyl-3,6-dihydro-2H-1,4-thiazine 1,1-dioxide;

(R)-5-amino-3-(2-fluoro-5-((Z)-2-fluoro-2-(5-((S)-1-hydroxypropan-2-yl)oxy)pyrazin-2-yl)vinyl)phenyl)-3,6,6-trimethyl-3,6-dihydro-2H-1,4-thiazine 1,1-dioxide;

(R)-5-amino-3-(2-fluoro-5-((Z)-2-fluoro-2-(5-((S)-2-hydroxypropoxy)pyrazin-2-yl)vinyl)phenyl)-3,6,6-trimethyl-3,6-dihydro-2H-1,4-thiazine 1,1-dioxide;

(R,Z)-3-amino-5-(2,3-difluoro-5-(2-fluoro-2-(5-(thiazol-4-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methylisoxazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methylisoxazol-3-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((3-methyl-1,2,4-oxadiazol-5-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(oxazol-4-ylmethoxy)pyrazin-2-yl)vinyl)phenyl)-2,5-dimethyl-5,6-dihydro-2H-1,2,4-thiadiazine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-4-fluoro-3-pyridinecarbonitrile;

(R,Z)-5-(5-(2-(5-(allyloxy)pyrazin-2-yl)-2-fluorovinyl)-2,3-difluorophenyl)-3-amino-2,5-dimethyl-5,6-dihydro-2H-1,2,4-thiadiazine 1,1-dioxide;

(R,Z)-3-amino-5-(2,3-difluoro-5-(2-fluoro-2-(5-(pyrimidin-2-ylmethoxy)pyrazin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((5-methyl-1,2,4-oxadiazol-3-yl)methoxy)pyrazin-2-yl)vinyl)phenyl)-2,5-dimethyl-5,6-dihydro-2H-1,2,4-thiadiazine 1,1-dioxide;

(R,Z)-2-(2-(3-(3-amino-2,5-dimethyl-1,1-dioxido-5,6-dihydro-2H-1,2,4-thiadiazin-5-yl)-4-fluorophenyl)-1-fluorovinyl)-5-chloroisonicotinonitrile;

(R,Z)-3-amino-5-(2,3-difluoro-5-(2-fluoro-2-(5-((5-methyl-1,3,4-oxadiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-Amino-5-(5-(2-(6,7-dihydro-[1,4]dioxino[2,3-d]pyrimidin-2-yl)-2-fluorovinyl)-2-fluorophenyl)-2,5-dimethyl-5,6-dihydro-2H-1,2,4-thiadiazine 1,1-dioxide;

(R)-3-amino-5-(2-fluoro-5-((Z)-2-fluoro-2-((R)-6-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R)-3-amino-5-(2-fluoro-5-((Z)-2-fluoro-2-((S)-7-methyl-6,7-dihydro-[1,4]dioxino[2,3-d]pyrimidin-2-yl)vinyl)phenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((4-methylthiazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-((2,5-dimethyloxazol-4-yl)methoxy)pyrazin-2-yl)-2-fluorovinyl)-2,3-difluorophenyl)-2,5-dimethyl-5,6-dihydro-2H-1,2,4-thiadiazine 1,1-dioxide;

(5R)-5-(5-((Z)-2-(3-chloro-5-(trifluoromethyl)-2-pyridinyl)-2-fluoroethenyl)-2-fluorophenyl)-2,5-dimethyl-5,6-dihydro-2H-1,2,4-thiadiazin-3-amine 1,1-dioxide;

(R,Z)-ethyl 2-((5-(2-(3-(3-amino-2,5-dimethyl-1,1-dioxido-5,6-dihydro-2H-1,2,4-thiadiazin-5-yl)-4,5-difluorophenyl)-1-fluorovinyl)pyrazin-2-yl)oxy)acetate;

(5R)-5-(2-fluoro-5-((Z)-2-fluoro-2-(5-(trifluoromethyl)-2-pyridinyl)ethenyl)phenyl)-2,5-dimethyl-5,6-dihydro-2H-1,2,4-thiadiazin-3-amine 1,1-dioxide;

6-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-5-methyl-3-pyridinecarbonitrile;

(R,Z)-3-amino-5-(2,3-difluoro-5-(2-fluoro-2-(5-((5-methyloxazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-bromopyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(5-(2-(5-(cyclopropylethynyl)pyrazin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-((1-methyl-1H-imidazol-2-yl)methoxy)pyrazin-2-yl)vinyl)phenyl)-2,5-dimethyl-5,6-dihydro-2H-1,2,4-thiadiazine 1,1-dioxide;

(R,Z)-3-amino-5-(5-(2-(5-(cyclopropylethynyl)pyridin-2-yl)-2-fluorovinyl)-2-fluorophenyl)-2,5-dimethyl-5,6-dihydro-2H-1,2,4-thiadiazine 1,1-dioxide;

(R,Z)-3-amino-5-(2-fluoro-5-(2-fluoro-2-(5-((4-hydroxybut-2-yn-1-yl)oxy)pyrazin-2-yl)vinyl)phenyl)-2,5-dimethyl-5,6-dihydro-2H-1,2,4-thiadiazine 1,1-dioxide;

2-((Z)-2-(3-((5R)-3-amino-2,5-dimethyl-1,1-dioxido-5,6-dihydro-2H-1,2,4-thiadiazin-5-yl)-4-fluorophenyl)-1-fluoroethenyl)-1,3-thiazole-5-carbonitrile;

(R,Z)-3-amino-5-(2-fluoro-5-(2-fluoro-2-(5-((4-fluorobut-2-yn-1-yl)oxy)pyrazin-2-yl)vinyl)phenyl)-2,5-dimethyl-5,6-dihydro-2H-1,2,4-thiadiazine 1,1-dioxide;

(5R)-5-(5-((Z)-2-([1,3]dioxolo[4,5-c]pyridin-6-yl)-2-fluoroethenyl)-2-fluorophenyl)-2,5-dimethyl-5,6-dihydro-2H-1,2,4-thiadiazin-3-amine 1,1-dioxide;

(R,Z)-3-amino-5-(2-fluoro-5-(2-fluoro-2-(5-(trifluoromethoxy)pyridin-2-yl)vinyl)phenyl)-2,5-dimethyl-5,6-dihydro-2H-1,2,4-thiadiazine 1,1-dioxide;

6-((Z)-2-(4-((4aS,7aS)-3-amino-2,2-dimethyl-1,1-dioxido-4a,5,7,7a-tetrahydro-2H-furo[3,4-b][1,4]thiazin-4a-yl)-3-fluorophenyl)-1-fluorovinyl)nicotinonitrile;

(R,Z)-5-amino-3-(5-(2-(3-chloro-5-(trifluoromethyl)pyridin-2-yl)-2-fluorovinyl)-2-fluorophenyl)-3,6,6-trimethyl-3,6-dihydro-2H-1,4-thiazine 1,1-dioxide;

317

(R,Z)-5-amino-3-(2-fluoro-5-(2-fluoro-2-(5-(trifluoromethyl)pyridin-2-yl)vinyl)phenyl)-3,6,6-trimethyl-3,6-dihydro-2H-1,4-thiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-chloronicotinonitrile;

(R,Z)-6-(2-(3-(3-amino-2,5-dimethyl-1,1-dioxido-5,6-dihydro-2H-1,2,4-thiadiazin-5-yl)-4-fluorophenyl)-1-fluorovinyl)-5-chloronicotinonitrile;

(R,Z)-3-amino-5-(2,3-difluoro-5-(2-fluoro-2-(5-methoxypyrazin-2-yl)vinyl)phenyl)-2,5-dimethyl-5,6-dihydro-2H-1,2,4-thiadiazine 1,1-dioxide;

(R,Z)-3-amino-5-(5-(2-(3-chloro-5-(trifluoromethyl)pyridin-2-yl)-2-fluorovinyl)-2,3-difluorophenyl)-2,5-dimethyl-5,6-dihydro-2H-1,2,4-thiadiazine 1,1-dioxide;

(R,Z)-3-amino-5-(2,3-difluoro-5-(2-fluoro-2-(5-(trifluoromethyl)pyridin-2-yl)vinyl)phenyl)-2,5-dimethyl-5,6-dihydro-2H-1,2,4-thiadiazine 1,1-dioxide;

(R,Z)-6-(2-(3-(5-amino-3,6,6-trimethyl-1,1-dioxido-3,6-dihydro-2H-1,4-thiazin-3-yl)-4-fluorophenyl)-1-fluorovinyl)-5-methylnicotinonitrile;

(R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-methylnicotinonitrile; or (R,Z)-6-(2-(3-(3-amino-2,5-dimethyl-1,1-dioxido-5,6-dihydro-2H-1,2,4-thiadiazin-5-yl)-4,5-difluorophenyl)-1-fluorovinyl)-5-chloronicotinonitrile.

28. The compound of claim 1, or a tautomer, or a pharmaceutically acceptable salt of said compound or tautomer, selected from

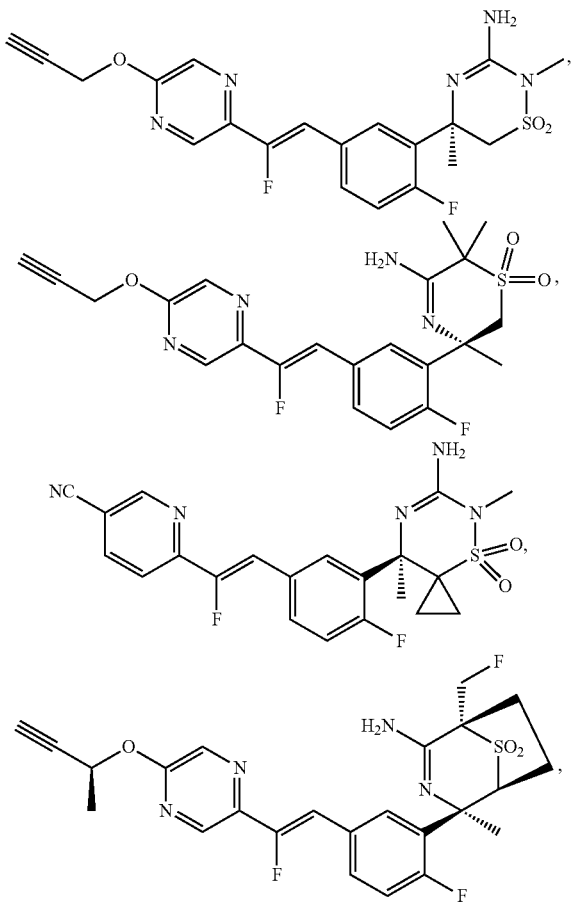

318

-continued

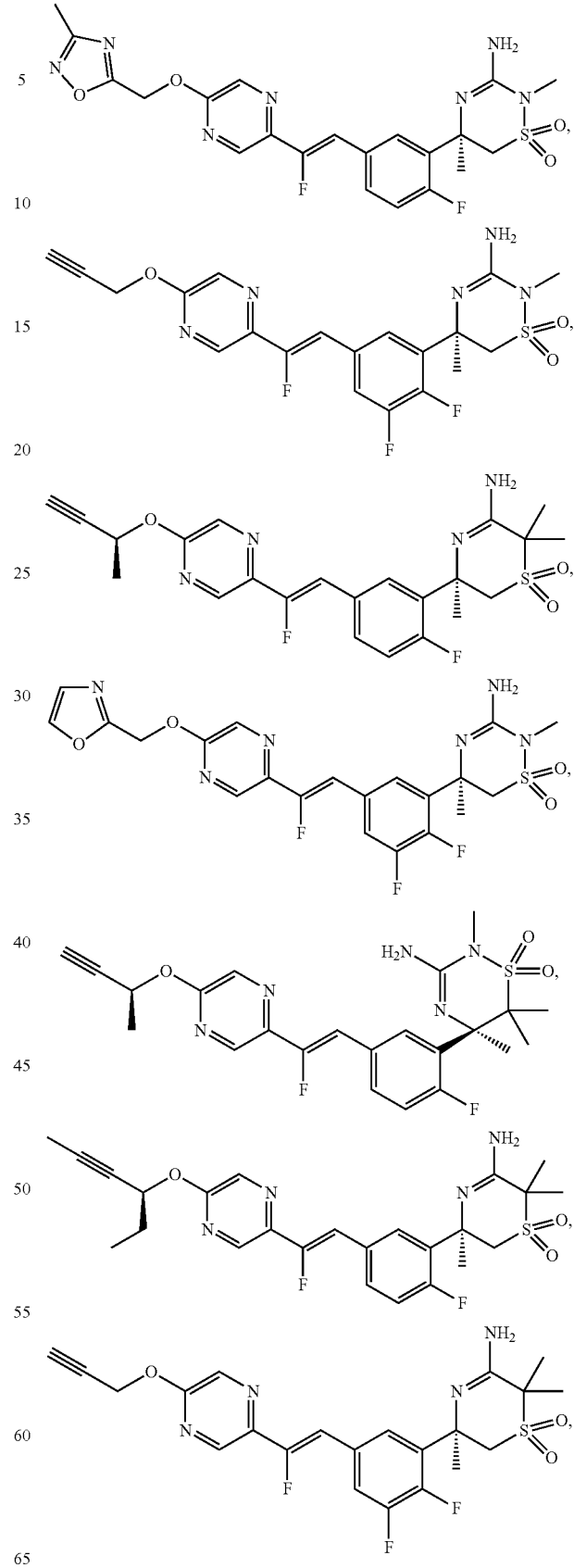

-continued

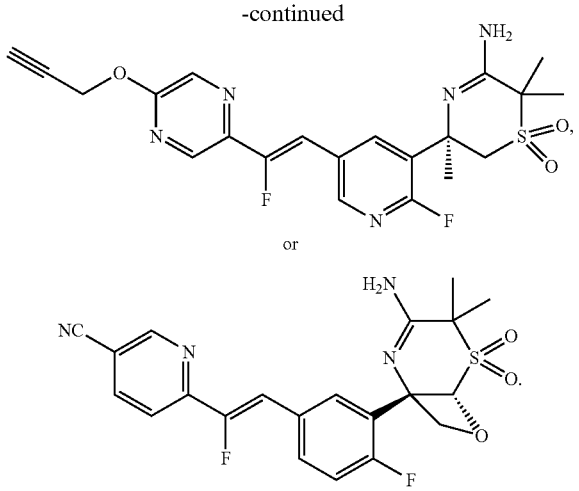

or

29. A pharmaceutical composition comprising the compound according to claim 1, or a tautomer, or a pharmaceutically acceptable salt of said compound or tautomer, and a pharmaceutically acceptable excipient.

30. A method of reducing beta amyloid peptide levels in the cerebral spinal fluid of a subject in need thereof, the method comprising administering to the subject a therapeutically effective amount of the compound according to claim 1, or a tautomer, or a pharmaceutically acceptable salt of said compound or tautomer.

31. A method of treating Alzheimer's disease, cognitive impairment or a combination thereof in a subject in need thereof, the method comprising administering to the subject a therapeutically effective amount of the compound according to claim 1, or a tautomer, or a pharmaceutically acceptable salt of said compound or tautomer.

32. A method of treating a neurological disorder selected from mild cognitive impairment, Down's syndrome, hereditary cerebral hemorrhage with Dutch-type amyloidosis, cerebral amyloid angiopathy, degenerative dementia, dementia associated with Parkinson's disease, dementia associated with supranuclear palsy, dementia associated with cortical basal degeneration, diffuse Lewy body type of Alzheimer's disease, or a combination thereof in a subject in need thereof, the method comprising administering to the subject a therapeutically effective amount of the compound according to claim 1, or a tautomer, or a pharmaceutically acceptable salt of said compound or tautomer.

33. A method of reducing the formation of plaque on the brain of a subject in need thereof, the method comprising administering to the subject a therapeutically effective amount of the compound according to claim 1, or a tautomer, or a pharmaceutically acceptable salt of said compound or tautomer.

* * * * *